US006555556B1

(12) United States Patent
Fujimoto et al.

(10) Patent No.: US 6,555,556 B1
(45) Date of Patent: Apr. 29, 2003

(54) BENZAMIDINE DERIVATIVES

(75) Inventors: Koichi Fujimoto, Yokohama (JP); Fumitoshi Asai, Nishitokyo (JP); Hayao Matsuhashi, Kawasaki (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/132,042

(22) Filed: Apr. 25, 2002

Related U.S. Application Data

(63) Continuation-in-part of application No. PCT/JP00/07469, filed on Oct. 25, 2000.

(30) Foreign Application Priority Data

Oct. 28, 1999 (JP) .......................................... 11-307192

(51) Int. Cl.[7] ...................... A61K 31/445; A61K 31/40; C07D 211/40; C07D 207/12

(52) U.S. Cl. ....................... 514/327; 546/221; 546/216; 548/541; 514/424

(58) Field of Search ................................ 514/327, 424; 546/221, 216; 548/541

(56) References Cited

U.S. PATENT DOCUMENTS 6,350,761 B1 * 2/2002 Guilford et al. ............ 514/327

FOREIGN PATENT DOCUMENTS

| | | |
|---|---|---|
| EP | 0 540 051 A1 | 5/1993 |
| EP | 0 798 295 A1 | 10/1997 |
| EP | 0 976 722 A1 | 2/2000 |
| WO | WO 00/47553 | 8/2000 |
| WO | WO 00-47554 | 8/2000 |

OTHER PUBLICATIONS

Harder et al., "Clinically Important Drug Interactions with Anticoagulants", *Clin. Pharmacokinet.*, (1996) 30, pp. 416–444.

Verstraete et al., "Novel Antithrombotic Drugs in Development", Drugs, (1996) 49, pp. 856–884.

Bouygues, et al., "Syntheses of new modified Phe–Pro peptides", *Bioorg. Med. Chem. Lett.*, 8, (1998), pp. 277–280.

Wells, et al., "Regioselective Nucleophilic Substitutions of Fluorobenzene Derivatives", *Tetrahedron Letters*, (1996), 37, No. 36, pp. 6439–6442.

Makosza, et al., "Hydroxylation of Nitroarenes with Alkyl Hydroperoxide Anions via Vicarious Nucleophilic Substitution of Hydrogen", *J. Org. Chem.* (1998), 63, pp. 4199–4208.

Coutrot et al., "2–Diethoxyphosphoryl alcanoic acid dianions (lithium α–lithiocarboxylates)", *Journal of Organometallic Chemistry*, (1987), 332, pp. 1–8.

Hara, et al., "DX–9065a, a New Synthetic, Potent Anticoagulant and Selective Inhibitor for Factor Xa", *Thombosis and Haemostasis*, (1994), 71, pp. 314–319.

Taniuchi, et al, "Biochemical and Pharmacological Characterization of YM–60828, a Newly Synthesized and Orally Active Inhibitor of Human Factor Xa", *Thromb Haemost*, (1998), 79, pp. 543–548.

*Drugs*, 53, 736 (1997).

*N. Engl. J. Med.*, 333, 1588 (1995).

*Circulation*, 98, 287 (1998).

*Drugs*, 52, 276 (1996).

*Thromb. Res.*, 86, 1 (1997).

*J. Enzyme Inhibition*, 14, 15 (1998).

* cited by examiner

*Primary Examiner*—Charanjit S. Aulakh
(74) *Attorney, Agent, or Firm*—Frishauf, Holtz, Goodman & Chick, P.C.

(57) ABSTRACT

Benzamidine derivatives of formula (I) or pharmaceutically acceptable salts thereof exhibit excellent inhibitory activity against factor Xa and are useful for treating or preventing blood coagulation disorders:

(I)

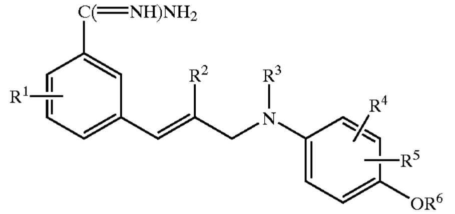

wherein $R^1$ represents a hydrogen atom, a halogen atom, an alkyl group or a hydroxyl group; $R^2$ represents a hydrogen atom, a halogen atom or an alkyl group, $R^3$ represents a hydrogen atom, an optionally substituted alkyl group, an aralkyl group, an optionally substituted alkanoyl group or an optionally substituted alkylsulfonyl group, $R^4$ and $R^5$ are the same as or different from each other and each represent a hydrogen atom, a halogen atom, an optionally substituted alkyl group, an alkoxy group, a carboxyl group, an alkoxycarbonyl group or an optionally substituted carbamoyl group, and $R^6$ represents a substituted pyrrolidine group or substituted piperidine group.

48 Claims, No Drawings

BENZAMIDINE DERIVATIVES

This is a Continuation-in-Part Application of International Application No. PCT/JP00/07469 filed Oct. 25, 2000 (not published in English).

BACKGROUND OF THE INVENTION

The present invention relates to benzamidine derivatives and their pharmaceutically acceptable salts having excellent inhibitory activity against factor Xa. This invention further relates to pharmaceutical compositions comprising said compounds as an active ingredient for prevention or treatment of a blood coagulation disorder. In another aspect, this invention relates to the use of said compounds in the preparation of a medicament for the prevention or treatment of a blood coagulation disorder. In another aspect, this invention relates to a method for the prevention or treatment of a blood coagulation disorder, which method comprises administering a pharmaceutically effective amount of said compounds to a warm-blooded animal in need of such treatment. In yet another aspect, this invention relates to a process for the preparation of said compounds.

Recently the number of patients with cardiovascular diseases is increasing in accordance with the increase in the elderly population. Among these diseases, thrombotic diseases such as cerebral infarction, myocardial infarction and peripheral occlusive diseases not only lead to death, but also cause a significant limitation in the individual and social lives of patients which have a poor prognosis. Thus, it is suggested that anticoagulant therapy against thrombotic diseases is becoming increasingly important.

Blood coagulation involves a complex cascade of enzymatic reactions that can be triggered by an initial stimulus, and amplified to terminate in the thrombin-catalyzed conversion of the soluble fibrinogen to the insoluble plasma protein fibrin. This process is known as the blood coagulation cascade and comprises the intrinsic and the extrinsic pathways. The activated factor X (factor Xa) is a key enzyme at the point of convergence of both coagulation pathways. It forms a complex with bivalent calcium ions, phospholipids and factor Va to efficiently convert prothrombin to thrombin, and thereby accelerates blood coagulation [e.g., E. L. Smith, A. White et al., 'Principles of Biochemistry': Mammalian Biochemistry, $7^{th}$ edition, McGraw-Hill, Inc. (1983), etc.].

Warfarin and thrombin inhibitors are currently used as anti-coagulants. Although warfarin is a widely used as an orally active anti-thrombotic agent, it has significant clinical limitations. The anti-coagulant activity of warfarin is antagonized by vitamin K, and is often affected by interactions with the diet or commonly used drugs [e.g., *Clin. Pharmacokinet*., 30, 416 (1996)]. In addition, currently available thrombin inhibitors carry a hemorrhage risk as adverse events associated with their pharmacological actions, and thus novel anti-coagulants need to be developed. Since factor Xa affects thrombin formation and factor Xa inhibitors are known to exert anti-coagulant activities, factor Xa inhibitors are suggested to become a novel type of anti-coagulant [e.g., *Drugs*, 49, 856 (1995)].

Aromatic amidine derivatives or amidinonaphthyl derivatives are described as competitive factor Xa inhibitors in Japanese Patent Application Publication No. Hei 5-208946 (EP 540051), WO 96/16940 (EP 798295) or WO 00/47553. Further, benzamidine derivatives such as N-[4-[1-acetimidoyl-4-piperidyloxy]phenyl]-N-[2-(3-amidinophenoxy)ethyl]sulfamoylacetic acid bis (trifluoroacetate) are described in WO 98/31661 (EP 976722).

DISCLOSURE OF THE INVENTION

The inventors studied the pharmacological actions of various benzamidine derivatives for many years to develop compounds with excellent anti-factor Xa activity. Our study resulted in the finding that benzamidine derivatives with specific substituents exhibit excellent anti-factor Xa activity, but do not exhibit anti-trypsin activity which is associated with adverse events. Furthermore, these derivatives are useful for the prophylaxis and therapy (particularly therapy) of blood coagulation disorders. These results led to the present invention.

The present invention relates to benzamidine derivatives and their pharmaceutically acceptable salts having excellent inhibitory activity against factor Xa. This invention further relates to pharmaceutical compositions comprising said compounds as an active ingredient for the prevention or treatment of a blood coagulation disorder. In another aspect, this invention relates to the use of said compounds in the preparation of a medicament for the prevention or treatment of a blood coagulation disorder. In another aspect, this invention relates to a method for the prevention or treatment of a blood coagulation disorder, which method comprises administering a pharmaceutically effective amount of said compounds to a warm-blooded animal in need of such treatment. In yet another aspect, this invention relates to a process for the preparation of said compounds.

Benzamidine derivatives of the present invention have the following formula (I):

(I)

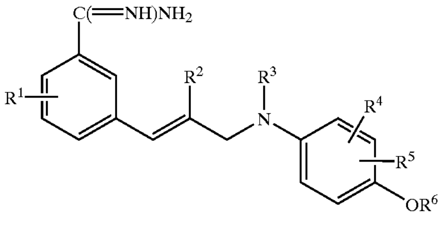

wherein:

$R^1$ represents a hydrogen atom, a halogen atom, a $C_1$–$C_6$ alkyl group or a hydroxyl group;

$R^2$ represents a hydrogen atom, a halogen atom or a $C_1$–$C_6$ alkyl group;

$R^3$ represents a hydrogen atom; a $C_1$–$C_6$ alkyl group; a $C_1$–$C_6$ alkyl group which is substituted with a hydroxyl group, a carboxyl group or a ($C_1$–$C_6$ alkoxy)carbonyl group; a group of formula (II)

(II)

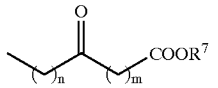

(wherein $R^7$ represents a $C_1$–$C_6$ alkyl group, m and n are the same as or different from each other and each represent an integer from 1 to 6); a $C_7$–$C_{15}$ aralkyl group; a $C_1$–$C_6$ alkanoyl group; a hydroxy $C_2$–$C_6$ alkanoyl group; a $C_1$–$C_6$ alkylsulfonyl group; or a $C_1$–$C_6$ alkylsulfonyl group which is substituted with a carboxyl group or a ($C_1$–$C_6$ alkoxy)carbonyl group; and $R^4$ and $R^5$ are the same as or different from each other and each represent a hydrogen atom, a halogen atom, a $C_1$–$C_6$ alkyl group, a halogeno-$C_1$–$C_6$ alkyl group, a $C_1$–$C_6$ alkoxy group, a carboxyl group, a ($C_1$–$C_6$ alkoxy)carbonyl group, a carbamoyl group, a ($C_1$–$C_6$ alkyl)carbamoyl group or a di($C_1$–$C_6$ alkyl)carbamoyl group; and $R^6$ represents a 1-acetimidoylpyrrolidin-3-yl group or 1-acetimidoylpiperidin-4-yl group.

The active ingredients of the pharmaceutical composition for prevention or treatment of a blood coagulation disorder of the present invention are the benzamidine derivatives of formula (I) or their pharmaceutically acceptable salts.

The "halogen atom" in the definition of $R^1$ may be, for example, a fluorine, chlorine, bromine or iodine atom; preferably a fluorine, chlorine or bromine atom; more preferably a fluorine or chlorine atom; and most preferably a fluorine atom.

The "$C_1$–$C_6$ alkyl group" in the definition of $R^1$ is, for example, a straight or branched chain alkyl group having from one to six carbon atoms such as a methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group; preferably a $C_1$–$C_4$ alkyl group; more preferably a methyl or ethyl group; and most preferably a methyl group.

The "halogen atom" in the definition of $R^2$ may be, for example, as described in the definition of $R^1$; preferably a fluorine or chlorine atom; and most preferably a fluorine atom.

The "$C_1$–$C_6$ alkyl group" in the definition of $R^2$ may be, for example, as described in the definition of $R^1$; preferably a $C_1$–$C_4$ alkyl group; more preferably a methyl or ethyl group; and most preferably a methyl group.

The $C_1$–$C_6$ alkyl moiety of the "$C_1$–$C_6$ alkyl group" and the "$C_1$–$C_6$ alkyl group which is substituted with a hydroxyl group, a carboxyl group or a ($C_1$–$C_6$ alkoxy)carbonyl group" in the definition of $R^3$ may be, for example, as described in the definition of $R^1$. Preferably the "$C_1$–$C_6$ alkyl group" is a $C_1$–$C_4$ alkyl group; more preferably a methyl, ethyl or isopropyl group; and most preferably an isopropyl group. On the other hand, preferably the $C_1$–$C_6$ alkyl moiety of the "$C_1$–$C_6$ alkyl group which is substituted with a hydroxyl group, a carboxyl group or a ($C_1$–$C_6$ alkoxy)carbonyl group" is a $C_1$–$C_4$ alkyl group; more preferably a methyl or ethyl group; and most preferably a methyl group.

The "($C_1$–$C_6$ alkoxy)carbonyl group" of the substituents of the "$C_1$–$C_6$ alkyl group which is substituted with a hydroxyl group, a carboxyl group or a ($C_1$–$C_6$ alkoxy) carbonyl group" and the "$C_1$–$C_6$ alkylsulfonyl group which is substituted with a carboxyl group or a ($C_1$–$C_6$ alkoxy) carbonyl group" in the definition of $R^3$ may be, for example, a carbonyl group attached to straight or branched chain alkoxy group having from one to six carbon atoms such as a methoxycarbonyl, ethoxycarbonyl, propoxycarbonyl, isopropoxycarbonyl, butoxycarbonyl, isobutoxycarbonyl, s-butoxycarbonyl, t-butoxycarbonyl, pentyloxycarbonyl, isopentyloxycarbonyl, 2-methylbutoxycarbonyl, neopentyloxycarbonyl, 1-ethylpropoxycarbonyl, hexyloxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl or 2-ethylbutoxycarbonyl group; preferably a ($C_1$–$C_4$ alkoxy)carbonyl group; more preferably a methoxycarbonyl or ethoxycarbonyl group; and most preferably an ethoxycarbonyl group.

The "$C_1$–$C_6$ alkyl group which is substituted with a hydroxyl group, a carboxyl group or a ($C_1$–$C_6$ alkoxy) carbonyl group" in the definition of $R^3$ may be, for example, a $C_1$–$C_6$ alkyl group described above which is substituted with a hydroxyl, carboxyl or ($C_1$–$C_6$ alkoxy)carbonyl group, such as a hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl, 5-hydroxypentyl, 6-hydroxyhexyl, carboxymethyl, 1-carboxyethyl, 2-carboxyethyl, 1-carboxypropyl, 2-carboxypropyl, 3-carboxypropyl, 1-carboxybutyl, 2-carboxybutyl, 3-carboxybutyl, 4-carboxybutyl, 5-carboxypentyl, 6-carboxyhexyl, methoxycarbonylmethyl, ethoxycarbonylmethyl, propoxycarbonylmethyl, isopropoxycarbonylmethyl, butoxycarbonylmethyl, isobutoxycarbonylmethyl, s-butoxycarbonylmethyl, t-butoxycarbonylmethyl, pentyloxycarbonylmethyl, isopentyloxycarbonylmethyl, 2-methylbutoxycarbonylmethyl, neopentyloxycarbonylmethyl, 1-ethylpropoxycarbonylmethyl, hexyloxycarbonylmethyl, 4-methylpentyloxycarbonylmethyl, 3-methylpentyloxycarbonylmethyl, 2-methylpentyloxycarbonylmethyl, 1-methylpentyloxycarbonylmethyl, 3,3-dimethylbutoxycarbonylmethyl, 2,2-dimethylbutoxycarbonylmethyl, 1,1-dimethyl- butoxycarbonylmethyl, 1,2-dimethylbutoxycarbonylmethyl, 1,3-dimethylbutoxycarbonylmethyl, 2,3-dimethylbutoxycarbonylmethyl, 2-ethylbutoxycarbonylmethyl, 1-(methoxycarbonyl)ethyl, 1-(ethoxycarbonyl)ethyl, 1-(propoxycarbonyl)ethyl, 1-(isopropoxycarbonyl)ethyl, 1-(butoxy- carbonyl)ethyl, 1-(isobutoxycarbonyl)ethyl, 1-(s-butoxycarbonyl)ethyl, 1-(t-butoxycarbonyl)ethyl, 1-(pentyloxycarbonyl)ethyl, 1-(isopentyloxycarbonyl)ethyl, 1-(2-methylbutoxycarbonyl)ethyl, 1-(neopentyloxycarbonyl)ethyl, 1-(1-ethylpropoxycarbonyl)ethyl, 1-(hexyloxycarbonyl)ethyl, 1-(4-methylpentyloxycarbonyl)ethyl, 1-(3-methylpentyloxycarbonyl)ethyl, 1-(2-methylpentyloxycarbonyl)ethyl, 1-(1-methylpentyloxycarbonyl)ethyl, 1-(3,3-dimethylbutoxycarbonyl)ethyl, 1-(2,2-dimethylbutoxycarbonyl)ethyl, 1-(1,1-dimethylbutoxycarbonyl)ethyl, 1-(1,2-dimethylbutoxycarbonyl)ethyl, 1-(1,3-dimethylbutoxycarbonyl)ethyl, 1-(2,3-dimethylbutoxycarbonyl)ethyl, 1-(2-ethylbutoxycarbonyl)ethyl, 2-(methoxycarbonyl)ethyl, 2-(ethoxycarbonyl)ethyl, 2-(propoxycarbonyl)ethyl, 2-(isopropoxycarbonyl) ethyl, 2-(butoxycarbonyl)ethyl, 2-(isobutoxycarbonyl)ethyl, 2-(s-butoxycarbonyl)ethyl, 2-(t-butoxycarbonyl)ethyl, 2-(pentyloxycarbonyl)ethyl, 2-(isopentyloxycarbonyl)ethyl, 2-(2-methylbutoxycarbonyl)ethyl, 2-(neopentyloxycarbonyl)ethyl, 2-(1-ethylpropoxycarbonyl)ethyl, 2-(hexyloxycarbonyl)ethyl, 2-(4-methylpentyloxycarbonyl)ethyl, 2-(3-methylpentyloxycarbonyl)ethyl, 2-(2-methylpentyloxycarbonyl)ethyl, 2-(1-methylpentyloxycarbonyl)ethyl, 2-(3,3-dimethylbutoxycarbonyl)ethyl, 2-(2,2-dimethylbutoxycarbonyl)ethyl, 2-(1,1-dimethylbutoxycarbonyl)ethyl, 2-(1,2-dimethylbutoxycarbonyl)ethyl, 2-(1,3-dimethylbutoxycarbonyl)ethyl, 2-(2,3-dimethylbutoxycarbonyl)ethyl, 2-(2-ethylbutoxycarbonyl)

ethyl, 3-(methoxycarbonyl)propyl, 3-(ethoxycarbonyl)propyl, 3-(propoxycarbonyl)propyl, 3-(isopropoxycarbonyl)propyl, 3-(butoxycarbonyl)propyl, 3-(isobutoxycarbonyl)propyl, 3-(s-butoxycarbonyl)propyl, 3-(t-butoxycarbonyl)propyl, 3-(pentyloxycarbonyl)propyl, 3-(isopentyloxycarbonyl)propyl, 3-(hexyloxycarbonyl)propyl, 4-(methoxycarbonyl)butyl, 4-(ethoxycarbonyl)butyl, 4-(propoxycarbonyl)butyl, 4-(isopropoxycarbonyl)butyl, 4-(butoxycarbonyl)butyl, 4-(isobutoxycarbonyl)butyl, 4-(s-butoxycarbonyl)butyl, 4-(t-butoxycarbonyl)butyl, 4-(pentyloxycarbonyl)butyl, 4-(isopentyloxycarbonyl)butyl, 4-(hexyloxycarbonyl)butyl, 5-(methoxycarbonyl)pentyl, 5-(ethoxycarbonyl)pentyl, 5-(propoxycarbonyl)pentyl, 5-(butoxycarbonyl)pentyl, 5-(pentyloxycarbonyl)pentyl, 5-(hexyloxycarbonyl)pentyl, 6-(methoxycarbonyl)hexyl, 6-(ethoxycarbonyl)hexyl, 6-(propoxycarbonyl)hexyl, 6-(butoxycarbonyl)hexyl, 6-(pentyloxycarbonyl)hexyl or 6-(hexyloxycarbonyl)hexyl group.

Preferably the "$C_1$–$C_6$ alkyl group which is substituted with a hydroxyl group, a carboxyl group or a ($C_1$–$C_6$) alkoxycarbonyl group" is a hydroxy-$C_1$–$C_4$-alkyl, carboxy-$C_1$–$C_4$-alkyl or ($C_1$–$C_4$ alkoxy)carbonyl-$C_1$–$C_4$-alkyl group; more preferably a hydroxy-$C_1$–$C_4$-alkyl or ($C_1$–$C_4$ alkoxy)carbonylmethyl group; further more preferably a 2-hydroxyethyl, carboxymethyl, methoxycarbonylmethyl, ethoxycarbonylmethyl, propoxycarbonylmethyl or butoxycarbonylmethyl group; still more preferably a 2-hydroxyethyl, carboxymethyl, methoxycarbonylmethyl or ethoxycarbonylmethyl group; and most preferably a carboxymethyl or ethoxycarbonylmethyl group.

The "$C_1$–$C_6$ alkyl group" in the definition of $R^7$ may be, for example, as described in the definition of $R^1$; preferably a $C_1$–$C_4$ alkyl group; more preferably a methyl or ethyl group; and most preferably an ethyl group.

Preferably m is an integer from 1 to 4; and more preferably 1 or 2.

Preferably n is an integer from 1 to 4; and more preferably 1 or 2.

The "$C_7$–$C_{15}$ aralkyl group" in the definition of $R^3$ may be, for example, a "$C_1$–$C_6$ alkyl group" described above which is substituted with one or two aromatic hydrocarbon rings having from 6 to 14 carbon atoms, such as a benzyl, naphthylmethyl, indenylmethyl, phenanthrenylmethyl, anthracenylmethyl, diphenylmethyl, phenethyl, naphthylethyl, phenylpropyl, naphthylpropyl, phenylbutyl, naphthylbutyl, phenylpentyl, naphthylpentyl or phenylhexyl group; preferably a benzyl, naphthylmethyl, diphenylmethyl or phenethyl group; more preferably a benzyl or phenethyl group; and most preferably a benzyl group.

The "$C_1$–$C_6$ alkanoyl group" in the definition of $R^3$ may be, for example, a straight or branched chain alkanoyl group having from 1 to 6 carbon atoms such as a formyl, acetyl, propionyl, butyryl, isobutyryl, pivaloyl, valeryl, isovaleryl or hexanoyl group; preferably a $C_1$–$C_4$ alkanoyl group; more preferably a formyl or acetyl group; and most preferably an acetyl group.

The "hydroxy-$C_2$–$C_6$ alkanoyl group" in the definition of $R^3$ may be, for example, the "$C_1$–$C_6$ alkanoyl group" described above which is substituted with hydroxyl such as a hydroxyacetyl, 2-hydroxypropionyl, 3-hydroxypropionyl, 4-hydroxybutyryl, 5-hydroxyvaleryl or 6-hydroxyhexanoyl group; preferably a hydroxyacetyl, 3-hydroxypropionyl or 4-hydroxybutyryl group; and most preferably a hydroxyacetyl group.

The "$C_1$–$C_6$ alkylsulfonyl group" in the definition of $R^3$ may be, for example, the "$C_1$–$C_6$ alkyl group" described above which is attached to a sulfonyl group, such as a methanesulfonyl, ethanesulfonyl, propanesulfonyl, isopropanesulfonyl, butanesulfonyl, isobutanesulfonyl, pentanesulfonyl, isopentanesulfonyl, neopentanesulfonyl, hexanesulfonyl or isohexanesulfonyl group; preferably a methanesulfonyl, ethanesulfonyl, propanesulfonyl, butanesulfonyl, pentanesulfonyl or hexanesulfonyl group; more preferably a methanesulfonyl, ethanesulfonyl or butanesulfonyl group; and most preferably an ethanesulfonyl group.

The "$C_1$–$C_6$ alkylsulfonyl group which is substituted with a carboxy group or a ($C_1$–$C_6$ alkoxy)carbonyl group" in the definition of $R^3$ may be, for example, the "$C_1$–$C_6$ alkylsulfonyl group" described above which is attached to a group selected from the carboxyl or the ($C_1$–$C_6$ alkoxy)carbonyl group described above such as a methoxycarbonylmethanesulfonyl, ethoxycarbonylmethanesulfonyl, propoxycarbonylmethanesulfonyl, isopropoxycarbonylmethanesulfonyl, butoxycarbonylmethanesulfonyl, isobutoxycarbonylmethanesulfonyl, s-butoxycarbonylmethanesulfonyl, t-butoxycarbonylmethanesulfonyl, pentyloxycarbonylmethanesulfonyl, isopentyloxycarbonylmethanesulfonyl, 2-methylbutoxycarbonylmethanesulfonyl, neopentyloxycarbonylmethanesulfonyl, 1-ethylpropoxycarbonylmethanesulfonyl, hexyloxycarbonylmethanesulfonyl, 4-methylpentyloxycarbonylmethanesulfonyl, 3-methylpentyloxycarbonylmethanesulfonyl, 2-methylpentyloxycarbonylmethanesulfonyl, 1-methylpentyloxycarbonylmethanesulfonyl, 3,3-dimethylbutoxycarbonylmethanesulfonyl, 2,2-dimethylbutoxycarbonylmethanesulfonyl, 1,1-dimethylbutoxycarbonylmethanesulfonyl, 1,2-dimethylbutoxycarbonylmethanesulfonyl, 1,3-dimethylbutoxycarbonylmethanesulfonyl, 2,3-dimethylbutoxycarbonylmethanesulfonyl, 2-ethylbutoxycarbonylmethanesulfonyl, 1-(metoxycarbonyl)ethanesulfonyl, 1-(ethoxycarbonyl)ethanesulfonyl, 1-(propoxycarbonyl)ethanesulfonyl, 1-(isopropoxycarbonyl)ethanesulfonyl, 1-(butoxycarbonyl)ethanesulfonyl, 1-(isobutoxycarbonyl)ethanesulfonyl, 1-(s-butoxycarbonyl)ethanesulfonyl, 1-(t-butoxycarbonyl)ethanesulfonyl, 1-(pentyloxycarbonyl)ethanesulfonyl, 1-(isopentyloxycarbonyl)ethanesulfonyl, 1-(2-methylbutoxycarbonyl)ethanesulfonyl, 1-(neopentyloxycarbonyl)ethanesulfonyl, 1-(1-ethylpropoxycarbonyl)ethanesulfonyl, 1-(hexyloxycarbonyl)ethanesulfonyl, 1-(4-methylpentyloxycarbonyl)ethanesulfonyl, 1-(3-methylpentyloxycarbonyl)ethanesulfonyl, 1-(2-methylpentyloxycarbonyl)ethanesulfonyl, 1-(1-methylpentyloxycarbonyl)ethanesulfonyl, 1-(3,3-dimethylbutoxycarbonyl)ethanesulfonyl, 1-(2,2-dimethylbutoxycarbonyl)ethanesulfonyl, 1-(1,1-dimethylbutoxycarbonyl)ethanesulfonyl, 1-(1,2-dimethylbutoxycarbonyl)ethanesulfonyl, 1-(1,3-dimethylbutoxycarbonyl)ethanesulfonyl, 1-(2,3-dimethylbutoxycarbonyl)ethanesulfonyl, 1-(2-ethylbutoxycarbonyl)ethanesulfonyl, 2-(methoxycarbonyl)ethanesulfonyl, 2-(ethoxycarbonyl)ethanesulfonyl, 2-(propoxycarbonyl)ethanesulfonyl, 2-(isopropoxycarbonyl)ethanesulfonyl, 2-(butoxycarbonyl)ethanesulfonyl, 2-(isobutoxycarbonyl)ethanesulfonyl, 2-(s-butoxycarbonyl)ethanesulfonyl, 2-(t-butoxycarbonyl)ethanesulfonyl, 2-(pentyloxycarbonyl)ethanesulfonyl, 2-(isopentyloxycarbonyl)ethanesulfonyl, 2-(2-methylbutoxycarbonyl)ethanesulfonyl, 2-(neopentyloxycarbonyl)ethanesulfonyl, 2-(1-ethylpropoxycarbonyl)ethanesulfonyl, 2-(hexyloxycarbonyl)ethanesulfonyl, 2-(4-methylpentyloxycarbonyl)ethanesulfonyl, 2-(3-methylpentyloxycarbonyl)ethanesulfonyl, 2-(2-methylpentyloxycarbonyl)ethanesulfonyl, 2-(1-methylpentyloxycarbonyl)ethanesulfonyl, 2-(3,3-dimethylbutoxycarbonyl)ethanesulfonyl, 2-(2,2-dimethylbutoxycarbonyl)ethanesulfonyl, 2-( 1,1-dimethylbutoxycarbonyl)ethanesulfonyl, 2-(1,2-dimethylbutoxycarbonyl)ethanesulfonyl, 2-(1,3-dimethylbutoxycarbonyl)ethanesulfonyl, 2-(2,3-dimethylbutoxycarbonyl)ethanesulfonyl, 2-(2-ethylbutoxycarbonyl)ethanesulfonyl, 1-(methoxycarbonyl)propanesulfonyl, 1-(ethoxycarbonyl)propanesulfonyl, 1-(propoxycarbonyl)propanesulfonyl, 1(-(butoxycarbonyl)propanesulfonyl, 1-(pentyloxycarbonyl)propanesulfonyl, 1-(hexyloxycarbonyl)propanesulfonyl, 2-(methoxycarbonyl)propanesulfonyl, 2-(ethoxycarbonyl)propanesulfonyl, 2-(propoxycarbonyl)propanesulfonyl, 2-(butoxycarbonyl)propanesulfonyl, 2-(pentyloxycarbonyl)propanesulfonyl, 2-(hexyloxycarbonyl)propanesulfonyl, 3-(methoxycarbonyl)propanesulfonyl, 3-(ethoxycarbonyl)propanesulfonyl, 3-(propoxycarbonyl)propanesulfonyl, 3-(isopropoxycarbonyl)propanesulfonyl, 3-(butoxycarbonyl)propanesulfonyl, 3-(isobutoxycarbonyl)propanesulfonyl, 3-(s-butoxycarbonyl)propanesulfonyl, 3-(t-butoxycarbonyl)propanesulfonyl, 3-(pentyloxycarbonyl)propanesulfonyl, 3-(isopentyloxycarbonyl)propanesulfonyl, 3-(2-methylbutoxycarbonyl)propanesulfonyl, 3-(neopentyloxycarbonyl)propanesulfonyl, 3-(1-ethylpropoxycarbonyl)propanesulfonyl, 3-(hexyloxycarbonyl)propanesulfonyl, 3-(4-methylpentyloxycarbonyl)propanesulfonyl, 3-(3-methylpentyloxycarbonyl)propanesulfonyl, 3-(2-methylpentyloxycarbonyl)propanesulfonyl, 3-(1-methylpentyloxycarbonyl)propanesulfonyl, 3-(3,3-dimethylbutoxycarbonyl)propanesulfonyl, 3-(2,2-dimethylbutoxycarbonyl)propanesulfonyl, 3-(1,1-dimethylbutoxycarbonyl)propanesulfonyl, 3-(1,2-dimethylbutoxycarbonyl)propanesulfonyl, 3-(1,3-dimethylbutoxycarbonyl)propanesulfonyl, 3-(2,3-dimethylbutoxycarbonyl)propanesulfonyl, 3-(2-ethylbutoxycarbonyl)propanesulfonyl, 2-methoxycarbonyl-1-methylethanesulfonyl, 2-ethoxycarbonyl-1-methylethanesulfonyl, 2-propoxycarbonyl-1-methylethanesulfonyl, 2-butoxycarbonyl-1-methylethanesulfonyl, 1-(methoxycarbonyl)butanesulfonyl, 1-(ethoxycarbonyl)butanesulfonyl, 1-(propoxycarbonyl)butanesulfonyl, 1-(butoxycarbonyl)butanesulfonyl, 1-(pentyloxycarbonyl)butanesulfonyl, 1-(hexyloxycarbonyl)butanesulfonyl, 2-(methoxycarbonyl)butanesulfonyl, 2-(ethoxycarbonyl)butanesulfonyl, 2-(propoxycarbonyl)butanesulfonyl, 2-(butoxycarbonyl)butanesulfonyl, 2-(pentyloxycarbonyl)butanesulfonyl, 2-(hexyloxycarbonyl)butanesulfonyl, 3-(methoxycarbonyl)butanesulfonyl, 3-(ethoxycarbonyl)butanesulfonyl, 3-(propoxycarbonyl)butanesulfonyl, 3-(butoxycarbonyl)butanesulfonyl, 3-(pentyloxycarbonyl)butanesulfonyl, 3-(hexyloxycarbonyl)butanesulfonyl, 4-(methoxycarbonyl)butanesulfonyl, 4-(ethoxycarbonyl)butanesulfonyl, 4-(propoxycarbonyl)butanesulfonyl, 4-(isopropoxycarbonyl)butanesulfonyl, 4-(butoxycarbonyl)butanesulfonyl, 4-(isobutoxycarbonyl)butanesulfonyl, 4-(s-butoxycarbonyl)butanesulfonyl, 4-(t-butoxycarbonyl)butanesulfonyl, 4-(pentyloxycarbonyl)butanesulfonyl, 4-(isopentyloxycarbonyl)butanesulfonyl, 4-(2-methylbutoxycarbonyl)butanesulfonyl, 4-(neopentyloxycarbonyl)butanesulfonyl, 4-(1-ethylpropoxycarbonyl)butanesulfonyl, 4-(hexyloxycarbonyl)butanesulfonyl, 4-(4-methylpentyloxycarbonyl)butanesulfonyl, 4-(3-methylpentyloxycarbonyl)butanesulfonyl, 4-(2-methylpentyloxycarbonyl)butanesulfonyl, 4-(1-methylpentyloxycarbonyl)butanesulfonyl, 4-(3,3-dimethylbutoxycarbonyl)butanesulfonyl, 4-(2,2-dimethylbutoxycarbonyl)butanesulfonyl, 4-(1,1-dimethylbutoxycarbonyl)butanesulfonyl, 4-(1,2-dimethylbutoxycarbonyl)butanesulfonyl, 4-(1,3-dimethylbutoxycarbonyl)butanesulfonyl, 4-(2,3-dimethylbutoxycarbonyl)butanesulfonyl, 4-(2-ethylbutoxycarbonyl)butanesulfonyl, 3-methoxycarbonyl-2-methylpropanesulfonyl, 3-ethoxycarbonyl-2-methylpropanesulfonyl, 5-(methoxycarbonyl)pentanesulfonyl, 5-(ethoxycarbonyl)pentanesulfony, 5-(propoxycarbonyl)pentanesulfonyl, 5-(butoxycarbonyl)pentanesulfonyl, 5-(pentyloxycarbonyl)pentanesulfonyl, 5-(hexyloxycarbonyl)pentanesuhfonyl, 6-(methoxycarbonyl)hexanesulfonyl, 6-(ethoxycarbonyl)hexanesulfonyl, 6-(propoxycarbonyl)hexanesulfonyl, 6-(butoxycarbonyl)hexanesulfonyl, 6-(pentyloxycarbonyl)hexanesulfonyl, 6-(hexyloxycarbonyl)hexanesulfonyl, carboxymethanesulfonyl, 2-carboxyethanesulfonyl, 3-carboxypropanesulfonyl, 2-carboxy-1-methylethanesulfonyl, 4-carboxybutanesulfonyl, 3-carboxy-2-methylpropanesulfonyl, 5-carboxypentanesulfonyl or 6-carboxyhexanesulfonyl group;

preferably a $C_1$–$C_4$ alkylsulfonyl group which is substituted with a carboxyl or ($C_1$–$C_4$ alkoxy)carbonyl group; more preferably a methanesulfonyl or ethanesulfonyl group which is substituted with a carboxyl or ($C_1$–$C_4$ alkoxy)carbonyl group; still more preferably a methoxycarbonylmethanesulfonyl, ethoxycarbonylmethanesulfonyl, carboxymethanesulfonyl, 2-methoxycarbonylethanesulfonyl, 2-ethoxycarbonylethanesulfonyl or 2-carboxyethanesulfonyl group; and most preferably an ethoxycarbonylmethanesulfonyl or carboxymethanesulfonyl group.

The "halogen atom" in the definition of $R^4$ and $R^5$ may be, for example, as described in the definition of $R^1$; preferably a fluorine, chlorine or bromine atom; more preferably a fluorine or chlorine atom; and most preferably a fluorine atom.

The "$C_1$–$C_6$ alkyl group" in the definition of $R^4$ and $R^5$ may be, for example, as described in the definition of $R^1$; preferably a $C_1$–$C_4$ alkyl group; more preferably a methyl or ethyl group; and most preferably a methyl group.

The "halogeno-$C_1$–$C_6$ alkyl group" in the definition of $R^4$ and $R^5$ may be, for example, the "$C_1$–$C_6$ alkyl group" described above which is substituted with from 1 to 5 halogen atoms described above, such as a fluoromethyl, difluoromethyl, trifluoromethyl, 2-fluoroethyl, 2,2-difluoroethyl, 2,2,2-trifluoroethyl, pentafluoroethyl, 3-fluoropropyl, 4-fluorobutyl, 6-fluorohexyl, chloromethyl, 2-chloroethyl, 3-chloropropyl, 4-chlorobutyl, bromomethyl, 3-bromopropyl, dibromopentyl, iodomethyl or 2-fluoro-1- chloroethyl group; preferably a $C_1$–$C_4$ alkyl group which is substituted with from 1 to 3 halogen atoms selected from fluorine and chlorine atoms; more preferably a fluoromethyl, difluoromethyl, trifluoromethyl, 2-fluoroethyl, 2,2-difluoroethyl or 2,2,2-trifluoroethyl group; and most preferably a trifluoromethyl group.

The "$C_1$–$C_6$ alkoxy group" in the definition of $R^4$ and $R^5$ may be, for example, an oxygen atom which is attached to the "$C_1$–$C_6$ alkyl group" described above, such as a methoxy, ethoxy, propoxy, isopropoxy, butoxy, isobutoxy, s-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy group; preferably a $C_1$–$C_4$ alkoxy group; more preferably a methoxy or ethoxy group; and most preferably a methoxy group.

The "($C_1$–$C_6$ alkoxy)carbonyl group" in the definition of $R^4$ and $R^5$ may be, for example, as described in the definition of $R^3$; preferably a ($C_1$–$C_4$ alkoxy)carbonyl group; more preferably a methoxycarbonyl or ethoxycarbonyl group; and most preferably an ethoxycarbonyl group.

The "($C_1$–$C_6$ alkyl)carbamoyl group" in the definition of $R^4$ and $R^5$ may be, for example, carbamoyl group which is substituted with a "$C_1$–$C_6$ alkyl group" described above, such as a methylcarbamoyl, ethylcarbamoyl, propylcarbamoyl, isopropylcarbamoyl, butylcarbamoyl, isobutylcarbamoyl, s-butylcarbamoyl, t-butylcarbamoyl, pentylcarbamoyl or hexylcarbamoyl group; preferably a ($C_1$–$C_4$ alkyl)carbamoyl group; more preferably a methylcarbamoyl or ethylcarbamoyl group; and most preferably a methylcarbamoyl group.

The "di($C_1$–$C_6$ alkyl)carbamoyl group" in the definition of $R^4$ and $R^5$ may be, for example, a carbamoyl group which is substituted with two "$C_1$–$C_6$ alkyl groups" described above, which may be the same or different, such as an N,N-dimethylcarbamoyl, N-ethyl-N-methylcarbamoyl, N,N-diethylcarbamoyl, N,N-dipropylcarbamoyl, N,N-diisopropylcarbamoyl, N,N-dibutylcarbamoyl, N,N-diisobutylcarbamoyl, N,N-di-s-butylcarbamoyl, N,N-di-t-butylcarbamoyl, N,N-dipentylcarbamoyl or N,N-dihexylcarbamoyl group; preferably a di($C_1$–$C_4$ alkyl) carbamoyl group; more preferably an N,N-dimethylcarbamoyl, N-ethyl-N-methylcarbamoyl or N,N-diethylcarbamoyl group; and most preferably an N,N-dimethylcarbamoyl group.

The compounds of formula (I) can be converted their to corresponding pharmaceutically acceptable salts by treatment with an acid in a conventional manner.

For example, a solution of the compound of formula (I) in a solvent (for example, an ether, an ester or an alcohol; preferably an ether or an alcohol) may be treated with a corresponding acid at room temperature for from 1 to 30 minutes. The resulting precipitate is collected by filtration or the resulting solution is concentrated in vacuo to give such a salt. Examples of such salts include carbonate; mineral acid salts such as hydrofluoride, hydrochloride, hydrobromide, hydroiodide, nitrate, perchlorate, sulfate or phosphate; sulfonates such as methanesulfonate, trifluoromethanesulfonate, ethanesulfonate, benzenesulfonate or p-toluenesulfonate; carboxylates such as acetate, propionate, butyrate, fumarate, succinate, citrate, tartrate, oxalate, maleate or benzoate; or amino acid salts such as a glutamic acid salt or aspartic acid salt.

When compounds of formula (I) have a carboxyl group etc. in $R^3$, such compounds can be converted to their corresponding pharmaceutically acceptable salts by treatment with a base in a conventional manner. For example, a solution of the compound of formula (I) in a solvent (for example, an ether, an ester or an alcohol; preferably an alcohol) is treated with a corresponding base at room temperature for from 1 to 30 minutes. The resulting precipitate is collected by filtration or the resulting solution is concentrated in vacuo to give such a salt. Examples of such salts include alkali metal salts such as a sodium salt, a potassium salt or a lithium salt; alkaline earth metal salts such as a calcium salt or a magnesium salt; metal salts such as an aluminum salt, an iron salt, a zinc salt, a copper salt, a nickel salt or a cobalt salt; an ammonium salt; organic amine salts such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzylphenethylamine salt, a piperazine salt, a tetramethylammonium salt or a tris(hydroxymethyl)aminomethane salt; preferably an alkali metal salts (especially a sodium or potassium salt).

When a compound of formula (I) or a pharmaceutically acceptable salt thereof has asymmetric carbon(s), each of said carbon atoms can exist in an (R) or (S) configuration. The present invention includes each of the individual isomers and mixtures of two or more isomers in any proportion. These optically active isomers of formula (I) can be produced using a starting material optically resolved or can be isolated from a racemic mixture of compounds of formula (I) by conventional optical resolution techniques.

When a compound of formula (I) or a pharmaceutically acceptable salt thereof is recrystallized or allowed to stand so that it is open to the atmosphere, it may absorb water to form a hydrate. The present invention also encompasses these hydrates.

Preferred compounds of formula (I) are:

(1) a compound wherein $R^1$ represents a hydrogen atom, a fluorine atom, a chlorine atom, a bromine atom, a $C_1$–$C_4$ alkyl group or a hydroxyl group;

(2) a compound wherein $R^1$ represents a hydrogen atom, a fluorine atom, a chlorine atom, a methyl group, an ethyl group or a hydroxyl group;

(3) a compound wherein $R^1$ represents a hydrogen atom, a fluorine atom, a methyl group or a hydroxyl group;

(4) a compound wherein $R^1$ represents a hydrogen atom or a hydroxyl group;

(5) a compound wherein $R^2$ represents a hydrogen atom, a fluorine atom, a chlorine atom, a bromine atom or a $C_1$–$C_4$ alkyl group;

(6) a compound wherein $R^2$ represents a hydrogen atom, a fluorine atom, a chlorine atom, a methyl group or an ethyl group;

(7) a compound wherein $R^2$ represents a hydrogen atom, a fluorine atom or a methyl group;

(8) a compound wherein $R^2$ represents a hydrogen atom or a fluorine atom;

(9) a compound wherein $R^2$ represents a hydrogen atom;

(10) a compound wherein $R^3$ represents a hydrogen atom; a $C_1$–$C_4$ alkyl group; a hydroxy-$C_1$–$C_4$-alkyl group; a carboxy-$C_1$–$C_4$-alkyl group; a ($C_1$–$C_4$ alkoxy)carbonyl-$C_1$–$C_4$-alkyl group; a group of formula (II)

(II)

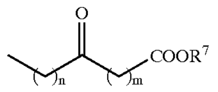

(wherein $R^7$ represents a $C_1$–$C_4$ alkyl group, m and n are the same as or different from and each other and each represent an integer from 1 to 4); a benzyl group, a naphthylmethyl group, a diphenylmethyl group or a phenethyl group; a $C_1$–$C_4$ alkanoyl group; a hydroxyacetyl group, a 3-hydroxypropionyl group or a 4-hydroxybutyryl group; a methanesulfonyl group, an ethanesulfonyl group, a propanesulfonyl group, a butanesulfonyl group, a pentanesulfonyl group or a hexanesulfonyl group; or a $C_1$–$C_4$ alkylsulfonyl group which is substituted with a carboxyl group or a ($C_1$–$C_4$ alkoxy)carbonyl group;

(11) a compound wherein $R^3$ represents a hydrogen atom; a $C_1$–$C_4$ alkyl group; a 2-hydroxyethyl group, a carboxymethyl group, a methoxycarbonylmethyl group, an ethoxycarbonylmethyl group, a propoxycarbonylmethyl group or a butoxycarbonylmethyl group; a group of formula (II)

(II)

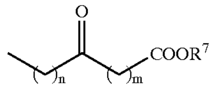

(wherein $R^7$ represents a methyl group or ethyl group, m and n are the same as or different from each other and each represent an integer 1 or 2); a benzyl group or a phenethyl group; a formyl group or an acetyl group; a hydroxyacetyl group; a methanesulfonyl group, an ethanesulfonyl group or a butanesulfonyl group; or a methanesulfonyl group or an ethanesulfonyl group which is substituted with a carboxyl group or a ($C_1$–$C_4$ alkoxy)carbonyl group;

(12) a compound wherein $R^3$ represents a hydrogen atom, a methyl group, an ethyl group, an isopropyl group, a 2-hydroxyethyl group, a carboxymethyl group, a methoxycarbonylmethyl group, an ethoxycarbonylmethyl group, a propoxycarbonylmethyl group, a butoxycarbonylmethyl group, an acetyl group, a hydroxyacetyl group, a methanesulfonyl group, an ethanesulfonyl group, a butanesulfonyl group, a methoxycarbonylmethanesulfonyl group, an ethoxycarbonylmethanesulfonyl group, a carboxymethanesulfonyl group, a 2-methoxycarbonylethanesulfonyl group, a 2-ethoxycarbonylethanesulfonyl group or a 2-carboxyethanesulfonyl group;

(13) a compound wherein $R^3$ represents an isopropyl group, a 2-hydroxyethyl group, a carboxymethyl group, a methoxycarbonylmethyl group, an ethoxycarbonylmethyl group, an ethanesulfonyl group, a methoxycarbonylmethanesulfonyl group, an ethoxycarbonylmethanesulfonyl group, a carboxymethanesulfonyl group, a 2-methoxycarbonylethanesulfonyl group, a 2-ethoxycarbonylethanesulfonyl group or a 2-carboxyethanesulfonyl group;

(14) a compound wherein $R^3$ represents an isopropyl group, a carboxymethyl group, an ethoxycarbonylmethyl group, an ethoxycarbonylmethanesulfonyl group or a carboxymethanesulfonyl group;

(15) a compound wherein $R^3$ represents an ethoxycarbonylmethanesulfonyl group or a carboxymethanesulfonyl group;

(16) a compound wherein $R^4$ and $R^5$ are the same as or different from each other and each represent a hydrogen atom, a fluorine atom, a chlorine atom, a bromine atom, a $C_1$–$C_4$ alkyl group, a fluoromethyl group, a difluoromethyl group, a trifluoromethyl group, a 2-fluoroethyl group, a 2,2-difluoroethyl group, a 2,2,2-trifluoroethyl group, a $C_1$–$C_4$ alkoxy group, a carboxyl group, a methoxycarbonyl group, an ethoxycarbonyl group, a carbamoyl group, a methylcarbamoyl group or an N,N-dimethylcarbamoyl group;

(17) a compound wherein $R^4$ represents a hydrogen atom, a fluorine atom, a chlorine atom or a trifluoromethyl group, and $R^5$ represents a hydrogen atom, a fluorine atom, a chlorine atom, a bromine atom, a C1–$C_4$ alkyl group, a fluoromethyl group, a difluoromethyl group, a trifluoromethyl group, a 2-fluoroethyl group, a 2,2-difluoroethyl group, a 2,2,2-trifluoroethyl group, a $C_1$–$C_4$ alkoxy group, a carboxyl group, a methoxycarbonyl group, an ethoxycarbonyl group, a carbamoyl group, a methylcarbamoyl group or an N,N-dimethylcarbamoyl group;

(18) a compound wherein $R^4$ represents a hydrogen atom, a fluorine atom or a chlorine atom, and $R^5$ represents a hydrogen atom, a fluorine atom, a chlorine atom, a bromine atom, a methyl group, an ethyl group, a trifluoromethyl group, a methoxy group, an ethoxy group or a carbamoyl group;

(19) a compound wherein $R^4$ represents a hydrogen atom, and $R^5$ represents a hydrogen atom, a fluorine atom, a chlorine atom, a methyl group, a trifluoromethyl group or a carbamoyl group;

(20) a compound wherein $R^4$ represents a hydrogen atom, and $R^5$ represents a hydrogen atom, a chlorine atom, a methyl group or a carbamoyl group; and

(21) a compound wherein $R^6$ represents a 1-acetimidoylpiperidin-4-yl group.

The preferred order of $R^1$ is from (1) to (4), the preferred order of $R^2$ is from (5) to (9), the preferred order of $R^3$ is from (10) to (15), and the preferred order of $R^4$ and $R^5$ is from (16) to (20). Examples of compounds of formula (I) include any combination of 2 to 5 substituent definitions selected from the groups consisting of (1) to (4), (5) to (9), (10) to (15), (16) to (20) and (21). The following compounds are preferred combinations:

(22) a compound wherein $R^1$ represents a hydrogen atom, a fluorine atom, a chlorine atom, a bromine atom, a $C_1$–$C_4$ alkyl group or a hydroxyl group;

$R^2$ represents a hydrogen atom, a fluorine atom, a chlorine atom, a bromine atom or a $C_1$–$C_4$ alkyl group;

$R^3$ represents a hydrogen atom, a $C_1$–$C_4$ alkyl group, a hydroxy-$C_1$–$C_4$-alkyl group, a carboxy-$C_1$–$C_4$-alkyl group, a ($C_1$–$C_4$ alkoxy)carbonyl-$C_1$–$C_4$-alkyl group, a group of formula (II)

(II)

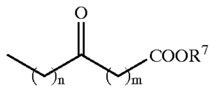

(wherein $R^7$ represents a $C_1$–$C_4$ alkyl group, m and n are the same as or different from each other and each represents an integer from 1 to 4), a benzyl group, a naphthylmethyl group, a diphenylmethyl group, a phenethyl group, a $C_1$–$C_4$ alkanoyl group, a hydroxyacetyl group, a 3-hydroxypropionyl group, a 4-hydroxybutyryl group, a methanesulfonyl group, an ethanesulfonyl group, a propanesulfonyl group, a butanesulfonyl group, a pentanesulfonyl group, a hexanesulfonyl group or a $C_1$–$C_4$ alkylsulfonyl group which is substituted with a carboxyl group or a ($C_1$–$C_4$ alkoxy)carbonyl group;

$R^4$ and $R^5$ are the same as or different from each other and each represent a hydrogen atom, a fluorine atom, a chlorine atom, a bromine atom, a $C_1$–$C_4$ alkyl group, a fluoromethyl group, a difluoromethyl group, a trifluoromethyl group, a 2-fluoroethyl group, a 2,2-difluoroethyl group, a 2,2,2-trifluoroethyl group, a $C_1$–$C_4$ alkoxy group, a carboxyl group, a methoxycarbonyl group, an ethoxycarbonyl group, a carbamoyl group, a methylcarbamoyl group or an N,N-dimethylcarbamoyl group;

(23) a compound wherein $R^1$ represents a hydrogen atom, a fluorine atom, a chlorine atom, a methyl group, an ethyl group or a hydroxyl group;

$R^2$ represents a hydrogen atom, a fluorine atom, a chlorine atom, a methyl group or an ethyl group;

$R^3$ represents a hydrogen atom, a $C_1$–$C_4$ alkyl group, a 2-hydroxyethyl group, a carboxymethyl group, a methoxycarbonylmethyl group, an ethoxycarbonylmethyl group, a propoxycarbonylmethyl group, a butoxycarbonylmethyl group, a group of formula (II)

(II)

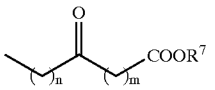

(wherein $R^7$ represents a methyl group or ethyl group, m and n are the same as or different from each other and each represent an integer 1 or 2), a benzyl group, a phenethyl group, a formyl group, an acetyl group, a hydroxyacetyl group, a methanesulfonyl group, an ethanesulfonyl group, a butanesulfonyl group, or a methanesulfonyl group or an ethanesulfonyl group which is substituted with a carboxyl group or a ($C_1$–$C_4$ alkoxy)carbonyl group;

$R^4$ represents a hydrogen atom, a fluorine atom, a chlorine atom or a trifluoromethyl group, and $R^5$ represents a hydrogen atom, a fluorine atom, a chlorine atom, a bromine atom, a $C_1$–$C_4$ alkyl group, a fluoromethyl group, a difluoromethyl group, a trifluoromethyl group, a 2-fluoroethyl group, a 2,2-difluoroethyl group, a 2,2,2-trifluoroethyl group, a $C_1$–$C_4$ alkoxy group, a carboxyl group, a methoxycarbonyl group, an ethoxycarbonyl group, a carbamoyl group, a methylcarbamoyl group or a N,N-dimethylcarbamoyl group; and $R^6$ represents a 1-acetimidoylpiperidin-4-yl group;

(24) a compound wherein $R^1$ represents a hydrogen atom, a fluorine atom, a methyl group or a hydroxyl group;

$R^2$ represents a hydrogen atom, a fluorine atom or a methyl group;

$R^3$ represents a hydrogen atom, a methyl group, an ethyl group, an isopropyl group, a 2-hydroxyethyl group, a carboxymethyl group, a methoxycarbonylmethyl group, an ethoxycarbonylmethyl group, a propoxycarbonylmethyl group, a butoxycarbonylmethyl group, an acetyl group, a hydroxyacetyl group, a methanesulfonyl group, an ethanesulfonyl group, a butanesulfonyl group, a methoxycarbonylmethanesulfonyl group, an ethoxycarbonylmethanesulfonyl group, a carboxymethanesulfonyl group, a 2-methoxycarbonylethanesulfonyl group, a 2-ethoxycarbonylethanesulfonyl group or a 2-carboxyethanesulfonyl group;

$R^4$ represents a hydrogen atom, a fluorine atom or a chlorine atom, and $R^5$ represents a hydrogen atom, a fluorine atom, a chlorine atom, a bromine atom, a methyl group, an ethyl group, a trifluoromethyl group, a methoxy group, an ethoxy group or a carbamoyl group; and $R^6$ represents a 1-acetimidoylpiperidin-4-yl group;

(25) a compound wherein $R^1$ represents a hydrogen atom or a hydroxyl group;

$R^2$ represents a hydrogen atom or a fluorine atom;

$R^3$ represents an isopropyl group, a 2-hydroxyethyl group, a carboxymethyl group, a methoxycarbonylmethyl group, an ethoxycarbonylmethyl group, an ethanesulfonyl group, a methoxycarbonylmethanesulfonyl group, an ethoxycarbonylmethanesulfonyl group, a carboxymethanesulfonyl group, 2-methoxycarbonylethanesulfonyl group, a 2-ethoxycarbonylethanesulfonyl group or a 2-carboxyethanesulfonyl group;

$R^4$ represents a hydrogen atom, and $R^5$ represents a hydrogen atom, a fluorine atom, a chlorine atom, a methyl group, a trifluoromethyl group or a carbamoyl group; and $R^6$ represents a 1-acetimidoylpiperidin-4-yl group;

(26) a compound wherein $R^1$ represents a hydrogen atom or a hydroxyl group;

$R^2$ represents a hydrogen atom or a fluorine atom;

$R^3$ represents an isopropyl group, a carboxymethyl group, an ethoxycarbonylmethyl group, an ethoxycarbonylmethanesulfonyl group or a carboxymethanesulfonyl group; and $R^4$ represents a hydrogen atom, and $R^5$ represents a hydrogen atom, a chlorine atom, a methyl group or a carbamoyl group; and $R^6$ represents a 1-acetimidoylpiperidin-4-yl group;

(27) a compound wherein $R^1$ represents a hydrogen atom or a hydroxyl group;

$R^2$ represents a hydrogen atom or a fluorine atom;

$R^3$ represents an ethoxycarbonylmethanesulfonyl group or a carboxymethanesulfonyl group;

$R^4$ represents an hydrogen atom, and $R^5$ represents a hydrogen atom, chlorine atom, methyl group or a carbamoyl group; and $R^6$ represents a 1-acetimidoylpiperidin-4-yl group.

The order of preferred compounds of formula (I) is from (22) to (27).

Typical examples of compounds of formula (I) of the present invention are given in the following tables. The present invention, however, is not limited to those compounds. Throughout the tables the following abbreviations are used with the following meanings.

| | |
|---|---|
| Ac | acetyl group |
| Al | acetimidoyl group |
| 1-Al-Pip(4) | 1-acetimidoylpiperidin-4-yl group |
| 1-Al-Pyrd(3) | 1-acetimidoylpyrrolidin-3-yl group |
| Bn | benzyl group |
| Bu | butyl group |
| i-Bu | isobutyl group |
| sBu | secondary butyl group |
| t-Bu | tertiary butyl group |
| Byr | butyryl group |
| Et | ethyl group |
| Hx | hexyl group |
| Me | methyl group |
| Np(1) | 1-naphthyl group |
| Np(2) | 2-naphthyl group |
| Ph | phenyl group |
| Pn | pentyl group |
| Pr | propyl group |
| iPr | isopropyl group |
| Prn | propionyl group |
| Va | valeryl group |

TABLE 1

(I)

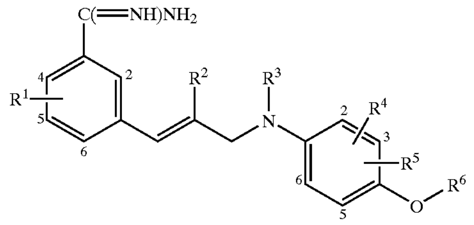

| Cpd. No. | $R^1$ | $R^2$ | $R^3$ | $R^4$ | $R^5$ | $R^6$ |
|---|---|---|---|---|---|---|
| 1 | H | H | H | H | H | 1-Al—Pyrd(3) |
| 2 | H | H | Me | H | H | 1-Al—Pyrd(3) |
| 3 | H | H | Et | H | H | 1-Al—Pyrd(3) |
| 4 | H | H | iPr | H | H | 1-Al—Pyrd(3) |
| 5 | H | H | iPr | 3-Cl | H | 1-Al—Pyrd(3) |
| 6 | H | H | iPr | 3-Me | H | 1-Al—Pyrd(3) |
| 7 | H | H | iPr | 3-$CONH_2$ | H | 1-Al—Pyrd(3) |
| 8 | H | H | iPr | 3-F | 5-F | 1-Al—Pyrd(3) |
| 9 | H | H | iPr | 3-Cl | 5-Cl | 1-Al—Pyrd(3) |
| 10 | H | H | iPr | 3-Me | 5-Me | 1-Al—Pyrd(3) |
| 11 | H | H | iPr | 3-Cl | 5-$CONH_2$ | 1-Al—Pyrd(3) |
| 12 | H | H | iPr | 2-Me | 5-$CONH_2$ | 1-Al—Pyrd(3) |
| 13 | H | H | iPr | 3-Me | 5-$CONH_2$ | 1-Al—Pyrd(3) |
| 14 | H | H | iPr | 3-$CONH_2$ | 5-$CONH_2$ | 1-Al—Pyrd(3) |
| 15 | 6-OH | H | iPr | H | H | 1-Al—Pyrd(3) |
| 16 | 6-OH | H | iPr | 3-Cl | H | 1-Al—Pyrd(3) |
| 17 | 6-OH | H | iPr | 3-Me | H | 1-Al—Pyrd(3) |
| 18 | 6-OH | H | iPr | 3-$CONH_2$ | H | 1-Al—Pyrd(3) |
| 19 | H | H | Bu | H | H | 1-Al—Pyrd(3) |
| 20 | H | H | Pn | H | H | 1-Al—Pyrd(3) |
| 21 | H | H | Hx | H | H | 1-Al—Pyrd(3) |
| 22 | H | H | $CH_2OH$ | H | H | 1-Al—Pyrd(3) |
| 23 | H | H | $(CH_2)_2OH$ | H | H | 1-Al—Pyrd(3) |
| 24 | 6-OH | H | $(CH_2)_2OH$ | H | H | 1-Al—Pyrd(3) |
| 25 | H | H | $(CH_2)_3OH$ | H | H | 1-Al—Pyrd(3) |
| 26 | H | H | $(CH_2)_4OH$ | H | H | 1-Al—Pyrd(3) |
| 27 | H | H | $(CH_2)_5OH$ | H | H | 1-Al—Pyrd(3) |
| 28 | H | H | $(CH_2)_6OH$ | H | H | 1-Al—Pyrd(3) |
| 29 | H | H | $CH_2COOH$ | H | H | 1-Al—Pyrd(3) |
| 30 | H | H | $CH_2COOH$ | 3-Cl | H | 1-Al—Pyrd(3) |
| 31 | H | H | $CH_2COOH$ | 3-Me | H | 1-Al—Pyrd(3) |
| 32 | H | H | $CH_2COOH$ | 3-$CONH_2$ | H | 1-Al—Pyrd(3) |
| 33 | H | H | $CH_2COOH$ | 3-F | 5-F | 1-Al—Pyrd(3) |
| 34 | H | H | $CH_2COOH$ | 3-Cl | 5-Cl | 1-Al—Pyrd(3) |
| 35 | H | H | $CH_2COOH$ | 3-Me | 5-Me | 1-Al—Pyrd(3) |
| 36 | H | H | $CH_2COOH$ | 3-Cl | 5-$CONH_2$ | 1-Al—Pyrd(3) |
| 37 | H | H | $CH_2COOH$ | 2-Me | 5-$CONH_2$ | 1-Al—Pyrd(3) |
| 38 | H | H | $CH_2COOH$ | 3-Me | 5-$CONH_2$ | 1-Al—Pyrd(3) |
| 39 | H | H | $CH_2COOH$ | 3-$CONH_2$ | 5-$CONH_2$ | 1-Al—Pyrd(3) |
| 40 | 6-OH | H | $CH_2COOH$ | H | H | 1-Al—Pyrd(3) |
| 41 | 6-OH | H | $CH_2COOH$ | 3-Cl | H | 1-Al—Pyrd(3) |
| 42 | 6-OH | H | $CH_2COOH$ | 3-Me | H | 1-Al—Pyrd(3) |
| 43 | 6-OH | H | $CH_2COOH$ | 3-$CONH_2$ | H | 1-Al—Pyrd(3) |
| 44 | H | H | $(CH_2)_2COOH$ | H | H | 1-Al—Pyrd(3) |
| 45 | H | H | $(CH_2)_3COOH$ | H | H | 1-Al—Pyrd(3) |
| 46 | H | H | $(CH_2)_4COOH$ | H | H | 1-Al—Pyrd(3) |
| 47 | H | H | $(CH_2)_5COOH$ | H | H | 1-Al—Pyrd(3) |
| 48 | H | H | $(CH_2)_6COOH$ | H | H | 1-Al—Pyrd(3) |
| 49 | H | H | $CH_2COOMe$ | H | H | 1-Al—Pyrd(3) |
| 50 | H | H | $CH_2COOEt$ | H | H | 1-Al—Pyrd(3) |
| 51 | H | H | $CH_2COOEt$ | 3-Cl | H | 1-Al—Pyrd(3) |
| 52 | H | H | $CH_2COOEt$ | 3-Me | H | 1-Al—Pyrd(3) |
| 53 | H | H | $CH_2COOEt$ | 3-$CONH_2$ | H | 1-Al—Pyrd(3) |
| 54 | H | H | $CH_2COOEt$ | 3-F | 5-F | 1-Al—Pyrd(3) |
| 55 | H | H | $CH_2COOEt$ | 3-Cl | 5-Cl | 1-Al—Pyrd(3) |
| 56 | H | H | $CH_2COOEt$ | 3-Me | 5-Me | 1-Al—Pyrd(3) |
| 57 | H | H | $CH_2COOEt$ | 3-Cl | 5-$CONH_2$ | 1-Al—Pyrd(3) |
| 58 | H | H | $CH_2COOEt$ | 2-Me | 5-$CONH_2$ | 1-Al—Pyrd(3) |
| 59 | H | H | $CH_2COOEt$ | 3-Me | 5-$CONH_2$ | 1-Al—Pyrd(3) |
| 60 | H | H | $CH_2COOEt$ | 3-$CONH_2$ | 5-$CONH_2$ | 1-Al—Pyrd(3) |
| 61 | 6-OH | H | $CH_2COOEt$ | H | H | 1-Al—Pyrd(3) |
| 62 | 6-OH | H | $CH_2COOEt$ | 3-Cl | H | 1-Al—Pyrd(3) |
| 63 | 6-OH | H | $CH_2COOEt$ | 3-Me | H | 1-Al—Pyrd(3) |

TABLE 1-continued (I)

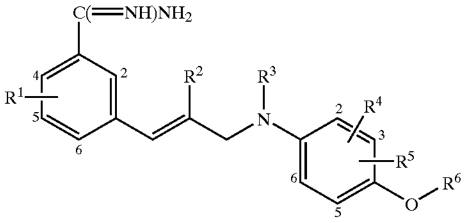

| Cpd. No. | $R^1$ | $R^2$ | $R^3$ | $R^4$ | $R^5$ | $R^6$ |
|---|---|---|---|---|---|---|
| 64 | 6-OH | H | $CH_2COOEt$ | 3-$CONH_2$ | H | 1-Al—Pyrd(3) |
| 65 | H | H | $CH_2COOPr$ | H | H | 1-Al—Pyrd(3) |
| 66 | H | H | $CH_2COOBu$ | H | H | 1-Al—Pyrd(3) |
| 67 | H | H | $CH_2COOPn$ | H | H | 1-Al—Pyrd(3) |
| 68 | H | H | $CH_2COOHx$ | H | H | 1-Al—Pyrd(3) |
| 69 | H | H | $(CH_2)_2COOEt$ | H | H | 1-Al—Pyrd(3) |
| 70 | H | H | $(CH_2)_3COOMe$ | H | H | 1-Al—Pyrd(3) |
| 71 | H | H | $(CH_2)_4COOPr$ | H | H | 1-Al—Pyrd(3) |
| 72 | H | H | $(CH_2)_5COOBu$ | H | H | 1-Al—Pyrd(3) |
| 73 | H | H | $(CH_2)_6COOHx$ | H | H | 1-Al—Pyrd(3) |
| 74 | H | H | Bn | H | H | 1-Al—Pyrd(3) |
| 75 | H | H | $(CH_2)_2Ph$ | H | H | 1-Al—Pyrd(3) |
| 76 | H | H | $(CH_2)_3Ph$ | H | H | 1-Al—Pyrd(3) |
| 77 | H | H | $(CH_2)_4Ph$ | H | H | 1-Al—Pyrd(3) |
| 78 | H | H | CHO | H | H | 1-Al—Pyrd(3) |
| 79 | H | H | Ac | H | H | 1-Al—Pyrd(3) |
| 80 | H | H | Pm | H | H | 1-Al—Pyrd(3) |
| 81 | H | H | Va | H | H | 1-Al—Pyrd(3) |
| 82 | H | H | $SO_2Me$ | H | H | 1-Al—Pyrd(3) |
| 83 | H | H | $SO_2Et$ | H | H | 1-Al—Pyrd(3) |
| 84 | 6-OH | H | $SO_2Et$ | H | H | 1-Al—Pyrd(3) |
| 85 | H | H | $SO_2Pr$ | H | H | 1-Al—Pyrd(3) |
| 86 | H | H | $SO_2Bu$ | H | H | 1-Al—Pyrd(3) |
| 87 | H | H | $SO_2Pn$ | H | H | 1-Al—Pyrd(3) |
| 88 | H | H | $SO_2Hx$ | H | H | 1-Al—Pyrd(3) |
| 89 | H | H | $SO_2CH_2COOMe$ | H | H | 1-Al—Pyrd(3) |
| 90 | H | H | $SO_2CH_2COOEt$ | H | H | 1-Al—Pyrd(3) |
| 91 | H | H | $SO_2CH_2COOEt$ | 3-F | H | 1-Al—Pyrd(3) |
| 92 | H | H | $SO_2CH_2COOEt$ | 2-Cl | H | 1-Al—Pyrd(3) |
| 93 | H | H | $SO_2CH_2COOEt$ | 3-Cl | H | 1-Al—Pyrd(3) |
| 94 | H | H | $SO_2CH_2COOEt$ | 2-Me | H | 1-Al—Pyrd(3) |
| 95 | H | H | $SO_2CH_2COOEt$ | 3-Me | H | 1-Al—Pyrd(3) |
| 96 | H | H | $SO_2CH_2COOEt$ | 3-Et | H | 1-Al—Pyrd(3) |
| 97 | H | H | $SO_2CH_2COOEt$ | 3-$CF_3$ | H | 1-Al—Pyrd(3) |
| 98 | H | H | $SO_2CH_2COOEt$ | 2-OEt | H | 1-Al—Pyrd(3) |
| 99 | H | H | $SO_2CH_2COOEt$ | 3-OMe | H | 1-Al—Pyrd(3) |
| 100 | H | H | $SO_2CH_2COOEt$ | 2-$CONH_2$ | H | 1-Al—Pyrd(3) |
| 101 | H | H | $SO_2CH_2COOEt$ | 3-$CONH_2$ | H | 1-Al—Pyrd(3) |
| 102 | H | H | $SO_2CH_2COOEt$ | 3-F | 5-F | 1-Al—Pyrd(3) |
| 103 | H | H | $SO_2CH_2COOEt$ | 3-Cl | 5-Cl | 1-Al—Pyrd(3) |
| 104 | H | H | $SO_2CH_2COOEt$ | 3-Me | 5-Me | 1-Al—Pyrd(3) |
| 105 | H | H | $SO_2CH_2COOEt$ | 3-Cl | 5-$CONH_2$ | 1-Al—Pyrd(3) |
| 106 | H | H | $SO_2CH_2COOEt$ | 2-Me | 5-$CONH_2$ | 1-Al—Pyrd(3) |
| 107 | H | H | $SO_2CH_2COOEt$ | 3-Me | 5-$CONH_2$ | 1-Al—Pyrd(3) |
| 108 | H | H | $SO_2CH_2COOEt$ | 3-$CONH_2$ | 5-$CONH_2$ | 1-Al—Pyrd(3) |
| 109 | H | F | $SO_2CH_2COOEt$ | H | H | 1-Al—Pyrd(3) |
| 110 | H | Cl | $SO_2CH_2COOEt$ | H | H | 1-Al—Pyrd(3) |
| 111 | H | Me | $SO_2CH_2COOEt$ | H | H | 1-Al—Pyrd(3) |
| 112 | H | Et | $SO_2CH_2COOEt$ | H | H | 1-Al—Pyrd(3) |
| 113 | 2-F | H | $SO_2CH_2COOEt$ | H | H | 1-Al—Pyrd(3) |
| 114 | 4-F | H | $SO_2CH_2COOEt$ | H | H | 1-Al—Pyrd(3) |
| 115 | 5-F | H | $SO_2CH_2COOEt$ | H | H | 1-Al—Pyrd(3) |
| 116 | 6-F | H | $SO_2CH_2COOEt$ | H | H | 1-Al—Pyrd(3) |
| 117 | 2-Cl | H | $SO_2CH_2COOEt$ | H | H | 1-Al—Pyrd(3) |
| 118 | 6-Cl | H | $SO_2CH_2COOEt$ | H | H | 1-Al—Pyrd(3) |
| 119 | 4-Me | H | $SO_2CH_2COOEt$ | H | H | 1-Al—Pyrd(3) |
| 120 | 6-Me | H | $SO_2CH_2COOEt$ | H | H | 1-Al—Pyrd(3) |
| 121 | 5-Et | H | $SO_2CH_2COOEt$ | H | H | 1-Al—Pyrd(3) |
| 122 | 6-Pr | H | $SO_2CH_2COOEt$ | H | H | 1-Al—Pyrd(3) |
| 123 | 2-OH | H | $SO_2CH_2COOEt$ | H | H | 1-Al—Pyrd(3) |
| 124 | 4-OH | H | $SO_2CH_2COOEt$ | H | H | 1-Al—Pyrd(3) |
| 125 | 5-OH | H | $SO_2CH_2COOEt$ | H | H | 1-Al—Pyrd(3) |
| 126 | 6-OH | H | $SO_2CH_2COOEt$ | H | H | 1-Al—Pyrd(3) |

TABLE 1-continued (I)

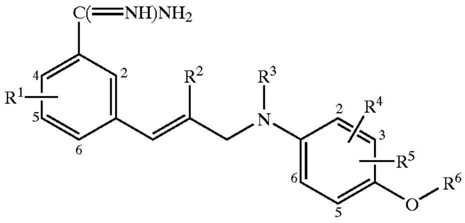

| Cpd. No. | $R^1$ | $R^2$ | $R^3$ | $R^4$ | $R^5$ | $R^6$ |
|---|---|---|---|---|---|---|
| 127 | H | H | $SO_2CH_2COOPr$ | H | H | 1-Al—Pyrd(3) |
| 128 | H | H | $SO_2CH_2COOBu$ | H | H | 1-Al—Pyrd(3) |
| 129 | H | H | $SO_2CH_2COOPn$ | H | H | 1-Al—Pyrd(3) |
| 130 | H | H | $SO_2CH_2COOHx$ | H | H | 1-Al—Pyrd(3) |
| 131 | H | H | $SO_2(CH_2)_2COOMe$ | H | H | 1-Al—Pyrd(3) |
| 132 | H | H | $SO_2(CH_2)_2COOEt$ | H | H | 1-Al—Pyrd(3) |
| 133 | H | H | $SO_2(CH_2)_2COOPr$ | H | H | 1-Al—Pyrd(3) |
| 134 | H | H | $SO_2(CH_2)_2COOBu$ | H | H | 1-Al—Pyrd(3) |
| 135 | H | H | $SO_2(CH_2)_2COOPn$ | H | H | 1-Al—Pyrd(3) |
| 136 | H | H | $SO_2(CH_2)_2COOHx$ | H | H | 1-Al—Pyrd(3) |
| 137 | H | H | $SO_2CH_2COOH$ | H | H | 1-Al—Pyrd(3) |
| 138 | H | H | $SO_2CH_2COOH$ | 3-F | H | 1-Al—Pyrd(3) |
| 139 | H | H | $SO_2CH_2COOH$ | 2-Cl | H | 1-Al—Pyrd(3) |
| 140 | H | H | $SO_2CH_2COOH$ | 3-Cl | H | 1-Al—Pyrd(3) |
| 141 | H | H | $SO_2CH_2COOH$ | 2-Me | H | 1-Al—Pyrd(3) |
| 142 | H | H | $SO_2CH_2COOH$ | 3-Me | H | 1-Al—Pyrd(3) |
| 143 | H | H | $SO_2CH_2COOH$ | 3-Et | H | 1-Al—Pyrd(3) |
| 144 | H | H | $SO_2CH_2COOH$ | $3-CF_3$ | H | 1-Al—Pyrd(3) |
| 145 | H | H | $SO_2CH_2COOH$ | 2-OMe | H | 1-Al—Pyrd(3) |
| 146 | H | H | $SO_2CH_2COOH$ | 3-OEt | H | 1-Al—Pyrd(3) |
| 147 | H | H | $SO_2CH_2COOH$ | $2-CONH_2$ | H | 1-Al—Pyrd(3) |
| 148 | H | H | $SO_2CH_2COOH$ | $3-CONH_2$ | H | 1-Al—Pyrd(3) |
| 149 | H | H | $SO_2CH_2COOH$ | 3-F | 5-F | 1-Al—Pyrd(3) |
| 150 | H | H | $SO_2CH_2COOH$ | 3-Cl | 5-Cl | 1-Al—Pyrd(3) |
| 151 | H | H | $SO_2CH_2COOH$ | 3-Me | 5-Me | 1-Al—Pyrd(3) |
| 152 | H | H | $SO_2CH_2COOH$ | 3-Cl | $5-CONH_2$ | 1-Al—Pyrd(3) |
| 153 | H | H | $SO_2CH_2COOH$ | 2-Me | $5-CONH_2$ | 1-Al—Pyrd(3) |
| 154 | H | H | $SO_2CH_2COOH$ | 3-Me | $5-CONH_2$ | 1-Al—Pyrd(3) |
| 155 | H | H | $SO_2CH_2COOH$ | $3-CONH_2$ | $5-CONH_2$ | 1-Al—Pyrd(3) |
| 156 | H | F | $SO_2CH_2COOH$ | H | H | 1-Al—Pyrd(3) |
| 157 | H | Cl | $SO_2CH_2COOH$ | H | H | 1-Al—Pyrd(3) |
| 158 | H | Me | $SO_2CH_2COOH$ | H | H | 1-Al—Pyrd(3) |
| 159 | H | Et | $SO_2CH_2COOH$ | H | H | 1-Al—Pyrd(3) |
| 160 | 2-F | H | $SO_2CH_2COOH$ | H | H | 1-Al—Pyrd(3) |
| 161 | 4-F | H | $SO_2CH_2COOH$ | H | H | 1-Al—Pyrd(3) |
| 162 | 5-F | H | $SO_2CH_2COOH$ | H | H | 1-Al—Pyrd(3) |
| 163 | 6-F | H | $SO_2CH_2COOH$ | H | H | 1-Al—Pyrd(3) |
| 164 | 2-Cl | H | $SO_2CH_2COOH$ | H | H | 1-Al—Pyrd(3) |
| 165 | 6-Cl | H | $SO_2CH_2COOH$ | H | H | 1-Al—Pyrd(3) |
| 166 | 4-Me | H | $SO_2CH_2COOH$ | H | H | 1-Al—Pyrd(3) |
| 167 | 6-Me | H | $SO_2CH_2COOH$ | H | H | 1-Al—Pyrd(3) |
| 168 | 5-Et | H | $SO_2CH_2COOH$ | H | H | 1-Al—Pyrd(3) |
| 169 | 6-Pr | H | $SO_2CH_2COOH$ | H | H | 1-Al—Pyrd(3) |
| 170 | 2-OH | H | $SO_2CH_2COOH$ | H | H | 1-Al—Pyrd(3) |
| 171 | 4-OH | H | $SO_2CH_2COOH$ | H | H | 1-Al—Pyrd(3) |
| 172 | 5-OH | H | $SO_2CH_2COOH$ | H | H | 1-Al—Pyrd(3) |
| 173 | 6-OH | H | $SO_2CH_2COOH$ | H | H | 1-Al—Pyrd(3) |
| 174 | H | H | $SO_2CH_2COOH$ | H | H | 1-Al—Pyrd(3) |
| 175 | H | H | $SO_2CH_2COOH$ | H | H | 1-Al—Pyrd(3) |
| 176 | H | H | $SO_2(CH_2)_2COOH$ | H | H | 1-Al—Pyrd(3) |
| 177 | H | H | H | H | H | 1-Al—Pip(4) |
| 178 | H | H | H | 2-F | H | 1-Al—Pip(4) |
| 179 | H | H | H | 3-F | H | 1-Al—Pip(4) |
| 180 | H | H | H | 2-Cl | H | 1-Al—Pip(4) |
| 181 | H | H | H | 3-Cl | H | 1-Al—Pip(4) |
| 182 | H | H | H | 2-Br | H | 1-Al—Pip(4) |
| 183 | H | H | H | 3-Br | H | 1-Al—Pip(4) |
| 184 | H | H | H | 2-I | H | 1-Al—Pip(4) |
| 185 | H | H | H | 3-I | H | 1-Al—Pip(4) |
| 186 | H | H | H | 2-Me | H | 1-Al—Pip(4) |
| 187 | H | H | H | 3-Me | H | 1-Al—Pip(4) |
| 188 | H | H | H | 2-Et | H | 1-Al—Pip(4) |
| 189 | H | H | H | 3-Et | H | 1-Al—Pip(4) |

TABLE 1-continued (I)

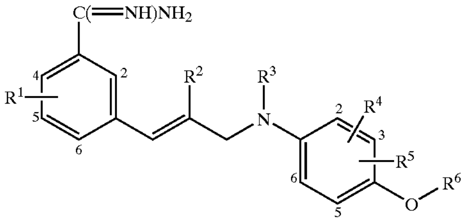

| Cpd. No. | $R^1$ | $R^2$ | $R^3$ | $R^4$ | $R^5$ | $R^6$ |
|---|---|---|---|---|---|---|
| 190 | H | H | H | 2-Pr | H | 1-Al—Pip(4) |
| 191 | H | H | H | 3-Pr | H | l-Al—Pip(4) |
| 192 | H | H | H | 2-Bu | H | 1-Al—Pip(4) |
| 193 | H | H | H | 3-Bu | H | 1-Al—Pip(4) |
| 194 | H | H | H | 2-Pn | H | 1-Al—Pip(4) |
| 195 | H | H | H | 3-Pn | H | 1-Al—Pip(4) |
| 196 | H | H | H | 2-Hx | H | 1-Al—Pip(4) |
| 197 | H | H | H | 3-Hx | H | 1-Al—Pip(4) |
| 198 | H | H | H | 2-$CF_3$ | H | 1-Al—Pip(4) |
| 199 | H | H | H | 3-$CF_3$ | H | 1-Al—Pip(4) |
| 200 | H | H | H | 2-OMe | H | 1-Al—Pip(4) |
| 201 | H | H | H | 3-OMe | H | 1-Al—Pip(4) |
| 202 | H | H | H | 2-OEt | H | 1-Al—Pip(4) |
| 203 | H | H | H | 3-OEt | H | 1-Al—Pip(4) |
| 204 | H | H | H | 2-COOH | H | 1-Al—Pip(4) |
| 205 | H | H | H | 3-COOH | H | 1-Al—Pip(4) |
| 206 | H | H | H | 2-COOMe | H | 1-Al—Pip(4) |
| 207 | H | H | H | 3-COOMe | H | 1-Al—Pip(4) |
| 208 | H | H | H | 2-COOEt | H | 1-Al—Pip(4) |
| 209 | H | H | H | 3-COOEt | H | 1-Al—Pip(4) |
| 210 | H | H | H | 2-COOPr | H | 1-Al—Pip(4) |
| 211 | H | H | H | 3-COOPr | H | 1-Al—Pip(4) |
| 212 | H | H | H | 2-COOBu | H | 1-Al—Pip(4) |
| 213 | H | H | H | 3-COOBu | H | 1-Al—Pip(4) |
| 214 | H | H | H | 2-COOPn | H | 1-Al—Pip(4) |
| 215 | H | H | H | 3-COOPn | H | 1-Al—Pip(4) |
| 216 | H | H | H | 2-COOHx | H | 1-Al—Pip(4) |
| 217 | H | H | H | 3-COOHx | H | 1-Al—Pip(4) |
| 218 | H | H | H | 2-$CONH_2$ | H | 1-Al—Pip(4) |
| 219 | H | H | H | 3-$CONH_2$ | H | 1-Al—Pip(4) |
| 220 | H | H | H | 2-CONHMe | H | 1-Al—Pip(4) |
| 221 | H | H | H | 3-CONHMe | H | 1-Al—Pip(4) |
| 222 | H | H | H | 2-CONHEt | H | 1-Al—Pip(4) |
| 223 | H | H | H | 3-CONHEt | H | 1-Al—Pip(4) |
| 224 | H | H | H | 2-$CON(Me)_2$ | H | 1-Al—Pip(4) |
| 225 | H | H | H | 3-$CON(Me)_2$ | H | 1-Al—Pip(4) |
| 226 | H | H | H | 2-CON(Me)Et | H | 1-Al—Pip(4) |
| 227 | H | H | H | 3-CON(Me)Et | H | 1-Al—Pip(4) |
| 228 | H | H | H | 2-$CON(Et)_2$ | H | 1-Al—Pip(4) |
| 229 | H | H | H | 3-$CON(Et)_2$ | H | 1-Al—Pip(4) |
| 230 | H | H | H | 3-F | 5-F | 1-Al—Pip(4) |
| 231 | H | H | H | 3-Cl | 5-Cl | 1-Al—Pip(4) |
| 232 | H | H | H | 3-Me | 5-Me | 1-Al—Pip(4) |
| 233 | H | H | H | 3-Cl | 5-$CONH_2$ | 1-Al—Pip(4) |
| 234 | H | H | H | 2-Me | 5-$CONH_2$ | 1-Al—Pip(4) |
| 235 | H | H | H | 3-Me | 5-$CONH_2$ | 1-Al—Pip(4) |
| 236 | H | H | H | 3-$CONH_2$ | 5-$CONH_2$ | 1-Al—Pip(4) |
| 237 | H | H | Me | H | H | 1-Al—Pip(4) |
| 238 | H | H | Me | 2-F | H | 1-Al—Pip(4) |
| 239 | H | H | Me | 3-F | H | 1-Al—Pip(4) |
| 240 | H | H | Me | 2-Cl | H | 1-Al—Pip(4) |
| 241 | H | H | Me | 3-Cl | H | 1-Al—Pip(4) |
| 242 | H | H | Me | 2-Br | H | 1-Al—Pip(4) |
| 243 | H | H | Me | 3-Br | H | 1-Al—Pip(4) |
| 244 | H | H | Me | 2-I | H | 1-Al—Pip(4) |
| 245 | H | H | Me | 3-I | H | 1-Al—Pip(4) |
| 246 | H | H | Me | 2-Me | H | 1-Al—Pip(4) |
| 247 | H | H | Me | 3-Me | H | 1-Al—Pip(4) |
| 248 | H | H | Me | 2-Et | H | 1-Al—Pip(4) |
| 249 | H | H | Me | 3-Et | H | 1-Al—Pip(4) |
| 250 | H | H | Me | 2-Pr | H | 1-Al—Pip(4) |
| 251 | H | H | Me | 3-Pr | H | 1-Al—Pip(4) |
| 252 | H | H | Me | 2-Bu | H | 1-Al—Pip(4) |

TABLE 1-continued (I)

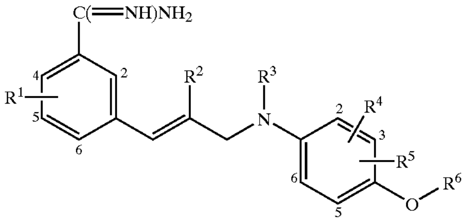

| Cpd. No. | $R^1$ | $R^2$ | $R^3$ | $R^4$ | $R^5$ | $R^6$ |
|---|---|---|---|---|---|---|
| 253 | H | H | Me | 3-Bu | H | 1-Al—Pip(4) |
| 254 | H | H | Me | 2-Pn | H | 1-Al—Pip(4) |
| 255 | H | H | Me | 3-Pn | H | 1-Al—Pip(4) |
| 256 | H | H | Me | 2-Hx | H | 1-Al—Pip(4) |
| 257 | H | H | Me | 3-Hx | H | 1-Al—Pip(4) |
| 258 | H | H | Me | 2-$CF_3$ | H | 1-Al—Pip(4) |
| 259 | H | H | Me | 3-$CF_3$ | H | 1-Al—Pip(4) |
| 260 | H | H | Me | 2-OMe | H | 1-Al—Pip(4) |
| 261 | H | H | Me | 3-OMe | H | 1-Al—Pip(4) |
| 262 | H | H | Me | 2-OEt | H | 1-Al—Pip(4) |
| 263 | H | H | Me | 3-OEt | H | 1-Al—Pip(4) |
| 264 | H | H | Me | 2-COOH | H | 1-Al—Pip(4) |
| 265 | H | H | Me | 3-COOH | H | 1-Al—Pip(4) |
| 266 | H | H | Me | 2-COOMe | H | 1-Al—Pip(4) |
| 267 | H | H | Me | 3-COOMe | H | 1-Al—Pip(4) |
| 268 | H | H | Me | 2-COOEt | H | 1-Al—Pip(4) |
| 269 | H | H | Me | 3-COOEt | H | 1-Al—Pip(4) |
| 270 | H | H | Me | 2-COOPr | H | 1-Al—Pip(4) |
| 271 | H | H | Me | 3-COOPr | H | 1-Al—Pip(4) |
| 272 | H | H | Me | 2-COOBu | H | 1-Al—Pip(4) |
| 273 | H | H | Me | 3-COOBu | H | 1-Al—Pip(4) |
| 274 | H | H | Me | 2-COOPn | H | 1-Al—Pip(4) |
| 275 | H | H | Me | 3-COOPn | H | 1-Al—Pip(4) |
| 276 | H | H | Me | 2-COOHx | H | 1-Al—Pip(4) |
| 277 | H | H | Me | 3-COOHx | H | 1-Al—Pip(4) |
| 278 | H | H | Me | 2-$CONH_2$ | H | 1-Al—Pip(4) |
| 279 | H | H | Me | 3-$CONH_2$ | H | 1-Al—Pip(4) |
| 280 | H | H | Me | 2-CONHMe | H | 1-Al—Pip(4) |
| 281 | H | H | Me | 3-CONHMe | H | 1-Al—Pip(4) |
| 282 | H | H | Me | 2-CONHEt | H | 1-Al—Pip(4) |
| 283 | H | H | Me | 3-CONHEt | H | 1-Al—Pip(4) |
| 284 | H | H | Me | 2-$CON(Me)_2$ | H | 1-Al—Pip(4) |
| 285 | H | H | Me | 3-$CON(Me)_2$ | H | 1-Al—Pip(4) |
| 286 | H | H | Me | 2-CON(Me)Et | H | 1-Al—Pip(4) |
| 287 | H | H | Me | 3-CON(Me)Et | H | 1-Al—Pip(4) |
| 288 | H | H | Me | 2-$CON(Et)_2$ | H | 1-Al—Pip(4) |
| 289 | H | H | Me | 3-$CON(Et)_2$ | H | 1-Al—Pip(4) |
| 290 | H | H | Me | 3-F | 5-F | 1-Al—Pip(4) |
| 291 | H | H | Me | 3-Cl | 5-Cl | 1-Al—Pip(4) |
| 292 | H | H | Me | 3-Me | 5-Me | 1-Al—Pip(4) |
| 293 | H | H | Me | 3-Cl | 5-$CONH_2$ | 1-Al—Pip(4) |
| 294 | H | H | Me | 2-Me | 5-$CONH_2$ | 1-Al—Pip(4) |
| 295 | H | H | Me | 3-Me | 5-$CONH_2$ | 1-Al—Pip(4) |
| 296 | H | H | Me | 3-$CONH_2$ | 5-$CONH_2$ | 1-Al—Pip(4) |
| 297 | H | H | Et | H | H | 1-Al—Pip(4) |
| 298 | H | H | Et | 2-F | H | 1-Al—Pip(4) |
| 299 | H | H | Et | 3-F | H | 1-Al—Pip(4) |
| 300 | H | H | Et | 2-Cl | H | 1-Al—Pip(4) |
| 301 | H | H | Et | 3-Cl | H | 1-Al—Pip(4) |
| 302 | H | H | Et | 2-Br | H | 1-Al—Pip(4) |
| 303 | H | H | Et | 3-Br | H | 1-Al—Pip(4) |
| 304 | H | H | Et | 2-I | H | 1-Al—Pip(4) |
| 305 | H | H | Et | 3-I | H | 1-Al—Pip(4) |
| 306 | H | H | Et | 2-Me | H | 1-Al—Pip(4) |
| 307 | H | H | Et | 3-Me | H | 1-Al—Pip(4) |
| 308 | H | H | Et | 2-Et | H | 1-Al—Pip(4) |
| 309 | H | H | Et | 3-Et | H | 1-Al—Pip(4) |
| 310 | H | H | Et | 2-Pr | H | 1-Al—Pip(4) |
| 311 | H | H | Et | 3-Pr | H | 1-Al—Pip(4) |
| 312 | H | H | Et | 2-Bu | H | 1-Al—Pip(4) |
| 313 | H | H | Et | 3-Bu | H | 1-Al—Pip(4) |
| 314 | H | H | Et | 2-Pn | H | 1-Al—Pip(4) |
| 315 | H | H | Et | 3-Pn | H | 1-Al—Pip(4) |

TABLE 1-continued (I)

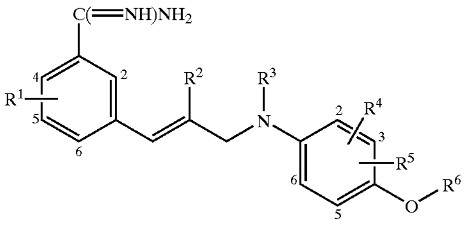

| Cpd. No. | $R^1$ | $R^2$ | $R^3$ | $R^4$ | $R^5$ | $R^6$ |
|---|---|---|---|---|---|---|
| 316 | H | H | Et | 2-Hx | H | 1-Al—Pip(4) |
| 317 | H | H | Et | 3-Hx | H | 1-Al—Pip(4) |
| 318 | H | H | Et | 2-$CF_3$ | H | 1-Al—Pip(4) |
| 319 | H | H | Et | 3-$CF_3$ | H | 1-Al—Pip(4) |
| 320 | H | H | Et | 2-OMe | H | 1-Al—Pip(4) |
| 321 | H | H | Et | 3-OMe | H | 1-Al—Pip(4) |
| 322 | H | H | Et | 2-OEt | H | 1-Al—Pip(4) |
| 323 | H | H | Et | 3-OEt | H | 1-Al—Pip(4) |
| 324 | H | H | Et | 2-COOH | H | 1-Al—Pip(4) |
| 325 | H | H | Et | 3-COOH | H | 1-Al—Pip(4) |
| 326 | H | H | Et | 2-COOMe | H | 1-Al—Pip(4) |
| 327 | H | H | Et | 3-COOMe | H | 1-Al—Pip(4) |
| 328 | H | H | Et | 2-COOEt | H | 1-Al—Pip(4) |
| 329 | H | H | Et | 3-COOEt | H | 1-Al—Pip(4) |
| 330 | H | H | Et | 2-COOPr | H | 1-Al—Pip(4) |
| 331 | H | H | Et | 3-COOPr | H | 1-Al—Pip(4) |
| 332 | H | H | Et | 2-COOBu | H | 1-Al—Pip(4) |
| 333 | H | H | Et | 3-COOBu | H | 1-Al—Pip(4) |
| 334 | H | H | Et | 2-COOPn | H | 1-Al—Pip(4) |
| 335 | H | H | Et | 3-COOPn | H | 1-Al—Pip(4) |
| 336 | H | H | Et | 2-COOHx | H | 1-Al—Pip(4) |
| 337 | H | H | Et | 3-COOHx | H | 1-Al—Pip(4) |
| 338 | H | H | Et | 2-$CONH_2$ | H | 1-Al—Pip(4) |
| 339 | H | H | Et | 3-$CONH_2$ | H | 1-Al—Pip(4) |
| 340 | H | H | Et | 2-CONHMe | H | 1-Al—Pip(4) |
| 341 | H | H | Et | 3-CONHMe | H | 1-Al—Pip(4) |
| 342 | H | H | Et | 2-CONHEt | H | 1-Al—Pip(4) |
| 343 | H | H | Et | 3-CONHEt | H | 1-Al—Pip(4) |
| 344 | H | H | Et | 2-$CON(Me)_2$ | H | 1-Al—Pip(4) |
| 345 | H | H | Et | 3-$CON(Me)_2$ | H | 1-Al—Pip(4) |
| 346 | H | H | Et | 2-CON(Me)Et | H | 1-Al—Pip(4) |
| 347 | H | H | Et | 3-CON(Me)Et | H | 1-Al—Pip(4) |
| 348 | H | H | Et | 2-$CON(Et)_2$ | H | 1-Al—Pip(4) |
| 349 | H | H | Et | 3-$CON(Et)_2$ | H | 1-Al—Pip(4) |
| 350 | H | H | Et | 3-F | 5-F | 1-Al—Pip(4) |
| 351 | H | H | Et | 3-Cl | 5-Cl | 1-Al—Pip(4) |
| 352 | H | H | Et | 3-Me | 5-Me | 1-Al—Pip(4) |
| 353 | H | H | Et | 3-Cl | 5-$CONH_2$ | 1-Al—Pip(4) |
| 354 | H | H | Et | 2-Me | 5-$CONH_2$ | 1-Al—Pip(4) |
| 355 | H | H | Et | 3-Me | 5-$CONH_2$ | 1-Al—Pip(4) |
| 356 | H | H | Et | 3-$CONH_2$ | 5-$CONH_2$ | 1-Al—Pip(4) |
| 357 | H | H | Pr | H | H | 1-Al—Pip(4) |
| 358 | H | H | iPr | H | H | 1-Al—Pip(4) |
| 359 | H | H | iPr | 2-F | H | 1-Al—Pip(4) |
| 360 | H | H | iPr | 3-F | H | 1-Al—Pip(4) |
| 361 | H | H | iPr | 2-Cl | H | 1-Al—Pip(4) |
| 362 | H | H | iPr | 3-Cl | H | 1-Al—Pip(4) |
| 363 | H | H | iPr | 2-Br | H | 1-Al—Pip(4) |
| 364 | H | H | iPr | 3-Br | H | 1-Al—Pip(4) |
| 365 | H | H | iPr | 2-I | H | 1-Al—Pip(4) |
| 366 | H | H | iPr | 3-I | H | 1-Al—Pip(4) |
| 367 | H | H | iPr | 2-Me | H | 1-Al—Pip(4) |
| 368 | H | H | iPr | 3-Me | H | 1-Al—Pip(4) |
| 369 | H | H | iPr | 2-Et | H | 1-Al—Pip(4) |
| 370 | H | H | iPr | 3-Et | H | 1-Al—Pip(4) |
| 371 | H | H | iPr | 2-Pr | H | 1-Al—Pip(4) |
| 372 | H | H | iPr | 3-Pr | H | 1-Al—Pip(4) |
| 373 | H | H | iPr | 2-Bu | H | 1-Al—Pip(4) |
| 374 | H | H | iPr | 3-Bu | H | 1-Al—Pip(4) |
| 375 | H | H | iPr | 2-Pn | H | 1-Al—Pip(4) |
| 376 | H | H | iPr | 3-Pn | H | 1-Al—Pip(4) |
| 377 | H | H | ipr | 2-Hx | H | 1-Al—Pip(4) |
| 378 | H | H | iPr | 3-Hx | H | 1-Al—Pip(4) |

TABLE 1-continued (I)

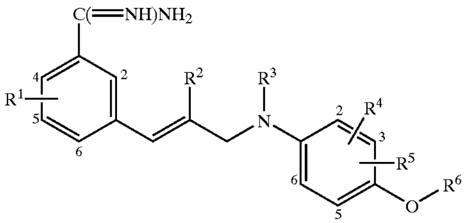

| Cpd. No. | $R^1$ | $R^2$ | $R^3$ | $R^4$ | $R^5$ | $R^6$ |
|---|---|---|---|---|---|---|
| 379 | H | H | iPr | 2-$CF_3$ | H | 1-Al—Pip(4) |
| 380 | H | H | iPr | 3-$CF_3$ | H | 1-Al—Pip(4) |
| 381 | H | H | iPr | 2-OMe | H | 1-Al—Pip(4) |
| 382 | H | H | iPr | 3-OMe | H | 1-Al—Pip(4) |
| 383 | H | H | iPr | 2-OEt | H | 1-Al—Pip(4) |
| 384 | H | H | iPr | 3-OEt | H | 1-Al—Pip(4) |
| 385 | H | H | iPr | 2-COOH | H | 1-Al—Pip(4) |
| 386 | H | H | iPr | 3-COOH | H | 1-Al—Pip(4) |
| 387 | H | H | iPr | 2-COOMe | H | 1-Al—Pip(4) |
| 388 | H | H | iPr | 3-COOMe | H | 1-Al—Pip(4) |
| 389 | H | H | iPr | 2-COOEt | H | 1-Al—Pip(4) |
| 390 | H | H | iPr | 3-COOEt | H | 1-Al—Pip(4) |
| 391 | H | H | iPr | 2-COOPr | H | 1-Al—Pip(4) |
| 392 | H | H | iPr | 3-COOPr | H | 1-Al—Pip(4) |
| 393 | H | H | iPr | 2-COOBu | H | 1-Al—Pip(4) |
| 394 | H | H | iPr | 3-COOBu | H | 1-Al—Pip(4) |
| 395 | H | H | iPr | 2-COOPn | H | 1-Al—Pip(4) |
| 396 | H | H | iPr | 3-COOPn | H | 1-Al—Pip(4) |
| 397 | H | H | iPr | 2-COOHx | H | 1-Al—Pip(4) |
| 398 | H | H | iPr | 3-COOHx | H | 1-Al—Pip(4) |
| 399 | H | H | iPr | 2-$CONH_2$ | H | 1-Al—Pip(4) |
| 400 | H | H | iPr | 3-$CONH_2$ | H | 1-Al—Pip(4) |
| 401 | H | H | iPr | 2-CONHMe | H | 1-Al—Pip(4) |
| 402 | H | H | iPr | 3-CONHMe | H | 1-Al—Pip(4) |
| 403 | H | H | iPr | 2-CONHEt | H | 1-Al—Pip(4) |
| 404 | H | H | iPr | 3-CONHEt | H | 1-Al—Pip(4) |
| 405 | H | H | iPr | 2-$CON(Me)_2$ | H | 1-Al—Pip(4) |
| 406 | H | H | iPr | 3-$CON(Me)_2$ | H | 1-Al—Pip(4) |
| 407 | H | H | iPr | 2-CON(Me)Et | H | 1-Al—Pip(4) |
| 408 | H | H | iPr | 3-CON(Me)Et | H | 1-Al—Pip(4) |
| 409 | H | H | iPr | 2-$CON(Et)_2$ | H | 1-Al—Pip(4) |
| 410 | H | H | iPr | 3-$CON(Et)_2$ | H | 1-Al—Pip(4) |
| 411 | H | H | iPr | 3-F | 5-F | 1-Al—Pip(4) |
| 412 | H | H | iPr | 3-Cl | 5-Cl | 1-Al—Pip(4) |
| 413 | H | H | iPr | 3-Me | 5-Me | 1-Al—Pip(4) |
| 414 | H | H | iPr | 3-Cl | 5-$CONH_2$ | 1-Al—Pip(4) |
| 415 | H | H | iPr | 2-Me | 5-$CONH_2$ | 1-Al—Pip(4) |
| 416 | H | H | iPr | 3-Me | 5-$CONH_2$ | 1-Al—Pip(4) |
| 417 | H | H | iPr | 3-$CONH_2$ | 5-$CONH_2$ | 1-Al—Pip(4) |
| 418 | 6-OH | H | iPr | H | H | 1-Al—Pip(4) |
| 419 | 6-OH | H | iPr | 2-F | H | 1-Al—Pip(4) |
| 420 | 6-OH | H | iPr | 3-F | H | 1-Al—Pip(4) |
| 421 | 6-OH | H | iPr | 2-Cl | H | 1-Al—Pip(4) |
| 422 | 6-OH | H | iPr | 3-Cl | H | 1-Al—Pip(4) |
| 423 | 6-OH | H | iPr | 2-Br | H | 1-Al—Pip(4) |
| 424 | 6-OH | H | iPr | 3-Br | H | 1-Al—Pip(4) |
| 425 | 6-OH | H | iPr | 2-I | H | 1-Al—Pip(4) |
| 426 | 6-OH | H | iPr | 3-I | H | 1-Al—Pip(4) |
| 427 | 6-OH | H | iPr | 2-Me | H | 1-Al—Pip(4) |
| 428 | 6-OH | H | iPr | 3-Me | H | 1-Al—Pip(4) |
| 429 | 6-OH | H | iPr | 2-Et | H | 1-Al—Pip(4) |
| 430 | 6-OH | H | iPr | 3-Et | H | 1-Al—Pip(4) |
| 431 | 6-OH | H | iPr | 2-Pr | H | 1-Al—Pip(4) |
| 432 | 6-OH | H | iPr | 3-Pr | H | 1-Al—Pip(4) |
| 433 | 6-OH | H | iPr | 2-Bu | H | 1-Al—Pip(4) |
| 434 | 6-OH | H | iPr | 3-Bu | H | 1-Al—Pip(4) |
| 435 | 6-OH | H | iPr | 2-Pn | H | 1-Al—Pip(4) |
| 436 | 6-OH | H | iPr | 3-Pn | H | 1-Al—Pip(4) |
| 437 | 6-OH | H | iPr | 2-Hx | H | 1-Al—Pip(4) |
| 438 | 6-OH | H | iPr | 3-Hx | H | 1-Al—Pip(4) |
| 439 | 6-OH | H | iPr | 2-$CF_3$ | H | 1-Al—Pip(4) |
| 440 | 6-OH | H | iPr | 3-$CF_3$ | H | 1-Al—Pip(4) |
| 441 | 6-OH | H | iPr | 2-OMe | H | 1-Al—Pip(4) |

TABLE 1-continued (I)

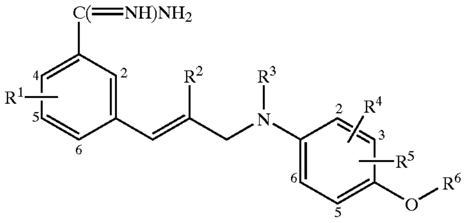

| Cpd. No. | $R^1$ | $R^2$ | $R^3$ | $R^4$ | $R^5$ | $R^6$ |
|---|---|---|---|---|---|---|
| 442 | 6-OH | H | iPr | 3-OMe | H | 1-Al—Pip(4) |
| 443 | 6-OH | H | iPr | 2-OEt | H | 1-Al—Pip(4) |
| 444 | 6-OH | H | iPr | 3-OEt | H | 1-Al—Pip(4) |
| 445 | 6-OH | H | iPr | 2-COOH | H | 1-Al—Pip(4) |
| 446 | 6-OH | H | iPr | 3-COOH | H | 1-Al—Pip(4) |
| 447 | 6-OH | H | iPr | 2-COOMe | H | 1-Al—Pip(4) |
| 448 | 6-OH | H | iPr | 3-COOMe | H | 1-Al—Pip(4) |
| 449 | 6-OH | H | iPr | 2-COOEt | H | 1-Al—Pip(4) |
| 450 | 6-OH | H | iPr | 3-COOEt | H | 1-Al—Pip(4) |
| 451 | 6-OH | H | iPr | 2-COOPr | H | 1-Al—Pip(4) |
| 452 | 6-OH | H | iPr | 3-COOPr | H | 1-Al—Pip(4) |
| 453 | 6-OH | H | iPr | 2-COOBu | H | 1-Al—Pip(4) |
| 454 | 6-OH | H | iPr | 3-COOBu | H | 1-Al—Pip(4) |
| 455 | 6-OH | H | iPr | 2-COOPn | H | 1-Al—Pip(4) |
| 456 | 6-OH | H | iPr | 3-COOPn | H | 1-Al—Pip(4) |
| 457 | 6-OH | H | iPr | 2-COOHx | H | 1-Al—Pip(4) |
| 458 | 6-OH | H | iPr | 3-COOHx | H | 1-Al—Pip(4) |
| 459 | 6-OH | H | iPr | 2-$CONH_2$ | H | 1-Al—Pip(4) |
| 460 | 6-OH | H | iPr | 3-$CONH_2$ | H | 1-Al—Pip(4) |
| 461 | 6-OH | H | ipr | 2-CONHMe | H | 1-Al—Pip(4) |
| 462 | 6-OH | H | iPr | 3-CONHMe | H | 1-Al—Pip(4) |
| 463 | 6-OH | H | iPr | 2-CONHEt | H | 1-Al—Pip(4) |
| 464 | 6-OH | H | iPr | 3-CONHEt | H | 1-Al—Pip(4) |
| 465 | 6-OH | H | iPr | 2-$CON(Me)_2$ | H | 1-Al—Pip(4) |
| 466 | 6-OH | H | iPr | 3-$CON(Me)_2$ | H | 1-Al—Pip(4) |
| 467 | 6-OH | H | iPr | 2-CON(Me)Et | H | 1-Al—Pip(4) |
| 468 | 6-OH | H | iPr | 3-CON(Me)Et | H | 1-Al—Pip(4) |
| 469 | 6-OH | H | iPr | 2-$CON(Et)_2$ | H | 1-Al—Pip(4) |
| 470 | 6-OH | H | iPr | 3-$CON(Et)_2$ | H | 1-Al—Pip(4) |
| 471 | H | H | Bu | H | H | 1-Al—Pip(4) |
| 472 | H | H | iBu | H | H | 1-Al—Pip(4) |
| 473 | H | H | sBu | H | H | 1-Al—Pip(4) |
| 474 | H | H | tBu | H | H | 1-Al—Pip(4) |
| 475 | H | H | Pn | H | H | 1-Al—Pip(4) |
| 476 | H | H | Hx | H | H | 1-Al—Pip(4) |
| 477 | H | H | $CH_2OH$ | H | H | 1-Al—Pip(4) |
| 478 | H | H | $(CH_2)_2OH$ | H | H | 1-Al—Pip(4) |
| 479 | H | H | $(CH_2)_2OH$ | 2-F | H | 1-Al—Pip(4) |
| 480 | H | H | $(CH_2)_2OH$ | 3-F | H | 1-Al—Pip(4) |
| 481 | H | H | $(CH_2)_2OH$ | 2-Cl | H | 1-Al—Pip(4) |
| 482 | H | H | $(CH_2)_2OH$ | 3-Cl | H | 1-Al—Pip(4) |
| 483 | H | H | $(CH_2)_2OH$ | 2-Br | H | 1-Al—Pip(4) |
| 484 | H | H | $(CH_2)_2OH$ | 3-Br | H | 1-Al—Pip(4) |
| 485 | H | H | $(CH_2)_2OH$ | 2-I | H | 1-Al—Pip(4) |
| 486 | H | H | $(CH_2)_2OH$ | 3-I | H | 1-Al—Pip(4) |
| 487 | H | H | $(CH_2)_2OH$ | 2-Me | H | 1-Al—Pip(4) |
| 488 | H | H | $(CH_2)_2OH$ | 3-Me | H | 1-Al—Pip(4) |
| 489 | H | H | $(CH_2)_2OH$ | 2-Et | H | 1-Al—Pip(4) |
| 490 | H | H | $(CH_2)_2OH$ | 3-Et | H | 1-Al—Pip(4) |
| 491 | H | H | $(CH_2)_2OH$ | 2-Pr | H | 1-Al—Pip(4) |
| 492 | H | H | $(CH_2)_2OH$ | 3-Pr | H | 1-Al—Pip(4) |
| 493 | H | H | $(CH_2)_2OH$ | 2-Bu | H | 1-Al—Pip(4) |
| 494 | H | H | $(CH_2)_2OH$ | 3-Bu | H | 1-Al—Pip(4) |
| 495 | H | H | $(CH_2)_2OH$ | 2-Pn | H | 1-Al—Pip(4) |
| 496 | H | H | $(CH_2)_2OH$ | 3-Pn | H | 1-Al—Pip(4) |
| 497 | H | H | $(CH_2)_2OH$ | 2-Hx | H | 1-Al—Pip(4) |
| 498 | H | H | $(CH_2)_2OH$ | 3-Hx | H | 1-Al—Pip(4) |
| 499 | H | H | $(CH_2)_2OH$ | 2-$CF_3$ | H | 1-Al—Pip(4) |
| 500 | H | H | $(CH_2)_2OH$ | 3-$CF_3$ | H | 1-Al—Pip(4) |
| 501 | H | H | $(CH_2)_2OH$ | 2-OMe | H | 1-Al—Pip(4) |
| 502 | H | H | $(CH_2)_2OH$ | 3-OMe | H | 1-Al—Pip(4) |
| 503 | H | H | $(CH_2)_2OH$ | 2-OEt | H | 1-Al—Pip(4) |
| 504 | H | H | $(CH_2)_2OH$ | 3-OEt | H | 1-Al—Pip(4) |

TABLE 1-continued (I)

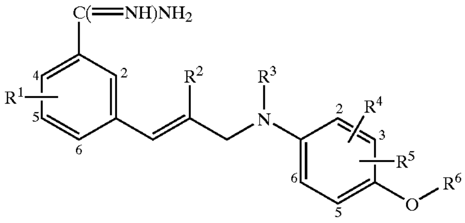

| Cpd. No. | $R^1$ | $R^2$ | $R^3$ | $R^4$ | $R^5$ | $R^6$ |
|---|---|---|---|---|---|---|
| 505 | H | H | $(CH_2)_2OH$ | 2-COOH | H | 1-Al—Pip(4) |
| 506 | H | H | $(CH_2)_2OH$ | 3-COOH | H | 1-Al—Pip(4) |
| 507 | H | H | $(CH_2)_2OH$ | 2-COOMe | H | 1-Al—Pip(4) |
| 508 | H | H | $(CH_2)_2OH$ | 3-COOMe | H | 1-Al—Pip(4) |
| 509 | H | H | $(CH_2)_2OH$ | 2-COOEt | H | 1-Al—Pip(4) |
| 510 | H | H | $(CH_2)_2OH$ | 3-COOEt | H | 1-Al—Pip(4) |
| 511 | H | H | $(CH_2)_2OH$ | 2-COOPr | H | 1-Al—Pip(4) |
| 512 | H | H | $(CH_2)_2OH$ | 3-COOPr | H | 1-Al—Pip(4) |
| 513 | H | H | $(CH_2)_2OH$ | 2-COOBu | H | 1-Al—Pip(4) |
| 514 | H | H | $(CH_2)_2OH$ | 3-COOBu | H | 1-Al—Pip(4) |
| 515 | H | H | $(CH_2)_2OH$ | 2-COOPn | H | 1-Al—Pip(4) |
| 516 | H | H | $(CH_2)_2OH$ | 3-COOPn | H | 1-Al—Pip(4) |
| 517 | H | H | $(CH_2)_2OH$ | 2-COOHx | H | 1-Al—Pip(4) |
| 518 | H | H | $(CH_2)_2OH$ | 3-COOHx | H | 1-Al—Pip(4) |
| 519 | H | H | $(CH_2)_2OH$ | 2-$CONH_2$ | H | 1-Al—Pip(4) |
| 520 | H | H | $(CH_2)_2OH$ | 3-$CONH_2$ | H | 1-Al—Pip(4) |
| 521 | H | H | $(CH_2)_2OH$ | 2-CONHMe | H | 1-Al—Pip(4) |
| 522 | H | H | $(CH_2)_2OH$ | 3-CONHMe | H | 1-Al—Pip(4) |
| 523 | H | H | $(CH_2)_2OH$ | 2-CONHEt | H | 1-Al—Pip(4) |
| 524 | H | H | $(CH_2)_2OH$ | 3-CONHEt | H | 1-Al—Pip(4) |
| 525 | H | H | $(CH_2)_2OH$ | 2-$CON(Me)_2$ | H | 1-Al—Pip(4) |
| 526 | H | H | $(CH_2)_2OH$ | 3-$CON(Me)_2$ | H | 1-Al—Pip(4) |
| 527 | H | H | $(CH_2)_2OH$ | 2-CON(Me)Et | H | 1-Al—Pip(4) |
| 528 | H | H | $(CH_2)_2OH$ | 3-CON(Me)Et | H | 1-Al—Pip(4) |
| 529 | H | H | $(CH_2)_2OH$ | 2-$CON(Et)_2$ | H | 1-Al—Pip(4) |
| 530 | H | H | $(CH_2)_2OH$ | 3-$CON(Et)_2$ | H | 1-Al—Pip(4) |
| 531 | H | H | $(CH_2)_2OH$ | 3-F | 5-F | 1-Al—Pip(4) |
| 532 | H | H | $(CH_2)_2OH$ | 3-Cl | 5-Cl | 1-Al—Pip(4) |
| 533 | H | H | $(CH_2)_2OH$ | 3-Me | 5-Me | 1-Al—Pip(4) |
| 534 | H | H | $(CH_2)_2OH$ | 3-Cl | 5-$CONH_2$ | 1-Al—Pip(4) |
| 535 | H | H | $(CH_2)_2OH$ | 2-Me | 5-$CONH_2$ | 1-Al—Pip(4) |
| 536 | H | H | $(CH_2)_2OH$ | 3-Me | 5-$CONH_2$ | 1-Al—Pip(4) |
| 537 | H | H | $(CH_2)_2OH$ | 3-$CONH_2$ | 5-$CONH_2$ | 1-Al—Pip(4) |
| 538 | H | H | $(CH_2)_3OH$ | H | H | 1-Al—Pip(4) |
| 539 | H | H | $(CH_2)_4OH$ | H | H | 1-Al—Pip(4) |
| 540 | H | H | $(CH_2)_5OH$ | H | H | 1-Al—Pip(4) |
| 541 | H | H | $(CH_2)_6OH$ | H | H | 1-Al—Pip(4) |
| 542 | H | H | $CH_2COOH$ | H | H | 1-Al—Pip(4) |
| 543 | H | H | $CH_2COOH$ | 2-F | H | 1-Al—Pip(4) |
| 544 | H | H | $CH_2COOH$ | 3-F | H | 1-Al—Pip(4) |
| 545 | H | H | $CH_2COOH$ | 2-Cl | H | 1-Al—Pip(4) |
| 546 | H | H | $CH_2COOH$ | 3-Cl | H | 1-Al—Pip(4) |
| 547 | H | H | $CH_2COOH$ | 2-Br | H | 1-Al—Pip(4) |
| 548 | H | H | $CH_2COOH$ | 3-Br | H | 1-Al—Pip(4) |
| 549 | H | H | $CH_2COOH$ | 2-I | H | 1-Al—Pip(4) |
| 550 | H | H | $CH_2COOH$ | 3-I | H | 1-Al—Pip(4) |
| 551 | H | H | $CH_2COOH$ | 2-Me | H | 1-Al—Pip(4) |
| 552 | H | H | $CH_2COOH$ | 3-Me | H | 1-Al—Pip(4) |
| 553 | H | H | $CH_2COOH$ | 2-Et | H | 1-Al—Pip(4) |
| 554 | H | H | $CH_2COOH$ | 3-Et | H | 1-Al—Pip(4) |
| 555 | H | H | $CH_2COOH$ | 2-Pr | H | 1-Al—Pip(4) |
| 556 | H | H | $CH_2COOH$ | 3-Pr | H | 1-Al—Pip(4) |
| 557 | H | H | $CH_2COOH$ | 2-Bu | H | 1-Al—Pip(4) |
| 558 | H | H | $CH_2COOH$ | 3-Bu | H | 1-Al—Pip(4) |
| 559 | H | H | $CH_2COOH$ | 2-Pn | H | 1-Al—Pip(4) |
| 560 | H | H | $CH_2COOH$ | 3-Pn | H | 1-Al—Pip(4) |
| 561 | H | H | $CH_2COOH$ | 2-Hx | H | 1-Al—Pip(4) |
| 562 | H | H | $CH_2COOH$ | 3-Hx | H | 1-Al—Pip(4) |
| 563 | H | H | $CH_2COOH$ | 2-$CF_3$ | H | 1-Al—Pip(4) |
| 564 | H | H | $CH_2COOH$ | 3-$CF_3$ | H | 1-Al—Pip(4) |
| 565 | H | H | $CH_2COOH$ | 2-OMe | H | 1-Al—Pip(4) |
| 566 | H | H | $CH_2COOH$ | 3-OMe | H | 1-Al—Pip(4) |
| 567 | H | H | $CH_2COOH$ | 2-OEt | H | 1-Al—Pip(4) |

TABLE 1-continued (I)

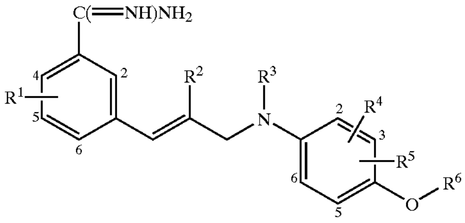

| Cpd. No. | $R^1$ | $R^2$ | $R^3$ | $R^4$ | $R^5$ | $R^6$ |
|---|---|---|---|---|---|---|
| 568 | H | H | $CH_2COOH$ | 3-OEt | H | 1-Al—Pip(4) |
| 569 | H | H | $CH_2COOH$ | 2-COOH | H | 1-Al—Pip(4) |
| 570 | H | H | $CH_2COOH$ | 3-COOH | H | 1-Al—Pip(4) |
| 571 | H | H | $CH_2COOH$ | 2-COOMe | H | 1-Al—Pip(4) |
| 572 | H | H | $CH_2COOH$ | 3-COOMe | H | 1-Al—Pip(4) |
| 573 | H | H | $CH_2COOH$ | 2-COOEt | H | 1-Al—Pip(4) |
| 574 | H | H | $CH_2COOH$ | 3-COOEt | H | 1-Al—Pip(4) |
| 575 | H | H | $CH_2COOH$ | 2-COOPr | H | 1-Al—Pip(4) |
| 576 | H | H | $CH_2COOH$ | 3-COOPr | H | 1-Al—Pip(4) |
| 577 | H | H | $CH_2COOH$ | 2-COOBu | H | 1-Al—Pip(4) |
| 578 | H | H | $CH_2COOH$ | 3-COOBu | H | 1-Al—Pip(4) |
| 579 | H | H | $CH_2COOH$ | 2-COOPn | H | 1-Al—Pip(4) |
| 580 | H | H | $CH_2COOH$ | 3-COOPn | H | 1-Al—Pip(4) |
| 581 | H | H | $CH_2COOH$ | 2-COOHx | H | 1-Al—Pip(4) |
| 582 | H | H | $CH_2COOH$ | 3-COOHx | H | 1-Al—Pip(4) |
| 583 | H | H | $CH_2COOH$ | 2-$CONH_2$ | H | 1-Al—Pip(4) |
| 584 | H | H | $CH_2COOH$ | 3-$CONH_2$ | H | 1-Al—Pip(4) |
| 585 | H | H | $CH_2COOH$ | 2-CONHMe | H | 1-Al—Pip(4) |
| 586 | H | H | $CH_2COOH$ | 3-CONHMe | H | 1-Al—Pip(4) |
| 587 | H | H | $CH_2COOH$ | 2-CONHEt | H | 1-Al—Pip(4) |
| 588 | H | H | $CH_2COOH$ | 3-CONHEt | H | 1-Al—Pip(4) |
| 589 | H | H | $CH_2COOH$ | 2-$CON(Me)_2$ | H | 1-Al—Pip(4) |
| 590 | H | H | $CH_2COOH$ | 3-$CON(Me)_2$ | H | 1-Al—Pip(4) |
| 591 | H | H | $CH_2COOH$ | 2-CON(Me)Et | H | 1-Al—Pip(4) |
| 592 | H | H | $CH_2COOH$ | 3-CON(Me)Et | H | 1-Al—Pip(4) |
| 593 | H | H | $CH_2COOH$ | 2-$CON(Et)_2$ | H | 1-Al—Pip(4) |
| 594 | H | H | $CH_2COOH$ | 3-$CON(Et)_2$ | H | 1-Al—Pip(4) |
| 595 | H | H | $CH_2COOH$ | 3-F | 5-F | 1-Al—Pip(4) |
| 596 | H | H | $CH_2COOH$ | 3-Cl | 5-Cl | 1-Al—Pip(4) |
| 597 | H | H | $CH_2COOH$ | 3-Me | 5-Me | 1-Al—Pip(4) |
| 598 | H | H | $CH_2COOH$ | 3-Cl | 5-$CONH_2$ | 1-Al—Pip(4) |
| 599 | H | H | $CH_2COOH$ | 2-Me | 5-$CONH_2$ | 1-Al—Pip(4) |
| 600 | H | H | $CH_2COOH$ | 3-Me | 5-$CONH_2$ | 1-Al—Pip(4) |
| 601 | H | H | $CH_2COOH$ | 3-$CONH_2$ | 5-$CONH_2$ | 1-Al—Pip(4) |
| 602 | 6-OH | H | $CH_2COOH$ | H | H | 1-Al—Pip(4) |
| 603 | 6-OH | H | $CH_2COOH$ | 2-F | H | 1-Al—Pip(4) |
| 604 | 6-OH | H | $CH_2COOH$ | 3-F | H | 1-Al—Pip(4) |
| 605 | 6-OH | H | $CH_2COOH$ | 2-Cl | H | 1-Al—Pip(4) |
| 606 | 6-OH | H | $CH_2COOH$ | 3-Cl | H | 1-Al—Pip(4) |
| 607 | 6-OH | H | $CH_2COOH$ | 2-Br | H | 1-Al—Pip(4) |
| 608 | 6-OH | H | $CH_2COOH$ | 3-Br | H | 1-Al—Pip(4) |
| 609 | 6-OH | H | $CH_2COOH$ | 2-I | H | 1-Al—Pip(4) |
| 610 | 6-OH | H | $CH_2COOH$ | 3-I | H | 1-Al—Pip(4) |
| 611 | 6-OH | H | $CH_2COOH$ | 2-Me | H | 1-Al—Pip(4) |
| 612 | 6-OH | H | $CH_2COOH$ | 3-Me | H | 1-Al—Pip(4) |
| 613 | 6-OH | H | $CH_2COOH$ | 2-Et | H | 1-Al—Pip(4) |
| 614 | 6-OH | H | $CH_2COOH$ | 3-Et | H | 1-Al—Pip(4) |
| 615 | 6-OH | H | $CH_2COOH$ | 2-Pr | H | 1-Al—Pip(4) |
| 616 | 6-OH | H | $CH_2COOH$ | 3-Pr | H | 1-Al—Pip(4) |
| 617 | 6-OH | H | $CH_2COOH$ | 2-Bu | H | 1-Al—Pip(4) |
| 618 | 6-OH | H | $CH_2COOH$ | 3-Bu | H | 1-Al—Pip(4) |
| 619 | 6-OH | H | $CH_2COOH$ | 2-Pn | H | 1-Al—Pip(4) |
| 620 | 6-OH | H | $CH_2COOH$ | 3-Pn | H | 1-Al—Pip(4) |
| 621 | 6-OH | H | $CH_2COOH$ | 2-Hx | H | 1-Al—Pip(4) |
| 622 | 6-OH | H | $CH_2COOH$ | 3-Hx | H | 1-Al—Pip(4) |
| 623 | 6-OH | H | $CH_2COOH$ | 2-$CF_3$ | H | 1-Al—Pip(4) |
| 624 | 6-OH | H | $CH_2COOH$ | 3-$CF_3$ | H | 1-Al—Pip(4) |
| 625 | 6-OH | H | $CH_2COOH$ | 2-OMe | H | 1-Al—Pip(4) |
| 626 | 6-OH | H | $CH_2COOH$ | 3-OMe | H | 1-Al—Pip(4) |
| 627 | 6-OH | H | $CH_2COOH$ | 2-OEt | H | 1-Al—Pip(4) |
| 628 | 6-OH | H | $CH_2COOH$ | 3-OEt | H | 1-Al—Pip(4) |
| 629 | 6-OH | H | $CH_2COOH$ | 2-COOH | H | 1-Al—Pip(4) |
| 630 | 6-OH | H | $CH_2COOH$ | 3-COOH | H | 1-Al—Pip(4) |

TABLE 1-continued (I)

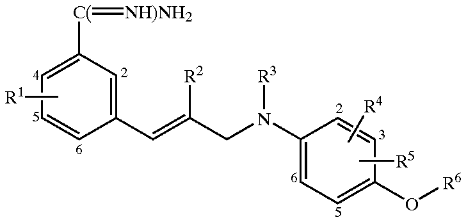

| Cpd. No. | $R^1$ | $R^2$ | $R^3$ | $R^4$ | $R^5$ | $R^6$ |
|---|---|---|---|---|---|---|
| 631 | 6-OH | H | $CH_2COOH$ | 2-COOMe | H | 1-Al—Pip(4) |
| 632 | 6-OH | H | $CH_2COOH$ | 3-COOMe | H | 1-Al—Pip(4) |
| 633 | 6-OH | H | $CH_2COOH$ | 2-COOEt | H | 1-Al—Pip(4) |
| 634 | 6-OH | H | $CH_2COOH$ | 3-COOEt | H | 1-Al—Pip(4) |
| 635 | 6-OH | H | $CH_2COOH$ | 2-COOPr | H | 1-Al—Pip(4) |
| 636 | 6-OH | H | $CH_2COOH$ | 3-COOPr | H | 1-Al—Pip(4) |
| 637 | 6-OH | H | $CH_2COOH$ | 2-COOBu | H | 1-Al—Pip(4) |
| 638 | 6-OH | H | $CH_2COOH$ | 3-COOBu | H | 1-Al—Pip(4) |
| 639 | 6-OH | H | $CH_2COOH$ | 2-COOPn | H | 1-Al—Pip(4) |
| 640 | 6-OH | H | $CH_2COOH$ | 3-COOPn | H | 1-Al—Pip(4) |
| 641 | 6-OH | H | $CH_2COOH$ | 2-COOHx | H | 1-Al—Pip(4) |
| 642 | 6-OH | H | $CH_2COOH$ | 3-COOHx | H | 1-Al—Pip(4) |
| 643 | 6-OH | H | $CH_2COOH$ | $2\text{-}CONH_2$ | H | 1-Al—Pip(4) |
| 644 | 6-OH | H | $CH_2COOH$ | $3\text{-}CONH_2$ | H | 1-Al—Pip(4) |
| 645 | 6-OH | H | $CH_2COOH$ | 2-CONHMe | H | 1-Al—Pip(4) |
| 646 | 6-OH | H | $CH_2COOH$ | 3-CONHMe | H | 1-Al—Pip(4) |
| 647 | 6-OH | H | $CH_2COOH$ | 2-CONHEt | H | 1-Al—Pip(4) |
| 648 | 6-OH | H | $CH_2COOH$ | 3-CONHEt | H | 1-Al—Pip(4) |
| 649 | 6-OH | H | $CH_2COOH$ | $2\text{-}CON(Me)_2$ | H | 1-Al—Pip(4) |
| 650 | 6-OH | H | $CH_2COOH$ | $3\text{-}CON(Me)_2$ | H | 1-Al—Pip(4) |
| 651 | 6-OH | H | $CH_2COOH$ | 2-CON(Me)Et | H | 1-Al—Pip(4) |
| 652 | 6-OH | H | $CH_2COOH$ | 3-CON(Me)Et | H | 1-Al—Pip(4) |
| 653 | 6-OH | H | $CH_2COOH$ | $2\text{-}CON(Et)_2$ | H | 1-Al—Pip(4) |
| 654 | 6-OH | H | $CH_2COOH$ | $3\text{-}CON(Et)_2$ | H | 1-Al—Pip(4) |
| 655 | 6-OH | H | $CH_2COOH$ | 3-F | 5-F | 1-Al—Pip(4) |
| 656 | 6-OH | H | $CH_2COOH$ | 3-Cl | 5-Cl | 1-Al—Pip(4) |
| 657 | 6-OH | H | $CH_2COOH$ | 3-Me | 5-Me | 1-Al—Pip(4) |
| 658 | 6-OH | H | $CH_2COOH$ | 3-Cl | $5\text{-}CONH_2$ | 1-Al—Pip(4) |
| 659 | 6-OH | H | $CH_2COOH$ | 2-Me | $5\text{-}CONH_2$ | 1-Al—Pip(4) |
| 660 | 6-OH | H | $CH_2COOH$ | 3-Me | $5\text{-}CONH_2$ | 1-Al—Pip(4) |
| 661 | 6-OH | H | $CH_2COOH$ | $3\text{-}CONH_2$ | $5\text{-}CONH_2$ | 1-Al—Pip(4) |
| 662 | H | H | $(CH_2)_2COOH$ | H | H | 1-Al—Pip(4) |
| 663 | H | H | $(CH_2)_3COOH$ | H | H | 1-Al—Pip(4) |
| 664 | H | H | $(CH_2)_4COOH$ | H | H | 1-Al—Pip(4) |
| 665 | H | H | $(CH_2)_5COOH$ | H | H | 1-Al—Pip(4) |
| 666 | H | H | $(CH_2)_6COOH$ | H | H | 1-Al—Pip(4) |
| 667 | H | H | $CH_2COOMe$ | H | H | 1-Al—Pip(4) |
| 668 | H | H | $CH_2COOEt$ | H | H | 1-Al—Pip(4) |
| 669 | H | H | $CH_2COOEt$ | 2-F | H | 1-Al—Pip(4) |
| 670 | H | H | $CH_2COOEt$ | 3-F | H | 1-Al—Pip(4) |
| 671 | H | H | $CH_2COOEt$ | 2-Cl | H | 1-Al—Pip(4) |
| 672 | H | H | $CH_2COOEt$ | 3-Cl | H | 1-Al—Pip(4) |
| 673 | H | H | $CH_2COOEt$ | 2-Br | H | 1-Al—Pip(4) |
| 674 | H | H | $CH_2COOEt$ | 3-Br | H | 1-Al—Pip(4) |
| 675 | H | H | $CH_2COOEt$ | 2-I | H | 1-Al—Pip(4) |
| 676 | H | H | $CH_2COOEt$ | 3-I | H | 1-Al—Pip(4) |
| 677 | H | H | $CH_2COOEt$ | 2-Me | H | 1-Al—Pip(4) |
| 678 | H | H | $CH_2COOEt$ | 3-Me | H | 1-Al—Pip(4) |
| 679 | H | H | $CH_2COOEt$ | 2-Et | H | 1-Al—Pip(4) |
| 680 | H | H | $CH_2COOEt$ | 3-Et | H | 1-Al—Pip(4) |
| 681 | H | H | $CH_2COOEt$ | 2-Pr | H | 1-Al—Pip(4) |
| 682 | H | H | $CH_2COOEt$ | 3-Pr | H | 1-Al—Pip(4) |
| 683 | H | H | $CH_2COOEt$ | 2-Bu | H | 1-Al—Pip(4) |
| 684 | H | H | $CH_2COOEt$ | 3-Bu | H | 1-Al—Pip(4) |
| 685 | H | H | $CH_2COOEt$ | 2-Pn | H | 1-Al—Pip(4) |
| 686 | H | H | $CH_2COOEt$ | 3-Pn | H | 1-Al—Pip(4) |
| 687 | H | H | $CH_2COOEt$ | 2-Hx | H | 1-Al—Pip(4) |
| 688 | H | H | $CH_2COOEt$ | 3-Hx | H | 1-Al—Pip(4) |
| 689 | H | H | $CH_2COOEt$ | $2\text{-}CF_3$ | H | 1-Al—Pip(4) |
| 690 | H | H | $CH_2COOEt$ | $3\text{-}CF_3$ | H | 1-Al—Pip(4) |
| 691 | H | H | $CH_2COOEt$ | 2-OMe | H | 1-Al—Pip(4) |
| 692 | H | H | $CH_2COOEt$ | 3-OMe | H | 1-Al—Pip(4) |
| 693 | H | H | $CH_2COOEt$ | 2-OEt | H | 1-Al—Pip(4) |

TABLE 1-continued (I)

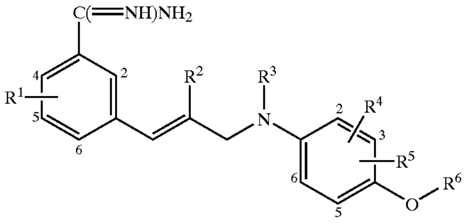

| Cpd. No. | $R^1$ | $R^2$ | $R^3$ | $R^4$ | $R^5$ | $R^6$ |
|---|---|---|---|---|---|---|
| 694 | H | H | $CH_2COOEt$ | 3-OEt | H | 1-Al—Pip(4) |
| 695 | H | H | $CH_2COOEt$ | 2-COOH | H | 1-Al—Pip(4) |
| 696 | H | H | $CH_2COOEt$ | 3-COOH | H | 1-Al—Pip(4) |
| 697 | H | H | $CH_2COOEt$ | 2-COOMe | H | 1-Al—Pip(4) |
| 698 | H | H | $CH_2COOEt$ | 3-COOMe | H | 1-Al—Pip(4) |
| 699 | H | H | $CH_2COOEt$ | 2-COOEt | H | 1-Al—Pip(4) |
| 700 | H | H | $CH_2COOEt$ | 3-COOEt | H | 1-Al—Pip(4) |
| 701 | H | H | $CH_2COOEt$ | 2-COOPr | H | 1-Al—Pip(4) |
| 702 | H | H | $CH_2COOEt$ | 3-COOPr | H | 1-Al—Pip(4) |
| 703 | H | H | $CH_2COOEt$ | 2-COOBu | H | 1-Al—Pip(4) |
| 704 | H | H | $CH_2COOEt$ | 3-COOBu | H | 1-Al—Pip(4) |
| 705 | H | H | $CH_2COOEt$ | 2-COOPn | H | 1-Al—Pip(4) |
| 706 | H | H | $CH_2COOEt$ | 3-COOPn | H | 1-Al—Pip(4) |
| 707 | H | H | $CH_2COOEt$ | 2-COOHx | H | 1-Al—Pip(4) |
| 708 | H | H | $CH_2COOEt$ | 3-COOHx | H | 1-Al—Pip(4) |
| 709 | H | H | $CH_2COOEt$ | $2-CONH_2$ | H | 1-Al—Pip(4) |
| 710 | H | H | $CH_2COOEt$ | $3-CONH_2$ | H | 1-Al—Pip(4) |
| 711 | H | H | $CH_2COOEt$ | 2-CONHMe | H | 1-Al—Pip(4) |
| 712 | H | H | $CH_2COOEt$ | 3-CONHMe | H | 1-Al—Pip(4) |
| 713 | H | H | $CH_2COOEt$ | 2-CONHEt | H | 1-Al—Pip(4) |
| 714 | H | H | $CH_2COOEt$ | 3-CONHEt | H | 1-Al—Pip(4) |
| 715 | H | H | $CH_2COOEt$ | $2-CON(Me)_2$ | H | 1-Al—Pip(4) |
| 716 | H | H | $CH_2COOEt$ | $3-CON(Me)_2$ | H | 1-Al—Pip(4) |
| 717 | H | H | $CH_2COOEt$ | 2-CON(Me)Et | H | 1-Al—Pip(4) |
| 718 | H | H | $CH_2COOEt$ | 3-CON(Me)Et | H | 1-Al—Pip(4) |
| 719 | H | H | $CH_2COOEt$ | $2-CON(Et)_2$ | H | 1-Al—Pip(4) |
| 720 | H | H | $CH_2COOEt$ | $3-CON(Et)_2$ | H | 1-Al—Pip(4) |
| 721 | H | H | $CH_2COOEt$ | 3-F | 5-F | 1-Al—Pip(4) |
| 722 | H | H | $CH_2COOEt$ | 3-Cl | 5-Cl | 1-Al—Pip(4) |
| 723 | H | H | $CH_2COOEt$ | 3-Me | 5-Me | 1-Al—Pip(4) |
| 724 | H | H | $CH_2COOEt$ | 3-Cl | $5-CONH_2$ | 1-Al—Pip(4) |
| 725 | H | H | $CH_2COOEt$ | 2-Me | $5-CONH_2$ | 1-Al—Pip(4) |
| 726 | H | H | $CH_2COOEt$ | 3-Me | $5-CONH_2$ | 1-Al—Pip(4) |
| 727 | H | H | $CH_2COOEt$ | $3-CONH_2$ | $5-CONH_2$ | 1-Al—Pip(4) |
| 728 | 6-OH | H | $CH_2COOEt$ | H | H | 1-Al—Pip(4) |
| 729 | 6-OH | H | $CH_2COOEt$ | 2-F | H | 1-Al—Pip(4) |
| 730 | 6-OH | H | $CH_2COOEt$ | 3-F | H | 1-Al—Pip(4) |
| 731 | 6-OH | H | $CH_2COOEt$ | 2-Cl | H | 1-Al—Pip(4) |
| 732 | 6-OH | H | $CH_2COOEt$ | 3-Cl | H | 1-Al—Pip(4) |
| 733 | 6-OH | H | $CH_2COOEt$ | 2-Br | H | 1-Al—Pip(4) |
| 734 | 6-OH | H | $CH_2COOEt$ | 3-Br | H | 1-Al—Pip(4) |
| 735 | 6-OH | H | $CH_2COOEt$ | 2-I | H | 1-Al—Pip(4) |
| 736 | 6-OH | H | $CH_2COOEt$ | 3-I | H | l-Al—Pip(4) |
| 737 | 6-OH | H | $CH_2COOEt$ | 2-Me | H | 1-Al—Pip(4) |
| 738 | 6-OH | H | $CH_2COOEt$ | 3-Me | H | 1-Al—Pip(4) |
| 739 | 6-OH | H | $CH_2COOEt$ | 2-Et | H | 1-Al—Pip(4) |
| 740 | 6-OH | H | $CH_2COOEt$ | 3-Et | H | 1-Al—Pip(4) |
| 741 | 6-OH | H | $CH_2COOEt$ | 2-Pr | H | 1-Al—Pip(4) |
| 742 | 6-OH | H | $CH_2COOEt$ | 3-Pr | H | 1-Al—Pip(4) |
| 743 | 6-OH | H | $CH_2COOEt$ | 2-Bu | H | 1-Al—Pip(4) |
| 744 | 6-OH | H | $CH_2COOEt$ | 3-Bu | H | 1-Al—Pip(4) |
| 745 | 6-OH | H | $CH_2COOEt$ | 2-Pn | H | 1-Al—Pip(4) |
| 746 | 6-OH | H | $CH_2COOEt$ | 3-Pn | H | 1-Al—Pip(4) |
| 747 | 6-OH | H | $CH_2COOEt$ | 2-Hx | H | 1-Al—Pip(4) |
| 748 | 6-OH | H | $CH_2COOEt$ | 3-Hx | H | 1-Al—Pip(4) |
| 749 | 6-OH | H | $CH_2COOEt$ | $2-CF_3$ | H | 1-Al—Pip(4) |
| 750 | 6-OH | H | $CH_2COOEt$ | $3-CF_3$ | H | 1-Al—Pip(4) |
| 751 | 6-OH | H | $CH_2COOEt$ | 2-OMe | H | 1-Al—Pip(4) |
| 752 | 6-OH | H | $CH_2COOEt$ | 3-OMe | H | 1-Al—Pip(4) |
| 753 | 6-OH | H | $CH_2COOEt$ | 2-OEt | H | 1-Al—Pip(4) |
| 754 | 6-OH | H | $CH_2COOEt$ | 3-OEt | H | 1-Al—Pip(4) |
| 755 | 6-OH | H | $CH_2COOEt$ | 2-COOH | H | 1-Al—Pip(4) |
| 756 | 6-OH | H | $CH_2COOEt$ | 3-COOH | H | 1-Al—Pip(4) |

TABLE 1-continued (I)

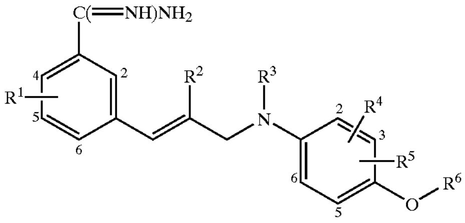

| Cpd. No. | $R^1$ | $R^2$ | $R^3$ | $R^4$ | $R^5$ | $R^6$ |
|---|---|---|---|---|---|---|
| 757 | 6-OH | H | $CH_2COOEt$ | 2-COOMe | H | 1-Al—Pip(4) |
| 758 | 6-OH | H | $CH_2COOEt$ | 3-COOMe | H | 1-Al—Pip(4) |
| 759 | 6-OH | H | $CH_2COOEt$ | 2-COOEt | H | 1-Al—Pip(4) |
| 760 | 6-OH | H | $CH_2COOEt$ | 3-COOEt | H | 1-Al—Pip(4) |
| 761 | 6-OH | H | $CH_2COOEt$ | 2-COOPr | H | 1-Al—Pip(4) |
| 762 | 6-OH | H | $CH_2COOEt$ | 3-COOPr | H | 1-Al—Pip(4) |
| 763 | 6-OH | H | $CH_2COOEt$ | 2-COOBu | H | 1-Al—Pip(4) |
| 764 | 6-OH | H | $CH_2COOEt$ | 3-COOBu | H | 1-Al—Pip(4) |
| 765 | 6-OH | H | $CH_2COOEt$ | 2-COOPn | H | 1-Al—Pip(4) |
| 766 | 6-OH | H | $CH_2COOEt$ | 3-COOPn | H | 1-Al—Pip(4) |
| 767 | 6-OH | H | $CH_2COOEt$ | 2-COOHx | H | 1-Al—Pip(4) |
| 768 | 6-OH | H | $CH_2COOEt$ | 3-COOHx | H | 1-Al—Pip(4) |
| 769 | 6-OH | H | $CH_2COOEt$ | 2-$CONH_2$ | H | 1-Al—Pip(4) |
| 770 | 6-OH | H | $CH_2COOEt$ | 3-$CONH_2$ | H | 1-Al—Pip(4) |
| 771 | 6-OH | H | $CH_2COOEt$ | 2-CONHMe | H | 1-Al—Pip(4) |
| 772 | 6-OH | H | $CH_2COOEt$ | 3-CONHMe | H | 1-Al—Pip(4) |
| 773 | 6-OH | H | $CH_2COOEt$ | 2-CONHEt | H | 1-Al—Pip(4) |
| 774 | 6-OH | H | $CH_2COOEt$ | 3-CONHEt | H | 1-Al—Pip(4) |
| 775 | 6-OH | H | $CH_2COOEt$ | 2-$CON(Me)_2$ | H | 1-Al—Pip(4) |
| 776 | 6-OH | H | $CH_2COOEt$ | 3-$CON(Me)_2$ | H | 1-Al—Pip(4) |
| 777 | 6-OH | H | $CH_2COOEt$ | 2-CON(Me)Et | H | 1-Al—Pip(4) |
| 778 | 6-OH | H | $CH_2COOEt$ | 3-CON(Me)Et | H | 1-Al—Pip(4) |
| 779 | 6-OH | H | $CH_2COOEt$ | 2-$CON(Et)_2$ | H | 1-Al—Pip(4) |
| 780 | 6-OH | H | $CH_2COOEt$ | 3-$CON(Et)_2$ | H | 1-Al—Pip(4) |
| 781 | 6-OH | H | $CH_2COOEt$ | 3-F | 5-F | 1-Al—Pip(4) |
| 782 | 6-OH | H | $CH_2COOEt$ | 3-Cl | 5-Cl | 1-Al—Pip(4) |
| 783 | 6-OH | H | $CH_2COOEt$ | 3-Me | 5-Me | 1-Al—Pip(4) |
| 784 | 6-OH | H | $CH_2COOEt$ | 3-Cl | 5-$CONH_2$ | 1-Al—Pip(4) |
| 785 | 6-OH | H | $CH_2COOEt$ | 2-Me | 5-$CONH_2$ | 1-Al—Pip(4) |
| 786 | 6-OH | H | $CH_2COOEt$ | 3-Me | 5-$CONH_2$ | 1-Al—Pip(4) |
| 787 | 6-OH | H | $CH_2COOEt$ | 3-$CONH_2$ | 5-$CONH_2$ | 1-Al—Pip(4) |
| 788 | H | H | $CH(CH_3)COOEt$ | H | H | 1-Al—Pip(4) |
| 789 | H | H | $CH(CH_3)COOEt$ | 2-F | H | 1-Al—Pip(4) |
| 790 | H | H | $CH(CH_3)COOEt$ | 3-F | H | 1-Al—Pip(4) |
| 791 | H | H | $CH(CH_3)COOEt$ | 2-Cl | H | 1-Al—Pip(4) |
| 792 | H | H | $CH(CH_3)COOEt$ | 3-Cl | H | 1-Al—Pip(4) |
| 793 | H | H | $CH(CH_3)COOEt$ | 2-Br | H | 1-Al—Pip(4) |
| 794 | H | H | $CH(CH_3)COOEt$ | 3-Br | H | 1-Al—Pip(4) |
| 795 | H | H | $CH(CH_3)COOEt$ | 2-I | H | 1-Al—Pip(4) |
| 796 | H | H | $CH(CH_3)COOEt$ | 3-I | H | 1-Al—Pip(4) |
| 797 | H | H | $CH(CH_3)COOEt$ | 2-Me | H | 1-Al—Pip(4) |
| 798 | H | H | $CH(CH_3)COOEt$ | 3-Me | H | 1-Al—Pip(4) |
| 799 | H | H | $CH(CH_3)COOEt$ | 2-Et | H | 1-Al—Pip(4) |
| 800 | H | H | $CH(CH_3)COOEt$ | 3-Et | H | 1-Al—Pip(4) |
| 801 | H | H | $CH(CH_3)COOEt$ | 2-Pr | H | 1-Al—Pip(4) |
| 802 | H | H | $CH(CH_3)COOEt$ | 3-Pr | H | 1-Al—Pip(4) |
| 803 | H | H | $CH(CH_3)COOEt$ | 2-Bu | H | 1-Al—Pip(4) |
| 804 | H | H | $CH(CH_3)COOEt$ | 3-Bu | H | 1-Al—Pip(4) |
| 805 | H | H | $CH(CH_3)COOEt$ | 2-Pn | H | 1-Al—Pip(4) |
| 806 | H | H | $CH(CH_3)COOEt$ | 3-Pn | H | 1-Al—Pip(4) |
| 807 | H | H | $CH(CH_3)COOEt$ | 2-Hx | H | 1-Al—Pip(4) |
| 808 | H | H | $CH(CH_3)COOEt$ | 3-Hx | H | 1-Al—Pip(4) |
| 809 | H | H | $CH(CH_3)COOEt$ | 2-$CF_3$ | H | 1-Al—Pip(4) |
| 810 | H | H | $CH(CH_3)COOEt$ | 3-$CF_3$ | H | 1-Al—Pip(4) |
| 811 | H | H | $CH(CH_3)COOEt$ | 2-OMe | H | 1-Al—Pip(4) |
| 812 | H | H | $CH(CH_3)COOEt$ | 3-OMe | H | 1-Al—Pip(4) |
| 813 | H | H | $CH(CH_3)COOEt$ | 2-OEt | H | 1-Al—Pip(4) |
| 814 | H | H | $CH(CH_3)COOEt$ | 3-OEt | H | 1-Al—Pip(4) |
| 815 | H | H | $CH(CH_3)COOEt$ | 2-COOH | H | 1-Al—Pip(4) |
| 816 | H | H | $CH(CH_3)COOEt$ | 3-COOH | H | 1-Al—Pip(4) |
| 817 | H | H | $CH(CH_3)COOEt$ | 2-COOMe | H | 1-Al—Pip(4) |
| 818 | H | H | $CH(CH_3)COOEt$ | 3-COOMe | H | 1-Al—Pip(4) |
| 819 | H | H | $CH(CH_3)COOEt$ | 2-COOEt | H | 1-Al—Pip(4) |

TABLE 1-continued (I)

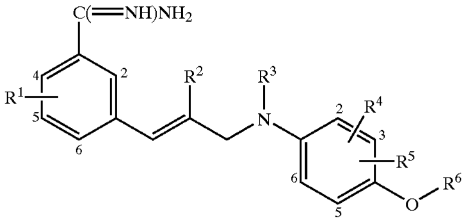

| Cpd. No. | $R^1$ | $R^2$ | $R^3$ | $R^4$ | $R^5$ | $R^6$ |
|---|---|---|---|---|---|---|
| 820 | H | H | $CH(CH_3)COOEt$ | 3-COOEt | H | 1-Al—Pip(4) |
| 821 | H | H | $CH(CH_3)COOEt$ | 2-COOPr | H | 1-Al—Pip(4) |
| 822 | H | H | $CH(CH_3)COOEt$ | 3-COOPr | H | 1-Al—Pip(4) |
| 823 | H | H | $OH(CH_3)COOEt$ | 2-COOBu | H | 1-Al—Pip(4) |
| 824 | H | H | $CH(CH_3)COOEt$ | 3-COOBu | H | 1-Al—Pip(4) |
| 825 | H | H | $CH(CH_3)COOEt$ | 2-COOPn | H | 1-Al—Pip(4) |
| 826 | H | H | $CH(CH_3)COOEt$ | 3-COOPn | H | 1-Al—Pip(4) |
| 827 | H | H | $CH(CH_3)COOEt$ | 2-COOHx | H | 1-Al—Pip(4) |
| 828 | H | H | $CH(CH_3)COOEt$ | 3-COOHx | H | 1-Al—Pip(4) |
| 829 | H | H | $CH(CH_3)COOEt$ | 2-$CONH_2$ | H | 1-Al—Pip(4) |
| 830 | H | H | $CH(CH_3)COOEt$ | 3-$CONH_2$ | H | 1-Al—Pip(4) |
| 831 | H | H | $CH(CH_3)COOEt$ | 2-CONHMe | H | 1-Al—Pip(4) |
| 832 | H | H | $CH(CH_3)COOEt$ | 3-CONHMe | H | 1-Al—Pip(4) |
| 833 | H | H | $CH(CH_3)COOEt$ | 2-CONHEt | H | 1-Al—Pip(4) |
| 834 | H | H | $CH(CH_3)COOEt$ | 3-CONHEt | H | 1-Al—Pip(4) |
| 835 | H | H | $CH(CH_3)COOEt$ | 2-$CON(Me)_2$ | H | 1-Al—Pip(4) |
| 836 | H | H | $CH(CH_3)COOEt$ | 3-$CON(Me)_2$ | H | 1-Al—Pip(4) |
| 837 | H | H | $CH(CH_3)COOEt$ | 2-CON(Me)Et | H | 1-Al—Pip(4) |
| 838 | H | H | $CH(CH_3)COOEt$ | 3-CON(Me)Et | H | 1-Al—Pip(4) |
| 839 | H | H | $CH(CH_3)COOEt$ | 2-$CON(Et)_2$ | H | 1-Al—Pip(4) |
| 840 | H | H | $CH(CH_3)COOEt$ | 3-$CON(Et)_2$ | H | 1-Al—Pip(4) |
| 841 | H | H | $CH(CH_3)COOEt$ | 3-F | 5-F | 1-Al—Pip(4) |
| 842 | H | H | $CH(CH_3)COOEt$ | 3-Cl | 5-Cl | 1-Al—Pip(4) |
| 843 | H | H | $CH(CH_3)COOEt$ | 3-Me | 5-Me | 1-Al—Pip(4) |
| 844 | H | H | $CH(CH_3)COOEt$ | 3-Cl | 5-$CONH_2$ | 1-Al—Pip(4) |
| 845 | H | H | $CH(CH_3)COOEt$ | 2-Me | 5-$CONH_2$ | 1-Al—Pip(4) |
| 846 | H | H | $CH(CH_3)COOEt$ | 3-Me | 5-$CONH_2$ | 1-Al—Pip(4) |
| 847 | H | H | $CH(CH_3)COOEt$ | 3-$CONH_2$ | 5-$CONH_2$ | 1-Al—Pip(4) |
| 848 | H | H | $(CH_2)_2COOEt$ | H | H | 1-Al—Pip(4) |
| 849 | H | H | $(CH_2)_3COOEt$ | H | H | 1-Al—Pip(4) |
| 850 | H | H | $(CH_2)_4COOEt$ | H | H | 1-Al—Pip(4) |
| 851 | H | H | $(CH_2)_5CCOEt$ | H | H | 1-Al—Pip(4) |
| 852 | H | H | $(CH_2)_6COOEt$ | H | H | 1-Al—Pip(4) |
| 853 | H | H | $CH_2COCH_2COOMe$ | H | H | 1-Al—Pip(4) |
| 854 | H | H | $CH_2COCH_2COOEt$ | H | H | 1-Al—Pip(4) |
| 855 | H | H | $CH_2COCH_2COOPr$ | H | H | 1-Al—Pip(4) |
| 856 | H | H | $CH_2COCH_2COOBu$ | H | H | 1-Al—Pip(4) |
| 857 | H | H | $CH_2COCH_2COOPn$ | H | H | 1-Al—Pip(4) |
| 858 | H | H | $CH_2COCH_2COOHx$ | H | H | 1-Al—Pip(4) |
| 859 | H | H | $(CH_2)_2COCH_2COOEt$ | H | H | 1-Al—Pip(4) |
| 860 | H | H | $(CH_2)_3COCH_2COOEt$ | H | H | 1-Al—Pip(4) |
| 861 | H | H | $(CH_2)_4COCH_2COOEt$ | H | H | 1-Al—Pip(4) |
| 862 | H | H | $(CH_2)_5COCH_2COOEt$ | H | H | 1-Al—Pip(4) |
| 863 | H | H | $(CH_2)_6COCH_2COOEt$ | H | H | 1-Al—Pip(4) |
| 864 | H | H | Bn | H | H | 1-Al—Pip(4) |
| 865 | H | H | Bn | 2-F | H | 1-Al—Pip(4) |
| 866 | H | H | Bn | 3-F | H | 1-Al—Pip(4) |
| 867 | H | H | Bn | 2-Cl | H | 1-Al—Pip(4) |
| 868 | H | H | Bn | 3-Cl | H | 1-Al—Pip(4) |
| 869 | H | H | Bn | 2-Br | H | 1-Al—Pip(4) |
| 870 | H | H | Bn | 3-Br | H | 1-Al—Pip(4) |
| 871 | H | H | Bn | 2-I | H | 1-Al—Pip(4) |
| 872 | H | H | Bn | 3-I | H | 1-Al—Pip(4) |
| 873 | H | H | Bn | 2-Me | H | 1-Al—Pip(4) |
| 874 | H | H | Bn | 3-Me | H | 1-Al—Pip(4) |
| 875 | H | H | Bn | 2-Et | H | 1-Al—Pip(4) |
| 876 | H | H | Bn | 3-Et | H | 1-Al—Pip(4) |
| 877 | H | H | Bn | 2-Pr | H | 1-Al—Pip(4) |
| 878 | H | H | Bn | 3-Pr | H | 1-Al—Pip(4) |
| 879 | H | H | Bn | 2-Bu | H | 1-Al—Pip(4) |
| 880 | H | H | Bn | 3-Bu | H | 1-Al—Pip(4) |
| 881 | H | H | Bn | 2-Pn | H | 1-Al—Pip(4) |
| 882 | H | H | Bn | 3-Pn | H | 1-Al—Pip(4) |

TABLE 1-continued (I)

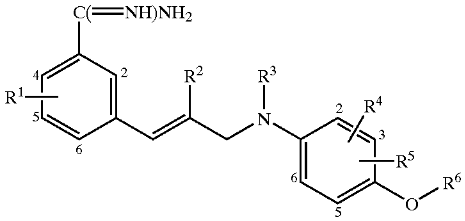

| Cpd. No. | $R^1$ | $R^2$ | $R^3$ | $R^4$ | $R^5$ | $R^6$ |
|---|---|---|---|---|---|---|
| 883 | H | H | Bn | 2-Hx | H | 1-Al—Pip(4) |
| 884 | H | H | Bn | 3-Hx | H | 1-Al—Pip(4) |
| 885 | H | H | Bn | 2-$CF_3$ | H | 1-Al—Pip(4) |
| 886 | H | H | Bn | 3-$CF_3$ | H | 1-Al—Pip(4) |
| 887 | H | H | Bn | 2-OMe | H | 1-Al—Pip(4) |
| 888 | H | H | Bn | 3-OMe | H | 1-Al—Pip(4) |
| 889 | H | H | Bn | 2-OEt | H | 1-Al—Pip(4) |
| 890 | H | H | Bn | 3-OEt | H | 1-Al—Pip(4) |
| 891 | H | H | Bn | 2-COOH | H | 1-Al—Pip(4) |
| 892 | H | H | Bn | 3-COOH | H | 1-Al—Pip(4) |
| 893 | H | H | Bn | 2-COOMe | H | 1-Al—Pip(4) |
| 894 | H | H | Bn | 3-COOMe | H | 1-Al—Pip(4) |
| 895 | H | H | Bn | 2-COOEt | H | 1-Al—Pip(4) |
| 896 | H | H | Bn | 3-COOEt | H | 1-Al—Pip(4) |
| 897 | H | H | Bn | 2-COOPr | H | 1-Al—Pip(4) |
| 898 | H | H | Bn | 3-COOPr | H | 1-Al—Pip(4) |
| 899 | H | H | Bn | 2-COOBu | H | 1-Al—Pip(4) |
| 900 | H | H | Bn | 3-COOBu | H | 1-Al—Pip(4) |
| 901 | H | H | Bn | 2-COOPn | H | 1-Al—Pip(4) |
| 902 | H | H | Bn | 3-COOPn | H | 1-Al—Pip(4) |
| 903 | H | H | Bn | 2-COOHx | H | 1-Al—Pip(4) |
| 904 | H | H | Bn | 3-COOHx | H | 1-Al—Pip(4) |
| 905 | H | H | Bn | 2-$CONH_2$ | H | 1-Al—Pip(4) |
| 906 | H | H | Bn | 3-$CONH_2$ | H | 1-Al—Pip(4) |
| 907 | H | H | Bn | 2-CONHMe | H | 1-Al—Pip(4) |
| 908 | H | H | Bn | 3-CONHMe | H | 1-Al—Pip(4) |
| 909 | H | H | Bn | 2-CONHEt | H | 1-Al—Pip(4) |
| 910 | H | H | Bn | 3-CONHEt | H | 1-Al—Pip(4) |
| 911 | H | H | Bn | 2-$CON(Me)_2$ | H | 1-Al—Pip(4) |
| 912 | H | H | Bn | 3-$CON(Me)_2$ | H | 1-Al—Pip(4) |
| 913 | H | H | Bn | 2-CON(Me)Et | H | 1-Al—Pip(4) |
| 914 | H | H | Bn | 3-CON(Me)Et | H | 1-Al—Pip(4) |
| 915 | H | H | Bn | 2-$CON(Et)_2$ | H | 1-Al—Pip(4) |
| 916 | H | H | Bn | 3-$CON(Et)_2$ | H | 1-Al—Pip(4) |
| 917 | H | H | Bn | 3-F | 5-F | 1-Al—Pip(4) |
| 918 | H | H | Bn | 3-Cl | 5-Cl | 1-Al—Pip(4) |
| 919 | H | H | Bn | 3-Me | 5-Me | 1-Al—Pip(4) |
| 920 | H | H | Bn | 3-Cl | 5-$CONH_2$ | 1-Al—Pip(4) |
| 921 | H | H | Bn | 2-Me | 5-$CONH_2$ | 1-Al—Pip(4) |
| 922 | H | H | Bn | 3-Me | 5-$CONH_2$ | 1-Al—Pip(4) |
| 923 | H | H | Bn | 3-$CONH_2$ | 5-$CONH_2$ | 1-Al—Pip(4) |
| 924 | H | H | $CH_2Np(1)$ | H | H | 1-Al—Pip(4) |
| 925 | 6-OH | H | $CH_2Np(1)$ | H | H | 1-Al—Pip(4) |
| 926 | H | H | $CH_2Np(2)$ | H | H | 1-Al—Pip(4) |
| 927 | 6-OH | H | $CH_2Np(2)$ | H | H | 1-Al—Pip(4) |
| 928 | H | H | $(CH_2)_2Ph$ | H | H | 1-Al—Pip(4) |
| 929 | 6-OH | H | $(CH_2)_2Ph$ | H | H | 1-Al—Pip(4) |
| 930 | H | H | $(CH_2)_2Np(1)$ | H | H | 1-Al—Pip(4) |
| 931 | 6-OH | H | $(CH_2)_2Np(1)$ | H | H | 1-Al—Pip(4) |
| 932 | H | H | $(CH_2)_2Np(2)$ | H | H | 1-Al—Pip(4) |
| 933 | 6-OH | H | $(CH_2)_2Np(2)$ | H | H | 1-Al—Pip(4) |
| 934 | H | H | $(CH_2)_3Ph$ | H | H | 1-Al—Pip(4) |
| 935 | 6-OH | H | $(CH_2)_3Ph$ | H | H | 1-Al—Pip(4) |
| 936 | H | H | $(CH_2)_3Np(1)$ | H | H | 1-Al—Pip(4) |
| 937 | 6-OH | H | $(CH_2)_3Np(1)$ | H | H | 1-Al—Pip(4) |
| 938 | H | H | $(CH_2)_3Np(2)$ | H | H | 1-Al—Pip(4) |
| 939 | 6-OH | H | $(CH_2)_3Np(2)$ | H | H | 1-Al—Pip(4) |
| 940 | H | H | $(CH_2)_4Ph$ | H | H | 1-Al—Pip(4) |
| 941 | 6-OH | H | $(CH_2)_4Ph$ | H | H | 1-Al—Pip(4) |
| 942 | H | H | $(CH_2)_4Ph$ | H | H | 1-Al—Pip(4) |
| 943 | 6-OH | H | $(CH_2)_5Ph$ | H | H | 1-Al—Pip(4) |
| 944 | H | H | $(CH_2)_6Ph$ | H | H | 1-Al—Pip(4) |
| 945 | 6-OH | H | $(CH_2)_6Ph$ | H | H | 1-Al—Pip(4) |

TABLE 1-continued (I)

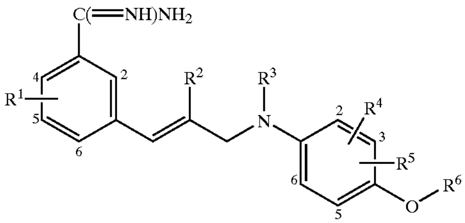

| Cpd. No. | $R^1$ | $R^2$ | $R^3$ | $R^4$ | $R^5$ | $R^6$ |
|---|---|---|---|---|---|---|
| 946 | H | H | CHO | H | H | 1-Al—Pip(4) |
| 947 | 6-OH | H | CHO | H | H | 1-Al—Pip(4) |
| 948 | H | H | Ac | H | H | 1-Al—Pip(4) |
| 949 | H | H | Ac | 2-F | H | 1-Al—Pip(4) |
| 950 | H | H | Ac | 3-F | H | 1-Al—Pip(4) |
| 951 | H | H | Ac | 2-Cl | H | 1-Al—Pip(4) |
| 952 | H | H | Ac | 3-Cl | H | 1-Al—Pip(4) |
| 953 | H | H | Ac | 2-Br | H | 1-Al—Pip(4) |
| 954 | H | H | Ac | 3-Br | H | 1-Al—Pip(4) |
| 955 | H | H | Ac | 2-I | H | 1-Al—Pip(4) |
| 956 | H | H | Ac | 3-I | H | 1-Al—Pip(4) |
| 957 | H | H | Ac | 2-Me | H | 1-Al—Pip(4) |
| 958 | H | H | Ac | 3-Me | H | 1-Al—Pip(4) |
| 959 | H | H | Ac | 2-Et | H | 1-Al—Pip(4) |
| 960 | H | H | Ac | 3-Et | H | 1-Al—Pip(4) |
| 961 | H | H | Ac | 2-Pr | H | 1-Al—Pip(4) |
| 962 | H | H | Ac | 3-Pr | H | 1-Al—Pip(4) |
| 963 | H | H | Ac | 2-Bu | H | 1-Al—Pip(4) |
| 964 | H | H | Ac | 3-Bu | H | 1-Al—Pip(4) |
| 965 | H | H | Ac | 2-Pn | H | 1-Al—Pip(4) |
| 966 | H | H | Ac | 3-Pn | H | 1-Al—Pip(4) |
| 967 | H | H | Ac | 2-Hx | H | 1-Al—Pip(4) |
| 968 | H | H | Ac | 3-Hx | H | 1-Al—Pip(4) |
| 969 | H | H | Ac | 2-$CF_3$ | H | 1-Al—Pip(4) |
| 970 | H | H | Ac | 3-$CF_3$ | H | 1-Al—Pip(4) |
| 971 | H | H | Ac | 2-OMe | H | 1-Al—Pip(4) |
| 972 | H | H | Ac | 3-OMe | H | 1-Al—Pip(4) |
| 973 | H | H | Ac | 2-OEt | H | 1-Al—Pip(4) |
| 974 | H | H | Ac | 3-OEt | H | 1-Al—Pip(4) |
| 975 | H | H | Ac | 2-COOH | H | 1-Al—Pip(4) |
| 976 | H | H | Ac | 3-COOH | H | 1-Al—Pip(4) |
| 977 | H | H | Ac | 2-COOMe | H | 1-Al—Pip(4) |
| 978 | H | H | Ac | 3-COOMe | H | 1-Al—Pip(4) |
| 979 | H | H | Ac | 2-COOEt | H | 1-Al—Pip(4) |
| 980 | H | H | Ac | 3-COOEt | H | 1-Al—Pip(4) |
| 981 | H | H | Ac | 2-COOPr | H | 1-Al—Pip(4) |
| 982 | H | H | Ac | 3-COOPr | H | 1-Al—Pip(4) |
| 983 | H | H | Ac | 2-COOBu | H | 1-Al—Pip(4) |
| 984 | H | H | Ac | 3-COOBu | H | 1-Al—Pip(4) |
| 985 | H | H | Ac | 2-COOPn | H | 1-Al—Pip(4) |
| 986 | H | H | Ac | 3-COOPn | H | 1-Al—Pip(4) |
| 987 | H | H | Ac | 2-COOHx | H | 1-Al—Pip(4) |
| 988 | H | H | Ac | 3-COOHx | H | 1-Al—Pip(4) |
| 989 | H | H | Ac | 2-$CONH_2$ | H | 1-Al—Pip(4) |
| 990 | H | H | Ac | 3-$CONH_2$ | H | 1-Al—Pip(4) |
| 991 | H | H | Ac | 2-CONHMe | H | 1-Al—Pip(4) |
| 992 | H | H | Ac | 3-CONHMe | H | 1-Al—Pip(4) |
| 993 | H | H | Ac | 2-CONHEt | H | 1-Al—Pip(4) |
| 994 | H | H | Ac | 3-CONHEt | H | 1-Al—Pip(4) |
| 995 | H | H | Ac | 2-$CON(Me)_2$ | H | 1-Al—Pip(4) |
| 996 | H | H | Ac | 3-$CON(Me)_2$ | H | 1-Al—Pip(4) |
| 997 | H | H | Ac | 2-CON(Me)Et | H | 1-Al—Pip(4) |
| 998 | H | H | Ac | 3-CON(Me)Et | H | 1-Al—Pip(4) |
| 999 | H | H | Ac | 2-$CON(Et)_2$ | H | 1-Al—Pip(4) |
| 1000 | H | H | Ac | 3-$CON(Et)_2$ | H | 1-Al—Pip(4) |
| 1001 | H | H | Ac | 3-F | 5-F | 1-Al—Pip(4) |
| 1002 | H | H | Ac | 3-Cl | 5-Cl | 1-Al—Pip(4) |
| 1003 | H | H | Ac | 3-Me | 5-Me | 1-Al—Pip(4) |
| 1004 | H | H | Ac | 3-Cl | 5-$CONH_2$ | 1-Al—Pip(4) |
| 1005 | H | H | Ac | 2-Me | 5-$CONH_2$ | 1-Al—Pip(4) |
| 1006 | H | H | Ac | 3-Me | 5-$CONH_2$ | 1-Al—Pip(4) |
| 1007 | H | H | Ac | 3-$CONH_2$ | 5-$CONH_2$ | 1-Al—Pip(4) |
| 1008 | H | H | Pm | H | H | 1-Al—Pip(4) |

TABLE 1-continued (I)

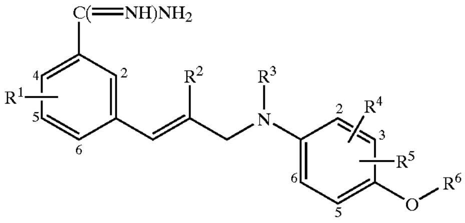

| Cpd. No. | $R^1$ | $R^2$ | $R^3$ | $R^4$ | $R^5$ | $R^6$ |
|---|---|---|---|---|---|---|
| 1009 | 6-OH | H | Pm | H | H | 1-Al—Pip(4) |
| 1010 | H | H | Byr | H | H | 1-Al—Pip(4) |
| 1011 | 6-OH | H | Byr | H | H | 1-Al—Pip(4) |
| 1012 | H | H | Va | H | H | 1-Al—Pip(4) |
| 1013 | 6-OH | H | Va | H | H | 1-Al—Pip(4) |
| 1014 | H | H | $COCH_2OH$ | H | H | 1-Al—Pip(4) |
| 1015 | H | H | $COCH_2OH$ | 2-F | H | 1-Al—Pip(4) |
| 1016 | H | H | $COCH_2OH$ | 3-F | H | 1-Al—Pip(4) |
| 1017 | H | H | $COCH_2OH$ | 2-Cl | H | 1-Al—Pip(4) |
| 1018 | H | H | $COCH_2OH$ | 3-Cl | H | 1-Al—Pip(4) |
| 1019 | H | H | $CCH_2OH$ | 2-Br | H | 1-Al—Pip(4) |
| 1020 | H | H | $COCH_2OH$ | 3-Br | H | 1-Al—Pip(4) |
| 1021 | H | H | $COCH_2OH$ | 2-I | H | 1-Al—Pip(4) |
| 1022 | H | H | $COCH_2OH$ | 3-I | H | 1-Al—Pip(4) |
| 1023 | H | H | $COCH_2OH$ | 2-Me | H | 1-Al—Pip(4) |
| 1024 | H | H | $COCH_2OH$ | 3-Me | H | 1-Al—Pip(4) |
| 1025 | H | H | $COCH_2OH$ | 2-Et | H | 1-Al—Pip(4) |
| 1026 | H | H | $COCH_2OH$ | 3-Et | H | 1-Al—Pip(4) |
| 1027 | H | H | $COCH_2OH$ | 2-Pr | H | 1-Al—Pip(4) |
| 1028 | H | H | $COCH_2OH$ | 3-Pr | H | 1-Al—Pip(4) |
| 1029 | H | H | $COCH_2OH$ | 2-Bu | H | 1-Al—Pip(4) |
| 1030 | H | H | $COCH_2OH$ | 3-Bu | H | 1-Al—Pip(4) |
| 1031 | H | H | $COCH_2OH$ | 2-Pn | H | 1-Al—Pip(4) |
| 1032 | H | H | $COCH_2OH$ | 3-Pn | H | 1-Al—Pip(4) |
| 1033 | H | H | $COCH_2OH$ | 2-Hx | H | 1-Al—Pip(4) |
| 1034 | H | H | $COCH_2OH$ | 3-Hx | H | 1-Al—Pip(4) |
| 1035 | H | H | $COCH_2OH$ | 2-$CF_3$ | H | 1-Al—Pip(4) |
| 1036 | H | H | $COCH_2OH$ | 3-$CF_3$ | H | 1-Al—Pip(4) |
| 1037 | H | H | $COCH_2OH$ | 2-OMe | H | 1-Al—Pip(4) |
| 1038 | H | H | $COCH_2OH$ | 3-OMe | H | 1-Al—Pip(4) |
| 1039 | H | H | $COCH_2OH$ | 2-OEt | H | 1-Al—Pip(4) |
| 1040 | H | H | $COCH_2OH$ | 3-OEt | H | 1-Al—Pip(4) |
| 1041 | H | H | $COCH_2OH$ | 2-COOH | H | 1-Al—Pip(4) |
| 1042 | H | H | $COCH_2OH$ | 3-COOH | H | 1-Al—Pip(4) |
| 1043 | H | H | $COCH_2OH$ | 2-COOMe | H | 1-Al—Pip(4) |
| 1044 | H | H | $COCH_2OH$ | 3-COOMe | H | 1-Al—Pip(4) |
| 1045 | H | H | $COCH_2OH$ | 2-COOEt | H | 1-Al—Pip(4) |
| 1046 | H | H | $COCH_2OH$ | 3-COOEt | H | 1-Al—Pip(4) |
| 1047 | H | H | $COCH_2OH$ | 2-COOPr | H | 1-Al—Pip(4) |
| 1048 | H | H | $COCH_2OH$ | 3-COOPr | H | 1-Al—Pip(4) |
| 1049 | H | H | $COCH_2OH$ | 2-COOBu | H | 1-Al—Pip(4) |
| 1050 | H | H | $COCH_2OH$ | 3-COOBu | H | 1-Al—Pip(4) |
| 1051 | H | H | $COCH_2OH$ | 2-COOPn | H | 1-Al—Pip(4) |
| 1052 | H | H | $COCH_2OH$ | 3-COOPn | H | 1-Al—Pip(4) |
| 1053 | H | H | $COCH_2OH$ | 2-COOHx | H | 1-Al—Pip(4) |
| 1054 | H | H | $COCH_2OH$ | 3-COOHx | H | 1-Al—Pip(4) |
| 1055 | H | H | $COCH_2OH$ | 2-$CONH_2$ | H | 1-Al—Pip(4) |
| 1056 | H | H | $COCH_2OH$ | 3-$CONH_2$ | H | 1-Al—Pip(4) |
| 1057 | H | H | $COCH_2OH$ | 2-CONHMe | H | 1-Al—Pip(4) |
| 1058 | H | H | $COCH_2OH$ | 3-CONHMe | H | 1-Al—Pip(4) |
| 1059 | H | H | $COCH_2OH$ | 2-CONHEt | H | 1-Al—Pip(4) |
| 1060 | H | H | $COCH_2OH$ | 3-CONHEt | H | 1-Al—Pip(4) |
| 1061 | H | H | $COCH_2OH$ | 2-$CON(Me)_2$ | H | 1-Al—Pip(4) |
| 1062 | H | H | $COCH_2OH$ | 3-$CON(Me)_2$ | H | 1-Al—Pip(4) |
| 1063 | H | H | $COCH_2OH$ | 2-CON(Me)Et | H | 1-Al—Pip(4) |
| 1064 | H | H | $COCH_2OH$ | 3-CON(Me)Et | H | 1-Al—Pip(4) |
| 1065 | H | H | $COCH_2OH$ | 2-$CON(Et)_2$ | H | 1-Al—Pip(4) |
| 1066 | H | H | $COCH_2OH$ | 3-$CON(Et)_2$ | H | 1-Al—Pip(4) |
| 1067 | H | H | $COCH_2CH$ | 3-F | 5-F | 1-Al—Pip(4) |
| 1068 | H | H | $COCH_2OH$ | 3-Cl | 5-Cl | 1-Al—Pip(4) |
| 1069 | H | H | $COCH_2OH$ | 3-Me | 5-Me | 1-Al—Pip(4) |
| 1070 | H | H | $COCH_2OH$ | 3-Cl | 5-$CONH_2$ | 1-Al—Pip(4) |
| 1071 | H | H | $COCH_2OH$ | 2-Me | 5-$CONH_2$ | 1-Al—Pip(4) |

TABLE 1-continued (I)

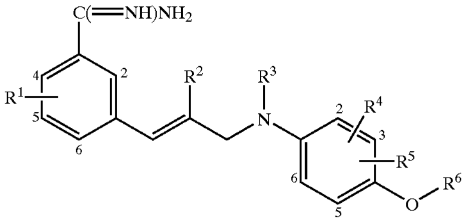

| Cpd. No. | $R^1$ | $R^2$ | $R^3$ | $R^4$ | $R^5$ | $R^6$ |
|---|---|---|---|---|---|---|
| 1072 | H | H | $COCH_2OH$ | 3-Me | 5-$CONH_2$ | 1-Al—Pip(4) |
| 1073 | H | H | $COCH_2OH$ | 3-$CONH_2$ | 5-$CONH_2$ | 1-Al—Pip(4) |
| 1074 | H | H | $CO(CH_2)_2OH$ | H | H | 1-Al—Pip(4) |
| 1075 | H | H | $CO(CH_2)_3OH$ | H | H | 1-Al—Pip(4) |
| 1076 | H | H | $CO(CH_2)_4OH$ | H | H | 1-Al—Pip(4) |
| 1077 | H | H | $CO(CH_2)_5OH$ | H | H | 1-Al—Pip(4) |
| 1078 | H | H | $SO_2Me$ | H | H | 1-Al—Pip(4) |
| 1079 | 6-OH | H | $SO_2Me$ | H | H | 1-Al—Pip(4) |
| 1080 | H | H | $SO_2Et$ | H | H | 1-Al—Pip(4) |
| 1081 | H | H | $SO_2Et$ | 2-F | H | 1-Al—Pip(4) |
| 1082 | H | H | $SO_2Et$ | 3-F | H | 1-Al—Pip(4) |
| 1083 | H | H | $SO_2Et$ | 2-Cl | H | 1-Al—Pip(4) |
| 1084 | H | H | $SO_2Et$ | 3-Cl | H | 1-Al—Pip(4) |
| 1085 | H | H | $SO_2Et$ | 2-Br | H | 1-Al—Pip(4) |
| 1086 | H | H | $SO_2Et$ | 3-Br | H | 1-Al—Pip(4) |
| 1087 | H | H | $SO_2Et$ | 2-I | H | 1-Al—Pip(4) |
| 1088 | H | H | $SO_2Et$ | 3-I | H | 1-Al—Pip(4) |
| 1089 | H | H | $SO_2Et$ | 2-Me | H | 1-Al—Pip(4) |
| 1090 | H | H | $SO_2Et$ | 3-Me | H | 1-Al—Pip(4) |
| 1091 | H | H | $SO_2Et$ | 2-Et | H | 1-Al—Pip(4) |
| 1092 | H | H | $SO_2Et$ | 3-Et | H | 1-Al—Pip(4) |
| 1093 | H | H | $SO_2Et$ | 2-Pr | H | 1-Al—Pip(4) |
| 1094 | H | H | $SO_2Et$ | 3-Pr | H | 1-Al—Pip(4) |
| 1095 | H | H | $SO_2Et$ | 2-Bu | H | 1-Al—Pip(4) |
| 1096 | H | H | $SO_2Et$ | 3-Bu | H | 1-Al—Pip(4) |
| 1097 | H | H | $SO_2Et$ | 2-Pn | H | 1-Al—Pip(4) |
| 1098 | H | H | $SO_2Et$ | 3-Pn | H | 1-Al—Pip(4) |
| 1099 | H | H | $SO_2Et$ | 2-Hx | H | 1-Al—Pip(4) |
| 1100 | H | H | $SO_2Et$ | 3-Hx | H | 1-Al—Pip(4) |
| 1101 | H | H | $SO_2Et$ | 2-$CF_3$ | H | 1-Al—Pip(4) |
| 1102 | H | H | $SO_2Et$ | 3-$CF_3$ | H | 1-Al—Pip(4) |
| 1103 | H | H | $SO_2Et$ | 2-OMe | H | 1-Al—Pip(4) |
| 1104 | H | H | $SO_2Et$ | 3-OMe | H | 1-Al—Pip(4) |
| 1105 | H | H | $SO_2Et$ | 2-OEt | H | 1-Al—Pip(4) |
| 1106 | H | H | $SO_2Et$ | 3-OEt | H | 1-Al—Pip(4) |
| 1107 | H | H | $SO_2Et$ | 2-COOH | H | 1-Al—Pip(4) |
| 1108 | H | H | $SO_2Et$ | 3-COOH | H | 1-Al—Pip(4) |
| 1109 | H | H | $SO_2Et$ | 2-COOMe | H | 1-Al—Pip(4) |
| 1110 | H | H | $SO_2Et$ | 3-COOMe | H | 1-Al—Pip(4) |
| 1111 | H | H | $SO_2Et$ | 2-COOEt | H | 1-Al—Pip(4) |
| 1112 | H | H | $SO_2Et$ | 3-COOEt | H | 1-Al—Pip(4) |
| 1113 | H | H | $SO_2Et$ | 2-COOPr | H | 1-Al—Pip(4) |
| 1114 | H | H | $SO_2Et$ | 3-COOPr | H | 1-Al—Pip(4) |
| 1115 | H | H | $SO_2Et$ | 2-COOBu | H | 1-Al—Pip(4) |
| 1116 | H | H | $SO_2Et$ | 3-COOBu | H | 1-Al—Pip(4) |
| 1117 | H | H | $SO_2Et$ | 2-COOPn | H | 1-Al—Pip(4) |
| 1118 | H | H | $SO_2Et$ | 3-COOPn | H | 1-Al—Pip(4) |
| 1119 | H | H | $SO_2Et$ | 2-COOHx | H | 1-Al—Pip(4) |
| 1120 | H | H | $SO_2Et$ | 3-COOHx | H | 1-Al—Pip(4) |
| 1121 | H | H | $SO_2Et$ | 2-$CONH_2$ | H | 1-Al—Pip(4) |
| 1122 | H | H | $SO_2Et$ | 3-$CONH_2$ | H | 1-Al—Pip(4) |
| 1123 | H | H | $SO_2Et$ | 2-CONHMe | H | 1-Al—Pip(4) |
| 1124 | H | H | $SO_2Et$ | 3-CONHMe | H | 1-Al—Pip(4) |
| 1125 | H | H | $SO_2Et$ | 2-CONHEt | H | 1-Al—Pip(4) |
| 1126 | H | H | $SO_2Et$ | 3-CONHEt | H | 1-Al—Pip(4) |
| 1127 | H | H | $SO_2Et$ | 3-CONHPr | H | 1-Al—Pip(4) |
| 1128 | H | H | $SO_2Et$ | 3-CONHBu | H | 1-Al—Pip(4) |
| 1129 | H | H | $SO_2Et$ | 3-CONHPn | H | 1-Al—Pip(4) |
| 1130 | H | H | $SO_2Et$ | 3-CONHHx | H | 1-Al—Pip(4) |
| 1131 | H | H | $SO_2Et$ | 2-$CON(Me)_2$ | H | 1-Al—Pip(4) |
| 1132 | H | H | $SO_2Et$ | 3-$CON(Me)_2$ | H | 1-Al—Pip(4) |
| 1133 | H | H | $SO_2Et$ | 2-CON(Me)Et | H | 1-Al—Pip(4) |
| 1134 | H | H | $SO_2Et$ | 3-CON(Me)Et | H | 1-Al—Pip(4) |

TABLE 1-continued (I)

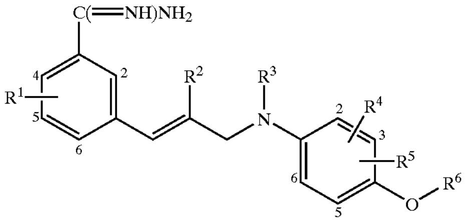

| Cpd. No. | $R^1$ | $R^2$ | $R^3$ | $R^4$ | $R^5$ | $R^6$ |
|---|---|---|---|---|---|---|
| 1135 | H | H | $SO_2Et$ | 2-CON(Et)$_2$ | H | 1-Al—Pip(4) |
| 1136 | H | H | $SO_2Et$ | 3-CON(Et)$_2$ | H | 1-Al—Pip(4) |
| 1137 | H | H | $SO_2Et$ | 3-CON(Pr)$_2$ | H | 1-Al—Pip(4) |
| 1138 | H | H | $SO_2Et$ | 3-CON(Bu)$_2$ | H | 1-Al—Pip(4) |
| 1139 | H | H | $SO_2Et$ | 3-CON(Pn)$_2$ | H | 1-Al—Pip(4) |
| 1140 | H | H | $SO_2Et$ | 3-CON(Hx)$_2$ | H | 1-Al—Pip(4) |
| 1141 | H | H | $SO_2Et$ | 2-F | 3-F | 1-Al—Pip(4) |
| 1142 | H | H | $SO_2Et$ | 2-F | 5-F | 1-Al—Pip(4) |
| 1143 | H | H | $SO_2Et$ | 2-F | 6-F | 1-Al—Pip(4) |
| 1144 | H | H | $SO_2Et$ | 3-F | 5-F | 1-Al—Pip(4) |
| 1145 | H | H | $SO_2Et$ | 2-Cl | 3-Cl | 1-Al—Pip(4) |
| 1146 | H | H | $SO_2Et$ | 2-Cl | 5-Cl | 1-Al—Pip(4) |
| 1147 | H | H | $SO_2Et$ | 2-Cl | 6-Cl | 1-Al—Pip(4) |
| 1148 | H | H | $SO_2Et$ | 3-Cl | 5-Cl | 1-Al—Pip(4) |
| 1149 | H | H | $SO_2Et$ | 2-Me | 3-Me | 1-Al—Pip(4) |
| 1150 | H | H | $SO_2Et$ | 2-Me | 5-Me | 1-Al—Pip(4) |
| 1151 | H | H | $SO_2Et$ | 2-Me | 6-Me | 1-Al—Pip(4) |
| 1152 | H | H | $SO_2Et$ | 3-Me | 5-Me | 1-Al—Pip(4) |
| 1153 | H | H | $SO_2Et$ | 2-Cl | 5-$CONH_2$ | 1-Al—Pip(4) |
| 1154 | H | H | $SO_2Et$ | 2-Cl | 6-$CONH_2$ | 1-Al—Pip(4) |
| 1155 | H | H | $SO_2Et$ | 3-Cl | 5-$CONH_2$ | 1-Al—Pip(4) |
| 1156 | H | H | $SO_2Et$ | 2-Me | 5-$CONH_2$ | 1-Al—Pip(4) |
| 1157 | H | H | $SO_2Et$ | 3-Me | 5-$CONH_2$ | 1-Al—Pip(4) |
| 1158 | H | H | $SO_2Et$ | 2-$CONH_2$ | 5-$CONH_2$ | 1-Al—Pip(4) |
| 1159 | H | H | $SO_2Et$ | 3-$CONH_2$ | 5-$CONH_2$ | 1-Al—Pip(4) |
| 1160 | H | F | $SO_2Et$ | H | H | 1-Al—Pip(4) |
| 1161 | H | F | $SO_2Et$ | 2-F | H | 1-Al—Pip(4) |
| 1162 | H | F | $SO_2Et$ | 3-F | H | 1-Al—Pip(4) |
| 1163 | H | F | $SO_2Et$ | 2-Cl | H | 1-Al—Pip(4) |
| 1164 | H | F | $SO_2Et$ | 3-Cl | H | 1-Al—Pip(4) |
| 1165 | H | F | $SO_2Et$ | 2-Br | H | 1-Al—Pip(4) |
| 1166 | H | F | $SO_2Et$ | 3-Br | H | 1-Al—Pip(4) |
| 1167 | H | F | $SO_2Et$ | 2-I | H | 1-Al—Pip(4) |
| 1168 | H | F | $SO_2Et$ | 3-I | H | 1-Al—Pip(4) |
| 1169 | H | F | $SO_2Et$ | 2-Me | H | 1-Al—Pip(4) |
| 1170 | H | F | $SO_2Et$ | 3-Me | H | 1-Al—Pip(4) |
| 1171 | H | F | $SO_2Et$ | 2-Et | H | 1-Al—Pip(4) |
| 1172 | H | F | $SO_2Et$ | 3-Et | H | 1-Al—Pip(4) |
| 1173 | H | F | $SO_2Et$ | 2-Pr | H | 1-Al—Pip(4) |
| 1174 | H | F | $SO_2Et$ | 3-Pr | H | 1-Al—Pip(4) |
| 1175 | H | F | $SO_2Et$ | 2-Bu | H | 1-Al—Pip(4) |
| 1176 | H | F | $SO_2Et$ | 3-Bu | H | 1-Al—Pip(4) |
| 1177 | H | F | $SO_2Et$ | 2-Pn | H | 1-Al—Pip(4) |
| 1178 | H | F | $SO_2Et$ | 3-Pn | H | 1-Al—Pip(4) |
| 1179 | H | F | $SO_2Et$ | 2-Hx | H | 1-Al—Pip(4) |
| 1180 | H | F | $SO_2Et$ | 3-Hx | H | 1-Al—Pip(4) |
| 1181 | H | F | $SO_2Et$ | 2-$CF_3$ | H | 1-Al—Pip(4) |
| 1182 | H | F | $SO_2Et$ | 3-$CF_3$ | H | 1-Al—Pip(4) |
| 1183 | H | F | $SO_2Et$ | 2-OMe | H | 1-Al—Pip(4) |
| 1184 | H | F | $SO_2Et$ | 3-OMe | H | 1-Al—Pip(4) |
| 1185 | H | F | $SO_2Et$ | 2-OEt | H | 1-Al—Pip(4) |
| 1186 | H | F | $SO_2Et$ | 3-OEt | H | 1-Al—Pip(4) |
| 1187 | H | F | $SO_2Et$ | 2-COOH | H | 1-Al—Pip(4) |
| 1188 | H | F | $SO_2Et$ | 3-COOH | H | 1-Al—Pip(4) |
| 1189 | H | F | $SO_2Et$ | 2-COOMe | H | 1-Al—Pip(4) |
| 1190 | H | F | $SO_2Et$ | 3-COOMe | H | 1-Al—Pip(4) |
| 1191 | H | F | $SO_2Et$ | 2-COOEt | H | 1-Al—Pip(4) |
| 1192 | H | F | $SO_2Et$ | 3-COOEt | H | 1-Al—Pip(4) |
| 1193 | H | F | $SO_2Et$ | 2-COOPr | H | 1-Al—Pip(4) |
| 1194 | H | F | $SO_2Et$ | 3-COOPr | H | 1-Al—Pip(4) |
| 1195 | H | F | $SO_2Et$ | 2-COOBu | H | 1-Al—Pip(4) |
| 1196 | H | F | $SO_2Et$ | 3-COOBu | H | 1-Al—Pip(4) |
| 1197 | H | F | $SO_2Et$ | 2-COOPn | H | 1-Al—Pip(4) |

TABLE 1-continued (I)

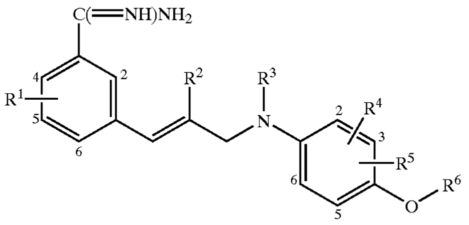

| Cpd. No. | $R^1$ | $R^2$ | $R^3$ | $R^4$ | $R^5$ | $R^6$ |
|---|---|---|---|---|---|---|
| 1198 | H | F | $SO_2Et$ | 3-COOPn | H | 1-Al—Pip(4) |
| 1199 | H | F | $SO_2Et$ | 2-COOHx | H | 1-Al—Pip(4) |
| 1200 | H | F | $SO_2Et$ | 3-COOHx | H | 1-Al—Pip(4) |
| 1201 | H | F | $SO_2Et$ | 2-$CONH_2$ | H | 1-Al—Pip(4) |
| 1202 | H | F | $SO_2Et$ | 3-$CONH_2$ | H | 1-Al—Pip(4) |
| 1203 | H | F | $SO_2Et$ | 2-CONHMe | H | 1-Al—Pip(4) |
| 1204 | H | F | $SO_2Et$ | 3-CONHMe | H | 1-Al—Pip(4) |
| 1205 | H | F | $SO_2Et$ | 2-CONHEt | H | 1-Al—Pip(4) |
| 1206 | H | F | $SO_2Et$ | 3-CONHEt | H | 1-Al—Pip(4) |
| 1207 | H | F | $SO_2Et$ | 2-$CON(Me)_2$ | H | 1-Al—Pip(4) |
| 1208 | H | F | $SO_2Et$ | 3-$CON(Me)_2$ | H | 1-Al—Pip(4) |
| 1209 | H | F | $SO_2Et$ | 2-CON(Me)Et | H | 1-Al—Pip(4) |
| 1210 | H | F | $SO_2Et$ | 3-CON(Me)Et | H | 1-Al—Pip(4) |
| 1211 | H | F | $SO_2Et$ | 2-$CON(Et)_2$ | H | 1-Al—Pip(4) |
| 1212 | H | F | $SO_2Et$ | 3-$CON(Et)_2$ | H | 1-Al—Pip(4) |
| 1213 | H | F | $SO_2Et$ | 3-F | 5-F | 1-Al—Pip(4) |
| 1214 | H | F | $SO_2Et$ | 3-Cl | 5-Cl | 1-Al—Pip(4) |
| 1215 | H | F | $SO_2Et$ | 3-Me | 5-Me | 1-Al—Pip(4) |
| 1216 | H | F | $SO_2Et$ | 3-Cl | 5-$CONH_2$ | 1-Al—Pip(4) |
| 1217 | H | F | $SO_2Et$ | 2-Me | 5-$CONH_2$ | 1-Al—Pip(4) |
| 1218 | H | F | $SO_2Et$ | 3-Me | 5-$CONH_2$ | 1-Al—Pip(4) |
| 1219 | H | F | $SO_2Et$ | 3-$CONH_2$ | 5-$CONH_2$ | 1-Al—Pip(4) |
| 1220 | H | Me | $SO_2Et$ | H | H | 1-Al—Pip(4) |
| 1221 | H | Me | $SO_2Et$ | 2-F | H | 1-Al—Pip(4) |
| 1222 | H | Me | $SO_2Et$ | 3-F | H | 1-Al—Pip(4) |
| 1223 | H | Me | $SO_2Et$ | 2-Cl | H | 1-Al—Pip(4) |
| 1224 | H | Me | $SO_2Et$ | 3-Cl | H | 1-Al—Pip(4) |
| 1225 | H | Me | $SO_2Et$ | 2-Br | H | 1-Al—Pip(4) |
| 1226 | H | Me | $SO_2Et$ | 3-Br | H | 1-Al—Pip(4) |
| 1227 | H | Me | $SO_2Et$ | 2-I | H | 1-Al—Pip(4) |
| 1228 | H | Me | $SO_2Et$ | 3-I | H | 1-Al—Pip(4) |
| 1229 | H | Me | $SO_2Et$ | 2-Me | H | 1-Al—Pip(4) |
| 1230 | H | Me | $SO_2Et$ | 3-Me | H | 1-Al—Pip(4) |
| 1231 | H | Me | $SO_2Et$ | 2-Et | H | 1-Al—Pip(4) |
| 1232 | H | Me | $SO_2Et$ | 3-Et | H | 1-Al—Pip(4) |
| 1233 | H | Me | $SO_2Et$ | 2-Pr | H | 1-Al—Pip(4) |
| 1234 | H | Me | $SO_2Et$ | 3-Pr | H | 1-Al—Pip(4) |
| 1235 | H | Me | $SO_2Et$ | 2-Bu | H | 1-Al—Pip(4) |
| 1236 | H | Me | $SO_2Et$ | 3-Bu | H | 1-Al—Pip(4) |
| 1237 | H | Me | $SO_2Et$ | 2-Pn | H | 1-Al—Pip(4) |
| 1238 | H | Me | $SO_2Et$ | 3-Pn | H | 1-Al—Pip(4) |
| 1239 | H | Me | $SO_2Et$ | 2-Hx | H | 1-Al—Pip(4) |
| 1240 | H | Me | $SO_2Et$ | 3-Hx | H | 1-Al—Pip(4) |
| 1241 | H | Me | $SO_2Et$ | 2-$CF_3$ | H | 1-Al—Pip(4) |
| 1242 | H | Me | $SO_2Et$ | 3-$CF_3$ | H | 1-Al—Pip(4) |
| 1243 | H | Me | $SO_2Et$ | 2-OMe | H | 1-Al—Pip(4) |
| 1244 | H | Me | $SO_2Et$ | 3-OMe | H | 1-Al—Pip(4) |
| 1245 | H | Me | $SO_2Et$ | 2-OEt | H | 1-Al—Pip(4) |
| 1246 | H | Me | $SO_2Et$ | 3-OEt | H | 1-Al—Pip(4) |
| 1247 | H | Me | $SO_2Et$ | 2-COOH | H | 1-Al—Pip(4) |
| 1248 | H | Me | $SO_2Et$ | 3-COOH | H | 1-Al—Pip(4) |
| 1249 | H | Me | $SO_2Et$ | 2-COOMe | H | 1-Al—Pip(4) |
| 1250 | H | Me | $SO_2Et$ | 3-COOMe | H | 1-Al—Pip(4) |
| 1251 | H | Me | $SO_2Et$ | 2-COOEt | H | 1-Al—Pip(4) |
| 1252 | H | Me | $SO_2Et$ | 3-COOEt | H | 1-Al—Pip(4) |
| 1253 | H | Me | $SO_2Et$ | 2-COOPr | H | 1-Al—Pip(4) |
| 1254 | H | Me | $SO_2Et$ | 3-COOPr | H | 1-Al—Pip(4) |
| 1255 | H | Me | $SO_2Et$ | 2-COOBu | H | 1-Al—Pip(4) |
| 1256 | H | Me | $SO_2Et$ | 3-COOBu | H | 1-Al—Pip(4) |
| 1257 | H | Me | $SO_2Et$ | 2-COOPn | H | 1-Al—Pip(4) |
| 1258 | H | Me | $SO_2Et$ | 3-COOPn | H | 1-Al—Pip(4) |
| 1259 | H | Me | $SO_2Et$ | 2-COOHx | H | 1-Al—Pip(4) |
| 1260 | H | Me | $SO_2Et$ | 3-COOHx | H | 1-Al—Pip(4) |

TABLE 1-continued (I)

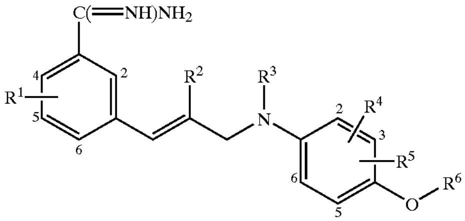

| Cpd. No. | $R^1$ | $R^2$ | $R^3$ | $R^4$ | $R^5$ | $R^6$ |
|---|---|---|---|---|---|---|
| 1261 | H | Me | $SO_2Et$ | 2-$CONH_2$ | H | 1-Al—Pip(4) |
| 1262 | H | Me | $SO_2Et$ | 3-$CONH_2$ | H | 1-Al—Pip(4) |
| 1263 | H | Me | $SO_2Et$ | 2-CONHMe | H | 1-Al—Pip(4) |
| 1264 | H | Me | $SO_2Et$ | 3-CONHMe | H | 1-Al—Pip(4) |
| 1265 | H | Me | $SO_2Et$ | 2-CONHEt | H | 1-Al—Pip(4) |
| 1266 | H | Me | $SO_2Et$ | 3-CONHEt | H | 1-Al—Pip(4) |
| 1267 | H | Me | $SO_2Et$ | 2-$CON(Me)_2$ | H | 1-Al—Pip(4) |
| 1268 | H | Me | $SO_2Et$ | 3-$CON(Me)_2$ | H | 1-Al—Pip(4) |
| 1269 | H | Me | $SO_2Et$ | 2-CON(Me)Et | H | 1-Al—Pip(4) |
| 1270 | H | Me | $SO_2Et$ | 3-CON(Me)Et | H | 1-Al—Pip(4) |
| 1271 | H | Me | $SO_2Et$ | 2-$CON(Et)_2$ | H | 1-Al—Pip(4) |
| 1272 | H | Me | $SO_2Et$ | 3-$CON(Et)_2$ | H | 1-Al—Pip(4) |
| 1273 | H | Me | $SO_2Et$ | 3-F | 5-F | 1-Al—Pip(4) |
| 1274 | H | Me | $SO_2Et$ | 3-Cl | 5-Cl | 1-Al—Pip(4) |
| 1275 | H | Me | $SO_2Et$ | 3-Me | 5-Me | 1-Al—Pip(4) |
| 1276 | H | Me | $SO_2Et$ | 3-Cl | 5-$CONH_2$ | 1-Al—Pip(4) |
| 1277 | H | Me | $SO_2Et$ | 2-Me | 5-$CONH_2$ | 1-Al—Pip(4) |
| 1278 | H | Me | $SO_2Et$ | 3-Me | 5-$CONH_2$ | 1-Al—Pip(4) |
| 1279 | H | Me | $SO_2Et$ | 3-$CONH_2$ | 5-$CONH_2$ | 1-Al—Pip(4) |
| 1280 | 6-F | H | $SO_2Et$ | H | H | 1-Al—Pip(4) |
| 1281 | 6-F | H | $SO_2Et$ | 2-F | H | 1-Al—Pip(4) |
| 1282 | 6-F | H | $SO_2Et$ | 3-F | H | 1-Al—Pip(4) |
| 1283 | 6-F | H | $SO_2Et$ | 2-Cl | H | 1-Al—Pip(4) |
| 1284 | 6-F | H | $SO_2Et$ | 3-Cl | H | 1-Al—Pip(4) |
| 1285 | 6-F | H | $SO_2Et$ | 2-Br | H | 1-Al—Pip(4) |
| 1286 | 6-F | H | $SO_2Et$ | 3-Br | H | 1-Al—Pip(4) |
| 1287 | 6-F | H | $SO_2Et$ | 2-I | H | 1-Al—Pip(4) |
| 1288 | 6-F | H | $SO_2Et$ | 3-I | H | 1-Al—Pip(4) |
| 1289 | 6-F | H | $SO_2Et$ | 2-Me | H | 1-Al—Pip(4) |
| 1290 | 6-F | H | $SO_2Et$ | 3-Me | H | 1-Al—Pip(4) |
| 1291 | 6-F | H | $SO_2Et$ | 2-Et | H | 1-Al—Pip(4) |
| 1292 | 6-F | H | $SO_2Et$ | 3-Et | H | 1-Al—Pip(4) |
| 1293 | 6-F | H | $SO_2Et$ | 2-Pr | H | 1-Al—Pip(4) |
| 1294 | 6-F | H | $SO_2Et$ | 3-Pr | H | 1-Al—Pip(4) |
| 1295 | 6-F | H | $SO_2Et$ | 2-Bu | H | 1-Al—Pip(4) |
| 1296 | 6-F | H | $SO_2Et$ | 3-Bu | H | 1-Al—Pip(4) |
| 1297 | 6-F | H | $SO_2Et$ | 2-Pn | H | l-Al—Pip(4) |
| 1298 | 6-F | H | $SO_2Et$ | 3-Pn | H | 1-Al—Pip(4) |
| 1299 | 6-F | H | $SO_2Et$ | 2-Hx | H | 1-Al—Pip(4) |
| 1300 | 6-F | H | $SO_2Et$ | 3-Hx | H | 1-Al—Pip(4) |
| 1301 | 6-F | H | $SO_2Et$ | 2-$CF_3$ | H | 1-Al—Pip(4) |
| 1302 | 6-F | H | $SO_2Et$ | 3-$CF_3$ | H | 1-Al—Pip(4) |
| 1303 | 6-F | H | $SO_2Et$ | 2-OMe | H | 1-Al—Pip(4) |
| 1304 | 6-F | H | $SO_2Et$ | 3-OMe | H | 1-Al—Pip(4) |
| 1305 | 6-F | H | $SO_2Et$ | 2-OEt | H | 1-Al—Pip(4) |
| 1306 | 6-F | H | $SO_2Et$ | 3-OEt | H | 1-Al—Pip(4) |
| 1307 | 6-F | H | $SO_2Et$ | 2-COOH | H | 1-Al—Pip(4) |
| 1308 | 6-F | H | $SO_2Et$ | 3-COOH | H | 1-Al—Pip(4) |
| 1309 | 6-F | H | $SO_2Et$ | 2-COOMe | H | 1-Al—Pip(4) |
| 1310 | 6-F | H | $SO_2Et$ | 3-COOMe | H | 1-Al—Pip(4) |
| 1311 | 6-F | H | $SO_2Et$ | 2-COOEt | H | 1-Al—Pip(4) |
| 1312 | 6-F | H | $SO_2Et$ | 3-COOEt | H | 1-Al—Pip(4) |
| 1313 | 6-F | H | $SO_2Et$ | 2-COOPr | H | 1-Al—Pip(4) |
| 1314 | 6-F | H | $SO_2Et$ | 3-COOPr | H | 1-Al—Pip(4) |
| 1315 | 6-F | H | $SO_2Et$ | 2-COOBu | H | 1-Al—Pip(4) |
| 1316 | 6-F | H | $SO_2Et$ | 3-COOBu | H | 1-Al—Pip(4) |
| 1317 | 6-F | H | $SO_2Et$ | 2-COOPn | H | 1-Al—Pip(4) |
| 1318 | 6-F | H | $SO_2Et$ | 3-COOPn | H | 1-Al—Pip(4) |
| 1319 | 6-F | H | $SO_2Et$ | 2-COOHx | H | 1-Al—Pip(4) |
| 1320 | 6-F | H | $SO_2Et$ | 3-COOHx | H | 1-Al—Pip(4) |
| 1321 | 6-F | H | $SO_2Et$ | 2-$CONH_2$ | H | 1-Al—Pip(4) |
| 1322 | 6-F | H | $SO_2Et$ | 3-$CONH_2$ | H | l-Al—Pip(4) |
| 1323 | 6-F | H | $SO_2Et$ | 2-CONHMe | H | 1-Al—Pip(4) |

TABLE 1-continued (I)

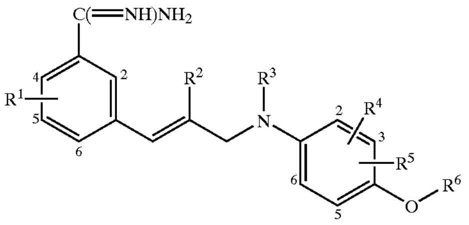

| Cpd. No. | $R^1$ | $R^2$ | $R^3$ | $R^4$ | $R^5$ | $R^6$ |
|---|---|---|---|---|---|---|
| 1324 | 6-F | H | $SO_2Et$ | 3-CONHMe | H | 1-Al—Pip(4) |
| 1325 | 6-F | H | $SO_2Et$ | 2-CONHEt | H | 1-Al—Pip(4) |
| 1326 | 6-F | H | $SO_2Et$ | 3-CONHEt | H | 1-Al—Pip(4) |
| 1327 | 6-F | H | $SO_2Et$ | 2-CON(Me)$_2$ | H | 1-Al—Pip(4) |
| 1328 | 6-F | H | $SO_2Et$ | 3-CON(Me)$_2$ | H | l-Al—Pip(4) |
| 1329 | 6-F | H | $SO_2Et$ | 2-CON(Me)Et | H | 1-Al—Pip(4) |
| 1330 | 6-F | H | $SO_2Et$ | 3-CON(Me)Et | H | 1-Al—Pip(4) |
| 1331 | 6-F | H | $SO_2Et$ | 2-CON(Et)$_2$ | H | 1-Al—Pip(4) |
| 1332 | 6-F | H | $SO_2Et$ | 3-CON(Et)$_2$ | H | 1-Al—Pip(4) |
| 1333 | 6-F | H | $SO_2Et$ | 3-F | 5-F | 1-Al—Pip(4) |
| 1334 | 6-F | H | $SO_2Et$ | 3-Cl | 5-Cl | 1-Al—Pip(4) |
| 1335 | 6-F | H | $SO_2Et$ | 3-Me | 5-Me | 1-Al—Pip(4) |
| 1336 | 6-F | H | $SO_2Et$ | 3-Cl | 5-$CONH_2$ | 1-Al—Pip(4) |
| 1337 | 6-F | H | $SO_2Et$ | 2-Me | 5-$CONH_2$ | 1-Al—Pip(4) |
| 1338 | 6-F | H | $SO_2Et$ | 3-Me | 5-$CONH_2$ | 1-Al—Pip(4) |
| 1339 | 6-F | H | $SO_2Et$ | 3-$CONH_2$ | 5-$CONH_2$ | 1-Al—Pip(4) |
| 1340 | 6-OH | H | $SO_2Et$ | H | H | 1-Al—Pip(4) |
| 1341 | 6-OH | H | $SO_2Et$ | 2-F | H | 1-Al—Pip(4) |
| 1342 | 6-OH | H | $SO_2Et$ | 3-F | H | 1-Al—Pip(4) |
| 1343 | 6-OH | H | $SO_2Et$ | 2-Cl | H | 1-Al—Pip(4) |
| 1344 | 6-OH | H | $SO_2Et$ | 3-Cl | H | 1-Al—Pip(4) |
| 1345 | 6-OH | H | $SO_2Et$ | 2-Br | H | 1-Al—Pip(4) |
| 1346 | 6-OH | H | $SO_2Et$ | 3-Br | H | 1-Al—Pip(4) |
| 1347 | 6-OH | H | $SO_2Et$ | 2-I | H | 1-Al—Pip(4) |
| 1346 | 6-OH | H | $SO_2Et$ | 3-I | H | 1-Al—Pip(4) |
| 1349 | 6-OH | H | $SO_2Et$ | 2-Me | H | 1-Al—Pip(4) |
| 1350 | 6-OH | H | $SO_2Et$ | 3-Me | H | 1-Al—Pip(4) |
| 1351 | 6-OH | H | $SO_2Et$ | 2-Et | H | 1-Al—Pip(4) |
| 1352 | 6-OH | H | $SO_2Et$ | 3-Et | H | 1-Al—Pip(4) |
| 1353 | 6-OH | H | $SO_2Et$ | 2-Pr | H | 1-Al—Pip(4) |
| 1354 | 6-OH | H | $SO_2Et$ | 3-Pr | H | 1-Al—Pip(4) |
| 1355 | 6-OH | H | $SO_2Et$ | 2-Bu | H | 1-Al—Pip(4) |
| 1356 | 6-OH | H | $SO_2Et$ | 3-Bu | H | 1-Al—Pip(4) |
| 1357 | 6-OH | H | $SO_2Et$ | 2-Pn | H | 1-Al—Pip(4) |
| 1358 | 6-OH | H | $SO_2Et$ | 3-Pn | H | 1-Al—Pip(4) |
| 1359 | 6-OH | H | $SO_2Et$ | 2-Hx | H | 1-Al—Pip(4) |
| 1360 | 6-OH | H | $SO_2Et$ | 3-Hx | H | 1-Al—Pip(4) |
| 1361 | 6-OH | H | $SO_2Et$ | 2-$CF_3$ | H | 1-Al—Pip(4) |
| 1362 | 6-OH | H | $SO_2Et$ | 3-$CF_3$ | H | 1-Al—Pip(4) |
| 1363 | 6-OH | H | $SO_2Et$ | 2-OMe | H | 1-Al—Pip(4) |
| 1364 | 6-OH | H | $SO_2Et$ | 3-OMe | H | 1-Al—Pip(4) |
| 1365 | 6-OH | H | $SO_2Et$ | 2-OEt | H | 1-Al—Pip(4) |
| 1366 | 6-OH | H | $SO_2Et$ | 3-OEt | H | 1-Al—Pip(4) |
| 1367 | 6-OH | H | $SO_2Et$ | 2-COOH | H | 1-Al—Pip(4) |
| 1368 | 6-OH | H | $SO_2Et$ | 3-COOH | H | 1-Al—Pip(4) |
| 1369 | 6-OH | H | $SO_2Et$ | 2-COOMe | H | 1-Al—Pip(4) |
| 1370 | 6-OH | H | $SO_2Et$ | 3-COOMe | H | 1-Al—Pip(4) |
| 1371 | 6-OH | H | $SO_2Et$ | 2-COOEt | H | 1-Al—Pip(4) |
| 1372 | 6-OH | H | $SO_2Et$ | 3-COOEt | H | 1-Al—Pip(4) |
| 1373 | 6-OH | H | $SO_2Et$ | 2-COOPr | H | 1-Al—Pip(4) |
| 1374 | 6-OH | H | $SO_2Et$ | 3-COOPr | H | 1-Al—Pip(4) |
| 1375 | 6-OH | H | $SO_2Et$ | 2-COOBu | H | 1-Al—Pip(4) |
| 1376 | 6-OH | H | $SO_2Et$ | 3-COOBu | H | 1-Al—Pip(4) |
| 1377 | 6-OH | H | $SO_2Et$ | 2-COOPn | H | 1-Al—Pip(4) |
| 1378 | 6-OH | H | $SO_2Et$ | 3-COOPn | H | 1-Al—Pip(4) |
| 1379 | 6-OH | H | $SO_2Et$ | 2-COOHx | H | 1-Al—Pip(4) |
| 1380 | 6-OH | H | $SO_2Et$ | 3-COOHx | H | 1-Al—Pip(4) |
| 1381 | 6-OH | H | $SO_2Et$ | 2-$CONH_2$ | H | 1-Al—Pip(4) |
| 1382 | 6-OH | H | $SO_2Et$ | 3-$CONH_2$ | H | 1-Al—Pip(4) |
| 1383 | 6-OH | H | $SO_2Et$ | 2-CONHMe | H | 1-Al—Pip(4) |
| 1384 | 6-OH | H | $SO_2Et$ | 3-CONHMe | H | 1-Al—Pip(4) |
| 1385 | 6-OH | H | $SO_2Et$ | 2-CONHEt | H | 1-Al—Pip(4) |
| 1386 | 6-OH | H | $SO_2Et$ | 3-CONHEt | H | 1-Al—Pip(4) |

TABLE 1-continued (I)

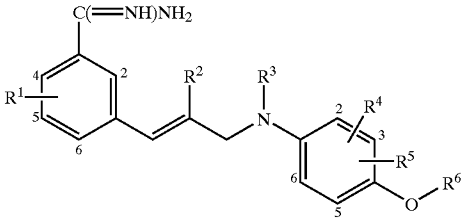

| Cpd. No. | $R^1$ | $R^2$ | $R^3$ | $R^4$ | $R^5$ | $R^6$ |
|---|---|---|---|---|---|---|
| 1387 | 6-OH | H | $SO_2Et$ | 2-CON(Me)$_2$ | H | 1-Al—Pip(4) |
| 1388 | 6-OH | H | $SO_2Et$ | 3-CON(Me)$_2$ | H | 1-Al—Pip(4) |
| 1389 | 6-OH | H | $SO_2Et$ | 2-CON(Me)Et | H | 1-Al—Pip(4) |
| 1390 | 6-OH | H | $SO_2Et$ | 3-CON(Me)Et | H | 1-Al—Pip(4) |
| 1391 | 6-OH | H | $SO_2Et$ | 2-CON(Et)$_2$ | H | 1-Al—Pip(4) |
| 1392 | 6-OH | H | $SO_2Et$ | 3-CON(Et)$_2$ | H | 1-Al—Pip(4) |
| 1393 | 6-OH | H | $SO_2Et$ | 3-F | 5-F | 1-Al—Pip(4) |
| 1394 | 6-OH | H | $SO_2Et$ | 3-Cl | 5-Cl | 1-Al—Pip(4) |
| 1395 | 6-OH | H | $SO_2Et$ | 3-Me | 5-Me | 1-Al—Pip(4) |
| 1396 | 6-OH | H | $SO_2Et$ | 3-Cl | 5-$CONH_2$ | 1-Al—Pip(4) |
| 1397 | 6-OH | H | $SO_2Et$ | 2-Me | 5-$CONH_2$ | 1-Al—Pip(4) |
| 1398 | 6-OH | H | $SO_2Et$ | 3-Me | 5-$CONH_2$ | 1-Al—Pip(4) |
| 1399 | 6-OH | H | $SO_2Et$ | 3-$CONH_2$ | 5-$CONH_2$ | 1-Al—Pip(4) |
| 1400 | H | H | $SO_2Pr$ | H | H | 1-Al—Pip(4) |
| 1401 | H | H | $SO_2$iPr | H | H | 1-Al—Pip(4) |
| 1402 | H | H | $SO_2Bu$ | H | H | 1-Al—Pip(4) |
| 1403 | H | H | $SO_2$sBu | H | H | 1-Al—Pip(4) |
| 1404 | H | H | $SO_2$iBu | H | H | 1-Al—Pip(4) |
| 1405 | H | H | $SO_2$tBu | H | H | 1-Al—Pip(4) |
| 1406 | H | H | $SO_2Pn$ | H | H | 1-Al—Pip(4) |
| 1407 | H | H | $SO_2Hx$ | H | H | 1-Al—Pip(4) |
| 1408 | H | H | $SO_2CH_2COOMe$ | H | H | 1-Al—Pip(4) |
| 1409 | 6-OH | H | $SO_2CH_2COOMe$ | H | H | 1-Al—Pip(4) |
| 1410 | H | H | $SO_2CH_2COOEt$ | H | H | 1-Al—Pip(4) |
| 1411 | H | H | $SO_2CH_2COOEt$ | 2-F | H | 1-Al—Pip(4) |
| 1412 | H | H | $SO_2CH_2COOEt$ | 3-F | H | 1-Al—Pip(4) |
| 1413 | H | H | $SO_2CH_2COOEt$ | 2-Cl | H | 1-Al—Pip(4) |
| 1414 | H | H | $SO_2CH_2COOEt$ | 3-Cl | H | 1-Al—Pip(4) |
| 1415 | H | H | $SO_2CH_2COOEt$ | 2-Br | H | 1-Al—Pip(4) |
| 1416 | H | H | $SO_2CH_2COOEt$ | 3-Br | H | 1-Al—Pip(4) |
| 1417 | H | H | $SO_2CH_2COOEt$ | 2-I | H | 1-Al—Pip(4) |
| 1418 | H | H | $SO_2CH_2COOEt$ | 3-I | H | 1-Al—Pip(4) |
| 1419 | H | H | $SO_2CH_2COOEt$ | 2-Me | H | 1-Al—Pip(4) |
| 1420 | H | H | $SO_2CH_2COOEt$ | 3-Me | H | 1-Al—Pip(4) |
| 1421 | H | H | $SO_2CH_2COOEt$ | 2-Et | H | 1-Al—Pip(4) |
| 1422 | H | H | $SO_2CH_2COOEt$ | 3-Et | H | 1-Al—Pip(4) |
| 1423 | H | H | $SO_2CH_2COOEt$ | 2-Pr | H | 1-Al—Pip(4) |
| 1424 | H | H | $SO_2CH_2COOEt$ | 3-Pr | H | 1-Al—Pip(4) |
| 1425 | H | H | $SO_2CH_2COOEt$ | 2-iPr | H | 1-Al—Pip(4) |
| 1426 | H | H | $SO_2CH_2COOEt$ | 3-iPr | H | 1-Al—Pip(4) |
| 1427 | H | H | $SO_2CH_2COOEt$ | 2-Bu | H | 1-Al—Pip(4) |
| 1425 | H | H | $SO_2CH_2COOEt$ | 3-Bu | H | 1-Al—Pip(4) |
| 1429 | H | H | $SO_2CH_2COOEt$ | 2-iBu | H | 1-Al—Pip(4) |
| 1430 | H | H | $SO_2CH_2COOEt$ | 3-iBu | H | 1-Al—Pip(4) |
| 1431 | H | H | $SO_2CH_2COOEt$ | 2-sBu | H | 1-Al—Pip(4) |
| 1432 | H | H | $SO_2CH_2COOEt$ | 3-sBu | H | 1-Al—Pip(4) |
| 1433 | H | H | $SO_2CH_2COOEt$ | 2-tBu | H | 1-Al—Pip(4) |
| 1434 | H | H | $SO_2CH_2COOEt$ | 3-tBu | H | 1-Al—Pip(4) |
| 1435 | H | H | $SO_2CH_2COOEt$ | 2-Pn | H | 1-Al—Pip(4) |
| 1436 | H | H | $SO_2CH_2COOEt$ | 3-Pn | H | 1-Al—Pip(4) |
| 1437 | H | H | $SO_2CH_2COOEt$ | 2-Hx | H | 1-Al—Pip(4) |
| 1438 | H | H | $SO_2CH_2COOEt$ | 3-Hx | H | 1-Al—Pip(4) |
| 1439 | H | H | $SO_2CH_2COOEt$ | 2-$CF_3$ | H | 1-Al—Pip(4) |
| 1440 | H | H | $SO_2CH_2COOEt$ | 3-$CF_3$ | H | 1-Al—Pip(4) |
| 1441 | H | H | $SO_2CH_2COOEt$ | 2-OMe | H | 1-Al—Pip(4) |
| 1442 | H | H | $SO_2CH_2COOEt$ | 3-OMe | H | 1-Al—Pip(4) |
| 1443 | H | H | $SO_2CH_2COOEt$ | 2-OEt | H | 1-Al—Pip(4) |
| 1444 | H | H | $SO_2CH_2COOEt$ | 3-OEt | H | 1-Al—Pip(4) |
| 1445 | H | H | $SO_2CH_2COOEt$ | 2-COOH | H | 1-Al—Pip(4) |
| 1446 | H | H | $SO_2CH_2COOEt$ | 3-COOH | H | 1-Al—Pip(4) |
| 1447 | H | H | $SO_2CH_2COOEt$ | 2-COOMe | H | 1-Al—Pip(4) |
| 1448 | H | H | $SO_2CH_2COOEt$ | 3-COOMe | H | 1-Al—Pip(4) |
| 1449 | H | H | $SO_2CH_2COOEt$ | 2-COOEt | H | 1-Al—Pip(4) |

TABLE 1-continued (I)

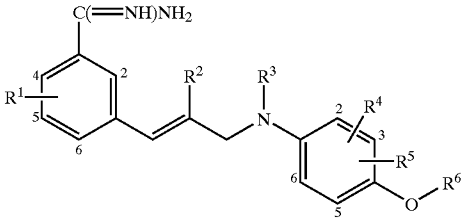

| Cpd. No. | $R^1$ | $R^2$ | $R^3$ | $R^4$ | $R^5$ | $R^6$ |
|---|---|---|---|---|---|---|
| 1450 | H | H | $SO_2CH_2COOEt$ | 3-COOEt | H | 1-Al—Pip(4) |
| 1451 | H | H | $SO_2CH_2COOEt$ | 2-COOPr | H | 1-Al—Pip(4) |
| 1452 | H | H | $SO_2CH_2COOEt$ | 3-COOPr | H | 1-Al—Pip(4) |
| 1453 | H | H | $SO_2CH_2COOEt$ | 2-COOBu | H | 1-Al—Pip(4) |
| 1454 | H | H | $SO_2CH_2COOEt$ | 3-COOBu | H | 1-Al—Pip(4) |
| 1455 | H | H | $SO_2CH_2COOEt$ | 2-COOPn | H | 1-Al—Pip(4) |
| 1456 | H | H | $SO_2CH_2COOEt$ | 3-COOPn | H | 1-Al—Pip(4) |
| 1457 | H | H | $SO_2CH_2COOEt$ | 2-COOHx | H | 1-Al—Pip(4) |
| 1458 | H | H | $SO_2CH_2COOEt$ | 3-COOHx | H | 1-Al—Pip(4) |
| 1459 | H | H | $SO_2CH_2COOEt$ | 2-$CONH_2$ | H | 1-Al—Pip(4) |
| 1460 | H | H | $SO_2CH_2COOEt$ | 3-$CONH_2$ | H | 1-Al—Pip(4) |
| 1461 | H | H | $SO_2CH_2COOEt$ | 2-CONHMe | H | 1-Al—Pip(4) |
| 1462 | H | H | $SO_2CH_2COOEt$ | 3-CONHMe | H | 1-Al—Pip(4) |
| 1463 | H | H | $SO_2CH_2COOEt$ | 2-CONHEt | H | 1-Al—Pip(4) |
| 1464 | H | H | $SO_2CH_2COOEt$ | 3-CONHEt | H | 1-Al—Pip(4) |
| 1465 | H | H | $SO_2CH_2COOEt$ | 2-$CON(Me)_2$ | H | 1-Al—Pip(4) |
| 1466 | H | H | $SO_2CH_2COOEt$ | 3-$CON(Me)_2$ | H | 1-Al—Pip(4) |
| 1467 | H | H | $SO_2CH_2COOEt$ | 2-CON(Me)Et | H | 1-Al—Pip(4) |
| 1468 | H | H | $SO_2CH_2COOEt$ | 3-CON(Me)Et | H | 1-Al—Pip(4) |
| 1469 | H | H | $SO_2CH_2COOEt$ | 2-$CON(Et)_2$ | H | 1-Al—Pip(4) |
| 1470 | H | H | $SO_2CH_2COOEt$ | 3-$CON(Et)_2$ | H | 1-Al—Pip(4) |
| 1471 | H | H | $SO_2CH_2COOEt$ | 2-F | 3-F | 1-Al—Pip(4) |
| 1472 | H | H | $SO_2CH_2COOEt$ | 2-F | 5-F | 1-Al—Pip(4) |
| 1473 | H | H | $SO_2CH_2COOEt$ | 2-F | 6-F | 1-Al—Pip(4) |
| 1474 | H | H | $SO_2CH_2COOEt$ | 3-F | 5-F | 1-Al—Pip(4) |
| 1475 | H | H | $SO_2CH_2COOEt$ | 2-Cl | 3-Cl | 1-Al—Pip(4) |
| 1476 | H | H | $SO_2CH_2COOEt$ | 2-Cl | 5-Cl | 1-Al—Pip(4) |
| 1477 | H | H | $SO_2CH_2COOEt$ | 2-Cl | 6-Cl | 1-Al—Pip(4) |
| 1478 | H | H | $SO_2CH_2COOEt$ | 3-Cl | 5-Cl | 1-Al—Pip(4) |
| 1479 | H | H | $SO_2CH_2COOEt$ | 2-Me | 3-Me | 1-Al—Pip(4) |
| 1480 | H | H | $SO_2CH_2COOEt$ | 2-Me | 5-Me | 1-Al—Pip(4) |
| 1481 | H | H | $SO_2CH_2COOEt$ | 2-Me | 6-Me | 1-Al—Pip(4) |
| 1482 | H | H | $SO_2CH_2COOEt$ | 3-Me | 5-Me | 1-Al—Pip(4) |
| 1483 | H | H | $SO_2CH_2COOEt$ | 2-Cl | 5-$CONH_2$ | 1-Al—Pip(4) |
| 1484 | H | H | $SO_2CH_2COOEt$ | 3-Cl | 5-$CONH_2$ | 1-Al—Pip(4) |
| 1485 | H | H | $SO_2CH_2COOEt$ | 3-Cl | 5-CONHMe | 1-Al—Pip(4) |
| 1486 | H | H | $SO_2CH_2COOEt$ | 3-Cl | 5-CONHEt | 1-Al—Pip(4) |
| 1487 | H | H | $SO_2CH_2COOEt$ | 3-Cl | 5-CONHPr | 1-Al—Pip(4) |
| 1488 | H | H | $SO_2CH_2COOEt$ | 3-Cl | 5-CONHBu | 1-Al—Pip(4) |
| 1489 | H | H | $SO_2CH_2COOEt$ | 3-Cl | 5-CONHPn | 1-Al—Pip(4) |
| 1490 | H | H | $SO_2CH_2COOEt$ | 3-Cl | 5-CONHHx | 1-Al—Pip(4) |
| 1491 | H | H | $SO_2CH_2COOEt$ | 2-Me | 5-$CONH_2$ | 1-Al—Pip(4) |
| 1492 | H | H | $SO_2CH_2COOEt$ | 2-Me | 5-CONHMe | 1-Al—Pip(4) |
| 1493 | H | H | $SO_2CH_2COOEt$ | 2-Me | 5-CONHEt | 1-Al—Pip(4) |
| 1494 | H | H | $SO_2CH_2COOEt$ | 2-Me | 5-CONHPr | 1-Al—Pip(4) |
| 1495 | H | H | $SO_2CH_2COOEt$ | 2-Me | 3-CONHBu | 1-Al—Pip(4) |
| 1496 | H | H | $SO_2CH_2COOEt$ | 2-Me | 5-CONHPn | 1-Al—Pip(4) |
| 1497 | H | H | $SO_2CH_2COOEt$ | 2-Me | 5-CONHHx | 1-Al—Pip(4) |
| 1498 | H | H | $SO_2CH_2COOEt$ | 3-Me | 5-$CONH_2$ | 1-Al—Pip(4) |
| 1499 | H | H | $SO_2CH_2COOEt$ | 3-Me | 5-CONHMe | 1-Al—Pip(4) |
| 1500 | H | H | $SO_2CH_2COOEt$ | 3-Me | 5-CONHEt | 1-Al—Pip(4) |
| 1501 | H | H | $SO_2CH_2COOEt$ | 3-Me | 5-CONHPr | 1-Al—Pip(4) |
| 1502 | H | H | $SO_2CH_2COOEt$ | 3-Me | 5-CONHBu | 1-Al—Pip(4) |
| 1503 | H | H | $SO_2CH_2COOEt$ | 3-Me | 5-CONHPn | 1-Al—Pip(4) |
| 1504 | H | H | $SO_2CH_2COOEt$ | 3-Me | 5-CONHHx | 1-Al—Pip(4) |
| 1505 | H | H | $SO_2CH_2COOEt$ | 2-$CONH_2$ | 6-$CONH_2$ | 1-Al—Pip(4) |
| 1506 | H | H | $SO_2CH_2COOEt$ | 3-$CONH_2$ | 5-$CONH_2$ | 1-Al—Pip(4) |
| 1507 | H | H | $SO_2CH_2COOEt$ | 3-CONHMe | 5-CONHMe | 1-Al—Pip(4) |
| 1508 | H | H | $SO_2CH_2COOEt$ | 3-CONHEt | 5-CONHEt | 1-Al—Pip(4) |
| 1509 | H | F | $SO_2CH_2COOEt$ | H | H | 1-Al—Pip(4) |
| 1510 | H | F | $SO_2CH_2COOEt$ | 2-F | H | 1-Al—Pip(4) |
| 1511 | H | F | $SO_2CH_2COOEt$ | 3-F | H | 1-Al—Pip(4) |
| 1512 | H | F | $SO_2CH_2COOEt$ | 2-Cl | H | 1-Al—Pip(4) |

TABLE 1-continued (I)

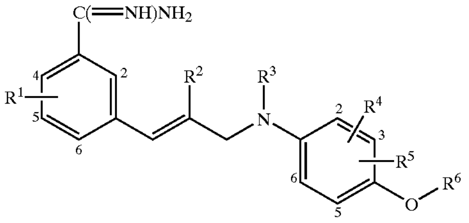

| Cpd. No. | $R^1$ | $R^2$ | $R^3$ | $R^4$ | $R^5$ | $R^6$ |
|---|---|---|---|---|---|---|
| 1513 | H | F | $SO_2CH_2COOEt$ | 3-Cl | H | 1-Al—Pip(4) |
| 1514 | H | F | $SO_2CH_2COOEt$ | 2-Br | H | 1-Al—Pip(4) |
| 1515 | H | F | $SO_2CH_2COOEt$ | 3-Br | H | 1-Al—Pip(4) |
| 1516 | H | F | $SO_2CH_2COOEt$ | 2-I | H | 1-Al—Pip(4) |
| 1517 | H | F | $SO_2CH_2COOEt$ | 3-I | H | 1-Al—Pip(4) |
| 1518 | H | F | $SO_2CH_2COOEt$ | 2-Me | H | 1-Al—Pip(4) |
| 1519 | H | F | $SO_2CH_2COOEt$ | 3-Me | H | 1-Al—Pip(4) |
| 1520 | H | F | $SO_2CH_2COOEt$ | 2-Et | H | 1-Al—Pip(4) |
| 1521 | H | F | $SO_2CH_2COOEt$ | 3-Et | H | 1-Al—Pip(4) |
| 1522 | H | F | $SO_2CH_2COOEt$ | 2-Pr | H | 1-Al—Pip(4) |
| 1523 | H | F | $SO_2CH_2COOEt$ | 3-Pr | H | 1-Al—Pip(4) |
| 1524 | H | F | $SO_2CH_2COOEt$ | 2-iPr | H | 1-Al—Pip(4) |
| 1525 | H | F | $SO_2CH_2COOEt$ | 3-iPr | H | 1-Al—Pip(4) |
| 1526 | H | F | $SO_2CH_2COOEt$ | 2-Bu | H | 1-Al—Pip(4) |
| 1527 | H | F | $SO_2CH_2COOEt$ | 3-Bu | H | 1-Al—Pip(4) |
| 1528 | H | F | $SO_2CH_2COOEt$ | 2-iBu | H | 1-Al—Pip(4) |
| 1529 | H | F | $SO_2CH_2COOEt$ | 3-iBu | H | 1-Al—Pip(4) |
| 1530 | H | F | $SO_2CH_2COOEt$ | 2-sBu | H | 1-Al—Pip(4) |
| 1531 | H | F | $SO_2CH_2COOEt$ | 3-sBu | H | 1-Al—Pip(4) |
| 1532 | H | F | $SO_2CH_2COOEt$ | 2-tBu | H | 1-Al—Pip(4) |
| 1533 | H | F | $SO_2CH_2COOEt$ | 3-tBu | H | 1-Al—Pip(4) |
| 1534 | H | F | $SO_2CH_2COOEt$ | 2-Pn | H | 1-Al—Pip(4) |
| 1535 | H | F | $SO_2CH_2COOEt$ | 3-Pn | H | 1-Al—Pip(4) |
| 1536 | H | F | $SO_2CH_2COOEt$ | 2-Hx | H | 1-Al—Pip(4) |
| 1537 | H | F | $SO_2CH_2COOEt$ | 3-Hx | H | 1-Al—Pip(4) |
| 1538 | H | F | $SO_2CH_2COOEt$ | $2-CF_3$ | H | 1-Al—Pip(4) |
| 1539 | H | F | $SO_2CH_2COOEt$ | $3-CF_3$ | H | 1-Al—Pip(4) |
| 1540 | H | F | $SO_2CH_2COOEt$ | 2-OMe | H | 1-Al—Pip(4) |
| 1541 | H | F | $SO_2CH_2COOEt$ | 3-OMe | H | 1-Al—Pip(4) |
| 1542 | H | F | $SO_2CH_2COOEt$ | 2-OEt | H | 1-Al—Pip(4) |
| 1543 | H | F | $SO_2CH_2COOEt$ | 3-OEt | H | 1-Al—Pip(4) |
| 1544 | H | F | $SO_2CH_2COOEt$ | 2-COOH | H | 1-Al—Pip(4) |
| 1545 | H | F | $SO_2CH_2COOEt$ | 3-COOH | H | 1-Al—Pip(4) |
| 1546 | H | F | $SO_2CH_2COOEt$ | 2-COOMe | H | 1-Al—Pip(4) |
| 1547 | H | F | $SO_2CH_2COOEt$ | 3-COOMe | H | 1-Al—Pip(4) |
| 1548 | H | F | $SO_2CH_2COOEt$ | 2-COOEt | H | 1-Al—Pip(4) |
| 1549 | H | F | $SO_2CH_2COOEt$ | 3-COOEt | H | 1-Al—Pip(4) |
| 1550 | H | F | $SO_2CH_2COOEt$ | 2-COOPr | H | 1-Al—Pip(4) |
| 1551 | H | F | $SO_2CH_2COOEt$ | 3-COOPr | H | 1-Al—Pip(4) |
| 1552 | H | F | $SO_2CH_2COOEt$ | 2-COOBu | H | 1-Al—Pip(4) |
| 1553 | H | F | $SO_2CH_2COOEt$ | 3-COOBu | H | 1-Al—Pip(4) |
| 1554 | H | F | $SO_2CH_2COOEt$ | 2-COOPn | H | 1-Al—Pip(4) |
| 1555 | H | F | $SO_2CH_2COOEt$ | 3-COOPn | H | 1-Al—Pip(4) |
| 1556 | H | F | $SO_2CH_2COOEt$ | 2-COOHx | H | 1-Al—Pip(4) |
| 1557 | H | F | $SO_2CH_2COOEt$ | 3-COOHx | H | 1-Al—Pip(4) |
| 1558 | H | F | $SO_2CH_2COOEt$ | $2-CONH_2$ | H | 1-Al—Pip(4) |
| 1559 | H | F | $SO_2CH_2COOEt$ | $3-CONH_2$ | H | 1-Al—Pip(4) |
| 1560 | H | F | $SO_2CH_2COOEt$ | 2-CONHMe | H | 1-Al—Pip(4) |
| 1561 | H | F | $SO_2CH_2COOEt$ | 3-CONHMe | H | 1-Al—Pip(4) |
| 1562 | H | F | $SO_2CH_2CCOEt$ | 2-CONHEt | H | 1-Al—Pip(4) |
| 1563 | H | F | $SO_2CH_2COOEt$ | 3-CONHEt | H | 1-Al—Pip(4) |
| 1564 | H | F | $SO_2CH_2COOEt$ | $2-CON(Me)_2$ | H | 1-Al—Pip(4) |
| 1565 | H | F | $SO_2CH_2COOEt$ | $3-CON(Me)_2$ | H | 1-Al—Pip(4) |
| 1566 | H | F | $SO_2CH_2COOEt$ | 2-CON(Me)Et | H | 1-Al—Pip(4) |
| 1567 | H | F | $SO_2CH_2COOEt$ | 3-CON(Me)Et | H | 1-Al—Pip(4) |
| 1568 | H | F | $SO_2CH_2COOEt$ | $2-CON(Et)_2$ | H | 1-Al—Pip(4) |
| 1569 | H | F | $SO_2CH_2COOEt$ | $3-CON(Et)_2$ | H | 1-Al—Pip(4) |
| 1570 | H | F | $SO_2CH_2COOEt$ | 3-F | 5-F | 1-Al—Pip(4) |
| 1571 | H | F | $SO_2CH_2COOEt$ | 3-Cl | 5-Cl | 1-Al—Pip(4) |
| 1572 | H | F | $SO_2CH_2COOEt$ | 3-Me | 5-Me | 1-Al—Pip(4) |
| 1573 | H | F | $SO_2CH_2COOEt$ | 3-Cl | $5-CONH_2$ | 1-Al—Pip(4) |
| 1574 | H | F | $SO_2CH_2COOEt$ | 2-Me | $5-CONH_2$ | 1-Al—Pip(4) |
| 1575 | H | F | $SO_2CH_2COOEt$ | 3-Me | $5-CONH_2$ | 1-Al—Pip(4) |

TABLE 1-continued (I)

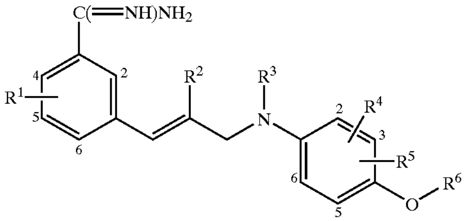

| Cpd. No. | $R^1$ | $R^2$ | $R^3$ | $R^4$ | $R^5$ | $R^6$ |
|---|---|---|---|---|---|---|
| 1576 | H | F | $SO_2CH_2COOEt$ | 3-$CONH_2$ | 5-$CONH_2$ | 1-Al—Pip(4) |
| 1577 | H | Me | $SO_2CH_2COOEt$ | H | H | 1-Al—Pip(4) |
| 1578 | H | Me | $SO_2CH_2COOEt$ | 2-F | H | 1-Al—Pip(4) |
| 1579 | H | Me | $SO_2CH_2COOEt$ | 3-F | H | 1-Al—Pip(4) |
| 1580 | H | Me | $SO_2CH_2COOEt$ | 2-Cl | H | 1-Al—Pip(4) |
| 1581 | H | Me | $SO_2CH_2COOEt$ | 3-Cl | H | 1-Al—Pip(4) |
| 1582 | H | Me | $SO_2CH_2COOEt$ | 2-Br | H | 1-Al—Pip(4) |
| 1583 | H | Me | $SO_2CH_2COOEt$ | 3-Br | H | 1-Al—Pip(4) |
| 1584 | H | Me | $SO_2CH_2COOEt$ | 2-I | H | 1-Al—Pip(4) |
| 1585 | H | Me | $SO_2CH_2COOEt$ | 3-I | H | 1-Al—Pip(4) |
| 1586 | H | Me | $SO_2CH_2COOEt$ | 2-Me | H | 1-Al—Pip(4) |
| 1587 | H | Me | $SO_2CH_2COOEt$ | 3-Me | H | 1-Al—Pip(4) |
| 1588 | H | Me | $SO_2CH_2COOEt$ | 2-Et | H | 1-Al—Pip(4) |
| 1589 | H | Me | $SO_2CH_2COOEt$ | 3-Et | H | 1-Al—Pip(4) |
| 1590 | H | Me | $SO_2CH_2COOEt$ | 2-Pr | H | 1-Al—Pip(4) |
| 1591 | H | Me | $SO_2CH_2COOEt$ | 3-Pr | H | 1-Al—Pip(4) |
| 1592 | H | Me | $SO_2CH_2COOEt$ | 2-Bu | H | 1-Al—Pip(4) |
| 1593 | H | Me | $SO_2CH_2COOEt$ | 3-Bu | H | 1-Al—Pip(4) |
| 1594 | H | Me | $SO_2CH_2COOEt$ | 2-Pn | H | 1-Al—Pip(4) |
| 1595 | H | Me | $SO_2CH_2COOEt$ | 3-Pn | H | 1-Al—Pip(4) |
| 1596 | H | Me | $SO_2CH_2COOEt$ | 2-Hx | H | 1-Al—Pip(4) |
| 1597 | H | Me | $SO_2CH_2COOEt$ | 3-Hx | H | 1-Al—Pip(4) |
| 1598 | H | Me | $SO_2CH_2COOEt$ | 2-$CF_3$ | H | 1-Al—Pip(4) |
| 1599 | H | Me | $SO_2CH_2COOEt$ | 3-$CF_3$ | H | 1-Al—Pip(4) |
| 1600 | H | Me | $SO_2CH_2COOEt$ | 2-OMe | H | 1-Al—Pip(4) |
| 1601 | H | Me | $SO_2CH_2COOEt$ | 3-OMe | H | 1-Al—Pip(4) |
| 1602 | H | Me | $SO_2CH_2COOEt$ | 2-OEt | H | 1-Al—Pip(4) |
| 1603 | H | Me | $SO_2CH_2COOEt$ | 3-OEt | H | 1-Al—Pip(4) |
| 1604 | H | Me | $SO_2CH_2COOEt$ | 2-COOH | H | 1-Al—Pip(4) |
| 1605 | H | Me | $SO_2CH_2COOEt$ | 3-COOH | H | 1-Al—Pip(4) |
| 1606 | H | Me | $SO_2CH_2COOEt$ | 2-COOMe | H | 1-Al—Pip(4) |
| 1607 | H | Me | $SO_2CH_2COOEt$ | 3-COOMe | H | 1-Al—Pip(4) |
| 1608 | H | Me | $SO_2CH_2COOEt$ | 2-COOEt | H | 1-Al—Pip(4) |
| 1609 | H | Me | $SO_2CH_2COOEt$ | 3-COOEt | H | 1-Al—Pip(4) |
| 1610 | H | Me | $SO_2CH_2COOEt$ | 2-COOPr | H | 1-Al—Pip(4) |
| 1611 | H | Me | $SO_2CH_2COOEt$ | 3-COOPr | H | 1-Al—Pip(4) |
| 1612 | H | Me | $SO_2CH_2COOEt$ | 2-COOBu | H | 1-Al—Pip(4) |
| 1613 | H | Me | $SO_2CH_2COOEt$ | 3-COOBu | H | 1-Al—Pip(4) |
| 1614 | H | Me | $SO_2CH_2COOEt$ | 2-COOPn | H | 1-Al—Pip(4) |
| 1615 | H | Me | $SO_2CH_2COOEt$ | 3-COOPn | H | 1-Al—Pip(4) |
| 1616 | H | Me | $SO_2CH_2COOEt$ | 2-COOHx | H | 1-Al—Pip(4) |
| 1617 | H | Me | $SO_2CH_2COOEt$ | 3-COOHx | H | 1-Al—Pip(4) |
| 1618 | H | Me | $SO_2CH_2COOEt$ | 2-$CONH_2$ | H | 1-Al—Pip(4) |
| 1619 | H | Me | $SO_2CH_2COOEt$ | 3-$CONH_2$ | H | 1-Al—Pip(4) |
| 1620 | H | Me | $SO_2CH_2COOEt$ | 2-CONHMe | H | 1-Al—Pip(4) |
| 1621 | H | Me | $SO_2CH_2COOEt$ | 3-CONHMe | H | 1-Al—Pip(4) |
| 1622 | H | Me | $SO_2CH_2COOEt$ | 2-CONHEt | H | 1-Al—Pip(4) |
| 1623 | H | Me | $SO_2CH_2COOEt$ | 3-CONHEt | H | 1-Al—Pip(4) |
| 1624 | H | Me | $SO_2CH_2COOEt$ | 2-$CON(Me)_2$ | H | 1-Al—Pip(4) |
| 1625 | H | Me | $SO_2CH_2COOEt$ | 3-$CON(Me)_2$ | H | 1-Al—Pip(4) |
| 1626 | H | Me | $SO_2CH_2COOEt$ | 2-CON(Me)Et | H | 1-Al—Pip(4) |
| 1627 | H | Me | $SO_2CH_2COOEt$ | 3-CON(Me)Et | H | 1-Al—Pip(4) |
| 1628 | H | Me | $SO_2CH_2COOEt$ | 2-$CON(Et)_2$ | H | 1-Al—Pip(4) |
| 1629 | H | Me | $SO_2CH_2COOEt$ | 3-$CON(Et)_2$ | H | 1-Al—Pip(4) |
| 1630 | H | Me | $SO_2CH_2COOEt$ | 3-F | 5-F | 1-Al—Pip(4) |
| 1631 | H | Me | $SO_2CH_2COOEt$ | 3-Cl | 5-Cl | 1-Al—Pip(4) |
| 1632 | H | Me | $SO_2CH_2COOEt$ | 3-Me | 5-Me | 1-Al—Pip(4) |
| 1633 | H | Me | $SO_2CH_2COOEt$ | 3-Cl | 5-$CONH_2$ | 1-Al—Pip(4) |
| 1634 | H | Me | $SO_2CH_2COOEt$ | 2-Me | 5-$CONH_2$ | 1-Al—Pip(4) |
| 1635 | H | Me | $SO_2CH_2COOEt$ | 3-Me | 5-$CONH_2$ | 1-Al—Pip(4) |
| 1636 | H | Me | $SO_2CH_2COOEt$ | 3-$CONH_2$ | 5-$CONH_2$ | 1-Al—Pip(4) |
| 1637 | 2-F | H | $SO_2CH_2COOEt$ | H | H | 1-Al—Pip(4) |
| 1638 | 4-F | H | $SO_2CH_2COOEt$ | H | H | 1-Al—Pip(4) |

TABLE 1-continued (I)

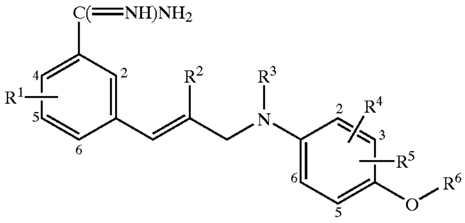

| Cpd. No. | $R^1$ | $R^2$ | $R^3$ | $R^4$ | $R^5$ | $R^6$ |
|---|---|---|---|---|---|---|
| 1639 | 4-F | H | $SO_2CH_2COOEt$ | 2-F | H | 1-Al—Pip(4) |
| 1640 | 4-F | H | $SO_2CH_2COOEt$ | 3-F | H | 1-Al—Pip(4) |
| 1641 | 4-F | H | $SO_2CH_2COOEt$ | 2-Cl | H | 1-Al—Pip(4) |
| 1642 | 4-F | H | $SO_2CH_2COOEt$ | 3-Cl | H | 1-Al—Pip(4) |
| 1643 | 4-F | H | $SO_2CH_2COOEt$ | 2-Br | H | 1-Al—Pip(4) |
| 1644 | 4-F | H | $SO_2CH_2COOEt$ | 3-Br | H | 1-Al—Pip(4) |
| 1645 | 4-F | H | $SO_2CH_2COOEt$ | 2-I | H | 1-Al—Pip(4) |
| 1646 | 4-F | H | $SO_2CH_2COOEt$ | 3-I | H | 1-Al—Pip(4) |
| 1647 | 4-F | H | $SO_2CH_2COOEt$ | 2-Me | H | 1-Al—Pip(4) |
| 1648 | 4-F | H | $SO_2CH_2COOEt$ | 3-Me | H | 1-Al—Pip(4) |
| 1649 | 4-F | H | $SO_2CH_2COOEt$ | 2-Et | H | 1-Al—Pip(4) |
| 1650 | 4-F | H | $SO_2CH_2COOEt$ | 3-Et | H | 1-Al—Pip(4) |
| 1651 | 4-F | H | $SO_2CH_2COOEt$ | 2-Pr | H | 1-Al—Pip(4) |
| 1652 | 4-F | H | $SO_2CH_2COOEt$ | 3-Pr | H | 1-Al—Pip(4) |
| 1653 | 4-F | H | $SO_2CH_2COOEt$ | 2-Bu | H | 1-Al—Pip(4) |
| 1654 | 4-F | H | $SO_2CH_2COOEt$ | 3-Bu | H | 1-Al—Pip(4) |
| 1655 | 4-F | H | $SO_2CH_2COOEt$ | 2-Pn | H | 1-Al—Pip(4) |
| 1656 | 4-F | H | $SO_2CH_2COOEt$ | 3-Pn | H | 1-Al—Pip(4) |
| 1657 | 4-F | H | $SO_2CH_2COOEt$ | 2-Hx | H | 1-Al—Pip(4) |
| 1658 | 4-F | H | $SO_2CH_2COOEt$ | 3-Hx | H | 1-Al—Pip(4) |
| 1659 | 4-F | H | $SO_2CH_2COOEt$ | 2-$CF_3$ | H | 1-Al—Pip(4) |
| 1660 | 4-F | H | $SO_2CH_2COOEt$ | 3-$CF_3$ | H | 1-Al—Pip(4) |
| 1661 | 4-F | H | $SO_2CH_2COOEt$ | 2-OMe | H | 1-Al—Pip(4) |
| 1662 | 4-F | H | $SO_2CH_2COOEt$ | 3-OMe | H | 1-Al—Pip(4) |
| 1663 | 4-F | H | $SO_2CH_2COOEt$ | 2-OEt | H | 1-Al—Pip(4) |
| 1664 | 4-F | H | $SO_2CH_2COOEt$ | 3-OEt | H | 1-Al—Pip(4) |
| 1665 | 4-F | H | $SO_2CH_2COOEt$ | 2-COOH | H | 1-Al—Pip(4) |
| 1666 | 4-F | H | $SO_2CH_2COOEt$ | 3-COOH | H | 1-Al—Pip(4) |
| 1667 | 4-F | H | $SO_2CH_2COOEt$ | 2-COOMe | H | 1-Al—Pip(4) |
| 1668 | 4-F | H | $SO_2CH_2COOEt$ | 3-COOMe | H | 1-Al—Pip(4) |
| 1669 | 4-F | H | $SO_2CH_2COOEt$ | 2-COOEt | H | 1-Al—Pip(4) |
| 1670 | 4-F | H | $SO_2CH_2COOEt$ | 3-COOEt | H | 1-Al—Pip(4) |
| 1671 | 4-F | H | $SO_2CH_2COOEt$ | 2-COOPr | H | 1-Al—Pip(4) |
| 1672 | 4-F | H | $SO_2CH_2COOEt$ | 3-COOPr | H | 1-Al—Pip(4) |
| 1673 | 4-F | H | $SO_2CH_2COOEt$ | 2-COOBu | H | 1-Al—Pip(4) |
| 1674 | 4-F | H | $SO_2CH_2COOEt$ | 3-COOBu | H | 1-Al—Pip(4) |
| 1675 | 4-F | H | $SO_2CH_2COOEt$ | 2-COOPn | H | 1-Al—Pip(4) |
| 1676 | 4-F | H | $SO_2CH_2COOEt$ | 3-COOPn | H | 1-Al—Pip(4) |
| 1677 | 4-F | H | $SO_2CH_2COOEt$ | 2-COOHx | H | 1-Al—Pip(4) |
| 1678 | 4-F | H | $SO_2CH_2COOEt$ | 3-COOHx | H | 1-Al—Pip(4) |
| 1679 | 4-F | H | $SO_2CH_2COOEt$ | 2-$CONH_2$ | H | 1-Al—Pip(4) |
| 1680 | 4-F | H | $SO_2CH_2COOEt$ | 3-$CONH_2$ | H | 1-Al—Pip(4) |
| 1681 | 4-F | H | $SO_2CH_2COOEt$ | 2-CONHMe | H | 1-Al—Pip(4) |
| 1682 | 4-F | H | $SO_2CH_2COOEt$ | 3-CONHMe | H | 1-Al—Pip(4) |
| 1683 | 4-F | H | $SO_2CH_2COOEt$ | 2-CONHEt | H | 1-Al—Pip(4) |
| 1684 | 4-F | H | $SO_2CH_2COOEt$ | 3-CONHEt | H | 1-Al—Pip(4) |
| 1685 | 4-F | H | $SO_2CH_2COOEt$ | 2-$CON(Me)_2$ | H | 1-Al—Pip(4) |
| 1686 | 4-F | H | $SO_2CH_2COOEt$ | 3-$CON(Me)_2$ | H | 1-Al—Pip(4) |
| 1687 | 4-F | H | $SO_2CH_2COOEt$ | 2-CON(Me)Et | H | 1-Al—Pip(4) |
| 1688 | 4-F | H | $SO_2CH_2COOEt$ | 3-CON(Me)Et | H | 1-Al—Pip(4) |
| 1689 | 4-F | H | $SO_2CH_2COOEt$ | 2-$CON(Et)_2$ | H | 1-Al—Pip(4) |
| 1690 | 4-F | H | $SO_2CH_2COOEt$ | 3-$CON(Et)_2$ | H | 1-Al—Pip(4) |
| 1691 | 4-F | Me | $SO_2CH_2COOEt$ | 3-F | 5-F | 1-Al—Pip(4) |
| 1692 | 4-F | Me | $SO_2CH_2COOEt$ | 3-Cl | 5-Cl | 1-Al—Pip(4) |
| 1693 | 4-F | Me | $SO_2CH_2COOEt$ | 3-Me | 5-Me | 1-Al—Pip(4) |
| 1694 | 4-F | Me | $SO_2CH_2COOEt$ | 3-Cl | 5-$CONH_2$ | 1-Al—Pip(4) |
| 1695 | 4-F | Me | $SO_2CH_2COOEt$ | 2-Me | 5-$CONH_2$ | 1-Al—Pip(4) |
| 1696 | 4-F | Me | $SO_2CH_2COOEt$ | 3-Me | 5-$CONH_2$ | 1-Al—Pip(4) |
| 1697 | 4-F | Me | $SO_2CH_2COOEt$ | 3-$CONH_2$ | 5-$CONH_2$ | 1-Al—Pip(4) |
| 1698 | 5-F | H | $SO_2CH_2COOEt$ | H | H | 1-Al—Pip(4) |
| 1699 | 6-F | H | $SO_2CH_2COOEt$ | H | H | 1-Al—Pip(4) |
| 1700 | 2-Cl | H | $SO_2CH_2COOEt$ | H | H | 1-Al—Pip(4) |
| 1701 | 4-Cl | H | $SO_2CH_2COOEt$ | H | H | 1-Al—Pip(4) |

TABLE 1-continued (I)

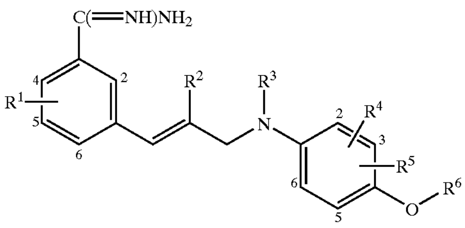

| Cpd. No. | $R^1$ | $R^2$ | $R^3$ | $R^4$ | $R^5$ | $R^6$ |
|---|---|---|---|---|---|---|
| 1702 | 5-Cl | H | $SO_2CH_2COOEt$ | H | H | 1-Al—Pip(4) |
| 1703 | 6-Cl | H | $SO_2CH_2COOEt$ | H | H | 1-Al—Pip(4) |
| 1704 | 2-Br | H | $SO_2CH_2COOEt$ | H | H | 1-Al—Pip(4) |
| 1705 | 4-Br | H | $SO_2CH_2COOEt$ | H | H | 1-Al—Pip(4) |
| 1706 | 5-Br | H | $SO_2CH_2COOEt$ | H | H | 1-Al—Pip(4) |
| 1707 | 6-Br | H | $SO_2CH_2COOEt$ | H | H | 1-Al—Pip(4) |
| 1708 | 2-Me | H | $SO_2CH_2COOEt$ | H | H | 1-Al—Pip(4) |
| 1709 | 3-Me | H | $SO_2CH_2COOEt$ | H | H | 1-Al—Pip(4) |
| 1710 | 4-Me | H | $SO_2CH_2COOEt$ | H | H | 1-Al—Pip(4) |
| 1711 | 5-Me | H | $SO_2CH_2COOEt$ | H | H | 1-Al—Pip(4) |
| 1712 | 5-Me | H | $SO_2CH_2COOEt$ | 2-F | H | 1-Al—Pip(4) |
| 1713 | 5-Me | H | $SO_2CH_2COOEt$ | 3-F | H | 1-Al—Pip(4) |
| 1714 | 5-Me | H | $SO_2CH_2COCEt$ | 2-Cl | H | 1-Al—Pip(4) |
| 1715 | 5-Me | H | $SO_2CH_2COOEt$ | 3-Cl | H | 1-Al—Pip(4) |
| 1716 | 5-Me | H | $SO_2CH_2COOEt$ | 2-Br | H | 1-Al—Pip(4) |
| 1717 | 5-Me | H | $SO_2CH_2COOEt$ | 3-Br | H | 1-Al—Pip(4) |
| 1718 | 5-Me | H | $SO_2CH_2COOEt$ | 2-I | H | 1-Al—Pip(4) |
| 1719 | 5-Me | H | $SO_2CH_2COOEt$ | 3-I | H | 1-Al—Pip(4) |
| 1720 | 5-Me | H | $SO_2CH_2COOEt$ | 2-Me | H | 1-Al—Pip(4) |
| 1721 | 5-Me | H | $SO_2CH_2COOEt$ | 3-Me | H | 1-Al—Pip(4) |
| 1722 | 5-Me | H | $SO_2CH_2COOEt$ | 2-Et | H | 1-Al—Pip(4) |
| 1723 | 5-Me | H | $SO_2CH_2COOEt$ | 3-Et | H | 1 Al—Pip(4) |
| 1724 | 5-Me | H | $SO_2CH_2COOEt$ | 2-Pr | H | 1-Al—Pip(4) |
| 1725 | 5-Me | H | $SO_2CH_2COOEt$ | 3-Pr | H | 1-Al—Pip(4) |
| 1726 | 5-Me | H | $SO_2CH_2COOEt$ | 2-Bu | H | 1-Al—Pip(4) |
| 1727 | 5-Me | H | $SO_2CH_2COOEt$ | 3-Bu | H | 1-Al—Pip(4) |
| 1728 | 5-Me | H | $SO_2CH_2COOEt$ | 2-Pn | H | 1-Al—Pip(4) |
| 1729 | 5-Me | H | $SO_2CH_2COOEt$ | 3-Pn | H | 1-Al—Pip(4) |
| 1730 | 5-Me | H | $SO_2CH_2COOEt$ | 2-Hx | H | 1-Al—Pip(4) |
| 1731 | 5-Me | H | $SO_2CH_2COOEt$ | 3-Hx | H | 1-Al—Pip(4) |
| 1732 | 5-Me | H | $SO_2CH_2COOEt$ | 2-$CF_3$ | H | 1-Al—Pip(4) |
| 1733 | 5-Me | H | $SO_2CH_2COOEt$ | 3-$CF_3$ | H | 1-Al—Pip(4) |
| 1734 | 5-Me | H | $SO_2CH_2COOEt$ | 2-OMe | H | 1-Al—Pip(4) |
| 1735 | 5-Me | H | $SO_2CH_2COOEt$ | 3-OMe | H | 1-Al—Pip(4) |
| 1736 | 5-Me | H | $SO_2CH_2COOEt$ | 2-OEt | H | 1-Al—Pip(4) |
| 1737 | 5-Me | H | $SO_2CH_2COOEt$ | 3-OEt | H | 1-Al—Pip(4) |
| 1738 | 5-Me | H | $SO_2CH_2COOEt$ | 2-COOH | H | 1-Al—Pip(4) |
| 1739 | 5-Me | H | $SO_2CH_2COOEt$ | 3-COOH | H | 1-Al—Pip(4) |
| 1740 | 5-Me | H | $SO_2CH_2COOEt$ | 2-COOMe | H | 1-Al—Pip(4) |
| 1741 | 5-Me | H | $SO_2CH_2COOEt$ | 3-COOMe | H | 1-Al—Pip(4) |
| 1742 | 5-Me | H | $SO_2CH_2COOEt$ | 2-COOEt | H | 1-Al—Pip(4) |
| 1743 | 5-Me | H | $SO_2CH_2COOEt$ | 3-COOEt | H | 1-Al—Pip(4) |
| 1744 | 5-Me | H | $SO_2CH_2COOEt$ | 2-COOPr | H | 1-Al—Pip(4) |
| 1745 | 5-Me | H | $SO_2CH_2COOEt$ | 3-COOPr | H | 1-Al—Pip(4) |
| 1746 | 5-Me | H | $SO_2CH_2COOEt$ | 2-COOBu | H | 1-Al—Pip(4) |
| 1747 | 5-Me | H | $SO_2CH_2COOEt$ | 3-COOBu | H | 1-Al—Pip(4) |
| 1748 | 5-Me | H | $SO_2CH_2COOEt$ | 2-COOPn | H | 1-Al—Pip(4) |
| 1749 | 5-Me | H | $SO_2CH_2COOEt$ | 3-COOPn | H | 1-Al—Pip(4) |
| 1750 | 5-Me | H | $SO_2CH_2COOEt$ | 2-COOHx | H | 1-Al—Pip(4) |
| 1751 | 5-Me | H | $SO_2CH_2COOEt$ | 3-COOHx | H | 1-Al—Pip(4) |
| 1752 | 5-Me | H | $SO_2CH_2COOEt$ | 2-$CONH_2$ | H | 1-Al—Pip(4) |
| 1753 | 5-Me | H | $SO_2CH_2COOEt$ | 3-$CONH_2$ | H | 1-Al—Pip(4) |
| 1754 | 5-Me | H | $SO_2CH_2COOEt$ | 2-CONHMe | H | 1-Al—Pip(4) |
| 1755 | 5-Me | H | $SO_2CH_2COOEt$ | 3-CONHMe | H | 1-Al—Pip(4) |
| 1756 | 5-Me | H | $SO_2CH_2COOEt$ | 2-CONHEt | H | 1-Al—Pip(4) |
| 1757 | 5-Me | H | $SO_2CH_2COOEt$ | 3-CONHEt | H | 1-Al—Pip(4) |
| 1758 | 5-Me | H | $SO_2CH_2COOEt$ | 2-$CON(Me)_2$ | H | 1-Al—Pip(4) |
| 1759 | 5-Me | H | $SO_2CH_2COOEt$ | 3-$CON(Me)_2$ | H | 1-Al—Pip(4) |
| 1760 | 5-Me | H | $SO_2CH_2COOEt$ | 2-CON(Me)Et | H | 1-Al—Pip(4) |
| 1761 | 5-Me | H | $SO_2CH_2COOEt$ | 3-CON(Me)Et | H | 1-Al—Pip(4) |
| 1762 | 5-Me | H | $SO_2CH_2COOEt$ | 2-$CON(Et)_2$ | H | 1-Al—Pip(4) |
| 1763 | 5-Me | H | $SO_2CH_2COOEt$ | 3-$CON(Et)_2$ | H | 1-Al—Pip(4) |
| 1764 | 5-Me | Me | $SO_2CH_2COOEt$ | 3-F | 5-F | 1-Al—Pip(4) |

TABLE 1-continued (I)

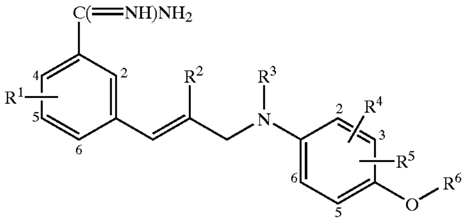

| Cpd. No. | $R^1$ | $R^2$ | $R^3$ | $R^4$ | $R^5$ | $R^6$ |
|---|---|---|---|---|---|---|
| 1765 | 5-Me | Me | $SO_2CH_2COOEt$ | 3-Cl | 5-Cl | 1-Al—Pip(4) |
| 1766 | 5-Me | Me | $SO_2CH_2COOEt$ | 3-Me | 5-Me | 1-Al—Pip(4) |
| 1767 | 5-Me | Me | $SO_2CH_2COOEt$ | 3-Cl | 5-$CONH_2$ | 1-Al—Pip(4) |
| 1768 | 5-Me | Me | $SO_2CH_2COOEt$ | 2-Me | 5-$CONH_2$ | 1-Al—Pip(4) |
| 1769 | 5-Me | Me | $SO_2CH_2COOEt$ | 3-Me | 5-$CONH_2$ | 1-Al—Pip(4) |
| 1770 | 5-Me | Me | $SO_2CH_2COOEt$ | 3-$CONH_2$ | 5-$CONH_2$ | 1-Al—Pip(4) |
| 1771 | 6-Me | H | $SO_2CH_2COOEt$ | H | H | 1-Al—Pip(4) |
| 1772 | 6-Me | H | $SO_2CH_2COOEt$ | 2-F | H | 1-Al—Pip(4) |
| 1773 | 6-Me | H | $SO_2CH_2COOEt$ | 3-F | H | 1-Al—Pip(4) |
| 1774 | 6-Me | H | $SO_2CH_2COOEt$ | 2-Cl | H | 1-Al—Pip(4) |
| 1775 | 6-Me | H | $SO_2CH_2COOEt$ | 3-Cl | H | 1-Al—Pip(4) |
| 1776 | 6-Me | H | $SO_2CH_2COOEt$ | 2-Br | H | 1-Al—Pip(4) |
| 1777 | 6-Me | H | $SO_2CH_2COOEt$ | 3-Br | H | 1-Al—Pip(4) |
| 1778 | 6-Me | H | $SO_2CH_2COOEt$ | 2-I | H | 1-Al—Pip(4) |
| 1779 | 6-Me | H | $SO_2CH_2COOEt$ | 3-I | H | 1-Al—Pip(4) |
| 1780 | 6-Me | H | $SO_2CH_2COOEt$ | 2-Me | H | 1-Al—Pip(4) |
| 1781 | 6-Me | H | $SO_2CH_2COOEt$ | 3-Me | H | 1-Al—Pip(4) |
| 1782 | 6-Me | H | $SO_2CH_2COOEt$ | 2-Et | H | 1-Al—Pip(4) |
| 1783 | 6-Me | H | $SO_2CH_2COOEt$ | 3-Et | H | 1-Al—Pip(4) |
| 1784 | 6-Me | H | $SO_2CH_2COOEt$ | 2-Pr | H | 1-Al—Pip(4) |
| 1785 | 6-Me | H | $SO_2CH_2COOEt$ | 3-Pr | H | 1-Al—Pip(4) |
| 1786 | 6-Me | H | $SO_2CH_2COOEt$ | 2-Bu | H | 1-Al—Pip(4) |
| 1787 | 6-Me | H | $SO_2CH_2COOEt$ | 3-Bu | H | 1-Al—Pip(4) |
| 1788 | 6-Me | H | $SO_2CH_2COOEt$ | 2-Pn | H | 1-Al—Pip(4) |
| 1789 | 6-Me | H | $SO_2CH_2COOEt$ | 3-Pn | H | 1-Al—Pip(4) |
| 1790 | 6-Me | H | $SO_2CH_2COOEt$ | 2-Hx | H | 1-Al—Pip(4) |
| 1791 | 6-Me | H | $SO_2CH_2COOEt$ | 3-Hx | H | 1-Al—Pip(4) |
| 1792 | 6-Me | H | $SO_2CH_2COOEt$ | 2-$CF_3$ | H | 1-Al—Pip(4) |
| 1793 | 6-Me | H | $SO_2CH_2COOEt$ | 3-$CF_3$ | H | 1-Al—Pip(4) |
| 1794 | 6-Me | H | $SO_2CH_2COOEt$ | 2-OMe | H | 1-Al—Pip(4) |
| 1795 | 6-Me | H | $SO_2CH_2COOEt$ | 3-OMe | H | 1-Al—Pip(4) |
| 1796 | 6-Me | H | $SO_2CH_2COOEt$ | 2-OEt | H | 1-Al—Pip(4) |
| 1797 | 6-Me | H | $SO_2CH_2COOEt$ | 3-OEt | H | 1-Al—Pip(4) |
| 1798 | 6-Me | H | $SO_2CH_2COOEt$ | 2-COOH | H | 1-Al—Pip(4) |
| 1799 | 6-Me | H | $SO_2CH_2COOEt$ | 3-COOH | H | 1-Al—Pip(4) |
| 1800 | 6-Me | H | $SO_2CH_2COOEt$ | 2-COOMe | H | 1-Al—Pip(4) |
| 1801 | 6-Me | H | $SO_2CH_2COOEt$ | 3-COOMe | H | 1-Al—Pip(4) |
| 1802 | 6-Me | H | $SO_2CH_2COOEt$ | 2-COOEt | H | 1-Al—Pip(4) |
| 1803 | 6-Me | H | $SO_2CH_2COOEt$ | 3-COOEt | H | 1-Al—Pip(4) |
| 1804 | 6-Me | H | $SO_2CH_2COOEt$ | 2-COOPr | H | 1-Al—Pip(4) |
| 1805 | 6-Me | H | $SO_2CH_2COOEt$ | 3-COOPr | H | 1-Al—Pip(4) |
| 1806 | 6-Me | H | $SO_2CH_2COOEt$ | 2-COOBu | H | 1-Al—Pip(4) |
| 1807 | 6-Me | H | $SO_2CH_2COOEt$ | 3-COOBu | H | 1-Al—Pip(4) |
| 1808 | 6-Me | H | $SO_2CH_2COOEt$ | 2-COOPn | H | 1-Al—Pip(4) |
| 1809 | 6-Me | H | $SO_2CH_2COOEt$ | 3-COOPn | H | 1-Al—Pip(4) |
| 1810 | 6-Me | H | $SO_2CH_2COOEt$ | 2-COOHx | H | 1-Al—Pip(4) |
| 1811 | 6-Me | H | $SO_2CH_2COOEt$ | 3-COOHx | H | 1-Al—Pip(4) |
| 1812 | 6-Me | H | $SO_2CH_2COOEt$ | 2-$CONH_2$ | H | 1-Al—Pip(4) |
| 1813 | 6-Me | H | $SO_2CH_2COOEt$ | 3-$CONH_2$ | H | 1-Al—Pip(4) |
| 1814 | 6-Me | H | $SO_2CH_2COOEt$ | 2-CONHMe | H | 1-Al—Pip(4) |
| 1815 | 6-Me | H | $SO_2CH_2COOEt$ | 3-CONHMe | H | 1-Al—Pip(4) |
| 1816 | 6-Me | H | $SO_2CH_2COOEt$ | 2-CONHEt | H | 1-Al—Pip(4) |
| 1817 | 6-Me | H | $SO_2CH_2COOEt$ | 3-CONHEt | H | 1-Al—Pip(4) |
| 1818 | 6-Me | H | $SO_2CH_2COOEt$ | 2-$CON(Me)_2$ | H | 1-Al—Pip(4) |
| 1819 | 6-Me | H | $SO_2CH_2COOEt$ | 3-$CON(Me)_2$ | H | 1-Al—Pip(4) |
| 1820 | 6-Me | H | $SO_2CH_2COOEt$ | 2-CON(Me)Et | H | 1-Al—Pip(4) |
| 1821 | 6-Me | H | $SO_2CH_2COOEt$ | 3-CON(Me)Et | H | 1-Al—Pip(4) |
| 1822 | 6-Me | H | $SO_2CH_2COOEt$ | 2-$CON(Et)_2$ | H | 1-Al—Pip(4) |
| 1823 | 6-Me | H | $SO_2CH_2COOEt$ | 3-$CON(Et)_2$ | H | 1-Al—Pip(4) |
| 1824 | 6-Me | Me | $SO_2CH_2COOEt$ | 3-F | 5-F | 1-Al—Pip(4) |
| 1825 | 6-Me | Me | $SO_2CH_2COOEt$ | 3-Cl | 5-Cl | 1-Al—Pip(4) |
| 1826 | 6-Me | Me | $SO_2CH_2COOEt$ | 3-Me | 5-Me | 1-Al—Pip(4) |
| 1827 | 6-Me | Me | $SO_2CH_2COOEt$ | 3-Cl | 5-$CONH_2$ | 1-Al—Pip(4) |

TABLE 1-continued (I)

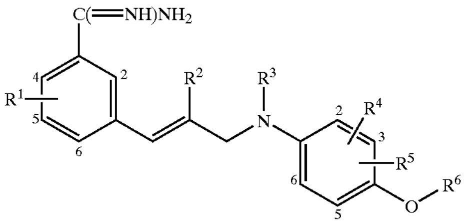

| Cpd. No. | $R^1$ | $R^2$ | $R^3$ | $R^4$ | $R^5$ | $R^6$ |
|---|---|---|---|---|---|---|
| 1828 | 6-Me | Me | $SO_2CH_2COOEt$ | 2-Me | 5-$CONH_2$ | 1-Al—Pip(4) |
| 1829 | 6-Me | Me | $SO_2CH_2COOEt$ | 3-Me | 5-$CONH_2$ | 1-Al—Pip(4) |
| 1830 | 6-Me | Me | $SO_2CH_2COOEt$ | 3-$CONH_2$ | 5-$CONH_2$ | 1-Al—Pip(4) |
| 1831 | 2-Et | H | $SO_2CH_2COOEt$ | H | H | 1-Al—Pip(4) |
| 1832 | 4-Et | H | $SO_2CH_2COOEt$ | H | H | 1-Al—Pip(4) |
| 1833 | 5-Et | H | $SO_2CH_2COOEt$ | H | H | 1-Al—Pip(4) |
| 1834 | 6-Et | H | $SO_2CH_2COOEt$ | H | H | 1-Al—Pip(4) |
| 1835 | 2-Pr | H | $SO_2CH_2COOEt$ | H | H | 1-Al—Pip(4) |
| 1836 | 4-Bu | H | $SO_2CH_2COOEt$ | H | H | 1-Al—Pip(4) |
| 1837 | 5-Pn | H | $SO_2CH_2COOEt$ | H | H | 1-Al—Pip(4) |
| 1838 | 6-Hx | H | $SO_2CH_2COOEt$ | H | H | 1-Al—Pip(4) |
| 1839 | 6-OH | H | $SO_2CH_2COOEt$ | H | H | 1-Al—Pip(4) |
| 1840 | 6-OH | H | $SO_2CH_2COOEt$ | 2-F | H | 1-Al—Pip(4) |
| 1841 | 6-OH | H | $SO_2CH_2COOEt$ | 3-F | H | 1-Al—Pip(4) |
| 1842 | 6-OH | H | $SO_2CH_2COOEt$ | 2-Cl | H | 1-Al—Pip(4) |
| 1843 | 6-OH | H | $SO_2CH_2COOEt$ | 3-Cl | H | 1-Al—Pip(4) |
| 1844 | 6-OH | H | $SO_2CH_2COOEt$ | 2-Br | H | 1-Al—Pip(4) |
| 1845 | 6-OH | H | $SO_2CH_2COOEt$ | 3-Br | H | 1-Al—Pip(4) |
| 1846 | 6-OH | H | $SO_2CH_2COOEt$ | 2-I | H | 1-Al—Pip(4) |
| 1847 | 6-OH | H | $SO_2CH_2COOEt$ | 3-I | H | 1-Al—Pip(4) |
| 1848 | 6-OH | H | $SO_2CH_2COOEt$ | 2-Me | H | 1-Al—Pip(4) |
| 1849 | 6-OH | H | $SO_2CH_2COOEt$ | 3-Me | H | 1-Al—Pip(4) |
| 1850 | 6-OH | H | $SO_2CH_2COOEt$ | 2-Et | H | 1-Al—Pip(4) |
| 1851 | 6-OH | H | $SO_2CH_2COOEt$ | 3-Et | H | 1-Al—Pip(4) |
| 1852 | 6-OH | H | $SO_2CH_2COOEt$ | 2-Pr | H | 1-Al—Pip(4) |
| 1853 | 6-OH | H | $SO_2CH_2COOEt$ | 3-Pr | H | 1-Al—Pip(4) |
| 1854 | 6-OH | H | $SO_2CH_2COOEt$ | 2-Bu | H | 1-Al—Pip(4) |
| 1855 | 6-OH | H | $SO_2CH_2COOEt$ | 3-Bu | H | 1-Al—Pip(4) |
| 1856 | 6-OH | H | $SO_2CH_2COOEt$ | 2-Pn | H | 1-Al—Pip(4) |
| 1857 | 6-OH | H | $SO_2CH_2COOEt$ | 3-Pn | H | 1-Al—Pip(4) |
| 1858 | 6-OH | H | $SO_2CH_2COOEt$ | 2-Hx | H | 1-Al—Pip(4) |
| 1859 | 6-OH | H | $SO_2CH_2COCEt$ | 3-Hx | H | 1-Al—Pip(4) |
| 1860 | 6-OH | H | $SO_2CH_2COOEt$ | 2-$CF_3$ | H | 1-Al—Pip(4) |
| 1861 | 6-OH | H | $SO_2CH_2COOEt$ | 3-$CF_3$ | H | 1-Al—Pip(4) |
| 1862 | 6-OH | H | $SO_2CH_2COOEt$ | 2-OMe | H | 1-Al—Pip(4) |
| 1863 | 6-OH | H | $SO_2CH_2COOEt$ | 3-OMe | H | 1-Al—Pip(4) |
| 1864 | 6-OH | H | $SO_2CH_2COOEt$ | 2-OEt | H | 1-Al—Pip(4) |
| 1865 | 6-OH | H | $SO_2CH_2COOEt$ | 3-OEt | H | 1-Al—Pip(4) |
| 1866 | 6-OH | H | $SO_2CH_2COOEt$ | 2-COOH | H | 1-Al—Pip(4) |
| 1867 | 6-OH | H | $SO_2CH_2COOEt$ | 3-COOH | H | 1-Al—Pip(4) |
| 1868 | 6-OH | H | $SO_2CH_2COOEt$ | 2-COOMe | H | 1-Al—Pip(4) |
| 1869 | 6-OH | H | $SO_2CH_2COOEt$ | 3-COOMe | H | 1-Al—Pip(4) |
| 1870 | 6-OH | H | $SO_2CH_2COOEt$ | 2-COOEt | H | 1-Al—Pip(4) |
| 1871 | 6-OH | H | $SO_2CH_2COOEt$ | 3-COOEt | H | 1-Al—Pip(4) |
| 1872 | 6-OH | H | $SO_2CH_2COOEt$ | 2-COOPr | H | 1-Al—Pip(4) |
| 1873 | 6-OH | H | $SO_2CH_2COOEt$ | 3-COOPr | H | 1-Al—Pip(4) |
| 1874 | 6-OH | H | $SO_2CH_2COOEt$ | 2-COOBu | H | 1-Al—Pip(4) |
| 1875 | 6-OH | H | $SO_2CH_2COOEt$ | 3-COOBu | H | 1-Al—Pip(4) |
| 1876 | 6-OH | H | $SO_2CH_2COOEt$ | 2-COOPn | H | 1-Al—Pip(4) |
| 1877 | 6-OH | H | $SO_2CH_2COOEt$ | 3-COOPn | H | 1-Al—Pip(4) |
| 1878 | 6-OH | H | $SO_2CH_2COOEt$ | 2-COOHx | H | 1-Al—Pip(4) |
| 1879 | 6-OH | H | $SO_2CH_2COOEt$ | 3-COOHx | H | 1-Al—Pip(4) |
| 1880 | 6-OH | H | $SO_2CH_2COOEt$ | 2-$CONH_2$ | H | 1-Al—Pip(4) |
| 1881 | 6-OH | H | $SO_2CH_2COOEt$ | 3-$CONH_2$ | H | 1-Al—Pip(4) |
| 1882 | 6-OH | H | $SO_2CH_2COOEt$ | 2-CONHMe | H | 1-Al—Pip(4) |
| 1883 | 6-OH | H | $SO_2CH_2COOEt$ | 3-CONHMe | H | 1-Al—Pip(4) |
| 1884 | 6-OH | H | $SO_2CH_2COOEt$ | 2-CONHEt | H | 1-Al—Pip(4) |
| 1885 | 6-OH | H | $SO_2CH_2COOEt$ | 3-CONHEt | H | 1-Al—Pip(4) |
| 1886 | 6-OH | H | $SO_2CH_2COOEt$ | 2-$CON(Me)_2$ | H | 1-Al—Pip(4) |
| 1887 | 6-OH | H | $SO_2CH_2COOEt$ | 3-$CON(Me)_2$ | H | 1-Al—Pip(4) |
| 1888 | 6-OH | H | $SO_2CH_2COOEt$ | 2-CON(Me)Et | H | 1-Al—Pip(4) |
| 1889 | 6-OH | H | $SO_2CH_2COOEt$ | 3-CON(Me)Et | H | 1-Al—Pip(4) |
| 1890 | 6-OH | H | $SO_2CH_2COOEt$ | 2-$CON(Et)_2$ | H | 1-Al—Pip(4) |

TABLE 1-continued (I)

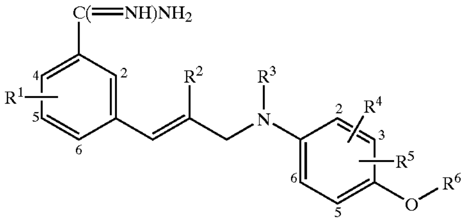

| Cpd. No. | $R^1$ | $R^2$ | $R^3$ | $R^4$ | $R^5$ | $R^6$ |
|---|---|---|---|---|---|---|
| 1891 | 6-OH | H | $SO_2CH_2COOEt$ | 3-CON(Et)$_2$ | H | 1-Al—Pip(4) |
| 1892 | 6-OH | H | $SO_2CH_2COOEt$ | 2-F | 3-F | 1-Al—Pip(4) |
| 1893 | 6-OH | H | $SO_2CH_2COOEt$ | 2-F | 5-F | 1-Al—Pip(4) |
| 1894 | 6-OH | H | $SO_2CH_2COOEt$ | 2-F | 6-F | 1-Al—Pip(4) |
| 1895 | 6-OH | H | $SO_2CH_2COOEt$ | 3-F | 5-F | 1-Al—Pip(4) |
| 1896 | 6-OH | H | $SO_2CH_2COOEt$ | 2-Cl | 3-Cl | 1-Al—Pip(4) |
| 1897 | 6-OH | H | $SO_2CH_2COOEt$ | 2-Cl | 5-Cl | 1-Al—Pip(4) |
| 1898 | 6-OH | H | $SO_2CH_2COOEt$ | 2-Cl | 6-Cl | 1-Al—Pip(4) |
| 1899 | 6-OH | H | $SO_2CH_2COOEt$ | 3-Cl | 5-Cl | 1-Al—Pip(4) |
| 1900 | 6-OH | H | $SO_2CH_2COOEt$ | 2-Me | 3-Me | 1-Al—Pip(4) |
| 1901 | 6-OH | H | $SO_2CH_2COOEt$ | 2-Me | 5-Me | 1-Al—Pip(4) |
| 1902 | 6-OH | H | $SO_2CH_2COOEt$ | 2-Me | 6-Me | 1-Al—Pip(4) |
| 1903 | 6-OH | H | $SO_2CH_2COOEt$ | 3-Me | 5-Me | 1-Al—Pip(4) |
| 1904 | 6-OH | H | $SO_2CH_2COOEt$ | 2-Cl | 5-CONH$_2$ | 1-Al—Pip(4) |
| 1905 | 6-OH | H | $SO_2CH_2COOEt$ | 3-Cl | 5-CONH$_2$ | 1-Al—Pip(4) |
| 1906 | 6-OH | H | $SO_2CH_2COOEt$ | 3-Cl | 5-CONHMe | 1-Al—Pip(4) |
| 1907 | 6-OH | H | $SO_2CH_2COOEt$ | 3-Cl | 5-CONHEt | 1-Al—Pip(4) |
| 1908 | 6-OH | H | $SO_2CH_2COOEt$ | 3-Cl | 5-CONHPr | 1-Al—Pip(4) |
| 1909 | 6-OH | H | $SO_2CH_2COOEt$ | 3-Cl | 5-CONHBu | 1-Al—Pip(4) |
| 1910 | 6-OH | H | $SO_2CH_2COOEt$ | 3-Cl | 5-CONHPn | 1-Al—Pip(4) |
| 1911 | 6-OH | H | $SO_2CH_2COOEt$ | 3-Cl | 5-CONHHx | 1-Al—Pip(4) |
| 1912 | 6-OH | H | $SO_2CH_2COOEt$ | 2-Me | 5-CONH$_2$ | 1-Al—Pip(4) |
| 1913 | 6-OH | H | $SO_2CH_2COOEt$ | 2-Me | 5-CONHMe | 1-Al—Pip(4) |
| 1914 | 6-OH | H | $SO_2CH_2COOEt$ | 2-Me | 5-CONHEt | 1-Al—Pip(4) |
| 1915 | 6-OH | H | $SO_2CH_2COOEt$ | 2-Me | 5-CONHPr | 1-Al—Pip(4) |
| 1916 | 6-OH | H | $SO_2CH_2COOEt$ | 2-Me | 5-CONHBu | 1-Al—Pip(4) |
| 1917 | 6-OH | H | $SO_2CH_2COOEt$ | 2-Me | 5-CONHPn | 1-Al—Pip(4) |
| 1918 | 6-OH | H | $SO_2CH_2COOEt$ | 2-Me | 5-CONHHx | 1-Al—Pip(4) |
| 1919 | 6-OH | H | $SO_2CH_2COOEt$ | 3-Me | 5-CONH$_2$ | 1-Al—Pip(4) |
| 1920 | 6-OH | H | $SO_2CH_2COOEt$ | 3-Me | 5-CONHMe | 1-Al—Pip(4) |
| 1921 | 6-OH | H | $SO_2CH_2COOEt$ | 3-Me | 5-CONHEt | 1-Al—Pip(4) |
| 1922 | 6-OH | H | $SO_2CH_2COOEt$ | 3-Me | 5-CONHPr | 1-Al—Pip(4) |
| 1923 | 6-OH | H | $SO_2CH_2COOEt$ | 3-Me | 5-CONHBu | 1-Al—Pip(4) |
| 1924 | 6-OH | H | $SO_2CH_2COOEt$ | 3-Me | 5-CONHPn | 1-Al—Pip(4) |
| 1925 | 6-OH | H | $SO_2CH_2COOEt$ | 3-Me | 5-CONHHx | 1-Al—Pip(4) |
| 1926 | 6-OH | H | $SO_2CH_2COOEt$ | 2-CONH$_2$ | 6-CONH$_2$ | 1-Al—Pip(4) |
| 1927 | 6-OH | H | $SO_2CH_2COOEt$ | 3-CONH$_2$ | 5-CONH$_2$ | 1-Al—Pip(4) |
| 1928 | 6-OH | H | $SO_2CH_2COOEt$ | 3-CONHMe | 5-CONHMe | 1-Al—Pip(4) |
| 1929 | 6-OH | H | $SO_2CH_2COOEt$ | 3-CONHEt | 5-CONHEt | 1-Al—Pip(4) |
| 1930 | H | H | $SO_2CH_2COOPr$ | H | H | 1-Al—Pip(4) |
| 1931 | H | H | $SO_2CH_2COOBu$ | H | H | 1-Al—Pip(4) |
| 1932 | H | H | $SO_2CH_2COOPn$ | H | H | 1-Al—Pip(4) |
| 1933 | H | H | $SO_2CH_2COOHx$ | H | H | 1-Al—Pip(4) |
| 1934 | H | H | $SO_2(CH_2)_2COOEt$ | H | H | 1-Al—Pip(4) |
| 1935 | H | H | $SO_2(CH_2)_3COOEt$ | H | H | 1-Al—Pip(4) |
| 1936 | H | H | $SO_2(CH_2)_4COOEt$ | H | H | 1-Al—Pip(4) |
| 1937 | H | H | $SO_2(CH_2)_5COOEt$ | H | H | 1-Al—Pip(4) |
| 1938 | H | H | $SO_2(CH_2)_6COOEt$ | H | H | 1-Al—Pip(4) |
| 1939 | H | H | $SO_2CH_2COOH$ | H | H | 1-Al—Pip(4) |
| 1940 | H | H | $SO_2CH_2COOH$ | 2-F | H | 1-Al—Pip(4) |
| 1941 | H | H | $SO_2CH_2COOH$ | 3-F | H | 1-Al—Pip(4) |
| 1942 | H | H | $SO_2CH_2COOH$ | 2-Cl | H | 1-Al—Pip(4) |
| 1943 | H | H | $SO_2CH_2COOH$ | 3-Cl | H | 1-Al—Pip(4) |
| 1944 | H | H | $SO_2CH_2COOH$ | 2-Br | H | 1-Al—Pip(4) |
| 1945 | H | H | $SO_2CH_2COOH$ | 3-Br | H | 1-Al—Pip(4) |
| 1946 | H | H | $SO_2CH_2COOH$ | 2-I | H | 1-Al—Pip(4) |
| 1947 | H | H | $SO_2CH_2COOH$ | 3-I | H | 1-Al—Pip(4) |
| 1948 | H | H | $SO_2CH_2COOH$ | 2-Me | H | 1-Al—Pip(4) |
| 1949 | H | H | $SO_2CH_2COOH$ | 3-Me | H | 1-Al—Pip(4) |
| 1950 | H | H | $SO_2CH_2COOH$ | 2-Et | H | 1-Al—Pip(4) |
| 1951 | H | H | $SO_2CH_2COOH$ | 3-Et | H | 1-Al—Pip(4) |
| 1952 | H | H | $SO_2CH_2COOH$ | 2-Pr | H | 1-Al—Pip(4) |
| 1953 | H | H | $SO_2CH_2COOH$ | 3-Pr | H | 1-Al—Pip(4) |

TABLE 1-continued (I)

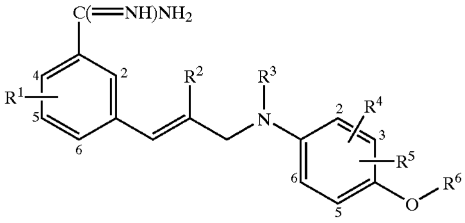

| Cpd. No. | $R^1$ | $R^2$ | $R^3$ | $R^4$ | $R^5$ | $R^6$ |
|---|---|---|---|---|---|---|
| 1954 | H | H | $SO_2CH_2COOH$ | 2-iPr | H | 1-Al—Pip(4) |
| 1955 | H | H | $SO_2CH_2COOH$ | 3-iPr | H | 1-Al—Pip(4) |
| 1956 | H | H | $SO_2CH_2COOH$ | 2-Bu | H | 1-Al—Pip(4) |
| 1957 | H | H | $SO_2CH_2COOH$ | 3-Bu | H | 1-Al—Pip(4) |
| 1958 | H | H | $SO_2CH_2COOH$ | 2-iBu | H | 1-Al—Pip(4) |
| 1959 | H | H | $SO_2CH_2COOH$ | 3-iBu | H | 1-Al—Pip(4) |
| 1960 | H | H | $SO_2CH_2COOH$ | 2-sBu | H | 1-Al—Pip(4) |
| 1961 | H | H | $SO_2CH_2COOH$ | 3-sBu | H | 1-Al—Pip(4) |
| 1962 | H | H | $SO_2CH_2COOH$ | 2-tBu | H | 1-Al—Pip(4) |
| 1963 | H | H | $SO_2CH_2COOH$ | 3-tBu | H | 1-Al—Pip(4) |
| 1964 | H | H | $SO_2CH_2COOH$ | 2-Pn | H | 1-Al—Pip(4) |
| 1965 | H | H | $SO_2CH_2COOH$ | 3-Pn | H | 1-Al—Pip(4) |
| 1966 | H | H | $SO_2CH_2COOH$ | 2-Hx | H | 1-Al—Pip(4) |
| 1967 | H | H | $SO_2CH_2COOH$ | 3-Hx | H | 1-Al—Pip(4) |
| 1968 | H | H | $SO_2CH_2COOH$ | 2-$CF_3$ | H | 1-Al—Pip(4) |
| 1969 | H | H | $SO_2CH_2COOH$ | 3-$CF_3$ | H | 1-Al—Pip(4) |
| 1970 | H | H | $SO_2CH_2COOH$ | 2-OMe | H | 1-Al—Pip(4) |
| 1971 | H | H | $SO_2CH_2COOH$ | 3-OMe | H | 1-Al—Pip(4) |
| 1972 | H | H | $SO_2CH_2COOH$ | 2-OEt | H | 1-Al—Pip(4) |
| 1973 | H | H | $SO_2CH_2COOH$ | 3-OEt | H | 1-Al—Pip(4) |
| 1974 | H | H | $SO_2CH_2COOH$ | 2-COOH | H | 1-Al—Pip(4) |
| 1975 | H | H | $SO_2CH_2COOH$ | 3-COOH | H | 1-Al—Pip(4) |
| 1976 | H | H | $SO_2CH_2COOH$ | 2-COOMe | H | 1-Al—Pip(4) |
| 1977 | H | H | $SO_2CH_2COOH$ | 3-COOMe | H | 1-Al—Pip(4) |
| 1978 | H | H | $SO_2CH_2COOH$ | 2-COOEt | H | 1-Al—Pip(4) |
| 1979 | H | H | $SO_2CH_2COOH$ | 3-COOEt | H | 1-Al—Pip(4) |
| 1980 | H | H | $SO_2CH_2COOH$ | 2-COOPr | H | 1-Al—Pip(4) |
| 1981 | H | H | $SO_2CH_2COOH$ | 3-COOPr | H | 1-Al—Pip(4) |
| 1982 | H | H | $SO_2CH_2COOH$ | 2-COOBu | H | 1-Al—Pip(4) |
| 1983 | H | H | $SO_2CH_2COOH$ | 3-COOBu | H | 1-Al—Pip(4) |
| 1984 | H | H | $SO_2CH_2COOH$ | 2-COOPn | H | 1-Al—Pip(4) |
| 1985 | H | H | $SO_2CH_2COOH$ | 3-COOPn | H | 1-Al—Pip(4) |
| 1986 | H | H | $SO_2CH_2COOH$ | 2-COOHx | H | 1-Al—Pip(4) |
| 1987 | H | H | $SO_2CH_2COOH$ | 3-COOHx | H | 1-Al—Pip(4) |
| 1988 | H | H | $SO_2CH_2COOH$ | 2-$CONH_2$ | H | 1-Al—Pip(4) |
| 1989 | H | H | $SO_2CH_2COOH$ | 3-$CONH_2$ | H | 1-Al—Pip(4) |
| 1990 | H | H | $SO_2CH_2COOH$ | 2-CONHMe | H | 1-Al—Pip(4) |
| 1991 | H | H | $SO_2CH_2COOH$ | 3-CONHMe | H | 1-Al—Pip(4) |
| 1992 | H | H | $SO_2CH_2COOH$ | 2-CONHEt | H | 1-Al—Pip(4) |
| 1993 | H | H | $SO_2CH_2COOH$ | 3-CONHEt | H | 1-Al—Pip(4) |
| 1994 | H | H | $SO_2CH_2COOH$ | 2-$CON(Me)_2$ | H | 1-Al—Pip(4) |
| 1995 | H | H | $SO_2CH_2COOH$ | 3-$CON(Me)_2$ | H | 1-Al—Pip(4) |
| 1996 | H | H | $SO_2CH_2COOH$ | 2-CON(Me)Et | H | 1-Al—Pip(4) |
| 1997 | H | H | $SO_2CH_2COOH$ | 3-CON(Me)Et | H | 1-Al—Pip(4) |
| 1998 | H | H | $SO_2CH_2COOH$ | 2-$CON(Et)_2$ | H | 1-Al—Pip(4) |
| 1999 | H | H | $SO_2CH_2COOH$ | 3-$CON(Et)_2$ | H | 1-Al—Pip(4) |
| 2000 | H | H | $SO_2CH_2COOH$ | 2-F | 3-F | 1-Al—Pip(4) |
| 2001 | H | H | $SO_2CH_2COOH$ | 2-F | 5-F | 1-Al—Pip(4) |
| 2002 | H | H | $SO_2CH_2COOH$ | 2-F | 6-F | 1-Al—Pip(4) |
| 2003 | H | H | $SO_2CH_2COOH$ | 3-F | 5-F | 1-Al—Pip(4) |
| 2004 | H | H | $SO_2CH_2COOH$ | 2-Cl | 3-Cl | 1-Al—Pip(4) |
| 2005 | H | H | $SO_2CH_2COOH$ | 2-Cl | 5-Cl | 1-Al—Pip(4) |
| 2006 | H | H | $SO_2CH_2COOH$ | 2-Cl | 6-Cl | 1-Al—Pip(4) |
| 2007 | H | H | $SO_2CH_2COOH$ | 3-Cl | 5-Cl | 1-Al—Pip(4) |
| 2008 | H | H | $SO_2CH_2COOH$ | 2-Me | 3-Me | 1-Al—Pip(4) |
| 2009 | H | H | $SO_2CH_2COOH$ | 2-Me | 5-Me | 1-Al—Pip(4) |
| 2010 | H | H | $SO_2CH_2COOH$ | 2-Me | 6-Me | 1-Al—Pip(4) |
| 2011 | H | H | $SO_2CH_2COOH$ | 3-Me | 5-Me | 1-Al—Pip(4) |
| 2012 | H | H | $SO_2CH_2COOH$ | 2-Cl | 5-$CONH_2$ | 1-Al—Pip(4) |
| 2013 | H | H | $SO_2CH_2COOH$ | 3-Cl | 5-$CONH_2$ | 1-Al—Pip(4) |
| 2014 | H | H | $SO_2CH_2COOH$ | 3-Cl | 5-CONHMe | 1-Al—Pip(4) |
| 2015 | H | H | $SO_2CH_2COOH$ | 3-Cl | 5-CONHEt | 1-Al—Pip(4) |
| 2016 | H | H | $SO_2CH_2COOH$ | 3-Cl | 5-CONHPr | 1-Al—Pip(4) |

TABLE 1-continued (I)

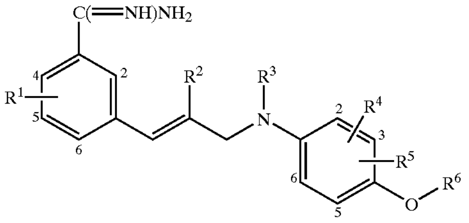

| Cpd. No. | $R^1$ | $R^2$ | $R^3$ | $R^4$ | $R^5$ | $R^6$ |
|---|---|---|---|---|---|---|
| 2017 | H | H | $SO_2CH_2COOH$ | 3-Cl | 5-CONHBu | 1-Al—Pip(4) |
| 2018 | H | H | $SO_2CH_2COOH$ | 3-Cl | 5-CONHPn | 1-Al—Pip(4) |
| 2019 | H | H | $SO_2CH_2COOH$ | 3-Cl | 5-CONHHx | 1-Al—Pip(4) |
| 2020 | H | H | $SO_2CH_2COOH$ | 2-Me | $5\text{-}CONH_2$ | 1-Al—Pip(4) |
| 2021 | H | H | $SO_2CH_2COOH$ | 2-Me | 5-CONHMe | 1-Al—Pip(4) |
| 2022 | H | H | $SO_2CH_2COOH$ | 2-Me | 5-CONHEt | 1-Al—Pip(4) |
| 2023 | H | H | $SO_2CH_2COOH$ | 2-Me | 5-CONHPr | 1-Al—Pip(4) |
| 2024 | H | H | $SO_2CH_2COOH$ | 2-Me | 5-CONHBu | 1-Al—Pip(4) |
| 2025 | H | H | $SO_2CH_2COOH$ | 2-Me | 5-CONHPn | 1-Al—Pip(4) |
| 2026 | H | H | $SO_2CH_2COOH$ | 2-Me | 5-CONHHx | 1-Al—Pip(4) |
| 2027 | H | H | $SO_2CH_2COOH$ | 3-Me | $5\text{-}CONH_2$ | 1-Al—Pip(4) |
| 2028 | H | H | $SO_2CH_2COOH$ | 3-Me | 5-CONHMe | 1-Al—Pip(4) |
| 2029 | H | H | $SO_2CH_2COOH$ | 3-Me | 5-CONHEt | 1-Al—Pip(4) |
| 2030 | H | H | $SO_2CH_2COOH$ | 3-Me | 5-CONHPr | 1-Al—Pip(4) |
| 2031 | H | H | $SO_2CH_2COOH$ | 3-Me | 5-CONHBu | 1-Al—Pip(4) |
| 2032 | H | H | $SO_2CH_2COOH$ | 3-Me | 5-CONHPn | 1-Al—Pip(4) |
| 2033 | H | H | $SO_2CH_2COOH$ | 3-Me | 5-CONHHx | 1-Al—Pip(4) |
| 2034 | H | H | $SO_2CH_2COOH$ | $2\text{-}CONH_2$ | $6\text{-}CONH_2$ | 1-Al—Pip(4) |
| 2035 | H | H | $SO_2CH_2COOH$ | $3\text{-}CONH_2$ | $5\text{-}CONH_2$ | 1-Al—Pip(4) |
| 2036 | H | H | $SO_2CH_2COOH$ | 3-CONHMe | 5-CONHMe | 1-Al—Pip(4) |
| 2037 | H | H | $SO_2CH_2COOH$ | 3-CONHEt | 5-CONHEt | 1-Al—Pip(4) |
| 2038 | H | F | $SO_2CH_2COOH$ | H | H | 1-Al—Pip(4) |
| 2039 | H | F | $SO_2CH_2COOH$ | 2-F | H | 1-Al—Pip(4) |
| 2040 | H | F | $SO_2CH_2COOH$ | 3-F | H | 1-Al—Pip(4) |
| 2041 | H | F | $SO_2CH_2COOH$ | 2-Cl | H | 1-Al—Pip(4) |
| 2042 | H | F | $SO_2CH_2COOH$ | 3-Cl | H | 1-Al—Pip(4) |
| 2043 | H | F | $SO_2CH_2COOH$ | 2-Br | H | 1-Al—Pip(4) |
| 2044 | H | F | $SO_2CH_2COOH$ | 3-Br | H | 1-Al—Pip(4) |
| 2045 | H | F | $SO_2CH_2COOH$ | 2-I | H | 1-Al—Pip(4) |
| 2046 | H | F | $SO_2CH_2COOH$ | 3-I | H | 1-Al—Pip(4) |
| 2047 | H | F | $SO_2CH_2COOH$ | 2-Me | H | 1-Al—Pip(4) |
| 2048 | H | F | $SO_2CH_2COOH$ | 3-Me | H | 1-Al—Pip(4) |
| 2049 | H | F | $SO_2CH_2COOH$ | 2-Et | H | 1-Al—Pip(4) |
| 2050 | H | F | $SO_2CH_2COOH$ | 3-Et | H | 1-Al—Pip(4) |
| 2051 | H | F | $SO_2CH_2COOH$ | 2-Pr | H | 1-Al—Pip(4) |
| 2052 | H | F | $SO_2CH_2COOH$ | 3-Pr | H | 1-Al—Pip(4) |
| 2053 | H | F | $SO_2CH_2COOH$ | 2-iPr | H | 1-Al—Pip(4) |
| 2054 | H | F | $SO_2CH_2COOH$ | 3-iPr | H | 1-Al—Pip(4) |
| 2055 | H | F | $SO_2CH_2COOH$ | 2-Bu | H | 1-Al—Pip(4) |
| 2056 | H | F | $SO_2CH_2COOH$ | 3-Bu | H | 1-Al—Pip(4) |
| 2057 | H | F | $SO_2CH_2COOH$ | 2-iBu | H | 1-Al—Pip(4) |
| 2058 | H | F | $SO_2CH_2COOH$ | 3-iBu | H | 1-Al—Pip(4) |
| 2059 | H | F | $SO_2CH_2COOH$ | 2-sBu | H | 1-Al—Pip(4) |
| 2060 | H | F | $SO_2CH_2COOH$ | 3-sBu | H | 1-Al—Pip(4) |
| 2061 | H | F | $SO_2CH_2COOH$ | 2-tBu | H | 1-Al—Pip(4) |
| 2062 | H | F | $SO_2CH_2COOH$ | 3-tBu | H | 1-Al—Pip(4) |
| 2063 | H | F | $SO_2CH_2COOH$ | 2-Pn | H | 1-Al—Pip(4) |
| 2064 | H | F | $SO_2CH_2COOH$ | 3-Pn | H | 1-Al—Pip(4) |
| 2065 | H | F | $SO_2CH_2COOH$ | 2-Hx | H | 1-Al—Pip(4) |
| 2066 | H | F | $SO_2CH_2COOH$ | 3-Hx | H | 1-Al—Pip(4) |
| 2067 | H | F | $SO_2CH_2COOH$ | $2\text{-}CF_3$ | H | 1-Al—Pip(4) |
| 2068 | H | F | $SO_2CH_2COOH$ | $3\text{-}CF_3$ | H | 1-Al—Pip(4) |
| 2069 | H | F | $SO_2CH_2COOH$ | 2-OMe | H | 1-Al—Pip(4) |
| 2070 | H | F | $SO_2CH_2COOH$ | 3-OMe | H | 1-Al—Pip(4) |
| 2071 | H | F | $SO_2CH_2COOH$ | 2-OEt | H | 1-Al—Pip(4) |
| 2072 | H | F | $SO_2CH_2COOH$ | 3-OEt | H | 1-Al—Pip(4) |
| 2073 | H | F | $SO_2CH_2COOH$ | 2-COOH | H | 1-Al—Pip(4) |
| 2074 | H | F | $SO_2CH_2COOH$ | 3-COOH | H | 1-Al—Pip(4) |
| 2075 | H | F | $SO_2CH_2COOH$ | 2-COOMe | H | 1-Al—Pip(4) |
| 2076 | H | F | $SO_29H_2COOH$ | 3-COOMe | H | 1-Al—Pip(4) |
| 2077 | H | F | $SO_2CH_2COOH$ | 2-COOEt | H | 1-Al—Pip(4) |
| 2078 | H | F | $SO_2CH_2COOH$ | 3-COOEt | H | 1-Al—Pip(4) |
| 2079 | H | F | $SO_2CH_2COOH$ | 2-COOPr | H | 1-Al—Pip(4) |

TABLE 1-continued (I)

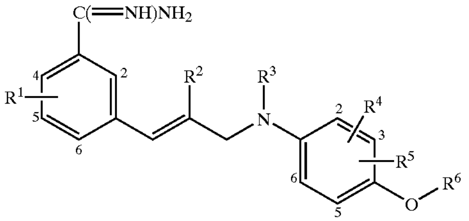

| Cpd. No. | $R^1$ | $R^2$ | $R^3$ | $R^4$ | $R^5$ | $R^6$ |
|---|---|---|---|---|---|---|
| 2080 | H | F | $SO_2CH_2COOH$ | 3-COOPr | H | 1-Al—Pip(4) |
| 2081 | H | F | $SO_2CH_2COOH$ | 2-COOBu | H | 1-Al—Pip(4) |
| 2082 | H | F | $SO_2CH_2COOH$ | 3-COOBu | H | 1-Al—Pip(4) |
| 2083 | H | F | $SO_2CH_2COOH$ | 2-COOPn | H | 1-Al—Pip(4) |
| 2084 | H | F | $SO_2CH_2COOH$ | 3-COOPn | H | 1-Al—Pip(4) |
| 2085 | H | F | $SO_2CH_2COOH$ | 2-COOHx | H | 1-Al—Pip(4) |
| 2086 | H | F | $SO_2CH_2COOH$ | 3-COOHx | H | 1-Al—Pip(4) |
| 2087 | H | F | $SO_2CH_2COOH$ | 2-$CONH_2$ | H | 1-Al—Pip(4) |
| 2088 | H | F | $SO_2CH_2COOH$ | 3-$CONH_2$ | H | 1-Al—Pip(4) |
| 2089 | H | F | $SO_2CH_2COOH$ | 2-CONHMe | H | 1-Al—Pip(4) |
| 2090 | H | F | $SO_2CH_2COOH$ | 3-CONHMe | H | 1-Al—Pip(4) |
| 2091 | H | F | $SO_2CH_2COOH$ | 2-CONHEt | H | 1-Al—Pip(4) |
| 2092 | H | F | $SO_2CH_2COOH$ | 3-CONHEt | H | 1-Al—Pip(4) |
| 2093 | H | F | $SO_2CH_2COOH$ | 2-$CON(Me)_2$ | H | 1-Al—Pip(4) |
| 2094 | H | F | $SO_2CH_2COOH$ | 3-$CON(Me)_2$ | H | 1-Al—Pip(4) |
| 2095 | H | F | $SO_2CH_2COOH$ | 2-CON(Me)Et | H | 1-Al—Pip(4) |
| 2096 | H | F | $SO_2CH_2COOH$ | 3-CON(Me)Et | H | 1-Al—Pip(4) |
| 2097 | H | F | $SO_2CH_2COOH$ | 2-$CON(Et)_2$ | H | 1-Al—Pip(4) |
| 2098 | H | F | $SO_2CH_2COOH$ | 3-$CON(Et)_2$ | H | 1-Al—Pip(4) |
| 2099 | H | Me | $SO_2CH_2COOH$ | H | H | 1-Al—Pip(4) |
| 2100 | H | Me | $SO_2CH_2COOH$ | 2-F | H | 1-Al—Pip(4) |
| 2101 | H | Me | $SO_2CH_2COOH$ | 3-F | H | 1-Al—Pip(4) |
| 2102 | H | Me | $SO_2CH_2COOH$ | 2-Cl | H | 1-Al—Pip(4) |
| 2103 | H | Me | $SO_2CH_2COOH$ | 3-Cl | H | 1-Al—Pip(4) |
| 2104 | H | Me | $SO_2CH_2COOH$ | 2-Br | H | 1-Al—Pip(4) |
| 2105 | H | Me | $SO_2CH_2COOH$ | 3-Br | H | 1-Al—Pip(4) |
| 2106 | H | Me | $SO_2CH_2COOH$ | 2-I | H | 1-Al—Pip(4) |
| 2107 | H | Me | $SO_2CH_2COOH$ | 3-I | H | 1-Al—Pip(4) |
| 2108 | H | Me | $SO_2CH_2COQH$ | 2-Me | H | 1-Al—Pip(4) |
| 2109 | H | Me | $SO_2CH_2COOH$ | 3-Me | H | 1-Al—Pip(4) |
| 2110 | H | Me | $SO_2CH_2COOH$ | 2-Et | H | 1-Al—Pip(4) |
| 2111 | H | Me | $SO_2CH_2COOH$ | 3-Et | H | 1-Al—Pip(4) |
| 2112 | H | Me | $SO_2CH_2COOH$ | 2-Pr | H | 1-Al—Pip(4) |
| 2113 | H | Me | $SO_2CH_2COOH$ | 3-Pr | H | 1-Al—Pip(4) |
| 2114 | H | Me | $SO_2CH_2COOH$ | 2-Bu | H | 1-Al—Pip(4) |
| 2115 | H | Me | $SO_2CH_2COOH$ | 3-Bu | H | 1-Al—Pip(4) |
| 2116 | H | Me | $SO_2CH_2COOH$ | 2-Pn | H | 1-Al—Pip(4) |
| 2117 | H | Me | $SO_2CH_2COOH$ | 3-Pn | H | 1-Al—Pip(4) |
| 2118 | H | Me | $SO_2CH_2COOH$ | 2-Hx | H | 1-Al—Pip(4) |
| 2119 | H | Me | $SO_2CH_2COOH$ | 3-Hx | H | 1-Al—Pip(4) |
| 2120 | H | Me | $SO_2CH_2COOH$ | 2-$CF_3$ | H | 1-Al—Pip(4) |
| 2121 | H | Me | $SO_2CH_2COOH$ | 3-$CF_3$ | H | 1-Al—Pip(4) |
| 2122 | H | Me | $SO_2CH_2COOH$ | 2-OMe | H | 1-Al—Pip(4) |
| 2123 | H | Me | $SO_2CH_2COOH$ | 3-OMe | H | 1-Al—Pip(4) |
| 2124 | H | Me | $SO_2CH_2COOH$ | 2-OEt | H | 1-Al—Pip(4) |
| 2125 | H | Me | $SO_2CH_2COOH$ | 3-OEt | H | 1-Al—Pip(4) |
| 2126 | H | Me | $SO_2CH_2COOH$ | 2-COOH | H | 1-Al—Pip(4) |
| 2127 | H | Me | $SO_2CH_2COOH$ | 3-COOH | H | 1-Al—Pip(4) |
| 2128 | H | Me | $SO_2CH_2COOH$ | 2-COOMe | H | 1-Al—Pip(4) |
| 2129 | H | Me | $SO_2CH_2COOH$ | 3-COOMe | H | 1-Al—Pip(4) |
| 2130 | H | Me | $SO_2CH_2COOH$ | 2-COOEt | H | 1-Al—Pip(4) |
| 2131 | H | Me | $SO_2CH_2COOH$ | 3-COOEt | H | 1-Al—Pip(4) |
| 2132 | H | Me | $SO_2CH_2COOH$ | 2-COOPr | H | 1-Al—Pip(4) |
| 2133 | H | Me | $SO_2CH_2COOH$ | 3-COOPr | H | 1-Al—Pip(4). |
| 2134 | H | Me | $SO_2CH_2COOH$ | 2-COOBu | H | 1-Al—Pip(4) |
| 2135 | H | Me | $SO_2CH_2COOH$ | 3-COOBu | H | 1-Al—Pip(4) |
| 2136 | H | Me | $SO_2CH_2COOH$ | 2-COOPn | H | 1-Al—Pip(4) |
| 2137 | H | Me | $SO_2CH_2COOH$ | 3-COOPn | H | 1-Al—Pip(4) |
| 2138 | H | Me | $SO_2CH_2COOH$ | 2-COOHx | H | 1-Al—Pip(4) |
| 2139 | H | Me | $SO_2CH_2COOH$ | 3-COOHx | H | 1-Al—Pip(4) |
| 2140 | H | Me | $SO_2CH_2COOH$ | 2-$CONH_2$ | H | 1-Al—Pip(4) |
| 2141 | H | Me | $SO_2CH_2COOH$ | 3-$CONH_2$ | H | 1-Al—Pip(4) |
| 2142 | H | Me | $SO_2CH_2COOH$ | 2-CONHMe | H | 1-Al—Pip(4) |

TABLE 1-continued (I)

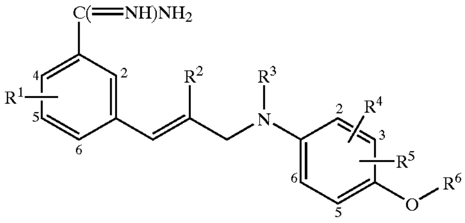

| Cpd. No. | $R^1$ | $R^2$ | $R^3$ | $R^4$ | $R^5$ | $R^6$ |
|---|---|---|---|---|---|---|
| 2143 | H | Me | $SO_2CH_2COOH$ | 3-CONHMe | H | 1-Al—Pip(4) |
| 2144 | H | Me | $SO_2CH_2COOH$ | 2-CONHEt | H | 1-Al—Pip(4) |
| 2145 | H | Me | $SO_2CH_2COOH$ | 3-CONHEt | H | 1-Al—Pip(4) |
| 2146 | H | Me | $SO_2CH_2COOH$ | 2-CON(Me)$_2$ | H | 1-Al—Pip(4) |
| 2147 | H | Me | $SO_2CH_2COOH$ | 3-CON(Me)$_2$ | H | 1-Al—Pip(4) |
| 2148 | H | Me | $SO_2CH_2COOH$ | 2-CON(Me)Et | H | 1-Al—Pip(4) |
| 2149 | H | Me | $SO_2CH_2COOH$ | 3-CON(Me)Et | H | 1-Al—Pip(4) |
| 2150 | H | Me | $SO_2CH_2COOH$ | 2-CON(Et)$_2$ | H | 1-Al—Pip(4) |
| 2151 | H | Me | $SO_2CH_2COOH$ | 3-CON(Et)$_2$ | H | 1-Al—Pip(4) |
| 2152 | 6-F | H | $SO_2CH_2COOH$ | H | H | 1-Al—Pip(4) |
| 2153 | 6-F | H | $SO_2CH_2COOH$ | 2-F | H | 1-Al—Pip(4) |
| 2154 | 6-F | H | $SO_2CH_2COOH$ | 3-F | H | 1-Al—Pip(4) |
| 2155 | 6-F | H | $SO_2CH_2COOH$ | 2-Cl | H | 1-Al—Pip(4) |
| 2156 | 6-F | H | $SO_2CH_2COOH$ | 3-Cl | H | 1-Al—Pip(4) |
| 2157 | 6-F | H | $SO_2CH_2COOH$ | 2-Br | H | 1-Al—Pip(4) |
| 2158 | 6-F | H | $SO_2CH_2COOH$ | 3-Br | H | 1-Al—Pip(4) |
| 2159 | 6-F | H | $SO_2CH_2COOH$ | 2-I | H | 1-Al—Pip(4) |
| 2160 | 6-F | H | $SO_2CH_2COOH$ | 3-I | H | 1-Al—Pip(4) |
| 2161 | 6-F | H | $SO_2CH_2COOH$ | 2-Me | H | 1-Al—Pip(4) |
| 2162 | 6-F | H | $SO_2CH_2COOH$ | 3-Me | H | 1-Al—Pip(4) |
| 2163 | 6-F | H | $SO_2CH_2COOH$ | 2-Et | H | 1-Al—Pip(4) |
| 2164 | 6-F | H | $SO_2CH_2COOH$ | 3-Et | H | 1-Al—Pip(4) |
| 2165 | 6-F | H | $SO_2CH_2COOH$ | 2-Pr | H | 1-Al—Pip(4) |
| 2166 | 6-F | H | $SO_2CH_2COOH$ | 3-Pr | H | 1-Al—Pip(4) |
| 2167 | 6-F | H | $SO_2CH_2COOH$ | 2-Bu | H | 1-Al—Pip(4) |
| 2168 | 6-F | H | $SO_2CH_2COOH$ | 3-Bu | H | 1-Al—Pip(4) |
| 2169 | 6-F | H | $SO_2CH_2COOH$ | 2-Pn | H | 1-Al—Pip(4) |
| 2170 | 6-F | H | $SO_2CH_2COOH$ | 3-Pn | H | 1-Al—Pip(4) |
| 2171 | 6-F | H | $SO_2CH_2COOH$ | 2-Hx | H | 1-Al—Pip(4) |
| 2172 | 6-F | H | $SO_2CH_2COOH$ | 3-Hx | H | 1-Al—Pip(4) |
| 2173 | 6-F | H | $SO_2CH_2COOH$ | 2-CF$_3$ | H | 1-Al—Pip(4) |
| 2174 | 6-F | H | $SO_2CH_2COOH$ | 3-CF$_3$ | H | 1-Al—Pip(4) |
| 2175 | 6-F | H | $SO_2CH_2COOH$ | 2-OMe | H | 1-Al—Pip(4) |
| 2176 | 6-F | H | $SO_2CH_2COOH$ | 3-OMe | H | 1-Al—Pip(4) |
| 2177 | 6-F | H | $SO_2CH_2COOH$ | 2-OEt | H | 1-Al—Pip(4) |
| 2178 | 6-F | H | $SO_2CH_2COOH$ | 3-OEt | H | 1-Al—Pip(4) |
| 2179 | 6-F | H | $SO_2CH_2COOH$ | 2-COOH | H | 1-Al—Pip(4) |
| 2180 | 6-F | H | $SO_2CH_2COOH$ | 3-COOH | H | 1-Al—Pip(4) |
| 2181 | 6-F | H | $SO_2CH_2COOH$ | 2-COOMe | H | 1-Al—Pip(4) |
| 2182 | 6-F | H | $SO_2CH_2COOH$ | 3-COOMe | H | 1-Al—Pip(4) |
| 2183 | 6-F | H | $SO_2CH_2COOH$ | 2-COOEt | H | 1-Al—Pip(4) |
| 2184 | 6-F | H | $SO_2CH_2COOH$ | 3-COOEt | H | 1-Al—Pip(4) |
| 2185 | 6-F | H | $SO_2CH_2COOH$ | 2-COOPr | H | 1-Al—Pip(4) |
| 2186 | 6-F | H | $SO_2CH_2COOH$ | 3-COOPr | H | 1-Al—Pip(4) |
| 2187 | 6-F | H | $SO_2CH_2COOH$ | 2-COOBu | H | 1-Al—Pip(4) |
| 2188 | 6-F | H | $SO_2CH_2COOH$ | 3-COOBu | H | 1-Al—Pip(4) |
| 2189 | 6-F | H | $SO_2CH_2COOH$ | 2-COOPn | H | 1-Al—Pip(4) |
| 2190 | 6-F | H | $SO_2CH_2COOH$ | 3-COOPn | H | 1-Al—Pip(4) |
| 2191 | 6-F | H | $SO_2CH_2COOH$ | 2-COOHx | H | 1-Al—Pip(4) |
| 2192 | 6-F | H | $SO_2CH_2COOH$ | 3-COOHx | H | 1-Al—Pip(4) |
| 2193 | 6-F | H | $SO_2CH_2COOH$ | 2-CONH$_2$ | H | 1-Al—Pip(4) |
| 2194 | 6-F | H | $SO_2CH_2COOH$ | 3-CONH$_2$ | H | 1-Al—Pip(4) |
| 2195 | 6-F | H | $SO_2CH_2COOH$ | 2-CONHMe | H | 1-Al—Pip(4) |
| 2196 | 6-F | H | $SO_2CH_2COOH$ | 3-CONHMe | H | 1-Al—Pip(4) |
| 2197 | 6-F | H | $SO_2CH_2COOH$ | 2-CONHEt | H | 1-Al—Pip(4) |
| 2198 | 6-F | H | $SO_2CH_2COOH$ | 3-CONHEt | H | 1-Al—Pip(4) |
| 2199 | 6-F | H | $SO_2CH_2COOH$ | 2-CON(Me)$_2$ | H | 1-Al—Pip(4) |
| 2200 | 6-F | H | $SO_2CH_2COOH$ | 3-CON(Me)$_2$ | H | 1-Al—Pip(4) |
| 2201 | 6-F | H | $SO_2CH_2COOH$ | 2-CON(Me)Et | H | 1-Al—Pip(4) |
| 2202 | 6-F | H | $SO_2CH_2COOH$ | 3-CON(Me)Et | H | 1-Al—Pip(4) |
| 2203 | 6-F | H | $SO_2CH_2COOH$ | 2-CON(Et)$_2$ | H | 1-Al—Pip(4) |
| 2204 | 6-F | H | $SO_2CH_2COOH$ | 3-CON(Et)$_2$ | H | 1-Al—Pip(4) |
| 2205 | 2-Me | H | $SO_2CH_2COOH$ | H | H | 1-Al—Pip(4) |

TABLE 1-continued (I)

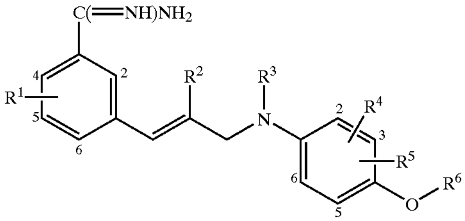

| Cpd. No. | $R^1$ | $R^2$ | $R^3$ | $R^4$ | $R^5$ | $R^6$ |
|---|---|---|---|---|---|---|
| 2206 | 3-Me | H | $SO_2CH_2COOH$ | H | H | 1-Al—Pip(4) |
| 2207 | 4-Me | H | $SO_2CH_2COOH$ | H | H | 1-Al—Pip(4) |
| 2208 | 5-Me | H | $SO_2CH_2COOH$ | H | H | 1-Al—Pip(4) |
| 2209 | 5-Me | H | $SO_2CH_2COOH$ | 2-F | H | 1-Al—Pip(4) |
| 2210 | 5-Me | H | $SO_2CH_2COOH$ | 3-F | H | 1-Al—Pip(4) |
| 2211 | 5-Me | H | $SO_2CH_2COOH$ | 2-Cl | H | 1-Al—Pip(4) |
| 2212 | 5-Me | H | $SO_2CH_2COOH$ | 3-Cl | H | 1-Al—Pip(4) |
| 2213 | 5-Me | H | $SO_2CH_2COOH$ | 2-Br | H | 1-Al—Pip(4) |
| 2214 | 5-Me | H | $SO_2CH_2COOH$ | 3-Br | H | 1-Al—Pip(4) |
| 2215 | 5-Me | H | $SO_2CH_2COOH$ | 2-I | H | 1-Al—Pip(4) |
| 2216 | 5-Me | H | $SO_2CH_2COOH$ | 3-I | H | 1-Al—Pip(4) |
| 2217 | 5-Me | H | $SO_2CH_2COOH$ | 2-Me | H | 1-Al—Pip(4) |
| 2218 | 5-Me | H | $SO_2CH_2COOH$ | 3-Me | H | 1-Al—Pip(4) |
| 2219 | 5-Me | H | $SO_2CH_2COOH$ | 2-Et | H | 1-Al—Pip(4) |
| 2220 | 5-Me | H | $SO_2CH_2COOH$ | 3-Et | H | 1-Al—Pip(4) |
| 2221 | 5-Me | H | $SO_2CH_2COOH$ | 2-Pr | H | 1-Al—Pip(4) |
| 2222 | 5-Me | H | $SO_2CH_2COOH$ | 3-Pr | H | 1-Al—Pip(4) |
| 2223 | 5-Me | H | $SO_2CH_2COOH$ | 2-Bu | H | 1-Al—Pip(4) |
| 2224 | 5-Me | H | $SO_2CH_2COOH$ | 3-Bu | H | 1-Al—Pip(4) |
| 2225 | 5-Me | H | $SO_2CH_2COOH$ | 2-Pn | H | 1-Al—Pip(4) |
| 2226 | 5-Me | H | $SO_2CH_2COOH$ | 3-Pn | H | 1-Al—Pip(4) |
| 2227 | 5-Me | H | $SO_2CH_2COOH$ | 2-Hx | H | 1-Al—Pip(4) |
| 2228 | 5-Me | H | $SO_2CH_2COOH$ | 3-Hx | H | 1-Al—Pip(4) |
| 2229 | 5-Me | H | $SO_2CH_2COOH$ | $2-CF_3$ | H | 1-Al—Pip(4) |
| 2230 | 5-Me | H | $SO_2CH_2COOH$ | $3-CF_3$ | H | 1-Al—Pip(4) |
| 2231 | 5-Me | H | $SO_2CH_2COOH$ | 2-OMe | H | 1-Al—Pip(4) |
| 2232 | 5-Me | H | $SO_2CH_2COOH$ | 3-OMe | H | 1-Al—Pip(4) |
| 2233 | 5-Me | H | $SO_2CH_2COOH$ | 2-OEt | H | 1-Al—Pip(4) |
| 2234 | 5-Me | H | $SO_2CH_2COOH$ | 3-OEt | H | 1-Al—Pip(4) |
| 2235 | 5-Me | H | $SO_2CH_2COOH$ | 2-COOH | H | 1-Al—Pip(4) |
| 2236 | 5-Me | H | $SO_2CH_2COOH$ | 3-COOH | H | 1-Al—Pip(4) |
| 2237 | 5-Me | H | $SO_2CH_2COOH$ | 2-COOMe | H | 1-Al—Pip(4) |
| 2238 | 5-Me | H | $SO_2CH_2COOH$ | 3-COOMe | H | 1-Al—Pip(4) |
| 2239 | 5-Me | H | $SO_2CH_2COOH$ | 2-COOEt | H | 1-Al—Pip(4) |
| 2240 | 5-Me | H | $SO_2CH_2COOH$ | 3-COOEt | H | 1-Al—Pip(4) |
| 2241 | 5-Me | H | $SO_2CH_2COOH$ | 2-COOPr | H | 1-Al—Pip(4) |
| 2242 | 5-Me | H | $SO_2CH_2COOH$ | 3-COOPr | H | 1-Al—Pip(4) |
| 2243 | 5-Me | H | $SO_2CH_2COOH$ | 2-COOBu | H | 1-Al—Pip(4) |
| 2244 | 5-Me | H | $SO_2CH_2COOH$ | 3-COOBu | H | 1-Al—Pip(4) |
| 2245 | 5-Me | H | $SO_2CH_2COOH$ | 2-COOPn | H | 1-Al—Pip(4) |
| 2246 | 5-Me | H | $SO_2CH_2COOH$ | 3-COOPn | H | 1-Al—Pip(4) |
| 2247 | 5-Me | H | $SO_2CH_2COOH$ | 2-COOHx | H | 1-Al—Pip(4) |
| 2248 | 5-Me | H | $SO_2CH_2COOH$ | 3-COOHx | H | 1-Al—Pip(4) |
| 2249 | 5-Me | H | $SO_2CH_2COOH$ | $2-CONH_2$ | H | 1-Al—Pip(4) |
| 2250 | 5-Me | H | $SO_2CH_2COOH$ | $3-CONH_2$ | H | 1-Al—Pip(4) |
| 2251 | 5-Me | H | $SO_2CH_2COOH$ | 2-CONHMe | H | 1-Al—Pip(4) |
| 2252 | 5-Me | H | $SO_2CH_2COOH$ | 3-CONHMe | H | 1-Al—Pip(4) |
| 2253 | 5-Me | H | $SO_2CH_2COOH$ | 2-CONHEt | H | 1-Al—Pip(4) |
| 2254 | 5-Me | H | $SO_2CH_2COOH$ | 3-CONHEt | H | 1-Al—Pip(4) |
| 2255 | 5-Me | H | $SO_2CH_2COOH$ | $2-CON(Me)_2$ | H | 1-Al—Pip(4) |
| 2256 | 5-Me | H | $SO_2CH_2COOH$ | $3-CON(Me)_2$ | H | 1-Al—Pip(4) |
| 2257 | 5-Me | H | $SO_2CH_2COOH$ | 2-CON(Me)Et | H | 1-Al—Pip(4) |
| 2258 | 5-Me | H | $SO_2CH_2COOH$ | 3-CON(Me)Et | H | 1-Al—Pip(4) |
| 2259 | 5-Me | H | $SO_2CH_2COOH$ | $2-CON(Et)_2$ | H | 1-Al—Pip(4) |
| 2260 | 5-Me | H | $SO_2CH_2COOH$ | $3-CON(Et)_2$ | H | 1-Al—Pip(4) |
| 2261 | 6-Me | H | $SO_2CH_2COOH$ | H | H | 1-Al—Pip(4) |
| 2262 | 6-OH | H | $SO_2CH_2COOH$ | H | H | 1-Al—Pip(4) |
| 2263 | 6-OH | H | $SO_2CH_2COOH$ | 2-F | H | 1-Al—Pip(4) |
| 2264 | 6-OH | H | $SO_2CH_2COOH$ | 3-F | H | 1-Al—Pip(4) |
| 2265 | 6-OH | H | $SO_2CH_2COOH$ | 2-Cl | H | 1-Al—Pip(4) |
| 2266 | 6-OH | H | $SO_2CH_2COOH$ | 3-Cl | H | 1-Al—Pip(4) |
| 2267 | 6-OH | H | $SO_2CH_2COOH$ | 2-Br | H | 1-Al—Pip(4) |
| 2268 | 6-OH | H | $SO_2CH_2COOH$ | 3-Br | H | 1-Al—Pip(4) |

TABLE 1-continued

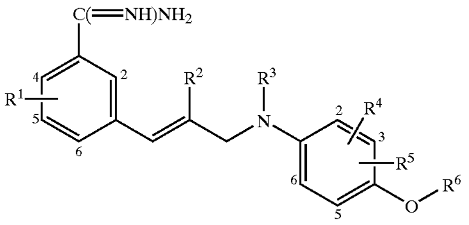

(I)

| Cpd. No. | $R^1$ | $R^2$ | $R^3$ | $R^4$ | $R^5$ | $R^6$ |
|---|---|---|---|---|---|---|
| 2269 | 6-OH | H | $SO_2CH_2COOH$ | 2-I | H | 1-Al—Pip(4) |
| 2270 | 6-OH | H | $SO_2CH_2COOH$ | 3-I | H | 1-Al—Pip(4) |
| 2271 | 6-OH | H | $SO_2CH_2COOH$ | 2-Me | H | 1-Al—Pip(4) |
| 2272 | 6-OH | H | $SO_2CH_2COOH$ | 3-Me | H | 1-Al—Pip(4) |
| 2273 | 6-OH | H | $SO_2CH_2COOH$ | 2-Et | H | 1-Al—Pip(4) |
| 2274 | 6-OH | H | $SO_2CH_2COOH$ | 3-Et | H | 1-Al—Pip(4) |
| 2275 | 6-OH | H | $SO_2CH_2COOH$ | 2-Pr | H | 1-Al—Pip(4) |
| 2276 | 6-OH | H | $SO_2CH_2COOH$ | 3-Pr | H | 1-Al—Pip(4) |
| 2277 | 6-OH | H | $SO_2CH_2COOH$ | 2-Bu | H | 1-Al—Pip(4) |
| 2278 | 6-OH | H | $SO_2CH_2COOH$ | 3-Bu | H | 1-Al—Pip(4) |
| 2279 | 6-OH | H | $SO_2CH_2COOH$ | 2-Pn | H | 1-Al—Pip(4) |
| 2280 | 6-OH | H | $SO_2CH_2COOH$ | 3-Pn | H | 1-Al—Pip(4) |
| 2281 | 6-OH | H | $SO_2CH_2COOH$ | 2-Hx | H | 1-Al—Pip(4) |
| 2282 | 6-OH | H | $SO_2CH_2COOH$ | 3-Hx | H | 1-Al—Pip(4) |
| 2283 | 6-OH | H | $SO_2CH_2COOH$ | 2-$CF_3$ | H | 1-Al—Pip(4) |
| 2284 | 6-OH | H | $SO_2CH_2COOH$ | 3-$CF_3$ | H | 1-Al—Pip(4) |
| 2285 | 6-OH | H | $SO_2CH_2COOH$ | 2-OMe | H | 1-Al—Pip(4) |
| 2286 | 6-OH | H | $SO_2CH_2COOH$ | 3-OMe | H | 1-Al—Pip(4) |
| 2287 | 6-OH | H | $SO_2CH_2COOH$ | 2-OEt | H | 1-Al—Pip(4) |
| 2288 | 6-OH | H | $SO_2CH_2COOH$ | 3-OEt | H | 1-Al—Pip(4) |
| 2289 | 6-OH | H | $SO_2CH_2COOH$ | 2-COOH | H | 1-Al—Pip(4) |
| 2290 | 6-OH | H | $SO_2CH_2COOH$ | 3-COOH | H | 1-Al—Pip(4) |
| 2291 | 6-OH | H | $SO_2CH_2COOH$ | 2-COOMe | H | 1-Al—Pip(4) |
| 2292 | 6-OH | H | $SO_2CH_2COOH$ | 3-COOMe | H | 1-Al—Pip(4) |
| 2293 | 6-OH | H | $SO_2CH_2COOH$ | 2-COOEt | H | 1-Al—Pip(4) |
| 2294 | 6-OH | H | $SO_2CH_2COOH$ | 3-COOEt | H | 1-Al—Pip(4) |
| 2295 | 6-OH | H | $SO_2CH_2COOH$ | 2-COOPr | H | 1-Al—Pip(4) |
| 2296 | 6-OH | H | $SO_2CH_2COOH$ | 3-COOPr | H | 1-Al—Pip(4) |
| 2297 | 6-OH | H | $SO_2CH_2COOH$ | 2-COOBu | H | 1-Al—Pip(4) |
| 2298 | 6-OH | H | $SO_2CH_2COOH$ | 3-COOBu | H | 1-Al—Pip(4) |
| 2299 | 6-OH | H | $SO_2CH_2COOH$ | 2-COOPn | H | 1-Al—Pip(4) |
| 2300 | 6-OH | H | $SO_2CH_2COOH$ | 3-COOPn | H | 1-Al—Pip(4) |
| 2301 | 6-OH | H | $SO_2CH_2COOH$ | 2-COOHx | H | 1-Al—Pip(4) |
| 2302 | 6-OH | H | $SO_2CH_2COOH$ | 3-COOHx | H | 1-Al—Pip(4) |
| 2303 | 6-OH | H | $SO_2CH_2COOH$ | 2-$CONH_2$ | H | 1-Al—Pip(4) |
| 2304 | 6-OH | H | $SO_2CH_2COOH$ | 3-$CONH_2$ | H | 1-Al—Pip(4) |
| 2305 | 6-OH | H | $SO_2CH_2COOH$ | 2-CONHMe | H | 1-Al—Pip(4) |
| 2306 | 6-OH | H | $SO_2CH_2COOH$ | 3-CONHMe | H | 1-Al—Pip(4) |
| 2307 | 6-OH | H | $SO_2CH_2COOH$ | 2-CONHEt | H | 1-Al—Pip(4) |
| 2308 | 6-OH | H | $SO_2CH_2COOH$ | 3-CONHEt | H | 1-Al—Pip(4) |
| 2309 | 6-OH | H | $SO_2CH_2COOH$ | 2-$CON(Me)_2$ | H | 1-Al—Pip(4) |
| 2310 | 6-OH | H | $SO_2CH_2COOH$ | 3-$CON(Me)_2$ | H | 1-Al—Pip(4) |
| 2311 | 6-OH | H | $SO_2CH_2COOH$ | 2-CON(Me)Et | H | 1-Al—Pip(4) |
| 2312 | 6-OH | H | $SO_2CH_2COOH$ | 3-CON(Me)Et | H | 1-Al—Pip(4) |
| 2313 | 6-OH | H | $SO_2CH_2COOH$ | 2-$CON(Et)_2$ | H | 1-Al—Pip(4) |
| 2314 | 6-OH | H | $SO_2CH_2COOH$ | 3-$CON(Et)_2$ | H | 1-Al—Pip(4) |
| 2315 | 6-OH | H | $SO_2CH_2COOH$ | 2-F | 3-F | 1-Al—Pip(4) |
| 2316 | 6-OH | H | $SO_2CH_2COOH$ | 2-F | 5-F | 1-Al—Pip(4) |
| 2317 | 6-OH | H | $SO_2CH_2COOH$ | 2-F | 6-F | 1-Al—Pip(4) |
| 2318 | 6-OH | H | $SO_2CH_2COOH$ | 3-F | 5-F | 1-Al—Pip(4) |
| 2319 | 6-OH | H | $SO_2CH_2COOH$ | 2-Cl | 3-Cl | 1-Al—Pip(4) |
| 2320 | 6-OH | H | $SO_2CH_2COOH$ | 2-Cl | 5-Cl | 1-Al—Pip(4) |
| 2321 | 6-OH | H | $SO_2CH_2COOH$ | 2-Cl | 6-Cl | 1-Al—Pip(4) |
| 2322 | 6-OH | H | $SO_2CH_2COOH$ | 3-Cl | 5-Cl | 1-Al—Pip(4) |
| 2323 | 6-OH | H | $SO_2CH_2COOH$ | 2-Me | 3-Me | 1-Al—Pip(4) |
| 2324 | 6-OH | H | $SO_2CH_2COOH$ | 2-Me | 5-Me | 1-Al—Pip(4) |
| 2325 | 6-OH | H | $SO_2CH_2COOH$ | 2-Me | 6-Me | 1-Al—Pip(4) |
| 2326 | 6-OH | H | $SO_2CH_2COOH$ | 3-Me | 5-Me | 1-Al—Pip(4) |
| 2327 | 6-OH | H | $SO_2CH_2COOH$ | 2-Cl | 5-$CONH_2$ | 1-Al—Pip(4) |
| 2328 | 6-OH | H | $SO_2CH_2COOH$ | 3-Cl | 5-$CONH_2$ | 1-Al—Pip(4) |
| 2329 | 6-OH | H | $SO_2CH_2COOH$ | 3-Cl | 5-CONHMe | 1-Al—Pip(4) |
| 2330 | 6-OH | H | $SO_2CH_2COOH$ | 3-Cl | 5-CONHEt | 1-Al—Pip(4) |
| 2331 | 6-OH | H | $SO_2CH_2COOH$ | 3-Cl | 5-CONHPr | 1-Al—Pip(4) |

TABLE 1-continued (I)

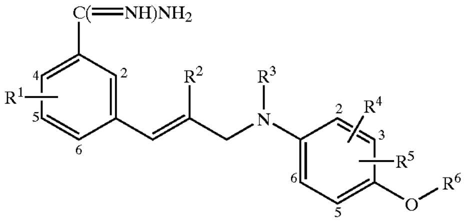

| Cpd. No. | $R^1$ | $R^2$ | $R^3$ | $R^4$ | $R^5$ | $R^6$ |
|---|---|---|---|---|---|---|
| 2332 | 6-OH | H | $SO_2CH_2COOH$ | 3-Cl | 5-CONHBu | 1-Al—Pip(4) |
| 2333 | 6-OH | H | $SO_2CH_2COOH$ | 3-Cl | 5-CONHPn | 1-Al—Pip(4) |
| 2334 | 6-OH | H | $SO_2CH_2COOH$ | 3-Cl | 5-CONHHx | 1-Al—Pip(4) |
| 2335 | 6-OH | H | $SO_2CH_2COOH$ | 2-Me | 5-$CONH_2$ | 1-Al—Pip(4) |
| 2336 | 6-OH | H | $SO_2CH_2COOH$ | 2-Me | 5-CONHMe | 1-Al—Pip(4) |
| 2337 | 6-OH | H | $SO_2CH_2COOH$ | 2-Me | 5-CONHEt | 1-Al—Pip(4) |
| 2338 | 6-OH | H | $SO_2CH_2COOH$ | 2-Me | 5-CONHPr | 1-Al—Pip(4) |
| 2339 | 6-OH | H | $SO_2CH_2COOH$ | 2-Me | 5-CONHBu | 1-Al—Pip(4) |
| 2340 | 6-OH | H | $SO_2CH_2COOH$ | 2-Me | 5-CONHPn | 1-Al—Pip(4) |
| 2341 | 6-OH | H | $SO_2CH_2COOH$ | 2-Me | 5-CONHHx | 1-Al—Pip(4) |
| 2342 | 6-OH | H | $SO_2CH_2COOH$ | 3-Me | 5-$CONH_2$ | 1-Al—Pip(4) |
| 2343 | 6-OH | H | $SO_2CH_2COOH$ | 3-Me | 5-CONHMe | 1-Al—Pip(4) |
| 2344 | 6-OH | H | $SO_2CH_2COOH$ | 3-Me | 5-CONHEt | 1-Al—Pip(4) |
| 2345 | 6-OH | H | $SO_2CH_2COOH$ | 3-Me | 5-CONHPr | 1-Al—Pip(4) |
| 2346 | 6-OH | H | $SO_2CH_2COOH$ | 3-Me | 5-CONHBu | 1-Al—Pip(4) |
| 2347 | 6-OH | H | $SO_2CH_2COOH$ | 3-Me | 5-CONHPn | 1-Al—Pip(4) |
| 2348 | 6-OH | H | $SO_2CH_2COOH$ | 3-Me | 5-CONHHx | 1-Al—Pip(4) |
| 2349 | 6-OH | H | $SO_2CH_2COOH$ | 2-$CONH_2$ | 6-$CONH_2$ | 1-Al—Pip(4) |
| 2350 | 6-OH | H | $SO_2CH_2COOH$ | 3-$CONH_2$ | 5-$CONH_2$ | 1-Al—Pip(4) |
| 2351 | 6-OH | H | $SO_2CH_2COOH$ | 3-CONHMe | 5-CONHMe | 1-Al—Pip(4) |
| 2352 | 6-OH | H | $SO_2CH_2COOH$ | 3-CONHEt | 5-CONHEt | 1-Al—Pip(4) |
| 2353 | H | H | $SO_2(CH_2)_2COOH$ | H | H | 1-Al—Pip(4) |
| 2354 | H | H | $SO_2(CH_2)_3COOH$ | H | H | 1-Al—Pip(4) |
| 2355 | H | H | $SO_2(CH_2)_4COOH$ | H | H | 1-Al—Pip(4) |
| 2356 | H | H | $SO_2(CH_2)_5COOH$ | H | H | 1-Al—Pip(4) |
| 2357 | H | H | $SO_2(CH_2)_6COOH$ | H | H | 1-Al—Pip(4) |
| 2358 | H | H | $SO_2CH_2COOMe$ | 2-F | H | 1-Al—Pip(4) |
| 2359 | H | H | $SO_2CH_2COOMe$ | 3-F | H | 1-Al—Pip(4) |
| 2360 | H | H | $SO_2CH_2COOMe$ | 2-Cl | H | 1-Al—Pip(4) |
| 2361 | H | H | $SO_2CH_2COOMe$ | 3-Cl | H | 1-Al—Pip(4) |
| 2362 | H | H | $SO_2CH_2COOMe$ | 2-Br | H | 1-Al—Pip(4) |
| 2363 | H | H | $SO_2CH_2COOMe$ | 3-Br | H | 1-Al—Pip(4) |
| 2364 | H | H | $SO_2CH_2COOMe$ | 2-I | H | 1-Al—Pip(4) |
| 2365 | H | H | $SO_2CH_2COOMe$ | 3-I | H | 1-Al—Pip(4) |
| 2366 | H | H | $SO_2CH_2COOMe$ | 2-Me | H | 1-Al—Pip(4) |
| 2367 | H | H | $SO_2CH_2COOMe$ | 3-Me | H | 1-Al—Pip(4) |
| 2368 | H | H | $SO_2CH_2COOMe$ | 2-Et | H | 1-Al—Pip(4) |
| 2369 | H | H | $SO_2CH_2COOMe$ | 3-Et | H | 1-Al—Pip(4) |
| 2370 | H | H | $SO_2CH_2COOMe$ | 2-Pr | H | 1-Al—Pip(4) |
| 2371 | H | H | $SO_2CH_2COOMe$ | 3-Pr | H | 1-Al—Pip(4) |
| 2372 | H | H | $SO_2CH_2COOMe$ | 2-iPr | H | 1-Al—Pip(4) |
| 2373 | H | H | $SO_2CH_2COOMe$ | 3-iPr | H | 1-Al—Pip(4) |
| 2374 | H | H | $SO_2CH_2COOMe$ | 2-Bu | H | 1-Al—Pip(4) |
| 2375 | H | H | $SO_2CH_2COOMe$ | 3-Bu | H | 1-Al—Pip(4) |
| 2376 | H | H | $SO_2CH_2COOMe$ | 2-iBu | H | 1-Al—Pip(4) |
| 2377 | H | H | $SO_2CH_2COOMe$ | 3-iBu | H | 1-Al—Pip(4) |
| 2378 | H | H | $SO_2CH_2COOMe$ | 2-sBu | H | 1-Al—Pip(4) |
| 2379 | H | H | $SO_2CH_2COOMe$ | 3-sBu | H | 1-Al—Pip(4) |
| 2380 | H | H | $SO_2CH_2COOMe$ | 2-tBu | H | 1-Al—Pip(4) |
| 2381 | H | H | $SO_2CH_2COOMe$ | 3-tBu | H | 1-Al—Pip(4) |
| 2382 | H | H | $SO_2CH_2COOMe$ | 2-Pn | H | 1-Al—Pip(4) |
| 2383 | H | H | $SO_2CH_2COOMe$ | 3-Pn | H | 1-Al—Pip(4) |
| 2384 | H | H | $SO_2CH_2COOMe$ | 2-Hx | H | 1-Al—Pip(4) |
| 2385 | H | H | $SO_2CH_2COOMe$ | 3-Hx | H | 1-Al—Pip(4) |
| 2386 | H | H | $SO_2CH_2COOMe$ | 2-$CF_3$ | H | 1-Al—Pip(4) |
| 2387 | H | H | $SO_2CH_2COOMe$ | 3-$CF_3$ | H | 1-Al—Pip(4) |
| 2388 | H | H | $SO_2CH_2COOMe$ | 2-OMe | H | 1-Al—Pip(4) |
| 2389 | H | H | $SO_2CH_2COOMe$ | 3-OMe | H | 1-Al—Pip(4) |
| 2390 | H | H | $SO_2CH_2COOMe$ | 2-OEt | H | 1-Al—Pip(4) |
| 2391 | H | H | $SO_2CH_2COOMe$ | 3-OEt | H | 1-Al—Pip(4) |
| 2392 | H | H | $SO_2CH_2COOMe$ | 2-COOH | H | 1-Al—Pip(4) |
| 2393 | H | H | $SO_2CH_2COOMe$ | 3-COOH | H | 1-Al—Pip(4) |
| 2394 | H | H | $SO_2CH_2COOMe$ | 2-COOMe | H | 1-Al—Pip(4) |

TABLE 1-continued (I)

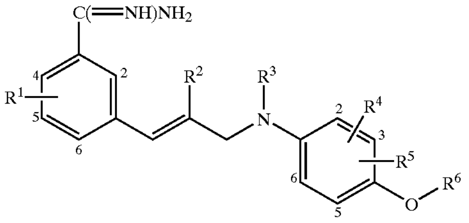

| Cpd. No. | $R^1$ | $R^2$ | $R^3$ | $R^4$ | $R^5$ | $R^6$ |
|---|---|---|---|---|---|---|
| 2395 | H | H | $SO_2CH_2COOMe$ | 3-COOMe | H | 1-Al—Pip(4) |
| 2396 | H | H | $SO_2CH_2COOMe$ | 2-COOEt | H | 1-Al—Pip(4) |
| 2397 | H | H | $SO_2CH_2COOMe$ | 3-COOEt | H | 1-Al—Pip(4) |
| 2398 | H | H | $SO_2CH_2COOMe$ | 2-COOPr | H | 1-Al—Pip(4) |
| 2399 | H | H | $SO_2CH_2COOMe$ | 3-COOPr | H | 1-Al—Pip(4) |
| 2400 | H | H | $SO_2CH_2COOMe$ | 2-COOBu | H | 1-Al—Pip(4) |
| 2401 | H | H | $SO_2CH_2COOMe$ | 3-COOBu | H | 1-Al—Pip(4) |
| 2402 | H | H | $SO_2CH_2COOMe$ | 2-COOPn | H | 1-Al—Pip(4) |
| 2403 | H | H | $SO_2CH_2COOMe$ | 3-COOPn | H | 1-Al—Pip(4) |
| 2404 | H | H | $SO_2CH_2COOMe$ | 2-COOHx | H | 1-Al—Pip(4) |
| 2405 | H | H | $SO_2CH_2COOMe$ | 3-COOHx | H | 1-Al—Pip(4) |
| 2406 | H | H | $SO_2CH_2COOMe$ | $2-CONH_2$ | H | 1-Al—Pip(4) |
| 2407 | H | H | $SO_2CH_2COOMe$ | $3-CONH_2$ | H | 1-Al—Pip(4) |
| 2408 | H | H | $SO_2CH_2COOMe$ | 2-CONHMe | H | 1-Al—Pip(4) |
| 2409 | H | H | $SO_2CH_2COOMe$ | 3-CONHMe | H | 1-Al—Pip(4) |
| 2410 | H | H | $SO_2CH_2COOMe$ | 2-CONHEt | H | 1-Al—Pip(4) |
| 2411 | H | H | $SO_2CH_2COOMe$ | 3-CONHEt | H | 1-Al—Pip(4) |
| 2412 | H | H | $SO_2CH_2COOMe$ | $2-CON(Me)_2$ | H | 1-Al—Pip(4) |
| 2413 | H | H | $SO_2CH_2COOMe$ | $3-CON(Me)_2$ | H | 1-Al—Pip(4) |
| 2414 | H | H | $SO_2CH_2COOMe$ | 2-CON(Me)Et | H | 1-Al—Pip(4) |
| 2415 | H | H | $SO_2CH_2COOMe$ | 3-CON(Me)Et | H | 1-Al—Pip(4) |
| 2416 | H | H | $SO_2CH_2COOMe$ | $2-CON(Et)_2$ | H | 1-Al—Pip(4) |
| 2417 | H | H | $SO_2CH_2COOMe$ | $3-CON(Et)_2$ | H | 1-Al—Pip(4) |
| 2418 | H | H | $SO_2CH_2COOMe$ | 2-F | 3-F | 1-Al—Pip(4) |
| 2419 | H | H | $SO_2CH_2COOMe$ | 2-F | 5-F | 1-Al—Pip(4) |
| 2420 | H | H | $SO_2CH_2COOMe$ | 2-F | 6-F | 1-Al—Pip(4) |
| 2421 | H | H | $SO_2CH_2COOMe$ | 3-F | 5-F | 1-Al—Pip(4) |
| 2422 | H | H | $SO_2CH_2COOMe$ | 2-Cl | 3-Cl | 1-Al—Pip(4) |
| 2423 | H | H | $SO_2CH_2COOMe$ | 2-Cl | 5-Cl | 1-Al—Pip(4) |
| 2424 | H | H | $SO_2CH_2COOMe$ | 2-Cl | 6-Cl | 1-Al—Pip(4) |
| 2425 | H | H | $SO_2CH_2COOMe$ | 3-Cl | 5-Cl | 1-Al—Pip(4) |
| 2426 | H | H | $SO_2CH_2COOMe$ | 2-Me | 3-Me | 1-Al—Pip(4) |
| 2427 | H | H | $SO_2CH_2COOMe$ | 2-Me | 5-Me | 1-Al—Pip(4) |
| 2428 | H | H | $SO_2CH_2COOMe$ | 2-Me | 6-Me | 1-Al—Pip(4) |
| 2429 | H | H | $SO_2CH_2COOMe$ | 3-Me | 5-Me | 1-Al—Pip(4) |
| 2430 | H | H | $SO_2CH_2COOMe$ | 2-Cl | $5-CONH_2$ | 1-Al—Pip(4) |
| 2431 | H | H | $SO_2CH_2COOMe$ | 3-Cl | $5-CONH_2$ | 1-Al—Pip(4) |
| 2432 | H | H | $SO_2CH_2COOMe$ | 3-Cl | 5-CONHMe | 1-Al—Pip(4) |
| 2433 | H | H | $SO_2CH_2COOMe$ | 3-Cl | 5-CONHEt | 1-Al—Pip(4) |
| 2434 | H | H | $SO_2CH_2COOMe$ | 3-Cl | 5-CONHPr | 1-Al—Pip(4) |
| 2435 | H | H | $SO_2CH_2COOMe$ | 3-Cl | 5-CONHBu | 1-Al—Pip(4) |
| 2436 | H | H | $SO_2CH_2COOMe$ | 3-Cl | 5-CONHPn | 1-Al—Pip(4) |
| 2437 | H | H | $SO_2CH_2COOMe$ | 3-Cl | 5-CONHHx | 1-Al—Pip(4) |
| 2438 | H | H | $SO_2CH_2COOMe$ | 2-Me | $5-CONH_2$ | 1-Al—Pip(4) |
| 2439 | H | H | $SO_2CH_2COOMe$ | 2-Me | 5-CONHMe | 1-Al—Pip(4) |
| 2440 | H | H | $SO_2CH_2COOMe$ | 2-Me | 5-CONHEt | 1-Al—Pip(4) |
| 2441 | H | H | $SO_2CH_2COOMe$ | 2-Me | 5-CONHPr | 1-Al—Pip(4) |
| 2442 | H | H | $SO_2CH_2COOMe$ | 2-Me | 5-CONHBu | 1-Al—Pip(4) |
| 2443 | H | H | $SO_2CH_2COOMe$ | 2-Me | 5-CONHPn | 1-Al—Pip(4) |
| 2444 | H | H | $SO_2CH_2COOMe$ | 2-Me | 5-CONHHx | 1-Al—Pip(4) |
| 2445 | H | H | $SO_2CH_2COOMe$ | 3-Me | $5-CONH_2$ | 1-Al—Pip(4) |
| 2446 | H | H | $SO_2CH_2COOMe$ | 3-Me | 5-CONHMe | 1-Al—Pip(4) |
| 2447 | H | H | $SO_2CH_2COOMe$ | 3-Me | 5-CONHEt | 1-Al—Pip(4) |
| 2448 | H | H | $SO_2CH_2COOMe$ | 3-Me | 5-CONHPr | 1-Al—Pip(4) |
| 2449 | H | H | $SO_2CH_2COOMe$ | 3-Me | 5-CONHBu | 1-Al—Pip(4) |
| 2450 | H | H | $SO_2CH_2COOMe$ | 3-Me | 5-CONHPn | 1-Al—Pip(4) |
| 2451 | H | H | $SO_2CH_2COOMe$ | 3-Me | 5-CONHHx | 1-Al—Pip(4) |
| 2452 | H | H | $SO_2CH_2COOMe$ | $2-CONH_2$ | $6-CONH_2$ | 1-Al—Pip(4) |
| 2453 | H | H | $SO_2CH_2COOMe$ | $3-CONH_2$ | $5-CONH_2$ | 1-Al—Pip(4) |
| 2454 | H | H | $SO_2CH_2COOMe$ | 3-CONHMe | 5-CONHMe | 1-Al—Pip(4) |
| 2455 | H | H | $SO_2CH_2COOMe$ | 3-CONHEt | 5-CONHEt | 1-Al—Pip(4) |
| 2456 | 6-OH | H | $SO_2CH_2COOMe$ | 2-F | H | 1-Al—Pip(4) |
| 2457 | 6-OH | H | $SO_2CH_2COOMe$ | 3-F | H | 1-Al—Pip(4) |

TABLE 1-continued (I)

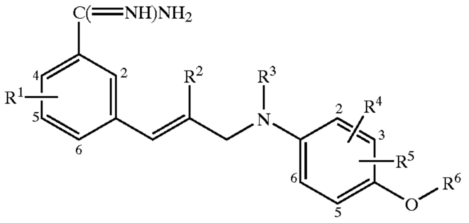

| Cpd. No. | $R^1$ | $R^2$ | $R^3$ | $R^4$ | $R^5$ | $R^6$ |
|---|---|---|---|---|---|---|
| 2458 | 6-OH | H | $SO_2CH_2COOMe$ | 2-Cl | H | 1-Al—Pip(4) |
| 2459 | 6-OH | H | $SO_2CH_2COOMe$ | 3-Cl | H | 1-Al—Pip(4) |
| 2460 | 6-OH | H | $SO_2CH_2COOMe$ | 2-Br | H | 1-Al—Pip(4) |
| 2461 | 6-OH | H | $SO_2CH_2COOMe$ | 3-Br | H | 1-Al—Pip(4) |
| 2462 | 6-OH | H | $SO_2CH_2COOMe$ | 2-I | H | 1-Al—Pip(4) |
| 2463 | 6-OH | H | $SO_2CH_2COOMe$ | 3-I | H | 1-Al—Pip(4) |
| 2464 | 6-OH | H | $SO_2CH_2COOMe$ | 2-Me | H | 1-Al—Pip(4) |
| 2465 | 6-OH | H | $SO_2CH_2COOMe$ | 3-Me | H | 1-Al—Pip(4) |
| 2466 | 6-OH | H | $SO_2CH_2COOMe$ | 2-Et | H | 1-Al—Pip(4) |
| 2467 | 6-OH | H | $SO_2CH_2COOMe$ | 3-Et | H | 1-Al—Pip(4) |
| 2468 | 6-OH | H | $SO_2CH_2COOMe$ | 2-Pr | H | 1-Al—Pip(4) |
| 2469 | 6-OH | H | $SO_2CH_2COOMe$ | 3-Pr | H | 1-Al—Pip(4) |
| 2470 | 6-OH | H | $SO_2CH_2COOMe$ | 2-iPr | H | 1-Al—Pip(4) |
| 2471 | 6-OH | H | $SO_2CH_2COOMe$ | 3-iPr | H | 1-Al—Pip(4) |
| 2472 | 6-OH | H | $SO_2CH_2COOMe$ | 2-Bu | H | 1-Al—Pip(4) |
| 2473 | 6-OH | H | $SO_2CH_2COOMe$ | 3-Bu | H | 1-Al—Pip(4) |
| 2474 | 6-OH | H | $SO_2CH_2COOMe$ | 2-iBu | H | 1-Al—Pip(4) |
| 2475 | 6-OH | H | $SO_2CH_2COOMe$ | 3-iBu | H | 1-Al—Pip(4) |
| 2476 | 6-OH | H | $SO_2CH_2COOMe$ | 2-sBu | H | 1-Al—Pip(4) |
| 2477 | 6-OH | H | $SO_2CH_2COOMe$ | 3-sBu | H | 1-Al—Pip(4) |
| 2478 | 6-OH | H | $SO_2CH_2COOMe$ | 2-tBu | H | 1-Al—Pip(4) |
| 2479 | 6-OH | H | $SO_2CH_2COOMe$ | 3-tBu | H | 1-Al—Pip(4) |
| 2480 | 6-OH | H | $SO_2CH_2COOMe$ | 2-Pn | H | 1-Al—Pip(4) |
| 2481 | 6-OH | H | $SO_2CH_2COOMe$ | 3-Pn | H | 1-Al—Pip(4) |
| 2482 | 6-OH | H | $SO_2CH_2COOMe$ | 2-Hx | H | 1-Al—Pip(4) |
| 2483 | 6-OH | H | $SO_2CH_2COOMe$ | 3-Hx | H | 1-Al—Pip(4) |
| 2484 | 6-OH | H | $SO_2CH_2COOMe$ | $2-CF_3$ | H | 1-Al—Pip(4) |
| 2485 | 6-OH | H | $SO_2CH_2COOMe$ | $3-CF_3$ | H | 1-Al—Pip(4) |
| 2486 | 6-OH | H | $SO_2CH_2COOMe$ | 2-OMe | H | 1-Al—Pip(4) |
| 2487 | 6-OH | H | $SO_2CH_2COOMe$ | 3-OMe | H | 1-Al—Pip(4) |
| 2488 | 6-OH | H | $SO_2CH_2COOMe$ | 2-OEt | H | 1-Al—Pip(4) |
| 2489 | 6-OH | H | $SO_2CH_2COOMe$ | 3-OEt | H | 1-Al—Pip(4) |
| 2490 | 6-OH | H | $SO_2CH_2COOMe$ | 2-COOH | H | 1-Al—Pip(4) |
| 2491 | 6-OH | H | $SO_2CH_2COOMe$ | 3-COOH | H | 1-Al—Pip(4) |
| 2492 | 6-OH | H | $SO_2CH_2COOMe$ | 2-COOMe | H | 1-Al—Pip(4) |
| 2493 | 6-OH | H | $SO_2CH_2COOMe$ | 3-COOMe | H | 1-Al—Pip(4) |
| 2494 | 6-OH | H | $SO_2CH_2COOMe$ | 2-COOEt | H | 1-Al—Pip(4) |
| 2495 | 6-OH | H | $SO_2CH_2COOMe$ | 3-COOEt | H | 1-Al—Pip(4) |
| 2496 | 6-OH | H | $SO_2CH_2COOMe$ | 2-COOPr | H | 1-Al—Pip(4) |
| 2497 | 6-OH | H | $SO_2CH_2COOMe$ | 3-COOPr | H | 1-Al—Pip(4) |
| 2498 | 6-OH | H | $SO_2CH_2COOMe$ | 2-COOBu | H | 1-Al—Pip(4) |
| 2499 | 6-OH | H | $SO_2CH_2COOMe$ | 3-COOBu | H | 1-Al—Pip(4) |
| 2500 | 6-OH | H | $SO_2CH_2COOMe$ | 2-COOPn | H | 1-Al—Pip(4) |
| 2501 | 6-OH | H | $SO_2CH_2COOMe$ | 3-COOPn | H | 1-Al—Pip(4) |
| 2502 | 6-OH | H | $SO_2CH_2COOMe$ | 2-COOHx | H | 1-Al—Pip(4) |
| 2503 | 6-OH | H | $SO_2CH_2COOMe$ | 3-COOHx | H | 1-Al—Pip(4) |
| 2504 | 6-OH | H | $SO_2CH_2COOMe$ | $2-CONH_2$ | H | 1-Al—Pip(4) |
| 2505 | 6-OH | H | $SO_2CH_2COOMe$ | $3-CONH_2$ | H | 1-Al—Pip(4) |
| 2506 | 6-OH | H | $SO_2CH_2COOMe$ | 2-CONHMe | H | 1-Al—Pip(4) |
| 2507 | 6-OH | H | $SO_2CH_2COOMe$ | 3-CONHMe | H | 1-Al—Pip(4) |
| 2508 | 6-OH | H | $SO_2CH_2COOMe$ | 2-CONHEt | H | 1-Al—Pip(4) |
| 2509 | 6-OH | H | $SO_2CH_2COOMe$ | 3-CONHEt | H | 1-Al—Pip(4) |
| 2510 | 6-OH | H | $SO_2CH_2COOMe$ | $2-CON(Me)_2$ | H | 1-Al—Pip(4) |
| 2511 | 6-OH | H | $SO_2CH_2COOMe$ | $3-CON(Me)_2$ | H | 1-Al—Pip(4) |
| 2512 | 6-OH | H | $SO_2CH_2COOMe$ | 2-CON(Me)Et | H | 1-Al—Pip(4) |
| 2513 | 6-OH | H | $SO_2CH_2COOMe$ | 3-CON(Me)Et | H | 1-Al—Pip(4) |
| 2514 | 6-OH | H | $SO_2CH_2COOMe$ | $2-CON(Et)_2$ | H | 1-Al—Pip(4) |
| 2515 | 6-OH | H | $SO_2CH_2COOMe$ | $3-CON(Et)_2$ | H | 1-Al—Pip(4) |
| 2516 | 6-OH | H | $SO_2CH_2COOMe$ | 2-F | 3-F | 1-Al—Pip(4) |
| 2517 | 6-OH | H | $SO_2CH_2COOMe$ | 2-F | 5-F | 1-Al—Pip(4) |
| 2518 | 6-OH | H | $SO_2CH_2COOMe$ | 2-F | 6-F | 1-Al—Pip(4) |
| 2519 | 6-OH | H | $SO_2CH_2COOMe$ | 3-F | 5-F | 1-Al—Pip(4) |
| 2520 | 6-OH | H | $SO_2CH_2COOMe$ | 2-Cl | 3-Cl | 1-Al—Pip(4) |

TABLE 1-continued (I)

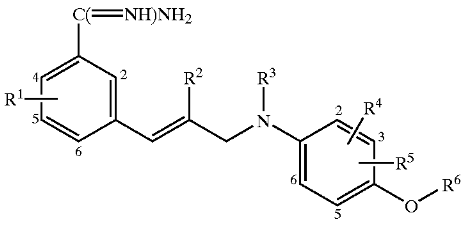

| Cpd. No. | $R^1$ | $R^2$ | $R^3$ | $R^4$ | $R^5$ | $R^6$ |
|---|---|---|---|---|---|---|
| 2521 | 6-OH | H | $SO_2CH_2COOMe$ | 2-Cl | 5-Cl | 1-Al—Pip(4) |
| 2522 | 6-OH | H | $SO_2CH_2COOMe$ | 2-Cl | 6-Cl | 1-Al—Pip(4) |
| 2523 | 6-OH | H | $SO_2CH_2COOMe$ | 3-Cl | 5-Cl | 1-Al—Pip(4) |
| 2524 | 6-OH | H | $SO_2CH_2COOMe$ | 2-Me | 3-Me | 1-Al—Pip(4) |
| 2525 | 6-OH | H | $SO_2CH_2COOMe$ | 2-Me | 5-Me | 1-Al—Pip(4) |
| 2526 | 6-OH | H | $SO_2CH_2COOMe$ | 2-Me | 6-Me | 1-Al—Pip(4) |
| 2527 | 6-OH | H | $SO_2CH_2COOMe$ | 3-Me | 5-Me | 1-Al—Pip(4) |
| 2528 | 6-OH | H | $SO_2CH_2COOMe$ | 2-Cl | 5-$CONH_2$ | 1-Al—Pip(4) |
| 2529 | 6-OH | H | $SO_2CH_2COOMe$ | 3-Cl | 5-$CONH_2$ | 1-Al—Pip(4) |
| 2530 | 6-OH | H | $SO_2CH_2COOMe$ | 3-Cl | 5-CONHMe | 1-Al—Pip(4) |
| 2531 | 6-OH | H | $SO_2CH_2COOMe$ | 3-Cl | 5-CONHEt | 1-Al—Pip(4) |
| 2532 | 6-OH | H | $SO_2CH_2COOMe$ | 3-Cl | 5-CONHPr | 1-Al—Pip(4) |
| 2533 | 6-OH | H | $SO_2CH_2COOMe$ | 3-Cl | 5-CONHBu | 1-Al—Pip(4) |
| 2534 | 6-OH | H | $SO_2CH_2COOMe$ | 3-Cl | 5-CONHPn | 1-Al—Pip(4) |
| 2535 | 6-OH | H | $SO_2CH_2COOMe$ | 3-Cl | 5-CONHHx | 1-Al—Pip(4) |
| 2536 | 6-OH | H | $SO_2CH_2COOMe$ | 2-Me | 5-$CONH_2$ | 1-Al—Pip(4) |
| 2537 | 6-OH | H | $SO_2CH_2COOMe$ | 2-Me | 5-CONHMe | 1-Al—Pip(4) |
| 2538 | 6-OH | H | $SO_2CH_2COOMe$ | 2-Me | 5-CONHEt | 1-Al—Pip(4) |
| 2539 | 6-OH | H | $SO_2CH_2COOMe$ | 2-Me | 5-CONHPr | 1-Al—Pip(4) |
| 2540 | 6-OH | H | $SO_2CH_2COOMe$ | 2-Me | 5-CONHBu | 1-Al—Pip(4) |
| 2541 | 6-OH | H | $SO_2CH_2COOMe$ | 2-Me | 5-CONHPn | 1-Al—Pip(4) |
| 2542 | 6-OH | H | $SO_2CH_2COOMe$ | 2-Me | 5-CONHHX | 1-Al—Pip(4) |
| 2543 | 6-OH | H | $SO_2CH_2COOMe$ | 3-Me | 5-$CONH_2$ | 1-Al—Pip(4) |
| 2544 | 6-OH | H | $SO_2CH_2COOMe$ | 3-Me | 5-CONHMe | 1-Al—Pip(4) |
| 2545 | 6-OH | H | $SO_2CH_2COOMe$ | 3-Me | 5-CONHEt | 1-Al—Pip(4) |
| 2546 | 6-OH | H | $SO_2CH_2COOMe$ | 3-Me | 3-CONHPr | 1-Al—Pip(4) |
| 2547 | 6-OH | H | $SO_2CH_2COOMe$ | 3-Me | 5-CONHBu | 1-Al—Pip(4) |
| 2548 | 6-OH | H | $SO_2CH_2COOMe$ | 3-Me | 5-CONHPn | 1-Al—Pip(4) |
| 2549 | 6-OH | H | $SO_2CH_2COOMe$ | 3-Me | 5-CONHHx | 1-Al—Pip(4) |
| 2550 | 6-OH | H | $SO_2CH_2COOMe$ | 2-$CONH_2$ | 6-$CONH_2$ | 1-Al—Pip(4) |
| 2551 | 6-OH | H | $SO_2CH_2COOMe$ | 3-$CONH_2$ | 5-$CONH_2$ | 1-Al—Pip(4) |
| 2552 | 6-OH | H | $SO_2CH_2COOMe$ | 3-CONHMe | 5-CONHMe | 1-Al—Pip(4) |
| 2553 | 6-OH | H | $SO_2CH_2COOMe$ | 3-CONHEt | 5-CONHEt | 1-Al—Pip(4) |

Exemplification compound numbers of preferred compounds are 83, 90, 93, 101, 137, 140, 142, 148, 177, 237, 297, 358, 478, 542, 663; 668, 788, 849, 864, 948, 1014, 1080, 1220, 1280, 1408, 1410, 1411, 1412, 1413, 1414, 1415, 1416, 1419, 1420, 1422, 1424, 1426, 1434, 1440, 1442, 1448, 1450, 1460, 1462, 1466, 1474, 1478, 1482, 1484, 1492, 1498, 1509, 1513, 1539, 1638, 1711, 1771, 1839, 1843, 1849, 1881, 1939, 1941, 1943, 1945, 1949, 1951, 1955, 1963, 1969, 1971, 1975, 1977, 1979, 1989, 1991, 1995, 2003, 2007, 2011, 2013, 2027, 2038, 2040, 2042, 2044, 2048, 2054, 2068, 2070, 2076, 2078, 2088, 2094, 2109, 2208, 2262, 2266, 2272, 2304 or 2353.

Exemplification compound numbers of more preferred compounds are 90, 137, 177, 237, 297, 358, 478, 542, 663, 668, 788, 849, 864, 948, 1014, 1080, 1408, 1410, 1412, 1414, 1416, 1419, 1420, 1426, 1440, 1442, 1450, 1460, 1462, 1466, 1474, 1478, 1482, 1484, 1492, 1498, 1509, 1513, 1638, 1711, 1771, 1839, 1843, 1849, 1881, 1939, 1941, 1943, 1945, 1949, 1951, 1955, 1969, 1971, 1975, 1979, 1989, 1991, 1995, 2003, 2007, 2011, 2013, 2027, 2038, 2040, 2042, 2094, 2208, 2262, 2266, 2272 or 2304.

Exemplification compound numbers of still more preferred compounds are 668, 849, 1014, 1410, 1412, 1414, 1420, 1426, 1440, 1442, 1450, 1460, 1462, 1466, 1474, 1478, 1482, 1484, 1498, 1509, 1839, 1843, 1939, 1941, 1943, 1945, 1949, 1955, 1969, 1971, 1975, 1979, 1989, 1991, 1995, 2003, 2007, 2011, 2013, 2027 or 2038.

Exemplification compound numbers of the most preferred compounds are:

1410: ethyl N-[4-(1-acetimidoylpiperidin-4-yloxy)phenyl]-N-[3-(3-amidinophenyl)-2-(E)-propenyl]sulfamoylacetate, 1414: ethyl N-[4-(1-acetimidoylpiperidin-4-yloxy)-3-chlorophenyl]-N-[3-(3-amidinophenyl)-2-(E)-propenyl]sulfamoylacetate, 1420: ethyl N-[4-(1-acetimidoylpiperidin-4-yloxy)-3-methylphenyl]-N-[3-(3-amidinophenyl)-2-(E)-propenyl]sulfamoylacetate, 1460: ethyl N-[4-(1-acetimidoylpiperidin-4-yloxy)-3-carbamoylphenyl]-N-[3-(3-amidinophenyl)-2-(E)-propenyl]sulfamoylacetate, 1939: N-[4-(1-acetimidoylpiperidin-4-yloxy)phenyl]-N-[3-(3-amidinophenyl)-2-(E)-propenyl]sulfamoylacetic acid, 1941: N-[4-(1-acetimidoylpiperidin-4-yloxy)-3-fluorophenyl]-N-[3-(3-amidinophenyl)-2-(E)-propenyl]sulfamoylacetic acid, 1943: N-[4-(1-acetimidoylpiperidin-4-yloxy)-3-chlorophenyl]-N-[3-(3-amidinophenyl)-2-(E)-propenyl]sulfamoylacetic acid, 1949: N-[4-(1-acetimidoylpiperidin-4-yloxy)-3-methylphenyl]-N-[3-(3-amidinophenyl)-2-(E)-propenyl]sulfamoylacetic acid, 1969: N-[4-(1-acetimidoylpiperidin-4-yloxy)-3-trifluoromethylphenyl]-N-[3-(3-amidinophenyl)-2-(E)-propenyl]sulfamoylacetic acid, 1989: N-[4-(1-acetimidoylpiperidin-4-yloxy)-3-carbamoylphenyl]-N-[3-(3-amidinophenyl)-2-(E)-propenyl]sulfamoylacetic acid, 2003: ethyl N-[4-(1-acetimidoylpiperidin-4-yloxy)-3,5-dichlorophenyl]-N-[3-(3-amidinophenyl)-2-(E)-propenyl]sulfamoylacetate, 2007: N-[4-(1-acetimidoylpiperidin-4-yloxy)-3,5-dichlorophenyl]-N-[3-(3-amidinophenyl)-2-(E)-propenyl]sulfamoylacetic acid or 2038: N-[4-(1-acetimidoylpiperidin-4-yloxy)phenyl]-N-[3-(3-amidinophenyl)-2-fluoro-2-(Z)-propenyl]sulfamoylacetic acid.

The compound of formula (I) of the present invention can be easily prepared according to the following methods.

Method A

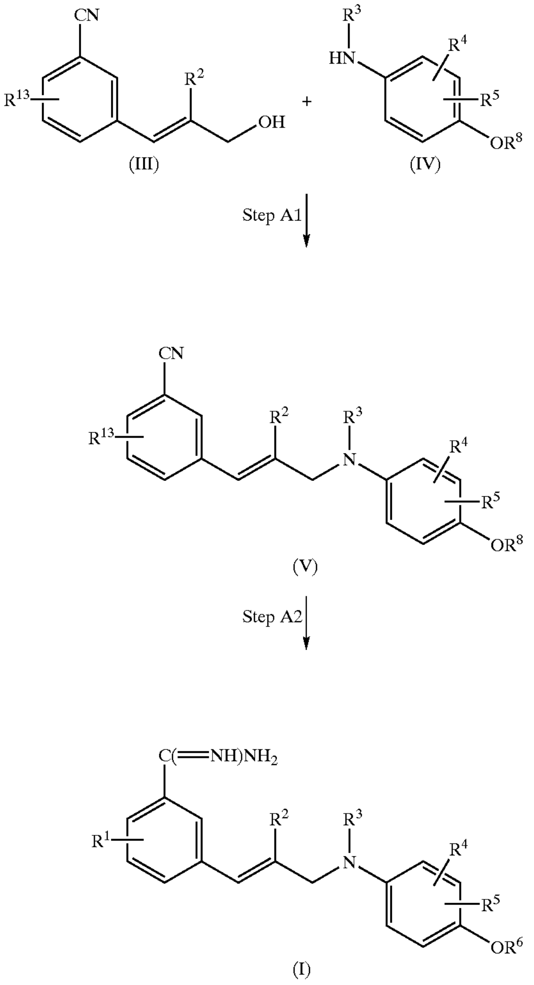

-continued

Method B

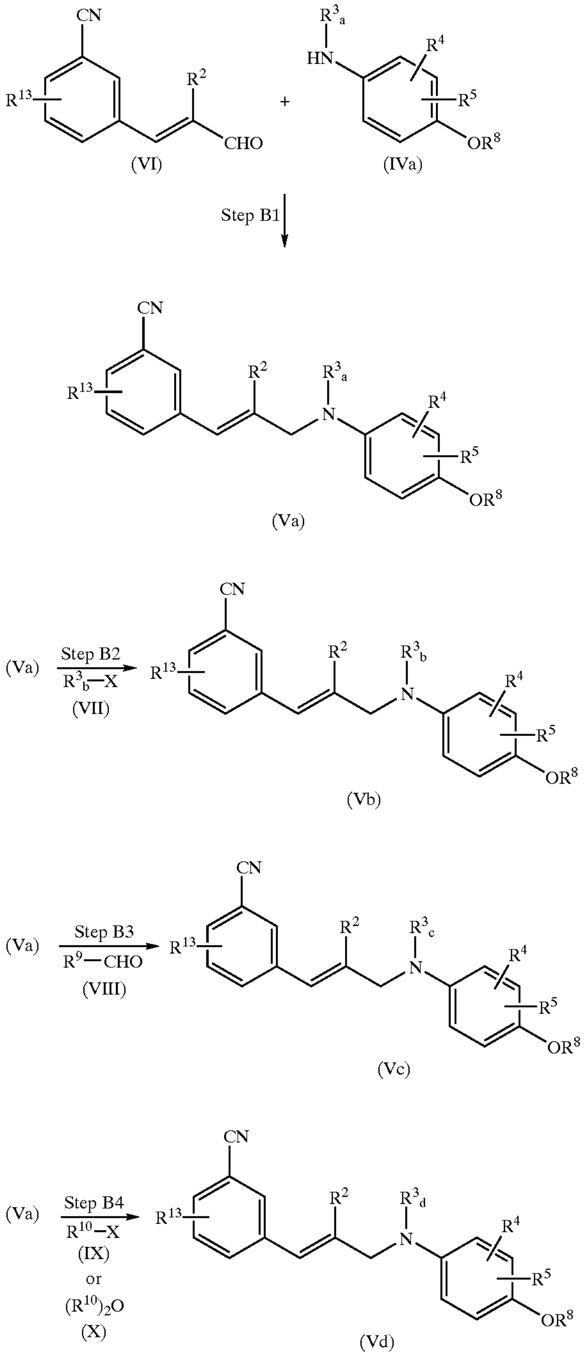

[Method C]

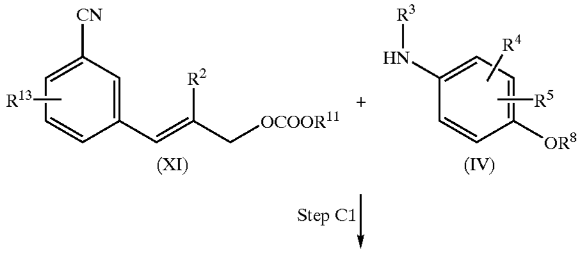

-continued

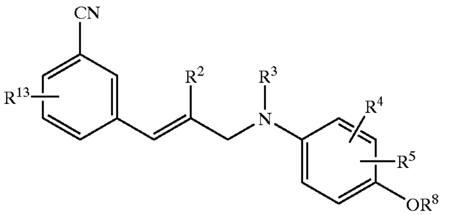

(V)

[Method D]

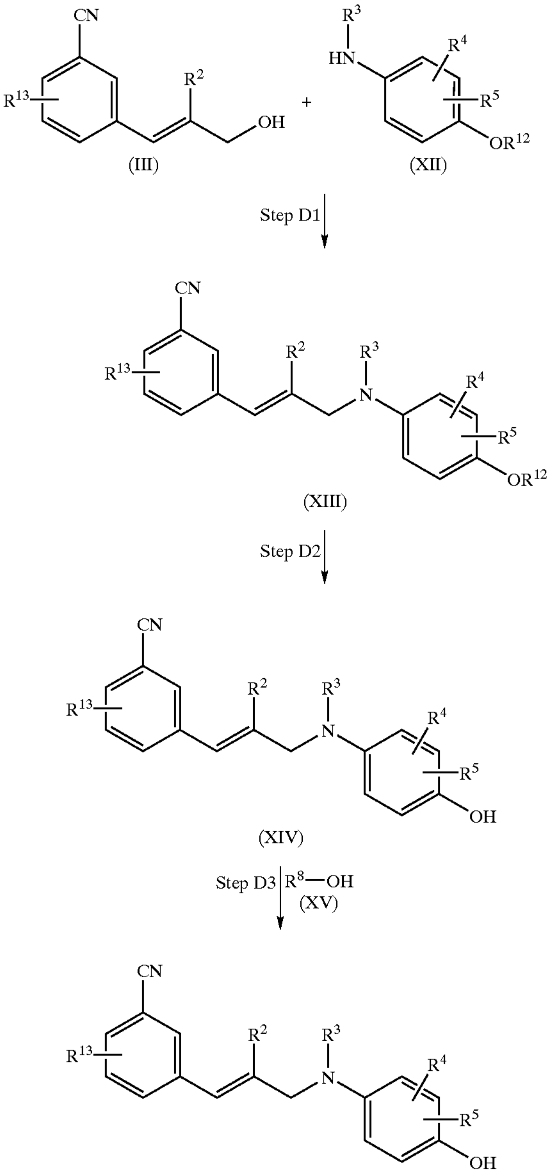

(III) (XII) (XIII) (XIV) (V)

In the above reaction schemes:

$R^1$, $R^2$, $R^3$, $R^4$, $R^5$ and $R^6$ are as defined above;

$R^3{}_a$ represents a hydrogen atom;

$R^3{}_b$ represents a $C_1$–$C_6$ alkyl group; a $C_1$–$C_6$ alkyl group which is substituted with a protected hydroxyl group or a ($C_1$–$C_6$ alkoxy)carbonyl group; a group of formula (II)

(II)

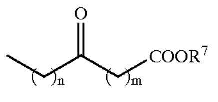

(wherein $R^7$, m and n are as defined above); a $C_7$–$C_{15}$ aralkyl group; a $C_1$–$C_6$ alkylsulfonyl group; or a $C_1$–$C_6$ alkylsulfonyl group which is substituted with a ($C_1$–$C_6$ alkoxy)carbonyl group;

$R^3{}_c$ represents a $C_1$–$C_6$ alkyl group or a $C_7$–$C_{15}$ aralkyl group;

$R^3{}_d$ represents a $C_1$–$C_6$ alkanoyl group or a $C_2$–$C_6$ alkanoyl group substituted with a protected hydroxyl group;

$R^8$ is the same as $R^6$ except that the pyrrolidine or piperidine group has a protecting group instead of the acetimidoyl group;

$R^9$ represents a $C_1$–$C_5$ alkyl group, a $C_6$–$C_{14}$ aryl group or a $C_7$–$C_{14}$ aralkyl group;

$R^{10}$ represents a $C_1$–$C_6$ alkanoyl group; or a $C_2$–$C_6$ alkanoyl group substituted with a protected hydroxyl group;

$R^{11}$ represents a $C_1$–$C_6$ alkyl group;

$R^{12}$ represents a protecting group for a hydroxyl group;

$R^{13}$ is the same as $R^1$ except that any hydroxyl group is protected; and

X represents a halogen atom.

The "$C_1$–$C_6$ alkyl group", the "$C_1$–$C_6$ alkyl group substituted with a ($C_1$–$C_6$ alkoxy)carbonyl group", the "a group of formula (II)

(II)

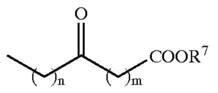

(wherein $R^7$, m and n are as defined above)", the "$C_7$–$C_{15}$ aralkyl group", the "$C_1$–$C_6$ alkylsulfonyl group" and the "$C_1$–$C_6$ alkylsulfonyl group substituted with ($C_1$–$C_6$ alkoxy) carbonyl group" in the definition of $R^3{}_b$; the "$C_1$–$C_6$ alkyl group" and the "$C_7$–$C_{15}$ aralkyl group" in the definition of $R^3{}_c$, and the "$C_1$–$C_6$ alkanoyl group" in the definition of $R^3{}_d$ have the same meaning as in the definition of $R^3$ above.

The "$C_1$–$C_6$ alkyl group which is substituted with a protected hydroxyl group" in the definition of $R^3{}_b$ has the same meaning as in the definition of $R^3$ above except that the hydroxyl group is protected.

The "$C_2$–$C_6$ alkanoyl group which is substituted with a protected hydroxyl group" in the definition of $R^3{}_d$ has the same meaning as the "hydroxyl $C_2$–$C_6$ alkanoyl group" in the definition of $R^3$ except that the hydroxyl group is protected.

The hydroxyl protecting groups of the "$C_1$–$C_6$ alkyl group which is substituted with a protected hydroxyl group" in the definition of $R^3{}_b$, the "$C_2$–$C_6$ alkanoyl group which is substituted with a protected hydroxyl group" in the definition of $R^3{}_d$ and $R^{10}$, the "hydroxyl protecting group" in the definition of $R^{12}$, and the "hydroxyl protecting group" included in $R^{13}$ are not particularly limited provided that they can usually function as a hydroxyl protecting group. Examples such protecting groups include, for example, alkanoyl groups such as the formyl, acetyl, propionyl, butyryl, isobutyryl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl or henicosanoyl groups; carboxyalkanoyl groups such as the succinoyl, glutaroyl or adipoyl groups; halogenoalkanoyl groups such as the chloroacetyl, dichloroacetyl, trichloroacetyl or trifluoroacetyl groups; alkoxyalkanoyl groups such as the methoxyacetyl group; alkenoyl or alkynoyl groups such as the (E)-2-methyl-2-butenoyl group; arylcarbonyl groups such as the benzoyl, α-naphthoyl or β-naphthoyl groups; halogenoarylcarbonyl groups such as the 2-bromobenzoylor 4-chlorobenzoyl groups; alkylarylcarbonyl groups such as the 2,4,6-trimethylbenzoyl or 4-toluoyl groups; alkoxyarylcarbonyl groups such as the 4-anisoyl group; carboxyarylcarbonyl groups such as the 2-carboxybenzoyl, 3-carboxybenzoyl or 4-carboxybenzoyl; nitroarylcarbonyl groups such as the 2-nitrobenzoyl or 4-nitrobenzoyl groups; (alkoxycarbonyl)arylcarbonyl groups such as the 2-(methoxycarbonyl)benzoyl group; arylarylcarbonyl groups such as the 4-phenylbenzoyl group; tetrahydropyranyl or tetrahydrothiopyranyl groups such as the tetrahydropyran-2-yl, 3-bromotetrahydropyran-2-yl, 4-methoxytetrahydropyran-4-yl, tetrahydrothiopyran-2-yl or 4-methoxytetrahydrothiopyran-4-yl groups; tetrahydrofuranyl or tetrahydrothiofuranyl groups such as the tetrahyrofuran-2-yl or tetrahyrothiofuran-2-yl group; alkoxymethyl groups such as the methoxymethyl, 1,1-dimethyl-1-methoxymethyl, ethoxymethyl, propoxymethyl, isopropoxymethyl, butoxymethyl or t-butoxymethyl groups; alkoxyalkoxymethyl groups such as the 2-methoxyethoxymethyl groups; halogenoalkoxymethyl groups such as the 2,2,2-trichloroethoxymethyl or bis(2-chloroethoxy)methyl groups; alkoxyethyl groups such as the 1-ethoxyethyl or 1-(isopropoxy)ethyl groups; halogenoethyl groups such as the 2,2,2-trichloroethyl group; aralkyl groups including 1 to 3 aryl groups such as the benzyl, α-naphthylmethyl, β-naphthylmethyl, diphenylmethyl, triphenylmethyl, α-naphthyldiphenylmethyl or 9-anthrylmethyl groups; aralkyl groups wherein the aryl moiety is substituted with one or more alkyl, alkoxy, halogeno or cyano groups, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl or 4-cyanobenzyl groups; alkoxycarbonyl groups such as the methoxycarbonyl, ethoxycarbonyl, t-butoxycarbonyl or isobutoxycarbonyl groups; halogenoalkoxycarbonyl groups such as the 2,2,2-trichloroethoxycarbonyl group; alkenyloxycarbonyl groups such as the vinyloxycarbonyl or allyloxycarbonyl groups; aralkyloxycarbonyl groups wherein the aryl moiety is optionally substituted with 1 or 2 substituents selected from alkoxy or nitro such as the benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl groups; or silyl groups such as the trimethylsilyl, triethylsilyl, isopropyldimethylsilyl, t-butyldimethylsilyl, methyldiisopropylsilyl, methyl-di-t-butylsilyl, triisopropylsilyl, diphenylmethylsilyl, diphenylbutylsilyl, diphenylisopropylsilyl or phenyldiisopropylsilyl groups.

Preferred "hydroxyl protecting groups" of the "$C_1$–$C_6$ alkyl group which is substituted with a protected hydroxyl group" in the definition of $R^3{}_b$, preferred "hydroxyl protecting groups" of the "$C_2$–$C_6$ alkanoyl group which is substituted with a protected hydroxyl group" in the definition of $R^3{}_d$ and $R^{10}$ are alkanoyl groups; and most preferably the acetyl group. Preferred "hydroxyl protecting groups" in the definition of $R^{12}$ and $R^{13}$ are alkoxymethyl groups; and most preferably the methoxymethyl group.

The "amino protecting groups" in the definition of $R^8$ are not particularly limited provided that they can usually function as amino protecting groups. Examples such protecting groups include, for example, $C_1$–$C_6$ alkanoyl groups such as the formyl, acetyl, propionyl, butyryl, isobutyryl, pivaloyl, valeryl, isovaleryl or hexanoyl groups; $C_1$–$C_4$ alkanoyl groups which are substituted with one or more halogen atoms or $C_1$–$C_4$ alkoxy groups such as the chloroacetyl, dichloroacetyl, trichloroacetyl, trifluoroacetyl, 3-fluoropropionyl, 4,4-dichlorobutyryl, methoxyacetyl, butoxyacetyl, ethoxypropionyl or propoxybutyryl groups; $C_3$–$C_4$ alkenoyl or alkynoyl groups such as the acryloyl, propioloyl, methacryloyl, crotonoyl or isocrotonoyl groups; $C_6$–$C_{10}$ arylcarbonyl groups which are optionally substituted with one or more substituents selected from a halogen atom, $C_1$–$C_4$ alkyl group, a $C_1$–$C_4$ alkoxy group, a $C_1$–$C_4$ alkoxycarbonyl group, a $C_6$–$C_{10}$ aryl group or a nitro group, such as the benzoyl, α-naphthoyl, β-naphthoyl, 2-fluorobenzoyl, 2-bromobenzoyl, 2,4-dichlorobenzoyl, 6-chloro-α-naphthoyl, 4-toluoyl, 4-propylbenzoyl, 4-t-butylbenzoyl, 2,4,6-trimethylbenzoyl, 6-ethyl-α-naphthoyl, 4-anisoyl, 4-propoxybenzoyl, 4-t-butoxybenzoyl, 6-ethoxy-α-naphthoyl, 2-ethoxycarbonylbenzoyl, 4-t-butoxycarbonylbenzoyl, 6-methoxycarbonyl-α-naphthoyl, 4-phenylbenzoyl, 4-phenyl-α-naphthoyl, 6-α-naphthylbenzoyl, 4-nitrobenzoyl, 2-nitrobenzoyl or 6-nitro-α-naphthoyl groups; $C_1$–$C_4$ alkoxycarbonyl groups which are optionally substituted with one or more halogen atoms or tri($C_1$–$C_4$)alkylsilyl groups, such as the methoxycarbonyl, ethoxycarbonyl, propoxycarbonyl, isopropoxycarbonyl, butoxycarbonyl, isobutoxycarbonyl, s-butoxycarbonyl, t-butoxycarbonyl, chloromethoxycarbonyl, 2,2,2-trichloroethoxycarbonyl, 2-fluoropropoxycarbonyl, 2-bromo-t-butoxycarbonyl, 2,2-dibromo-t-butoxycarbonyl, triethylsilylmethoxycarbonyl, 2-trimethylsilylethoxycarbonyl, 4-tripropylsilylbutoxycarbonyl or t-butyidimethylsilylpropoxycarbonyl groups; $C_2$–$C_5$ alkenyloxycarbonyl groups such as the vinyloxycarbonyl, allyloxycarbonyl, 1,3-butadienyloxycarbonyl or 2-pentenyloxycarbonyl groups; aryldicarbonyl groups such as the phthaloyl group; aralkyl groups such as the benzyl, phenethyl, 3-phenylpropyl, 4-phenylbutyl, α-naphthylmethyl, β-naphthylmethyl, diphenylmethyl, triphenylmethyl, α-naphthyldiphenylmethyl or 9-anthrylmethyl groups; $C_7$–$C_{15}$ aralkyloxycarbonyl groups which are optionally substituted with a methoxy or nitro group, such as benzyloxycarbonyl, (1-phenyl) benzyloxycarbonyl, α-naphthylmethyloxycarbonyl, β-naphthylmethyfoxycarbonyl, 9-anthrylmethyloxycarbonyl, p-methoxybenzyloxycarbonyl or p-nitrobenzyloxycarbonyl groups.

Preferred amino protecting groups in the definition of $R^8$ are the $C_1$–$C_4$ alkanoyl, trifluoroacetyl, methoxyacetyl, benzoyl, α-naphthoyl, β-naphthoyl, anisoyl, nitrobenzoyl, $C_1$–$C_4$ alkoxycarbonyl, 2,2,2-trichloroethoxycarbonyl, triethylsilylmethoxycarbonyl, 2-trimethylsilylethoxycarbonyl, vinyloxycarbonyl, allyloxycarbonyl, phthaloyl, benzyl, benzyloxycarbonyl or nitrobenzyloxycarbonyl groups; more preferably the formyl, acetyl, benzoyl, 4-anisoyl, 4-nitrobenzoyl, methoxycarbonyl, ethoxycarbonyl, butoxycarbonyl, t-butoxycarbonyl, phthaloyl, benzyl, benzyloxycarbonyl or p-nitrobenzyloxycarbonyl groups; and most preferably the t-butoxycarbonyl group.

The "$C_1$–$C_5$ alkyl group" in the definition of $R^9$ may be, for example, a straight or branched chain alkyl group having from 1 to 5 carbon atoms such as the methyl, ethyl, propyl, isopropyl, butyl, isobutyl, s-butyl, t-butyl, pentyl, isopentyl, 2-methylbutyl, neopentyl or 1-ethylpropyl groups; preferably a $C_1$–$C_3$ alkyl group; and more preferably the methyl, ethyl or propyl group.

The "$C_6$–$C_{14}$ aryl group" in the definition of $R^9$ may be an aromatic hydrocarbon ring having fom 6 to 14 carbon atoms such as the phenyl, indenyl, naphthyl, phenanthrenyl or anthracenyl groups; preferably the phenyl or naphthyl groups; and more preferably the phenyl group.

The "$C_7$–$C_{14}$ aralkyl group" in the definition of $R^9$ may be, for example, a $C_1$–$C_5$ alkyl group which is attached to 1 or 2 aromatic hydrocarbon rings having from 6 to 10 carbon atoms and which has a total of 7 to 14 carbon atoms, such as the benzyl, α-naphthylmethyl, indenylmethyl, diphenylmethyl, 2-phenethyl, 2-α-naphthylethyl, 3-phenylpropyl, 3-α-naphthylpropyl, phenylbutyl, 4-α-naphthylbutyl or 5-phenylpentyl groups; preferably the benzyl, α-naphthylmethyl, diphenylmethyl or 2-phenethyl groups; more preferably the benzyl or 2-phenethyl groups; and most preferably the benzyl group.

The "$C_1$–$C_6$ alkanoyl group" in the definition of $R^{10}$ may be, for example, straight or branched chain alkanoyl having from 1 to 6 carbon atoms such as the formyl, acetyl, propionyl, butyryl, isobutyryl, pivaloyl, valeryl, isovaleryl or hexanoyl groups; preferably a $C_1$–$C_4$ alkanoyl group; and most preferably the acetyl group.

The "$C_2$–$C_6$ alkanoyl" moiety of the "$C_2$–$C_6$ alkanoyl group substituted with a protected hydroxyl group" in the definition of $R^{10}$ is the straight or branched chain alkanoyl group having from 2 to 6 carbon atoms as described in the above "$C_1$–$C_6$ alkanoyl group"; preferably a $C_2$–$C_4$ alkanoyl group; and most preferably the acetyl group.

The "$C_1$–$C_6$ alkyl group" in the definition of $R^{11}$ may be, for example, a straight or branched chain alkyl group having from 1 to 6 carbon atoms, such as the methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl groups; preferably a $C_1$–$C_4$ alkyl group; more preferably the methyl or ethyl groups; and most preferably the ethyl group.

The "halogen atom" in the definition of X may be, for example, a fluorine atom, chlorine atom, bromine atom or iodine atom.

A compound of formula (I) is prepared by Method A.

In Step A1 a compound of formula (V) can be prepared by condensation of a compound of formula (III) with a compound of formula (IV) in the presence of a phosphine derivative and an azo compound in an inert solvent.

The inert solvent employed in Step A1 is not particularly limited provided that it has no adverse effect on the reaction and dissolves the starting material to some extent. Examples of such a solvent include an aliphatic hydrocarbon such as hexane, heptane, ligroin or petroleum ether; an aromatic hydrocarbon such as benzene, toluene or xylene; a halogenohydrocarbon such as dichloromethane, chloroform, carbon tetrachloride, dichloroethane, chlorobenzene or dichlorobenzene; or an ether such as diethyl ether, diisopropyl ether, tetrahydrofuran, dioxane, dimethoxyethane or di(ethylene glycol)dimethyl ether; preferably an aliphatic hydrocarbon, an aromatic hydrocarbon, a halogenohydrocarbon or an ether, more preferably a halogenohydrocarbon (dichloromethane) or an ether (particularly diethyl ether or tetrahydrofuran).

The phosphine derivative employed in Step A1 may be, for example, a tri-$C_1$–$C_6$-alkylphosphine such as trimethylphosphine, triethylphosphine, tripropylphosphine, tributylphosphine, tripentylphosphine or trihexylphosphine; a tri-$C_6$–$C_{10}$-arylphosphine such as triphenylphosphine, triindenylphosphine or trinaphthylphosphine; or a tri-$C_6$–$C_{10}$-aryl phosphine which may be substituted with $C_1$–$C_4$ alkyl such as tolyldiphenylphosphine, tritolylphosphine, trimesitylphosphine, tributylphenylphosphine or tri-(6-ethyl-2-naphthyl)phosphine; preferably a tri-$C_1$–$C_6$-alkylphosphine (particularly trimethylphosphine, triethylphosphine, tripropylphosphine or tributylphosphine) or a tri-$C_6$–$C_{10}$-arylphosphine (particularly triphenyiphosphine, triindenylphosphine or trinaphthylphosphine); and more preferably tributylphosphine or triphenylphosphine.

The azo compound employed in Step A1 may be, for example, azodicarbonyldipiperidine, or a di-$C_1$–$C_4$-alkyl azodicarboxylate such as dimethyl azodicarboxylate, diethyl azodicarboxylate, dipropyl azodicarboxylate or dibutyl azodicarboxylate; preferably azodicarbonyldipiperidine, dimethyl azodicarboxylate or diethyl azodicarboxylate.

The reaction temperature employed in Step A1 varies depends on the nature of the starting materials and the reagents, but is usually between −50° C. and 100° C., and is preferably between 0° C. and 60° C.

The reaction time employed in Step A1 varies depends on the nature of the starting materials, the reagents, and the reaction temperature. It is usually from 5 minutes to 24 hours, and is preferably from 10 minutes to 6 hours.

After the completion of the reaction, the desired product of Step A1 can be isolated in a conventional manner. For example, after the reaction, when insoluble materials exist in the reaction mixture, the reaction mixture is filtered and the filtrate is concentrated to give the desired product; or, after the reaction, the solvent is evaporated, the residue is partitioned between water and a solvent immiscible with water (for example, benzene, ether, ethyl acetate or the like), the extract is washed with water, dried over anhydrous magnesium sulfate or the like and concentrated to give the desired compound. The product thus obtained, if necessary, can be further purified in a conventional manner such as recrystallization, reprecipitation, chromatography or the like.

In Step A2, a compound of formula (I) can be prepared by an appropriate combination of the following reactions:

(a) conversion of the cyano group into an amidino group, (b) removal of the protecting group of the protected amino group, and (c) conversion of the amino group into an acetimidoyl group; and if desired, (d) hydrolysis of any ester group, and (e) removal of the protecting group of any protected hydroxyl group.

The essential reaction (a), which is the conversion of the cyano group into an amidino group, can be accomplished according to the following conventional methods:

(1) ammonolysis of an intermediate imino ether compound, which is obtained by a reaction of the starting material with an alcohol in the presence of an acid, in an inert solvent or in the absence of a solvent (preferably in an inert solvent) or (2) hydrogenolysis of an intermediate amidoxime compound which is obtained by reaction of the starting material with a hydroxylamine compound in the presence or absence of a base in an inert solvent.

The reaction (a)(1) is a two-step reaction. In the first step, an imino ether derivative is obtatained by a reaction of the nitrile with an alcohol in the presence of an acid.

The inert solvent employed in the first step of reaction (a)(1) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; an ester such as methyl acetate or ethyl acetate; a nitro compound such as nitromethane; an amide such as formamide, N,N-dimethylformamide, N,N-dimethylacetamide or N-methyl-2-pyrrolidinone; a sulfoxide such as dimethyl sulfoxide; or sulfolane; or mixtures thereof; preferably an aromatic hydrocarbon (particularly benzene) or a halogenohydrocarbon (particularly dichloromethane); and most preferably a halogenohydrocarbon (particularly dichloromethane).

This reaction can be conducted in an excess of alcohol, as a reagent and a solvent, and is usually conducted in an alcohol provided that there is no adverse effect on the reaction. Examples of such an alcohol include methanol, ethanol, propanol, 2-propanol, butanol, isobutanol or the like, preferably methanol or ethanol.

The acid employed in the first step of reaction (a)(1) is a mineral acid such as hydrogen chloride, hydrochloric acid, hydrobromic acid, hydroiodic acid, nitric acid, perchloric acid, sulfuric acid or phosphoric acid; a sulfonic acid such as methanesulfonic acid, trifluoromethanesulfonic acid, ethanesulfonic acid, benzenesulfonic acid or p-toluenesulfonic acid; or a Lewis acid such as boron trifluoride, aluminum chloride, iron (III) chloride, zinc chloride, mercury (II) chloride or the like; preferably a mineral acid or Lewis acid; and most preferably hydrogen chloride.

The reaction temperature employed in the first step of reaction (a)(1) varies depending on the nature of the starting materials and the reagents, but is usually between −10° C. and 100° C., and is preferably between 0° C. and 50° C.

The reaction time employed in first step of reaction (a)(1) varies depending on the nature of the starting materials, the reagents, and the reaction temperature. It is usually from 10 minutes to 48 hours, and is preferably from 1 hour to 15 hours.

After completion of the reaction, the desired product of the first step of reaction (a)(1) can be isolated in a conventional manner (for example, evaporation of the solvent). In certain cases, the reaction product can be used in the next reaction step without isolation or purification.

The second step of reaction (a)(1) is ammonolysis of the imino ether derivative obtained in the first step. This reaction is usually carried out in the presence of an ammonium compound in an inert solvent.

The inert solvent employed in the second step of reaction (a)(1) is not particularly limited provided that it has no adverse effect on the reaction and dissolves the starting material to some extent. Examples of such a solvent include an alcohol such as methanol, ethanol, propanol, 2-propanol, butanol or isobutanol; water; or mixtures of water and an alcohol; preferably methanol, ethanol, water, aqueous methanol or aqueous ethanol; and most preferably aqueous methanol or aqueous ethanol.

The ammonium compound, ie the source of ammonium ion, employed in the second step of reaction (a)(1) is, for example, aqueous ammonia solution, ammonium chloride, ammonium carbonate or mixtures thereof; preferably ammonium chloride.

The pH of the second step of reaction (a)(1) is neutral or weakly basic; preferably from 7 to 9 adjusted with aqueous ammonia solution or hydrochloric acid.

The reaction temperature of the second step of reaction (a)(1) varies depending on the nature of the starting materials and the reagents, but is usually between −10° C. and 100° C., and is preferably between 0° C. and 50° C.

The reaction time of the second step of reaction (a)(1) varies depending on the nature of the starting materials, the reagents and the reaction temperature. It is usually from 10 minutes to 48 hours, and is preferably from 1 hour to 15 hours.

After completion of the reaction, the desired product of the second step of reaction (a)(1) can be isolated in a conventional manner. For example, after the reaction, the solvent of the reaction mixture is evaporated to give the desired product; or, after completion of the reaction, the reaction mixture is partitioned between water and a solvent immiscible with water (for example, benzene, ether, ethyl acetate or the like), the extractant is washed with water, dried over anhydrous magnesium sulfate or the like, and concentrated to give the desired compound. The product thus obtained, if necessary, can be further purified in a conventional manner such as recrystallization, reprecipitation or chromatography.

The reaction (a)(2) is a two-step reaction. In the first step, an amidoxime derivative is obtained by reaction of the nitrile with a hydroxylamine compound in an inert solvent, if desired, in the presence of a base.

The inert solvent used in the first step of reaction (a)(2) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile such as acetonitrile or isobutyronitrile; an alcohol such as methanol, ethanol, propanol, 2-propanol, butanol or isobutanol; an amide such as formamide, N,N-dimethylformamide, N,N-dimethylacetamide or N-methyl-2-pyrrolidinone; a sulfoxide such as dimethyl sulfoxide; or sulfolane; or water; preferably an alcohol (particularly methanol or ethanol).

The hydroxylamine compound used in the first step of reaction (a)(2) is an aqueous hydroxylamine solution, a solution of hydroxylamine in an organic solvent or an acid addition salt thereof.

The base used in the first step of reaction (a)(2) is not particularly limited provided that when an acid addition salt of hydroxylamine is used in this step, the base can neutralize it (when a solution of hydroxylamine is directly used, the base is not always necessary). Examples of such a base include an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal acetate such as sodium acetate; an alkali metal hydroxide such as sodium hydroxide, potassium hydroxide or lithium hydroxide; an alkali metal alkoxide such as sodium methoxide, sodium ethoxide, potassium t-butoxide or lithium methoxide; or an organic base such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane (DABCO) or 1,8-diazabicyclo[5.4.0]undec-7-ene (DBU); preferably an alkali metal carbonate (particularly sodium carbonate) or an alkali metal alkoxide (particularly potassium t-butoxide).

The reaction temperature of the first step of reaction (a)(2) varies depending on the nature of the starting materials and the reagents, but is usually between 0° C. and 150° C., and is preferably between 50° C. and 100° C.

The reaction time of the first step of reaction (a)(2) varies depending on the nature of the starting materials, the reagents, and the reaction temperature. It is usually from 1 hour to 24 hours, and is preferably from 5 hours to 12 hours.

After the completion of the reaction, the desired product of the first step of reaction (a)(2) can be isolated in a conventional manner (for example, evaporation of the solvent). In certain cases, the reaction product can be used in the next reaction step without isolation or purification.

The second step of reaction (a)(2) is hydrogenolysis of the amidoxime compound obtained in the first step. Before this reaction, the hydroxy group is converted to a leaving group, and an acetyl group is usually used. Acetylation is usually carried out using acetic anhydride in acetic acid: if necessary, it can be conducted in a solvent.

The solvent employed in the acetylation reaction is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; or a nitrile such as acetonitrile or isobutyronitrile; preferably a halogenohydrocarbon (particularly dichloromethane) or an ether (particularly tetrahydrofuran).

The reaction temperature of the acetylation varies depending on the nature of the starting materials and the reagents, but is usually between 0° C. and 150° C., and is preferably between 10° C. and 50° C.

The reaction time of the acetylation varies depending on the nature of the starting materials, the reagents, and the reaction temperature. It is usually from 1 hour to 24 hours, and is preferably from 5 hours to 12 hours.

After completion of the reaction, the desired product of the acetylation reaction can be isolated in a conventional manner (for example, evaporation of the solvent after completion of the reaction). In certain cases, the reaction product can be used in the next reaction step without isolation or purification.

The hydrogenolysis of the amidoxime compound (when the hydroxyl group is acetylated, deacetylation) can be conducted without changing the solvent or, if desired, the solvent of the reaction mixture is evaporated, the residue is dissolved in an inert solvent and then the hydrogenolysis can also be conducted in the solvent.

The inert solvent used in the second step of the reaction (a)(2) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile such as acetonitrile or isobutyronitrile; an alcohol such as methanol, ethanol, propanol, 2-propanol, butanol or isobutanol; an amide such as formamide, N,N-dimethylformamide, N,N-dimethylacetamide or N-methyl-2-pyrrolidinone; a sulfoxide such as dimethyl sulfoxide; or sulfolane; a carboxylic acid such as formic acid or acetic acid; water; or mixtures thereof; preferably an alcohol (particularly methanol or ethanol), acetic acid or mixtures thereof.

The catalyst used in the hydrogenolysis is not particularly limited provided that it can usually be used in catalytic reduction. Examples of such a catalyst inlcude palladium black, palladium on carbon, palladium hydroxide, palladium hydroxide on carbon, Raney nickel, rhodium-aluminum oxide, palladium-barium sulfate, platinum oxide or platinum black; preferably palladium on carbon.

The reaction temperature of the second step of reaction (a)(2) varies depending on the nature of the starting materials and the reagents, but is usually between −10° C. and 100° C., and is preferably between 0° C. and 80° C.

The reaction time of the second step of reaction (a)(2) varies depending on the nature of the starting materials, the reagents, and the reaction temperature. It is usually from 1 hour to 24 hours, and is preferably from 5 hours to 12 hours.

After completion of the reaction, the desired product of the second step of reaction (a)(2) can be isolated in a conventional manner. For example, after completion of the reaction, the reaction mixture is filtered to remove the catalyst, the filtrate is concentrated to give the desired product, or after completion of the reaction, the reaction mixture is filtered to remove the catalyst, the filtrate is partitioned between water and a solvent immiscible with water (for example, benzene, ether, ethyl acetate or the like), the extract is washed with water, dried over anhydrous magnesium sulfate or the like and concentrated to give the desired compound. The product thus obtained, if necessary, can be further purified in a conventional manner such as recrystallization, reprecipitation or chromatography.

The essential reaction, reaction (b), that is, removal of the protecting group of the protected amino group, is conducted according to techniques known to those skilled in the art as follows.

When the amino protecting group is a formyl, acetyl, benzoyl, methoxycarbonyl, ethoxycarbonyl, t-butoxycarbonyl, 2-trimethylsilylethoxycarbonyl, 2-bromo-t-butoxycarbonyl, 2,2-dibromo-t-butoxycarbonyl, vinyloxycarbonyl, benzyloxycarbonyl, (1-phenyl) benzyloxycarbonyl, 9-anthrylmethyloxycarbonyl, p-methoxybenzyloxycarbonyl or p-nitrobenzyloxycarbonyl group, the reaction to remove the protecting group can be accomplished by treatment with an acid in an inert solvent or in an aqueous solvent. In certain case, an acid addition salt of the desired compound can be obtained.

The acid used in step (b) may be, for example, hydrochloric acid, sulfuric acid, phosphoric acid, hydrobromic acid or trifluoroacetic acid; preferably hydrochloric acid, sulfuric acid, hydrobromic acid or trifluoroacetic acid.

The inert solvent used in step (b) is not particularly limited provided that it has no adverse effect on the reaction and dissolves the starting material to some extent. Example of such a solvent include an aliphatic hydrocarbon such as hexane, heptane, ligroin or petroleum ether; an aromatic hydrocarbon such as benzene, toluene or xylene; a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an ester such as methyl acetate or ethyl acetate; an alcohol such as methanol, ethanol, propanol, 2-propanol or butanol; an amide such as formamide, N,N-dimethylformamide, N,N-dimethylacetamide or hexamethylphosphoric triamide; a sulfoxide such as dimethyl sulfoxide; or sulfolane; an aliphatic acid such as formic acid or acetic acid; water; or mixtures of water and the solvent described above; preferably a halogenohydrocarbon, an ether, an alcohol, an aliphatic acid or mixtures of water and the solvent described above; and more preferably a halogenohydrocarbon (particularly dichloromethane), an ether (particularly tetrahydrofuran or dioxane), an aliphatic acid (particularly acetic acid), an alcohol (particularly methanol or ethanol), water or mixtures of water and the solvent described above.

The reaction temperature of step (b) varies depending on the nature of the starting materials, the solvent and the acid, but is usually between −10° C. and 150° C., and is preferably between 0° C. and 100° C.

The reaction time of the step (b) varies depend on the nature of the starting materials, the solvent and the acid. It is usually from 5 minutes to 48 hours, and is preferably from 10 minutes to 15 hours.

After completion of the reaction, the desired product of step (b) can be isolated in a conventional manner. For example, after completion of the reaction, the precipitate of the reaction mixture is filtered, if necessary, is neutralized in a solvent, the solvent is evaporated and the residue is dried to give the desired compound; or, after completion of the reaction, the reaction mixture is poured into water, if necessary neutralized, and the resulting mixture is extracted with a solvent immiscible with water (for example, benzene, ether, ethyl acetate or the like), the extract containing the desired compound is washed with water, dried over anhydrous magnesium sulfate or the like, and concentrated to give the desired compound. The product thus obtained, if necessary, can be further purified in a conventional manner such as recrystallization, reprecipitation or chromatography.

When the amino-protecting group is an alkanoyl, arylcarbonyl, alkoxycarbonyl, alkenyloxycarbonyl, aryldicarbonyl, aralkyl or aralkyloxycarbonyl group, the reaction to remove the protecting group can be accomplished by treatment with a base in an inert solvent or in an aqueous solvent.

The base used in step (b) may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; an alkali metal mercaptan such as sodium methyl mercaptan or sodium ethyl mercaptan; or an organic base such as hydrazine, methylamine, dimethylamine, ethylamine, triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); preferably an alkali metal carbonate (particularly sodium carbonate or potassium carbonate), an alkali metal hydroxide (particularly sodium hydroxide or potassium hydroxide), an alkali metal alkoxide (particularly sodium methoxide, sodium ethoxide or potassium t-butoxide) or an organic base (particularly hydrazine or methylamine).

The inert solvent used in step (b) is not particularly limited provided that it has no adverse effect on the reaction and dissolves the starting material to some extent. Examples of such a solvent include an aliphatic hydrocarbon such as hexane, heptane, ligroin or petroleum ether; an aromatic hydrocarbon such as benzene, toluene or xylene; a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol or butanol; an amide such as formamide, N,N-dimethylformamide, N,N-dimethylacetamide or hexamethylphosphoric triamide; a sulfoxide such as dimethyl sulfoxide; or sulfolane; water; or mixtures of water and the solvent described above; preferably a halogenohydrocarbon, an ether, an alcohol, or mixtures of water and the solvent described above; and more preferably an ether (particularly tetrahydrofuran or dioxane), an alcohol (particularly methanol or ethanol) or mixtures of water and the solvent described above.

The reaction temperature of step (b) varies depending on the nature of the starting materials, the base, and the solvent, but is usually between −10° C. and 50° C., and is preferably between −5° C. and 10° C.

The reaction time of step (b) varies depending on the nature of the starting materials, the base, and the solvent. It is usually from 5 minutes to 20 hours, and is preferably from 10 minutes to 3 hours.

After completion of the reaction, the desired product of step (b) can be isolated in a conventional manner. For example, after completion of the reaction, the precipitate of the reaction mixture is filtered, if necessary, is neutralized in a solvent, the solvent is evaporated to give the desired compound; or, after completion of the reaction, the reaction mixture is poured into water, the pH of the resulting mixture is adjusted, the precipitate is collected by filtration to give the desired compound; or; after the neutralization, the resulting mixture is extracted with a solvent immiscible with water (for example, benzene, ether, ethyl acetate or the like), the extract containing the desired compound is washed with water, dried over anhydrous magnesium sulfate or the like, and concentrated to give the desired compound. The product thus obtained, if necessary, can be further purified in a conventional manner such as recrystallization, reprecipitation or chromatography.

When the amino protecting group is a t-butoxycarbonyl group, the reaction to remove the protecting group can also be accomplished by treatment with a silyl compound or a Lewis acid in an inert solvent.

The silyl compound employed in step (b) is, for example, trimethylsilyl chloride, trimethylsilyl iodide or trimethylsilyl trifluoromethanesulfonate.

The Lewis acid employed in step (b) is, for example, aluminum chloride.

The solvent used in step (b) is not particularly limited provided that it has no adverse effect on the reaction and dissolves the starting material to some extent. Examples of such a solvent include, a halogenohydrocarbon such as dichloromethane, chloroform or carbon tetrachloride; an ether such as diethyl ether, tetrahydrofuran or dioxane; or a nitrile such as acetonitrile; preferably a halogenohydrocarbon (particularly dichloromethane or chloroform) or a nitrile (particularly acetonitrile).

The reaction temperature of step (b) varies depending on the nature of the starting materials, the reagents, and the solvent, but is usually between −20° C. and 100° C., and is preferably between 0° C. and 50° C.

The reaction time of step (b) varies depending on the nature of the starting materials, the reagents, the solvent, and the reaction temperature. It is usually from 10 minutes to 10 hours, and is preferably from 30 minutes to 3 hours.

After completion of the reaction, the desired product of step (b) can be isolated in a conventional manner. For example, after distillation of the solvent, water is added to the reaction mixture, the resulting mixture is basified and then filtered to give the desired compound; or, after the basification, the resulting mixture is extraxted with a solvent immiscible with water (for example, benzene, ether, ethyl acetate or the like), the extract containing the desired compound is washed with water, dried over anhydrous magnesium sulfate or the like, and concentrated to give the desired compound. The product thus obtained, if necessary, can be further purified in a conventional manner such as recrystallization, reprecipitation or chromatography.

When the amino-protecting group is an allyloxycarbonyl group, removal of the protecting group can be accomplished by a similar method to the catalytic reduction of the aralkyl group. For example, the allyloxycarbonyl group can be removed by palladium and triphenylphosphine or nickel tetracarbonyl.

When the amino-protecting group is an aralkyl group or a $C_7$–$C_{11}$ aralkyloxycarbonyl group, the reaction to remove the protecting group can be accomplished by contact with a reducing agent (preferably catalytic reduction in the presence of a catalyst) or treatment with an oxidizing agent in an inert solvent.

The inert solvent employed in the removal of the protecting group by catalytic reduction is not particularly limited provided that it has no adverse effect on the reaction. Examples of such a solvent include an aliphatic hydrocarbon such as hexane or cyclohexane; an aromatic hydrocarbon such as toluene, benzene or xylene; an ether such as diethyl ether, tetrahydrofuran or dioxane; an ester such as ethyl acetate or propyl acetate; an alcohol such as methanol, ethanol or 2-propanol; an aliphatic acid such as formic acid or acetic acid; or mixtures of water and the solvent described above; preferably an aliphatic hydrocarbon, an aromatic hydrocarbon, an ether, an ester, an alcohol, an aliphatic acid or mixtures of water and the solvent described above; and more preferably an alcohol (particularly methanol or ethanol), an aliphatic acid (particularly formic acid or acetic acid) or mixtures of water and the solvent described above.

The catalyst employed in the hydrogenolysis is not particularly limited provided that it can usually be used in catalytic reduction. Examples of such a catalyst include palladium on carbon, Raney nickel, rhodium-aluminum oxide or palladium-barium sulfate; preferably palladium on carbon or Raney nickel.

The pressure employed in the hydrogenolysis is not particularly limited and is usually between 1 and 10 atmospheres pressure; preferably 1 atmosphere pressure.

The reaction temperature of the hydrogenolysis varies depending on the nature of the starting material, the solvent, and the reducing agent, but is usually between 0° C. and 100° C., and is preferably between 10° C. and 50° C.

The reaction time of the hydrogenolysis varies depending on the nature of the starting material, the solvent, the reducing agent, and the reaction temperature. It is usually from 15 minutes to 24 hours, and is preferably from 30 minutes to 12 hours.

After completion of the reaction, the desired product of hydrogenolysis can be isolated in a conventional manner. For example, after the reaction, the reaction mixture is filtered to remove the catalyst, the filtrate is concentrated, poured into water, and the aqueous layer is basified and the precipitate is collected by filtration to give the desired compound; or, after the basification, the resulting mixture is extracted with a solvent immiscible with water (for example, benzene, ether, ethyl acetate or the like), the extract containing the desired compound is washed with water, dried over anhydrous magnesium sulfate or the like, and concentrated to give the desired compound. The product thus obtained, if necessary, can be further purified in a conventional manner such as recrystallization, reprecipitation or chromatography.

The inert solvent used in removal of the protecting group by oxidation is not particularly limited provided that it has no adverse effect on the reaction. Examples of such a solvent include a ketone such as acetone; a halogenohydrocarbon such as dichloromethane, chloroform or carbon tetrachloride; a nitrile such as acetonitrile; an ether such as diethyl ether, tetrahydrofuran or dioxane; an amide such as N,N-dimethylformamide, N,N-dimethylacetamide, hexamethylphosphoric triamide; a sulfoxide such as dimethyl sulfoxide; or mixtures of water and the solvent described above; preferably a ketone, a halogenohydrocarbon, a nitrile, an ether, an amide, a sulfoxide or mixtures of water and the solvents described above; and more preferably a ketone (particularly acetone), an halogenohydrocarbon (particularly dichloromethane), a nitrile (particularly acetonitrile), an amide (particularly hexamethylphosphoric triamide), a sulfoxide (particularly dimethyl sulfoxide) or mixtures of water and the solvents described above.

The oxidizing agent employed in the oxidation is, for example, potassium persulfate, sodium persulfate, ceric ammonium nitrate (CAN) or 2,3-dichloro-5,6-dicyano-p-benzoquinone (DDQ); preferably CAN or DDQ.

The reaction temperature of the oxidation reaction varies depending on the nature of the starting material, the solvent, and the oxidizing agent, but is usually between 0° C. and 150° C., and is preferably between 10° C. and 50° C.

The reaction time of the oxidation reaction varies depending on the nature of the starting material, the solvent, and the oxidizing agent. It is usually from 15 minutes to 24 hours, and is preferably from 30 minutes to 12 hours.

After completion of the reaction, the desired product of the oxidation reaction can be isolated in a conventional manner. For example, after the reaction the reaction, mixture is filtered to remove the oxidizing agent, the filtrate is concentrated, poured into water, and the aqueous layer is basified and the precipitate is collected by filtration to give the desired compound; or, after the basification, the resulting mixture is extracted with a solvent immiscible with water (for example, benzene, ether, ethyl acetate or the like), the extractant containing the desired compound is washed with water, dried over anhydrous magnesium sulfate or the like, and concentrated to give the desired compound. The product thus obtained, if necessary, can be further purified in a conventional manner such as recrystallization, reprecipitation or chromatography.

The essential reaction (c), that is the conversion of the amino group into an acetimidoyl group is accomplished by reaction of a starting material with ethyl acetimidate or ethyl acetimidate hydrochloride (preferably ethyl acetimidate hydrochloride) in an inert solvent in the presence or absence of a base (preferably in the presence of a base).

The inert solvent used in step (c) is not particularly limited provided that it has no adverse effect on the reaction and dissolves the starting material to some extent. Examples of such a solvent inlcude an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile such as acetonitrile or isobutyronitrile; an alcohol such as methanol, ethanol, propanol, 2-propanol, butanol or isobutanol; an amide such as formamide, N,N-dimethylformamide, N,N-dimethylacetamide or N-methyl-2-pyrrolidinone; or a sulfoxide such as dimethyl sulfoxide; or sulfolane; preferably an alcohol (particularly ethanol).

The base used in step (c) may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydroxide such as sodium hydroxide, potassium hydroxide or lithium hydroxide; or an organic base such as triethylamine, tributylamine, diisopropylethylamine, N-methylmorpholine, pyridine, 4-(N,N-dimethylamino) pyridine, N,N-dimethylaniline, N,N-diethylaniline, 1,5-diazabicyclo[4.3.0]non-5-ene, 1,4-diazabicyclo[2.2.2] octane (DABCO) or 1,8-diazabicyclo[5.4.0]undec-7-ene (DBU); preferably an alkali metal carbonate (particularly sodium carbonate or potassium carbonate) or an organic base (particularly triethylamine).

The reaction temperature of step (c) varies depending on the nature of the starting materials and the reagent, but is usually between −10° C. and 100° C., and is preferably between 0° C. and 50° C.

The reaction time of step (c) varies depending on the nature of the starting materials, the reagent, and the reaction temperature. It is usually from 1 hour to 48 hours, and is preferably from 5 hours to 15 hours.

After completion of the reaction, the desired product of step (c) can be isolated in a conventional manner. For example, after the reaction, the reaction mixture is concentrated to give the desired compound; or, after the reaction, the reaction mixture is partitioned between water and a solvent immiscible with water (for example, benzene, ether, ethyl acetate or the like), the extract containing the desired compound is washed with water, dried over anhydrous magnesium sulfate or the like, and concentrated to give the desired compound. The product thus obtained, if necessary, can be further purified in a conventional manner such as recrystallization, reprecipitation or chromatography.

The reaction (d), hydrolysis of any ester group (which is an optional process) is accomplished by treatment of a starting material with an acid or a base (preferably an acid) in the presence or absence of an inert solvent according to techniques known to those skilled in the art.

The inert solvent used in step (d) is not particularly limited provided that it has no adverse effect on the reaction and dissolves the starting material to some extent. Examples of such a solvent include an alcohol such as methanol, ethanol, propanol, 2-propanol, butanol or isobutanol; or mixtures of water and the solvent described above; preferably aqueous methanol or aqueous ethanol.

The acid used in step (d) may be, for example, a mineral acid such as hydrochloric acid, hydrobromic acid, hydroiodic acid, nitric acid, perchloric acid, sulfuric acid or phosphoric acid; a sulfonic acid such as methanesulfonic acid, trifluoromethanesulfonic acid, ethanesulfonic acid, benzenesulfonic acid or p-toluenesulfonic acid; or a carboxylic acid such as fumaric acid, succinic acid, citric acid, tartaric acid, oxalic acid or maleic acid; preferably a mineral acid (particularly hydrochloric acid).

The base used in step (d) may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; or an alkali metal hydroxide such as sodium hydroxide, potassium hydroxide or lithium hydroxide; preferably sodium hydroxide.

The reaction temperature of step (d) varies depending on the nature of the starting material and the reagent. In the hydrolysis reaction using an acid, it is usually between 0° C. and 150° C., and is preferably between 50° C. and 100° C. In the hydrolysis reaction using a base, it is usually between −10° C. and 50° C., and is preferably between −5° C. and 10° C.

The reaction time of step (d) varies depending on the nature of the starting material, the reagent, and the reaction temperature. In the hydrolysis reaction using an acid, it is usually from 30 minutes to 48 hours, and is preferably from 3 hours to 10 hours. In the hydrolysis reaction using a base, it is usually from 5 minutes to 10 hours, and is preferably from 10 minutes to 3 hours.

After completion of the reaction, the desired product of step (d) can be isolated in a conventional manner. For example, after the reaction the reaction mixture is concentrated to give the desired compound; or, after the reaction, the reaction mixture is acidified with an acid (for example, hydrochloric acid), the precipitate is collected by filtration to give the desired compound; or, after the acidification, the resulting mixture is extracted with a solvent immiscible with water (for example, benzene, ether, ethyl acetate or the like), the extract containing the desired compound is washed with water, dried over anhydrous magnesium sulfate or the like, and concentrated to give the desired compound.

In addition, after the reaction, carbon dioxide gas is passed through an aqueous solution of the reaction mixture or sodium carbonate or potassium carbonate is added to an aqueous solution of the reaction mixture to afford a carbonate of the desired product. The product thus obtained, if necessary, can be further purified by conventional manner such as recrystallization, reprecipitation or chromatography.

The reaction step (e), removal of the protecting group of a protected hydroxyl group (which is an optional process), can be carried out according to a method described in Protective Groups in Organic Synthesis, 3rd edition, T. W.Greene & P. G. M. Wuts; John Wiley & Sons, Inc.

When the hydroxyl-protecting group is a formyl, acetyl, benzoyl, tetrahydropyran-2-yl, 3-bromotetrahydropyran-2-yl, 4-methoxytetrahydropyran-4-yl, tetrahydrothiopyran-2-yl, 4-methoxytetrahydrothiopyran-4-yl, tetrahydrofuran-2-yl, tetrahydrothiofuran-2-yl, methoxymethyl, 1,1-dimethyl-1-methoxymethyl, ethoxymethyl, propoxymethyl, isopropoxymethyl, butoxymethyl, t-butoxymethyl, 2-methoxyethoxymethyl, 2,2,2-trichloroethoxymethyl, bis(2-chloroethoxy)methyl, 1-ethoxyethyl, 1-(isopropoxy)ethyl, methoxycarbonyl, ethoxycarbonyl, t-butoxycarbonyl, 2-trimethylsilylethoxycarbonyl, 2-bromo-t-butoxycarbonyl, 2,2-dibromo-t-butoxycarbonyl, vinyloxycarbonyl, benzyloxycarbonyl, (1-phenyl)benzyloxycarbonyl, 9-anthrylmethyloxycarbonyl, p-methoxybenzyloxycarbonyl or p-nitrobenzyloxycarbonyl group, the protecting group can be removed by treatment with an acid in an inert solvent or an aqueous solvent.

The acid employed in step (e) may be, for example, hydrochloric acid, sulfuric acid, phosphoric acid, hydrobromic acid or trifluoroacetic acid; preferably hydrochloric acid, sulfuric acid, hydrobromic acid or trifluoroacetic acid.

The inert solvent employed in step (e) is not particularly limited provided that it has no adverse effect on the reaction and dissolves the starting material to some extent. Examples of such a solvent include an aliphatic hydrocarbon such as hexane, heptane, ligroin or petroleum ether; an aromatic hydrocarbon such as benzene, toluene or xylene; a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an ester such as methyl acetate or ethyl acetate; an alcohol such as methanol, ethanol, propanol, 2-propanol or butanol; an amide such as formamide, N,N-dimethylformamide, N,N-dimethylacetamide or hexamethylphosphoric triamide; a sulfoxide such as dimethyl sulfoxide; or sulfolane; an aliphatic acid such as formic acid or acetic acid; water; or mixtures of water and the solvent described above; preferably a halogenohydrocarbon, an ether, an ester, an alcohol, an aliphatic acid or mixtures of water and the solvent described above; and more preferably a halogenohydrocarbon (particularly dichloromethane), an ether (particularly tetrahydrofuran or dioxane), an ester (particularly ethyl acetate), an aliphatic acid (particularly acetic acid), water or mixtures of water and the solvent described above.

The reaction temperature of step (e) varies depending on the nature of the starting material, the solvent, and the acid, but is usually between −10° C. and 150° C., and is preferably between 0° C. and 60° C.

The reaction time of step (e) varies depending on the nature of the starting material, the solvent and the acid. It is usually from 5 minutes to 20 hours, and is preferably from 10 minutes to 12 hours.

After completion of the reaction, the desired product of step (e) can be isolated in a conventional manner. For example, after the reaction, the reaction mixture is appropriately neutralized, concentrated, partitioned between water and a solvent immiscible with water (for example, benzene, ether, ethyl acetate or the like), the extract containing the desired compound is washed with water, dried over anhydrous magnesium sulfate or the like and concentrated to give the desired compound. The product thus obtained, if necessary, can be further purified in a conventional manner such as recrystallization, reprecipitation or chromatography.

When the hydroxyl-protecting group is an alkanoyl, carboxylated alkanoyl, halogenoalkanoyl, alkoxyalkanoyl, unsaturated alkanoyl, arylcarbonyl, halogenoarylcarbonyl, alkylated arylcarbonyl, carboxylated arylcarbonyl, nitroarylcarbonyl, alkoxycarbonylated arylcarbonyl, or arylated arylcarbonyl, the protecting group can be removed by treatment with a base in an inert solvent or aqueous solvent.

The base employed in step (e) may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; an alkali metal mercaptan such as sodium methyl mercaptan or sodium ethyl mercaptan; or an organic base such as hydrazine, methylamine, dimethylamine, ethylamine, triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); preferably an alkali metal carbonate (particularly sodium carbonate or potassium carbonate); an alkali metal hydroxide (particularly sodium hydroxide or potassium hydroxide); an alkali metal alkoxide (particularly sodium methoxide, sodium ethoxide or potassium t-butoxide) or an organic base (particularly hydrazine or methylamine).

The inert solvent of step (e) is not particularly limited provided that it has no adverse effect on the reaction and dissolves the starting material to some extent. Examples of such a solvent include an aliphatic hydrocarbon such as hexane, heptane, ligroin or petroleum ether; an aromatic hydrocarbon such as benzene, toluene or xylene; a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol or butanol; an amide such as formamide, N,N-dimethylformamide, N,N-dimethylacetamide or hexamethylphosphoric triamide; a sulfoxide such as dimethyl sulfoxide; or sulfolane; or mixtures of water and the solvent described above; preferably a halogenohydrocarbon, an ether, an alcohol, or mixtures of water and the solvent described above; and more preferably an ether (particularly tetrahydrofuran or dioxane), an alcohol (particularly methanol or ethanol) or mixtures of water and the solvent described above.

The reaction temperature of step (e) varies depending on the nature of the starting material, the solvent and the base, but is usually between −10° C. and 150° C., and is preferably between 0° C. and 50° C.

The reaction time of step (e) varies depending on the nature of the starting material, the solvent and the base. It is usually from 50 minutes to 20 hours, and is preferably from 10 minutes to 5 hours.

After completion of the reaction, the desired product of step (e) can be isolated in a conventional manner. For example, after the reaction, the reaction mixture is concentrated, partitioned between water and a solvent immiscible with water (for example, benzene, ether, ethyl acetate or the like), the extract containing the desired compound is washed with water, dried over anhydrous magnesium sulfate or the like, and concentrated to give the desired compound. The product thus obtained, if necessary, can be further purified in a conventional manner such as recrystallization, reprecipitation or chromatography.

When the hydroxyl-protecting group is an aralkyl group or aralkyloxycarbonyl group, the protecting group can be removed by contact with a reducing agent (preferably catalytic reduction in the presence of a catalyst) in an inert solvent or treatment with an oxidizing agent in an inert solvent.

The inert solvent used in the catalytic reduction is not particularly limited provided that it has no adverse effect on the reaction. Examples of such a solvent include an aliphatic hydrocarbon such as hexane or cyclohexane; an aromatic hydrocarbon such as benzene, toluene or xylene; an ether such as diethyl ether, tetrahydrofuran or dioxane; an ester such as ethyl acetate or propyl acetate; an alcohol such as methanol, ethanol or 2-propanol; an aliphatic acid such as formic acid or acetic acid; or mixtures of water and these organic solvents; preferably an aliphatic hydrocarbon, an aromatic hydrocarbon an ether, an ester, an alcohol, an aliphatic acid or mixtures of water and these organic solvents; and more preferably an alcohol (particularly methanol or ethanol), an aliphatic acid (particularly formic acid or acetic acid) or mixtures of water and these organic solvents.

The catalyst of the step (e) is not particularly limited provided that it can usually be used in catalytic reduction. Examples of such catalysts include palladium on carbon, Raney nickel, rhodium-aluminum oxide or palladium-barium sulfate; preferably palladium on carbon or Raney nickel.

The pressure of step (e) is not particularly limited and is usually between 1 and 10 atmospheres pressure; preferably 1 atmosphere pressure.

The reaction temperature of step (e) varies depending on the nature of the starting material, the solvents and the reducing agent, but is usually between 0° C. and 100C, and is preferably between 10° C. and 50° C.

The reaction time of step (e) varies depending on the nature of the starting material, the solvents, the reducing agents and the reaction temperature. It is usually from 15 minutes to 10 hours, and is preferably from 30 minutes to 3 hours.

After completion of the reaction, the desired product of step (e) can be isolated in a conventional manner. For example, after the reaction, the reaction mixture is filtered to remove the catalyst, the filtrate is concentrated, extracted with a solvent immiscible with water (for example, benzene, ether, ethyl acetate or the like), the extract containing the desired compound is washed with water, dried over anhydrous magnesium sulfate or the like, and concentrated to give the desired compound. The product thus obtained, if necessary, can be further purified in a conventional manner such as recrystallization, reprecipitation or chromatography.

The inert solvent used in removal of the protecting group by oxidation is not particularly limited provided that it has no adverse effect on the reaction. Examples of such a solvent include a ketone such as acetone; a halogenohydrocarbon such as dichloromethane, chloroform or carbon tetrachloride; a nitrile such as acetonitrile; an ether such as diethyl ether, tetrahydrofuran or dioxane; an amide such as N,N-dimethylformamide, N,N-dimethylacetamide, hexamethylphosphoric triamide; a sulfoxide such as dimethyl sulfoxide; or mixtures of water and these organic solvents; preferably a ketone, a halogenohydrocarbon, a nitrile, an ether, an amide, a sulfoxide or mixtures of water and these organic solvents; and more preferably a ketone (particularly acetone), a halogenohydrocarbon (particularly dichloromethane), a nitrile (particularly acetonitrile), an amide (particularly hexamethylphosphoric triamide), a sulfoxide (particularly dimethyl sulfoxide) or mixtures of water and these organic solvents.

The oxidizing agent employed in the oxidation may be, for example, potassium persulfate, sodium persulfate, ceric ammonium nitrate (CAN) or 2,3-dichloro-5,6-dicyano-p-benzoquinone (DDQ); preferably CAN or DDQ.

The reaction temperature of the oxidation reaction varies depending on the nature of the starting materials, the solvent and the oxidizing agent, but is usually between 0° C. and 150° C., and is preferably between 10° C. and 50° C.

The reaction time of the oxidation reaction varies depend on the nature of the starting material, the solvent and the oxidizing reagent. It is usually from 15 minutes to 24 hours, and is preferably from 30 minutes to 5 hours.

After completion of the reaction, the desired product of this step can be isolated in a conventional manner. For example, after the reaction, the reaction mixture is filtered to remove the oxidizing agent, the filtrate is concentrated, extracted with a solvent immiscible with water (for example, benzene, ether, ethyl acetate or the like), the extract containing the desired compound is washed with water, dried over anhydrous magnesium sulfate or the like, and concentrated to give the desired compound. The product thus obtained, if necessary, can be further purified in a conventional manner such as recrystallization, reprecipitation or chromatography.

When the hydroxyl-protecting group is a silyl group, the protecting group can be removed by reaction with a compound which produces fluoride ion in an inert solvent.

The inert solvent employed in removal of the silyl group is not particularly limited provided that it has no adverse effect on the reaction. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; or an ether such as diethyl ether, diisopropyl ether, tetrahydrofuran, dioxane, dimethoxyethane or di(ethylene glycol)dimethyl ether; preferably an ether (particularly tetrahydrofuran).

The compound which produces fluoride ion may be, for example, tetrabutylammonium fluoride, hydrofluoric acid, hydrofluoric acid-pyridine or potassium fluoride; preferably tetrabutylammonium fluoride.

The reaction temperature of step (e) varies depending on the nature of the starting materials and the reagent, but is usually between −50° C. and 100° C., and is preferably between −10° C. and 50° C.

The reaction time of step (e) varies depending on the nature of the starting materials, the reagent and the reaction temperature. It is usually from 5 minutes to 12 hours, and is preferably from 10 minutes to 1 hour.

After completion of the reaction, the desired product of this step can be isolated in a conventional manner. For example, after the reaction, the reaction mixture is partitioned between water and a solvent immiscible with water (for example, benzene, ether, ethyl acetate or the like), the extract is washed with water, dried over anhydrous magnesium sulfate or the like, and concentrated to give the desired compound. The product thus obtained, if necessary, can be further purified in a conventional manner such as recrystallization, reprecipitation or chromatography.

Compounds of formula (Va), (Vb), (Vc) or (Vd) each of which is an intermediate in Method A, are prepared by Method B.

In Step B1, a compound of formula (Va), which is a compound of formula (V) wherein $R^3$ is hydrogen, is prepared by Step B1(1), condensation of a compound of formula (VI) with a compound of formula (IVa) in an inert solvent in the presence or absence of molecular sieves (preferably in the presence of powder molecular sieves 5A) and then by Step B1(2), reduction of the product of Step B1(1) using a reducing agent in an inert solvent.

The inert solvent employed in step B1(1) is not particularly limited provided that it has no adverse effect on the reaction and dissolves the starting material to some extent. Examples of such a solvent include an aliphatic hydrocarbon such as hexane, heptane, ligroin or petroleum ether; an aromatic hydrocarbon such as benzene, toluene or xylene; a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an ester such as methyl acetate or ethyl acetate; an alcohol such as methanol, ethanol, propanol, 2-propanol or butanol; an amide such as formamide, N,N-dimethylformamide, N,N-dimethylacetamide or hexamethylphosphoric triamide; a sulfoxide such as dimethyl sulfoxide; or sulfolane; preferably a halogenohydrocarbon, an ether or an aromatic hydrocarbon; more preferably an ether or an aromatic hydrocarbon; still more preferably an aromatic hydrocarbon (particularly benzene or toluene).

The reaction temperature of Step B1(1) varies depending on the nature of the starting material and the solvent, but is usually between 0° C. and 150° C., and is preferably between 50° C. and 100° C.

The reaction time of Step B1(1) varies depending on the nature of the starting material and the solvent. It is usually from 5 minutes to 20 hours, and is preferably from 10 minutes to 12 hours.

After completion of the reaction, the desired product of this step can be isolated in a conventional manner. For example, after the reaction, the reaction mixture is concentrated and then partitioned between water and a solvent immiscible with water (for example, benzene, ether, ethyl acetate or the like). The extract is washed with water, dried over anhydrous magnesium sulfate or the like, and concentrated to give the desired compound. The product thus obtained, if necessary, can be further purified in a conventional manner such as recrystallization, reprecipitation or chromatography. In addition, the intermediate product of this step can be also used in the next reaction step without purification.

The inert solvent employed in Step B1(2) is not particularly limited provided that it has no adverse effect on the reaction and dissolves the starting material to some extent. Examples of such a solvent include an aliphatic hydrocarbon such as hexane, heptane, ligroin or petroleum ether; an aromatic hydrocarbon such as benzene, toluene or xylene; a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol or butanol; or mixtures thereof; preferably a halogenohydrocarbon, an ether, an alcohol, or a mixture thereof and more preferably an alcohol (particularly methanol or ethanol).

The reducing agent employed in this step may be, for example, an aluminum hydride compound such as lithium aluminum hydride or diisobutylaluminum hydride; sodium borohydride, diborane, or the like; preferably sodium borohydride. In addition, when sodium borohydride is used, cerium chloride can be used as a catalyst.

The reaction temperature of step B1(2) varies depending on the nature of the starting materials and the solvent, but is usually between −50° C. and 50° C., and is preferably between 0° C. and 30° C.

The reaction time of step B1(2) varies depending on the nature of the starting materials and the solvent. It is usually from 5 minutes to 20 hours, and is preferably from 10 minutes to 12 hours.

After completion of the reaction, the desired product of this step can be isolated in a conventional manner. For example, after the reaction, the reaction mixture is concentrated or partitioned between iced water and a solvent immiscible with water (for example, benzene, ether, ethyl acetate or the like), the extract is washed with water, dried over anhydrous magnesium sulfate or the like, and concentrated to give the desired compound. The product thus obtained, if necessary, can be further purified in a conventional manner such as recrystallization, reprecipitation or chromatography.

In step B2, a compound of formula (Vb), which is a compound of formula (V) wherein $R^3$ is a $C_1$–$C_6$ alkyl group; a $C_1$–$C_6$ alkyl group which is substituted with a protected hydroxyl group or a ($C_1$–$C_6$ alkoxy)carbonyl group; a group of formula (II)

(II)

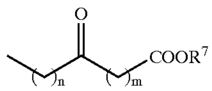

(wherein $R^7$, m and n are as defined above), a $C_7$–C $_5$ aralkyl group, a $C_1$–$C_6$ alkylsulfonyl group, or a $C_1$–$C_6$ alkylsulfonyl group substituted with a ($C_1$–$C_6$ alkoxy)carbonyl group, is prepared by reaction of a compound of formula (Va) with a compound of formula (VII) in an inert solvent in the presence or absence of a base (preferably in the presence of a base).

The inert solvent used in this step is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile such as acetonitrile or isobutyronitrile; an amide such as formamide, N,N-dimethylformamide, N,N-dimethylacetamide or N-methyl-2-pyrrolidinone; or a sulfoxide such as dimethyl sulfoxide; or sulfolane; preferably a halogenohydrocarbon (particularly dichloromethane), an ether (diethyl ether or tetrahydrofuran) or an amide (particularly N,N-dimethylformamide).

Examples of the base used in this step include an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; or an organic base such as methylamine, dimethylamine, ethylamine, triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo [5.4.0]undec-7-ene (DBU); preferably an alkali metal carbonate (particularly sodium carbonate or potassium carbonate), an alkali metal hydrogencarbonate (particularly sodium hydrogencarbonate or potassium hydrogencarbonate) or an alkali metal hydride (particularly lithium hydride or sodium hydride).

The reaction temperature of this step varies depending on the nature of the starting material and the reagents, but is usually between −10° C. and 100° C., and is preferably between 0° C. and 50° C.

The reaction time of this step varies depending on the nature of the starting materials, the reagents and the temperature. It is usually from 10 minutes to 24 hours, and is preferably from 1 hour to 12 hours.

After completion of the reaction, the desired product of this step can be isolated in a conventional manner. For example, after the reaction, the reaction mixture is partitioned between water and a solvent immiscible with water (for example, benzene, ether, ethyl acetate or the like). The extract is washed with water, dried over anhydrous magnesium sulfate or the like, and concentrated to give the desired compound. The product thus obtained, if necessary, can be further purified in a conventional manner such as recrystallization, reprecipitation or chromatography.

In Step B3, a compound of formula (Vc), which is a compound of formula (V) wherein $R^3$ is $C_1$–$C_6$ alkyl or $C_7$–$C_{15}$ aralkyl, is prepared by reaction of a compound of formula (Va) with a compound of formula (VIII) in the presence of acetic acid and sodium cyanoborohydride or sodium triacetoxyborohydride in an inert solvent.

The inert solvent used in this step is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol, butanol or isobutanol; an amide such as formamide, N,N-dimethylformamide, N,N-dimethylacetamide or N-methyl-2-pyrrolidinone; a sulfoxide such as dimethyl sulfoxide; or sulfolane; or mixtures thereof; preferably a halogenohydrocarbon (particularly dichloromethane), an alcohol (methanol or ethanol) or mixtures thereof (particularly a mixture of dichloromethane and methanol).

The reaction temperature of this step varies depending on the nature of the starting materials and the reagents, but is usually between −10° C. and 150° C., and is preferably between 0° C. and 100° C.

The reaction time of this step varies depending on the nature of the starting materials, the reagents and the temperature. It is usually from 10 minutes to 24 hours, and is preferably from 1 hour to 12 hours.

After completion of the reaction, the desired product of this step can be isolated in a conventional manner. For example, after the reaction, the reaction mixture is partitioned between water and a solvent immiscible with water (for example, benzene, ether, ethyl acetate or the like). The extract is washed with water, dried over anhydrous magnesium sulfate or the like, and concentrated to give the desired compound. The product thus obtained, if necessary, can be further purified in a conventional manner such as recrystallization, reprecipitation or chromatography.

In Step B4, a compound of formula (Vd), which is a compound of formula (V) wherein $R^3$ is a $C_1$–$C_6$ alkanoyl group or a $C_2$–$C_6$ alkanoyl group substituted with a protected hydroxyl group, is prepared by Step B4(1), reaction of a compound of formula (Va) with a compound of formula (IX) or (X) in an inert solvent in the presence or absence of a base (preferably in the presence of a base) and then, if necessary, Step B4(2), removal of the hydroxyl-protecting group of the product of Step B4(1).

The inert solvent employed in this step is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile such as acetonitrile or isobutyronitrile; an amide such as formamide, N,N-dimethylformamide, N,N-dimethylacetamide or N-methyl-2-pyrrolidinone; or a sulfoxide such as dimethyl sulfoxide; or sulfolane; preferably a halogenohydrocarbon (particularly dichloromethane) or an ether (diethyl ether or tetrahydrofuran).

The base used in this step may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydroxide such as sodium hydroxide, potassium hydroxide or lithium hydroxide; or an organic base such as methylamine, dimethylamine, ethylamine, triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); preferably an alkali metal carbonate (particularly sodium carbonate or potassium carbonate), an alkali metal hydrogencarbonate (particularly sodium hydrogencarbonate or potassium hydrogencarbonate) or an organic base (particularly triethylamine, pyridine or 4-(N,N-dimethylamino)pyridine).

The reaction temperature of this step varies depending on the nature of the starting materials and the reagents, but is usually between −10° C. and 100° C., and is preferably between 0° C. and 50° C.

The reaction time of this step varies depending on the nature of the starting materials, the reagents and the temperature. It is usually from 10 minutes to 24 hours, and is preferably from 1 hour to 12 hours.

After completion of the reaction, the desired product of this step can be isolated in a conventional manner. For example, after the reaction the reaction mixture is partitioned between water and a solvent immiscible with water (for example, benzene, ether, ethyl acetate or the like). The extract is washed with water, dried over anhydrous magnesium sulfate or the like, and concentrated to give the desired compound. The product thus obtained, if necessary, can be further purified in a conventional manner such as recrystallization, reprecipitation or chromatography.

In Step B4(2) removal of the protecting group of the hydroxyl group can be carried out under similar reaction conditions to that described in reaction (e) of Step A2.

Method C is another method for the preparation of the compound of formula (V) which is an intermediate in method A.

In Step C1, a compound of formula (V) can be prepared by condensation of a compound of formula (XI) with a compound of formula (IV) in the presence of a palladium catalyst and a phosphine derivative in an inert solvent.

The inert solvent of this step is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; or a nitrile such as acetonitrile or isobutyronitrile; preferably an ether (particularly tetrahydrofuran).

The palladium catalyst of this step may be, for example, tris(dibenzylideneacetone)dipalladium-chloroform complex, bis(dibenzylideneacetone)palladium, palladium acetate or π-allylpalladium chloride dimer; preferably tris(dibenzylideneacetone)dipalladium-chloroform complex.

The phosphine derivative used in this step may be, for example, a tri-$C_1$–$C_6$-alkylphosphine such as trimethylphosphine, triethylphosphine, tripropylphosphine, tributylphosphine, tripentylphosphine, trihexylphosphine or the like; a tri-$C_6$–$C_{10}$-arylphosphine such as triphenylphosphine, triindenylphosphine, trinaphthylphosphine or the like; or a tri-$C_6$–$C_{10}$-aryl phosphine which may be substituted with $C_1$–$C_4$ alkyl such as tolyidiphenylphosphine, tritolylphosphine, trimesitylphosphine, tributylphenylphosphine, tri-6-ethyl-2-naphthylphosphine or the like; preferably a tri-$C_1$–$C_6$-alkylphosphine (particularly trimethylphosphine, triethylphosphine, tripropylphosphine or tributylphosphine) or a tri-$C_6$–$C_{10}$ -arylphosphine (particularly triphenylphosphine, triindenylphosphine or trinaphthylphosphine); more preferably tributylphosphine or triphenylphosphine; and the most preferably triphenylphosphine.

The reaction temperature of this step varies depending on the nature of the starting materials and the reagents, but is usually between −10° C. and 100° C., and is preferably between 0° C. and 50° C.

The reaction time of this step varies depending on the nature of the starting materials, the reagents and the temperature. It is usually from 10 minutes to 10 hours, and is preferably from 30 minutes to 5 hours.

After completion of the reaction, the desired product of this step can be isolated in a conventional manner. For example, after the reaction, the reaction mixture is concentrated to give the desired compound. The product thus obtained, if necessary, can be further purified in a conventional manner such as recrystallization, reprecipitation or chromatography.

Method D is another method for the preparation of a compound of formula (V) which is an intermediate in Method A.

In Step D1, a compound of formula (XIII) can be prepared by condensation of a compound of formula (III) with a compound of formula (XII) in the presence of a phosphine derivative and an azo compound in an inert solvent under similar conditions to those described in Step A1.

In Step D2, a compound of formula (XIV) can be prepared by removal of a protecting group for a hydroxyl group of the compound of formula (XIII) under similar conditions to those described in Step A2(e).

In Step D3, a compound of formula (V) can be prepared by condensation of a compound of formula (XIV) with a compound of formula (XV) in the presence of a phosphine derivative and an azo compound in an inert solvent under similar conditions to those described in Step A1.

A compound of formula (III), (IV), (IVa), (VI), (XI) or (XII), each of which is a starting material of this invention, can be easily prepared as follows.

Method E

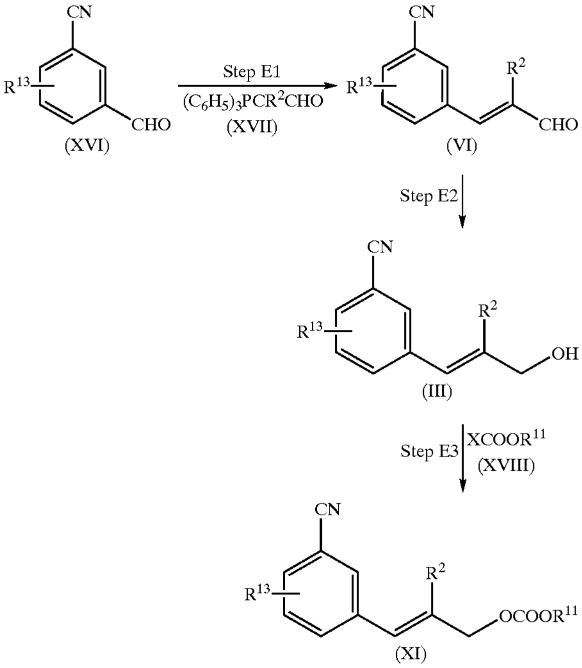

Method G

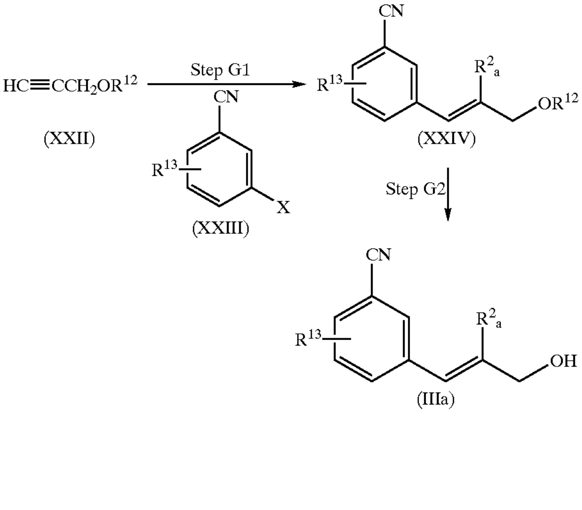

-continued
Method H
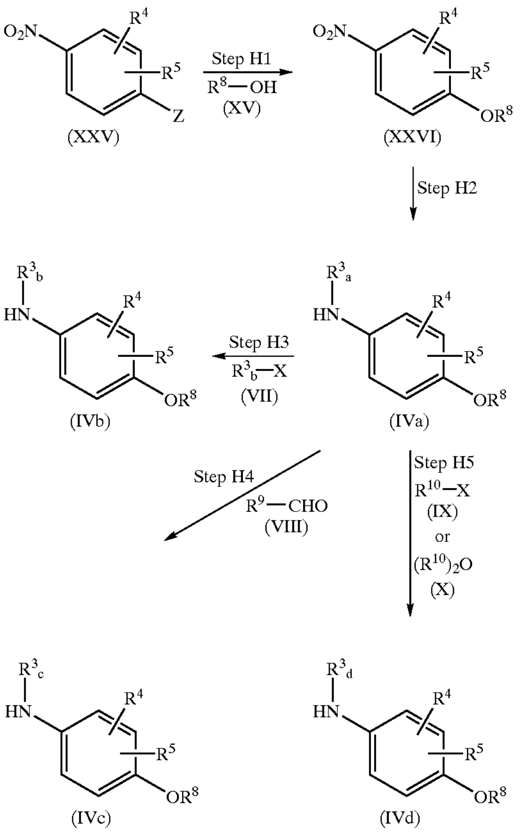
(XXV) (XXVI) (IVb) (IVa) (IVc) (IVd)
Method J
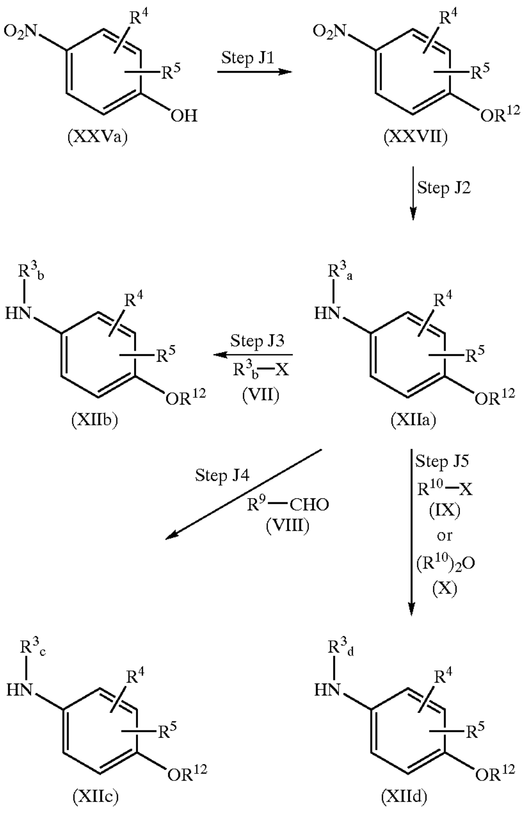
(XXVa) (XXVII) (XIIb) (XIIa) (XIIc) (XIId)
-continued
Method K
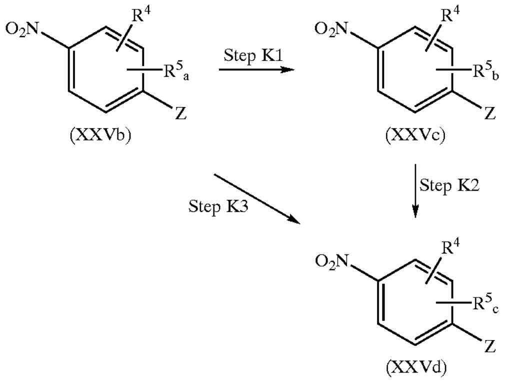
(XXVb) (XXVc) (XXVd)
Method L
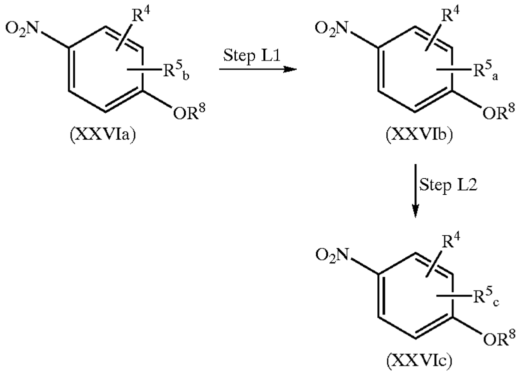
(XXVIa) (XXVIb) (XXVIc)
Method M
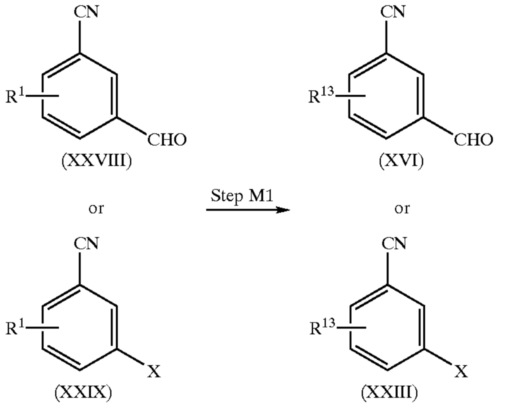
(XXVIII) (XVI)
or or
(XXIX) (XXIII)
Method N
$(R^{11}O)_2P(O)CH(R^2)COOEt$ (XXX) → Step N1 → $(R^{11}O)_2P(O)CH(R^2)COOH$ (XXXI)
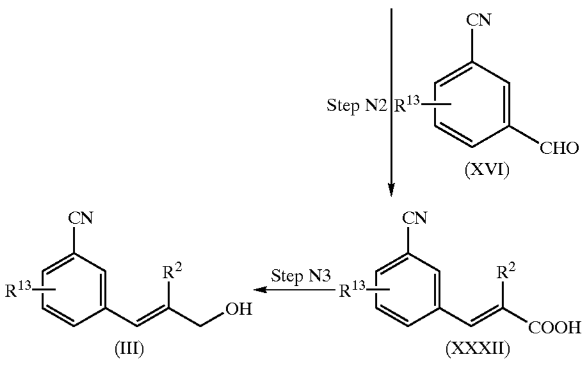
(XVI) (III) (XXXII)

-continued

Method O

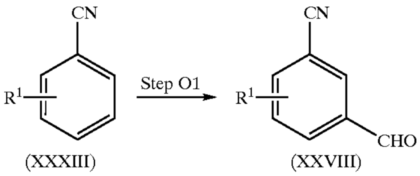

(XXXIII) (XXVIII)

In the above reaction schemes:

$R^1$, $R^2$, $R^3$, $R^3_a$, $R^3_b$, $R^3_c$, $R^3_d$, $R^4$, $R^5$, $R^6$, R8, $R^9$, $R^{10}$, $R^{11}$, $R^{12}$, $R^{13}$ and X are as defined above;

$R^2_a$ represents a hydrogen atom;

$R^5_a$ represents a carboxyl group;

$R^5_b$ represents a ($C_1$–$C_6$ alkoxy)carbonyl group;

$R^5_c$ represents a carbamoyl group, a ($C_1$–$C_6$ alkyl) carbamoyl group or a di ($C_1$–$C_6$ alkyl)carbamoyl group; and Z represents a hydroxyl group or a leaving group.

The "($C_1$–$C_6$ alkoxy)carbonyl group" in the definition of $R^5_b$ and the "($C_1$–$C_6$ alkyl)carbamoyl group" and "di($C_1$–$C_6$ alkyl)carbamoyl group" in the definition of $R^5_c$ have the same meaning as those in $R^5$ defined above, respectively.

The "leaving group" in the definition of Z is not particularly limited provided that it can leave as a nucleophilic group. Examples of such a leaving group include a halogen atom such as a chlorine, bromine or iodine atom; a $C_1$–$C_4$ alkanesulfonyloxy group such as methanesulfonyloxy, ethanesulfonyloxy, propanesulfonyloxy or butanesulfonyloxy; a halogeno $C_1$–$C_4$ alkanesulfonyloxy group such as trifluoromethanesulfonyloxy, 2,2,2-trichloroethanesulfonyloxy, 3,3,3-tribromopropanesulfonyloxy or 4,4,4-trifluorobutanesulfonyloxy; or a $C_6$–$C_{10}$ arylsulfonyloxy group which is optionally substituted with from 1 to 3 $C_1$–$C_4$ alkyl groups such as benzenesulfonyloxy, α-naphthylsulfonyloxy, β-naphthylsulfonyloxy, p-toluenesulfonyloxy, 4-t-butylbenzenesulfonyloxy, mesitylenesulfonyloxy or 6-ethyl-α-naphthylsulfonyloxy; preferably a halogen atom, methanesulfonyloxy, ethanesulfonyloxy, trifluoromethanesulfonyloxy, 2,2,2-trichloroethanesulfonyloxy, benzenesulfonyloxy, toluenesulfonyloxy or mesitylenesulfonyloxy; more preferably a halogen atom, methanesulfonyloxy, trifluoromethanesulfonyloxy, benzenesulfonyloxy, p-toluenesulfonyloxy or mesitylenesulufonyloxy; and still more preferably a fluorine or chlorine atom.

Compounds of formulae (VI), (III) and (XI) are prepared by method E.

In Step E1, a compound of formula (VI) can be prepared by reaction of a compound of formula (XVI) with a compound of formula (XVII) in an inert solvent.

The inert solvent used in Step E1 is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; or a nitrile such as acetonitrile, propionitrile or butyronitrile; preferably an aromatic hydrocarbon (particularly benzene or toluene).

The reaction temperature of Step E1 varies depending on the nature of the starting material and the reagent, but is usually between 0° C. and 150° C., and is preferably between 30° C. and 100° C.

The reaction time of Step E1 varies depending on the nature of the starting material, the reagent and the temperature. It is usually from 10 minutes to 10 hours, and is preferably from 30 minutes to 5 hours.

After completion of the reaction, the desired product of this step can be isolated in a conventional manner. For example, after the reaction, the reaction mixture is concentrated to give the desired compound. The product thus obtained, if necessary, can be further purified in a conventional manner such as recrystallization, reprecipitation or chromatography.

In Step E2, a compound of formula (III) is prepared by reduction of a compound of formula (VI) in the presence of a reducing agent in an inert solvent.

The inert solvent used in Step E2 is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol, butanol or isobutanol; or mixtures thereof. When the reducing agent is an aluminum hydride or diborane, the inert solvent is an aliphatic hydrocarbon (particularly hexane or cyclohexane), an aromatic hydrocarbon (particularly benzene, toluene or xylene) or an ether (particularly diethyl ether, tetrahydrofuran or dioxane). When the reducing agent is sodium borohydride, the inert solvent is an alcohol (particularly methanol or ethanol) or a mixture of a halogenohydrocarbon and an alcohol (particularly a mixture of dichloromethane and ethanol).

The reducing agent used in Step E2 may be, for example, an aluminum hydride compound such as lithium aluminum hydride or diisobutylaluminum hydride; sodium borohydride or diborane; preferably sodium borohydride. In addition, when sodium borohydride is used, cerium chloride can be used as a catalyst.

The reaction temperature of Step E2 varies depending on the nature of the starting material and the reagent, but is usually between −78° C. and 100° C., and is preferably between 0° C. and 50° C.

The reaction time of Step E2 varies depending on the nature of the starting material, the reagents and the temperature. It is usually from 10 minutes to 12 hours, and is preferably from 30 minutes to 5 hours.

After completion of the reaction, the desired product of this step can be isolated in a conventional manner. For example, after the reaction, the reaction mixture is concentrated and the residue is partitioned between water and a solvent immiscible with water (for example, benzene, ether, ethyl acetate or the like). The extract is washed with water, dried over magnesium sulfate or the like, and then concentrated to give the desired compound. The product thus obtained, if necessary, can be further purified in a conventional manner such as recrystallization, reprecipitation or chromatography.

In Step E3, a compound of formula (XI) can be prepared by reaction of a compound of formula (III) with a compound of formula (XVIII) in the presence or absence of a base (preferably in the presence of a base) in an inert solvent.

The inert solvent used in this step is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile such as acetonitrile or isobutyronitrile; an amide such as formamide, N,N-dimethylformamide, N,N-dimethylacetamide or N-methyl-2-pyrrolidinone; or a sulfoxide such as dimethyl sulfoxide; or sulfolane; preferably a halogenohydrocarbon (particularly dichloromethane) or an ether (particularly diethyl ether or tetrahydrofuran).

The base used in this step may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; or an organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); preferably an organic amine (particularly triethylamine or pyridine).

The reaction temperature of this step varies depending on the nature of the starting material and the reagent, but is usually between −50° C. and 80° C., and is preferably between −20° C. and 50° C.

The reaction time of this step varies depending on the nature of the starting material, the reagent and the temperature. It is usually from 10 minutes to 10 hours, and is preferably from 30 minutes to 5 hours.

After completion of the reaction, the desired product of this step can be isolated in a conventional manner. For example, after the reaction, the reaction mixture is partitioned between water and a solvent immiscible with water (for example, benzene, ether, ethyl acetate or the like). The extract is washed with water, dried over magnesium sulfate or the like, and then concentrated to give the desired compound. The product thus obtained, if necessary, can be further purified in a conventional manner such as recrystallization, reprecipitation or chromatography.

Method G is another procedure to prepare a compound of formula (IIIa) which is a compound of formula (III) wherein $R^2$ is hydrogen.

In Step G1, a compound of formula (XXIV) can be prepared by Step G1(1), reaction of a compound of formula (XXII) with catecholborane in the presence or absence of an inert solvent (preferably in the absence of an inert solvent) and then by Step G1(2), reaction of the intermediate obtained in Step G1(1) with a compound of formula (XXIII) in the presence of a palladium catalyst and a base in an inert solvent.

The inert solvent used in Step G1(1) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; or an ether such as diethyl ether, diisopropyl ether, tetrahydrofuran, dioxane, dimethoxyethane or di(ethylene glycol)dimethyl ether; preferably an aliphatic hydrocarbon (particularly hexane or petroleum ether) or an aromatic hydrocarbon (particularly toluene).

The reaction temperature of Step G1(1) varies depending on the nature of the starting material and the reagent, but is usually between −10° C. and 100° C., and is preferably between 30° C. and 80° C.

The reaction time of step G1(1) varies depending on the nature of the starting material, the reagents and the temperature. It is usually from 10 minutes to 10 hours, and is preferably from 30 minutes to 5 hours.

After completion of the reaction, the desired product of Step G1(1) can be isolated in a conventional manner. For example, after the reaction, the reaction mixture is concentrated to give the desired compound. In addition, the product of this step can be used in the next reaction step without purification.

The inert solvent used in Step G1(2) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol, butanol or isobutanol; or mixtures thereof; preferably an aromatic hydrocarbon (particularly toluene).

The palladium catalyst used in Step G1(2) may be, for example, a palladium phosphine complex such as tetrakis(triphenylphosphine)palladium, bis(triphenylphosphine)palladium chloride complex, bis(diphenylphosphinoferrocene)palladium chloride complex or bis(triphenylphosphine)palladium acetate; tris(benzylideneacetone)dipalladium chloroform complex; bis(dibenzylideneacetone)palladium; palladium acetate or π-allylpalladium chloride dimer; preferably tetrakis(triphenylphosphine)palladium, bis(triphenylphosphine)palladium chloride complex or bis(diphenylphosphinoferrocene)palladium chloride complex; and more preferably tetrakis(triphenylphosphine)palladium.

The base used in Step G1(2) may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal alkoxide such as sodium methoxide, sodium ethoxide, potassium t-butoxide or lithum methoxide; or an organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); preferably an alkali metal alkoxide (particularly sodium ethoxide).

The reaction temperature of Step G1(2) varies depending on the nature of the starting material and the reagent, but is usually between 0° C. and 150° C., and is preferably between 50° C. and 120° C.

The reaction time of Step G1(2) varies depending on the nature of the starting material, the reagent and the temperature. It is usually from 10 minutes to 10 hours, and is preferably from 30 minutes to 5 hours.

After completion of the reaction, the desired product of Step G1(2) can be isolated in a conventional manner. For example, after completion of the reaction, the reaction mixture is partitioned between water and a solvent immiscible with water (for example, benzene, ether, ethyl acetate or the like). The extract is washed with water, dried over magnesium sulfate or the like, and then concentrated to give the desired compound. The product thus obtained, if necessary, can be further purified in a conventional manner such as recrystallization, reprecipitation or chromatography.

In Step G2, a compound of formula (IIIa) can be prepared by removal of the hydroxyl-protecting group of the compound of formula (XXIV) according to a similar procedure to that described in Step A2(e).

In Method H, a compound of formula (IVa), (IVb), (IVc) or (IVd) is prepared.

In Step H1, a compound of formula (XXVI) can be prepared by Step H1(1), reaction of a compound of formula (XXV), wherein Z is a leaving group, with a compound of formula (XV) in the presence of a base in an inert solvent, or by Step H1(2), condensation of a compound of formula (XXV) wherein Z is hydroxyl, with a compound of formula (XV) in the presence of a phosphine derivative and an azo compound in an inert solvent.

The inert solvent used in Step H1(1) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a nitro compound such as nitromethane; a nitrile such as acetonitrile or isobutyronitrile; an amide such as formamide, N,N-dimethylformamide, N,N-dimethylacetamide or N-methyl-2-pyrrolidinone; or a sulfoxide such as dimethyl sulfoxide; or sulfolane; preferably an amide (particularly N,N-dimethylformamide or N,N-dimethylacetamide).

The base used in Step H1(1) may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal acetate such as sodium acetate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; an organic amine such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo [5.4.0]undec-7-ene (DBU); an alkyllithium such as methyllithium, ethyllithium or butyllithium; or a lithium alkylamide such as lithium diisopropylamide or lithium dicyclohexylamide; preferably an alkali metal hydride (particularly lithium hydride or sodium hydride), an alkali metal alkoxide (particularly sodium methoxide) or an alkyllithium (particularly butyllithium).

The reaction temperature of Step H1(1) varies depending on the nature of the starting material and the reagent, but is usually between −10° C. and 100° C., and is preferably between −5° C. and 50° C.

The reaction time of Step H1(1) varies depending on the nature of the starting material, the reagent and the temperature. It is usually from 5 minutes to 24 hours, and is preferably from 10 minutes to 12 hours.

After completion of the reaction, the desired product of Step H1(1) can be isolated in a conventional manner. For example, after completion of the reaction, the reaction mixture is partitioned between water and a solvent immiscible with water (for example, benzene, ether, ethyl acetate or the like). The extract is washed with water, dried over magnesium sulfate or the like, and then concentrated to give the desired compound. The product thus obtained, if necessary, can be further purified in a conventional manner such as recrystallization, reprecipitation or chromatography.

The inert solvent used in Step H1(2) is not particularly limited provided that it has no adverse effect on the reaction and dissolves the starting material to some extent. Examples of such a solvent include an aliphatic hydrocarbon such as hexane, heptane, ligroin or petroleum ether; an aromatic hydrocarbon such as benzene, toluene or xylene; a halogenohydrocarbon such as dichloromethane, chloroform, carbon tetrachloride, dichloroethane, chlorobenzene or dichlorobenzene; an ether such as diethyl ether; diisopropyl ether, tetrahydrofuran, dioxane, dimethoxyethane or di(ethylene glycol)dimethyl ether; preferably an aliphatic hydrocarbon, an aromatic hydrocarbon, a halogenohydrocarbon or an ether and more preferably a halogenohydrocarbon (particularly dichloromethane) or an ether (particularly diethyl ether or tetrahydrofuran).

The phosphine derivative used in Step H1(2) may be, for example, a tri-$C_1$–$C_6$-alkylphosphine such as trimethylphosphine, triethylphosphine, tripropylphosphine, tributylphosphine, tripentylphosphine, trihexylphosphine or the like; a tri-$C_6$–$C_{10}$-arylphosphine such as triphenylphosphine, triindenylphosphine, trinaphthylphosphine or the like; or a tri-$C_6$–$C_{10}$-aryl phosphine which may be substituted with a $C_1$–$C_4$ alkyl group such as tolyldiphenylphosphine, tritolylphosphine, trimesitylphosphine, tributylphenylphosphine, tri-6-ethyl-2-naphthylphosphine or the like; preferably a tri-$C_1$–$C_6$-alkylphosphine (particularly trimethylphosphine, triethylphosphine, tripropylphosphine or tributylphosphine) or a tri-$C_6$–$C_{10}$-arylphosphine (particularly triphenylphosphine, triindenylphosphine or trinaphthylphosphine); and more preferably tributylphosphine or triphenylphosphine.

The azo compound used in Step H1(2) may be, for example, azodicarbonyldipiperidine, a di-$C_1$–$C_4$-alkyl azodicarboxylate such as dimethyl azodicarboxylate, diethyl azodicarboxylate, dipropyl azodicarboxylate or dibutyl azodicarboxylate; preferably dimethyl azodicarboxylate or diethyl azodicarboxylate.

The reaction temperature of Step H1(2) varies depending on the nature of the starting material and the reagents, but is usually between −20° C. and 100° C., and is preferably between −10° C. and 50° C.

The reaction time of Step H1(2) varies depending on the nature of the starting material, the reagents and the temperature. It is usually from 15 minutes to 48 hours, and is preferably from 30 minutes to 24 hours.

After completion of the reaction, the desired product of Step H1 (2) can be isolated in a conventional manner. For example, when there is insoluble material in the reaction mixure, the reaction mixture is filtered and the filtrate is concentrated to give the desired compound; or the reaction mixture is concentrated and the residue is partitioned between water and a solvent immiscible with water (for example, benzene, ether, ethyl acetate or the like), the extract is washed with water, dried over magnesium sulfate or the like, and then concentrated to give the desired compound. The product thus obtained, if necessary, can be further purified in a conventional manner such as recrystallization, reprecipitation or chromatography.

In Step H2, a compound of formula (IVa) can be prepared by Step H2(1), reduction of a compound of formula (XXVI) under a hydrogen atmosphere at between 1 and 5 atmospheres pressure (preferably 1 atomsphere pressure) using a catalyst for catalytic hydrogenation in an inert solvent or by Step H2(2), reduction of compound of formula (XXVI) according to a method known to those skilled in the art, for example, stirring in the presence of metal powder in acetic acid or the like.

The inert solvent used in Step H2(1) (catalytic reduction) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol, butanol or isobutanol; or mixtures thereof; preferably an alcohol (particularly methanol) or mixtures of an ether and an alcohol (particularly a mixture of tetahydrofuran and methanol or ethanol).

The catalyst used in the catalytic hydrogenation is not particularly limited provided that it can usually be used in catalytic reduction. Examples of such a catalyst may be, for example, palladium black, palladium on carbon, palladium hydroxide, palladium hydroxide on carbon, Raney nickel, rhodium-aluminum oxide, palladium-barium sulfate, platinum oxide or platinum black; preferably palladium on carbon.

The reaction temperature of Step H2(1) varies depending on the nature of the starting material and the reagents, but is usually between −10° C. and 100° C., and is preferably between 0° C. and 50° C.

The reaction time of Step H2(1) varies depending on the nature of the starting material, the reagents and the reaction temperature. It is usually from 10 minutes to 10 hours, and is preferably from 30 minutes to 6 hours.

After completion of the reaction, the desired product of this step can be isolated by conventional manner. For example, after completion of the reaction, the reaction mixture is filtered to remove the catalyst, the filtrate is concentrated to give the desired product. The product thus obtained, if necessary, can be further purified in a conventional manner such as recrystallization, reprecipitation or chromatography.

The inert solvent used in Step H2(2) (reduction using metal powder) may be, for example, acetic acid, hydrochloric acid, water, an alcohol or mixtures of an organic solvent miscible with water; preferably acetic acid.

The metal powder used in Step H2(2) may be, for example, zinc, tin or iron powder; preferably zinc or tin powder.

The reaction temperature of Step H2(2) varies depending on the nature of the starting material and the reagents, but is usually between −10° C. and 100° C., and is preferably between 0° C. and 50° C.

The reaction time of Step H2(2) varies depending on the nature of the starting material, the reagents and the reaction temperature. It is usually from 10 minutes to 10 hours, and is preferably from 30 minutes to 3 hours.

After completion of the reaction, the desired product of Step H2(2) can be isolated in a conventional manner. For example, after completion of the reaction, the reaction mixture is filtered to remove insoluble material and the filtrate is concentrated to give the desired product. The product thus obtained, if necessary, can be further purified in a conventional manner such as recrystallization, reprecipitation or chromatography.

In Step H3, a compound of formula (IVb) can be prepared by reaction of a compound of formula (IVa) with a compound of formula (VII) in the presence or absence of a base (preferably in the presence of a base) in an inert solvent under similar conditions to those described in Step B2.

In Step H4, a compound of formula (IVc) can be prepared by reaction of a compound of formula (IVa) with a compound of formula (VIII) in the presence of acetic acid and sodium cyanoborohydride in an inert solvent under similar conditions to those described in Step B3.

In Step H5, a compound of formula (IVd) can be prepared by Step H5(1), reaction of a compound of formula (IVa) with a compound of formula (IX) or (X) in the presence or absence of a base (preferably in the presence of a base) in an inert solvent and then, if necessary, by Step H5(2), removal of a hydroxyl protecting group of the product of Step H5(1) under similar conditions to those described in step B4(1) or A2(e), respectively.

Method J is a procedure to prepare a compound of formula (XIIa), (XIIb), (XIIc) or (XIId).

In Step J1, a compound of formula (XXVII) can be prepared by Step J1(1), reaction of a compound of formula (XXVa), which is a compound of formula (XXV) wherein Z is a hydroxyl group, with a compound of formula $R^{12}$—$Z_a$ (wherein $R^{12}$ is as defined above, and $Z_a$ is the leaving group defined in Z) or a compound of formula $R^2_a$—O—$R^{12}_a$ (wherein $R^{12}_a$ is the acyl group defined in $R^{12}$) in the presence or absence of a base (preferably in the presence of a base) in an inert solvent or by Step J1(2), reaction of a compound of formula (XXVa), which is a compound of formula (XXV) wherein Z is a hydroxyl group, with a compound of formula $R^{12}_a$—OH (wherein $R^{12}_a$ is as defined above) in the presence of a condensation reagent and in the presence or absence of a base (preferably in the presence of a base) in an inert solvent or by Step J1(3), reaction of a compound of formula (XXVa), which is a compound of formula (XXV) wherein Z is a hydroxyl group, with a compound of formula $R^{12}_a$—OH (wherein $R^{12}_a$ is as defined above) in the presence of a dialkyl halogenophosphate such as diethyl chlorophosphate and in the presence of a base in an inert solvent or by Step J1(4), reaction of a compound of formula (XXVa), which is a compound of formula (XXV) wherein Z is a hydroxyl group, with a dihydrofuran or dihydropyran derivative in the presence or absence of an acid (preferably in the presence of an acid) in an inert solvent.

The inert solvent used in Step J1(1) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an ester such as ethyl formate, ethyl acetate, propyl acetate, butyl acetate or diethyl carbonate; a ketone such as acetone or methyl ethyl ketone; a nitro compound such as nitromethane; a nitrile such as acetonitrile or isobutyronitrile; an alcohol such as methanol, ethanol, propanol, 2-propanol, butanol or isobutanol; an amide such as formamide, N,N-dimethylformamide, N,N-dimethylacetamide or N-methyl-2-pyrrolidinone; a sulfoxide such as dimethyl sulfoxide; or sulfolane; preferably a halogenohydrocarbon (particularly dichloromethane), an ether (particularly diethyl ether or teterahydrofuran) or an amide (particularly N,N-dimethylformamide).

The base employed in Step J1(1) may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal alkoxide such as sodium methoxide, sodium ethoxide, potassium t-butoxide or lithium methoxide; or an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); preferably an alkali metal hydride (particularly sodium hydride), an alkali metal alkoxide (particularly potassium t-butoxide) or an organic amine (particularly triethylamine or pyridine).

In addition, a catalytic amount of 4-(N,N-dimethylamino)pyridine or 4-pyrrolidinopyridine can be used in combination with another base. A quaternary ammonium salt such as benzyltriethylammonium chloride or tetrabutylammonium chloride or a crown ether such as dibenzo-18-crown-6 can be added in order to catalyse the reaction.

The reaction temperature of Step J1(1) varies depending on the nature of the starting material and the reagent, but is usually between −20° C. and 100° C., and is preferably between 0° C. and 50° C.

The reaction time of Step J1(1) varies depending on the nature of the starting material, the reagents and the reaction temperature. It is usually from 10 minutes to 24 hours, and is preferably from 30 minutes to 12 hours.

Typical examples of the compound of formula $R^{12}$—$Z_a$ may be, for example, an acyl halide such as acetyl chloride, propionyl chloride, butyryl bromide, valeryl chloride, hexanoyl chloride, methoxycarbonyl chloride, methoxycarbonyl bromide, ethoxycarbonyl chloride, propoxycarbonyl chloride, butoxycarbonyl chloride, hexyloxycarbonyl chloride, benzoyl chloride, benzoyl bromide or naphthoyl chloride; a silyl halide such as t-butyldimethylsilyl chloride, trimethylsilyl chloride, triethylsilyl chloride, triethylsilyl bromide, triisopropylsilyl chloride, dimethylisopropylsilyl chloride, diethylisopropylsilyl chloride, t-butyldiphenylsilyl chloride, diphenylmethylsilyl chloride, triphenylsilyl chloride; a silyl trifluoromethanesulfonate corresponding to one of the silyl halides described above; an aralkyl halide such as benzyl chloride or benzyl bromide; or a substituted alkyl halide which is substituted with a $C_1$–$C_4$ alkoxy, $C_1$–$C_4$ alkanoyloxy or $C_2$–$C_5$ alkoxycarbonyloxy group such as methoxymethyl chloride, ethoxymethyl chloride, pivaloyloxymethyl chloride or ethoxycarbonyloxymethyl chloride; preferably a substituted alkyl halide which is substituted with a $C_1$–$C_4$ alkoxy, $C_1$–$C_4$ alkanoyloxy or $C_2$–$C_5$ alkoxycarbonyloxy group (particularly methoxymethyl chloride).

Typical examples of the compound of formula $R^{12}_a$—O—$R^{12}_a$ may be, for example, an aliphatic and anhydride such as acetic anhydride, propionic anhydride, valeric anhydride or hexanoic anhydride. A mixed anhydride, such as a mixed anhydride, of formic acid and acetic acid, can also be used.

The inert solvent used in Step J1(2) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile such as acetonitrile or isobutyronitrile; an amide such as formamide, N,N-dimethylformamide, N,N-dimethylacetamide or N-methyl-2-pyrrolidinone or a sulfoxide such as dimethyl sulfoxide; or sulfolane; preferably an ether (particularly diethyl ether or tetrahydrofuran) or an amide (particularly N,N-dimethylacetamide or N-methyl-2-pyrrolidinone).

Examples of the condensation reagent used in Step J1(2) include 1,3-dicyclohexylcarbodiimide, 1,1'-carbonyldiimidazole or 2-chloro-1-methylpyridinium iodide; preferably 1,3-dicyclohexylcarbodiimide.

Examples of the base used in Step J1(2) include the same bases as those used in Step J1(1).

The reaction temperature of Step J1(2) varies depending on the nature of the starting materials and the reagents, but is usually between −20° C. and 100° C., and is preferably between 0° C. and 50° C.

The reaction time of Step J1(2) varies depending on the nature of the starting materials, the reagents and the reaction temperature. It is usually from 10 minutes to 24 hours, and is preferably from 30 minutes to 12 hours.

The inert solvent used in Step J1(3) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; an ester such as ethyl formate, ethyl acetate, propyl acetate, butyl acetate or diethyl carbonate; a nitro compound such as nitromethane; a nitrile such as acetonitrile or isobutyronitrile; an amide such as formamide, N,N-dimethylformamide, N,N-dimethylacetamide or N-methyl-2-pyrrolidinone or a sulfoxide such as dimethyl sulfoxide; or sulfolane; preferably an ether (particularly diethyl ether or tetrahydrofuran).

Examples of the base employed in Step J1(3) include the same bases as those used in Step J1(1).

The reaction temperature of Step J1(3) varies depending on the nature of the starting materials and the reagents, but is usually between −20° C. and 100° C., and is preferably between 0° C. and 50° C.

The reaction time of Step J1(3) varies depending on the nature of the starting materials, the reagents and the reaction temperature. It is usually from 10 minutes to 24 hours, and is preferably from 30 minutes to 12 hours.

The inert solvent used in Step J1(4) is not particularly limited provided that it has no adverse effect on the reaction and dissolves the starting material to some extent. Examples of such a solvent may be, for example, an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an ester such as ethyl formate, ethyl acetate, propyl acetate, butyl acetate or diethyl carbonate; a nitro compound such as nitromethane; a nitrile such as acetonitrile or isobutyronitrile; preferably a halogenohydrocarbon (particularly dichloromethane) or an ether (particularly diethyl ether or tetrahydrofuran).

The acid used in Step J1(4) may be, for example, a mineral acid such as hydrofluoric acid, hydrochloric acid, hydrobromic acid, hydroiodic acid, nitric acid, perchloric acid, sulfuric acid, phosphoric acid or the like; a sulfonic acid such as methanesulfonic acid, trifluoromethanesulfonic acid, ethanesulfonic acid, benzenesulfonic acid or p-toluenesulfonic acid; or a carboxylic acid such as acetic acid, propionic acid, butyric acid, fumaric acid, succinic acid, citric acid, tartaric acid, oxalic acid, maleic acid, benzoic acid or the like; preferably a sulfonic acid (particularly p-toluenesulfonic acid).

The reaction temperature of Step J1(4) varies depending on the nature of the starting materials and the reagents, but is usually between −20° C. and 100° C., and is preferably between 0° C. and 50° C.

The reaction time of Step J1(4) varies depending on the nature of the starting materials, the reagents and the reaction temperature. It is usually from 10 minutes to 24 hours, and is preferably from 30 minutes to 12 hours.

After completion of the reaction, the desired product of Step J1 can be isolated in a conventional manner. For example, after completion of the reaction, the reaction mixture is partitioned between water and a solvent immiscible with water (for example, benzene, ether, ethyl acetate or the like). The extract is washed with water, dried over anhydrous magnesium sulfate or the like, and then concentrated to give the desired product. The product thus obtained, if necessary, can be further purified in a conventional manner such as recrystallization, reprecipitation or chromatography.

In Step J2, a compound of formula (XIIa) can be prepared by Step J2(1), reduction of a compound of formula (XXVII) under a hydrogen atmosphere at between 1 and 5 atmospheres pressure (preferably 1 atomosphere pressure) using a catalyst for catalytic hydrogenation in an inert solvent, or by Step J2(2), reduction of a compound of formula (XXVII) according to a procedure which is a reduction of nitro group to amino group known to those skilled in the art, for example, stirring in the presence of metal powder in acetic acid or the like. Step J2 can be carried out by a similar procedure to that described in Step H2.

In Step J3, a compound of formula (XIIb) can be prepared by reaction of a compound of formula (XIIa) with a compound of formula (VII) in the presence or absence of a base (preferably in the presence of a base) in an inert solvent according to a similar procedure to that described in Step B2.

In Step J4, a compound of formula (XIIc) can be prepared by reaction of a compound of formula (XIIa) with a compound of formula (VIII) in the presence of acetic acid and sodium cyanoborohydride in an inert solvent according to a similar procedure to that described in Step B3.

In Step J5, a compound of formula (XIId) can be prepared by Step J5(1), reaction of a compound of formula (XIIa) with a compound of formula (IX) or (X) in the presence or absence of a base (preferably in the presence of a base) in an inert solvent and then, if necessary, by Step J5(2), removal of a protecting group for a hydroxyl group of the product of Step J5(1), according to a similar procedure to that described in Step B4(1) or A2(e), respectively.

In Method K, compounds of formula (XXVc) or (XXVd) can be prepared.

In Step K1, a compound of formula (XXVc) can be prepared by Step K1(1), reaction of a compound of formula (XXVb) with an alcohol in the presence of an esterification reagent in an inert solvent, or by Step K1(2), reaction of a compound of formula (XXVb) with an active ester formation reagent in an inert solvent and then by reaction of the active ester with an alcohol in an inert solvent, or by Step K1(3), reaction of a compound of formula (XXVb) with a halogenation reagent in an inert solvent and then by reaction of the acyl halide with an alcohol in an inert solvent, or by Step K1(4), reaction of a compound of formula (XXVb) with an alcohol in the presence of an acid in an inert solvent or without a solvent (preferably without a solvent).

The esterification reagent used in Step K1(1) is not limited provided that it can be usually used in the field of synthetic organic chemistry. Examples of such an esterification reagent include a diazoalkane or a trialkylsilyldiazoalkane; preferably a $C_1$–$C_6$ diazoalkane such as diazomethane, diazoethane, diazopropane, diazobutane, diazopentane or diazohexane; or trimethylsilyidiazomethane; more preferably a $C_1$–$C_4$ diazoalkane or trimethylsilyldiazomethane; and most preferably diazomethane.

The inert solvent used in the reaction with a $C_1$–$C_6$ diazoalkane is not particularly limited provided that it has no adverse effect on the reaction and dissolves the starting material to some extent. Example of such a solvent include an aliphatic hydrocarbon such as hexane, heptane, ligroin or petroleum ether; an aromatic hydrocarbon such as benzene, toluene or xylene; a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an ester such as methyl acetate or ethyl acetate; or mixtures thereof; preferably a halogenohydrocarbon, an ether, an ester or mixtures thereof and more preferably an ether (particularly diethyl ether), an ester (particularly ethyl acetate), or mixtures thereof.

The inert solvent used in the reaction with trimethylsilyldiazomethane is not particularly limited provided that it has no adverse effect on the reaction and dissolves the starting material to some extent. Examples of such a solvent include an alcohol such as methanol, ethanol, propanol, 2-propanol, butanol, isobutanol, t-butanol, pentanol or hexanol; or mixtures of an alcohol described above and an aliphatic hydrocarbon such as hexane, heptane, ligroin or petroleum ether, an aromatic hydrocarbon such as benzene, toluene or xylene, a halogenohydrocarbon such as dichloromethane, chloroform, carbon tetrachloride, dichloroethane, chlorobenzene or dichlorobenzene, an ether such as diethyl ether, diisopropyl ether, tetrahydrofuran, dioxane, dimethoxyethane or di(ethylene glycol)dimethyl ether, or an ester such as methyl acetate or ethyl acetate; preferably an alcohol (particularly methanol) or mixtures of an aromatic hydrocarbon (particularly benzene) and an alcohol (particularly methanol).

The reaction temperature of Step K1(1) varies depending on the nature of the starting materials and the reagents, but is usually between −10° C. and 100° C., and is preferably between 10° C. and 50° C.

The reaction time of Step K1(1) varies depending on the nature of the starting materials, the reagents and the reaction temperature. It is usually from 10 minutes to 10 hours, and is preferably from 15 minutes to 2 hours.

After completion of the reaction, the desired product of Step K1(1) can be isolated in a conventional manner. For example, after the completion of the reaction, the solvent of the reaction mixture is evaporated to give the desired product. The product thus obtained, if necessary, can be further purified in a conventional manner such as recrystallization, reprecipitation or chromatography.

The active ester formation reagent used in Step K1(2) is not limited provided that it can usually be used in the field of synthetic organic chemistry. Examples of such an active ester formation reagent include ethyl chloroformate; an N-hydroxy compound such as N-hydroxysuccinimide, 1-hydroxybenzotriazole or N-hydroxy-5-norbornene-2,3-dicarboximide; or a disulfide compound such as 2,2'-dipyridyl disulfide. Formation of an active ester is carried out in the presence of a condensation reagent such as 1,3-dicyclohexylcarbodiimide, 1,1'-carbonyldiimidazole or triphenylphosphine.

The inert solvent used in both reactions of Step K1(2) is not particularly limited provided that it has no adverse effect on the reaction and dissolves the starting material to some extent. Examples of such a solvent include a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an amide such as formamide, N,N-dimethylformamide, N,N-dimethylacetamide or hexamethylphosphoric triamide; or a nitrile such as acetonitrile; preferably an ether (particularly tetrahydrofuran) or an amide (particularly N,N-dimethylformamide).

The reaction temperature of Step K1(2) varies depending on the nature of the starting materials and the reagents. In the formation of the active ester, it is usually between −70° C. and 150° C., and is preferably between −10° C. and 100° C. In the reaction of the active ester with an alcohol, it is usually between −20° C. and 100° C., and is preferably between 0° C. and 50° C.

The reaction times of both reactions of Step K1(2) vary depending on the nature of the starting materials, the reagents and the reaction temperature. They are usually from 30 minutes to 80 hours, and are preferably from 1 hour to 48 hours.

After completion of the reaction, the desired product of Step K1(2) can be isolated in a conventional manner. For example, after completion of the reaction, the solvent of the reaction mixture is evaporated to give the desired product; or, after completion of the reaction, the reaction mixture is concentrated and the residue is partitioned between water and a solvent immiscible with water (for example, benzene, ether, ethyl acetate or the like), the extract is washed with water, dried over anhydrous magnesium sulfate or the like, and concentrated to give the desired compound. The product thus obtained, if necessary, can be further purified in a conventional manner such as recrystallization, reprecipitation or chromatography.

The halogenation reagent used in Step K1(3) is not limited provided that it can be usually used in the field of synthetic organic chemistry. Examples of such a halogenation reagent include oxalyl chloride, thionyl chloride, phosphoryl chloride or phosphorus pentachloride.

The inert solvent used in both reactions of Step K1 (3) is not particularly limited provided that it has no adverse effect on the reaction and dissolves the starting material to some extent. Examples of such a solvent include an aromatic hydrocarbon such as benzene, toluene or xylene; a halogenohydrocarbon such as dichloromethane, chloroform, carbon tetrachloride, dichloroethane, chlorobenzene or dichlorobenzene; or an ether such as diethyl ether, diisopropyl ether, tetrahydrofuran, dioxane, dimethoxyethane or di(ethylene glycol)dimethyl ether; preferably an ether (particularly tetrahydrofuran).

The reaction temperature of Step K1(3) varies depending on the nature of the starting materials and the reagents. The reaction temperature of formation for an acyl halide is between −70° C. and 150° C., and is preferably between −10° C. and 100° C.

The temperature for reaction of an acyl halide with an alcohol is between −20° C. and 100° C., and is preferably between 0° C. and 50° C.

Both reaction times of Step K1(3) vary depending on the nature of the starting materials, the reagents and the reaction temperature. They are usually from 30 minutes to 80 hours, and are preferably from 1 hour to 48 hours.

After completion of the reaction, the desired product of Step K1(3) can be isolated in a conventional manner. For example, after completion of the reaction, the solvent of the reaction mixture is evaporated to give the desired product; or, after completion of the reaction, the reaction mixture is evaporated, the residue is partitioned between water and a solvent immiscible with water (for example, benzene, ether, ethyl acetate or the like), the extract is washed with water, dried over anhydrous magnesium sulfate or the like, and concentrated to give the desired compound. The product thus obtained, if necessary, can be further purified in a conventional manner such as recrystallization, reprecipitation or chromatography.

The inert solvent used in Step K1(4) is not particularly limited provided that it has no adverse effect on the reaction and dissolves the starting material to some extent. Examples of such a solvent include a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an amide such as formamide, N,N-dimethylformamide, N,N-dimethylacetamide or hexamethylphosphoric triamide; or a nitrile such as acetonitrile; preferably an ether (particularly or diethyl ether or tetrahydrofuran).

The acid used in Step K1(4) may be, for example, a mineral acid such as hydrofluoric acid, hydrochloric acid, hydrobromic acid, hydroiodic acid, nitric acid, perchloric acid, sulfuric acid, phosphoric acid or the like; a sulfonic acid such as methanesulfonic acid, trifluoromethanesulfonic acid, ethanesulfonic acid, benzenesulfonic acid or p-toluenesulfonic acid; or a carboxylic acid such as acetic acid, propionic acid, butyric acid, fumaric acid, succinic acid, citric acid, tartaric acid, oxalic acid, maleic acid, benzoic acid or the like; preferably a mineral acid (particularly hydrochloric acid or sulfuric acid).

The reaction temperature of Step K1(4) varies depending on the nature of the starting materials and the reagents, but is usually between 0° C. and 150° C., and is preferably between 30° C. and 100° C.

The reaction time of Step K1(4) varies depending on the nature of the starting materials, the reagents and the reaction temperature. It is usually from 30 minutes to 80 hours, and is preferably from 1 hour to 48 hours.

After completion of the reaction, the desired product of Step K1(4) can be isolated in a conventional manner. For example, after completion of the reaction, the reaction mixture is evaporated to give the desired compound; or, after completion of the reaction, the reaction mixture is evaporated, the residue is partitioned between water and a solvent immiscible with water (for example, benzene, ether, ethyl acetate or the like), the extract is washed with water, dried over anhydrous magnesium sulfate or the like, and then concentrated to give the desired product. The product thus obtained, if necessary, can be further purified in a conventional manner such as recrystallization, reprecipitation or chromatography.

In Step K2, a compound of formula (XXVd) can be prepared by reaction of a compound of formula (XXVc) with ammonia, a $C_1$–$C_6$ alkylamine or a di($C_1$–$C_6$ alkyl) amine in the presence or absence of a base (preferably in the presence of a base) in an inert solvent.

The inert solvent used in this step is not particularly limited provided that it has no adverse effect on the reaction and dissolves the starting material to some extent. Examples of such a solvent include an aliphatic hydrocarbon such as hexane, heptane, ligroin or petroleum ether; an aromatic hydrocarbon such as benzene, toluene or xylene; a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol, butanol or isobutanol; an amide such as formamide, N,N-dimethylformamide, N,N-dimethylacetamide, hexamethylphosphoric triamide or hexamethylphosphorous triamide; or a sulfoxide such as dimethyl sulfoxide; or sulfolane; preferably a halogenohydrocarbon or an ether; and more preferably an ether (particularly tetrahydrofuran).

Examples of the base used in Step K2 include an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; or an alkali metal hydroxide such as sodium hydroxide, potassium hydroxide or lithium hydroxide; preferably an alkali metal carbonate (particularly sodium carbonate or potassium carbonate).

Examples of the ammonia used in Step K2 include ammonia gas or concentrated aqueous ammonia solution; preferably an aqueous ammonia solution.

Examples of the $C_1$–$C_6$ alkylamine employed in Step K2 include methylamine, ethylamine, propylamine, isopropylamine, butylamine, isobutylamine, s-butylamine, t-butylamine, pentylamine or hexylamine.

Examples of the di($C_1$–$C_6$ alkyl)amine used in Step K2 include N,N-dimethylamine, N-ethyl-N-methylamine, N,N-diethylamine, N,N-dipropylamine, N,N-diisopropylamine, N,N-dibutylamine, N,N-diisobutylamine, N,N-di-s-butylamine, N,N-di-t-butylamine, N,N-dipentylamine or N,N-dihexylamine.

The reaction temperature of this step varies depending on the nature of the starting material and the reagent, but is usually between −10° C. and 100° C., and is preferably between 0° C. and 50° C.

The reaction time of this step varies depending on the nature of the starting materials, the reagents and the reaction temperature. It is usually from 10 minutes to 10 hours, and is preferably from 30 minutes to 3 hours.

After completion of the reaction, the desired product of this step can be isolated in a conventional manner. For example, after completion of the reaction, the solvent is evaporated to give the desired compound; or, after completion of the reaction, the reaction mixture is evaporated, the residue is partitioned between water and a solvent immiscible with water (for example, benzene, ether, ethyl acetate or the like), the extractant is washed with water, dried over anhydrous magnesium sulfate or the like, and then concentrated to give the desired product. The product thus obtained, if necessary, can be further purified in a conventional manner such as recrystallization, reprecipitation or chromatography.

In Step K3, a compound of formula (XXVd) is also prepared by reaction of a compound of formula (XXVb) with ammonia, a $C_1$–$C_6$ alkylamine or a di($C_1$–$C_6$ alkyl) amine in an inert solvent according to a method known to those skilled in synthetic organic chemistry. Examples of such a method may be, for example, a method usual in the synthesis of peptides such as an azide method, an active ester method, a mixed anhydride method or a condensation method; preferably a mixed anhydride method.

In the azide method, reaction of a compound of formula (XXVb) with hydrazine in an inert solvent (for example, an amide such as formamide, N,N-dimethylformamide, N,N-dimethylacetamide or hexamethylphosphoric triamide, preferably N,N-dimethylformamide) at between −10° C. and 100° C. (preferably between 0° C. and 50° C.) affords a hydrazide derivative which is converted to an azide derivative by reaction with a nitrite compound. The product is treated with ammonia, a $C_1$–$C_6$ alkylamine or a di($C_1$–$C_6$ alkyl)amine.

Examples of the nitrite employed in the azide method include an alkali metal nitrite such as sodium nitrite or an alkyl nitrite such as isoamyl nitrite.

The inert solvent used in the azide method may be, for example, an amide such as formamide, N,N-dimethylformamide, N,N-dimethylacetamide or hexamethylphosphoric triamide; a sulfoxide such as dimethyl sulfoxide; or sulfolane; or a pyrrolidone derivative such as N-methyl-2-pyrrolidone; preferably an amide (particularly N,N-dimethylformamide).

The two reaction steps of azidation and reaction with ammonia or the like, a $C_1$–$C_6$ alkylamine or a di($C_1$–$C_6$ alkyl)amine are usually carried out in one pot.

The reaction temperature of this step varies depending on the nature of the starting materials and the reagents. The reaction temperature of the azidation reaction is usually between −70° C. and 50° C., and is preferably between −50° C. and 0° C. The reaction temperature of the reaction with ammonia or the like is between −70° C. and 50° C., and is preferably between −10° C. and 10° C.

The reaction time of this step varies depending on the nature of the starting materials, the reagents and the reaction temperature. The reaction time for the azidation is usually from 5 minutes to 3 hours, and is preferably from 10 minutes to 1 hour. The reaction time of the reaction with ammonia or the like is usually from 5 hours to 7 days, and is preferably from 10 hours to 5 days.

After completion of the reaction, the desired product of Step K3 can be isolated in a conventional manner. For example, after completion of the reaction, the reaction mixture is evaporated to give the desired compound; or, after the reaction, the solvent is evaporated, the residue is partitioned between water and a solvent immiscible with water (for example, benzene, ether or ethyl acetate or the like), the extract is washed with water, dried over anhydrous magnesium sulfate or the like, and then concentrated to give the desired product. The product thus obtained, if necessary, can be further purified in a conventional manner such as recrystallization, reprecipitation or chromatography.

In the active ester method, reaction of a compound of formula (XXVb) with an active ester formation reagent in an inert solvent affords an active ester. The product is then treated with ammonia, a $C_1$–$C_6$ alkylamine or a di($C_1$–$C_6$ alkyl)amine.

The inert solvent used in both reactions of the active ester method is not particularly limited provided that it has no adverse effect on the reaction and disolves the starting material to some extent. Examples of such a solvent include a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an amide such as formamide, N,N-dimethylformamide, N,N-dimethylacetamide or hexamethylphosphoric triamide; or a nitrile such as acetonitrile; preferably an ether (particularly tetrahydrofuran) or an amide (particularly N,N-dimethylformamide).

Examples of the active ester formation reagent used in the active ester method include an N-hydroxy compound such as N-hydroxysuccinimide, 1-hydroxybenzotriazole or N-hydroxy-5-norbornene-2,3-dicarboximide; or a disulfide compound such as 2,2'-dipyridyl disulfide. Formation of an active ester is carried out in the presence of a condensation reagent such as 1,3-dicyclohexylcarbodiimide, 1,1'-carbonyidiimidazole or triphenylphosphine.

The reaction temperature of the active ester method varies depending on the nature of the starting materials and the reagents. The reaction temperature for the formation of an active ester is usually between −70° C. and 150° C., and is preferably between −10° C. and 100° C. The reaction temperature for the reaction of the active ester with ammonia or the like is between −20° C. and 100° C., and is preferably between 0° C. and 50° C.

The reaction time of the active ester method varies depending on the nature of the starting materials, the reagents and the reaction temperature. The reaction times of both reactions are usually from 30 minutes to 80 hours, and are preferably from 1 hour to 48 hours.

After completion of the reaction, the desired product of the active ester method can be isolated in a conventional manner. For example, after completion of the reaction, the reaction mixture is evaporated to give the desired compound; or, after completion of the reaction, the reaction mixture is evaporated, the residue is partitioned between water and a solvent immiscible with water (for example, benzene, ether, ethyl acetate or the like), the extract is washed with water, dried over anhydrous magnesium sulfate or the like, and then concentrated to give the desired product. The product thus obtained, if necessary, can be further purified in a conventional manner such as recrystallization, reprecipitation or chromatography.

In the mixed anhydride method, reaction of a compound of formula (XXVb) with a mixed anhydride formation reagent in the presence of a base in an inert solvent affords a mixed anhydride. The product is then treated with ammonia, a $C_1$–$C_6$ alkylamine or a di($C_1$–$C_6$ alkyl)amine in an inert solvent.

The inert solvent used in the mixed anhydride method may be, for example, a halogenohydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; or an amide such as formamide, N,N-dimethylformamide, N,N-dimethylacetamide or hexamethylphosphoric triamide; preferably an ether (particularly tetrahydrofuran).

Example of the mixed anhydride formation reagent used in the mixed anhydride method may be, for example, a $C_1$–$C_4$ alkyl halogenoformate, such as ethyl chloroformate or isobutyl chloroformate; a $C_1$–$C_5$ alkanoyl halide such as pivaloyl chloride; or a $C_1$–$C_4$ alkyl or $C_6$–$C_{14}$ aryl cyanophosphonate such as diethyl cyanophosphonate or diphenyl cyanophosphonate; preferably a $C_1$–$C_4$ alkyl halogenoformate (particularly ethyl chloroformate).

The base employed in the mixed anhydride method may be, for example, an alkali metal carbonate such as sodium carbonate, potassium carbonate or lithium carbonate; or an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); preferably an organic amine (particularly triethylamine).

The reaction temperature for the formation of a mixed anhydride varies depending on the nature of the starting materials and the reagents. It is usually between −50° C. and 100° C., and is preferably between −10° C. and 50° C.

The reaction time for the formation of a mixed anhydride varies depending on the nature of the starting materials, the reagents and the reaction temperature. It is usually from 5 minutes to 20 hours, and is preferably from 10 minutes to 10 hours.

The inert solvent used in the reaction of the anhydride with ammonia or the like is not particularly limited provided that it has no adverse effect on the reaction and dissolves the starting materials to some extent. Examples of such a solvent include an ether such as diethyl ether, diisopropyl ether, tetrahydrofuran, dioxane, dimethoxyethane or di(ethylene glycol)dimethyl ether; or an amide such as formamide, N,N-dimethylformamide, N,N-dimethylacetamide or hexamethylphosphoric triamide; preferably an ether (particularly tetrahydrofuran).

The reaction temperature for the reaction of a mixed anhydride with ammonia or the like varies depending on the nature of the starting materials and the reagents. It is usually between −30° C. and 100° C., and is preferably between 0° C. and 80° C.

The reaction time for the reaction of a mixed anhydride with ammonia or the like varies depending on the nature of the starting materials, the reagents and the reaction temperature. It is usually from 5 minutes to 24 hours, and is preferably from 10 minutes to 5 hours.

After completion of the reaction, the desired product of the mixed anhydride method can be isolated in a conventional manner. For example, after completion of the reaction, the reaction mixture is evaporated to give the desired compound; or, after the completion of the reaction, the reaction mixture is evaporated, the residue is partitioned between water and a solvent immiscible with water (for example, benzene, ether, ethyl acetate or the like), the extract is washed with water, dried over anhydrous magnesium sulfate or the like, and then concentrated to give the desired product. The product thus obtained, if necessary, can be further purified in a conventional manner such as recrystallization, reprecipitation or chromatography.

In the condensation method, reaction of a compound of formula (XXVb) with ammonia, a $C_1$–$C_6$ alkylamine or a di($C_1$–$C_6$ alkyl)amine is carried out in the presence of a condensation reagent in an inert solvent.

The condensation reagent employed in the condensation method may be, for example, 1,3-dicyclohexylcarbodiimide, 1,1'-carbonyldiimidazole or 2-chloro-1-methylpyridinium iodide; preferably 1,3-dicyclohexylcarbodiimide.

The reaction of condensation method can be conducted by a similar procedure to that described in the active ester method.

After completion of the reaction, the desired product of the condensation method can be isolated in a conventional manner. For example, after the reaction, the solvent is evaporated to give the desired compound; or, after the reaction, the solvent is evaporated, the residue is partitioned between water and a solvent immiscible with water (for example, benzene, ether or ethyl acetate or the like), the extract is washed with water, dried over anhydrous magnesium sulfate or the like, and then concentrated to give the desired product. The product thus obtained, if necessary, can be further purified in a conventional manner such as recrystallization, reprecipitation or chromatography.

In Method L, compounds of formula (XXVIb) or (XXVIc) are prepared.

In Step L1, a compound of formula (XXVIb) is prepared by hydrolysis of a compound of formula (XXVIa) according to a method known to those skilled in synthetic organic chemistry. The hydrolysis can be accomplished by treatment of a compound of formula (XXVIa) with an acid or a base in the presence or absence of an inert solvent according to a similar procedure to that described in Step A2(d).

In Step L2, a compound of formula (XXVIC) is prepared by reaction of a compound of formula (XXVIb) with ammonia, a $C_1$–$C_6$ alkylamine or a di($C_1$–$C_6$ alkyl)amine in an inert solvent according to a method known to those skilled in synthetic organic chemistry. Example of such a method include the usual methods used in the synthesis of peptides, such as an azide method, an active ester method, a mixed anhydride method or a condensation method; preferably a mixed anhydride method. The reaction of Step L2 can be carried out in a similar procedure to that described in Step K3.

In Method M, a compound of formula (XVI) or (XXIII) is prepared.

In Step M1 a compound of formula (XVI) or (XXIII) can be prepared.

(1) by reaction of acompound of formula (XXVIII) or (XXIX) with a compound of formula $R^{12}$—$Z_a$ (wherein $R^{12}$ and $Z_a$ are as defined above) or a compound of formula $R^{12}_a$—O—$R^{12}_a$ (wherein $R^{12}_a$ is as defined above) in the presence or absence of a base (preferably in the presence of a base) in an inert solvent;

(2) by reaction of a compound of formula (XXVIII) or (XXIX) with a compound of formula $R^{12}_a$—OH (wherein $R^{12}_a$ is as defined above) in the presence of a condensation reagent and in the presence or absence of a base (preferably in the presence of a base) in an inert solvent;

(3) by reaction of a compound of formula (XXVIII) or (XXIX) with a compound of formula $R^{12}_a$—OH (wherein $R^{12}_a$ is as defined above) in the presence of a dialkyl halogenophosphate such as diethyl chlorophosphate and a base in an inert solvent; or (4) by reaction of a compound of formula (XXVIII) or (XXIX) with a dihydrofuran or dihydropyran derivative in the presence or absence of an acid (preferably in the presence of an acid) in an inert solvent.

The reaction of Step M1 is carried out by a similar procedure to that described in Step J1.

Method N is another method for preparing a compound of formula (III).

In Step N1, a compound of formula (XXXI) can be prepared by hydrolysis of a compound of formula (XXX) in the presence of an acid or a base in the presence or absence of an inert solvent according to a similar procedure to that described in Step A2(d).

In Step N2, a compound of formula (XXXII) can be prepared by reaction of a compound of formula (XXXI) with a compound of formula (XVI) in the presence of a base in an inert solvent.

The inert solvent used in this step is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an amide such as formamide, N,N-dimethylformamide, N,N-dimethylacetamide or N-methyl-2-pyrrolidinone; or a sulfoxide such as dimethyl sulfoxide; or sulfolane; preferably an ether (particularly diethyl ether or tetrahydrofuran).

The base used in this step may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as litium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); an alkyllithium such as methyllithium, ethyllithium or butyllithium; a lithium alkylamide such as lithium diisopropylamide or lithium dicyclohexylamide; or an alkali metal hexamethyldisilazide such as potassium hexamethyidisilazide or sodium hexamethyldisilazide; preferably an alkyllithium (particularly butyllithium) or a lithium alkylamide (particularly lithium diisopropylamide).

The reaction temperature of this step varies depending on the nature of the starting materials and the reagents, but is usually between −150° C. and 50° C., and is preferably between −100° C. and 0° C.

The reaction time of this step varies depending on the nature of the starting materials, the reagents and the reaction temperature. It is usually from 10 minutes to 10 hours, and is preferably from 30 minutes to 5 hours.

After completion of the reaction, the desired product of Step N2 can be isolated in a conventional manner. For example, after the reaction, the desired product is extracted with water. The aqueous layer is adjusted to an acidic pH using an acid (for example, hydrochloric acid) and then is extracted with a solvent immiscible with water (for example, benzene, ether or ethyl acetate or the like). The extract is washed with water, dried over anhydrous magnesium sulfate or the like, and then concentrated to give the desired product. The product thus obtained, if necessary, can be further purified in a conventional manner such as recrystallization, reprecipitation or chromatography.

In Step N3, a compound of formula (III) can be prepared by Step N3(1), reaction of a compound of formula (XXXII) with a ($C_1$–$C_6$ alkyl)halogenocarbonate in the presence of a base in an inert solvent and then Step N3(2), reaction of the intermediate obtained in Step N3(1) with sodium borohydride in an inert solvent.

The inert solvent used in Step N3(1) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; or an ether such as diethyl ether, diisopropyl ether, tetrahydrofuran, dioxane, dimethoxyethane or di(ethylene glycol)dimethyl ether; preferably a halogenohydrocarbon (particularly dichloromethane) or an ether (particularly diethyl ether or tetrahydrofuran).

The base employed in Step N3(1) may be, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydroxide such as sodium hydroxide, potassium hydroxide or lithium hydroxide; or an organic base such as methylamine, dimethylamine, ethylamine, triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); preferably an organic amine (particularly triethylamine).

Examples of the ($C_1$–$C_6$ alkyl)halogenocarbonate employed in Step N3(l) include methyl fluorocarbonate, methyl chlorocarbonate, methyl bromocarbonate, methyl iodocarbonate, ethyl fluorocarbonate, ethyl chlorocarbonate, ethyl bromocarbonate, ethyl iodocarbonate, propyl fluorocarbonate, butyl chlorocarbonate, pentyl bromocarbonate or hexyl iodocarbonate; preferably methyl chlorocarbonate or ethyl chlorocarbonate.

The reaction temperature of Step N3(1) varies depending on the nature of the starting materials and the reagents, but is usually between −10° C. and 150° C., and is preferably between 0° C. and 100° C.

The reaction time of Step N3(1) varies depending on the nature of the starting materials, the reagents and the reaction temperature. It is usually from 5 minutes to 12 hours, and is preferably from 10 minutes to 6 hours.

After completion of the reaction, the desired product of Step N3(1) can be isolated in a conventional manner. For example, after the reaction, if necessary, the reaction mixture is filtered, the solvent of the filtrate is evaporated to give the desired product; or, after the reaction, the reaction mixture is partitioned between water and a solvent immiscible with water (for example, benzene, ether or ethyl acetate or the like), the extract is washed with water, dried over anhydrous magnesium sulfate or the like, and then concentrated to give the desired product. The product thus obtained, if necessary, can be further purified in a conventional manner such as recrystallization, reprecipitation or chromatography.

The inert solvent used in Step N3(2) is not particularly limited provided that it has no adverse effect on the reaction and dissolves the starting material to some extent. Examples of such a solvent include an aliphatic hydrocarbon such as hexane, cyclohexane, heptane, ligroin or petroleum ether; an aromatic hydrocarbon such as benzene, toluene or xylene; a halogenohydrocarbon such as dichloromethane, chloroform, carbon tetrachloride, 1,2-dichloroethane, chlorobenzene or dichlorobenzene; or an ether such as diethyl ether, diisopropyl ether, tetrahydrofuran, dioxane, dimethoxyethane or di(ethylene glycol)dimethyl ether; preferably an ether (particularly diethyl ether or tetrahydrofuran).

The reaction temperature of Step N3(2) varies depending on the nature of the starting materials and the reagents, but is usually between −10° C. and 150° C., and is preferably between 0° C. and 100° C.

The reaction time of Step N3(2) varies depending on the nature of the starting materials, the reagents and the reaction temperature. It is usually from 1 hour to 48 hours, and is preferably from 6 hours to 24 hours.

After completion of the reaction, the desired product of Step N3(2) can be isolated in a conventional manner. For example, after the reaction, the reaction mixture is partitioned between water and a solvent immiscible with water (for example, benzene, ether or ethyl acetate or the like), the extract is washed with water, dried over anhydrous magnesium sulfate or the like, and then concentrated to give the desired product. The product thus obtained, if necessary, can be further purified in a conventional manner such as recrystallization, reprecipitation or chromatography.

Method O is a procedure for preparing a compound of formula (XXVIII) which is a starting material for method M.

In Step O1, a compound of formula (XXVIII) can be prepared by reaction of a compound of formula (XXXIII) with hexamethylenetetramine in trifluoroacetic acid.

The reaction temperature of this step varies depending on the nature of the starting material and the reagent. The temperature for the reaction with hexamethylenetetramine is usually between 0° C. and 150° C., and is preferably between 50° C. and 120° C.

The reaction time for the reaction with hexamethylenetetramine varies depending on the nature of the starting materials, the reagents and the reaction temperature. It is usually from 1 hour to 24 hours, and is preferably from 6 hours to 12 hours.

After completion of the reaction, the desired product of Step O1 can be isolated in a conventional manner. For example, after the reaction, the solvent is evaporated to give the desired product; or, after the reaction, the solvent is evaporated and the residue is partitioned between water and a solvent immiscible with water (for example, benzene, diethyl ether or ethyl acetate or the like), the extract is washed with water, dried over anhydrous magnesium sulfate or the like and then concentrated to give the desired product. The product thus obtained, if necessary, can be further purified in a conventional manner such as recrystallization, reprecipitation or chromatography.

Starting compounds of the present invention having formulae (VII), (VIII), (IX), (X), (XV), (XVI), (XVII), (XVIII), (XIX), (XXII), (XXIII), (XXV), (XXVIII), (XXIX), (XXX) and (XXXIII) are known or can easily be prepared by known methods [for example, *Bioorg. Med. Chem. Lett.*, 8, 277 (1998), *Tetrahedron Letters*, 37, 6439 (1996) and the like].

EXAMPLES

The following Examples and Formulation Examples are intended to further illustrate the present invention and are not intended to limit the scope of the invention.

NMR spectra are reported as δ values (ppm) relative to tetramethylsilane as the internal standard. Coupling constants (J values) are reported in Hertz (Hz), rounded to the nearest 0.5 Hz, using the following abbreviations:

| | |
|---|---|
| d | doublet |
| dd | doublet of doublets |
| ddd | doublet doublet of doublets |
| dt | doublet of triplets |
| t | triplet |
| q | quartet |
| m | multiplet |
| s | singlet |
| bs | broad singlet |

Example 1

N-[4-(1-Acetimidoylpiperidin-4-yloxy)phenyl]-N-[3-(3-amidinophenyl)-2-(E)-propenyl] ethanesulfonamide Dihydrochloride (Exemplification Compound Number 1080)

(a) N-[3-(3-Amidinophenyl)-2-(E)-propenyl]-N-[4-(piperidin-4-yloxy)phenyl]ethanesulfonamide Dihydrochloride N-[4-(1-t-butoxycarbonylpiperidin-4-yloxy)phenyl]-N-[3-(3-cyanophenyl)-2-(E)-propenyl]ethanesulfonamide (955 mg) was dissolved in a mixture of dichloromethane (40 ml) and ethanol (20 ml). Hydrogen chloride gas was passed through the mixture in an ice bath for 1 hour. The resulting mixture was stirred in a stoppered reaction vessel at room temperature for 9 hours. The reaction mixture was concentrated in vacuo, and to a solution of the residue in ethanol (30 ml) were added aqueous ammonium chloride solution (193 mg in 10 ml) and 28% aqueous ammonia solution (0.375 ml). The resulting mixture was allowed to stand at room temperature for 12 hours and concentrated in vacuo. To a solution of the residue in methanol (20 ml) was added a 4M solution of hydrogen chloride in dioxane (2 ml) and the mixture was concentrated in vacuo. The residue was purified by preparative HPLC (YMC-Pack ODS YMC) using 15% aqueous acetonitrile as an eluant to afford an amorphous solid. To a solution of the solid in methanol (10 ml) was added a 4M solution of hydrogen chloride in dioxane (1 ml) and the mixture was concentrated to dryness in vacuo. The resulting amorphous solid was dissolved in water (10 ml) and the solution was lyophilized to give the desired compound (354 mg, yield 44%) as a colorless amorphous solid.

$^1$H NMR (500 MHz, DMSO-$d_6$) δ ppm: 1.27 (3H, t, J=7.0), 1.83 (2H, m), 2.09 (2H, m), 3.03 (2H, m), 3.17 (2H, q, J=7.0), 3.19 (2H, m), 4.45 (2H, d, J=6.0), 4.64 (1H, m), 6.45 (1H, dt, J=16.0, 6.0), 6.55 (1H, d, J=16.0), 7.00 (2H, d, J=9.0), 7.37 (2H, d, J=9.0), 7.54 (1H, t, J=8.0), 7.70 (2H, m), 7.89 (1H, s); MS (FAB) m/z=443 $(M+H)^+$.

(b) N-[4-(1-Acetimidoylpiperidin-4-yloxy)phenyl]-N-[3-(3-amidinophenyl)-2-(E)-propenyl]ethanesulfonamide dihydrochloride To a solution of N-[3-(3-amidinophenyl)-2-(E)-propenyl]-N-[4-(piperidin-4-yloxy)phenyl] ethanesulfonamide dihydrochloride (311 mg) in ethanol (10 ml) were added ethyl acetimidate hydrochloride (260 mg) and triethylamine (0.500 ml). The resulting mixture was stirred at room temperature for 12 hours. After addition of a 4M solution of hydrogen chloride in dioxane (1 ml), the resulting mixture was concentrated in vacuo. The residue was purified by preparative HPLC (YMC-Pack ODS YMC) using 20% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. The resulting amorphous solid was dissolved in water (10 ml) and the solution was lyophilized to give the title compound (243 mg, yield 62%) as a colorless amorphous solid.

$^1$H NMR (500 MHz, DMSO-$d_6$) δ ppm: 1.27 (3H, t, J=7.0), 1.72 (2H, m), 2.04 (2H, m), 2.30 (3H, s), 3.18 (2H, q, J=7.0), 3.50–3.59 (2H, m), 3.72 (1H, m), 3.84 (1H, m), 4.45 (2H, d, J=6.0), 4.70 (1H, m), 6.46 (1H, dt, J=15.5, 6.0), 6.55 (1H, d, J=15.5), 7.01 (2H, d, J=9.0), 7.37 (2H, d, J=9.0), 7.54 (1H, t, J=8.0), 7.71 (2H, m), 7.91 (1H, s); IR (KBr, $cm^{-1}$): 1674, 1625.

Example 2

N-[4-(1-Acetimidoylpiperidin-4-yloxy)phenyl]-N-[3-(3-amidinophenyl)-2-methyl-2-(E)-propenyl] ethanesulfonamide Dihydrochloride (Exemplification Compound Number 1220)

(a) N-[3-(3-Amidinophenyl)-2-methyl-2-(E)-propenyl]-N-[4-(piperidin-4-yloxy)phenyl]ethanesulfonamide Dihydrochloride N-[4-(1-t-butoxycarbonylpiperidin-4-yloxy)phenyl]-N-[3-(3-cyanophenyl)-2-methyl-2-(E)-propenyl] ethanesulfonamide (839 mg) was dissolved in a mixture of dichloromethane (40 ml) and ethanol (20 ml). Hydrogen chloride gas was passed through the mixture in an ice bath for 1 hour. The resulting mixture was stirred in a stoppered reaction vessel at room temperature for 8 hours. The reaction mixture was concentrated in vacuo and to a solution of the residue in ethanol (30 ml) were added aqueous ammonium chloride solution (166 mg in 10 ml) and 28% aqueous ammonia solution (0.320 ml). The resulting mixture was allowed to stand at room temperature for 12 hours and concentrated in vacuo. To a solution of the residue in methanol (20 ml) was added a 4M solution of hydrogen chloride in dioxane (1 ml) and the mixture was concentrated in vacuo. The residue was purified by preparative HPLC (YMC-Pack ODS YMC) using 15% aqueous acetonitrile as an eluant to afford an amorphous solid. To a solution of the solid in methanol (20 ml) was added a 4M solution of hydrogen chloride in dioxane (1 ml) and the mixture was concentrated to dryness in vacuo. The resulting amorphous solid was dissolved in water (10 ml) and the solution was lyophilized to give the desired compound (514 mg, yield 63%) as a colorless amorphous solid.

$^1$H NMR (500 MHz, DMSO-$d_6$) δ ppm: 1.27 (3H, t, J=7.0), 1.84 (2H, m), 1.87 (3H, s), 2.09 (2H, m), 3.04 (2H, m), 3.16 (2H, q, J=7.0), 3.20 (2H, m), 4.39 (2H, s), 4.64 (1H, m), 6.35 (1H, s), 7.01 (2H, d, J=9.5), 7.39 (2H, d, J=9.5), 7.47 (1H, d, J=8.0), 7.55 (2H, m), 7.64 (1H, d, J=8.0); IR (KBr, $cm^{-1}$): 1675.

(b) N-[4-(1-Acetimidoylpiperidin-4-yloxy)phenyl]-N-[3-(3-amidinophenyl)-2-methyl-2-(E)-propenyl] ethanesulfonamide Dihydrochloride To a solution of N-[3-(3-amidinophenyl)-2-methyl-2-(E)-propenyl]-N-[4-(piperidin-4-yloxy)phenyl] ethanesulfonamide dihydrochloride (303 mg) in ethanol (10 ml) were added ethyl acetimidate hydrochloride (246 mg) and triethylamine (0.460 ml). The resulting mixture was stirred at room temperature for 12 hours. After addition of a 4M solution of hydrogen chloride in dioxane (0.9 ml), the resulting mixture was concentrated in vacuo. The residue was purified by preparative HPLC (YMC-Pack ODS YMC) using 20% aqueous acetonitrile as an eluant to afford an amorphous solid. To a solution of the solid in methanol (10 ml) was added a 4M solution of hydrogen chloride in dioxane (0.4 ml) and the mixture was concentrated to dryness in vacuo. The resulting amorphous solid was dissolved in water (10 ml) and the solution was lyophilized to give the title compound (170 mg, yield 45%) as a colorless amorphous solid.

$^1$H NMR (500 MHz, DMSO-$d_6$) δ ppm: 1.27 (3H, t, J=7.0), 1.71 (2H, m), 1.87 (3H, s), 2.04 (2H, m), 2.30 (3H, s), 3.17 (2H, q, J=7.0), 3.53 (2H, m), 3.72 (1H, m), 3.83 (1H, m), 4.39 (2H, s), 4.70 (1H, m), 6.35 (1H, s), 7.01 (2H, d, J=9.0), 7.39 (2H, d, J=9.0), 7.47 (1H, d, J=8.0), 7.55 (1H, s), 7.55 (1H, t, J=8.0), 7.65 (1H, d, J=8.0); IR (KBr, $cm^{-1}$): 1673, 1626.

Example 3

Ethyl N-[4-(1-Acetimidoylpiperidin-4-yloxy) phenyl]-N-[3-(3-amidinophenyl)-2-(E)-propenyl] sulfamoylacetate Dihydrochloride (Exemplification Compound Number 1410)

(a) Ethyl N-[3-(3-Amidinophenyl)-2-(E)-propenyl]-N-[4-(piperidin-4-yloxy)phenyl]sulfamoylacetate Dihydrochloride Ethyl N-[4-(1-t-butoxycarbonylpiperidin-4-yloxy) phenyl]-N-[3-(3-cyanophenyl)-2-(E)-propenyl] sulfamoylacetate (1.46 g) was dissolved in a mixture of dichloromethane (50 ml) and ethanol (25 ml). Hydrogen chloride gas was passed through the mixture in an ice bath for 1 hour. The resulting mixture was stirred in a stoppered reaction vessel at room temperature for 8 hours. The reaction mixture was concentrated in vacuo, and to a solution of the residue in ethanol (40 ml) were added aqueous ammonium chloride solution (0.3 g in 15 ml) and 28% aqueous ammonia solution (0.58 ml). The resulting mixture was allowed to stand at room temperature for 12 hours. To the reaction mixture was added a 4M solution of hydrogen chloride in dioxane (2 ml) and the mixture was concentrated in vacuo. The residue was purified by preparative HPLC (YMC-Pack ODS YMC) using 15% aqueous acetonitrile as an eluant to afford the desired compound (0.98 g, yield 68%) as a pale yellow amorphous solid.

$^1$H NMR (500 MHz, DMSO-$d_6$) δ ppm: 1.23 (3H, t, J=7.0), 1.83 (2H, m), 2.10 (2H, m), 3.05 (2H, m), 3.19 (2H, m), 4.20 (2H, q, J=7.0), 4.34 (2H, s), 4.45 (2H, d, J=6.0), 4.66 (1H, m), 6.45 (1H, dt, J=16.0, 6.0), 6.55 (1H, d, J=16.0), 7.04 (2H, d, J=8.5), 7.39 (2H, d, J=8.5), 7.55 (1H, t, J=8.0), 7.69 (1H, d, J=8.0), 7.72 (1H, d, J=8.0), 7.89 (1H, s); IR (KBr, $cm^{-1}$): 1737, 1675.

(b) Ethyl N-[4-(1-Acetimidoylpiperidin-4-yloxy)phenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[4-(piperidin-4-yloxy)phenyl]sulfamoylacetate dihydrochloride (1090 mg) in ethanol (40 ml) were added ethyl acetimidate hydrochloride (705 mg) and triethylamine (1.30 ml). The resulting mixture was stirred at room temperature for 6 hours and then concentrated to dryness in vacuo. To a solution of the residue in methanol (15 ml) was added a 4M solution of hydrogen chloride in dioxane (2 ml). The resulting mixture was concentrated in vacuo. The residue was purified by preparative HPLC (YMC-Pack ODS YMC) using 20% aqueous acetonitrile as an eluant to afford an amorphous solid. To a solution of the solid in methanol (15 ml) was added a 4M solution of hydrogen chloride in dioxane (1 ml) and the mixture was concentrated to dryness in vacuo to give the title compound (812 mg, yield 70%) as a colorless amorphous solid.

$^1$H NMR (500 MHz, DMSO-$d_6$) δ ppm: 1.23 (3H, t, J=7.0), 1.67–1.79 (2H, m), 2.04 (2H, m), 2.29 (3H, s), 3.50 (2H, m), 3.72 (1H, m), 3.81 (1H, m), 4.19 (2H, q, J=7.0), 4.34 (2H, s), 4.44 (2H, d, J=6.0), 4.70 (1H, m), 6.45 (1H, dt, J=16.5, 6.0), 6.55 (1H, d, J=16.5), 7.04 (2H, d, J=9.5), 7.39 (2H, d, J=9.5), 7.54 (1H, t, J=8.0), 7.69 (1H, d, J=8.0), 7.71 (1H, d, J=8.0), 7.88 (1H, s); IR (KBr, $cm^{-1}$): 1738, 1673, 1626.

Example 4

N-[4-(1-Acetimidoylpiperidin-4-yloxy)phenyl]-N-[3-(3-amidinophenyl)-2-(E)-propenyl] sulfamoylacetic Acid Dihydrochloride (Exemplification Compound Number 1939)

Ethyl N-[4-(1-acetimidoylpiperidin-4-yloxy)phenyl]-N-[3-(3-amidinophenyl)-2-(E)-propenyl]sulfamoylacetate dihydrochloride (440 mg) was dissolved in 3M hydrochloric acid (30 ml) and the mixture was stirred at 80° C. for 3 hours. The reaction mixture was cooled to room temperature and concentrated in vacuo. The residue was purified by preparative HPLC (YMC-Pack ODS YMC) using 15% aqueous acetonitrile as an eluant to afford an amorphous solid. To a solution of the solid in methanol (15 ml) was added a 4M solution of hydrogen chloride in dioxane (1 ml) and the mixture was concentrated to dryness in vacuo. The residue was dissolved in water (15 ml) and the solution was lyophilized to give the title compound (331 mg, yield 78%).

$^1$H NMR (500 MHz, DMSO-$d_6$) δ ppm: 1.73 (2H, m), 2.04 (2H, m), 2.29 (3H, s), 3.51 (2H, m), 3.72 (1H, m), 3.80 (1H, m), 4.18 (2H, s), 4.45 (2H, d, J=6.0), 4.70 (1H, m), 6.44 (1H, dt, J=16.5, 6.0), 6.55 (1H, d, J=16.5), 7.03 (2H, d, J=8.5), 7.40 (2H, d, J=8.5), 7.54 (1H, t, J=8.0), 7.68 (1H, d, J=8.0), 7.71 (1H, d, J=8.0), 7.87 (1H, s); IR (KBr, $cm^{-1}$): 1733, 1673, 1627.

Example 5

N-[4-(1-Acetimidoylpiperidin-4-yloxy)phenyl]-N-[3-(5-amidino-2-fluorophenyl)-2-(E)-propenyl] ethanesulfonamide Dihydrochloride (Exemplification Compound Number 1280)

(a) N-[3-(5-Amidino-2-fluorophenyl)-2-(E)-propenyl]-N-[4-(piperidin-4-yloxy)phenyl]ethanesulfonamide Dihydrochloride N-[4-(1-t-butoxycarbonylpiperidin-4-yloxy)phenyl]-N-[3-(5-cyano-2-fluorophenyl)-2-(E)-propenyl] ethanesulfonamide (2.00 g) was dissolved in a mixture of dichloromethane (60 ml) and ethanol (40 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (50 ml) were added aqueous ammonium chloride solution (0.39 g in 25 ml) and 28% aqueous ammonia solution (0.76 ml). The resulting mixture was allowed to stand at room temperature for 12 hours and concentrated in vacuo. To a solution of the residue in methanol (20 ml) was added a 4M solution of hydrogen chloride in dioxane (2 ml) and the mixture was concentrated in vacuo. The residue was purified by preparative HPLC (YMC-Pack ODS YMC) using 20% aqueous acetonitrile as an eluant to afford an amorphous solid. To a solution of the solid in methanol (10 ml) was added a 4M solution of hydrogen chloride in dioxane (1 ml) and the mixture was concentrated to dryness in vacuo. The resulting amorphous solid was dissolved in water (10 ml) and the solution was lyophilized to give the desired compound (1.20 g, yield 61%) as a pale brown amorphous solid.

$^1$H NMR (500 MHz, DMSO-$d_6$) δ ppm: 1.27 (3H, t, J=7.0), 1.82 (2H, m), 2.09 (2H, m), 3.04 (2H, m), 3.17 (2H, q, J=7.0), 3.18 (2H, m), 4.49 (2H, d, J=6.0), 4.64 (1H, m), 6.55 (1H, dt, J=16.0, 6.0), 6.61 (1H, d, J=16.0), 7.01 (2H, d, J=8.5), 7.37 (2H, d, J=8.5), 7.45 (1H, m), 7.78 (1H, m), 8.11 (1H, m); IR (KBr, $cm^{-1}$): 3056, 1676.

(b) N-[4-(1-Acetimidoylpiperidin-4-yloxy)phenyl]-N-[3-(5-amidino-2-fluorophenyl)-2-(E)-propenyl] ethanesulfonamide Dihydrochloride To a solution of N-[3-(5-amidino-2-fluorophenyl)-2-(E)-propenyl]-N-[4-(piperidin-4-yloxy)phenyl] ethanesulfonamide dihydrochloride (534 mg) in ethanol (20 ml) were added ethyl acetimidate hydrochloride (371 mg) and triethylamine (0.70 ml) at room temperature. The resulting mixture was stirred at room temperature for 12 hours. After addition of a 4M solution of hydrogen chloride in dioxane (2 ml), the resulting mixture was concentrated in vacuo. The residue was purified by preparative HPLC (YMC-Pack ODS YMC) using 20% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. The resulting amorphous solid was dissolved in water (10 ml) and the solution was lyophilized to give the title compound (415 mg, yield 75%) as a colorless amorphous solid.

$^1$H NMR (500 MHz, DMSO-$d_6$) δ ppm: 1.28 (3H, t, J=7.0), 1.74 (2H, m), 2.05 (2H, m), 2.30 (3H, s), 3.18 (2H, q, J=7.0), 3.52 (2H, m), 3.72 (1H, m), 3.81 (1H, m), 4.50 (2H, d, J=6.0), 4.70 (1H, m), 6.56 (1H, dt, J=16.5, 6.0), 6.62 (1H, d, J=16.5), 7.02 (2H, d, J=9.0), 7.37 (2H, d, J=9.0), 7.46 (1H, m), 7.78 (1H, m), 8.12 (1H, m); IR (KBr, $cm^{-1}$): 3113, 1674, 1625.

Example 6

Ethyl N-[4-(1-Acetimidoylpiperidin-4-yloxy)-2-methylphenyl]-N-[3-(3-amidinophenyl)-2-(E)-propenyl]sulfamoylacetate Dihydrochloride (Exemplification Compound Number 1419)

(a) Ethyl N-[3-(3-Amidinophenyl)-2-(E)-propenyl]-N-[2-methyl-4-(piperidin-4-yloxy)phenyl]sulfamoylacetate Dihydrochloride Ethyl N-[4-(1-t-butoxycarbonylpiperidin-4-yloxy)-2-methylphenyl]-N-[3-(3-cyanophenyl)-2-(E)-propenyl] sulfamoylacetate (1.80 g) was dissolved in a mixture of dichloromethane (60 ml) and ethanol (40 ml). Hydrogen chloride gas was passed through the mixture in an ice bath for 1 hour. The resulting mixture was stirred in a stoppered reaction vessel at room temperature for 6 hours. The reaction mixture was concentrated in vacuo, and to a solution of the residue in ethanol (50 ml) were added aqueous ammonium chloride solution (0.32 g in 25 ml) and 28% aqueous ammonia solution (0.62 ml). The resulting mixture was allowed to stand at room temperature for 12 hours and concentrated in vacuo. To a solution of the residue in methanol (30 ml) was added a 4M solution of hydrogen chloride in dioxane (2 ml) and the mixture was concentrated in vacuo. The residue was purified by preparative HPLC (YMC-Pack ODS YMC) using 20% aqueous acetonitrile as an eluant to give the desired compound (0.78 g, yield 45%) as a colorless amorphous solid.

$^1$H NMR (500 MHz, DMSO-$d_6$) δ ppm: 1.23 (3H, t, J=7.0), 1.73 (2H, m), 2.04 (2H, m), 2.27 (3H, s), 3.00 (2H, m), 3.18 (2H, m), 4.20 (2H, q, J=7.0), 4.25 (1H, m), 4.33 (1H, d, J=14.5), 4.45 (1H, m), 4.46 (1H, d, J=14.5), 4.59 (1H, m), 6.46 (2H, s), 6.88 (1H, d, J=9.0), 6.90 (1H, s), 7.39 (1H, d, J=9.0), 7.55 (1H, t, J=8.0), 7.67 (1H, d, J=8.0), 7.71 (1H, d, J=8.0), 7.81 (1H, s); IR (KBr, $cm^{-1}$): 1737, 1676.

(b) Ethyl N-[4-(1-Acetimidoylpiperidin-4-yloxy-2-methylphenyl]-N-[3-(3-amidinophenyl)-2-(E)-propenyl] sulfamoylacetate Dihydrochloride To a solution of ethyl N-[3-(3-amidinophenyl)-2-(E)-propenyl]-N-[2-methyl-4-(piperidin-4-yloxy)phenyl] sulfamoylacetate dihydrochloride (631 mg) in ethanol (30 ml) were added ethyl acetimidate hydrochloride (397 mg) and triethylamine (0.75 ml). The resulting mixture was stirred at room temperature for 64 hours. After addition of a 4M solution of hydrogen chloride in dioxane (2 ml), the resulting mixture was concentrated in vacuo. The residue was purified by preparative HPLC (YMC-Pack ODS YMC) using 24% aqueous acetonitrile as an eluant to afford an amorphous solid. To a solution of the solid in methanol (20 ml) was added a 4M solution of hydrogen chloride in dioxane (1 ml) and the mixture was concentrated to dryness in vacuo. The resulting amorphous solid was dissolved in water (15 ml) and the solution was lyophilized to give the title compound (423 mg, yield 60%) as a colorless amorphous solid.

$^1$H NMR (500 MHz, DMSO-$d_6$) δ ppm: 1.24 (3H, t, J=6.5), 1.65–1.79 (2H, m), 2.04 (2H, m), 2.28 (3H, s), 2.31 (3H, s), 3.48–3.59 (2H, m), 3.72 (1H, m), 3.85 (1H, m), 4.21 (2H, q, J=6.5), 4.28 (1H, dd, J=14.5, 6.0), 4.34 (1H, d, J=15.0), 4.43 (1H, dd, J=14.5, 4.5), 4.49 (1H, d, J=15.0), 4.70 (1H, m), 6.46 (1H, d, J=15.5), 6.49 (1H, m), 6.90 (1H, dd, J=9.0, 3.0), 6.93 (1H, d, J=3.0), 7.41 (1H, d, J=9.0), 7.55 (1H, t, J=8.0), 7.72 (2H, m), 7.88 (1H, s); IR (KBr, $cm^{-1}$): 1738, 1673, 1624.

Example 7

Ethyl N-[4-(1-Acetimidoylpiperidin-4-yloxy)-3-methoxyphenyl]-N-[3-(3-amidinophenyl)-2-(E)-propenyl]sulfamoylacetate Dihydrochloride (Exemplification Compound Number 1442)

(a) Ethyl N-[3-(3-Amidinophenyl)-2-(E)-propenyl]-N-[3-methoxy-4-(piperidin-4-yloxy)phenyl]sulfamoylacetate Dihydrochloride Ethyl N-[4-(1-t-butoxycarbonylpiperidin-4-yloxy)-3-methoxyphenyl]-N-[3-(3-cyanophenyl)-2-(E)-propenyl] sulfamoylacetate (985 mg) was dissolved in a mixture of dichloromethane (30 ml) and ethanol (15 ml). Hydrogen chloride gas was passed through the mixture in an ice bath for 40 minutes. The resulting mixture was stirred in a stoppered reaction vessel at room temperature for 6 hours. The reaction mixture was concentrated in vacuo, and to a solution of the residue in ethanol (20 ml) were added aqueous ammonium chloride solution (172 mg in 10 ml) and 28% aqueous ammonia solution (0.33 ml). The resulting mixture was allowed to stand at room temperature for 13 hours and concentrated in vacuo. To a solution of the residue in methanol (20 ml) was added a 4M solution of hydrogen chloride in dioxane (1.5 ml) and the mixture was concentrated in vacuo. The residue was purified by preparative HPLC (YMC-Pack ODS YMC) using 17% aqueous acetonitrile as an eluant to afford an amorphous solid. The solid was dissolved in a mixture of methanol (20 ml) and a 4M solution of hydrogen chloride in dioxane (0.4 ml) and the solution was concentrated to dryness in vacuo to give the desired compound (560 mg, yield 58%) as a pale yellow amorphous solid.

$^1H$ NMR (500 MHz, DMSO-$d_6$) δ ppm: 1.24 (3H, t, J=7.0), 1.84 (2H, m), 2.05 (2H, m), 3.03 (2H, m), 3.19 (2H, m), 3.79 (3H, s), 4.21 (2H, q, J=7.0), 4.38 (2H, s), 4.46 (2H, d, J=6.0), 4.56 (1H, m), 6.46 (1H, dt, J=15.5, 6.0), 6.57 (1H, d, J=15.5), 6.98 (1H, dd, J=9.0, 2.0), 7.08 (1H, d, J=9.0), 7.11 (1H, d, J=2.0), 7.55 (1H, t, J=7.5), 7.69 (1H, d, J=7.5), 7.73 (1H, d, J=7.5), 7.90 (1H, s); IR (KBr, $cm^{-1}$): 1737, 1675.

(b) Ethyl N-[4-(1-Acetimidoylpiperidin-4-yloxy)-3-methoxyphenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[3-methoxy-4-(piperidin-4-yloxy)phenyl]sulfamoylacetate dihydrochloride (392 mg) in ethanol (20 ml) were added ethyl acetimidate hydrochloride (241 mg) and triethylamine (0.452 ml). The resulting mixture was stirred at room temperature for 38 hours. After addition of a 4M solution of hydrogen chloride in dioxane (0.8 ml), the resulting mixture was concentrated in vacuo. The residue was purified by preparative HPLC (YMC-Pack ODS YMC) using 20% aqueous acetonitrile as an eluant to afford an amorphous solid. To a solution of the solid in methanol (20 ml) was added a 4M solution of hydrogen chloride in dioxane (0.3 ml) and the mixture was concentrated to dryness in vacuo. The resulting amorphous solid was dissolved in water (10 ml) and the solution was lyophilized to give the title compound (317 mg, yield 76%) as a colorless amorphous solid.

$^1H$ NMR (500 MHz, DMSO-$d_6$) δ ppm: 1.24 (3H, t, J=7.0), 1.66–1.80 (2H, m), 2.01 (2H, m), 2.30 (3H, s), 3.47–3.59 (2H, m), 3.72 (1H, m), 3.78 (3H, s), 3.82 (1H, m), 4.21 (2H, q, J=7.0), 4.39 (2H, s), 4.47 (2H, d, J=5.5), 4.62 (1H, m), 6.47 (1H, dt, J=15.5, 5.5), 6.57 (1H, d, J=15.5), 6.99 (1H, dd, J=9.0, 3.0), 7.11 (2H, m), 7.55 (1H, t, J=8.0), 7.71 (1H, d, J=8.0), 7.73 (1H, d, J=8.0), 7.91 (1H, s); IR (KBr, $cm^{-1}$): 1738, 1674, 1625.

Example 8

Ethyl N-[4-(1-Acetimidoylpiperidin-4-yloxy)-3-chlorophenyl]-N-[3-(3-amidinophenyl)-2-(E)-propenyl]sulfamoylacetate Dihydrochloride (Exemplification Compound Number 1414)

(a) Ethyl N-[3-(3-Amidinophenyl)-2-(E)-propenyl]-N-[3-chloro-4-(piperidin-4-yloxy)phenyl]sulfamoylacetate Dihydrochloride Ethyl N-[4-(1-t-butoxycarbonylpiperidin-4-yloxy)-3-chlorophenyl]-N-[3-(3-cyanophenyl)-2-(E)-propenyl]sulfamoylacetate (1200 mg) was dissolved in a mixture of dichloromethane (30 ml) and ethanol (20 ml). Hydrogen chloride gas was passed through the mixture in an ice bath for 2 hours. The resulting mixture was stirred in a stoppered reaction vessel at room temperature for 4 hours. The reaction mixture was concentrated in vacuo, and to a solution of the residue in ethanol (20 ml) were added aqueous ammonium chloride solution (208 mg in 10 ml) and 28% aqueous ammonia solution (0.40 ml). The resulting mixture was allowed to stand at room temperature for 13 hours and concentrated in vacuo. To a solution of the residue in methanol (25 ml) was added a 4M solution of hydrogen chloride in dioxane (1.6 ml) and the mixture was concentrated in vacuo. The residue was purified by preparative HPLC (YMC-Pack ODS YMC) using 20% aqueous acetonitrile as an eluant to afford an amorphous solid. To a solution of the solid in methanol (20 ml) was added a 4M solution of hydrogen chloride in dioxane (0.5 ml) and the solution was concentrated to dryness in vacuo. The resulting amorphous solid was dissolved in water and the solution was lyophilized to give the desired compound (662 mg, yield 56%) as a pale yellow amorphous solid.

$^1H$ NMR (500 MHz, DMSO-$d_6$) δ ppm: 1.23 (3H, t, J=7.0), 1.88 (2H, m), 2.10 (2H, m), 3.08 (2H, m), 3.17 (2H, m), 4.19 (2H, q, J=7.0), 4.41 (2H, s), 4.47 (2H, d, J=6.5), 4.78 (1H, m), 6.44 (1H, dt, J=16.0, 6.5), 6.57 (1H, d, J=16.0), 7.30 (1H, d, J=9.5), 7.41 (1H, dd, J=9.5, 2.5), 7.55 (1H, t, J=8.0), 7.59 (1H, d, J=2.5), 7.69 (1H, d, J=8.0), 7.73 (1H, d, J=8.0), 7.88 (1H, s); IR (KBr, $cm^{-1}$): 1737, 1675.

(b) Ethyl N-[4-(1-Acetimidoylpiperidin-4-yloxy)-3-chlorophenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[3-chloro-4-(piperidin-4-yloxy)phenyl]sulfamoylacetate dihydrochloride (387 mg) in ethanol (10 ml) were added ethyl acetimidate hydrochloride (232 mg) and triethylamine (0.440 ml). The resulting mixture was stirred at room temperature for 5 hours. After addition of a 4M solution of hydrogen chloride in dioxane (1 ml), the resulting mixture was concentrated in vacuo. The residue was purified by preparative HPLC (YMC-Pack ODS YMC) using 22% aqueous acetonitrile as an eluant to afford an amorphous solid. To a solution of the solid in methanol (20 ml) was added a 4M solution of hydrogen chloride in dioxane (0.25 ml) and the mixture was concentrated to dryness in vacuo. The resulting amorphous solid was dissolved in water (15 ml) and the solution was lyophilized to give the title compound (268 mg, yield 66%) as a colorless amorphous solid.

$^1H$ NMR (500 MHz, DMSO-$d_6$) δ ppm: 1.23 (3H, t, J=7.0), 1.80 (2H, m), 2.05 (2H, m), 2.30 (3H, s), 3.55–3.78 (4H, m), 4.19 (2H, q, J=7.0), 4.42 (2H, s), 4.47 (2H, d, J=6.0), 4.84 (1H, m), 6.45 (1H, dt, J=15.5, 6.0), 6.58 (1H, d, J=15.5), 7.33 (1H, d, J=9.0), 7.41 (1H, dd, J=9.0, 3.0), 7.55 (1H, t, J=8.0), 7.59 (1H, d, J=3.0), 7.70 (1H, d, J=8.0), 7.73 (1H, d, J=8.0), 7.90 (1H, s); IR (KBr, $cm^{-1}$): 1738, 1673, 1623.

Example 9

N-[4-(1-Acetimidoylpiperidin-4-yloxy)-3-chlorophenyl]-N-[3-(3-amidinophenyl)-2-(E)-propenyl]sulfamoylacetic Acid Dihydrochloride (Exemplification Compound Number 1943)

Ethyl N-[4-(1-acetimidoylpiperidin-4-yloxy)-3-chlorophenyl]-N-[3-(3-amidinophenyl)-2-(E)-propenyl]sulfamoylacetate dihydrochloride (187 mg) was dissolved in 3M hydrochloric acid (7 ml) and the mixture was stirred at 80° C. for 2 hours. The reaction mixture was cooled to room temperature and concentrated in vacuo. The residue was purified by preparative HPLC (YMC-Pack ODS YMC) using 15% aqueous acetonitrile as an eluant to afford an amorphous solid. To a solution of the solid in methanol (10 ml) was added a 4M solution of hydrogen chloride in dioxane (0.2 ml) and the mixture was concentrated to dryness in vacuo. The residue was dissolved in water (10 ml) and the solution was lyophilized to give the title compound (147 mg, yield 82%).

$^1H$ NMR (500 MHz, DMSO-$d_6$) δ ppm: 1.79 (2H, m), 2.05 (2H, m), 2.29 (3H, s), 3.54–3.75 (4H, m), 4.23 (2H, s), 4.47 (2H, d, J=6.0), 4.83 (1H, m), 6.45 (1H, dt, J=16.0, 6.0), 6.57 (1H, d, J=16.0), 7.32 (1H, d, J=9.0), 7.41 (1H, m), 7.55 (1H, t, J=8.0), 7.60 (1H, m), 7.68 (1H, d, J=8.0), 7.73 (1H, d, J=8.0), 7.88 (1H, s); IR (KBr, $cm^{-1}$): 1734, 1673, 1625.

Example 10

Ethyl N-[4-(1-Acetimidoylpiperidin-4-yloxy)-3-fluorophenyl]-N-[3-(3-amidinophenyl)-2-(E)-propenyl]sulfamoylacetate Dihydrochloride (Exemplification Compound Number 1412)

(a) Ethyl N-[3-(3-Amidinophenyl)-2-(E)-propenyl]-N-[3-fluoro-4-(piperidin-4-yloxy)phenyl]sulfamoylacetate Dihydrochloride Ethyl N-[4-(1-t-butoxycarbonylpiperidin-4-yloxy)-3-fluorophenyl]-N-[3-(3-cyanophenyl)-2-(E)-propenyl] sulfamoylacetate (1210 mg) was dissolved in a mixture of dichloromethane (30 ml) and ethanol (20 ml). Hydrogen chloride gas was passed through the mixture in an ice bath for 1 hour. The resulting mixture was stirred in a stoppered reaction vessel at room temperature for 6 hours. The reaction mixture was concentrated in vacuo, and to a solution of the residue in ethanol (20 ml) were added aqueous ammonium chloride solution (215 mg in 10 ml) and 28% aqueous ammonia solution (0.41 ml). The resulting mixture was allowed to stand at room temperature for 17 hours and concentrated in vacuo. To a solution of the residue in methanol (20 ml) was added a 4M solution of hydrogen chloride in dioxane (2 ml) and the mixture was concentrated in vacuo. The residue was purified by preparative HPLC (YMC-Pack ODS YMC) using 17% aqueous acetonitrile as an eluant to afford an amorphous solid. To a solution of the solid in methanol (15 ml) was added a 4M solution of hydrogen chloride in dioxane (0.3 ml) and the solution was concentrated to dryness in vacuo to give the desired compound (798 mg, yield 67%) as a pale yellow amorphous solid.

$^1$H NMR (500 MHz, DMSO-$d_6$) δ ppm: 1.23 (3H, t, J=7.0), 1.85 (2H, m), 2.09 (2H, m), 3.06 (2H, m), 3.19 (2H, m), 4.19 (2H, q, J=7.0), 4.40 (2H, s), 4.47 (2H, d, J=7.0), 4.68 (1H, m), 6.43 (1H, m), 6.58 (1H, d, J=16.0), 7.25 (1H, dd, J=9.0, 2.5), 7.31 (1H, t, J=9.0), 7.43 (1H, dd, J=12.5, 2.5), 7.55 (1H, t, J=8.0), 7.68 (1H, m), 7.73 (1H, d, J=8.0), 7.88 (1H, bs); IR (KBr, $cm^{-1}$): 1737, 1675.

(b) Ethyl N-[4-(1-Acetimidoylpiperidin-4-yloxy)-3-fluorophenyl]-N-[3-(3-amidinophenyl)-2-(E)-propenyl] sulfamoylacetate Dihydrochloride To a solution of ethyl N-[3-(3-amidinophenyl)-2-(E)-propenyl]-N-[3-fluoro-4-(piperidin-4-yloxy)phenyl] sulfamoylacetate dihydrochloride (467 mg) in ethanol (25 ml) were added ethyl acetimidate hydrochloride (293 mg) and triethylamine (0.550 ml). The resulting mixture was stirred at room temperature for 66 hours. After addition of a 4M solution of hydrogen chloride in dioxane (1.5 ml), the resulting mixture was concentrated in vacuo. The residue was purified by preparative HPLC (YMC-Pack ODS YMC) using 22% aqueous acetonitrile as an eluant to afford an amorphous solid. To a solution of the solid in methanol (15 ml) was added a 4M solution of hydrogen chloride in dioxane (0.3 ml) and the mixture was concentrated to dryness in vacuo. The resulting amorphous solid was dissolved in water (15 ml) and the solution was lyophilized to give the title compound (284 mg, yield 57%) as a colorless amorphous solid.

$^1$H NMR (500 MHz, DMSO-$d_6$) δ ppm: 1.22 (3H, t, J=7.0), 1.68–1.82 (2H, m), 2.06 (2H, m), 2.31 (3H, s), 3.51 (1H, m), 3.59 (1H, m), 3.71 (1H, m), 3.86 (1H, m), 4.19 (2H, q, J=7.0), 4.42 (2H, s), 4.47 (2H, d, J=6.0), 4.76 (1H, m), 6.46 (1H, dt, J=15.5, 6.0), 6.57 (1H, d, J=15.5), 7.26 (1H, d, J=9.0), 7.35 (1H, t, J=9.0), 7.43 (1H, dd, J=12.0, 2.5), 7.54 (1H, t, J=8.0), 7.73 (2H, m), 7.95 (1H, s); IR (KBr, $cm^{-1}$): 1738, 1673, 1623.

Example 11

N-[4-(1-Acetimidoylpiperidin-4-yloxy)-3-fluorophenyl]-N-[3-(3-amidinophenyl)-2-(E)-propenyl]sulfamoylacetic Acid Dihydrochloride (Exemplification Compound Number 1941)

Ethyl N-[4-(1-acetimidoylpiperidin-4-yloxy)-3-fluorophenyl]-N-[3-(3-amidinophenyl)-2-(E)-propenyl] sulfamoylacetate dihydrochloride (199 mg) was dissolved in 3M hydrochloric acid (7 ml) and the mixture was stirred at 80° C. for 2 hours. The reaction mixture was cooled to room temperature and concentrated in vacuo. The residue was purified by preparative HPLC (YMC-Pack ODS YMC) using 15% aqueous acetonitrile as an eluant to afford an amorphous solid. To a solution of the solid in methanol (10 ml) was added a 4M solution of hydrogen chloride in dioxane (0.2 ml) and the mixture was concentrated to dryness in vacuo. The residue was dissolved in water (10 ml) and the solution was lyophilized to give the title compound (163 mg, yield 86%).

$^1$H NMR (500 MHz, DMSO-$d_6$) δ ppm: 1.77 (2H, m), 2.05 (2H, m), 2.29 (3H, s), 3.52 (2H, m), 3.71 (1H, m), 3.80 (1H, m), 4.23 (2H, s), 4.47 (2H, d, J=6.0), 4.73 (1H, m), 6.44 (1H, dt, J=16.0, 6.0), 6.57 (1H, d, J=16.0), 7.26 (1H, m), 7.32 (1H, t, J=8.5), 7.43 (1H, dd, J=13.0, 2.0), 7.55 (1H, t, J=8.0), 7.68 (1H, d, J=8.0), 7.72 (1H, d, J=8.0), 7.88 (1H, s); IR (KBr, $cm^{-1}$): 3295, 1733, 1673 1624.

Example 12

Ethyl N-[4-(1-Acetimidoylpiperidin-4-yloxy) phenyl]-N-[3-(5-amidino-2-methylphenyl)-2-(E)-propenyl]sulfamoylacetate Dihydrochloride (Exemplification Compound Number 1771)

(a) Ethyl N-[3-(5-Amidino-2-methylphenyl)-2-(E)-propenyl]-N-[4-(piperidin-4-yloxy)phenyl]sulfamoylacetate Dihydrochloride Ethyl N-[4-(1-t-butoxycarbonylpiperidin-4-yloxy) phenyl]-N-[3-(5-cyano-2-methylphenyl)-2-(E)-propenyl] sulfamoylacetate (2.03 g) was dissolved in a mixture of dichloromethane (40 ml) and ethanol (40 ml). Hydrogen chloride gas was passed through the mixture in an ice bath for 1 hour. The resulting mixture was stirred in a stoppered reaction vessel at room temperature for 6 hours. The reaction mixture was concentrated in vacuo, and to a solution of the residue in ethanol (45 ml) were added aqueous ammonium chloride solution (0.36 g in 15 ml) and 28% aqueous ammonia solution (0.68 ml). The resulting mixture was allowed to stand at room temperature for 12 hours and concentrated in vacuo. To a solution of the residue in methanol (30 ml) was added a 4M solution of hydrogen chloride in dioxane (2 ml) and the mixture was concentrated in vacuo. The residue was purified by preparative HPLC (YMC-Pack ODS YMC) using 20% aqueous acetonitrile as an eluant to afford an amorphous solid. To a solution of the solid in methanol (20 ml) was added a 4M solution of hydrogen chloride in ethyl acetate (1 ml) and the solution was concentrated to dryness in vacuo to give the desired compound (1.49 g, yield 75%) as a colorless amorphous solid.

$^1$H NMR (500 MHz, DMSO-$d_6$) δ ppm: 1.23 (3H, t, J=7.0), 1.82 (2H, m), 2.09 (2H, m), 2.22 (3H, s), 3.05 (2H, m), 3.21 (2H, m), 4.19 (2H, q, J=7.0), 4.34 (2H, s), 4.46 (2H, d, J=6.5), 4.66 (1H, m), 6.30 (1H, dt, J=16.0, 6.5), 6.66 (1H, d, J=16.0), 7.05 (2H, d, J=9.5), 7.37 (1H, d, J=7.5), 7.38 (2H, d, J=9.5), 7.61 (1H, dd, J=7.5, 2.0), 7.86 (1H, d, J=2.0); IR (KBr, $cm^{-1}$): 1738, 1674.

(b) Ethyl N-[4-(1-Acetimidoylpiperidin-4-yloxy)phenyl-N-[3-(5-amidino-2-methylphenyl)-2-(E)-propenyl]sulfamoylacetate Dihydrochloride To a solution of ethyl N-(3-(5-amidino-2-methylphenyl)-2-(E)-propenyl]-N-[4-(piperidin-4-yloxy)phenyl]sulfamoylacetate dihydrochloride (1.43 g) in ethanol (40 ml) were added ethyl acetimidate hydrochloride (0.60 g) and triethylamine (1.4 ml). The resulting mixture was stirred at room temperature for 13 hours. After addition of a 4M solution of hydrogen chloride in ethyl acetate (2 ml), the resulting mixture was concentrated in vacuo. The residue was purified by preparative HPLC (YMC-Pack ODS YMC) using 25% aqueous acetonitrile as an eluant to afford an amorphous solid. To a solution of the solid in methanol (20 ml) was added a 4M solution of hydrogen chloride in ethyl acetate (0.8 ml) and the mixture was concentrated to dryness in vacuo to give the title compound (1.18 g, yield 77%) as a colorless amorphous solid.

$^1$H NMR (500 MHz, DMSO-$d_6$) δ ppm: 1.23 (3H, t, J=7.0), 1.67–1.80 (2H, m), 2.05 (2H, m), 2.22 (3H, s), 2.30 (3H, s), 3.49–3.61 (2H, m), 3.72 (1H, m), 3.83 (1H, m), 4.19 (2H, q, J=7.0), 4.35 (2H, s), 4.46 (2H, d, J=6.0), 4.72 (1H, m), 6.32 (1H, dt, J=16.0, 6.0), 6.66 (1H, d, J=16.0), 7.06 (2H, d, J=9.5), 7.38 (1H, d, J=9.0), 7.39 (2H, d, J=9.5), 7.64 (1H, dd, J=9.0, 2.0), 7.88 (1H, d, J=2.0); IR (KBr, $cm^{-1}$): 1738, 1675, 1626.

Example 13

Ethyl N-[4-(1-Acetimidoylpiperidin-4-yloxy)-3-trifluoromethylphenyl]-N-[3-(3-amidinophenyl)-2-(E)-propenyl]sulfamoylacetate Dihydrochloride (Exemplification Compound Number 1440)

(a) Ethyl N-[3-(3-Amidinophenyl)-2-(E)-propenyl]-N-[4-(piperidin-4-yloxy)-3-trifluoromethylphenyl]sulfamoylacetate Dihydrochloride Ethyl N-[4-(1-t-butoxycarbonylpiperidin-4-yloxy)-3-trifluoromethylphenyl]-N-[3-(3-cyanophenyl)-2-(E)-propenyl]sulfamoylacetate (2.06 g) was dissolved in a mixture of dichloromethane (50 ml) and ethanol (25 ml). Hydrogen chloride gas was passed through the mixture in an ice bath for 1 hour. The resulting mixture was stirred in a stoppered reaction vessel at room temperature for 6 hours. The reaction mixture was concentrated in vacuo, and to a solution of the residue in ethanol (45 ml) were added aqueous ammonium chloride solution (0.34 g in 15 ml) and 28% aqueous ammonia solution (0.63 ml). The resulting mixture was allowed to stand at room temperature for 12 hours and concentrated in vacuo. To a solution of the residue in methanol (30 ml) was added a 4M solution of hydrogen chloride in dioxane (2.5 ml) and the mixture was concentrated in vacuo. The residue was purified by preparative HPLC (YMC-Pack ODS YMC) using 25% aqueous acetonitrile as an eluant to afford an amorphous solid. To a solution of the solid in methanol (20 ml) was added a 4M solution of hydrogen chloride in dioxane (0.5 ml) and the solution was concentrated to dryness in vacuo to give the desired compound (1.21 g, yield 60%) as a colorless amorphous solid.

$^1$H NMR (500 MHz, DMSO-$d_6$) δ ppm: 1.22 (3H, t, J=7.0), 1.87 (2H, m), 2.08 (2H, m), 3.11 (2H, m), 3.33 (2H, m), 4.18 (2H, q, J=7.0), 4.44 (2H, s), 4.50 (2H, d, J=6.5), 4.89 (1H, m), 6.44 (1H, dt, J=16.0, 6.5), 6.57 (1H, d, J=16.0), 7.39 (1H, d, J=9.0), 7.55 (1H, t, J=8.0), 7.66–7.73 (4H, m), 7.85 (1H, s); IR (KBr, $cm^{-1}$): 1738, 1676.

(b) Ethyl N-[4-(1-Acetimidoylpiperidin-4-yloxy)-3-trifluoromethylphenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[4-(piperidin-4-yloxy)-3-trifluoromethylphenyl]sulfamoylacetate dihydrochloride (1.13 g) in ethanol (20 ml) were added ethyl acetimidate hydrochloride (0.65 g) and triethylamine (1.20 ml). The resulting mixture was stirred at room temperature for 13 hours. After addition of a 4M solution of hydrogen chloride in dioxane (2 ml), the resulting mixture was concentrated in vacuo. The residue was purified by preparative HPLC (YMC-Pack ODS YMC) using 30% aqueous acetonitrile as an eluant to afford an amorphous solid. To a solution of the solid in methanol (20 ml) was added a 4M solution of hydrogen chloride in ethyl acetate (0.5 ml) and the mixture was concentrated to dryness in vacuo to give the title compound (1.04 g, yield 87%) as a colorless amorphous solid.

$^1$H NMR (500 MHz, DMSO-$d_6$) δ ppm: 1.22 (3H, t, J=7.0), 1.81 (2H, m), 2.07 (2H, m), 2.30 (3H, s), 3.59–3.73 (4H, m), 4.19 (2H, q, J=7.0), 4.46 (2H, s), 4.50 (2H, d, J=6.5), 4.96 (1H, m), 6.47 (1H, dt, J=16.5, 6.5), 6.58 (1H, d, J=16.5), 7.44 (1H, d, J=9.5), 7.56 (1H, t, J=8.0), 7.71 (4H, m), 7.90 (1H, s); IR (KBr, $cm^{-1}$): 1739, 1673, 1618.

Example 14

Ethyl N-[4-(1-Acetimidoylpiperidin-4-yloxy)-3-methylphenyl]-N-[3-(3-amidinophenyl)-2-(E)-propenyl]sulfamoylacetate Dihydrochloride (Exemplification Compound Number 1420)

(a) Ethyl N-[3-(3-Amidinophenyl)-2-(E)-propenyl]-N-[3-methyl-4-(piperidin-4-yloxy)phenyl]sulfamoylacetate Dihydrochloride Ethyl N-(4-(1-t-butoxycarbonylpiperidin-4-yloxy)-3-methylphenyl]-N-[3-(3-cyanophenyl)-2-(E)-propenyl]sulfamoylacetate (1.90 g) was dissolved in a mixture of dichloromethane (40 ml) and ethanol (40 ml). Hydrogen chloride gas was passed through the mixture in an ice bath for 1 hour. The resulting mixture was stirred in a stoppered reaction vessel at room temperature for 5 hours. The reaction mixture was concentrated in vacuo, and to a solution of the residue in ethanol (45 ml) were added aqueous ammonium chloride solution (0.34 g in 15 ml) and 28% aqueous ammonia solution (0.64 ml). The resulting mixture was allowed to stand at room temperature for 13 hours and concentrated in vacuo. To a solution of the residue in methanol (20 ml) was added a 4M solution of hydrogen chloride in ethyl acetate (2 ml) and the mixture was concentrated in vacuo. The residue was purified by preparative HPLC (YMC-Pack ODS YMC) using 20% aqueous acetonitrile as an eluant to afford an amorphous solid. To a solution of the solid in methanol (20 ml) was added a 4M solution of hydrogen chloride in ethyl acetate (1 ml) and the solution was concentrated to dryness in vacuo to give the desired compound (1.36 g, yield 73%) as a colorless amorphous solid.

$^1$H NMR (400 MHz, DMSO-$d_6$) δ ppm: 1.23 (3H, t, J=7.0), 1.87 (2H, m), 2.10 (2H, m), 2.17 (3H, s), 3.07 (2H, m), 3.17 (2H, m), 4.20 (2H, q, J=7.0), 4.33 (2H, s), 4.44 (2H, d, J=6.0), 4.65 (1H, m), 6.44 (1H, dt, J=16.0, 6.0), 6.56 (1H, d, J=16.0), 7.05 (1H, d, J=9.0), 7.24 (1H, dd, J=9.0, 2.5), 7.29 (1H, d, J=2.5), 7.54 (1H, t, J=8.0), 7.71 (2H, m), 7.90 (1H, s); IR (KBr, $cm^{-1}$): 1738, 1675.

(b) Ethyl N-[4-(1-Acetimidoylpiperidin-4-yloxy)-3-methylphenyl]-N-[3-(3-amidinophenyl)-2-(E)-propenyl] sulfamoylacetate Dihydrochloride To a solution of ethyl N-[3-(3-amidinophenyl)-2-(E)-propenyl]-N-[3-methyl-4-(piperidin-4-yloxy)phenyl] sulfamoylacetate dihydrochloride (1.23 g) in ethanol (40 ml) were added ethyl acetimidate hydrochloride (0.52 g) and triethylamine (1.20 ml). The resulting mixture was stirred at room temperature for 13 hours. After addition of a 4M solution of hydrogen chloride in dioxane (2 ml), the resulting mixture was concentrated in vacuo. The residue was purified by preparative HPLC (YMC-Pack ODS YMC) using 22% aqueous acetonitrile as an eluant to afford an amorphous solid. To a solution of the solid in methanol (20 ml) was added a 4M solution of hydrogen chloride in ethyl acetate (0.6 ml) and the mixture was concentrated to dryness in vacuo to give the title compound (1.10 g, yield 84%) as a colorless amorphous solid.

$^1$H NMR (500 MHz, DMSO-$d_6$) δ ppm: 1.24 (3H, t, J=7.0), 1.77 (2H, m), 2.03 (2H, m), 2.16 (3H, s), 2.30 (3H, s), 3.60–3.80 (4H, m), 4.20 (2H, q, J=7.0), 4.33 (2H, s), 4.44 (2H, d, J=6.0), 4.73 (1H, m), 6.45 (1H, dt, J=16.0, 6.0), 6.56 (1H, d, J=16.0), 7.06 (1H, d, J=9.0), 7.25 (1H, dd, J=9.0, 2.5), 7.29 (1H, d, J=2.5), 7.55 (1H, t, J=8.0), 7.71 (2H, m), 7.91 (1H, s); IR (KBr, $cm^{-1}$): 1738, 1672, 1624.

Example 15

Ethyl N-[4-(1-Acetimidoylpiperidin-4-yloxy) phenyl]-N-[3-(3-amidino-5-methylphenyl)-2-(E)-propenyl]sulfamoylacetate Dihydrochloride (Exemplification Compound Number 1711)

(a) Ethyl N-[3-(3-Amidino-5-methylphenyl)-2-(E)-propenyl]-N-[4-(piperidin-4-yloxy)phenyl]sulfamoylacetate Dihydrochloride Ethyl N-[4-(1-t-butoxycarbonylpiperidin-4-yloxy) phenyl]-N-[3-(3-cyano-5-methylphenyl)-2-(E)-propenyl] sulfamoylacetate (1.59 g) was dissolved in a mixture of dichloromethane (15 ml) and ethanol (15 ml). Hydrogen chloride gas was passed through the mixture in an ice bath for 1 hour. The resulting mixture was stirred in a stoppered reaction vessel at room temperature for 4 hours. The reaction mixture was concentrated in vacuo, and to a solution of the residue in ethanol (20 ml) were added aqueous ammonium chloride solution (0.21 g in 4 ml) and 28% aqueous ammonia solution (0.53 ml). The resulting mixture was allowed to stand at room temperature overnight and concentrated in vacuo. The residue was purified by preparative HPLC (YMC-Pack ODS YMC) using 20% aqueous acetonitrile as an eluant to give the desired compound (1.10 g, yield 80%) as a colorless amorphous solid.

$^1$H NMR (270 MHz, DMSO-$d_6$) δ ppm: 1.23 (3H, t, J=7.0), 1.85 (2H, m), 2.10 (2H, m), 2.36 (3H, s), 3.06 (2H, m), 3.18 (2H, m), 4.19 (2H, q, J=7.0), 4.33 (2H, s), 4.44 (2H, d, J=5.5), 4.66 (1H, m), 6.41 (1H, dt, J=16.0, 5.5), 6.51 (1H, d, J=16.0), 7.04 (2H, d, J=9.0), 7.38 (2H, d, J=9.0), 7.54 (1H, s), 7.58 (1H, s), 7.68 (1H, s); IR (KBr, $cm^{-1}$): 1737, 1674.

(b) Ethyl N-[4-(1-Acetimidoylpiperidin4-yloxy)phenyl]-N-[3-(3-amidino-5-methylphenyl)-2-(E)-propenyl] sulfamoylacetate Dihydrochloride To a solution of ethyl N-[3-(3-amidino-5-methylphenyl)-2-(E)-propenyl]-N-[4-(piperidin-4-yloxy)phenyl] sulfamoylacetate dihydrochloride (800 mg) in ethanol (25 ml) were added ethyl acetimidate hydrochloride (1400 mg) and triethylamine (2.2 ml). The resulting mixture was stirred at room temperature for 27 hours and then concentrated in vacuo. The residue was purified by preparative HPLC (YMC-Pack ODS YMC) using 20% aqueous acetonitrile as an eluant to afford an amorphous solid. To a solution of the solid in ethanol (20 ml) was added a 4M solution of hydrogen chloride in ethyl acetate (1 ml) and the mixture was concentrated to dryness in vacuo. The residual solid was suspended in ethyl acetate and filtered to give the title compound (400 mg, yield 41%) as a colorless amorphous solid.

$^1$H NMR (270 MHz, DMSO-$d_6$) δ ppm: 1.23 (3H, t, J=7.0), 1.70 (2H, m), 2.05 (2H, m), 2.30 (3H, s), 2.36 (3H, s), 3.45–3.65 (2H, m), 3.65–3.95 (2H, m), 4.19 (2H, q, J=7.0), 4.34 (2H, s), 4.44 (2H, d, J=5.5), 4.71 (1H, m), 6.41 (1H, dt, J=16.0, 5.5), 6.51 (1H, d, J=16.0), 7.04 (2H, d, J=9.0), 7.39 (2H, d, J=9.0), 7.56 (2H, containing two singlets), 7.70 (1H, s); IR (KBr, $cm^{-1}$): 1738, 1672, 1625.

Example 16

N-[4-(1-Acetimidoylpiperidin-4-yloxy)phenyl]-N-[3-(3-amidino-5-methylphenyl)-2-(E)-propenyl] sulfamoylacetic Acid Dihydrochloride (Exemplification Compound Number 2208)

Ethyl N-[4-(1-acetimidoylpiperidin-4-yloxy)phenyl]-N-[3-(3-amidino-5-methylphenyl)-2-(E)-propenyl] sulfamoylacetate dihydrochloride (200 mg) was dissolved in 1M hydrochloric acid (8 ml) and the mixture was stirred at 80° C. for 8 hours. The reaction mixture was concentrated in vacuo. The residue was purified by preparative HPLC (YMC-Pack ODS YMC) using 20% aqueous acetonitrile as an eluant to afford an amorphous solid. To a solution of the solid in water was added a 4M solution of hydrogen chloride in ethyl acetate (0.2 ml) and the mixture was concentrated to dryness in vacuo to give the title compound (110 mg, yield 57%) as a colorless amorphous solid.

$^1$H NMR (270 MHz, DMSO-$d_6$) δ ppm: 1.60–1.85 (2H, m), 2.05 (2H, m), 2.30 (3H, s), 2.36 (3H, s), 3.40–3.65 (2H, m), 3.65–3.95 (2H, m), 4.20 (2H, s), 4.44 (2H, d, J=5.0), 4.70 (1H, m), 6.41 (1H, dt, J=16.0, 5.0), 6.51 (1H, d, J=16.0), 7.04 (2H, d, J=9.0), 7.39 (2H, d, J=9.0), 7.55 (2H, containing two singlets), 7.69 (1H, s); MS (FAB) m/z=528 $(M+H)^+$.

Example 17

Ethyl N-[4-(1-Acetimidoylpiperidin-4-yloxy) phenyl]-N-[3-(3-amidino-4-fluorophenyl)-2-(E)-propenyl]sulfamoylacetate Dihydrochloride (Exemplification Compound Number 1638)

(a) Ethyl N-[3-(3-Amidino-4-fluorophenyl)-2-(E)-propenyl]-N-[4-(piperidin-4-yloxy)phenyl]sulfamoylacetate Dihydrochloride Ethyl N-[4-(1-t-butoxycarbonylpiperidin-4-yloxy) phenyl]-N-[3-(3-cyano-4-fluorophenyl)-2-(E)-propenyl] sulfamoylacetate (1530 mg) was dissolved in a mixture of dichloromethane (15 ml) and ethanol (15 ml). Hydrogen chloride gas was passed through the mixture in an ice bath for 1.25 hours. The resulting mixture was stirred in a stoppered reaction vessel at room temperature for 4 hours. The reaction mixture was concentrated in vacuo, and to a solution of the residue in ethanol (20 ml) were added aqueous ammonium chloride solution (200 mg in 4 ml) and 28% aqueous ammonia solution (0.50 ml). The resulting mixture was allowed to stand at room temperature overnight and concentrated in vacuo. The residue was purified by preparative HPLC (YMC-Pack ODS YMC) using 20% aqueous acetonitrile as an eluant to give the desired compound (550 mg, yield 41%) as a colorless amorphous solid.

$^1$H NMR (270 MHz, DMSO-$d_6$) δ ppm: 1.23 (3H, t, J=7.0), 1.75–1.95 (2H, m), 2.00–2.20 (2H, m), 2.95–3.15

(2H, m), 3.15–3.30 (2H, m), 4.19 (2H, q, J=7.0), 4.33 (2H, s), 4.42 (2H, d, J=6.0), 4.65 (1H, m), 6.35 (1H, dt, J=16.0, 6.0), 6.53 (1H, d, J=16.0), 7.03 (2H, d, J=9.0), 7.38 (2H, d, J=9.0), 7.42 (1H, m), 7.73 (2H, m); IR (KBr, $cm^{-1}$): 1737, 1677.

(b) Ethyl N-[4-(1-Acetimidoylpiperidin-4-yloxy)phenyl]-N-[3-(3-amidino-4-fluorophenyl)-2-(E)-Propenyl] sulfamoylacetate Dihydrochloride To a solution of ethyl N-[3-(3-amidino-4-fluorophenyl)-2-(E)-propenyl]-N-[4-(piperidin-4-yloxy)phenyl] sulfamoylacetate dihydrochloride (350 mg) in ethanol (14 ml) were added ethyl acetimidate hydrochloride (160 mg) and triethylamine (0.36 ml). The resulting mixture was stirred at room temperature for 6 hours and then concentrated in vacuo. The residue was purified by preparative HPLC (YMC-Pack ODS YMC) using 20% aqueous acetonitrile as an eluant to afford an amorphous solid. To a solution of the solid in ethanol (8 ml) was added a 4M solution of hydrogen chloride in ethyl acetate (0.5 ml) and the mixture was concentrated to dryness in vacuo to give the title compound (279 mg, yield 65%) as a colorless amorphous solid.

$^1$H NMR (270 MHz, DMSO-$d_6$) δ ppm: 1.23 (3H, t, J=7.0), 1.73 (2H, m), 2.05 (2H, m), 2.29 (3H, s), 3.40–3.65 (2H, m), 3.65–3.90 (2H, m), 4.19 (2H, q, J=7.0), 4.33 (2H, s), 4.42 (2H, d, J=5.5), 4.71 (1H, m), 6.35 (1H, dt, J=16.0, 5.5), 6.54 (1H, d, J=16.0), 7.04 (2H, d, J=9.0), 7.38 (2H, d, J=9.0), 7.40 (1H, m), 7.73 (2H, m); IR (KBr, $cm^{-1}$): 1738, 1675, 1618.

Example 18

N-[4-(1-Acetimidoylpiperidin-4-yloxy)phenyl]-N-[3-(3-amidinophenyl)-2-(E)-propenyl]acetamide Dihydrochloride (Exemplification Compound Number 948)

(a) N-[3-(3-Amidinophenyl)-2-(E)-propenyl]-N-[4-(piperidin-4-yloxy)phenyl]acetamide Dihydrochloride N-[4-(1-t-butoxycarbonylpiperidin-4-yloxy)phenyl]-N-[3-(3-cyanophenyl)-2-(E)-propenyl]acetamide (1203 mg) was dissolved in a mixture of dichloromethane (60 ml) and ethanol (30 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (50 ml) were added aqueous ammonium chloride solution (271 mg in 25 ml) and 28% aqueous ammonia solution (0.51 ml). The resulting mixture was allowed to stand at room temperature for 12 hours and then a 4M solution of hydrogen chloride in dioxane (1.5 ml) was added. The resulting solution was concentrated in vacuo. The residue was purified by preparative HPLC (YMC-Pack ODS YMC) using 13% aqueous acetonitrile as an eluant to afford an amorphous solid. To a solution of the solid in methanol (10 ml) was added a 4M solution of hydrogen chloride in dioxane (1.5 ml) and the solution was concentrated in vacuo. A solution of the residue in water (10 ml) was lyophilized to give the desired compound (853 mg, yield 72%) as a pale yellow amorphous solid.

$^1$H NMR (270 MHz, DMSO-$d_6$) δ ppm: 1.78 (3H, s), 1.83 (2H, m), 2.11 (2H, m), 2.90–3.30 (4H, m), 4.39 (2H, m), 4.50–4.80 (1H, m), 6.40–6.60 (2H, m), 7.04 (2H, d, J=9.0), 7.28 (2H, d, J=9.0), 7.55 (1H, t, J=7.5), 7.71 (1H, d, J=7.5), 7.73 (1H, d, J=7.5), 7.94 (1H, s); IR (KBr, $cm^{-1}$): 1675, 1626.

(b) N-[4-(1-Acetimidoylpiperidin-4-yloxy)phenyl]-N-[3-(3-amidinophenyl)-2-(E)-propenyl]acetamide Dihydrochloride To a solution of N-[3-(3-amidinophenyl)-2-(E)-propenyl]-N-[4-(piperidin-4-yloxy)phenyl]acetamide dihydrochloride (400 mg) in methanol (20 ml) were added ethyl acetimidate hydrochloride (320 mg) and triethylamine (0.60 ml) at room temperature. The resulting mixture was stirred at room temperature for 12 hours. To the reaction mixture was added a 4M solution of hydrogen chloride in dioxane (1 ml) and the solution was concentrated in vacuo. The residue was purified by preparative HPLC (YMC-Pack ODS YMC) using 15% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (342 mg, yield 79%) as a colorless amorphous solid.

$^1$H NMR (270 MHz, DMSO-$d_6$) δ ppm: 1.74 (2H, m), 1.78 (3H, s), 2.04 (2H, m), 2.31 (3H, s), 3.45–3.95 (4H, m), 4.39 (2H, m), 4.60–4.80 (1H, m), 6.40–6.60 (2H, m), 7.05 (2H, d, J=8.5), 7.28 (2H, d, J=8.5), 7.55 (1H, t, J=7.5), 7.65–7.80 (2H, m), 7.95 (1H, s); IR (KBr, $cm^{-1}$): 1672, 1624.

Example 19

N-[4-(1-Acetimidoylpiperidin-4-yloxy)phenyl]-N-[3-(3-amidinophenyl)-2-(E)-propenyl]-2-hydroxyacetamide Dihydrochloride (Exemplification Compound Number 1014)

(a) N-[3-(3-Amidinophenyl)-2-(E)-propenyl]-N-[4-(piperidin-4-yloxy)phenyl]-2-hydroxyacetamide Dihydrochloride N-[4-(1-t-butoxycarbonylpiperidin-4-yloxy)phenyl]-N-[3-(3-cyanophenyl)-2-(E)-propenyl]-2-hydroxyacetamide (977 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (20 ml) were added aqueous ammonium chloride solution (213 mg in 10 ml) and 28% aqueous ammonia solution (0.40 ml). The resulting mixture was allowed to stand at room temperature for 12 hours and then a 4M solution of hydrogen chloride in dioxane (1 ml) was added. The resulting solution was concentrated in vacuo. The residue was purified by preparative HPLC (YMC-Pack ODS YMC) using 11% aqueous acetonitrile as an eluant to afford an amorphous solid. To a solution of the solid in methanol (10 ml) was added a 4M solution of hydrogen chloride in dioxane (0.5 ml) and the solution was concentrated to dryness in vacuo. A solution of the residue in water (10 ml) was lyophilized to give the desired compound (685 mg, yield 72%) as a colorless amorphous solid.

$^1$H NMR (270 MHz, DMSO-d6) δ ppm : 1.84 (2H, m), 2.10 (2H, m), 2.90–3.80 (6H, m), 4.36 (2H, m), 4.65 (1H, m), 6.50 (2H, m), 7.03 (2H, d, J=8.5), 7.28 (2H, d, J=8.5), 7.55 (1H, t, J=7.5), 7.65–7.80 (2H, m), 7.92 (1H, s); IR (KBr, $cm^{-1}$): 1673.

(b) N-[4-(1-Acetimidoylpiperidin-4-yloxy)phenyl]-N-[3-(3-amidinophenyl)-2-(E)-propenyl]-2-hydroxyacetamide Dihydrochloride To a solution of N-[3-(3-amidinophenyl)-2-(E)-propenyl]-N-[4-(piperidin-4-yloxy)phenyl]-2-hydroxyacetamide dihydrochloride (385 mg) in methanol (20 ml) were added ethyl acetimidate hydrochloride (300 mg) and triethylamine (0.56 ml) at room temperature. The resulting mixture was stirred at room temperature for 12 hours. To the reaction mixture was added a 4M solution of hydrogen chloride in dioxane (1 ml) and the solution was concentrated in vacuo. The residue was purified by preparative HPLC (YMC-Pack ODS YMC) using 14% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (336 mg, yield 80%) as a colorless amorphous solid.

$^1$H NMR (270 MHz, DMSO-$d_6$) δ ppm: 1.73 (2H, m), 2.05 (2H, m), 2.30 (3H, s), 3.30–3.90 (6H, m), 4.39 (2H, m), 4.69 (1H, m), 6.40–6.60 (2H, m), 7.04 (2H, d, J=9.0), 7.28 (2H, d, J=9.0), 7.55 (1H, t, J=8.0), 7.65–7.80 (2H, m), 7.93 (1H, s); IR (KBr, $cm^{-1}$): 1671.

Example 20

3-[3-[N-[4-( 1-Acetimidoylpiperidin-4-yloxy) phenyl]-N-benzylamino]-1-(E)-propenyl] benzamidine Trihydrochloride (Exemplification Compound Number 864)

(a) 3-[3-[N-Benzyl-N-[4-(piperidin-4-yloxy)phenyl] amino]-1-(E)-propenyl]benzamidine Trihydrochloride 3-[3-[N-benzyl-N-[4-(1-t-butoxycarbonylpiperidin-4-yloxy)phenyl]amino]-1-(E)-propenyl]benzonitrile (916 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (20 ml) were added aqueous ammonium chloride solution (187 mg in 10 ml) and 28% aqueous ammonia solution (0.46 ml). The resulting mixture was allowed to stand at room temperature for 12 hours and then a 4M solution of hydrogen chloride in dioxane (1 ml) was added. The resulting solution was concentrated in vacuo. The residue was purified by chromatography on a silica gel column (Cosmosil (trade mark) 75C18-PREP; Nacalai Tesque) using 5% aqueous acetonitrile as an eluant to afford an amorphous solid. To a solution of the solid in methanol (10 ml) was added a 4M solution of hydrogen chloride in dioxane (0.5 ml) and the solution was concentrated in vacuo. A solution of the residue in water (about 10 ml) was lyophilized to give the desired compound (581 mg, yield 60%) as a pale brown amorphous solid.

$^1$H NMR (500 MHz, DMSO-$d_6$) δ ppm 1.78 (2H, m), 2.03 (2H, m), 2.98 (2H, m), 3.15 (2H, m), 4.35 (2H, m), 4.50 (1H, m), 4.76 (2H, m), 6.61 (1H, dt, J=16.0, 6.5), 6.70 (1H, d, J=16.0), 6.93 (2H, m), 7.20–7.35 (3H, m), 7.35–7.50 (4H, m), 7.57 (1H, t, J=8.0), 7.70 (1H, d, J=8.0), 7.73 (1H, d, J=8.0), 7.89 (1H, s); IR (KBr, $cm^{-1}$): 1675.

(b) 3-[3-[N-[4-(1-Acetimidoylpiperidin-4-yloxy)phenyl]-N-benzylamino]-1-(E)-propenyl]benzamidine Trihydrochloride To a solution of 3-[3-[N-benzyl-N-[4-(piperidin-4-yloxy) phenyl]amino]-1-(E)-propenyl]benzamidine trihydrochloride (335 mg) in methanol (20 ml) were added ethyl acetimidate hydrochloride (230 mg) and triethylamine (0.51 ml) at room temperature. The resulting mixture was stirred at room temperature for 12 hours. To the reaction mixture was added a 4M solution of hydrogen chloride in dioxane (1 ml) and the solution was concentrated in vacuo. The residue was purified by preparative HPLC (YMC-Pack ODS YMC) using 30% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (252 mg, yield 70%) as a colorless amorphous solid.

$^1$H NMR (270 MHz, DMSO-$d_6$) δ ppm: 1.50–1.75 (2H, m), 1.96 (2H, m), 2.29 (3H, s), 3.40–3.90 (4H, m), 4.40 (2H, m), 4.50–4.90 (3H, m), 6.63 (1H, dt, J=16.0, 6.0), 6.74 (1H, d, J=16.0), 6.97 (2H, d, J=8.5), 7.15–7.30 (3H, m), 7.40–7.60 (4H, m), 7.56 (1H, t, J=7.5), 7.66 (1H, d, J=7.5), 7.77 (1H, d, J=7.5), 7.92 (1H, s); IR (KBr, $cm^{-1}$): 1672, 1624.

Example 21

3-[3-[N-[4-(1-Acetimidoylpiperidin-4-yloxy)phenyl] amino]-1-(E)-propenyl]benzamidine Trihydrochloride (Exemplification Compound Number 177)

(a) 3-[3-[N-[4-(Piperidin-4-yloxy)phenyl]amino]-1-(E)-propenyl]benzamidine Trihydrochloride 3-[3-[N-[4-(1-t-butoxycarbonylpiperidin-4-yloxy) phenyl]amino]-1-(E)-propenyl]benzonitrile (900 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (20 ml) were added aqueous ammonium chloride solution (222 mg in 10 ml) and 28% aqueous ammonia solution (0.54 ml). The resulting mixture was allowed to stand at room temperature for 12 hours and then a 4M solution of hydrogen chloride in dioxane (1 ml) was added. The resulting solution was concentrated in vacuo. The residue was purified by preparative HPLC (YMC-Pack ODS YMC) using 15% aqueous acetonitrile as an eluant to afford an amorphous solid. To a solution of the solid in methanol (10 ml) was added a 4M solution of hydrogen chloride in dioxane (0.5 ml) and the solution was concentrated in vacuo to give the desired compound (735 mg, yield 77%) as a pale yellow amorphous solid.

$^1$H NMR (500 MHz, DMSO-$d_6$) δ ppm: 1.82 (2H, m), 2.05 (2H, m), 3.03 (2H, m), 3.20 (2H, m), 3.95–4.10 (2H, m), 4.50–4.65 (1H, m), 6.55 (1H, dt, J=16.0, 6.5), 6.79 (1H, d, J=16.0), 7.05 (2H, m), 7.20–7.45 (2H, m), 7.61 (1H, t, J=8.0), 7.70–7.80 (2H, m), 7.87 (1H, s); IR (KBr, $cm^{-1}$): 1675, (b) 3-[3-[N-[4-(1-Acetimidoylpiperidin-4-yloxy)phenyl] amino]-1-(E)-propenyl]benzamidine Trihydrochloride To a solution of 3-[3-[N-[4-(piperidin-4-yloxy)phenyl] amino]-1-(E)-propenyl]benzamidine trihydrochloride (345 mg) in methanol (20 ml) were added ethyl acetimidate hydrochloride (185 mg) and triethylamine (0.52 ml) at room temperature. The resulting mixture was stirred at room temperature for 12 hours. To the reaction mixture was added a 4M solution of hydrogen chloride in dioxane (1 ml) and the solution was concentrated in vacuo. The residue was purified by preparative HPLC (YMC-Pack ODS YMC) using 30% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (272 mg, yield 72%) as a yellow amorphous solid.

$^1$H NMR (270 MHz, DMSO-$d_6$) δ ppm: 1.73 (2H, m), 2.05 (2H, m), 2.30 (s, 3H), 3.40–3.95 (4H, m), 4.06 (2H, d, J=6.5), 4.69 (1H, m), 6.56 (1H, dt, J=16.0, 6.5), 6.80 (1H, d, J=16.0), 7.10 (2H, d, J=9.0), 7.35–7.55 (2H, m), 7.60 (1H, t, J=8.0), 7.70–7.80 (2H, m), 7.87 (1H, s); IR (KBr, $cm^{-1}$): 1672, 1625.

Example 22

3-[3-[N-[4-(1-Acetimidoylpiperidin-4-yloxy)phenyl]-N-isopropylamino]-1-(E)-propenyl]benzamidine Trihydrochloride (Exemplification Compound Number 358)

(a) 3-[3-[N-Isopropyl-N-[4-(piperidin-4-yloxy)phenyl]amino]-1-(E)-propenyl]benzamidine Trihydrochloride 3-[3-[N-[4-(1-t-butoxycarbonylpiperidin-4-yloxy)phenyl-N-isopropylamino]-1-(E)-propenyl]benzonitrile (705 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (20 ml) were added aqueous ammonium chloride solution (159 mg in 10 ml) and 28% aqueous ammonia solution (0.39 ml). The resulting mixture was allowed to stand at room temperature for 12 hours and then a 4M solution of hydrogen chloride in dioxane (1 ml) was added. The resulting solution was concentrated in vacuo. The residue was purified by preparative HPLC (YMC-Pack ODS YMC) using 15% aqueous acetonitrile as an eluant to afford an amorphous solid. To a solution of the solid in methanol (10 ml) was added a 4M solution of hydrogen chloride in dioxane (0.5 ml) and the solution was concentrated in vacuo. A solution of the residual solid in water (about 10 ml) was lyophilized to give the desired compound (570 mg, yield 70%) as a pale brown amorphous solid.

$^1$H NMR (270 MHz, DMSO-$d_6$) δ ppm: 1.16 (3H, m), 1.40 (3H, m), 1.82 (2H, m), 2.07 (2H, m), 3.03 (2H, m), 3.18 (2H, m), 3.98 (1H, m), 4.41 (2H, m), 4.68 (1H, m), 6.40 (1H, m), 6.72 (1H, d, J=16.0), 7.13 (2H, m), 7.50–7.65 (2H, m), 7.70–7.85 (4H, m); IR (KBr, $cm^{-1}$): 1675.

(b) 3-[3-[N-[4-(1-Acetimidoylpiperidin-4-yloxy)phenyl]-N-isopropylamino]-1-(E)-propenyl]benzamidine Trihydrochloride To a solution of 3-[3-[N-isopropyl-N-[4-(piperidin-4-yloxy)phenyl]amino]-1-(E)-propenyl]benzamidine trihydrochloride (310 mg) in methanol (20 ml) were added ethyl acetimidate hydrochloride (229 mg) and triethylamine (0.52 ml) at room temperature. The resulting mixture was stirred at room temperature for 12 hours. To the reaction mixture was added a 4M solution of hydrogen chloride in dioxane (1 ml) and the solution was concentrated in vacuo. The residue was purified by preparative HPLC (YMC-Pack ODS YMC) using 15% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (259 mg, yield 77%) as a pale brown amorphous solid.

$^1$H NMR (270 MHz, DMSO-$d_6$) δ ppm: 1.17 (3H, d, J=6.0), 1.43 (3H, d, J=6.0), 1.70 (2H, m), 2.04 (2H, m), 2.31 (3H, s), 3.45–4.05 (5H, m), 4.41 (2H, m), 4.74 (1H, m), 6.42 (1H, dt, J=16.0, 7.0), 6.73 (1H, d, J=16.0), 7.15 (2H, d, J=8.5), 7.50–7.65 (2H, m), 7.70–7.90 (4H, m); IR (KBr, $cm^{-1}$): 1672, 1623.

Example 23

Ethyl 2-[N-[4-(1-Acetimidoylpiperidin-4-yloxy)phenyl]-N-[3-(3-amidinophenyl)-2-(E)-propenyl]amino]acetate Trihydrochloride (Exemplification Compound Number 668)

(a) Ethyl 2-[N-[3-(3-Amidinophenyl)-2-(E)-propenyl]-N-[4-(piperidin-4-yloxy)phenyl]amino]acetate Trihydrochloride Ethyl 2-[N-[4-(1-t-butoxycarbonylpiperidin-4-yloxy)phenyl]-N-[3-(3-cyanophenyl)-2-(E)-propenyl]amino]acetate (1305 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (20 ml) were added aqueous ammonium chloride solution (269 mg in 10 ml) and 28% aqueous ammonia solution (0.66 ml). The resulting mixture was allowed to stand at room temperature for 12 hours and then a 4M solution of hydrogen chloride in dioxane (1 ml) was added. The resulting solution was concentrated in vacuo. The residue was purified by preparative HPLC (YMC-Pack ODS YMC) using 20% aqueous acetonitrile as an eluant to afford an amorphous solid. To a solution of the solid in methanol (10 ml) was added a 4M solution of hydrogen chloride in dioxane (0.5 ml) and the solution was concentrated to dryness in vacuo. A solution of the residual solid in water (about 10 ml) was lyophilized to give the desired compound (652 mg, yield 48%) as a pale yellow amorphous solid.

$^1$H NMR (270 MHz, DMSO-$d_6$) δ ppm: 1.18 (3H,t, J=7.0), 1.80 (2H, m), 2.04 (2H, m), 3.00 (2H, m), 3.17 (2H, m), 4.11 (2H, q, J=7.0), 4.10–4.20 (4H, m), 4.42 (1H, m), 6.55 (1H, dt, J=16.0, 5.0), 6.65 (2H, d, J=9.0), 6.67 (1H, d, J=16.0), 6.87 (2H, d, J=9.0), 7.56 (1H, t, J=7.5), 7.65–7.80 (2H, m), 7.91 (1H, s); IR (KBr, $cm^{-1}$): 1747, 1675.

(b) Ethyl 2-[N-[4-(1-acetimidoylpiperidin-4-yloxy)phenyl]-N-[3-(3-amidinophenyl)-2-(E)-propenyl]amino]acetate Trihydrochloride To a solution of ethyl 2-[N-[3-(3-amidinophenyl)-2-(E)-propenyl]-N-[4-(piperidin-4-yloxy)phenyl]amino]acetate trihydrochloride (400 mg) in methanol (20 ml) were added ethyl acetimidate hydrochloride (270 mg) and triethylamine (0.61 ml) at room temperature. The resulting mixture was stirred at room temperature for 12 hours. To the reaction mixture was added a 4M solution of hydrogen chloride in dioxane (1 ml) and the solution was concentrated in vacuo. The residue was purified by preparative HPLC (YMC-Pack ODS YMC) using 24% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (350 mg, yield 81%) as a pale yellow amorphous solid.

$^1$H NMR (270 MHz, DMSO-$d_6$) δ ppm: 1.18 (3H, t, J=7.0), 1.70 (2H, m), 1.99 (2H, m), 2.31 (3H, s), 3.45–3.85 (4H, m), 4.11 (2H, q, J=7.0), 4.15–4.25 (4H, m), 4.48 (1H, m), 6.56 (1H, dt, J=16.0, 4.5), 6.66 (2H, d, J=9.0), 6.67 (1H, d, J=16.0), 6.88 (2H, d, J=9.0), 7.56 (1H, t, J=8.0), 7.65–7.80 (2H, m), 7.92 (1H, s); IR (KBr, $cm^{-1}$): 1747, 1672, 1623.

Example 24

3-[3-[N-[4-(1-Acetimidoylpiperidin-4-yloxy)phenyl]-N-ethylamino]-1-(E)-propenyl]benzamidine Trihydrochloride (Exemplification Compound Number 297)

(a) 3-[3-[N-Ethyl-N-[4-(piperidin-4-yloxy)phenyl]amino-1-(E)-propenyl]benzamidine Trihydrochloride 3-(3-(N-[4-(1-t-butoxycarbonylpiperidin-4-yloxy)phenyl]-N-ethylamino]-1-(E)-propenyl]benzonitrile (700 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (20 ml) were added aqueous ammonium chloride solution (178 mg in 10 ml) and 28% aqueous ammonia solution (0.44 ml). The resulting mixture was allowed to stand at room temperature for 12 hours and then a 4M solution of hydrogen chloride in dioxane (1 ml) was added. The resulting solution was concentrated in vacuo. The residue was purified by preparative HPLC (YMC-Pack ODS YMC) using 20% aqueous acetonitrile as an eluant to afford an amorphous solid. To a solution of the solid in methanol (10 ml) was added a 4M solution of hydrogen chloride in dioxane (0.5 ml) and the solution was concentrated to dryness in vacuo. A solution of the residual solid in water (about 10 ml) was lyophilized to give the desired compound (570 mg, yield 70%) as a colorless amorphous solid.

$^1$H NMR (270 MHz, DMSO-$d_6$) δ ppm: 1.07 (3H, t, J=7.0), 1.83 (2H, m), 2.10 (2H, m), 2.95–3.25 (4H, m), 3.60 (2H, m), 4.30 (2H, m), 4.69 (1H, m), 6.48 (1H, dt, J=16.0, 7.0), 6.72 (1H, d, J=16.0), 7.15 (2H, d, J=8.5), 7.56 (1H, t, J=7.5), 7.66 (1H, d, J=7.5), 7.70–8.00 (4H, m); IR (KBr, $cm^{-1}$): 1675.

(b) 3-[3-[N-[4-(1-Acetimidoylpiperidin-4-yloxy)phenyl]-N-ethylamino]-1-(E)-propenyl]benzamidine Trihydrochloride To a solution of 3-[3-[N-ethyl-N-[4-(piperidin-4-yloxy) phenyl]amino]-1-(E)-propenyl]benzamidine trihydrochloride (420 mg) in methanol (20 ml) were added ethyl acetimidate hydrochloride (319 mg) and triethylamine (0.72 ml) at room temperature. The resulting mixture was stirred at room temperature for 12 hours. To the reaction mixture was added a 4M solution of hydrogen chloride in dioxane (1 ml) and the solution was concentrated in vacuo. The residue was purified by preparative HPLC (YMC-Pack ODS YMC) using 20% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (287 mg, yield 63%) as a colorless amorphous solid.

$^1$H NMR (270 MHz, DMSO-$d_6$) δ ppm: 1.09 (3H, t, J=7.0), 1.71 (2H, m), 2.03 (2H, m), 2.32 (3H, s), 3.50–3.95 (6H, m), 4.30 (2H, m), 4.75 (1H, m), 6.49 (1H, dt, J=16.0, 6.5), 6.73 (1H, d, J=16.0), 7.00–7.30 (2H, m), 7.58 (1H, t, J=7.5), 7.67 (1H, d, J=7.5), 7.75–7.90 (4H, m); IR (KBr, $cm^{-1}$): 1673, 1623.

Example 25

Ethyl N-[4-(1-Acetimidoylpyrrolidin-3-yloxy) phenyl]-N-[3-(3-amidinophenyl)-2-(E)-propenyl] sulfamoylacetate Dihydrochloride (Exemplification Compound Number 90)

(a) Ethyl N-[3-(3-Amidinophenyl)-2-(E)-propenyl]-N-[4-(pyrrolidin-3-yloxy)phenyl]sulfamoylacetate Dihydrochloride Ethyl N-[4-(1-t-butoxycarbonylpyrrolidin-3-yloxy) phenyl]-N-[3-(3-cyanophenyl)-2-(E)-propenyl] sulfamoylacetate (2349 mg) was dissolved in a mixture of dichloromethane (60 ml) and ethanol (30 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (100 ml) were added aqueous ammonium chloride solution (440 mg in 50 ml) and 28% aqueous ammonia solution (0.83 ml). The resulting mixture was allowed to stand at room temperature for 12 hours and then a 4M solution of hydrogen chloride in dioxane (2 ml) was added. The resulting solution was concentrated in vacuo. The residue was purified by preparative HPLC (YMC-Pack ODS YMC) using 18% aqueous acetonitrile as an eluant to afford an amorphous solid. To a solution of the solid in methanol (10 ml) was added a 4M solution of hydrogen chloride in dioxane (0.5 ml) and the solution was concentrated to dryness in vacuo to give the desired compound (272 mg, yield 12%) as a colorless amorphous solid.

$^1$H NMR (270 MHz, DMSO-$d_6$) δ ppm: 1.23 (3H, t, J=7.0), 2.05–2.25 (2H, m), 3.15–3.50 (4H, m), 4.20 (2H, q, J=7.0), 4.34 (2H, s), 4.45 (2H, d, J=5.5), 5.12 (1H, m), 6.44 (1H, dt, J=16.0, 5.5), 6.56 (1H, d, J=16.0), 7.01 (2H, d, J=9.0), 7.42 (2H, d, J=9.0), 7.54 (1H, t, J=8.0), 7.65–7.75 (2H, m), 7.90 (1H, s); IR (KBr, $cm^{-1}$): 1737, 1675.

(b) Ethyl N-[4-(1-Acetimidoylpyrrolidin-3-yloxy)phenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[4-(pyrrolidin-3-yloxy)phenyl] sulfamoylacetate dihydrochloride (400 mg) in methanol (20 ml) were added ethyl acetimidate hydrochloride (350 mg) and triethylamine (0.50 ml) at room temperature. The resulting mixture was stirred at room temperature for 12 hours. To the reaction mixture was added a 4M solution of hydrogen chloride in dioxane (1 ml) and the solution was concentrated in vacuo. The residue was purified by preparative HPLC (YMC-Pack ODS YMC) using 20% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (255 mg, yield 59%) as a colorless amorphous solid.

$^1$H NMR (270 MHz, DMSO-$d_6$) δ ppm: 1.23 (3H, t, J=7.0), 2.10–2.30 (2H, m), 2.26 and 2.29 (total 3H, each singlet), 3.40–4.05 (4H, m), 4.19 (2H, q, J=7.0), 4.34 (2H, s), 4.45 (2H, d, J=5.5), 5.10–5.30 (1H, m), 6.44 (1H, dt, J=16.0, 5.5), 6.56 (1H, d, J=16.0), 7.01 and 7.02 (total 2H, each doublet, J=9.0), 7.42 and 7.43 (total 2H, each doublet, J=9.0), 7.54 (1H, t, J=7.5), 7.65–7.75 (2H, m), 7.91 (1H, s); IR (KBr, $cm^{-1}$): 1738, 1672, 1629.

Example 26

Ethyl 2-[N-[4-(1-Acetimidoylpiperidin-4-yloxy) phenyl]-N-[3-(3-amidinophenyl)-2-(E)-propenyl] amino]propionate Trihydrochloride (Exemplification Compound Number 788)

(a) Ethyl 2-[N-[3-(3-Amidinophenyl)-2-(E)-propenyl]-N-[4-(piperidin-4-yloxy)phenyl]amino]propionate Trihydrochloride Ethyl 2-[N-[4-(1-t-butoxycarbonylpiperidin-4-yloxy) phenyl]-N-[3-(3-cyanophenyl)-2-(E)-propenyl]amino] propionate (882 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (20 ml) were added aqueous ammonium chloride solution (177 mg in 10 ml) and 28% aqueous ammonia solution (0.43 ml). The resulting mixture was allowed to stand at room temperature for 12 hours and then a 4M solution of hydrogen chloride in dioxane (1 ml) was added. The resulting solution was concentrated in vacuo. The residue was purified by preparative HPLC (YMC-Pack ODS YMC) using 25% aqueous acetonitrile as an eluant to afford an amorphous solid. To a solution of the solid in methanol (10 ml) was added a 4M solution of hydrogen chloride in dioxane (0.5 ml) and the solution was concentrated to dryness in vacuo to give the desired compound (384 mg) and crude desired product (200 mg, yield 41% above) as a brown amorphous solid, respectively.

$^1$H NMR (500 MHz, DMSO-$d_6$) δ ppm: 1.16 (3H, t, J=7.0), 1.44 (3H, d, J=7.0), 1.78 (2H, m), 2.04 (2H, m), 3.01 (2H, m), 3.18 (2H, m), 4.09 (2H, q, J=7.0), 3.96–4.15 (2H, m), 4.42 (1H, m), 4.55 (1H, q, J=7.0), 6.55 (1H, dt, J=16.0, 4.5), 6.64 (1H, d, J=16.0), 6.72 (2H, d, J=8.5), 6.86 (2H, d, J=8.5), 7.54 (1H, t, J=8.0), 7.67 (1H, d, J=8.0), 7.73 (1H, d, J=8.0), 7.86 (1H, s); IR (KBr, $cm^{-1}$): 1745, 1681.

(b) Ethyl 2-[N-[4-(1-Acetimidoylpiperidin-4-yloxy)phenyl]-N-[3-(3-amidinophenyl)-2-(E)-propenyl]amino]propionate Trihydrochloride To a solution of a mixture (544 mg) containing ethyl 2-[N-[3-(3-amidinophenyl)-2-(E)-propenyl]-N-[4-(piperidin-4-yloxy)phenyl]amino]propionate in methanol (30 ml) were added ethyl acetimidate hydrochloride (360 mg) and triethylamine (0.81 ml) at room temperature. The resulting mixture was stirred at room temperature for 12 hours. To the reaction mixture was added a 4M solution of hydrogen chloride in dioxane (1 ml) and the solution was concentrated in vacuo. The residue was purified by preparative HPLC (YMC-Pack ODS YMC) using 25% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (468 mg, yield of two steps 47%) as a pale brown amorphous solid.

$^1$H NMR (500 MHz, DMSO-$d_6$) δ ppm: 1.15 (3H, t, J=7.0), 1.45 (3H, d, J=7.0), 1.68 (2H, m), 1.98 (2H, m), 2.29 (3H, s), 3.45–3.60 (2H, m), 3.65–3.85 (2H, m), 4.09 (2H, q, J=7.0), 3.95–4.20 (2H, m), 4.49 (1H, m), 4.56 (1H, q, J=7.0), 6.56 (1H, dt, J=16.0, 4.5), 6.64 (1H, d, J=16.0), 6.76 (2H, d, J=9.0), 6.87 (2H, d, J=9.0), 7.54 (1H, t, J=8.0), 7.70 (1H, d, J=8.0), 7.73 (1H, d, J=8.0), 7.89 (1H, s); IR (KBr, $cm^{-1}$): 1745, 1673, 1623.

Example 27

3-[3-[N-[4-(1-Acetimidoylpiperidin-4-yloxy)phenyl]-N-methylamino]-1-(E)-propenyl]benzamidine Trihydrochloride (Exemplification Compound Number 237)

(a) 3-[3-[N-Methyl-N-[4-(piperidin-4-yloxy)phenyl]amino]-1-(E)-propenyl]benzamidine Trihydrochloride 3-[3-[N-[4-(1-t-butoxycarbonylpiperidin-4-yloxy)phenyl]-N-methylamino]-1-(E)-propenyl]benzonitrile (761 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 7 hours. The reaction mixture was concentrated in vacuo, and to a solution of the residue in ethanol (20 ml) were added aqueous ammonium chloride solution (181 mg in 10 ml) and 28% aqueous ammonia solution (0.44 ml). The resulting mixture was allowed to stand at room temperature for 12 hours and then a 4M solution of hydrogen chloride in dioxane (1 ml) was added. The resulting solution was concentrated in vacuo. The residue was purified by preparative HPLC (YMC-Pack ODS YMC) using 8% aqueous acetonitrile as an eluant to afford an amorphous solid. To a solution of the solid in methanol (10 ml) was added a 4M solution of hydrogen chloride in dioxane (0.5 ml) and the solution was concentrated to dryness in vacuo to give the desired compound (401 mg, yield 50%) as a yellow amorphous solid.

$^1$H NMR (270 MHz, DMSO-$d_6$) δ ppm: 1.83 (2H, m), 2.08 (2H, m), 2.95–3.25 (7H, m), 4.22 (2H, m), 4.60 (1H, m), 6.49 (1H, dt, J=16.0, 6.5), 6.71 (1H, d, J=16.0), 6.90–7.90 (8H, m); IR (KBr, $cm^{-1}$): 1675.

(b) 3-[3-[N-[4-(1-Acetimidoylpiperidin-4-yloxy)phenyl]-N-methylamino]-1-(E)-propenyl]benzamidine Trihydrochloride To a solution of 3-[3-[N-methyl-N-[4-(piperidin-4-yloxy)phenyl]amino]-1-(E)-propenyl]benzamidine trihydrochloride (368 mg) in methanol (20 ml) were added ethyl acetimidate hydrochloride (290 mg) and triethylamine (0.65 ml) at room temperature. The resulting mixture was stirred at room temperature for 12 hours. To the reaction mixture was added a 4M solution of hydrogen chloride in dioxane (1 ml) and the solution was concentrated in vacuo. The residue was purified by preparative HPLC (YMC-Pack ODS YMC) using 10% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (288 mg, yield 72%) as a pale brown amorphous solid.

$^1$H NMR (270 MHz, DMSO-$d_6$) δ ppm: 1.71 (2H, m), 2.02 (2H, m), 2.31 (3H, s), 3.13 (3H, s), 3.40–3.70 (4H, m), 4.29 (2H, d, J=7.0), 4.75 (1H, m), 6.50 (1H, dt, J=16.0, 7.0), 6.76 (1H, d, J=16.0), 7.15 (2H, d, J=9.0), 7.58 (1H, t, J=7.5), 7.69 (1H, d, J=7.5), 7.70–7.85 (3H, m), 7.92 (1H, s); IR (KBr, $cm^{-1}$) 1672, 1625.

Example 28

3-[3-[N-[4-(1-Acetimidoylpiperidin-4-yloxy)phenyl]-N-(2-hydroxyethyl)amino]-1-(E)-propenyl]benzamidine Trihydrochloride (Exemplification Compound Number 478)

(a) 3-[3-[N-(2-Hydroxyethyl)-N-[4-(piperidin-4-yloxy)phenyl]amino]-1-(E)-propenyl]benzamidine Trihydrochloride 3-[3-[N-[4-(1-t-butoxycarbonylpiperidin-4-yloxy)phenyl]-N-(2-hydroxyethyl)amino]-1-(E)-propenyl]benzonitrile (1098 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 6 hours. The reaction mixture was concentrated in vacuo, and to a solution of the residue in ethanol (20 ml) were added aqueous ammonium chloride solution (246 mg in 10 ml) and 28% aqueous ammonia solution (0.60 ml). The resulting mixture was allowed to stand at room temperature for 12 hours and then a 4M solution of hydrogen chloride in dioxane (1 ml) was added. The resulting solution was concentrated in vacuo. The residue was purified by preparative HPLC (YMC-Pack ODS YMC) using 12% aqueous acetonitrile as an eluant to afford an amorphous solid. To a solution of the solid in methanol (10 ml) was added a 4M solution of hydrogen chloride in dioxane (0.5 ml) and the solution was concentrated to dryness in vacuo. A solution of the residual solid in water (about 10 ml) was lyophilized to give the desired compound (555 mg, yield 48%) as a colorless amorphous solid.

$^1$H NMR (500 MHz, DMSO-$d_6$) δ ppm: 1.82 (2H, m), 2.07 (2H, m), 3.03 (2H, m), 3.18 (2H, m), 3.54 (2H, m), 3.60

(2H, m), 4.31 (2H, m), 4.62 (1H, m), 6.48 (1H, dt, J=16.0, 6.5), 6.69 (1H, d, J=16.0), 7.08 (2H, m), 7.50 (2H, m), 7.58 (1H, t, J=8.0), 7.70 (1H, d, J=8.0), 7.73 (1H, d, J=8.0), 7.86 (1H, s); IR (KBr, $cm^{-1}$): 1676.

(b) 3-[3-[N-[4-(1-Acetimidoylpiperidin-4-yloxy)phenyl]-N-(2-hydroxyethyl)amino]-1-(E)-propenyl]benzamidine Trihydrochloride To a solution of 3-[3-[N-(2-hydroxyethyl)-N-[4-(piperidin-4-yloxy)phenyl]amino]-1-(E)-propenyl] benzamidine trihydrochloride (295 mg) in methanol (20 ml) were added ethyl acetimidate hydrochloride (362 mg) and triethylamine (0.41 ml) at room temperature. The resulting mixture was stirred at room temperature for 2 hours. To the reaction mixture was added a 4M solution of hydrogen chloride in dioxane (1 ml) and the solution was concentrated in vacuo. The residue was purified by preparative HPLC (YMC-Pack ODS YMC) using 16% aqueous acetonitrile as an eluant to afford an amorphous solid. To a solution of the solid in methanol (10 ml) was added a 4M solution of hydrogen chloride in dioxane (0.5 ml) and the mixture was concentrated to dryness in vacuo. A solution of the residual solid in water (about 10 ml) was lyophilized to give the title compound (175 mg, yield 55%) as a pale yellow amorphous solid.

$^1$H NMR (500 MHz, DMSO-$d_6$) δ ppm: 1.71 (2H, m), 2.03 (2H, m), 2.31 (3H, s), 3.40–4.00 (8H, m), 4.32 (2H, m), 4.67 (1H, m), 6.50 (1H, dt, J=16.0, 6.5), 6.70 (1H, d, J=16.0), 7.08 (2H, m), 7.50 (2H, m), 7.58 (1H, t, J=8.0), 7.70 (1H, d, J=8.0), 7.75 (1H, d, J=8.0), 7.89 (1H, s); IR (KBr, $cm^{-1}$): 1673, 1626.

Example 29

Ethyl N-[4-(1-Acetimidoylpiperidin-4-yloxy)-3-ethoxycarbonylphenyl]-N-[3-(3-amidinophenyl)-2-(E)-propenyl]sulfamoylacetate Dihydrochloride (Exemplification Compound Number 1450)

(a) Ethyl N-[3-(3-Amidinophenyl)-2-(E)-propenyl]-N-[3-ethoxycarbonyl-4-(piperidin-4-yloxy)phenyl] sulfomoylacetate Dihydrochloride Ethyl N-[4-(1-t-butoxycarbonylpiperidin-4-yloxy)-3-ethoxycarbonylphenyl]-N-[3-(3-cyanophenyl)-2-(E)-propenyl]sulfamoylacetate (2.45 g) was dissolved in a mixture of dichloromethane (25 ml) and ethanol (25 ml). Hydrogen chloride gas was passed through the mixture in an ice bath for 1.5 hours. The resulting mixture was stirred in a stoppered reaction vessel at room temperature for 4.5 hours. The reaction mixture was concentrated in vacuo, and to a solution of the residue in ethanol (20 ml) were added aqueous ammonium chloride solution (0.44 gin 5 ml) and 28% aqueous ammonia solution (1.00 ml). The resulting mixture was stirred at room temperature for 0.5 hours and then allowed to stand for 13 hours. The reaction mixture was concentrated in vacuo. The residue was purified by preparative HPLC (YMC-Pack ODS YMC) using 22% aqueous acetonitrile as an eluant to afford an amorphous solid. To a solution of the solid in ethanol (20 ml) was added a 4M solution of hydrogen chloride in dioxane (1.90 ml) and the solution was concentrated to dryness in vacuo to give the desired compound (1.41 g, yield 58%).as a colorless amorphous solid.

$^1$H NMR (500 MHz, DMSO-$d_6$) δ ppm: 1.23 (3H, t, J=7.0), 1.29 (3H, t, J=7.0), 1.85–1.95 (2H, m), 2.05–2.15 (2H, m), 3.05–3.40 (4H, m), 4.19 (2H, q, J=7.0), 4.28 (2H, q, J=7.0), 4.41 (2H, s), 4.47 (2H, d, J=6.0), 4.86 (1H, m), 6.45 (1H, dt, J=16.0, 6.0), 6.57 (1H, d, J=16.0), 7.30 (1H, m), 7.55 (1H, m), 7.61 (1H, m), 7.65–7.80 (3H, m), 7.89 (1H, m); IR (KBr, $cm^{-1}$): 1729, 1676.

(b) Ethyl N-[4-(1-Acetimidoylpiperidin-4-yloxy)-3-ethoxycarbonylphenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[3-ethoxycarbonyl-4-(piperidin-4-yloxy) phenyl]sulfamoylacetate dihydrochloride (1.24 g) in ethanol (20 ml) were added ethyl acetimidate hydrochloride (0.72 g) and triethylamine (1.70 ml) in an ice bath. The resulting mixture was stirred at room temperature for 0.5 hours and allowed to stand for 15 hours. The reaction mixture was concentrated in vacuo. The residue was purified by preparative HPLC (YMC-Pack ODS YMC) using 22% aqueous acetonitrile as an eluant to afford an amorphous solid. To a solution of the solid in ethanol (10 ml) was added a 4M solution of hydrogen chloride in ethyl acetate (1.30 ml) and the mixture was concentrated to dryness in vacuo to give the title compound (1.01 g, yield 76%) as a colorless amorphous solid.

$^1$H NMR (500 MHz, DMSO-$d_6$) δ ppm: 1.23 (3H, t, J=7.0), 1.27 (3H, t, J=7.0), 1.75–1.90 (2H, m), 1.95–2.10 (2H, m), 2.31 (3H, s), 3.60–3.70 (3H, m), 3.70–3.80 (1H, m), 4.19 (2H, q, J=7.0), 4.26 (2H, q, J=7.0), 4.41 (2H, s), 4.47 (2H, d, J=6.0), 4.90 (1H, m), 6.45 (1H, dt, J=16.0, 6.0), 6.58 (1H, d, J=16.0), 7.32 (1H, m), 7.55 (1H, m), 7.62 (1H, m), 7.65–7.70 (3H, m), 7.90 (1H, m); IR (KBr, $cm^{-1}$): 1730, 1673, 1624.

Example 30

N-[4-(1-Acetimidoylpiperidin-4-yloxy)-3-carboxyphenyl]-N-[3-(3-amidinophenyl)-2-(E)-propenyl]sulfamoylacetic Acid Dihydrochloride (Exemplification Compound Number 1975)

Ethyl N-[4-(1-Acetimidoylpiperidin-4-yloxy)-3-ethoxycarbonylphenyl]-N-[3-(3-amidinophenyl)-2-(E)-propenyl]sulfamoylacetate Dihydrochloride (0.30 g) was dissolved in 3M hydrochloric acid (6 ml) and the mixture was stirred at 80° C. for 2 hours. The reaction mixture was cooled to room temperature and concentrated in vacuo. The residue was purified by preparative HPLC (YMC-Pack ODS YMC) using 10% aqueous acetonitrile as an eluant to afford an amorphous solid. A solution of the solid in 1M hydrochloric acid (1.10 ml) was concentrated to dryness in vacuo to give the title compound (0.22 g, yield 79%) as a colorless amorphous solid.

$^1$H NMR (500 MHz, DMSO-$d_6$) δ ppm: 1.75–1.90 (2H, m), 1.90–2.10 (2H, m), 2.29 (3H, s), 3.55–3.75 (4H, m), 4.26 (2H, s), 4.47 (2H, d, J=6.0), 4.87 (1H, m), 6.44 (1H, dt, J=16.0, 6.0), 6.57 (1H, d, J=16.0), 7.28 (1H, m), 7.50–7.65 (2H, m), 7.65–7.80 (3H, m), 7.86 (1H, m); IR (KBr, $cm^1$): 1726, 1673, 1627.

Example 31

Ethyl N-[4-(1-Acetimidoylpiperidin-4-yloxy)-3-bromophenyl]-N-[3-(3-amidinophenyl)-2-(E)-propenyl]sulfamoylacetate Dihydrochloride (Exemplification Compound Number 1416)

(a) Ethyl N-[3-(3-Amidinophenyl)-2-(E)-propenyl]-N-[3-bromo-4-(piperidin-4-yloxy)phenyl]sulfamoylacetate Dihydrochloride Ethyl N-[3-bromo-4-(1-t-butoxycarbonylpiperidin-4-yloxy)phenyl]-N-[3-(3-cyanophenyl)-2-(E)-propenyl] sulfamoylacetate (2.20 g) was dissolved in a mixture of dichloromethane (25 ml) and ethanol (25 ml). Hydrogen chloride gas was passed through the mixture in an ice bath for 1.5 hours. The resulting mixture was stirred in a stoppered reaction vessel at room temperature for 5 hours. The reaction mixture was concentrated in vacuo, and to a solution of the residue in ethanol (20 ml) were added aqueous ammonium chloride solution (0.40 g in 5 ml) and 28% aqueous ammonia solution (0.90 ml). The resulting mixture was stirred at room temperature for 0.5 hours and then allowed to stand for 15 hours. The reaction mixture was concentrated in vacuo. The residue was purified by preparative HPLC (YMC-Pack ODS YMC) using 22% aqueous acetonitrile as an eluant to afford an amorphous solid. To a solution of the solid in ethanol (20 ml) was added a 4M solution of hydrogen chloride in ethyl acetate (1.70 ml) and the solution was concentrated to dryness in vacuo to give the desired compound (1.34 g, yield 61%) as a colorless amorphous solid.

$^1$H NMR (500 MHz, DMSO-$d_6$) δ ppm: 1.23 (3H, t, J=7.0), 1.85–1.95 (2H, m), 2.05–2.15 (2H, m), 3.05–3.20 (4H, m), 4.20 (2H, q, J=7.0), 4.42 (2H, s), 4.47 (2H, d, J=6.0), 4.80 (1H, m), 6.44 (1H, dt. J=16.0, 6.0), 6.58 (1H, d, J=16.0), 7.27 (1H, m), 7.45 (1H, m), 7.55 (1H, m), 7.65–7.80 (3H, m), 7.90 (1H, m); IR (KBr, $cm^{-1}$): 1737, 1675.

(b) Ethyl N-[4-(1-Acetimidoylpiperidin-4-yloxy)-3-bromophenyl]-N-[3-(3-amidinophenyl)-2-(E)-propenyl] sulfamoylacetate Dihydrochloride To a solution of ethyl N-[3-(3-amidinophenyl)-2-(E)-propenyl]-N-[3-bromo-4-(piperidin-4-yloxy)phenyl] sulfamoylacetate dihydrochloride (1.17 g) in ethanol (30 ml) were added ethyl acetimidate hydrochloride (0.67 g) and triethylamine (1.50 ml) in an ice bath. The resulting mixture was stirred at room temperature for 2 hours and allowed to stand for 14 hours. The reaction mixture was concentrated in vacuo. The residue was purified by preparative HPLC (YMC-Pack ODS YMC) using 22% aqueous acetonitrile as an eluant to afford an amorphous solid. To a solution of the solid in ethanol (10 ml) was added a 4M solution of hydrogen chloride in ethyl acetate (1.20 ml) and the mixture was concentrated to dryness in vacuo to give the title compound (0.97 g, yield 77%) as a colorless amorphous solid.

$^1$H NMR (500 MHz, DMSO-$d_6$) δ ppm: 1.23 (3H, t, J=7.0), 1.70–1.90 (2H, m), 1.95–2.15 (2H, m), 2.30 (3H, s), 3.55–3.75 (4H, m), 4.19. (2H, q, J=7.0), 4.42 (2H, s), 4.47 (2H, d, J=6.0), 4.85 (1H, m), 6.44 (1H, dt, J=16.0, 6.0), 6.58 (1H, d, J=16.0), 7.29 (1H, m), 7.45 (1H, m), 7.55 (1H, m), 7.65–7.80 (3H, m), 7.90 (1H, m); IR (KBr, $cm^{-1}$): 1738, 1674, 1625.

Example 32

N-[4-(1-Acetimidoylpiperidin-4-yloxy)-3-bromophenyl]-N-[3-(3-amidinophenyl)-2-(E)-propenyl]sulfamoylacetic Acid Dihydrochloride (Exemplification Compound Number 1945)

Ethyl N-[4-(1-acetimidoylpiperidin-4-yloxy)-3-bromophenyl]-N-[3-(3-amidinophenyl)-2-(E)-propenyl] sulfamoylacetate dihydrochloride (0.80 g) was dissolved in 3M hydrochloric acid (15 ml) and the mixture was stirred at 90° C. for 2 hours. The reaction mixture was cooled to room temperature and concentrated in vacuo. The residue was purified by preparative HPLC (YMC-Pack ODS YMC) using 22% aqueous acetonitrile as an eluant to afford an amorphous solid. To a solution of the solid in ethanol (10 ml) was added a 4M solution of hydrogen chloride in ethyl acetate (0.5 ml) and the mixture was concentrated to dryness in vacuo to give the title compound (0.37 g, yield 48%) as a colorless amorphous solid.

$^1$H NMR (500 MHz, DMSO-$d_6$) ppm: δ 1.70–1.85 (2H, m), 1.95–2.10 (2H, m), 2.30 (3H, s), 3.55–3.75 (4H, m), 4.26 (2H, s), 4.47 (2H, d, J=6.0), 4.85 (1H, m), 6.45 (1H, dt, J=16.0, 6.0), 6.58 (1H, d, J=16.0), 7.29 (1H, m), 7.46 (1H, m), 7.55 (1H, m), 7.65–7.75 (3H, m), 7.89 (1H, m); IR (KBr, $cm^{-1}$): 1732, 1672, 1626.

Example 33

Ethyl N-[4-(1-Acetimidoylpiperidin-4-yloxy)-3-isopropylphenyl]-N-[3-(3-amidinophenyl)-2-(E)-propenyl]sulfamoylacetate Dihydrochloride (Exemplification Compound Number 1426)

(a) Ethyl N-[3-(3-Amidinophenyl)-2-(E)-propenyl]-N-[3-isopropyl-4-(piperidin-4-yloxy)phenyl]sulfamoylacetate Dihydrochloride Ethyl N-[4-(1-t-butoxycarbonylpiperidin-4-yloxy)-3-isopropylphenyl]-N-[3-(3-cyanophenyl)-2-(E)-propenyl] sulfamoylacetate (1.82 g) was dissolved in a mixture of dichloromethane (30 ml) and ethanol (30 ml). Hydrogen chloride gas was passed through the mixture in an ice bath for 1.5 hours. The resulting mixture was stirred in a stoppered reaction vessel at room temperature for 2 hours. The reaction mixture was concentrated in vacuo, and to a solution of the residue in ethanol (20 ml) were added aqueous ammonium chloride solution (0.35 g in 5 ml) and 28% aqueous ammonia solution (0.80 ml). The resulting mixture was stirred at room temperature for 0.5 hours and then allowed to stand for 13 hours. The reaction mixture was concentrated in vacuo. The residue was purified by preparative HPLC (YMC-Pack ODS YMC) using 25% aqueous acetonitrile as an eluant to afford an amorphous solid. To a solution of the solid in ethanol (20 ml) was added a 4M solution of hydrogen chloride in ethyl acetate (1.40 ml) and the solution was concentrated to dryness in vacuo to give the desired compound (0.92 g, yield 51%) as a colorless amorphous solid.

$^1$H NMR (500 MHz, DMSO-$d_6$) δ ppm: 1.15 (6H, d, J=7.0), 1.24 (3H, t, J=7.0), 1.80–1.95 (2H, m), 2.05–2.20 (2H, m), 3.00–3.20 (4H, m), 3.21 (1H, m), 4.21 (2H, q, J=7.0), 4.33 (2H, s), 4.43 (2H, d, J=6.0), 4.68 (1H, m), 6.45 (1H, dt, J=16.0, 6.0), 6.55 (1H, d, J=16.0), 7.04 (1H, d, J=9.0), 7.23 (1H, dd, J=9.0, 3.0), 7.29 (1H, d, J=3.0), 7.54 (1H, m), 7.65–7.75 (2H, m), 7.89 (1H, m); IR (KBr, $cm^{-1}$): 1738, 1676.

(b) Ethyl N-[4-(1-Acetimidoylpiperidin-4-yloxy)-3-isopropylphenyl]-N-[3-(3-amidinophenyl)-2-(E)-propenyl] sulfamoylacetate Dihydrochloride To a solution of ethyl N-[3-(3-amidinophenyl)-2-(E)-propenyl]-N-[3-isopropyl-4-(piperidin-4-yloxy)phenyl] sulfamoylacetate dihydrochloride (0.78 g) in ethanol (30 ml) were added ethyl acetimidate hydrochloride (0.50 g) and triethylamine (1.10 ml) in an ice bath. The resulting mixture was stirred at room temperature for 7 hours and allowed to stand for 17 hours. The reaction mixture was concentrated in vacuo. The residue was purified by preparative HPLC (YMC-Pack ODS YMC) using 25% aqueous acetonitrile as an eluant to afford an amorphous solid. To a solution of the solid in ethanol (20 ml) was added a 4M solution of hydrogen chloride in ethyl acetate (0.90 ml) and the mixture was concentrated to dryness in vacuo to give the title compound (0.67 g, yield 80%) as a colorless amorphous solid.

$^1$H NMR (500 MHz, DMSO-$d_6$) δ ppm: 1.14 (6H, d, J=7.0), 1.24 (3H, t, J=7.0), 1.70–1.85 (2H, m), 1.95–2.10 (2H, m), 2.30 (3H, s), 3.22 (1H, m), 3.50–3.60 (1H, m), 3.60–3.70 (2H, m), 3.70–3.80 (1H, m), 4.21 (2H, q, J=7.0), 4.33 (2H, s), 4.43 (2H, d, J=6.0), 4.74 (1H, m), 6.45 (1H, dt, J=16.0, 6.0), 6.55 (1H, d, J=16.0), 7.07 (1H, d, J=9.0), 7.23 (1H, dd, J=9.0, 3.0), 7.28 (1H, d, J=3.0), 7.55 (1H, m), 7.71 (2H, m), 7.90 (1H, m); IR (KBr, $cm^{-1}$): 1739, 1673, 1623.

Example 34

N-[4-(1-Acetimidoylpiperidin-4-yloxy)-3-isopropylphenyl]-N-[3-(3-amidinophenyl)-2-(E)-propenyl]sulfamoylacetic Acid Dihydrochloride (Exemplification Compound Number 1955)

Ethyl N-[4-(1-acetimidoylpiperidin-4-yloxy)-3-isopropylphenyl]-N-[3-(3-amidinophenyl)-2-(E)-propenyl] sulfamoylacetate dihydrochloride (0.51 g) was dissolved in 3M hydrochloric acid (20 ml) and the mixture was stirred at 90° C. for 2 hours. The reaction mixture was cooled to room temperature and concentrated in vacuo. The residue was purified by preparative HPLC (YMC-Pack ODS YMC) using 25% aqueous acetonitrile as an eluant to afford an amorphous solid. A solution of the solid in 1M hydrochloric acid (1.70 ml) was concentrated to dryness in vacuo to give the title compound (0.33 g, yield 66%) as a colorless amorphous solid.

$^1H$ NMR (500 MHz, DMSO-$d_6$) δ ppm: 1.14 (6H, d, J=7.0), 1.70–1.85 (2H, m), 1.95–2.10 (2H, m), 2.30 (3H, s), 3.21 (1H, m), 3.50–3.60 (1H, m), 3.60–3.70 (2H, m), 3.70–3.80 (1H, m), 4.21 (2H, s), 4.44 (2H, d, J=6.0), 4.73 (1H, m), 6.46 (1H, dt, J=16.0, 6.0), 6.54 (1H, d, J=16.0), 7.06 (1H, d, J=9.0), 7.24 (1H, dd, J=9.0, 3.0), 7.29 (1H, d, J=3.0), 7.54 (1H, m), 7.71 (2H, m), 7.90 (1H, m); IR (KBr, $cm^1$): 1733, 1673, 1625.

Example 35

Ethyl N-[4-(1-Acetimidoylpiperidin-4-yloxy)-3-carbamoylphenyl]-N-[3-(3-amidinophenyl)-2-(E)-propenyl]sulfamoylacetate Dihydrochloride (Exemplification Compound Number 1460)

(a) Ethyl N-[3-(3-Amidinophenyl)-2-(E)-propenyl]-N-[3-carbamoyl-4-(piperidin-4-yloxy)phenyl]sulfamoylacetate Dihydrochloride Ethyl N-[4-(1-t-butoxycarbonylpiperidin-4-yloxy)-3-carbamoylphenyl]-N-[3-(3-cyanophenyl)-2-(E)-propenyl] sulfamoylacetate (2.40 g) was dissolved in a mixture of dichloromethane (20 ml) and ethanol (20 ml). Hydrogen chloride gas was passed through the mixture in an ice bath for 2.5 hours. The resulting mixture was stirred in a stoppered reaction vessel at room temperature for 6 hours. The reaction mixture was concentrated in vacuo, and to a solution of the residue in ethanol (20 ml) were added aqueous ammonium chloride solution (0.50 g in 5 ml) and 28% aqueous ammonia solution (1.10 ml). The resulting mixture was stirred at room temperature for 0.5 hours and then allowed to stand for 13 hours. The reaction mixture was concentrated in vacuo. The residue was purified by preparative HPLC (YMC-Pack ODS YMC) using 15% aqueous acetonitrile as an eluant to afford an amorphous solid. To a solution of the solid in ethanol (20 ml) was added a 4M solution of hydrogen chloride in ethyl acetate (0.90 ml) and the solution was concentrated to dryness in vacuo to give the desired compound (0.60 g, yield 25%) as a colorless amorphous solid.

$^1H$ NMR (500 MHz, DMSO-$d_6$) δ ppm: 1.23 (3H, t, J=7.0), 1.85–2.00 (2H, m), 2.05–2.20 (2H, m), 3.00–3.10 (2H, m), 3.15–3.25 (2H, m), 4.20 (2H, q, J=7.0), 4.38 (2H, s), 4.47 (2H, d, J=6.0), 4.80 (1H, m), 6.45 (1H, dt, J=16.0, 6.0), 6.57 (1H, d, J=16.0), 7.24 (1H, m), 7.50 (1H, m), 7.54 (1H, m), 7.65–7.75 (3H, m), 7.90 (1H, m); IR (KBr, $cm^{-1}$): 1736, 1671, 1658.

(b) Ethyl N-[4-(1-Acetimidoylpiperidin-4-yloxy)-3-carbamoylphenyl]-N-[3-(3-amidinophenyl)-2-(E)-propenyl] sulfamoylacetate Dihydrochloride To a solution of ethyl N-[3-(3-amidinophenyl)-2-(E)-propenyl]-N-[3-carbamoyl-4-(piperidin-4-yloxy)phenyl] sulfamoylacetate dihydrochloride (0.44 g) in ethanol (20 ml) were added ethyl acetimidate hydrochloride (0.27 g) and triethylamine (0.60 ml) in an ice bath. The resulting mixture was stirred at room temperature for 0.5 hours and allowed to stand for 14 hours. The reaction mixture was concentrated in vacuo. The residue was purified by preparative HPLC (YMC-Pack ODS YMC) using 15% aqueous acetonitrile as an eluant to afford an amorphous solid. To a solution of the solid in ethanol (10 ml) was added a 4M solution of hydrogen chloride in ethyl acetate (0.50 ml) and the mixture was concentrated to dryness in vacuo to give the title compound (0.37 g, yield 78%) as a colorless amorphous solid.

$^1H$ NMR (400 MHz, DMSO-$d_6$) δ ppm: 1.24 (3H, t, J=7.0), 1.80–1.95 (2H, m), 2.00–2.15 (2H, m), 2.29 (3H, s), 3.45–3.65 (2H, m), 3.65–3.85 (2H, m), 4.20 (2H, q, J=7.0), 4.37 (2H, s), 4.47 (2H, d, J=6.0), 4.86 (1H, m), 6.44 (1H, dt, J=16.0, 6.0), 6.58 (1H, d, J=16.0), 7.28 (1H, m), 7.45–7.60 (2H, m), 7.70 (2H, m), 7.78 (1H, m), 7.88 (1H, m); IR (KBr, $cm^{-1}$): 1737, 1672.

Example 36

N-[4-(1-Acetimidolpiperdin-4-yloxy)-3-carbamoylphenyl]-N-[3-(3-amidinophenyl)-2-(E)-propenyl]sulfamoylacetic Acid Dihydrochloride (Exemplification Compound Number 1989)

Ethyl N-[4-(1-acetimidoylpiperidin-4-yloxy)-3-carbamoylphenyl]-N-[3-(3-amidinophenyl)-2-(E)-propenyl] sulfamoylacetate dihydrochloride (0.20 g) was dissolved in 1.5M hydrochloric acid (20 ml) and the mixture was stirred at 60° C. for 6 hours. The reaction mixture was cooled to room temperature and concentrated in vacuo. The residue was purified by preparative HPLC (YMC-Pack ODS YMC) using 15% aqueous acetonitrile as an eluant to afford an amorphous solid. A solution of the solid in 1M hydrochloric acid (0.75 ml) was concentrated to dryness in vacuo to give the title compound (0.14 g, yield 71%) as a colorless amorphous solid.

$^1H$ NMR (500 MHz, DMSO-$d_6$) δ ppm: 1.75–1.95 (2H, m), 2.00–2.15 (2H, m), 2.29 (3H, s), 3.45–3.65 (2H, m), 3.65–3.85 (2H, m), 4.24 (2H, s), 4.47 (2H, d, J=6.0), 4.85 (1H, m), 6.45 (1H, dt, J=16.0, 6.0), 6.57 (1H, d, J=16.0), 7.27 (1H, m), 7.45–7.60 (2H, m), 7.70 (2H, m), 7.77 (1H, m), 7.88 (1H, m); IR (KBr, $cm^{-1}$): 1729, 1672.

Example 37

Ethyl N-[4-(1-Acetimidoylpiperidin-4-yloxy)-3-(N'-methylcarbamoyl)phenyl]-N-[3-(3-amidinophenyl)-2-(E)-propenyl]sulfamoylacetate Dihydrochloride (Exemplification Compound Number 1462)

(a) Ethyl N-[3-(3-Amidinophenyl)-2-(E)-prophenyl]-N-[3-(N'-methylcarbamoyl)-4-(piperidin-4-yloxy)phenyl] sulfamoylacetate Dihydrochloride Ethyl N-[4-(1-t-butoxycarbonylpiperidin-4-yloxy)-3-(N'-methylcarbamoyl)phenyl]-N-[3-(3-cyanophenyl)-2-(E)-propenyl]sulfamoylacetate (1.50 g) was dissolved in a mixture of dichloromethane (20 ml) and ethanol (20 ml). Hydrogen chloride gas was passed through the mixture in an ice bath for 1.5 hours. The resulting mixture was stirred in a stoppered reaction vessel at room temperature for 3.5 hours. The reaction mixture was concentrated in vacuo, and to a solution of the residue in ethanol (20 ml) were added aqueous ammonium chloride solution (0.29 g in 5 ml) and 28% aqueous ammonia solution (0.66 ml). The resulting mixture was stirred at room temperature for 2 hours and then allowed to stand for 15 hours. The reaction mixture was concentrated in vacuo. The residue was purified by preparative HPLC (YMC-Pack ODS YMC) using 15% aqueous acetonitrile as an eluant to afford an amorphous solid. To a solution of the solid in ethanol (20 ml) was added a 4M solution of hydrogen chloride in ethyl acetate (1.55 ml) and the solution was concentrated to dryness in vacuo to give the desired compound (1.14 g, yield 73%) as a colorless amorphous solid.

$^1$H NMR (400 MHz, DMSO-$d_6$) δ ppm: 1.23 (3H, t, J=7.0), 1.85–1.95 (2H, m), 2.05–2.15 (2H, m), 2.79 (3H, m), 2.95–3.10 (2H, m), 3.10–3.25 (2H, m), 4.20 (2H, q, J=7.0), 4.38 (2H, s), 4.47 (2H, d, J=6.0), 4.79 (1H, m), 6.45 (1H, dt, J=16.0, 6.0), 6.58 (1H, d, J=16.0), 7.24 (1H, m), 7.48 (1H, m), 7.54 (1H, m), 7.62 (1H, m), 7.12 (2H, m), 7.92 (1H, m); IR (KBr, $cm^{-1}$) 1737, 1676, 1641.

(b) Ethyl N-[4-(1-Acetimidoylpiperidin-4-yloxy)-3-(N'-methylcarbamoyl)phenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[3-(N'-methylcarbamoyl)-4-(piperidin-4-yloxy)phenyl]sulfamoylacetate dihydrochloride (1.00 g) in ethanol (30 ml) were added ethyl acetimidate hydrochloride (0.60 g) and triethylamine (1.35 ml) in an ice bath. The resulting mixture was stirred at room temperature for 8 hours. The reaction mixture was concentrated in vacuo. The residue was purified by preparative HPLC (YMC-Pack ODS YMC) using 15% aqueous acetonitrile as an eluant to afford an amorphous solid. To a solution of the solid in ethanol (10 ml) was added a 4M solution of hydrogen chloride in ethyl acetate (1.00 ml) and the mixture was concentrated to dryness in vacuo to give the title compound (0.79 g, yield 74%) as a colorless amorphous solid.

$^1$H NMR (400 MHz, DMSO-$d_6$) δ ppm: 1.23 (3H, t, J=7.0), 1.75–1.90 (2H, m), 1.95–2.10 (2H, m), 2.30 (3H, s), 2.78 (3H, s), 3.50–3.80 (4H, m), 4.20 (2H, q, J=7.0), 4.37 (2H, s), 4.47 (2H, d, J=6.0), 4.84 (1H, m), 6.44 (1H, dt, J=16.0, 6.0), 6.58 (1H, d, J=16.0), 7.27 (1H, m), 7.50 (1H, m), 7.55 (1H, m), 7.65–7.75 (3H, m), 7.90 (1H. m); IR (KBr, $cm^{-1}$): 1738, 1673, 1633.

Example 38

N-[4-(1-Acetimidoylpiperidin-4-yloxy)-3-(N'-methylcarbamoyl)phenyl]-N-[3-(3-amidinophenyl)-2-(E)-propenyl]sulfamoylacetic Acid Dihydrochloride (Exemplification Compound Number 1991)

Ethyl N-[4-(1-acetimidoylpiperidin-4-yloxy)-3-(N'-methylcarbamoyl)phenyl]-N-[3-(3-amidinophenyl)-2-(E)-propenyl]sulfamoylacetate dihydrochloride (0.53 g) was dissolved in 1.5M hydrochloric acid (30 ml) and the mixture was stirred at 60° C. for 8 hours. The reaction mixture was cooled to room temperature and concentrated in vacuo. The residue was purified by preparative HPLC (YMC-Pack ODS YMC) using 15% aqueous acetonitrile as an eluant to afford an amorphous solid. A solution of the solid in 1M hydrochloric acid (2.20 ml) was concentrated to dryness in vacuo to give the title compound (0.42 g, yield 82%) as a colorless amorphous solid.

$^1$H NMR (400 MHz, DMSO-$d_6$) δ ppm: 1.75–1.90 (2H, m), 1.95–2.10 (2H, m), 2.30 (3H, s), 2.78 (3H, s), 3.50–3.85 (4H, m), 4.25 (2H, s), 4.47 (2H, d, J=6.0), 4.84 (1H, m), 6.45 (1H, dt, J=16.0, 6.0), 6.57 (1H, d, J=16.0), 7.27 (1H, m), 7.45–7.60 (2H, m), 7.65–7.75 (3H, m), 7.90 (1H, m); IR (KBr, $cm^{-1}$): 1732, 1673, 1628.

Example 39

Ethyl N-[4-(1-Acetimidoylpiperidin-4-yloxy)-3-(N',N'-dimethylcarbamoyl)phenyl]-N-[3-(3-amidinophenyl)-2-(E)-propenyl]sulfamoylacetate Dihydrochloride (Exemplification Compound Number 1466)

(a) Ethyl N-[3-(3-Amidinophenyl)-2-(E)-propenyl]-N-[3-(N',N'-dimethylcarbamoyl)-4-(piperidin-4-yloxy)phenyl]sulfamoylacetate Dihydrochloride Ethyl N-[4-(1-t-butoxycarbonylpiperidin-4-yloxy)-3-(N',N'-dimethylcarbamoyl)phenyl]-N-[3-(3-cyanophenyl)-2-(E)-propenyl]sulfamoylacetate (1.70 g) was dissolved in a mixture of dichloromethane (20 ml) and ethanol (20 ml). Hydrogen chloride gas was passed through the mixture in an ice bath for 1.5 hours. The resulting mixture was stirred in a stoppered reaction vessel at room temperature for 3.5 hours. The reaction mixture was concentrated in vacuo, and to a solution of the residue in ethanol (20 ml) were added aqueous ammonium chloride solution (0.30 g in 5 ml) and 28% aqueous ammonia solution (0.70 ml). The resulting mixture was stirred at room temperature for 5 hours and then allowed to stand for 13 hours. The reaction mixture was concentrated in vacuo. The residue was purified by preparative HPLC (YMC-Pack ODS YMC) using 15% aqueous acetonitrile as an eluant to afford an amorphous solid. To a solution of the solid in ethanol (20 ml) was added a 4M solution of hydrogen chloride in ethyl acetate (1.00 ml) and the solution was concentrated to dryness in vacuo to give the desired compound (0.75 g, yield 44%) as a colorless amorphous solid.

$^1$H NMR (400 MHz, DMSO-$d_6$) δ ppm: 1.22 (3H, t, J=7.0), 1.75–1.95 (2H, m), 1.95–2.15 (2H, m), 2.69 (3H, s), 2.97 (3H, s), 2.95–3.15 (4H, m), 4.19 (2H, q, J=7.0), 4.38 (2H, s), 4.35–4.55 (2H, m), 4.75 (1H, m), 6.43 (1H, dt, J=16.0, 6.0), 6.55 (1H, d, J=16.0), 7.22 (1H, d, J=9.0), 7.30 (1H, d, J=3.0), 7.45 (1H, dd, J=9.0, 3.0), 7.54 (1H, t, J=8.0), 7.70 (2H, d, J=8.0), 7.88 (1H, s); IR (KBr, $cm^{-1}$): 1738, 1676, 1618.

(b) Ethyl N-[4-(1-Acetimidoylpiperidin-4-yloxy)-3-(N',N'-dimethylcarbamoyl)phenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[3-(N',N'-dimethylcarbamoyl)-4-(piperidin-4-yloxy)phenyl]sulfamoylacetate dihydrochloride (0.60 g) in ethanol (20 ml) were added ethyl acetimidate hydrochloride (0.35 g) and triethylamine (0.80 ml) in an ice bath. The resulting mixture was stirred at room temperature for 0.5 hours and allowed to stand for 12 hours. The reaction mixture was concentrated in vacuo. The residue was purified by preparative HPLC (YMC-Pack ODS YMC) using 20% aqueous acetonitrile as an eluant to afford an amorphous solid. To a solution of the solid in ethanol (20 ml) was added a 4M solution of hydrogen chloride in ethyl acetate (0.60 ml) and the mixture was concentrated to dryness in vacuo to give the title compound (0.47 g, yield 73%) as a colorless amorphous solid.

$^1$H NMR (400 MHz, DMSO-$d_6$) δ ppm: 1.22 (3H, t, J=7.0), 1.60–1.85 (2H, m), 1.85–2.10 (2H, m), 2.29 (3H, s), 2.69 (3H, s), 2.95 (3H, s), 3.50–3.70 (4H, m), 4.19 (2H, q, J=7.0), 4.35–4.55 (2H, m), 4.39 (2H, s), 4.79 (1H, m), 6.44 (1H, dt, J=16.0, 6.0), 6.55 (1H, d, J=16.0), 7.25 (1H, d, J=9.0), 7.29 (1H, d, J=3.0), 7.45 (1H, dd, J=9.0, 3.0), 7.54

(1H, m), 7.65–7.75 (2H, m), 7.90 (1H, s); IR (KBr, $cm^{-1}$): 1738, 1673, 1618.

Example 40

N-[4-(1-Acetimidoylpiperidin-4-yloxy)-3-(N',N'-dimethylcarbamoyl)phenyl]-N-[3-(3-amidinophenyl)-2-(E)-propenyl]sulfamoylacetic Acid Dihydrochloride (Exemplification Compound Number 1995)

Ethyl N-[4-(1-acetimidoylpiperidin-4-yloxy)-3-(N',N'-dimethylcarbamoyl)phenyl]-N-[3-(3-amidinophenyl)-2-(E)-propenyl]sulfamoylacetate dihydrochloride (0.30 g) was dissolved in 1.5M hydrochloric acid (10 ml) and the mixture was stirred at 60° C. for 9.5 hours. The reaction mixture was cooled to room temperature and concentrated in vacuo. The residue was purified by preparative HPLC (YMC-Pack ODS YMC) using 10% aqueous acetonitrile as an eluant to afford an amorphous solid. A solution of the solid in 1M hydrochloric acid (1.20 ml) was concentrated to dryness in vacuo to give the title compound (0.24 g, yield 83%) as a colorless amorphous solid.

$^1$H NMR (400 MHz, DMSO-$d_6$) δ ppm: 1.65–1.85 (2H, m), 1.90–2.10 (2H, m), 2.28 (3H, s), 2.69 (3H, s), 2.95 (3H, s), 3.50–3.70 (4H, m), 4.25 (2H, s), 4.35–4.55 (2H, m), 4.78 (1H, m), 6.43 (1H, dt, J=16.0, 6.0), 6.55 (1H, d, J=16.0), 7.24 (1H, d, J=9.0), 7.29 (1H, d, J=3.0), 7.46 (1H, dd, J=9.0, 3.0), 7.54 (1H, m), 7.65–7.75 (2H, m), 7.88 (1H, s); IR (KBr, $cm^{-1}$): 1733, 1672, 1614.

Example 41

Ethyl N-[4-(1-Acetimidoylpiperidin-4-yloxy)-3-chlorophenyl]-N-[3-(5-amidino-2-hydroxyphenyl)-2-(E)-propenyl]sulfamoylacetate Dihydrochloride (Exemplification Compound Number 1843)

(a) Ethyl N-[3-(5-Amidino-2-hydroxyphenyl)-2-(E)-propenyl]-N-[3-chloro-4-(piperidin-4-yloxy)phenyl]sulfamoylacetate Ethyl N-[4-(1-t-butoxycarbonylpiperidin-4-yloxy)-3-chlorophenyl]-N-[3-(5-cyano-2-methoxymethoxyphenyl)-2-(E)-propenyl]sulfamoylacetate (1.4 g) was dissolved in a mixture of dichloromethane (20 ml) and ethanol (20 ml). Hydrogen chloride gas was passed through the mixture in an ice bath for 1.5 hours. The resulting mixture was stirred in a stoppered reaction vessel at room temperature for 2 hours. The reaction mixture was concentrated in vacuo, and to a solution of the residue in ethanol (40 ml) were added aqueous ammonium chloride solution (0.2 g in 10 ml) and 28% aqueous ammonia solution (0.5 ml). The resulting mixture was stirred at room temperature for 0.5 hours and then allowed to stand for 12 hours. The reaction mixture was concentrated in vacuo. The residue was purified by preparative HPLC (YMC-Pack ODS YMC) using 15% aqueous acetonitrile as an eluant to give the desired compound (0.1 g, yield 4%) as a colorless amorphous solid.

$^1$H NMR (500 MHz, DMSO-$d_6$) δ ppm: 1.23 (3H, t, J=7.0), 1.85–1.95 (2H, m), 2.05–2.15 (2H, m), 3.05–3.15 (2H, m), 3.15–3.25 (2H, m), 4.19 (2H, q, J=7.0), 4.40 (2H, s), 4.45 (2H, d, J=6.0), 4.78 (1H, m), 6.38 (1H, dt, J=16.0, 6.0), 6.66 (1H, d, J=16.0), 7.04 (1H, d, J=9.0), 7.31 (1H, d, J=9.0), 7.38 (1H, dd, J=9.0, 3.0), 7.56 (1H, d, J=3.0), 7.62 (1H, dd, J=9.0, 2.0), 7.94 (1H, d, J=2.0).

(b) Ethyl N-[4-(1-Acetimidoylpiperidin-4-yloxy)-3-chlorophenyl]-N-[3-(5-amidino-2-hydroxyphenyl)-2-(E)-propenyl]sulfamoylacetate Dihydrochloride To a solution of ethyl N-[3-(5-amidino-2-hydroxyphenyl)-2-(E)-propenyl]-N-[3-chloro-4-(piperidin-4-yloxy)phenyl]sulfamoylacetate (0.05 g) in ethanol (10 ml) were added ethyl acetimidate hydrochloride (0.04 g) and triethylamine (0.08 ml) in an ice bath. The resulting mixture was stirred at room temperature for 5 hours and allowed to stand for 13 hours. The reaction mixture was concentrated in vacuo. The residue was purified by preparative HPLC (YMC-Pack ODS YMC) using 20% aqueous acetonitrile as an eluant to afford an amorphous solid. To a solution of the solid in ethanol (10 ml) was added a 4M solution of hydrogen chloride in ethyl acetate (0.05 ml) and the mixture was concentrated to dryness in vacuo to give the title compound (0.04 g, yield 59%) as a colorless amorphous solid.

$^1$H NMR (500 MHz, DMSO-$d_6$) δ ppm: 1.23 (3H, t, J=7.0), 1.70–1.85 (2H, m), 2.00–2.15 (2H, m), 2.30 (3H, s), 3.50–3.80 (4H, m), 4.19 (2H, q, J=7.0), 4.41 (2H, s), 4.45 (2H, d, J=6.0), 4.84 (1H, m), 6.39 (1H, dt, J=16.0, 6.0), 6.65 (1H, d, J=16.0), 7.08 (1H, d, J=9.0), 7.33 (1H, d, J=9.0), 7.38 (1H, dd, J=9.0, 2.0), 7.56 (1H, d, J=2.0), 7.63 (1H, dd, J=9.0, 2.0), 7.95 (1H, d, J=2.0); IR (KBr, $cm^{-1}$): 1738, 1671.

Example 42

Ethyl N-[4-(1-Acetimidoylpiperidin-4-yloxy)-5-carbamoyl-3-chlorophenyl]-N-[3-(3-amidinophenyl)-2-(E)-propenyl]sulfamoylacetate Dihydrochloride (Exemplification Compound Number 1484)

(a) Ethyl N-[3-(3-Amidinophenyl)-2-(E)-propenyl]-N-[5-carbamoyl-3-chloro-4-(piperidin-4-yloxy)phenyl]sulfamoylacetate Dihydrochloride Ethyl N-[4-(1-t-butoxycarbonylpiperidin-4-yloxy)-5-carbamoyl-3-chlorophenyl]-N-[3-(3-cyanophenyl)-2-(E)-propenyl]sulfamoylacetate (1.50 g) was dissolved in a mixture of dichloromethane (20 ml) and ethanol (20 ml). Hydrogen chloride gas was passed through the mixture in an ice bath for 1.5 hours. The resulting mixture was stirred in a stoppered reaction vessel at room temperature for 4 hours. The reaction mixture was concentrated in vacuo, and to a solution of the residue in ethanol (20 ml) were added aqueous ammonium chloride solution (0.26 g in 5 ml) and 28% aqueous ammonia solution (0.60 ml). The resulting mixture was stirred at room temperature for 4 hours and then allowed to stand for 12 hours. The reaction mixture was concentrated in vacuo. The residue was purified by preparative HPLC (YMC-Pack ODS YMC) using 20% aqueous acetonitrile as an eluant to afford an amorphous solid. A solution of the solid in 1M hydrochloric acid was concentrated to dryness in vacuo to give the desired compound (0.55 g, yield 37%) as a colorless amorphous solid.

$^1$H NMR (500 MHz, DMSO-$d_6$) δ ppm: 1.23 (3H, t, J=7.0), 1.90–2.00 (2H, m), 2.00–2.10 (2H, m), 2.95–3.05 (2H, m), 3.20–3.30 (2H, m), 4.19 (2H, q, J=7.0), 4.35 (1H, m), 4.48 (2H, s), 4.51 (2H, d, J=6.0), 6.44 (1H, dt, J=16.0, 6.0), 6.62 (1H, d, J=16.0), 7.50–7.60 (2H, m), 7.65–7.80 (3H, m), 7.88 (1H, m); IR (KBr, $cm^{-1}$): 1737, 1672.

(b) Ethyl N-[4-(1-Acetimidoylpiperidin-4-yloxy)-5-carbamoyl-3-chlorophenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[5-carbamoyl-3-chloro-4-(piperidin-4-yloxy)phenyl]sulfamoylacetate dihydrochloride (0.51 g) in ethanol (25 ml) were added ethyl acetimidate hydrochloride (0.30 g) and triethylamine (0.70 ml) in an ice bath. The resulting mixture was stirred at room temperature for 1 hour then allowed to stand for 12 hours. The reaction mixture was concentrated in vacuo. The residue was purified by preparative HPLC (YMC-Pack ODS YMC) using 20% aqueous acetonitrile as an eluant to afford an amorphous solid. To a solution of the solid in ethanol (10 ml) was added a 4M solution of hydrogen chloride in ethyl acetate (0.50 ml) and the mixture was concentrated to dryness in vacuo to give the title compound (0.36 g, yield 66%) as a colorless amorphous solid.

$^1$H NMR (500 MHz, DMSO-$d_6$) δ ppm: 1.23 (3H, t, J=7.0), 1.75–1.90 (2H, m), 1.90–2.05 (2H, m), 2.29 (3H, s), 3.40–3.55 (2H, m), 3.75–3.90 (2H, m), 4.20 (2H, q, J=7.0), 4.42 (1H, m), 4.48 (2H, s), 4.52 (2H, d, J=6.0), 6.44 (1H, dt, J=16.0, 6.0), 6.62 (1H, d, J=16.0), 7.50–7.60 (2H, m), 7.65–7.80 (3H, m), 7.89 (1H, m); IR (KBr, $cm^{-1}$): 1738, 1671, 1622.

Example 43

N-[4-(1-Acetimidoylpiperidin-4-yloxy)-5-carbamoyl-3-chlorophenyl]-N-[3-(3-amidinophenyl)-2-(E)-propenyl]sulfamoylacetic Acid Dihydrochloride (Exemplification Compound Number 2013)

Ethyl N-[4-(1-acetimidoylpiperidin-4-yloxy)-5-carbamoyl-3-chlorophenyl]-N-[3-(3-amidinophenyl)-2-(E)-propenyl]sulfamoylacetate dihydrochloride (0.20 g) was dissolved in 3M hydrochloric acid (20 ml) and the mixture was stirred at 70° C. for 1.5 hours. The reaction mixture was cooled to room temperature and concentrated in vacuo. The residue was purified by preparative HPLC (YMC-Pack ODS YMC) using 15% aqueous acetonitrile as an eluant to afford an amorphous solid. A solution of the solid in 1M hydrochloric acid (0.80 ml) was concentrated to dryness in vacuo to give the title compound (0.16 g, yield 83%) as a colorless amorphous solid.

$^1$H NMR (500 MHz, DMSO-$d_6$) δ ppm: 1.75–1.90 (2H, m), 1.90–2.05 (2H. m), 2.28 (3H, s), 3.40–3.55 (2H, m), 3.75–3.90 (2H, m), 4.35 (2H, s), 4.42 (1H, m), 4.51 (2H, d, J=6.0), 6.44 (1H, dt, J=16.0, 6.0), 6.61 (1H, d, J=16.0), 7.50–7.60 (2H, m), 7.65–7.80 (3H, m), 7.87 (1H, m); IR (KBr, $cm^{-1}$): 1730, 1671, 1628.

Example 44

Ethyl N-[4-(1-Acetimidoylpiperidin-4-yloxy)-3-carbamoyl-5-methylphenyl]-N-[3-(3-amidinophenyl)-2-(E)-propenyl]sulfamoylacetate Dihydrochloride (Exemplification Compound Number 1498)

(a) Ethyl N-[3-(3-Amidinophenyl)-2-(E)-propenyl]-N-[3-carbamoyl-5-methyl-4-(piperidin-4-yloxy)phenyl]sulfamoylacetate Dihydrochloride Ethyl N-[4-(1-t-butoxycarbonylpiperidin-4-yloxy)-3-carbamoyl-5-methylphenyl]-N-[3-(3-cyanophenyl)-2-(E)-propenyl]sulfamoylacetate (3.20 g) was dissolved in a mixture of dichloromethane (30 ml) and ethanol (30 ml). Hydrogen chloride gas was passed through the mixture in an ice bath for 1.5 hours. The resulting mixture was stirred in a stoppered reaction vessel at room temperature for 2.5 hours. The reaction mixture was concentrated in vacuo, and to a solution of the residue in ethanol (30 ml) were added aqueous ammonium chloride solution (0.59 g in 8 ml) and 28% aqueous ammonia solution (1.34 ml). The resulting mixture was stirred at room temperature for 0.5 hours and then allowed to stand for 15 hours. The reaction mixture was concentrated in vacuo. The residue was purified by preparative HPLC (YMC-Pack ODS YMC) using 20% aqueous acetonitrile as an eluant to afford an amorphous solid. To a solution of the solid in ethanol (10 ml) was added a 4M solution of hydrogen chloride in dioxane (3.00 ml) and the solution was concentrated to dryness in vacuo to give the desired compound (2.85 g, yield 90%) as a colorless amorphous solid.

$^1$H NMR (500 MHz, DMSO-$d_6$) δ ppm: 1.23 (3H, t, J=7.0), 1.85–1.95 (2H, m), 1.95–2.05 (2H, m), 2.26 (3H, s), 2.90–3.00 (2H, m), 3.20–3.30 (2H, m), 4.15–4.20 (1H, m), 4.20 (2H, q, J=7.0), 4.39 (2H, s), 4.47 (2H, d, J=6.0), 6.43 (1H, dt, J=16.0, 6.0), 6.60 (1H, d, J=16.0), 7.54 (2H, m), 7.57 (1H, m), 7.68 (11H, m), 7.73 (1H, m), 7.87 (1H, m); IR (KBr, $cm^{-1}$) 1737, 1672.

(b) Ethyl N-[4-(1-Acetimidoylpiperidin-4-yloxy)-3-carbamoyl-5-methylphenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[3-carbamoyl-5-methyl-4-(piperidin-4-yloxy)phenyl]sulfamoylacetate dihydrochloride (2.68 g) in ethanol (40 ml) were added ethyl acetimidate hydrochloride (1.58 g) and triethylamine (3.55 ml) in an ice bath. The resulting mixture was stirred at room temperature for 1 hour and allowed to stand for 13 hours. The reaction mixture was concentrated in vacuo. The residue was purified by preparative HPLC (YMC-Pack ODS YMC) using 20% aqueous acetonitrile as an eluant to afford an amorphous solid. To a solution of the solid in ethanol (10 ml) was added a 4M solution of hydrogen chloride in dioxane (0.44 ml) and the mixture was concentrated to dryness in vacuo to give the title compound (0.38 g, yield 13%) as a colorless amorphous solid.

$^1$H NMR (500 MHz, DMSO-$d_6$) δ ppm: 1.23 (3H. t, J=7.0), 1.70–1.90 (2H, m), 1.90–2.00 (2H, m), 2.27 (3H. s), 2.29 (3H. s), 3.35–3.45 (2H, m), 3.75–3.95 (2H, m), 4.20 (2H, q, J=7.0), 4.25 (1H, m), 4.40 (2H, s), 4.48 (2H, d, J=6.0), 6.43 (1H, dt, J=16.0, 6.0), 6.60 (1H, d, J=16.0), 7.43 (2H, m), 7.55 (1H, m), 7.69 (1H, m), 7.73 (1H, m), 7.88 (1H, m); IR (KBr, $cm^{-1}$): 1738, 1672, 1625.

Example 45

N-[4-(1-Acetimidoylpiperidin-4-yloxy)-3-carbamoyl-5-methylphenyl]-N-[3-(3-amidinophenyl)-2-(E)-propenyl]sulfamoylacetic Acid Dihydrochloride (Exemplification Compound Number 2027)

Ethyl N-[4-(1-acetimidoylpiperidin-4-yloxy)-3-carbamoyl-5-methylphenyl]-N-[3-(3-amidinophenyl)-2-(E)-propenyl]sulfamoylacetate dihydrochloride (0.24 g) was dissolved in 3M hydrochloric acid (20 ml) and the mixture was stirred at 70° C. for 2.5 hours. The reaction mixture was cooled to room temperature and concentrated in vacuo. The residue was purified by preparative HPLC (YMC-Pack ODS YMC) using 15% aqueous acetonitrile as an eluant to afford an amorphous solid. A solution of the solid in 1M hydrochloric acid (1.00 ml) was concentrated to dryness in vacuo to give the title compound (0.18 g, yield 78%) as a colorless amorphous solid, $^1$H NMR (500 MHz, DMSO-$d_6$) δ ppm: 1.70–1.85 (2H, m), 1.90–2.00 (2H, m), 2.27 (3H, 5), 2.29 (3H, s), 3.30–3.45 (2H, m), 3.75–3.90 (2H, m), 4.25 (1H, m), 4.27 (2H, s), 4.48 (2H, d, J=6.0), 6.43 (1H, dt, J=16.0, 6.0). 6.60 (11H, d, J=16.0), 7.43 (2H, m), 7.55 (1H, m), 7.67 (1H, m), 7.72 (1H, m), 7.86 (1H, m); IR (KBr, $cm^{-1}$): 1731, 1672.

Example 46

Ethyl N-[4-(1-Acetimidoylpiperidin-4-yloxy)-3,5-difluorophenyl]-N-[3-(3-amidinophenyl)-2-(E)-propenyl]sulfamoylacetate Dihydrochloride (Exemplification Compound Number 1474)

(a) Ethyl N-[3-(3-Amidinophenyl)-2-(E)-propenyl]-N-[3,5-difluoro-4-(piperidin-4-yloxy)phenyl]sulfamoylacetate Dihydrochloride Ethyl N-[4-(1-t-butoxycarbonylpiperidin-4-yloxy)-3,5-difluorophenyl]-N-[3-(3-cyanophenyl)-2-(E)-propenyl] sulfamoylacetate (1823 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 5.5 hours. The reaction mixture was concentrated in vacuo, and to a solution of the residue in ethanol (20 ml) were added aqueous ammonium chloride solution (315 mg in 10 ml) and 28% aqueous ammonia solution (0.59 ml). The resulting mixture was allowed to stand at room temperature for 15 hours. To the reaction mixture was added a 4M solution of hydrogen chloride in dioxane (1 ml) and the mixture was concentrated in vacuo. The residue was purified by preparative HPLC (YMC-Pack ODS YMC) using 20% aqueous acetonitrile as an eluant to afford an amorphous solid. To a solution of the solid in ethanol (20 ml) was added 1M hydrochloric acid (2 ml) and the solution was concentrated to dryness in vacuo to give the desired compound (1214 mg, yield 68%) as a colorless amorphous solid.

$^1$H NMR (400 MHz, DMSO-$d_6$) δ ppm: 1.21 (3H, t, J=7.0), 1.85–1.91 (2H, m), 2.04–2.10 (2H, m), 2.99–3.05 (2H, m), 3.18–3.24 (2H, m), 4.18 (2H, q, J=7.0), 4.37 (1H, m), 4.50 (2H, s), 4.51 (2H, d, J=6.0), 6.42 (1H, dt, J=16.0, 6.0), 6.62 (1H, d, J=16.0), 7.39 (2H, m), 7.55 (1H, t, J=8.0), 7.68 (1H, d, J=8.0), 7.74 (1H, d, J=8.0), 7.88 (1H, s); IR (KBr, $cm^{-1}$): 1738, 1676.

(b) Ethyl N-[4-(1-Acetimidoylpiperidin-4-yloxy)-3,5-difluorophenyl]-N-[3-(3-amidinophenyl)-2-(E)-propenyl] sulfamoylacetate Dihydrochloride To a solution of ethyl N-[3-(3-amidinophenyl)-2-(E)-propenyl]-N-[3,5-difluoro-4-(piperidin-4-yloxy)phenyl] sulfamoylacetate dihydrochloride (1020 mg) in ethanol (30 ml) were added ethyl acetimidate hydrochloride (620 m) and triethylamine (1.17 ml). The resulting mixture was stirred at room temperature for 15 hours. To the reaction mixture was added a 4M solution of hydrogen chloride in dioxane (1.0 ml) and the mixture was concentrated in vacuo. The residue was purified by preparative HPLC (YMC-Pack ODS YMC) using 22% aqueous acetonitrile as an eluant to afford an amorphous solid. To a solution of the solid in ethanol (15 ml) was added 1M hydrochloric acid (1.0 ml) and the mixture was concentrated to dryness in vacuo. A solution of the residual solid in water (about 20 ml) was lyophilized to give the title compound (851 mg, yield 78%) as a colorless amorphous solid.

$^1$H NMR (400 MHz, DMSO-$d_6$) δ ppm: 1.22 (3H, t, J=7.0), 1.76–1.83 (2H, m), 1.98–2.03 (2H, m), 2.30 (3H, s), 3.52 (2H, m), 3.78 (2H, m), 4.18 (2H, q, J=7.0), 4.46 (1H, m), 4.51 (2H, s), 4.52 (2H, d, J=6.0), 6.43 (1H, dt, J=16.0, 6.0), 6.62 (1H, d, J=16.0), 7.39 (2H, m), 7.55 (1H, t, J=8.0), 7.70 (1H, d, J=8.0), 7.73 (1H, d, J=8.0), 7.91 (1H, s); IR (KBr, $cm^{-1}$): 1739, 1673, 1624.

Example 47

N-[4-(1-Acetimidoylpiperidin-4-yloxy)-3,5-difluorophenyl]-N-[3-(3-amidinophenyl)-2-(E)-propenyl]sulfamoylacetic Acid Dihydrochloride (Exemplification Compound Number 2003)

Ethyl N-[4-(1-acetimidoylpiperidin-4-yloxy)-3,5-difluorophenyl]-N-[3-(3-amidinophenyl)-2-(E)-propenyl] sulfamoylacetate dihydrochloride (415 mg) was dissolved in 2M hydrochloric acid (20 ml) and the mixture was stirred at 60° C. for 5 hours. The reaction mixture was cooled to room temperature and concentrated in vacuo. The residue was purified by preparative HPLC (YMC-Pack ODS YMC) using 15% aqueous acetonitrile as an eluant to afford an amorphous solid. To a solution of the solid in 15% aqueous acetonitrile (20 ml) was added 1M hydrochloric acid (1.0 ml) and the mixture was concentrated to dryness in vacuo. A solution of the residual solid in water (about 20 ml) was lyophilized to give the title compound (319 mg, yield 80%) as a colorless amorphous solid.

$^1$H NMR (400 MHz, DMSO-$d_6$) δ ppm: 1.70–1.90 (2H, m), 1.95–2.10 (2H, m), 2.29 (3H, s), 3.40–3.60 (2H, m), 3.78 (2H, m), 4.37 (2H, s), 4.46 (1H, m), 4.52 (2H, d, J=6.0), 6.43 (1H, dt, J=16.0, 6.0), 6.62 (1H, d, J=16.0), 7.38 (2H, m), 7.55 (1H, t, J=8.0), 7.69 (1H, d, J=8.0), 7.74 (1H, d, J=8.0), 7.89 (1H, s); IR (KBr, $cm^{-1}$): 3123, 1733, 1674, 1626.

Example 48

Ethyl N-[4-(1-Acetimidoylpiperidin-4-yloxy)-3,5-dichlorophenyl]-N-[3-(3-amidinophenyl)-2-(E)-propenyl]sulfamoylacetate Dihydrochloride (Exemplification Compound Number 1478)

(a) Ethyl N-[3-(3-Amidinophenyl)-2-(E)-prophenyl]-N-[3,5-dichloro-4-(piperidin-4-yloxy)phenyl]sulfamoylacetate Dihydrochloride Ethyl N-[4-(1-t-butoxycarbonylpiperidin-4-yloxy)-3,5-dichlorophenyl]-N-[3-(3-cyanophenyl)-2-(E)-propenyl] sulfamoylacetate (2057 mg) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 6 hours. The reaction mixture was concentrated in vacuo, and to a solution of the residue in ethanol (40 ml) were added aqueous ammonium chloride solution (337 mg in 20 ml) and 28% aqueous ammonia solution (0.63 ml). The resulting mixture was allowed to stand at room temperature for 15 hours. To the reaction mixture was added a 4M solution of hydrogen chloride in dioxane (2.0 ml) and the mixture was concentrated in vacuo. The residue was purified by preparative HPLC (YMC-Pack ODS YMC) using 23% aqueous acetonitrile as an eluant to afford an amorphous solid. To a solution of the solid in ethanol (20 ml) was added 1M hydrochloric acid (1.0 ml) and the solution was concentrated to dryness in vacuo to give the desired compound (1002 mg, yield 49%) as a colorless amorphous solid.

$^1$H NMR (400 MHz, DMSO-$d_6$) δ ppm: 1.21 (3H, t, J=7.0), 1.95–2.15 (4H, m), 2.95–3.10 (2H, m), 3.20–3.35 (2H, m), 4.18 (2H, q, J=7.0), 4.46 (1H, m), 4.53 (4H, m), 6.43 (1H, dt, J=16.0, 6.0), 6.62 (1H, d, J=16.0), 7.55 (1H, t, J=7.5), 7.67 (2H, s), 7.68 (1H, d, J=7.5), 7.74 (1H, d, J=7.5), 7.88 (1H, s); IR (KBr, $cm^{-1}$): 1738, 1676.

(b) Ethyl N-[4-(1-Acetimidoylpiperidin-4-yloxy)-3,5-dichlorophenyl]-N-[3-(3-amidinophenyl)-2-(E)-propenyl] sulfamoylacetate Dihydrochloride To a solution of ethyl N-[3-(3-amidinophenyl)-2-(E)-propenyl]-N-[3,5-dichloro-4-(piperidin-4-yloxy)phenyl]

sulfamoylacetate dihydrochloride (800 mg) in ethanol (30 ml) were added ethyl acetimidate hydrochloride (462 mg) and triethylamine (0.87 ml). The resulting mixture was stirred at room temperature for 15 hours. To the reaction mixture was added a 4M solution of hydrogen chloride in dioxane (1 ml) and the mixture was concentrated in vacuo. The residue was purified by preparative HPLC (YMC-Pack ODS YMC) using 25% aqueous acetonitrile as an eluant to afford an amorphous solid. To a solution of the solid in ethanol (20 ml) was added 1M hydrochloric acid (1.0 ml) and the mixture was concentrated to dryness in vacuo. A solution of the residual solid in water (about 20 ml) was lyophilized to give the title compound (722 mg, yield 85%) as a colorless amorphous solid.

$^1$H NMR (500 MHz, DMSO-$d_6$) δ ppm: 1.22 (3H, t, J=7.0), 1.80–2.00 (2H, m), 2.00–2.10 (2H, m), 2.29 (3H, s), 3.40–3.55 (2H, m), 3.80–4.00 (2H, m), 4.18 (2H, q, J=7.0), 4.53 (5H, m), 6.43 (1H, dt, J=16.0, 6.0), 6.63 (1H, d, J=16.0), 7.56 (1H, t, J=8.0), 7.67 (2H, s), 7.68 (1H, d, J=8.0), 7.74 (1H, d, J=8.0), 7.88 (1H, s); IR (KBr, $cm^{-1}$): 1739, 1674, 1624.

Example 49

N-[4-(1-Acetimidoylpiperidin-4-yloxy)-3,5-dichlorophenyl]-N-[3-(3-amidinophenyl)-2-(E)-propenyl]sulfamoylacetic Acid Dihydrochloride (Exemplification Compound Number 2007)

Ethyl N-[4-(1-acetimidoylpiperidin-4-yloxy)-3,5-dichlorophenyl]-N-[3-(3-amidinophenyl)-2-(E)-propenyl]sulfamoylacetate dihydrochloride (300 mg) was dissolved in 2M hydrochloric acid (20 ml) and the mixture was stirred at 60° C. for 6 hours. The reaction mixture was cooled to room temperature and concentrated in vacuo. The residue was purified by preparative HPLC (YMC-Pack ODS YMC) using 18% aqueous acetonitrile as an eluant to afford an amorphous solid. To a solution of the solid in 18% aqueous acetonitrile (20 ml) was added 1M hydrochloric acid (1.0 ml) and the mixture was concentrated to dryness in vacuo. A solution of the residual solid in water (about 20 ml) was lyophilized to give the title compound (233 mg, yield 81%) as a colorless amorphous solid.

$^1$H NMR (500 MHz, DMSO-$d_6$) δ ppm: 1.80–2.00 (2H, m), 2.00–2.10 (2H, m), 2.30 (3H, s), 3.40–3.55 (2H, m), 3.80–4.00 (2H, m), 4.39 (2H, s), 4.53 (2H, d, J=6.0), 4.53 (1H, m), 6.44 (1H, dt, J=16.0, 6.0), 6.62 (1H, d, J=16.0), 7.56 (1H, t, J=8.0), 7.67 (2H, s), 7.70 (1H, d, J=8.0), 7.74 (1H, d, J=8.0), 7.90 (1H, s); IR (KBr, $cm^{-1}$): 3127, 1733, 1673, 1625.

Example 50

Methyl N-(4-(1-Acetimidoylpiperidin-4-yloxy)-3,5-dimethylphenyl]-N-[3-(3-amidinophenyl)-2-(E)-propenyl]sulfamoylacetate Dihydrochloride (Exemplification Compound Number 2429)

(a) Ethyl N-[3-(3-Amidinophenyl)-2-(E)-propenyl]-N-[3,5-dimethyl-4-(piperidin-4-yloxy)phenyl]sulfamoylacetate Dihydrochloride Ethyl N-[4-(1-t-butoxycarbonylpiperidin-4-yloxy)-3,5-dimethylphenyl]-N-[3-(3-cyanophenyl)-2-(E)-propenyl]sulfamoylacetate (1.75 g) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 6 hours. The reaction mixture was concentrated in vacuo, and to a solution of the residue in ethanol (30 ml) were added aqueous ammonium chloride solution (0.31 g in 15 ml) and 28% aqueous ammonia solution (0.57 ml). The resulting mixture was allowed to stand at room temperature for 14 hours. To the reaction mixture was added a 4M solution of hydrogen chloride in dioxane (1 ml) and the mixture was concentrated in vacuo. The residue was purified by preparative HPLC (YMC-Pack ODS YMC) using 20% aqueous acetonitrile as an eluant to afford an amorphous solid. To a solution of the solid in ethanol (20 ml) was added 1M hydrochloric acid (1 ml) and the solution was concentrated to dryness in vacuo to give the desired compound (1.21 g, yield 70%) as a colorless amorphous solid.

$^1$H NMR (400 MHz, DMSO-$d_6$) δ ppm: 1.23 (3H, t, J=7.0), 1.80–1.95 (2H, m), 2.00–2.10 (2H, m), 2.22 (6H, s), 2.94 (2H, m), 3.26 (2H, m), 4.12 (1H, m), 4.19 (2H, q, J=7.0), 4.35 (2H, s), 4.44 (2H, d, J=6.0), 6.43 (1H, dt, J=16.0, 6.0), 6.59 (1H, d, J=16.0), 7.17 (2H, s), 7.55 (1H, t, J=8.0), 7.68 (1H, d, J=8.0), 7.73 (1H, d, J=8.0), 7.88 (1H, s); IR (KBr, $cm^{-1}$): 1738, 1676.

(b) Methyl N-[4-(1-Acetimidoylpiperidin-4-yloxy)-3,5-dimethylphenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[3,5-dimethyl-4-(piperidin-4-yloxy)phenyl]sulfamoylacetate dihydrochloride (1.00 g) in methanol (30 ml) were added ethyl acetimidate hydrochloride (0.62 g) and triethylamine (1.16 ml). The resulting mixture was stirred at room temperature for 14 hours. To the reaction mixture was added a 4M solution of hydrogen chloride in dioxane (2 ml) and the mixture was concentrated in vacuo. The residue was purified by preparative HPLC (YMC-Pack ODS YMC) using 20% aqueous acetonitrile as an eluant to afford an amorphous solid. To a solution of the solid in methanol (20 ml) was added 1M hydrochloric acid (1.0 ml) and the mixture was concentrated to dryness in vacuo. A solution of the residual solid in water (about 20 ml) was lyophilized to give the title compound (0.81 g, yield 78%) as a colorless amorphous solid.

$^1$H NMR (400 MHz, DMSO-$d_6$) δ ppm: 1.75 (2H, m), 1.98 (2H, m), 2.23 (6H, s), 2.29 (3H, s), 3.25–3.35 (2H, m), 3.73 (3H, s), 3.85 (1H, m), 4.02 (1H, m), 4.18 (1H, m), 4.38 (2H, s), 4.44 (2H, d, J=6.0), 6.42 (1H, dt, J=16.0, 6.0), 6.59 (1H, d, J=16.0), 7.16 (2H, s), 7.55 (1H, t, J=8.0), 7.68 (1H, d, J=8.0), 7.73 (1H, d, J=8.0), 7.88 (1H, s); IR (KBr, $cm^{-1}$): 1743, 1673, 1626.

Example 51

N-[4-(1-Acetimidoylpiperidin-4-yloxy)-3,5-dimethylphenyl]-N-[3-(3-amidinophenyl)-2-(E)-propenyl]sulfamoylacetic Acid Dihydrochloride (Exemplification Compound Number 2011)

Methyl N-[4-(1-acetimidoylpiperidin-4-yloxy)-3,5-dimethylphenyl]-N-[3-(3-amidinophenyl)-2-(E)-propenyl]sulfamoylacetate dihydrochloride (620 mg) was dissolved in 2M hydrochloric acid (20 ml) and the mixture was stirred at 60° C. for 5 hours. The reaction mixture was cooled to room temperature and concentrated in vacuo. The residue was purified by preparative HPLC (YMC-Pack ODS YMC) using 18% aqueous acetonitrile as an eluant to afford an amorphous solid. To a solution of the solid in 18% aqueous acetonitrile (20 ml) was added 1M hydrochloric acid (1.0 ml) and the mixture was concentrated to dryness in vacuo. A solution of the residual solid in water (about 20 ml) was lyophilized to give the title compound (220 mg, yield 57%) as a colorless amorphous solid.

$^1$H NMR (500 MHz, DMSO-$d_6$) δ ppm: 1.75 (2H, m), 1.98 (2H, m), 2.23 (6H, s), 2.29 (3H, s), 3.25–3.40 (2H, m), 3.85 (1H, m), 4.02 (1H, m), 4.17 (1H, m), 4.22 (2H, s), 4.44 (2H, d, J=6.0), 6.43 (1H, dt, J=16.0, 6.0), 6.58 (1H, d, J=16.0), 7.17 (2H, s), 7.55 (1H, t, J=8.0), 7.69 (1H, d, J=8.0), 7.72 (1H, d, J=8.0), 7.88 (1H, s); IR (KBr, $cm^{-1}$): 3131, 1733 1673, 1626.

Example 52

Ethyl 4-[N-[4-(1-Acetimidoylpiperidin-4-yloxy) phenyl]-N-[3-(3-amidinophenyl)-2-(E)-propenyl] amino]butyrate Trihydrochloride (Exemplification Compound Number 849)

(a) Ethyl 4-[N-[3-(3-Amidinophenyl)-2-(E)-prophenyl]-[N-[4-(piperidin-4-yloxy)phenyl]amino]butyrate Trihydrochloride Ethyl 4-[N-[4-(1-t-butoxycarbonylpiperidin-4-yloxy) phenyl]-N-[3-(3-cyanophenyl)-2-(E)-propenyl]amino] butyrate (2.19 g) was dissolved in a mixture of dichloromethane (30 ml) and ethanol (15 ml). Hydrogen chloride gas was passed through the mixture in an ice bath for 1 hour. The resulting mixture was stirred in a stoppered reaction vessel at room temperature for 5.5 hours. The reaction mixture was concentrated in vacuo, and to a solution of the residue in ethanol (20 ml) were added aqueous ammonium chloride solution (0.43 g in 10 ml) and 28% aqueous ammonia solution (1.04 ml). The resulting mixture was allowed to stand at room temperature for 14 hours. To the reaction mixture was added a 4M solution of hydrogen chloride in dioxane (1 ml) and the mixture was concentrated in vacuo. The residue was purified by preparative HPLC (YMC-Pack ODS YMC) using 25% aqueous acetonitrile as an eluant to afford an amorphous solid. To a solution of the solid in ethanol (20 ml) was added 1M hydrochloric acid (1.0 ml) and the solution was concentrated to dryness in vacuo. A solution of the residual solid in water (about 10 ml) was lyophilized to give the desired compound (1.52 g, yield 66%) as a pale yellow amorphous solid.

$^1$H NMR (400 MHz, DMSO-$d_6$) δ ppm: 1.19 (3H, t, J=7.0), 1.70–1.95 (4H, m), 2.00–2.15 (2H, m), 2.39 (2H, m), 3.00–3.15 (2H, m), 3.15–3.30 (2H, m), 3.30–3.40 (2H, m), 4.07 (2H, q, J=7.0), 4.00–4.20 (2H, m), 4.43 (1H, m), 6.52 (1H, dt, J=16.0, 5.5), 6.55–7.00 (5H, m), 7.59 (1H, t, J=8.0), 7.65–7.80 (2H, m), 7.88 (1H, s); IR (KBr, $cm^{-1}$): 1728, 1674.

(b) Ethyl 4-[N-[4-(1-Acetimidoylpiperidin-4-yloxy) phenyl]-N-[3-(3-amidinophenyl)-2-(E)-propenyl]amino] butyrate Trihydrochloride To a solution of ethyl 4-[N-[3-(3-amidinophenyl)-2-(E)-propenyl]-N-[4-(piperidin-4-yloxy)phenyl]amino]butyrate trihydrochloride (1378 mg) in ethanol (20 ml) were added ethyl acetimidate hydrochloride (890 mg) and triethylamine (2.01 ml). The resulting mixture was stirred at room temperature for 4 hours. To the reaction mixture was added a 4M solution of hydrogen chloride in dioxane (1 ml) and the mixture was concentrated in vacuo. The residue was purified by preparative HPLC (YMC-Pack ODS YMC) using 25% aqueous acetonitrile as an eluant to afford an amorphous solid. To a solution of the solid in ethanol (20 ml) was added 1M hydrochloric acid (1.0 ml) and the mixture was concentrated to dryness in vacuo. A solution of the residual solid in water (about 20 ml) was lyophilized to give the title compound (1072 mg, yield 73%) as a pale yellow amorphous solid.

$^1$H NMR (400 MHz, DMSO-$d_6$) δ ppm: 1.16 (3H, t, J=7.0), 1.60–1.90 (4H, m), 1.90–2.10 (2H, m), 2.29 (3H, s), 2.30–2.40 (2H, m), 3.20–3.40 (2H, m), 3.45–3.60 (2H, m), 3.70–3.85 (2H, m), 4.04 (2H, q, J=7.0), 4.00–4.10 (2H, m), 4.40–4.55 (1H, m), 6.49 (1H, dt, J=16.0, 6.0), 6.55–6.95 (5H, m), 7.57 (1H, t, J=7.5), 7.65–7.75 (2H, m), 7.85 (1H, s); IR (KBr, $cm^{-1}$): 1727, 1673, 1624.

Example 53

4-[N-[4-(1-Acetimidoylpiperidin-4-yloxy)phenyl]-N-[3-(3-amidinophenyl)-2-(E)-propenyl]amino] butyric Acid Trihydrochloride (Exemplification Compound Number 663)

Ethyl 4-[N-[4-(1-acetimidoylpiperidin-4-yloxy)phenyl]-N-[3-(3-amidinophenyl)-2-(E)-propenyl]amino]butyrate trihydrochloride (572 mg) was dissolved in 2M hydrochloric acid (20 ml) and the mixture was stirred at room temperature for 2 hours and then at 50° C. for 2 hours. The reaction mixture was cooled to room temperature and concentrated in vacuo. The residue was purified by preparative HPLC (YMC-Pack ODS YMC) using 18% aqueous acetonitrile as an eluant to afford an amorphous solid. To a solution of the solid in 18% aqueous acetonitrile (20 ml) was added 1M hydrochloric acid (1.0 ml) and the mixture was concentrated to dryness in vacuo. A solution of the residual solid in water (about 20 ml) was lyophilized to give the title compound (333 mg, yield 61%) as a pale brown amorphous solid.

$^1$H NMR (400 MHz, DMSO-$d_6$) δ ppm: 1.40–1.95 (4H, m), 1.95–2.10 (2H, m), 2.30 (3H, s), 2.25–2.35 (2H, m), 3.45–4.40 (8H, m), 4.65–4.80 (1H, m), 6.50 (1H, dt, J=15.5, 6.5), 6.55–7.30 (5H, m), 7.58 (1H, t, J=7.5), 7.65–7.75 (2H, m), 7.85 (1H, s); IR (KBr, $cm^{-1}$): 3119, 1726, 1673, 1625.

Example 54

N-[4-(1-Acetimidoylpiperidin-4-yloxy)-3-trifluoromethylphenyl]-N-[3-(3-amidinophenyl)-2-(E)-propenyl]sulfamoylacetic Acid Dihydrochloride (Exemplification Compound Number 1969)

Ethyl N-[4-(1-acetimidoylpiperidin-4-yloxy)-3-trifluoromethylphenyl]-N-[3-(3-amidinophenyl)-2-(E)-propenyl]sulfamoylacetate dihydrochloride (321 mg) was dissolved in 3M hydrochloric acid (15 ml) and the mixture was stirred at 80° C. for 3 hours. The reaction mixture was cooled to room temperature and concentrated in vacuo. The residue was purified by preparative HPLC (YMC-Pack ODS YMC) using 20% aqueous acetonitrile as an eluant to afford an amorphous solid. To a solution of the solid in methanol (10 ml) was added a solution of 4M hydrogen chloride in dioxane (0.5 ml) and the mixture was concentrated to dryness in vacuo. A solution of the residual solid in water (about 15 ml) was lyophilized to give the title compound (231 mg, yield 75%) as a colorless amorphous solid.

$^1$H NMR (500 MHz, DMSO-$d_6$) δ ppm: 1.79 (2H, m), 2.05 (2H, m), 2.31 (3H, s), 3.40–3.75 (4H, m), 4.32 (2H, s), 4.50 (2H, d, J=6.5), 4.96 (1H, m), 6.47 (1H, dt, J=17.0, 6.5), 6.57 (1H, d, J=17.0), 7.43 (1H, d, J=10.0), 7.54 (11H, d, J=7.5), 7.71 (4H, m), 7.92 (1H, s); IR (KBr, $cm^{-1}$): 3102, 1734, 1675, 1617.

Example 55

N-[4-(1-Acetimidoylpiperidin-4-yloxy)-3-methylphenyl]-N-[3-(3-amidinophenyl)-2-(E)-propenyl]sulfamoylacetic Acid Dihydrochloride (Exemplification Compound Number 1949)

Ethyl N-[4-(1-acetimidoylpiperidin-4-yloxy)-3-methylphenyl]-N-[3-(3-amidinophenyl)-2-(E)-propenyl] sulfamoylacetate dihydrochloride (480 mg) was dissolved in 3M hydrochloric acid (15 ml) and the mixture was stirred at 80° C. for 3 hours. The reaction mixture was cooled to room temperature and concentrated in vacuo. The residue was purified by preparative HPLC (YMC-Pack ODS YMC) using 20% aqueous acetonitrile as an eluant to afford an amorphous solid. To a solution of the solid in methanol (15 ml) was added a solution of 4M hydrogen chloride in dioxane (0.5 ml) and the mixture was concentrated to dryness in vacuo to give the title compound (315 mg, yield 69%) as a colorless amorphous solid.

$^1$H NMR (500 MHz, DMSO-$d_6$) δ ppm: 1.78 (2H, m), 2.02 (2H, m), 2.14 (3H, s), 2.29 (3H, s), 3.62 (4H, m), 3.71 (2H, s), 4.12 (1H, m), 4.46 (2H, d, J=6.0), 4.70 (1H, m), 6.45 (1H, dt, J=16.0, 6.0), 6.50 (1H, d, J=16.0), 7.02 (1H, d, J=8.5), 7.36 (1H, s), 7.37 (1H, d, J=8.5), 7.52 (1H, d, J=8.0), 7.67 (1H, d, J=7.5), 7.69 (1H, d, J=8.0), 7.86 (1H, s); IR (KBr, $cm^{-1}$): 3067, 1678, 1608, 1497.

Example 56

Ethyl N-[4-(1-Acetimidoylpiperidin-4-yloxy) phenyl]-N-[3-(3-amidinophenyl)-2-fluoro-2-(Z)-propenyl]sulfamoylacetate Dihydrochloride (Exemplification Compound Number 1509)

(a) Ethyl N-[3-(3-Amidinophenyl)-2-fluoro-2-(Z)-propenyl]-N-[4-(piperidin-4-yloxy)phenyl]sulfamoylacetate Dihydrochloride Ethyl N-[4-(1-t-butoxycarbonylpiperidin-4-yloxy) phenyl]-N-[3-(3-cyanophenyl)-2-fluoro-2-(Z)-propenyl] sulfamoylacetate (1.41 g) was dissolved in a mixture of dichloromethane (25 ml) and ethanol (25 ml). Hydrogen chloride gas was passed through the mixture in an ice bath for 1 hour. The resulting mixture was stirred in a stoppered reaction vessel at room temperature for 10 hours. The reaction mixture was concentrated in vacuo, and to a solution of the residue in ethanol (30 ml) were added aqueous ammonium chloride solution (0.25 g in 10 ml) and 28% aqueous ammonia solution (0.47 ml). The resulting mixture was allowed to stand at room temperature for 8 hours. To the reaction mixture was added a 4M solution of hydrogen chloride in dioxane (2.0 ml) and the mixture was concentrated in vacuo. The residue was purified by preparative HPLC (YMC-Pack ODS YMC) using 20% aqueous acetonitrile as an eluant to afford an amorphous solid. To a solution of the solid in methanol (15 ml) was added a solution of 4M hydrogen chloride in dioxane (0.5 ml) and the solution was concentrated to dryness in vacuo to give the desired compound (1.00 g, yield 75%) as a colorless amorphous solid.

$^1$H NMR (500 MHz, DMSO-$d_6$) δ ppm: 1.24 (3H, t, J=7.0), 1.81 (2H, m), 2.08 (2H, m), 3.06 (2H, m), 3.22 (2H, m), 4.20 (2H, q. J=7.0), 4.36 (2H, s), 4.56 (2H, d, J=16.5), 4.65 (1H, m), 5.94 (1H, d, J=39.0), 7.05 (2H, d, J=9.5), 7.40 (2H, d, J=9.5), 7.56 (1H, d, J=8.0), 7.74 (2H, m), 7.81 (1H, s); IR (KBr, $cm^{-1}$): 3061, 2985, 1737, 1676, 1507.

(b) Ethyl N-[4-(1-Acetimidoylpiperidin-4-yloxy)phenyl]-N-[3-(3-amidinophenyl)-2-fluoro-2-(Z)-prophenyl]-sulfamoylacetate Dihydrochloride To a solution of ethyl N-[3-(3-amidinophenyl)-2-fluoro-2-(Z)-propenyl]-N-[4-(piperidin-4-yloxy)phenyl] sulfamoylacetate dihydrochloride (800 mg) in ethanol (20 ml) were added ethyl acetimidate hydrochloride (515 mg) and triethylamine (0.97 ml). The resulting mixture was stirred at room temperature for 4 hours. To the reaction mixture was added a 4M solution of hydrogen chloride in dioxane (2 ml) and the mixture was concentrated in vacuo. The residue was purified by preparative HPLC (YMC-Pack ODS YMC) using 25% aqueous acetonitrile as an eluant to afford an amorphous solid. To a solution of the solid in methanol (15 ml) was added a 4M solution of hydrochloric acid in dioxane (0.5 ml) and the mixture was concentrated to dryness in vacuo to give the title compound (458 mg, yield 54%) as a pale yellow amorphous solid.

$^1$H NMR (500 MHz, DMSO-$d_6$) δ ppm: 1.24 (3H, t, J=7.0), 1.74 (2H, m), 2.05 (2H, m), 2.28 (3H, s), 3.52 (2H, m), 3.72 (1H, m), 3.78 (1H, m), 4.20 (2H, q, J=7.0), 4.36 (2H, s), 4.59 (2H, d, J=15.5), 4.71 (1H, m), 5.96 (1H, d, J=39.0), 7.05 (2H, d, J=9.5), 7.41 (2H, d, J=9.5), 7.59 (1H, t, J=7.5), 7.67 (1H, d, J=7.5), 7.76 (1H, d, J=7.5), 7.80 (1H, s); IR (KBr, $cm^{-1}$): 3103, 1738, 1673, 1627, 1606.

Example 57

N-[4-(1-Acetimidoylpiperidin-4-yloxy)phenyl]-N-[3-(3-amidinophenyl)-2-fluoro-2-(Z)-propenyl] sulfamoylacetic Acid Dihydrochloride (Exemplification Compound Number 2038)

Ethyl N-[4-(1-acetimidoylpiperidin-4-yloxy)phenyl]-N-[3-(3-amidinophenyl)-2-fluoro-2-(Z)-propenyl] sulfamoylacetate dihydrochloride (265 mg) was dissolved in 3M hydrochloric acid (15 ml) and the mixture was stirred at 80° C. for 2 hours. The reaction mixture was cooled to room temperature and concentrated in vacuo. The residue was purified by preparative HPLC (YMC-Pack ODS YMC) using 15% aqueous acetonitrile as an eluant to afford an amorphous solid. To a solution of the solid in methanol (10 ml) was added a 4M solution of hydrogen chloride in dioxane (0.2 ml) and the mixture was concentrated to dryness in vacuo. A solution of the residual solid in water (about 15 ml) was lyophilized to give the title compound (218 mg, yield 86%) as a colorless amorphous solid.

$^1$H NMR (500 MHz, DMSO-$d_6$) δ ppm: 1.74 (2H, m), 2.05 (2H, m), 2.29 (3H, s), 3.52 (2H, m), 3.72 (1H, m), 3.82 (1H, m), 4.20 (2H, s), 4.59 (2H, d, J=15.5), 4.71 (1H, m), 5.95 (1H, d, J=38.0), 7.06 (2H, d, J=9.0), 7.42 (2H, d, J=9.0), 7.59 (1H, t, J=8.0), 7.68 (1H, d, J=8.0), 7.76 (1H, d, J=8.0), 7.81 (1H, s); IR (KBr, $cm^{-1}$): 1734, 1673, 1627.

Example 58

Ethyl N-[4-(1-Acetimidoylpiperidin-4-yloxy)-3,5-dicarbamoylphenyl]-N-[3-(3-amidinophenyl)-2-(E)-propenyl]sulfamoylacetate Dihydrochloride (Exemplification Compound Number 1506)

(a) Ethyl N-[3-(3-Amidinophenyl)-2-(E)-propenyl-N-[3,5-dicarbamoyl-4-(piperidin-4-yloxy)phenyl]sulfamoylacetate Dihydrochloride Ethyl N-[4-(1-t-butoxycarbonylpiperidin-4-yloxy)-3,5-dicarbamoylphenyl]-N-[3-(3-cyanophenyl)-2-(E)-propenyl] sulfamoylacetate (0.84 g) was dissolved in a mixture of dichloromethane (25 ml) and ethanol (25 ml). Hydrogen chloride gas was passed through the mixture in an ice bath for 1.5 hours. The resulting mixture was stirred in a stoppered reaction vessel at room temperature for 3 hours. The reaction mixture was concentrated in vacuo, and to a solution of the residue in ethanol (25 ml) were added aqueous ammonium chloride solution (0.15 g in 5 ml) and 28% aqueous ammonia solution (0.35 ml). The resulting mixture was stirred at room temperature for 2.5 hours and allowed to stand for 12 hours. The reaction mixture was concentrated in vacuo. The residue was purified by preparative HPLC (YMC-Pack ODS YMC) using 17.5% aqueous acetonitrile as an eluant to afford an amorphous solid. To a solution of the solid in ethanol (10 ml) was added a 4M solution of hydrogen chloride in dioxane (0.20 ml) and the solution was concentrated to dryness in vacuo to give the desired compound (0.17 g, yield 20%) as a colorless amorphous solid.

$^1$H NMR (500 MHz, DMSO-$d_6$) δ ppm: 1.24 (3H, t, J=7.0), 1.85–2.00 (4H, m), 2.95–3.05 (2H, m), 3.20–3.30 (2H, m), 4.20 (2H, q, J=7.0), 4.25–4.35 (1H, m), 4.45 (2H, s), 4.50 (2H, d, J=6.0), 6.45 (1H, dt, J=16.0, 6.0), 6.61 (1H, d, J=16.0), 7.55 (1H, t, J=8.0), 7.61 (2H, s), 7.67 (1H, d, J=8.0), 7.72 (1H, d, J=8.0), 7.88 (1H, s); MASS (FAB, m/z): 587 [M+H].

(b) Ethyl N-[4-(1-Acetimidoylpiperidin-4-yloxy)-3,5-dicarbamoylphenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[3,5-dicarbamoyl-4-(piperidin-4-yloxy)phenyl]sulfamoylacetate dihydrochloride (0.17 g) in ethanol (20 ml) were added ethyl acetimidate hydrochloride (1.67 g) and triethylamine (1.68 ml). The resulting mixture was stirred at room temperature for 5.5 hours. The reaction mixture was concentrated in vacuo. The residue was purified by preparative HPLC (YMC-Pack ODS YMC) using 17.5% aqueous acetonitrile as an eluant to afford an amorphous solid. To a solution of the solid in ethanol (5 ml) was added a 4M solution of hydrogen chloride in dioxane (0.10 ml) and the mixture was concentrated to dryness in vacuo to give the title compound (0.08 g, yield 43%) as a colorless amorphous solid.

$^1$H NMR (500 MHz, DMSO-$d_6$) δ ppm: 1.24 (3H, t, J=7.0), 1.75–2.00 (4H, m), 2.28 (3H, s), 3.45–3.55 (2H, m), 3.70–3.80 (2H, m), 4.20 (2H, q, J=7.0), 4.30–4.40 (1H, m), 4.45 (2H, s), 4.51 (2H, d, J=6.0), 6.44 (1H, dt, J=16.0, 6.0), 6.61 (1H, d, J=16.0), 7.55 (1H, t, J=8.0), 7.64 (2H, s), 7.68 (1H, d, J=8.0), 7.72 (1H, d, J=8.0), 7.88 (1H, s); MASS (FAB, m/z): 628 [M+H].

Example 59

N-[4-(1-Acetimidoylpiperidin-4-yloxy)-3,5-dicarbamoylphenyl]-N-[3-(3-amidinophenyl)-2-(E)-propenyl]sulfamoylacetic Acid Dihydrochloride (Exemplification Compound Number 2035)

Ethyl N-[4-(1-acetimidoylpiperidin-4-yloxy)-3,5-dicarbamoylphenyl]-N-[3-(3-amidinophenyl)-2-(E)-propenyl]sulfamoylacetate dihydrochloride (0.07 g) was dissolved in 3M hydrochloric acid (10 ml) and the mixture was stirred at 70° C. for 2 hours. The reaction mixture was cooled to room temperature and concentrated in vacuo. The residue was purified by preparative HPLC (YMC-Pack ODS YMC) using 10% aqueous acetonitrile as an eluant to afford an amorphous solid. A solution of the solid in 1M hydrochloric acid (0.30 ml) was concentrated to dryness in vacuo to give the title compound (0.05 g, yield 69%) as a colorless amorphous solid.

$^1$H NMR (500 MHz, DMSO-$d_6$) δ ppm: 1.75–2.00 (4H, m), 2.27 (3H, s), 3.45–3.55 (2H, m), 3.70–3.80 (2H, m), 4.32 (2H, s), 4.35–4.40 (1H, m), 4.51 (2H, d, J=6.0), 6.45 (1H, dt, J=16.0, 6.0), 6.60 (1H, d, J=16.0), 7.55 (1H, t, J=8.0), 7.63 (2H, s), 7.67 (1H, d, J=8.0), 7.72 (1H, d, J=8.0), 7.87 (1H, s); IR (KBr, $cm^{-1}$): 1729, 1668.

Example 60

Ethyl N-[4-(1-Acetimidoylpiperidin-4-yloxy)-5-carbamoyl-2-methylphenyl]-N-[3-(3-amidinophenyl)-2-(E)-propenyl]sulfamoylacetate Dihydrochloride (Exemplification Compound Number 1491)

(a) Ethyl N-[3-(3-amidinophenyl)-2-(E)-prophenyl]-N-[5-carbamoyl-2-methyl-4-(piperidin-4-yloxy)phenyl]sulfamoylacetate Dihydrochloride Ethyl N-[4-(1-t-butoxycarbonylpiperidin-4-yloxy)-5-carbamoyl-2-methylphenyl]-N-[3-(3-cyanophenyl)-2-(E)-propenyl]sulfamoylacetate (2.10 g) was dissolved in a mixture of dichloromethane (25 ml) and ethanol (25 ml). Hydrogen chloride gas was passed through the mixture in an ice bath for 1 hour. The resulting mixture was stirred in a stoppered reaction vessel at room temperature for 3 hours. The reaction mixture was concentrated in vacuo, and to a solution of the residue in ethanol (25 ml) were added aqueous ammonium chloride solution (0.59 in 5 ml) and 28% aqueous ammonia solution (1.34 ml). The resulting mixture was stirred at room temperature for 7 hours and allowed to stand for 12 hours. The reaction mixture was concentrated in vacuo. The residue was purified by preparative HPLC (YMC-Pack ODS YMC) using 17.5% aqueous acetonitrile as an eluant to afford an amorphous solid. To a solution of the solid in ethanol (20 ml) was added a 4M solution of hydrogen chloride in dioxane (1.40 ml) and the solution was concentrated to dryness in vacuo to give the desired compound (1.18 g, yield 57%) as a colorless amorphous solid.

$^1$H NMR (500 MHz, DMSO-$d_6$) δ ppm: 1.24 (3H, t, J=7.0), 1.85–1.95 (2H, m), 2.10–2.20 (2H, m), 2.33 (3H, s), 3.05–3.15 (2H, m), 3.20–3.30 (2H, m), 4.21 (2H, q, J=7.0), 4.25–4.30 (1H, m), 4.36 (1H, d, J=14.0), 4.45–4.50 (1H, m), 4.51 (1H, d, J=14.0), 4.80 (1H, m), 6.40–6.55 (2H, m), 6.48 (1H, s), 7.55 (1H, t, J=8.0), 7.69 (1H, d, J=8.0), 7.72 (1H, d, J=8.0), 7.77 (1H, s), 7.83 (1H, s); IR (KBr, $cm^{-1}$): 1737, 1673, 1657.

(b) Ethyl N-[4-(1-Acetimidoylpiperidin-4-yloxy)-5-carbamoyl-2-methylphenyl]-N-[3-(3-amidinophenyl)-2-(E)-propenyl]sulfamoylacetate Dihydrochloride To a solution of ethyl N-[3-(3-amidinophenyl)-2-(E)-propenyl]-N-[5-carbamoyl-2-methyl-4-(piperidin-4-yloxy)phenyl]sulfamoylacetate dihydrochloride (1.00 g) in ethanol (50 ml) were added ethyl acetimidate hydrochloride (0.59 g) and triethylamine (1.33 ml). The resulting mixture was stirred at room temperature for 1 hour and allowed to stand for 14 hours. The reaction mixture was concentrated in vacuo. The residue was purified by preparative HPLC (YMC-Pack ODS YMC) using 20% aqueous acetonitrile as an eluant to afford an amorphous solid. To a solution of the solid in ethanol (10 ml) was added a 4M solution of hydrogen chloride in dioxane (1.00 ml) and the mixture was concentrated to dryness in vacuo to give the title compound (0.98 g, yield 92%) as a colorless amorphous solid.

$^1$H NMR (500 MHz, DMSO-$d_6$) δ ppm: 1.24 (3H, t, J=7.0), 1.75–1.90 (2H, m), 2.00–2.15 (2H, m), 2.30 (3H, s), 2.34 (3H, s), 3.50–3.60 (2H, m), 3.70–3.80 (1H, m), 3.80–3.90 (1H, m), 4.21 (2H, q, J=7.0), 4.25–4.30 (1H, m), 4.36 (1H, d, J=14.0), 4.45–4.50 (1H, m), 4.51 (1H, d, J=14.0), 4.87 (1H, m), 6.40–6.55 (2H, m), 7.19 (1H, s), 7.56 (1H, t, J=8.0), 7.70 (1H, d, J=8.0), 7.72 (1H, d, J=8.0), 7.82 (1H, s), 7.84 (1H, s); IR (KBr, $cm^{-1}$): 1737, 1672, 1622.

Example 61

N-[4-(1-Acetimidoylpiperidin-4-yloxy)-5-carbamoyl-2-methylphenyl]-N-[3-(3-amidinophenyl)-2-(E)-propenyl]sulfamoylacetic Acid Dihydrochloride (Exemplification Compound Number 2020)

Ethyl N-[4-(1-acetimidoylpiperidin-4-yloxy)-5-carbamoyl-2-methylphenyl]-N-[3-(3-amidinophenyl)-2-(E)-propenyl]sulfamoylacetate dihydrochloride (0.80 g) was dissolved in 3M hydrochloric acid (40 ml) and the mixture was stirred at 70° C. for 1.5 hours. The reaction mixture was cooled to room temperature and concentrated in vacuo. The residue was purified by preparative HPLC (YMC-Pack ODS YMC) using 12.5% aqueous acetonitrile as an eluant to afford an amorphous solid. A solution of the solid in 1M hydrochloric acid (3.00 ml) was concentrated to dryness in vacuo to give the title compound (0.71 g, yield 92%) as a colorless amorphous solid.

$^1$H NMR (500 MHz, DMSO-$d_6$) δ ppm: 1.75–1.90 (2H, m), 2.00–2.15 (2H, m), 2.30 (3H, s), 2.34 (3H, s), 3.45–3.55 (1H, m), 3.55–3.65 (1H, m), 3.65–3.80 (1H, m), 3.80–3.95 (1H, m), 4.20–4.30 (1H, m), 4.22 (1H, d, J=15.0), 4.41 (1H, d, J=15.0), 4.45–4.55 (1H, m), 4.86 (1H, m), 6.40–6.55 (2H, m), 7.18 (1H, s), 7.55 (1H, t, J=7.0), 7.70 (1H, d, J=7.0), 7.72 (1H, d, J=7.0), 7.83 (1H, s), 7.84 (1H, s); IR (KBr, $cm^{-1}$): 1730, 1672.

Reference Example 1

3-Cyanocinnamaldehyde

To a solution of 3-cyanobenzaldehyde (4.5 g) in toluene (200 ml) was added (triphenylphosphoranylidene) acetaldehyde (13.6 g) and the mixture was stirred at 70° C. for 4 hours. The reaction mixture was concentrated in vacuo. The residue was purified by chromatography on a silica gel column using dichloromethane as an eluant and then the product was recrystallized from a mixture of toluene and hexane to give the desired compound (3.09 g, yield 57%) as pale yellow needle crystals.

$^1$H NMR (500 MHz, $CDCl_3$) δ ppm: 6.76 (1H, dd, J=16.0, 7.5), 7.46 (1H, d, J=16.0), 7.58 (1H, t, J=8.0), 7.73 (1H, d, J=8.0), 7.80 (1H, d, J=8.0), 7.84 (1H, s), 9.75 (1H, d, J=7.5).

Reference Example 2

3-(3-Cyanophenyl)-2-(E)-propen-1-ol

To a solution of 3-cyanocinnamaldehyde (3.00 g) in a mixture of dichloromethane (30 ml) and ethanol (70 ml) were added sodium borohydride (1.32 g) and cerium chloride (2.49 g) in an ice bath and the mixture was stirred at the same temperature for 1.5 hours. After addition of saturated aqueous ammonium chloride, the reaction mixture was extracted with dichloromethane three times. The extractant was washed with brine, dried over anhydrous sodium sulfate and concentrated in vacuo. The residue was purified by chromatography on a silica gel column using hexane/ethyl acetate=3/2 as an eluant to give the desired compound (3.27 g, yield quantitative) as a pale yellow oil.

$^1$H NMR (500 MHz, $CDCl_3$) δ ppm: 4.37 (2H, m), 6.43 (1H, dt, J=16.0, 5.0), 6.62 (1H, d, J=16.0), 7.43 (1H, t, J=8.0), 7.52 (1H, d, J=8.0), 7.60 (1H, d, J=8.0), 7.65 (1H, s).

Reference Example 3

3-(3-Cyanophenyl)-2-(E)-propenyl]ethyl Carbonate

To a solution of 3-(3-cyanophenyl)-2-(E)-propen-1-ol (403 mg) in dichloromethane (6 ml) was added pyridine (1 ml) and then added dropwise ethyl chloroformate (0.38 ml) in an ice bath. The mixture was stirred at the same temperature for 2 hours. After this time, aqueous ammonium chloride was added to the reaction mixture and the mixture was extracted with ethyl acetate. The extractant was washed with water and brine. The organic layer was dried over anhydrous sodium sulfate, filtered and concentrated in vacuo. The residue was purified by chromatography on a silica gel column using hexane/ethyl acetate=4/1 as an eluant to give the desired compound (492 mg, yield 84%) as a colorless oil.

$^1$H NMR (500 MHz, $CDCl_3$) δ ppm: 1.34 (3H, t, J=7.0), 4.24 (2H, q, J=7.0), 4.80 (2H, d, J=5.5), 6.36 (1H, dt, J=16.0, 5.5), 6.67 (1H, d, J=16.0), 7.44 (1H, t, J=8.0), 7.55 (1H, d, J=8.0), 7.61 (1H, d, J=8.0), 7.66 (1H, s).

Reference Example 4

4-(1-t-Butoxycarbonylpiperidin-4-yloxy) nitrobenzene

To a suspension of sodium hydride (2.2 g) washed with hexane in N,N-dimethylacetamide (150 ml) was added 1-t-butoxycarbonyl-4-hydroxypiperidine (10.1 g) in an ice bath and the mixture was stirred at room temperature for 2 hours. To the reaction mixture was added 4-fluoronitrobenzene over 20 minutes, and the dark brown reaction solution was stirred for 4 hours. To the reaction mixture was added saturated aqueous ammonium chloride in order to stop the reaction. The resulting mixture was extracted with t-butyl methyl ether three times and the extractant was washed with water and brine. The organic layer was dried over anhydrous sodium sulfate and concentrated in vacuo. The residue was purified by chromatography on a silica gel column using hexane/ethyl acetate=2/1 as an eluant to give the desired compound (11.9 g, yield 74%) as a pale yellow solid.

$^1$H NMR (400 MHz, $CDCl_3$) δ ppm: 1.43 (9H, s), 1.76 (2H, m), 1.91 (2H, m), 3.34 (2H, m), 3.65 (2H, m), 4.56 (1H, m), 6.91 (2H, d, J=9.0), 8.15 (2H, d, J=9.0).

Reference Example 5

4-(1-t-Butoxycarbonylpiperidin-4-yloxy)aniline

To a solution of 4-(1-t-butoxycarbonylpiperidin-4-yloxy) nitrobenzene (11.9 g) in methanol (100 ml) was added palladium on carbon (1.9 g) and the mixture was stirred under a hydrogen atmosphere at room temperature for 4 hours. The reaction mixture was filtered and the filtrate was concentrated in vacuo. The residue was purified by chromatography on a silica gel column using hexane/ethyl acetate=1/1 as an eluant to give the desired compound (10.7 g, yield 99%) as a pale red solid.

$^1$H NMR (400 MHz, $CDCl_3$) δ ppm: 1.46 (9H, s), 1.71 (2H, m), 1.87 (2H, m), 3.27 (2H, m), 3.71 (2H, m), 4.26 (1H, m), 6.63 (2H, d, J=8.5), 6.76 (2H, d, J=8.5).

Reference Example 6

N-[4-(1-t-Butoxycarbonylpiperidin-4-yloxy)phenyl] ethanesulfonamide

To a solution of 4-(1-t-butoxycarbonylpiperidin-4-yloxy) aniline (10.6 g) and pyridine (8 ml) in dichloromethane (75 ml) was added dropwise ethanesulfonyl chloride (4.1 ml) in an ice bath and the mixture was stirred at room temperature for 5 hours. After addition of methanol (1 ml), the reaction mixture was concentrated in vacuo. The residue was purified by chromatography on a silica gel column using hexane/ethyl acetate=3/2 as an eluant to give the desired compound (11.7 g, yield 84%) as a pale pink solid.

$^1$H NMR (400 MHz, $CDCl_3$) δ ppm: 1.38 (3H, t, J=8.0), 1.47 (9H, s), 1.74 (2H, m), 1.90 (2H, m), 3.07 (2H, q, J=8.0), 3.34 (2H, m), 3.69 (2H, m), 4.42 (1H, m), 6.88 (2H, d, J=9.0), 7.17 (2H, d, J=9.0).

Reference Example 7

N-[4-(1-t-Butoxycarbonylpiperidin-4-yloxy)phenyl]-N-[3-(3-cyanophenyl)-2-(E)-propenyl] ethanesulfonamide To a suspension of [3-(3-cyanophenyl)-2-(E)-propenyl] ethyl carbonate (1.04 g) and N-[4-(1-t-butoxycarbonylpiperidin-4-yloxy)phenyl] ethanesulfonamide (1.15 g) in tetrahydrofuran (9 ml) were added tris(dibenzylideneacetone)palladium chloroform complex (0.077 g) and triphenylphosphine (0.039 g) and the mixture was stirred at room temperature for 3 hours. The reaction mixture was concentrated in vacuo. The residue was purified by chromatography on a silica gel column using dichloromethane/ethyl acetate=8/1 as an eluant to give the desired compound (1.57 g, yield quantitative) as a pale yellow oil.

$^1$H NMR (500 MHz, $CDCl_3$) δ ppm: 1.42 (3H, t, J=7.0), 1.47 (9H, s), 1.74 (2H, m), 1.90 (2H, m), 3.06 (2H, q, J=7.0), 3.34 (2H, m), 3.68 (2H, m), 4.42 (2H, d, J=7.0), 4.44 (1H, m), 6.28 (1H, dt, J=15.5, 7.0), 6.42 (1H, d, J=15.5), 6.89 (2H, d, J=9.0), 7.26 (2H, d, J=9.0), 7.40 (1H, t, J=7.5), 7.52 (2H, m), 7.56 (1H, s).

Reference Example 8

3-(3-Cyanophenyl)-2-methyl-2-(E)-propenal

To a solution of 3-cyanobenzaldehyde (2.62 g) in toluene (90 ml) was added 2-(triphenylphosphoranylidene) propionaldehyde (8.28 g) and the mixture was stirred at 70° C. for 11 hours. The reaction mixture was concentrated in vacuo. The residue was purified by chromatography on a silica gel column using dichloromethane as an eluant to give the desired compound (2.61 g, yield 76%) as pale yellow needle crystals.

$^1$H NMR (500 MHz, $CDCl_3$) δ ppm: 2.07 (3H, s), 7.25 (1H, bs), 7.59 (1H, t, J=8.0), 7.68 (1H, d, J=8.0), 7.74 (1H, d, J=8.0), 7.79 (1H, s), 9.63 (1H, s).

Reference Example 9

3-(3-Cyanophenyl)-2-methyl-2-(E)-propen-1-ol

To a solution of 3-(3-cyanophenyl)-2-methyl-2-(E)-propenal (2.00 g) in a mixture of dichloromethane (30 ml) and ethanol (60 ml) were added sodium borohydride (0.83 g) and cerium chloride (1.30 g) in an ice bath and stirred at the same temperature for 3 hours. After addition of saturated aqueous ammonium chloride, the reaction mixture was extracted with dichloromethane three times. The extractant was washed with water and brine. The organic layer was dried over anhydrous sodium sulfate, filtered and concentrated in vacuo. The residue was purified by chromatography on a silica gel column using hexane/ethyl acetate=1/1 as an eluant to give the desired compound (2.05 g, yield quantitative) as a pale yellow oil.

$^1$H NMR (500 MHz, $CDCl_3$) δ ppm: 1.87 (3H, s), 4.22 (2H, m), 6.52 (1H, bs), 7.42–7.52 (3H, m), 7.55 (1H, s).

Reference Example 10

[3-(3-Cyanophenyl)-2-methyl-2-(E)-propenyl]ethyl Carbonate

To a solution of 3-(3-cyanophenyl)-2-methyl-2-(E)-propen-1-ol (2.00 g) in dichloromethane (20 ml) was added pyridine (3 ml) and then added dropwise ethyl chloroformate (1.30 ml) in an ice bath. The mixture was stirred at room temperature for 12 hours. The reaction mixture was concentrated in vacuo. The residue was purified by chromatography on a silica gel column using hexane/ethyl acetate=4/1 as an eluant to give the desired compound (2.46 g, yield 87%) as a colorless oil.

$^1$H NMR (400 MHz, $CDCl_3$) δ ppm: 1.34 (3H, t, J=7.0), 1.90 (3H, s), 4.25 (2H, q, J=7.0), 4.70 (2H, s), 6.53 (1H, bs), 7.43–7.55 (4H, m).

Reference Example 11

N-[4-(1-t-Butoxycarbonylpiperidin-4-yloxy)phenyl]-N-[3-(3-cyanophenyl)-2-methyl-2-(E)-propenyl] ethanesulfonamide To a suspension of [3-(3-cyanophenyl)-2-methyl-2-(E)-propenyl]ethyl carbonate (1.10 g) and N-[4-(1-t-butoxycarbonylpiperidin-4-yloxy)phenyl] ethanesulfonamide (1.15 g) in tetrahydrofuran (9 ml) were added tris(dibenzylideneacetone)palladium chloroform complex (78 mg) and triphenylphosphine (39 mg) and the mixture was stirred at room temperature for 16 hours. The reaction mixture was concentrated in vacuo. The residue was purified by chromatography on a silica gel column using dichloromethane/ethyl acetate=12/1 as an eluant to give the desired compound (0.58 g, yield 36%) as a colorless amorphous solid.

$^1$H NMR (500 MHz, $CDCl_3$) δ ppm: 1.42 (3H, t, J=7.5), 1.47 (9H, s), 1.75 (2H, m), 1.89 (3H, s), 1.91 (2H, m), 3.07 (2H, q, J=7.5), 3.34 (2H, m), 3.69 (2H, m), 4.37 (2H, s), 4.45 (1H, m), 6.21 (1H, s), 6.89 (2H, d, J=9.0), 7.26 (2H, d, J=9.0), 7.32 (1H, d, J=8.0), 7.35 (1H, s), 7.38 (1H, t, J=8.0), 7.48 (1H, d, J=8.0).

Reference Example 12

Ethyl N-[4-(1-t-Butoxycarbonylpiperidin-4-yloxy) phenyl]sulfamoylacetate

To a solution of 4-(1-t-butoxycarbonylpiperidin-4-yloxy) aniline (4.39 g) and pyridine (2.4 ml) in dichloromethane (30 ml) was added dropwisely ethyl chlorosulfonylacetate (2.4 ml) in an ice bath and the mixture was stirred at room temperature for 13 hours. After addition of methanol (0.5 ml), the reaction mixture was concentrated in vacuo. The residue was purified by chromatography on a silica gel column using hexane/ethyl acetate=3/2 as an eluant to give the desired compound (4.96 g, yield 75%) as a pale red oil.

$^1$H NMR (400 MHz, $CDCl_3$) δ ppm 1.33 (3H, t, J=7.0), 1.47 (9H, s), 1.75 (2H, m), 1.90 (2H, m), 3.34 (2H, m), 3.69 (2H, m), 3.89 (2H, s), 4.29 (2H, q, J=7.0), 4.44 (1H, m), 6.89 (2H, d, J=8.5), 7.27 (2H, d, J=8.5).

Reference Example 13

Ethyl N-[4-(1-t-Butoxycarbonylpiperidin-4-yloxy) phenyl]-N-[3-(3-cyanophenyl)-2-(E)-propenyl] sulfamoylacetate To a solution of 3-(3-cyanophenyl)-2-(E)-propen-1-ol (0.80 g), ethyl N-[4-(1-t-butoxycarbonylpiperidin-4-yloxy) phenyl]sulfamoylacetate (2.21 g) and triphenylphosphine (1.70 g) in dichloromethane (40 ml) was added dropwise diethyl azodicarboxylate (1.0 ml) in an ice bath and the mixture was stirred at the same temperature for 2 hours. The reaction mixture was concentrated in vacuo. The residue was purified by chromatography on a silica gel column using dichloromethane/ethyl acetate=10/1 as an eluant to give the desired compound (2.15 g, yield 74%) as a colorless oil.

$^1$H NMR (500 MHz, $CDCl_3$) δ ppm: 1.35 (3H, t, J=7.0), 1.47 (9H, s), 1.75 (2H, m), 1.90 (2H, m), 3.34 (2H, m), 3.68 (2H, m), 3.98 (2H, s), 4.30 (2H, q, J=7.0), 4.45 (1H, m), 4.47 (2H, d, J=6.0), 6.24 (1H, dt, J=15.5, 6.0), 6.40 (1H, d, J=15.5), 6.90 (2H, d, J=8.5), 7.39 (3H, m), 7.51 (2H, m), 7.55 (1H, s).

Reference Example 14

4-(1-t-Butoxycarbonylpiperidin-4-yloxy)-2-methylnitrobenzene

To a solution of 1-t-butoxycarbonyl-4-hydroxypiperidine (6.04 g), 3-methyl-4-nitrophenol (4.59 g) and triphenylphosphine (10.20 g) in dichloromethane (100 ml) was added dropwise diethyl azodicarboxylate (6.1 ml) in an ice bath and the mixture was stirred at room temperature for 6 hours. The reaction mixture was concentrated in vacuo. The residue was purified by chromatography on a silica gel column using hexane/ethyl acetate=3/1 as an eluant to give the desired compound (6.04 g, yield 60%) as a pale yellow solid.

$^1$H NMR (400 MHz, $CDCl_3$) δ ppm: 1.48 (9H, s), 1.78 (2H, m), 1.94 (2H, m), 2.62 (3H, s), 3.38 (2H, m), 3.69 (2H, m), 4.58 (1H, m), 6.80 (2H, m), 8.08 (1H, d, J=9.5).

Reference Example 15

4-(1-t-Butoxycarbonylpiperidin-4-yloxy)-2-methylaniline

To a solution of 4-(1-t-butoxycarbonylpiperidin-4-yloxy)-2-methylnitrobenzene (3.23 g) in methanol (30 ml) was added palladium on carbon (0.21 g) and the mixture was stirred under a hydrogen atmosphere at room temperature for 4 hours. The reaction mixture was filtered and the filtrate concentrated in vacuo. The residue was purified by chromatography on a silica gel column using hexane/ethyl acetate=1/1 as an eluant to give the desired compound (3.02 g, yield 99%) as a pale red oil.

$^1$H NMR (400 MHz, $CDCl_3$) δ ppm: 1.47 (9H, s), 1.70 (2H, m), 1.87 (2H, m), 2.12 (3H, s), 3.27 (2H, m), 3.71 (2H, m), 4.26 (1H, m), 6.59–6.69 (3H, m).

Reference Example 16

Ethyl N-[4-(1-t-Butoxycarbonylpiperidin-4-yloxy)-2-methylphenyl]sulfamoylacetate To a solution of 4-(1-t-butoxycarbonylpiperidin-4-yloxy)-2-methylaniline (3.00 g) and pyridine (1.6 ml) in dichloromethane (20 ml) was added dropwise ethyl chlorosulfonylacetate (1.6 ml) in an ice bath and the mixture was stirred at room temperature for 13 hours. After addition of methanol (1 ml), the reaction mixture was concentrated in vacuo. The residue was purified by chromatography on a silica gel column using hexane/ethyl acetate=3/2 as an eluant to give the desired compound (2.35 g, yield 53%) as a pale yellow solid.

$^1$H NMR (500 MHz, $CDCl_3$) δ ppm: 1.33 (3H, t, J=7.0), 1.47 (9H, s), 1.74 (2H, m), 1.90 (2H, m), 2.38 (3H, s), 3.34 (2H, m), 3.68 (2H, m), 4.01 (2H, s), 4.29 (2H, q, J=7.0), 4.43 (1H, m), 6.73 (1H, dd, J=8.5, 3.0), 6.80 (1H, d, J=3.0), 7.34 (1H, d, J=8.0).

Reference Example 17

Ethyl N-[4-(1-t-Butoxycarbonylpiperidin-4-yloxy)-2-methylphenyl]-N-[3-(3-cyanophenyl)-2-(E)-propenyl]sulfamoylacetate To a solution of 3-(3-cyanophenyl)-2-(E)-propen-1-ol (0.48 g), ethyl N-[4-(1-t-butoxycarbonylpiperidin-4-yloxy)-2-methylphenyl]sulfamoylacetate (1.37 g) and triphenylphosphine (0.94 g) in dichloromethane (20 ml) was added dropwise diethyl azodicarboxylate (0.57 ml) in an ice bath and the mixture was stirred at the same temperature for 1 hour. The reaction mixture was concentrated in vacuo. The residue was purified by chromatography on a silica gel column using dichloromethane/ethyl acetate=11/1 as an eluant to give the desired compound (1.80 g, yield quantitative) as a pale yellow amorphous solid.

$^1$H NMR (500 MHz, $CDCl_3$) δ ppm: 1.36 (3H, t, J=7.0), 1.47 (9H, s), 1.74 (2H, m), 1.90 (2H, m), 2.35 (3H, s), 3.34 (2H, m), 3.68 (2H, m), 3.99 (1H, d, J=15.0), 4.12 (1H, d, J=15.0), 4.27 (1H, dd, J=15.0, 6.0), 4.31 (2H, m), 4.44 (1H, m), 4.50 (1H, dd, J=15.0, 6.0), 6.28 (1H, dt, J=16.5, 6.0), 6.32 (1H, d, J=16.5), 6.76 (1H, dd, J=9.0, 3.0), 6.79 (1H, d, J=3.0), 7.39 (1H, d, J=9.0), 7.41 (1H, d, J=7.5), 7.52 (3H, m).

Reference Example 18

4-(1-t-Butoxycarbonylpiperidin-4-yloxy)-3-methoxynitrobenzene

To a solution of 1-t-butoxycarbonyl-4-hydroxypiperidine (3.02 g), 2-methoxy-4-nitrophenol (2.54 g) and triphenylphosphine (10.20 g) in dichloromethane (60 ml) was added dropwise diethyl azodicarboxylate (3.1 ml) in an ice bath and the mixture was stirred at room temperature for 20 hours. The reaction mixture was concentrated in vacuo. The residue was purified by chromatography on a silica gel column using hexane/ethyl acetate=5/2 as an eluant to give the desired compound (4.36 g, yield 82%) as a pale yellow oil.

$^1$H NMR (500 MHz, $CDCl_3$) δ ppm: 1.47 (9H, s), 1.83 (2H, m), 1.96 (2H, m), 3.33 (2H, m), 3.77 (2H, m), 3.94 (3H, s), 4.61 (1H, m), 6.94 (1H, d, J=9.0), 7.76 (1H, d, J=2.0), 7.87 (1H, dd, J=9.0, 2.0).

Reference Example 19

4-(1-t-Butoxycarbonylpiperidin-4-yloxy)-3-methoxyaniline

To a solution of 4-(1-t-butoxycarbonylpiperidin-4-yloxy)-3-methoxynitrobenzene (4.36 g) in methanol (60 ml) was added palladium on carbon (0.25 g) and the mixture was stirred under a hydrogen atmosphere at room temperature for 65 hours. The reaction mixture was filtered and the filtrate concentrated in vacuo. The residue was purified by chromatography on a silica gel column using hexane/ethyl acetate=1/1 as an eluant to give the desired compound (2.03 g, yield 51%) as a pale red oil.

$^1$H NMR (500 MHz, $CDCl_3$) δ ppm: 1.46 (9H, s), 1.71 (2H, m), 1.87 (2H, m), 3.18 (2H, m), 3.78 (2H, m), 3.80 (3H, s), 4.15 (1H, m), 6.19 (1H, dd, J=8.5, 3.0), 6.29 (1H, d, J=3.0), 6.76 (1H, d, J=8.5).

Reference Example 20

Ethyl N-[4-(1-t-Butoxycarbonylpiperidin-4-yloxy)-3-methylphenyl]sulfamoylacetate To a solution of 4-(1-t-butoxycarbonylpiperidin-4-yloxy)-3-methoxyaniline (2.00 g) and pyridine (1.0 ml) in dichloromethane (40 ml) was added dropwise ethyl chlorosulfonylacetate (1.0 ml) in an ice bath and the mixture was stirred at the same temperature for 2 hours and then at room temperature for 5 hours. The reaction mixture was concentrated in vacuo. The residue was purified by chromatography on a silica gel column using hexane/ethyl acetate=2/1 as an eluant to give the desired compound (2.56 g, yield 87%) as a pale red oil.

$^1$H NMR (500 MHz, $CDCl_3$) δ ppm: 1.32 (3H, t, J=7.0), 1.47 (9H, s), 1.76 (2H, m), 1.90 (2H, m), 3.25 (2H, m), 3.78 (2H, m), 3.85 (3H, s), 3.92 (2H, s), 4.29 (2H, q, J=7.0), 4.36 (1H, m), 6.82 (1H, dd, J=9.0, 2.5), 6.88 (1H, d, J=9.0), 6.96 (1H, d, J=2.5).

Reference Example 21

Ethyl N-[4-(1-t-Butoxycarbonylpiperidin-4-yloxy)-3-methoxyphenyl]-N-[3-(3-cyanophenyl)-2-(E)-propenyl]sulfamoylacetate To a solution of 3-(3-cyanophenyl)-2-(E)-propen-1-ol (338 mg), ethyl N-[4-(1-t-butoxycarbonylpiperidin-4-yloxy)-3-methoxyphenyl]sulfamoylacetate (823 mg) and triphenylphosphine (1000 mg) in dichloromethane (20 ml) was added dropwise diethyl azodicarboxylate (0.43 ml) in an ice bath and the mixture was stirred at the same temperature for 1 hour. The reaction mixture was concentrated in vacuo. The residue was purified by chromatography on a silica gel column using dichloromethane/ethyl acetate=12/1 as an eluant to give the desired compound (985 mg, yield 76%) as a colorless amorphous solid.

$^1$H NMR (500 MHz, $CDCl_3$) δ ppm: 1.37 (3H, t, J=7.0), 1.48 (9H, s), 1.78 (2H, m), 1.93 (2H, m), 3.27 (2H, m), 3.80 (2H, m), 3.84 (3H, s), 4.02 (2H, s), 4.32 (2H, q, J=7.0), 4.43 (1H, m), 4.50 (2H, d, J=7.0), 6.27 (1H, dt, J=15.5, 7.0), 6.42 (1H, d, J=15.5), 6.92 (1H, d, J=8.0), 7.03 (1H, dd, J=8.0, 3.0), 7.05 (1H, d, J=3.0), 7.42 (1H, t, J=8.0), 7.53 (2H, m), 7.58 (1H, s).

Reference Example 22

4-(1-t-Butoxycarbonylpiperidin-4-yloxy-3-fluoronitrobenzene

To a solution of 1-t-butoxycarbonyl-4-hydroxypiperidine (3.02 g), 2-fluoro-4-nitrophenol (2.36 g) and triphenylphosphine (5.11 g) in dichloromethane (60 ml) was added dropwise diethyl azodicarboxylate (3.1 ml) in an ice bath and the mixture was stirred at room temperature for 14 hours. The reaction mixture was concentrated in vacuo. The residue was purified by chromatography on a silica gel column using hexane/ethyl acetate=5/2 as an eluant to give the desired compound (3.71 g, yield 73%) as a pale yellow solid.

$^1$H NMR (500 MHz, $CDCl_3$) δ ppm: 1.48 (9H, s), 1.84 (2H, m), 1.97 (2H, m), 3.41 (2H, m), 3.71 (2H, m), 4.66 (1H, m), 7.05 (1H, m), 8.04 (2H, m).

Reference Example 23

4-(1-t-Butoxycarbonylpiperidin-4-yloxy)-3-fluoroaniline

To a solution of 4-(1-t-butoxycarbonylpiperidin-4-yloxy)-3-fluoronitrobenzene (3.71 g) in methanol (50 ml) was added palladium on carbon (0.30 g) and the mixture was stirred under a hydrogen atmosphere at room temperature for 4 hours. The reaction mixture was filtered and the filtrate concentrated in vacuo. The residue was purified by chromatography on a silica gel column using hexane/ethyl acetate=1/1 as an eluant to give the desired compound (3.27 g, yield 97%) as a pale red solid.

$^1$H NMR (500 MHz, $CDCl_3$) δ ppm: 1.46 (9H, s), 1.72 (2H, m), 1.86 (2H, m), 3.23 (2H, m), 3.75 (2H, m), 4.17 (1H, m), 6.35 (1H, dd, J=8.5, 3.0), 6.44 (1H, dd, J=12.5, 3.0), 6.82 (1H, dd, J=9.0, 8.5).

Reference Example 24

Ethyl N-[4-(1-t-Butoxycarbonylpiperidin-4-yloxy)-3-fluorophenyl]sulfamoylacetate To a solution of 4-(1-t-butoxycarbonylpiperidin-4-yloxy)-3-fluoroaniline (1.49 g) and pyridine (0.77 ml) in dichloromethane (30 ml) was added dropwise ethyl chlorosulfonylacetate (0.77 ml) in an ice bath and the mixture was stirred at room temperature for 7 hours. The reaction mixture was concentrated in vacuo. The residue was purified by chromatography on a silica gel column using hexane/ethyl acetate=3/2 as an eluant to give the desired compound (1.58 g, yield 71%) as a pale red oil.

$^1$H NMR (500 MHz, $CDCl_3$) δ ppm: 1.33 (3H, t, J=7.0), 1.47 (9H, s), 1.77 (2H, m), 1.90 (2H, m), 3.32 (2H, m), 3.72 (2H, m), 3.92 (2H, s), 4.29 (2H, q, J=7.0), 4.42 (1H, m), 6.97 (1H, dd, J=9.0, 8.5), 7.04 (1H, dd, J=9.0, 3.0), 7.17 (1H, dd, J=11.5, 3.0).

Reference Example 25

Ethyl N-[4-(1-t-Butoxycarbonylpiperidin-4-yloxy)-3-fluorophenyl]-N-[3-(3-cyanophenyl)-2-(E)-propenyl]sulfamoylacetate To a solution of 3-(3-cyanophenyl)-2-(E)-propen-1-ol (0.40 g), ethyl N-[4-(1-t-butoxycarbonylpiperidin-4-yloxy)-3-fluorophenyl]sulfamoylacetate (1.15 g) and triphenylphosphine (0.85 g) in dichloromethane (20 ml) was added dropwise diethyl azodicarboxylate (0.51 ml) in an ice bath and the mixture was stirred at the same temperature for 3 hours. The reaction mixture was concentrated in vacuo. The residue was purified by chromatography on a silica gel column using dichloromethane/ethyl acetate≦10/1 as an eluant to give the desired compound (1.21 g, yield 81%) as a pale yellow amorphous solid.

$^1$H NMR (500 MHz, $CDCl_3$) δ ppm: 1.35 (3H, t, J=7.0), 1.47 (9H, s), 1.77 (2H, m), 1.91 (2H, m), 3.34 (2H, m), 3.70 (2H, m), 3.98 (2H, s), 4.31 (2H, q, J=7.0), 4.46 (1H, m), 4.47 (2H, d, J=7.0), 6.22 (1H, dt, J=16.0, 7.0), 6.41 (1H, d, J=16.0), 6.98 (1H, dd, J=9.0, 8.5), 7.20 (1H, dd, J=8.5, 2.0), 7.27 (1H, m), 7.40 (1H, dd, J=8.0, 7.0), 7.52 (1H, d, J=7.0), 7.53 (1H, d, J=8.0), 7.56 (1H, s).

Reference Example 26

4-(1-t-Butoxycarbonylpiperidin-4-yloxy)-3-chloronitrobenzene

To a solution of 1-t-butoxycarbonyl-4-hydroxypiperidine (3.32 g), 2-chloro-4-nitrophenol (2.36 g) and triphenylphosphine (5.11 g) in dichloromethane (60 ml) was added dropwise diethyl azodicarboxylate (3.1 ml) in an ice bath and the mixture was stirred at room temperature for 18 hours. The reaction mixture was concentrated in vacuo. The residue was purified by chromatography on a silica gel column using hexane/ethyl acetate=5/2 as an eluant to give the desired compound (3.90 g, yield 76%) as a pale yellow solid.

$^1$H NMR (500 MHz, $CDCl_3$) δ ppm: 1.48 (9H, s), 1.84–1.98 (4H, m), 3.54 (2H, m), 3.62 (2H, m), 4.73 (1H, m), 7.00 (1H, d, J=9.0), 8.14 (1H, dd, J=9.0, 3.0), 8.31 (1H, d, J=3.0).

Reference Example 27

4-(1-t-Butoxycarbonylpiperidin-4-yloxy)-3-chloroaniline

To a solution of 4-(1-t-butoxycarbonylpiperidin-4-yloxy)-3-chloronitrobenzene (2.40 g) in acetic acid (50 ml) was added zinc powder (5.60 g) in four portions at room temperature and the mixture was stirred for 2 hours. The reaction mixture was filtered and the filtrate concentrated in vacuo. The residue was purified by chromatography on a silica gel column using hexane/ethyl acetate=1/1 as an eluant to give the desired compound (1.99 g, yield 87%) as an orange oil.

$^1$H NMR (500 MHz, $CDCl_3$) δ ppm: 1.47 (9H, s), 1.77 (2H, m), 1.87 (2H, m), 3.31 (2H, m), 3.72 (2H, m), 4.26 (1H, m), 6.52 (1H, dd, J=9.0, 3.0), 6.73 (1H, d, J=3.0), 6.80 (1H, d, J=9.0).

Reference Example 28

Ethyl N-[4-(1-t-Butoxycarbonylpiperidin-4-yloxy)-3-chlorophenyl]sulfamoylacetate To a solution of 4-(1-t-butoxycarbonylpiperidin-4-yloxy)-3-chloroaniline (1.50 g) and pyridine (0.56 ml) in dichloromethane (20 ml) was added dropwise ethyl chlorosulfonylacetate (0.74 ml) in an ice bath and the mixture was stirred at room temperature for 5 hours. The reaction mixture was concentrated in vacuo. The residue was purified by chromatography on a silica gel column using hexane/ethyl acetate=3/2 as an eluant to give the desired compound (1.19 g, yield 54%) as a pale red oil.

$^1$H NMR (500 MHz, $CDCl_3$) δ ppm: 1.34 (3H, t, J=7.0), 1.47 (9H, s), 1.79–1.92 (4H, m), 3.46 (2H, m), 3.64 (2H, m), 3.92 (2H, s), 4.30 (2H, q, J=7.0), 4.52 (1H, m), 6.94 (1H, d, J=9.0), 7.22 (1H, dd, J=9.0, 2.5), 7.40 (1H, d, J=2.5).

Reference Example 29

Ethyl N-[4-(1-t-Butoxycarbonylpiperidin-4-yloxy)-3-chlorophenyl]-N-[3-(3-cyanophenyl)-2-(E)-propenyl]sulfamoylacetate To a solution of 3-(3-cyanophenyl)-2-(E)-propen-1-ol (0.40 g), ethyl N-[4-(1-t-butoxycarbonylpiperidin-4-yloxy)-3-chlorophenyl]sulfamoylacetate (1.19 g) and triphenylphosphine (0.79 g) in dichloromethane (20 ml) was added dropwise diethyl azodicarboxylate (0.50 ml) in an ice bath and the mixture was stirred at the same temperature for 2.5 hours. The reaction mixture was concentrated in vacuo. The residue was purified by chromatography on a silica gel column using dichloromethane/ethyl acetate=10/1 as an eluant to give the desired compound (1.20 g, yield 78%) as a pale red amorphous solid.

$^1$H NMR (500 MHz, $CDCl_3$) δ ppm: 1.36 (3H, t, J=7.0), 1.47 (9H, s), 1.79–1.92 (4H, m), 3.47 (2H, m), 3.62 (2H, m), 3.99 (2H, s), 4.31 (2H, q, J=7.0), 4.47 (2H, d, J=6.5), 4.55 (1H, m), 6.23 (1H, dt, J=16.0, 6.5), 6.41 (1H, d, J=16.0), 6.94 (1H, d, J=9.0), 7.32 (1H, dd, J=9.0, 3.0), 7.41 (1H, t, J=7.5), 7.50–7.58 (4H, m).

Reference Example 30

4-(1-t-Butoxycarbonylpiperidin-4-yloxy)-3-trifluoromethylnitrobenzene

To a solution of 1-t-butoxycarbonyl-4-hydroxypiperidine (1.45 g), 2-trifluoromethyl-4-nitrophenol (1.38 g) [which was prepared from 3-trifluoromethylnitrobenzene according to the method described in *J. Org. Chem.*, 63 4199 (1998)] and triphenylphosphine (2.27 g) in dichloromethane (65 ml) was added dropwise diethyl azodicarboxylate (1.4 ml) in an ice bath and the mixture was stirred at room temperature for 24 hours. The reaction mixture was concentrated in vacuo. The residue was purified by chromatography on a silica gel column using dichloromethane as an eluant to give the desired compound (2.28 g, yield 88%) as a pale yellow oil.

$^1$H NMR (500 MHz, $CDCl_3$) δ ppm: 1.49 (9H, s), 1.88–1.99 (4H, m), 3.51 (2H, m), 3.64 (2H, m), 4.83 (1H, m), 7.09 (1H, d, J=9.0), 8.41 (1H, dd, J=9.0, 3.0), 8.53 (1H, d, J=3.0).

Reference Example 31

4-(1-t-Butoxycarbonylpiperidin-4-yloxy)-3-trifluoromethylaniline

To a solution of 4-(1-t-butoxycarbonylpiperidin-4-yloxy)-3-trifluoromethylnitrobenzene (2.28 g) in methanol (50 ml) was added palladium on carbon (0.20 g) and the mixture was stirred under a hydrogen atmosphere at room temperature for 5 hours. The reaction mixture was filtered and the filtrate concentrated in vacuo. The residue was purified by chromatography on a silica gel column using hexane/ethyl acetate=3/2 as an eluant to give the desired compound (1.69 g, yield 80%) as a pale red oil.

$^1$H NMR (500 MHz, $CDCl_3$) δ ppm: 1.47 (9H, s), 1.76–1.88 (4H, m), 3.43 (2H, m), 3.59 (2H, m), 4.46 (1H, m), 6.78 (1H, dd, J=9.0, 3.0), 6.83 (1H, d, J=9.0), 6.91 (1H, d, J=3.0).

Reference Example 32

Ethyl N-[4-(1-t-Butoxycarbonylpiperidin-4-yloxy)-3-trifluoromethylphenyl]sulfamoylacetate To a solution of 4-(1-t-butoxycarbonylpiperidin-4-yloxy)-3-trifluoromethylaniline (1.69 g) and pyridine (0.49 ml) in dichloromethane (20 ml) was added dropwise ethyl chlorosulfonylacetate (0.76 ml) in an ice bath and the mixture was stirred at room temperature for 3 hours. The reaction mixture was concentrated in vacuo. The residue was purified by chromatography on a silica gel column using hexane/ethyl acetate=3/2 as an eluant to give the desired compound (1.74 g, yield 73%) as a pale red oil.

$^1$H NMR (500 MHz, $CDCl_3$) δ ppm: 1.34 (3H, t, J=7.0), 1.48 (9H, s), 1.83–1.94 (4H, m), 3.48–3.60 (4H, m), 3.91 (2H, s), 4.31 (2H, q, J=7.0), 4.65 (1H, m), 6.99 (1H, d, J=9.0), 7.52 (1H, dd, J=9.0, 2.5), 7.56 (1H, d, J=2.5).

Reference Example 33

Ethyl N-[4-(1-t-Butoxycarbonylpiperidin-4-yloxy)-3-trifluoromethylphenyl]-N-[3-(3-cyanophenyl)-2-(E)-propenyl]sulfamoylacetate To a solution of 3-(3-cyanophenyl)-2-(E)-propen-1-ol (0.57 g), ethyl N-[4-(1-t-butoxycarbonylpiperidin-4-yloxy)-3-trifluoromethylphenyl]sulfamoylacetate (1.74 g) and triphenylphosphine (1.07 g) in dichloromethane (27 ml) was added dropwise diethyl azodicarboxylate (0.65 ml) in an ice bath and the mixture was stirred at the same temperature for 3 hours. The reaction mixture was concentrated in vacuo. The residue was purified by chromatography on a silica gel column using dichloromethane/ethyl acetate=12/1 as an eluant to give the desired compound (2.06 g, yield 93%) as a colorless amorphous solid.

$^1$H NMR (500 MHz, $CDCl_3$) δ ppm: 1.35 (3H, t, J=7.0), 1.47 (9H, s), 1.82–1.92 (4H, m), 3.46–3.62 (4H, m), 3.98 (2H, s), 4.31 (2H, q, J=7.0), 4.48 (2H, d, J=6.5), 4.66 (1H, m), 6.22 (1H, dt, J=16.0, 6.5), 6.41 (1H, d, J=16.0), 6.98 (1H, d, J=7.5), 7.41 (1H, dd, J=8.0, 7.5), 7.52 (2H, m), 7.57 (1H, s), 7.58 (1H, dd, J=9.0, 2.0), 7.72 (1H, d, J=2.0).

Reference Example 34

4-(1-t-Butoxycarbonylpiperidin-4-yloxy)-3-methylnitrobenzene

To a solution of 1-t-butoxycarbonyl-4-hydroxypiperidine (3.62 g), 2-methyl-4-nitrophenol (2.55 g) and triphenylphosphine (5.25 g) in dichloromethane (100 ml) was added dropwise diethyl azodicarboxylate (3.2 ml) in an ice bath and the mixture was stirred at room temperature for 18 hours. The reaction mixture was concentrated in vacuo. The residue was purified by chromatography on a silica gel column using dichloromethane as an eluant to give the crude desired compound (4.07 g) as a pale yellow oil.

$^1$H NMR (500 MHz, $CDCl_3$) δ ppm: 1.48 (9H, s), 1.84 (2H, m), 1.95 (2H, m), 2.29 (3H, s), 3.49 (2H, m), 3.62 (2H, m), 4.66 (1H, m), 6.86 (1H, d, J=8.5), 8.07 (2H, m).

Reference Example 35

4-(1-t-Butoxycarbonylpiperidin-4-yloxy)-3-methylaniline

To a solution of 4-(1-t-butoxycarbonylpiperidin-4-yloxy)-3-methylnitrobenzene (4.07 g) in methanol (40 ml) was added palladium on carbon (0.41 g) and the mixture was stirred under a hydrogen atmosphere at room temperature for 4 hours. The reaction mixture was filtered and the filtrate concentrated in vacuo. The residue was purified by chromatography on a silica gel column using hexane/ethyl acetate=3/2 as an eluant to give the desired compound (2.73 g, two step yield, from Reference example 41, 53%) as a pale red oil.

$^1$H NMR (500 MHz, $CDCl_3$) δ ppm: 1.47 (9H, s), 1.74 (2H, m), 1.87 (2H, m), 2.17 (3H, s), 3.30 (2H, m), 3.68 (2H, m), 4.25 (1H, m), 6.47 (1H, dd, J=8.5, 2.5), 6.53 (1H, d, J=2.5), 6.68 (1H, d, J=8.5).

Reference Example 36

Ethyl N-[4-(1-t-Butoxycarbonylpiperidin-4-yloxy)-3-methylphenyl]sulfamoylacetate To a solution of 4-(1-t-butoxycarbonylpiperidin-4-yloxy)-3-methylaniline (1.63 g) and pyridine (0.81 ml) in dichloromethane (30 ml) was added dropwise ethyl chlorosulfonylacetate (0.86 ml) in an ice bath and the mixture was stirred at room temperature for 5 hours. After addition of methanol (0.5 ml), the reaction mixture was concentrated in vacuo. The residue was purified by chromatography on a silica gel column using hexane/ethyl acetate=3/2 as an eluant to give the desired compound (1.84 g, yield 76%) as a pale brown amorphous solid.

$^1$H NMR (500 MHz, $CDCl_3$) δ ppm: 1.34 (3H, t, J=7.0), 1.47 (9H, s), 1.78 (2H, m), 1.89 (2H, m), 2.22 (3H, s), 3.43 (2H, m), 3.62 (2H, m), 3.90 (2H, s), 4.29 (2H, q, J=7.0), 4.48 (1H, m), 6.79 (1H, d, J=8.0), 7.12 (2H, m).

Reference Example 37

Ethyl N-[4-(1-t-Butoxycarbonylpiperidin-4-yloxy)-3-methylphenyl]-N-[3-(3-cyanophenyl)-2-(E)-propenyl]sulfamoylacetate To a solution of 3-(3-cyanophenyl)-2-(E)-propen-1-ol (0.64 g), ethyl N-[4-(1-t-butoxycarbonylpiperidin-4-yloxy)-3-methylphenyl]sulfamoylacetate (1.84 g) and triphenylphosphine (1.26 g) in dichloromethane (40 ml) was added dropwise diethyl azodicarboxylate (0.76 ml) in an ice bath and the mixture was stirred at the same temperature for 1 hour. The reaction mixture was concentrated in vacuo. The residue was purified by chromatography on a silica gel column using dichloromethane/ethyl acetate=12/1 as an eluant to give the desired compound (1.90 g, yield 79%) as a colorless amorphous solid.

$^1$H NMR (500 MHz, $CDCl_3$) δ ppm: 1.36 (3H, t, J=7.0), 1.47 (9H, s), 1.78 (2H, m), 1.89 (2H, m), 2.21 (3H, s), 3.44 (2H, m), 3.60 (2H, m), 3.99 (2H, s), 4.31 (2H, q, J=7.0), 4.46 (2H, d, J=6.5), 4.50 (1H, m), 6.24 (1H, dt, J=16.0, 6.5), 6.41 (1H, d, J=16.0), 6.80 (1H, d, J=8.0), 7.24 (2H, m), 7.40 (1H, t, J=8.0), 7.50 (1H, d, J=7.5), 7.52 (1H, d, J=8.0), 7.56 (1H, s).

Reference Example 38

3-Bromo-5-cyanotoluene

To a solution of 3,5-dibromotoluene (10.00 g) in 1-methyl-2-pyrrolidone (70 ml) was added copper (I) cyanide (5.20) and the mixture was stirred at 200° C. for 1.5 hours. The reaction mixture was cooled to room temperature and partitioned between water and ethyl acetate. The extract was washed with 1M hydrochloric acid, water and brine, dried over anhydrous magnesium sulfate and then concentrated in vacuo. The residue was purified by chromatography on a silica gel column using hexane/ethyl acetate=9/1 as an eluant to give the desired compound (1.70 g, yield 21%).

$^1$H NMR (270 MHz, $CDCl_3$) δ ppm: 2.39 (3H, s), 7.40 (1H, s), 7.57 (1H, s), 7.60 (1H, s).

Reference Example 39

3-(3-Cyano-5-methylphenyl)-2-(E)-propen-1-ol

Catecholborane (1.07 ml) was added to 1-t-butyldimethylsilyloxy-2-propyne (1.70 g) and the mixture was stirred at 60° C. for 3 hours. The reaction mixture was cooled to room temperature and to this mixture were added toluene (20 ml), 3-bromo-5-cyanotoluene (1.40 g), tetrakis(triphenylphosphine)palladium complex (0.42 g) and a 20% solution of sodium ethoxide in ethanol (3.40 ml). The resulting mixture was stirred at 100° C. for 3 hours. The reaction mixture was partitioned between water and ether. The extract was washed with 1M aqueous sodium hydroxide, water and brine, dried over anhydrous sodium sulfate and then concentrated in vacuo. The residue was purified by chromatography on a silica gel column using hexane/ethyl acetate=19/1 as an eluant to give a silyl ether derivative (1.50 g).

To a solution of the silyl ether derivative in tetrahydrofuran (30 ml) was added a 1M solution of tetrabutylammonium fluoride in tetrahydrofuran (7 ml) and the mixture was stirred for 1 hour. The reaction mixture was partitioned between water and ethyl acetate. The extract was washed with water and brine, dried over anhydrous magnesium sulfate and then concentrated in vacuo. The residue was purified by chromatography on a silica gel column using hexane/ethyl acetate=3/2 as an eluant to give the desired compound (0.54 g, two step yield 43%) as a yellow oil.

$^1$H NMR (270 MHz, $CDCl_3$) δ ppm: 2.38 (3H, s), 4.35 (2H, d, J=5.0), 6.40 (1H, dt, J=16.0, 5.0), 6.58 (1H, d, J=16.0), 7.33 (1H, s), 7.40 (1H, s), 7.46 (1H, s).

Reference Example 40

Ethyl N-[4-(1-t-Butoxycarbonylpiperidin-4-yloxy)phenyl]-N-[3-(3-cyano-5-methylphenyl)-2-(E)-propenyl]sulfamoylacetate To a solution of 3-(3-cyano-5-methylphenyl)-2-(E)-propen-1-ol (0.54 g), ethyl N-[4-(1-t- butoxycarbonylpiperidin-4-yloxy)phenyl]sulfamoylacetate (1.50 g) and triphenylphosphine (1.10 g) in dichloromethane (30 ml) was added dropwise diethyl azodicarboxylate (0.66 ml) in an ice bath and the mixture was stirred at room temperature for 4.5 hours. The reaction mixture was concentrated in vacuo. The residue was purified by chromatography on a silica gel column using dichloromethane/ethyl acetate=19/1 as an eluant to give the desired compound (1.70 g, yield 91%) as an amorphous solid.

$^1$H NMR (270 MHz, $CDCl_3$) δ ppm: 1.35 (3H, t, J=7.0), 1.47 (9H, s), 1.65–1.80 (2H, m), 1.85–2.00 (2H, m), 2.36 (3H, s), 3.25–3.40 (2H, m), 3.60–3.75 (2H, m), 3.98 (2H, s), 4.30 (2H, q, J=7.0), 4.40–4.50 (3H, m), 6.21 (1H, dt, J=16.0, 6.0), 6.36 (1H, d, J=16.0), 6.90 (2H, m), 7.30–7.45 (5H, m).

Reference Example 41

3-(3-Cyano-4-fluorophenyl)-2-(E)-propen-1-ol

Catecholborane (1.07 ml) was added to 1-t-butyldimethylsilyloxy-2-propyne (1.70 g) and the mixture was stirred at 60° C. for 4 hours. The reaction mixture was cooled to room temperature and to this mixture were added toluene (20 ml), 5-bromo-2-fluorobenzonitrile (1.43 g), tetrakis(triphenylphosphine)palladium complex (0.42 g) and a 20% solution of sodium ethoxide in ethanol (3.4 ml). The resulting mixture was stirred at 100° C. for 4 hours. The reaction mixture was partitioned between water and ether. The extract was washed with 1M aqueous sodium hydroxide, water and brine, dried over anhydrous sodium sulfate and then concentrated in vacuo. The residue was purified by chromatography on a silica gel column using hexane/ethyl acetate=19/1 as an eluant to give a silyl ether derivative (1.33 g).

To a solution of the silyl ether derivative in tetrahydrofuran (20 ml) was added a 1M solution of tetrabutylammonium fluoride in tetrahydrofuran (6 ml) in an ice bath and the mixture was stirred at the same temperature for 1 hour. The reaction mixture was partitioned between water and ethyl acetate. The extract was washed with water and brine, dried over anhydrous magnesium sulfate and then concentrated in vacuo. The residue was purified by chromatography on a silica gel column using hexane/ethyl acetate=3.2 as an eluant to give the desired compound (0.48 g, two step yield 37%) as a yellow oil.

$^1$H NMR (270 MHz, $CDCl_3$) δ ppm: 4.30–4.40 (2H, m), 6.35 (1H, dt, J=16.0, 5.0), 6.59 (1H, d, J=16.0), 7.18 (1H, m), 7.55–7.65 (2H, m).

Reference Example 42

Ethyl N-[4-(1-t-Butoxycarbonylpiperidin-4-yloxy)phenyl]-N-[3-(3-cyano-4-fluorophenyl)-2-(E)-propenyl]sulfamoylacetate To a solution of 3-(3-cyano-4-fluorophenyl)-2-(E)-propen-1-ol (0.48 g), ethyl N-[4-(1-t-butoxycarbonylpiperidin-4-yloxy)phenyl]sulfamoylacetate (1.30 g) and triphenylphosphine (1.00 g) in dichloromethane (30 ml) was added dropwise diethyl azodicarboxylate (0.60 ml) in an ice bath and the mixture was stirred at room temperature for 1 hour. The reaction mixture was concentrated in vacuo. The residue was purified by chromatography on a silica gel column using dichloromethane/ethyl acetate=19/1 as an eluant to give the desired compound (1.53 g, yield 93%) as an amorphous solid.

$^1$H NMR (500 MHz, $CDCl_3$) δ ppm: 1.35 (3H, t, J=7.0), 1.47 (9H, s), 1.70–1.80 (2H, m), 1.85–1.95 (2H, m), 3.30–3.40 (2H, m), 3.65–3.75 (2H, m), 3.97 (2H, s), 4.30 (2H, q, J=7.0), 4.40–4.50 (3H, m), 6.16 (1H, dt, J=16.0, 6.0), 6.37 (1H, d, J=16.0), 6.91 (2H, d, J=9.0), 7.14 (1H, m), 7.38 (2H, d, J=9.0), 7.45–7.55 (2H, m).

Reference Example 43

3-[3-[N-[4-(1-t-Butoxycarbonylpiperidin-4-yloxy)phenyl]amino]-1-(E)-propenyl]benzonitrile A suspension of 3-cyanocinnamaldehyde (6.0 g), 4-(1-t-butoxycarbonylpiperidin-4-yloxy)aniline (11.3 g) and molecular sieves 5A (15.0 g) in toluene (30 ml) was heated under reflux for 2 hours. The reaction mixture was filtered through Celite (trade mark) and the filtrate concentrated in vacuo. The residue was recrystallized from a mixture of dichloromethane and ether to afford an imine derivative (12.9 g).

To a suspension of the imine derivative in ethanol (200 ml) was added a catalytic amount of cerium chloride and then sodium borohydride (1.1 g) in an ice bath. The mixture was stirred at the same temperature. The reaction mixture was concentrated in vacuo and partitioned between water and ethyl acetate. The extract was washed with brine, dried over anhydrous magnesium sulfate and then concentrated in vacuo. The residue was purified by chromatography on a silica gel column using hexane/ethyl acetate=3/2 as an eluant to afford a yellow solid. The solid was washed with diisopropyl ether to give the desired compound (10.0 g, yield 60%) as pale yellow crystals.

$^1$H NMR (270 MHz, $CDCl_3$) δ ppm: 1.46 (9H, s), 1.60–1.80 (2H, m), 1.80–1.95 (2H, m), 3.20–3.35 (2H, m), 3.65–3.80 (2H, m), 3.93 (2H, dd, J=5.5, 1.0), 4.28 (1H, m), 6.39 (1H, dt, J=16.0, 5.5), 6.61 (1H, d, J=16.0), 6.61 (2H, d, J=9.0), 6.81 (2H, d, J=9.0), 7.41 (1H, t, J=7.5), 7.51 (1H, d, J=7.5), 7.57 (1H, d, J=7.5), 7.63 (1H, s).

Reference Example 44

3-[3-[N-[4-(1-t-Butoxycarbonylpiperidin-4-yloxy)phenyl]-N-methylamino]-1-(E)-propenyl]benzonitrile To a suspension of 3-[3-[N-[4-(1-t-butoxycarbonylpiperidin-4-yloxy)phenyl]amino]-1-(E)-propenyl]benzonitrile (1000 mg) and paraformaldehyde (138 mg) in dichloromethane (20 ml) were added acetic acid (0.26 ml) and sodium cyanoborohydride (144 mg) in an ice bath. The mixture was stirred at room temperature overnight and then methanol (20 ml) was added. The resulting mixture was stirred at 30° C. for 5 hours. The reaction mixture was partitioned between water and ethyl acetate. The extract was washed with brine, dried over anhydrous magnesium sulfate and then concentrated in vacuo. The residue was purified by chromatography on a silica gel column using hexane/ethyl acetate=3/2 as an eluant to give the desired compound (761 mg, yield 74%) as a yellow oil.

$^1$H NMR (270 MHz, $CDCl_3$) δ ppm: 1.47 (9H, s), 1.72 (2H, m), 1.87 (2H, m), 2.92 (3H, s), 3.28 (2H, m), 3.71 (2H, m), 4.02 (2H, d, J=5.0), 4.29 (1H, m), 6.32 (1H, dt, J=16.0, 5.0), 6.51 (1H, d, J=16.0), 6.72 (2H, d, J=9.0), 6.86 (2H, d, J=9.0), 7.39 (1H, t, J=7.5), 7.49 (1H, d, J=7.5), 7.56 (1H, d, J=7.5), 7.62 (1H, s).

Reference Example 45

3-[3-[N-[4-(1-t-Butoxycarbonylpiperidin-4-yloxy)phenyl]-N-ethylamino]-1-(E)-propenyl]benzonitrile To a solution of 3-[3-[N-[4-(1-t-butoxycarbonylpiperidin-4-yloxy)phenyl]amino]-1-(E)-propenyl]benzonitrile (1000 mg) and acetaldehyde (0.52 ml) in a mixture of dichloromethane (10 ml) and methanol (20 ml) were added acetic acid (0.26 ml) and sodium cyanoborohydride (144 mg) in an ice bath. The mixture was stirred at the same temperature for 2 hours and then at room temperature overnight. To the reaction mixture was added water, and the mixture was then extracted with ethyl acetate. The extractant was washed with brine, dried over anhydrous magnesium sulfate and filtered, and the filtrate concentrated in vacuo. The residue was purified by chromatography on a silica gel column using hexane/ethyl acetate=4/1→2/1 as an eluant to give the desired compound (661 mg, yield 62%) as a yellow oil.

$^1$H NMR (270 MHz, $CDCl_3$) δ ppm: 1.16 (3H, t, J=7.0), 1.46 (9H, s), 1.72 (2H, m), 1.87 (2H, m), 3.25 (2H, m), 3.36 (2H, q, J=7.0), 3.71 (2H, m), 4.01 (2H, d, J=5.0), 4.26 (1H, m), 6.31 (1H, dt, J=16.0, 5.0), 6.50 (1H, d, J=16.0), 6.69 (2H, d, J=9.0), 6.84 (2H, d, J=9.0), 7.39 (1H, t, J=7.5), 7.49 (1H, d, J=7.5), 7.55 (1H, d, J=7.5), 7.61 (1H, s).

Reference Example 46

3-[3-[N-[4-(1-t-butoxycarbonylpiperidin-4-yloxy)phenyl]-N-isopropylamino]-1-(E)-propenyl]benzonitrile To a solution of 3-[3-[N-[4-(1-t-butoxycarbonylpiperidin-4-yloxy)phenyl]amino]-1-(E)-propenyl]benzonitrile (1500 mg) in acetone (20 ml) were added acetic acid (0.20 ml) and sodium cyanoborohydride (214 mg) in an ice bath. The mixture was stirred at room temperature overnight and then heated under reflux for 8 hours. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=4/1 as an eluant to give the desired compound (583 mg, yield 35%) as a pale yellow oil.

$^1$H NMR (270 MHz, $CDCl_3$) δ ppm: 1.18 (6H, d, J=6.5), 1.46 (9H, s), 1.60–1.80 (2H, m), 1.80–1.95 (2H, m), 3.26 (2H, m), 3.71 (2H, m), 3.91 (2H, d, J=4.5), 4.00 (1H, m), 4.26 (1H, m), 6.33 (1H, dt, J=16.0, 4.5), 6.53 (1H, d, J=16.0), 6.73 (2H, d, J=9.0), 6.82 (2H, d, J=9.0), 7.38 (1H, t, J=7.5), 7.47 (1H, d, J=7.5), 7.53 (1H, d, J=7.5), 7.60 (1H, s).

Reference Example 47

3-[3-[N-Benzyl-N-[4-(1-t-butoxycarbonylpiperidin-4-yloxy)phenyl]amino]-1-(E)-propenyl]benzonitrile To a solution of 3-[3-(N-[4-(1-t-butoxycarbonylpiperidin-4-yloxy)phenyl]amino]-1-(E)-propenylgbenzonitrile (1000 mg) and benzaldehyde (0.52 ml) in a mixture of dichloromethane (10 ml) and methanol (20 ml) were added acetic acid (0.26 ml) and sodium cyanoborohydride (144 mg) in an ice bath. The mixture was heated under reflux for 10 hours. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=4/1→2/1 as an eluant to give the desired compound (924 mg, yield 76%) as a yellow oil.

$^1$H NMR (270 MHz, $CDCl_3$) δ ppm: 1.46 (9H, s), 1.70 (2H, m), 1.87 (2H, m), 3.26 (2H, m), 3.69 (2H, m), 4.11 (2H, d, J=5.0), 4.26 (1H, m), 4.52 (2H, s), 6.32 (1H, dt, J=16.0, 5.0), 6.48 (1H, d, J=16.0), 6.71 (2H, d, J=9.0), 6.81 (2H, d, J=9.0), 7.20–7.60 (9H, m).

Reference Example 48

N-[4-(1-t-Butoxycarbonylpiperidin-4-yloxy)phenyl]-N-[3-(3-cyanophenyl)-2-(E)-propenyl]acetamide To a solution of 3-[3-[N-[4-(1-t-butoxycarbonylpiperidin-4-yloxy)phenyl]amino]-1-(E)-propenyl]benzonitrile (503 mg) and pyridine (0.14 ml) in dichloromethane (10 ml) was added acetic anhydride (0.13 ml) in an ice bath. The mixture was stirred at room temperature for 1 hour. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=1/1→ethyl acetate as an eluant to afford yellow crystals. The crystals were washed with diisopropyl ether to give the desired compound (403 mg, yield 50%) as pale yellow crystals.

$^1$H NMR (270 MHz, $CDCl_3$) δ ppm: 1.47 (9H, s), 1.88 (3H, s), 1.70–1.95 (4H, m), 3.33 (2H, m), 3.70 (2H, m), 4.41 (2H, d, J=5.5), 4.47 (1H, m), 6.32 (1H, dt, J=16.0, 5.5), 6.38 (1H, d, J=16.0), 6.91 (2H, d, J=9.0), 7.07 (2H, d, J=9.0), 7.40 (1H, t, J=8.0), 7.51 (1H, d, J=8.0), 7.55 (1H, d, J=8.0), 7.58 (1 H, s).

Reference Example 49

N-[4-(1-t-Butoxycarbonylpiperidin-4-yloxy)phenyl]-N-[3-(3-cyanophenyl)-2-(E)-propenyl]-2-hydroxyacetamide To a solution of 3-[3-[N-[4-(1-t-butoxycarbonylpiperidin-4-yloxy)phenyl]amino]-1-(E)-propenyl]benzonitrile (1000 mg) and pyridine (0.28 ml) in dichloromethane (20 ml) was added acetoxyacetyl chloride (0.27 ml) in an ice bath. The mixture was stirred at the same temperature for 1 hour. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=2/3 as an eluant to afford the desired intermediate (1232 mg) as a colorless amorphous solid.

To a solution of the intermediate in methanol (20 ml) was added potassium carbonate (640 mg). The mixture was stirred at room temperature for 1 hour. After addition of water, the reaction mixture was extracted with ethyl acetate. The extractant was washed with brine. The organic layer was dried over anhydrous magnesium sulfate, filtered and the filtrate concentrated in vacuo. The residue was purified by chromatography on a silica gel column using hexane/ethyl acetate=1/2 as an eluant to give the desired compound (977 mg, yield 86%) as a colorless amorphous solid.

$^1$H NMR (270 MHz, $CDCl_3$) δ ppm: 1.47 (9H, s), 1.76 (2H, m), 1.93 (2H, m), 3.28–3.40 (2H, m), 3.60–3.80 (2H, m), 3.81 (2H, d, J=4.5), 4.46 (2H, d, J=6.5), 4.47 (1H, m), 6.30 (1H, dt, J=16.0, 6.5), 6.44 (1H, d, J=16.0), 6.93 (2H, d, J=9.0), 7.07 (2H, d, J=9.0), 7.42 (1H, t, J=7.5), 7.53 (1H, d, J=7.5), 7.56 (1H, d, J=7.5), 7.59 (1H, s).

Reference Example 50

Ethyl 2-[N-[4-(1-t-Butoxycarbonylpiperidin-4-yloxy)phenyl]-N-[3-(3-cyanophenyl)-2-(E)-propenyl]amino]acetate To a solution of 3-[3-[N-[4-(1-t-butoxycarbonylpiperidin-4-yloxy)phenyl]amino]-1-(E)-propenyl]benzonitrile (1.00 g) in N,N-dimethylformamide (20 ml) were added potassium carbonate (0.96 g) and ethyl bromoacetate (0.62 ml). The mixture was stirred at 70° C. for 9 hours. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=2/1 as an eluant to give the desired compound (1.31 g, yield quantitative) as a yellow oil.

$^1$H NMR (270 MHz, $CDCl_3$) δ ppm: 1.26 (3H, t, J=7.0), 1.46 (9H, s), 1.71 (2H, m), 1.88 (2H, m), 3.27 (2H, m), 3.71 (2H, m), 4.03 (2H, m), 4.15–4.35 (5H, m), 6.36 (1H, dt, J=16.0, 5.0), 6.57 (1H, d, J=16.0), 6.65 (2H, d, J=9.0), 6.83 (2H, d, J=9.0), 7.40 (1H, t, J=7.5), 7.50 (1H, d, J=7.5), 7.57 (1H, d, J=7.5), 7.63 (1H, s).

Reference Example 51

Ethyl 2-[N-[4-(1-t-Butoxycarbonylpiperidin-4-yloxy)phenyl]-N-[3-(3-cyanophenyl)-2-(E)-propenyl]amino]propionate To a solution of 3-[3-[N-[4-(1-t-butoxycarbonylpiperidin-4-yloxy)phenyl]amino]-1-(E)-propenyl]benzonitrile (1200 mg) in N,N-dimethylformamide (20 ml) were added potassium carbonate (1710 mg) and ethyl 2-bromopropionate (1.5 ml). The mixture was stirred at 100° C. for 12 hours. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=2/1 as an eluant to give the desired compound (882 mg, yield 60%) as a yellow oil.

$^1$H NMR (270 MHz, $CDCl_3$) δ ppm: 1.24 (3H, t, J=7.0), 1.46 (9H, s), 1.50 (3H, d, J=7.0), 1.71 (2H, m), 1.87 (2H, m), 3.27 (2H, m), 3.70 (2H, m), 4.17 (2H, q, J=7.0), 4.01–4.32 (3H, m), 4.38 (1H, q, J=7.0), 6.36 (1H, dt, J=16.0, 4.5), 6.57 (1H, d, J=16.0), 6.73 (2H, d, J=9.0), 6.82 (2H, d, J=9.0), 7.39 (1H, t, J=8.0), 7.49 (1H, d, J=8.0), 7.55 (1H, d, J=8.0), 7.61 (1H, s).

Reference Example 52

Ethyl N-(4-Methoxymethoxyphenyl)sulfamoylacetate

To a solution of 4-methoxymethoxyaniline (20.9 g) and pyridine (33 ml) in dichloromethane (400 ml) was added dropwise ethyl chlorosulfonylacetate (18.0 ml) in an ice bath and the mixture was stirred at room temperature overnight. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=3/2 as an eluant to give the desired compound (28.0 g, yield 67%) as a brown oil.

$^1$H NMR (270 MHz, $CDCl_3$) δ ppm: 1.33 (3H, t, J=7.0), 3.48 (3H, s), 3.90 (2H, s), 4.29 (2H, q, J=7.0), 5.16 (2H, s), 7.03 (2H, d, J=9.0), 7.28 (2H, d, J=9.0).

Reference Example 53

Ethyl N-[3-(3-Cyanophenyl)-2-(E)-propenyl]-N-(4-methoxymethoxyphenyl)sulfamoylacetate To a solution of 3-(3-cyanophenyl)-2-(E)-propen-1-ol (0.525 g), ethyl N-(4-methoxymethoxyphenyl)sulfamoylacetate (1.00 g) and triphenylphosphine (1.12 g) in dichloromethane (30 ml) was added dropwisely diethyl azodicarboxylate (0.66 ml) and the mixture was stirred at room temperature for 3.5 hours. The reaction mixture was concentrated in vacuo. The residue was purified by chromatography on a silica gel column using hexane/ethyl acetate=3/2 as an eluant to give the desired compound (1.38 g, yield 94%) as a yellow oil.

$^1$H NMR (270 MHz, $CDCl_3$) δ ppm: 1.37 (3H, t, J=7.0), 3.48 (3H, s), 3.99 (2H, s), 4.32 (2H, q, J=7.0), 4.49 (2H, d, J=6.0), 5.18 (2H, s), 6.25 (1H, dt, J=16.0, 6.0), 6.42 (1H, d, J=16.0), 7.06 (2H, d, J=9.0), 7.40 (1H, t, J=7.0), 7.41 (2H, d, J=9.0), 7.52 (1H, d, J=7.0), 7.54 (1H, d, J=7.0), 7.56 (1H, s).

Reference Example 54

Ethyl N-[3-(3-Cyanophenyl)-2-(E)-propenyl]-N-(4-hydroxyphenyl)sulfamoylacetate

To a solution of N-[3-(3-cyanophenyl)-2-(E)-propenyl]-N-(4-methoxymethoxyphenyl)sulfamoylacetate (10.7 g) in ethyl acetate (120 ml) was added a 4M solution of hydrogen chloride in ethyl acetate (80 ml) in an ice bath and the mixture was stirred at room temperature for 4 hours. The reaction mixture was concentrated in vacuo. After addition of water, the residue was extracted with ethyl acetate. The extract was washed with brine. The organic layer was dried over anhydrous magnesium sulfate and concentrated in vacuo. The residue was purified by chromatography on a silica gel column using hexane/ethyl acetate=1/1 as an eluant to give the desired compound (9.1 g, yield 95%) as a yellow oil.

$^1$H NMR (270 MHz, $CDCl_3$) δ ppm: 1.35 (3H, t, J=7.0), 3.98 (2H, s), 4.30 (2H, q, J=7.0), 4.46 (2H, d, J=6.0), 6.23 (1H, dt, J=16.0, 6.0), 6.39 (1H, d, J=16.0), 6.84 (2H, d, J=9.0), 7.34 (2H, d, J=9.0), 7.39 (1H, t, J=7.5), 7.50 (2H, m), 7.54 (1H, s).

Reference Example 55

Ethyl N-[4-(1-t-Butoxycarbonylpyrrolidin-3-yloxy)phenyl]-N-[3-(3-cyanophenyl)-2-(E)-propenyl]sulfamoylacetate To a solution of ethyl N-[3-(3-cyanophenyl)-2-(E)-propenyl]-N-(4-hydroxyphenyl)sulfamoylacetate (800 mg), 1-t-butoxycarbonyl-3-hydroxypyrrolidine (450 mg) and triphenylphosphine (680 mg) in tetrahydrofuran (20 ml) was added dropwise diethyl azodicarboxylate (0.68 ml) and the mixture was stirred at room temperature overnight. The reaction mixture was concentrated in vacuo. The residue was purified by chromatography on a silica gel column using dichloromethane/ethyl acetate 10/1 as an eluant to give the desired compound (900 mg, yield 79%) as a colorless amorphous solid.

$^1$H NMR (270 MHz, $CDCl_3$) δ ppm: 1.36 (3H, t, J=7.0), 1.46 (9H, s), 2.00–2.25 (2H, m), 3.40–3.70 (4H, m), 3.98 (2H, s), 4.31 (2H, q, J=7.0), 4.48 (2H, d, J=6.5), 4.85 (1H, m), 6.24 (1H, dt, J=16.0, 6.5), 6.41 (1H, d, J=16.0), 6.87 (2H, d, J=9.0), 7.35–7.45 (3H, m), 7.45–7.60 (3H, m).

Reference Example 56

3-[3-[N-[4-(1-t-Butoxycarbonylpiperidin-4-yloxy)phenyl]-N-(2-hydroxyethyl)amino]-1-(E)-propenyl]benzonitrile To a solution of 3-[3-[N-[4-(1-t-butoxycarbonylpiperidin-4-yloxy)phenyl]amino]-1-(E)-propenyl]benzonitrile (1000 mg) and glycolaldehyde dimer (277 mg) in dichloromethane (20 ml) were added acetic acid (0.13 ml) and sodium cyanoborohydride (72 mg) in an ice bath. The mixture was stirred at the same temperature for 5 hours and then at room temperature for 4 hours. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=4/3 as an eluant to give the desired compound (1100 mg, yield 50%) as a pale yellow oil.

$^1$H NMR (500 MHz, $CDCl_3$) δ ppm: 1.46 (9H, s), 1.72 (2H, m), 1.89 (2H, m), 3.28 (2H, m), 3.45 (2H, t, J=5.5), 3.71 (2H, m), 3.79 (2H, m), 4.07 (2H, m), 4.30 (1H, m), 6.31 (1H, dt, J=16.0, 5.5), 6.48 (1H, d, J=16.0), 6.80 (2H, d, J=9.0), 6.84 (2H, d, J=9.0), 7.39 (1H, t, J=8.0), 7.49 (1H, d, J=8.0), 7.54 (1H, d, J=8.0), 7.60 (1H, s).

Reference Example 57

Ethyl 5-Nitrosalicylate

To a solution of 5-nitrosalicylic acid (10.8 g) in ethanol (100 ml) was added concentrated sulfuric acid (92.0 g) at room temperature and the mixture was heated under reflux for 7.5 hours. After neutralization with aqueous sodium hydroxide, the reaction mixture was extracted with ethyl acetate. The extractant was washed with saturated aqueous sodium hydrogencarbonate, 0.5M hydrochloric acid and brine. The organic layer was dried over anhydrous magnesium sulfate, filtered and the filtrate concentrated in vacuo to give the desired compound (10.7 g, yield 85%) as a yellow solid.

$^1$H NMR (400 MHz, $CDCl_3$) δ ppm: 1.47 (3H, t, J=7.0), 4.49 (2H, q, J=7.0), 7.09 (1H, d, J=9.0), 8.33 (1H, dd, J=9.0, 3.0), 8.79 (1H, d, J=3.0).

Reference Example 58

4-(1-t-Butoxycarbonylpiperidin-4-yloxy)-3-ethoxycarbonylnitrobenzene

To a solution of 1-t-butoxycarbonyl-4-hydroxypiperidine (10.2 g), ethyl 5-nitrosalicylate (10.7 g) and triphenylphosphine (17.3 g) in dichloromethane (200 ml) was added dropwise diethyl azodicarboxylate (10.4 ml) in an ice bath and the mixture was stirred at room temperature for 4 hours. The reaction mixture was concentrated in vacuo. The residue was purified by chromatography on a silica gel column using hexane/ethyl acetate=3/1 as an eluant to afford a yellow solid. A suspension of the solid in hexane was filtered to give the desired compound (12.3 g, yield 61%) as a white solid.

$^1$H NMR (400 MHz, $CDCl_3$) δ ppm: 1.40 (3H, t, J=7.0), 1.47 (9H, s), 1.91 (4H, m), 3.58 (4H, m), 4.39 (2H, q, J=7.0), 4.79 (1H, m), 7.04 (1H, d, J=9.0), 8.32 (1H, dd, J=9.0, 3.0), 8.69 (1H, d, J=3.0).

Reference Example 59

4-(1-t-Butoxycarbonylpiperidin-4-yloxy)-3-ethoxycarbonylaniline

To a solution of 4-(1-t-butoxycarbonylpiperidin-4-yloxy)-3-ethoxycarbonylnitrobenzene (5.0 g) in methanol (75 ml) was added palladium on carbon (0.5 g) and the mixture was stirred under a hydrogen atmosphere at room temperature for 2.5 hours. The reaction mixture was filtered and the filtrate concentrated in vacuo to give the desired compound (4.6 g, yield 99%) as a gray oil.

$^1$H NMR (400 MHz, $CDCl_3$) δ ppm: 1.37 (3H, t, J=7.0), 1.46 (9H, s), 1.70–1.95 (4H, m), 3.25–3.40 (2H, m), 3.60–3.75 (2H, m), 4.30–4.40 (1H, m), 4.34 (2H, q, J=7.0), 6.77 (1H, dd, J=9.0, 3.0), 6.83 (1H, d, J=9.0), 7.12 (1H, d, J=3.0).

Reference Example 60

Ethyl N-[4-(1-t-Butoxycarbonylpiperidin-4-yloxy)-3-ethoxycarbonylphenyl]sulfamoylacetate To a solution of 4-(1-t-butoxycarbonylpiperidin-4-yloxy)-3-ethoxycarbonylaniline (4.6 g) and pyridine (2.0 ml) in dichloromethane (70 ml) was added dropwise ethyl chlorosulfonylacetate (2.5 ml) in an ice bath and the mixture was stirred at room temperature for 6 hours. The reaction mixture was concentrated in vacuo. The residue was suspended in a mixture of hexane/ethyl acetate=1/1 and filtered. The filtrate was purified by chromatography on a silica gel column using hexane/ethyl acetate=1/1 as an eluant to give the desired compound (5.9 g, yield 90%) as an orange amorphous solid.

$^1$H NMR (400 MHz, $CDCl_3$) δ ppm 1.34 (3H, t, J=7.0), 1.37 (3H, t, J=7.0), 1.47 (9H, s), 1.75–1.95 (4H, m), 3.45–3.55 (2H, m), 3.55–3.65 (2H, m), 3.91 (2H, s), 4.30 (2H, q, J=7.0), 4.35 (2H, q, J=7.0), 4.59 (1H, m), 6.97 (1H, d, J=9.0), 7.47 (1H, dd, J=9.0, 3.0), 7.70 (1H, d, J=3.0).

Reference Example 61

Ethyl N-[4-(1-t-Butoxycarbonylpiperidin-4-yloxy)-3-ethoxycarbonylphenyl]-N-[3-(3-cyanaphenyl)-2-(E)-propenyl]sulfamoylacetate To a solution of 3-(3-cyanophenyl)-2-(E)-propen-1-ol (1.7 g), ethyl N-[4-(1-t-butoxycarbonylpiperidin-4-yloxy)-3-ethoxycarbonylphenyl]sulfamoylacetate (5.9 g) and triphenylphosphine (4.5 g) in dichloromethane (100 ml) was added dropwise diethyl azodicarboxylate (2.7 ml) and the mixture was stirred at the same temperature for 3 hours. The reaction mixture was concentrated in vacuo. The residue was purified by chromatography on a silica gel column using hexane/ethyl acetate=2/1 as an eluant to give the desired compound (5.7 g, yield 81%) as a yellow amorphous solid.

$^1$H NMR (500 MHz, $CDCl_3$) δ ppm: 1.35 (3H, t, J=7.0), 1.36 (3H, t, J=7.0), 1.46 (9H, s), 1.75–1.95 (4H, m), 3.45–3.65 (4H, m), 3.99 (2H, s), 4.31 (2H, q, J=7.0), 4.35 (2H, q, J=7.0), 4.49 (2H, d, J=7.0), 4.62 (1H, m), 6.23 (1H, dt, J=16.0, 7.0), 6.41 (1H, d, J=16.0), 6.97 (1H, m), 7.40 (1H, m), 7.45–7.60 (4H, m), 7.89 (1H, m).

Reference Example 62

3-Bromo-4-(1-t-butoxycarbonylpiperidin-4-yloxy)nitrobenzene

To a solution of 1-t-butoxycarbonyl-4-hydroxypiperidine (2.7 g), 3-bromo-4-hydroxynitrobenzene (1.9 g) [which was prepared from 3-bromonitrobenzene according to the method described in J. Org. Chem., 63 4199 (1998)] and triphenylphosphine (4.4 g) in dichloromethane (50 ml) was added dropwise diethyl azodicarboxylate (2.7 ml) and the mixture was stirred at room temperature for 11.5 hours. The reaction mixture was concentrated in vacuo. The residue was purified by chromatography on a silica gel column using hexane/ethyl acetate=2/1 as an eluant to give the desired compound (3.1 g, yield 91%) as a yellow oil.

$^1$H NMR (400 MHz, $CDCl_3$) δ ppm: 1.48 (9H, s), 1.91 (4H, m), 3.59 (4H, m), 4.75 (1H, m), 6.96 (1H, d, J=9.0), 8.19 (1H, dd, J=9.0, 3.0), 8.48 (1H, d, J=3.0).

Reference Example 63

3-Bromo-4-(1-t-butoxycarbonylpiperidin-4-yloxy)aniline

To a solution of 3-bromo-4-(1-t-butoxycarbonylpiperidin-4-yloxy)nitrobenzene (3.1 g) in acetic acid (40 ml) was added zinc powder (10.0 g) in ten portions and the mixture was stirred at room temperature for 5 hours. The reaction mixture was filtered through Celite (trade mark) and the filtrate was extracted with ethyl acetate. The extractant was washed with saturated aqueous potassium carbonate, water and brine, dried over anhydrous magnesium sulfate, filtered and the filtrate concentrated in vacuo. The residue was purified by chromatography on a silica gel column using hexane/ethyl acetate=1/1 as an eluant to give the desired compound (2.0 g, yield 69%) as a brown amorphous solid.

$^1H$ NMR (400 MHz, $CDCl_3$) δ ppm: 1.47 (9H, s), 1.70–1.90 (4H, m), 3.30–3.40 (2H, m), 3.65–3.75 (2H, m), 4.30 (1H, m), 6.57 (1H, dd, J=9.0, 3.0), 6.78 (1H, d, J=9.0), 6.91 (1H, d, J=3.0).

Reference Example 64

Ethyl N-[3-Bromo-4-(1-t-butoxycarbonylpiperidin-4-yloxy)phenyl]sulfamoylacetate

To a solution of 3-bromo-4-(1-t-butoxycarbonylpiperidin-4-yloxy)aniline (2.0 g) and pyridine (0.9 ml) in dichloromethane (60 ml) was added dropwise ethyl chlorosulfonylacetate (0.9 ml) in an ice bath and the mixture was stirred at room temperature for 2 hours. The reaction mixture was concentrated in vacuo. The residue was purified by chromatography on a silica gel column using hexane/ethyl acetate=1/1 as an eluant to give the desired compound (2.1 g, yield 74%) as a yellow amorphous solid.

$^1H$ NMR (500 MHz, $CDCl_3$) δ ppm: 1.34 (3H, t, J=7.0), 1.47 (9H, s), 1.75–1.95 (4H, m), 3.45–3.55 (2H, m), 3.55–3.65 (2H, m), 3.92 (2H, s), 4.29 (2H, q, J=7.0), 4.55 (1H, m), 6.85–6.95 (2H, m), 7.56 (1H, m).

Reference Example 65

Ethyl N-[3-Bromo-4-(1-t-butoxycarbonylpiperidin-4-yloxy)phenyl]-N-[3-(3-cyanophenyl)-2-(E)-propenyl]sulfamoylacetate To a solution of 3-(3-cyanophenyl)-2-(E)-propen-1-ol (0.7 g), ethyl N-[3-bromo-4-(1-t-butoxycarbonylpiperidin-4-yloxy)phenyl]sulfamoylacetate (2.1 g) and triphenylphosphine (1.4 g) in dichloromethane (30 ml) was added dropwise diethyl azodicarboxylate (0.9 ml) and the mixture was stirred at room temperature for 6 hours. The reaction mixture was concentrated in vacuo. The residue was purified by chromatography on a silica gel column using dichloromethane/ethyl acetate=19/1 as an eluant to give the desired compound (2.2 g, yield 82%) as a colorless amorphous solid.

$^1H$ NMR (400 MHz, $CDCl_3$) δ ppm: 1.36 (3H, t, J=7.0), 1.47 (9H, s), 1.75–1.95 (4H, m), 3.45–3.65 (4H, m), 3.99 (2H, s), 4.31 (2H, q, J=7.0), 4.46 (2H, d, J=6.0), 4.58 (1H, m), 6.22 (1H, dt, J=16.0, 6.0), 6.42 (1H, d, J=16.0), 6.90 (1H, m), 7.37 (1H, m), 7.42 (1H, m), 7.45–7.60 (3H, m), 7.71 (1H, m).

Reference Example 66

2-Isopropyl-4-nitrophenol

To a solution of 2-isopropylphenol (4.1 ml) in acetic acid (30 ml) was added 69% nitric acid (4 ml) in an ice bath and the mixture was stirred at the same temperature for 30 minutes. After addition of iced water, the reaction mixture was extracted with t-butyl methyl ether. The extractant was washed with water and brine, dried over anhydrous sodium sulfate, filtered and the filtrate concentrated in vacuo. The residue was purified by chromatography on a silica gel column using hexane/ethyl acetate=4/1 as an eluant to give the desired compound (2.66 g, yield 49%) as a yellow solid.

$^1H$ NMR (400 MHz, $CDCl_3$) δ ppm 1.30 (6H, d, J=7.0), 3.25 (1H, m), 6.82 (1H, d, J=9.0), 8.01 (1H, dd, J=9.0, 2.5), 8.13 (1H, d, J=2.5).

Reference Example 67

4-(1-t-Butoxycarbonylpiperidin-4-yloxy)-3-isopropylnitrobenzene

To a solution of 1-t-butoxycarbonyl-4-hydroxypiperidine (2.96 g), 2-isopropyl-4-nitrophenol (2.66 g) and triphenylphosphine (5.00 g) in dichloromethane (80 ml) was added diethyl azodicarboxylate (3.0 ml) and the mixture was stirred at room temperature for 2 hours. The reaction mixture was concentrated in vacuo. The residue was purified by chromatography on a silica gel column using dichloromethane as an eluant to give the desired compound (4.07 g, yield 76%) as a brown solid.

$^1H$ NMR (400 MHz, $CDCl_3$) δ ppm: 1.26 (6H, d, J=7.0), 1.48 (9H, s), 1.80–1.90 (2H, m), 1.90–2.05 (2H, m), 3.33 (1H, m), 3.52 (2H, m), 3.62 (2H, m), 4.67 (1H, m), 6.87 (1H, d, J=9.0), 8.08 (1H, dd, J=9.0, 3.0), 8.12 (1H, d, J=3.0).

Reference Example 68

4-(1-t-Butoxycarbonylpiperidin-4-yloxy)-3-isopropylaniline

To a solution of 4-(1-t-butoxycarbonylpiperidin-4-yloxy)-3-isopropylnitrobenzene (4.1 g) in methanol (70 ml) was added palladium on carbon (0.4 g) and the mixture was stirred under a hydrogen atmosphere at room temperature for 3 hours. The reaction mixture was filtered and the filtrate concentrated in vacuo. The residue was purified by chromatography on a silica gel column using hexane/ethyl acetate=3/2 as an eluant to give the desired compound (2.8 g, yield 74%) as a red oil.

$^1H$ NMR (400 MHz, $CDCl_3$) δ ppm: 1.18 (6H, d, J=7.0), 1.47 (9 H, s), 1.70–1.80 (2H, m), 1.85–1.95 (2H, m), 3.20–3.40 (3H, m), 3.60–3.75 (2H, m), 4.29 (1 H, m), 6.47 (1H, dd, J=9.0, 3.0), 6.60 (1H, d, J=3.0), 6.68 (1H, d, J=9.0).

Reference Example 69

Ethyl N-[4-(1-t-Butoxycarbonylpiperidin-4-yloxy)-3-isopropylphenyl]sulfamoylacetate To a solution of 4-(1-t-butoxycarbonylpiperidin-4-yloxy)-3-isopropylaniline (2.8 g) and pyridine (1.4 ml) in dichloromethane (80 ml) was added dropwise ethyl chlorosulfonylacetate (1.5 ml) in an ice bath and the mixture was stirred at room temperature for 4 hours. The reaction mixture was concentrated in vacuo. The residue was purified by chromatography on a silica gel column using dichloromethane/ethyl acetate=19/1 as an eluant to give the desired compound (3.3 g, yield 80%) as a yellow amorphous solid.

$^1H$ NMR (500 MHz, $CDCl_3$) δ ppm: 1.20 (6H, d, J=7.0), 1.37 (3H, t, J=7.0), 1.48 (9H, s), 1.75–1.85 (2H, m), 1.85–1.95 (2H, m), 3.30 (1H, m), 3.40–3.50 (2H, m), 3.55–3.65 (2H, m), 3.90 (2H, s), 4.30 (2H, q, J=7.0), 4.50 (1H, m), 6.80 (1H, d, J=9.0), 7.13 (1H, dd, J=9.0, 3.0), 7.17 (1H, d, J=3.0).

Reference Example 70

Ethyl N-[4-(1-t-Butoxycarbonylpiperidin-4-yloxy)-3-isopropylphenyl]-N-[3-(3-cyanophenyl)-2-(E)-propenyl]sulfamoylacetate To a solution of 3-(3-cyanophenyl)-2-(E)-propen-1-ol (0.5 g), ethyl N-[4-(1-t-butoxycarbonylpiperidin-4-yloxy)-3-isopropylphenyl]sulfamoylacetate (1.5 g) and triphenylphosphine (1.1 g) in dichloromethane (50 ml) was added dropwise diethyl azodicarboxylate (0.7 ml) in an ice bath and the mixture was stirred at the same temperature for 4 hours. The reaction mixture was concentrated in vacuo. The residue was purified by chromatography on a silica gel column using dichloromethane/ethyl acetate=19/1 as an eluant to give the desired compound (1.8 g, yield 96%) as a yellow amorphous solid.

$^1H$ NMR (500 MHz, $CDCl_3$) δ ppm: 1.18 (6H, d, J=7.0), 1.36 (3H, t, J=7.0), 1.47 (9H, s), 1.75–1.85 (2H, m), 1.85–1.95 (2H, m), 3.29 (1H, m), 3.40–3.50 (2H, m), 3.55–3.65 (2H, m), 3.99 (2H, s), 4.31 (2H, q, J=7.0), 4.46 (2H, d, J=6.0), 4.52 (1H, m), 6.25 (1H, dt, J=16.0, 6.0), 6.40 (1H, d, J=16.0), 6.81 (1H, d, J=9.0), 7.22 (1H, dd, J=9.0, 3.0), 7.31 (1H, d, J=3.0), 7.40 (1H, m), 7.45–7.60 (3H, m).

Reference Example 71

4-(1-t-Butoxycarbonylpiperidin-4-yloxy)-3-carboxynitrobenzene

To a solution of 4-(1-t-butoxycarbonylpiperidin-4-yloxy)-3-ethoxycarbonylnitrobenzene (1.0 g) in ethanol (10 ml) was added aqueous potassium hydroxide solution (0.2 g in 0.5 ml) and the mixture was heated under reflux for 2 hours. After neutralization with 1M hydrochloric acid, the reaction mixture was extracted with ethyl acetate. The extract was washed with water and brine. The organic layer was dried over anhydrous magnesium sulfate, filtered and the filtrate concentrated in vacuo to give the desired compound (0.9 g, yield 96%) as a yellow solid.

$^1H$ NMR (500 MHz, $CDCl_3$) δ ppm: 1.48 (9H, s), 1.85–1.95 (2H, m), 2.00–2.10 (2H, m), 3.45–3.55 (2H, m), 3.65–3.75 (2H, m), 4.87 (1H, m), 7.13 (1H, d, J=9.0), 8.39 (1H, dd, J=9.0, 3.0), 8.93 (1H, d, J=3.0).

Reference Example 72

4-(1-t-Butoxycarbonylpiperidin-4-yloxy)-3-carbamoylnitrobenzene

To a solution of 4-(1-t-butoxycarbonylpiperidin-4-yloxy)-3-carboxynitrobenzene (0.9 g) in dichloromethane (20 ml) were added isobutyl chloroformate (0.3 ml) and triethylamine (0.4 ml) in an ice bath and the mixture was stirred at the same temperature for 1 hour. To the reaction mixture was added 28% aqueous ammonia (0.2 ml) and the resulting mixture was stirred at room temperature for 1 hour. The reaction mixture was concentrated in vacuo. The residue was purified by chromatography on a silica gel column using dichloromethane/methanol=19/1 as an eluant to give the desired compound (0.9 g, yield 98%) as a pale yellow amorphous solid.

$^1H$ NMR (500 MHz, $CDCl_3$) δ ppm: 1.48 (9H, s), 1.80–1.90 (2H, m), 2.05–2.20 (2H, m), 3.30–3.40 (2H, m), 3.75–3.90 (2H, m), 4.81 (1H, m), 7.11 (1H, d, J=9.0), 8.33 (1H, dd, J=9.0, 3.0), 9.09 (1H, d, J=3.0).

Reference Example 73

4-(1-t-Butoxycarbonylpiperidin-4-yloxy)-3-carbamoylaniline

To a solution of 4-(1-t-butoxycarbonylpiperidin-4-yloxy)-3-carbamoylnitrobenzene (5.7 g) in methanol (80 ml) was added palladium on carbon (0.6 g) and the mixture was stirred under a hydrogen atmosphere at room temperature for 2.5 hours. The reaction mixture was filtered. The filtrate was purified by chromatography on a silica gel column using dichloromethane/methanol=19/1 as an eluant to give the desired compound (4.8 g, yield 91%) as a pale yellow amorphous solid.

$^1H$ NMR (500 MHz, $CDCl_3$) δ ppm: 1.47 (9H, s), 1.65–1.80 (2H, m), 1.95–2.05 (2H, m), 3.19 (2H, m), 3.75–3.85 (2H, m), 4.44 (1H, m), 6.78 (1H, dd, J=9.0, 3.0), 6.84 (1H, d, J=9.0), 7.50 (1H, d, J=3.0).

Reference Example 74

Ethyl N-[4-(1-t-Butoxycarbonylpiperidin-4-yloxy)-3-carbamoylphenyl]sulfamoylacetate To a solution of 4-(1-t-butoxycarbonylpiperidin-4-yloxy)-3-carbamoylaniline (4.8 g) and pyridine (2.3 ml) in dichloromethane (80 ml) was added dropwise ethyl chlorosulfonylacetate (2.5 ml) in an ice bath and the mixture was stirred at room temperature for 6 hours. The reaction mixture was concentrated in vacuo. The residue was purified by chromatography on a silica gel column using dichloromethane/methanol=19/1 as an eluant to give the desired compound (3.7 g, yield 53%) as a pale yellow solid.

$^1H$ NMR (500 MHz, $CDCl_3$) δ ppm 1.32 (3H, t, J=7.0), 1.47 (9H, s), 1.70–1.85 (2H, m), 2.00–2.15 (2H, m), 3.27 (2H, m), 3.75–3.85 (2H, m), 3.94 (2H, s), 4.28 (2H, q, J=7.0), 4.65 (1H, m), 7.02 (1H, d, J=9.0), 7.59 (1H, dd, J=9.0, 3.0), 8.12 (1H, d, J=3.0).

Reference Example 75

Ethyl N-[4-(1-t-Butoxycarbonylpiperidin-4-yloxy)-3-carbamoylphenyl]-N-[3-(3-cyanophenyl)-2-(E)-propenyl]sulfamoylacetate To a solution of 3-(3-cyanophenyl)-2-(E)-propen-1-ol (0.7 g), ethyl N-[4-(1 -t-butoxycarbonylpiperidin-4-yloxy)-3-carbamoylphenyl]sulfamoylacetate (2.0 g) and triphenylphosphine (1.5 g) in dichloromethane (30 ml) was added dropwise diethyl azodicarboxylate (0.9 ml) and the mixture was stirred at room temperature for 8 hours. The reaction mixture was concentrated in vacuo. The residue was purified by chromatography on a silica gel column using hexane/ethyl acetate=1/2 as an eluant to give the desired compound (2.5 g, yield 94%) as a yellow amorphous solid.

$^1H$ NMR (500 MHz, $CDCl_3$) δ ppm: 1.36 (3H, t, J=7.0), 1.47 (9H, s), 1.75–1.85 (2H, m), 2.00–2.10 (2H, m), 3.27 (2H, m), 3.75–3.85 (2H, m), 3.99 (2H, s), 4.31 (2H, q, J=7.0), 4.53 (2H, d, J=7.0), 4.66 (1H, m), 6.22 (1H, dt, J=16.0, 7.0), 6.42 (1H, d, J=16.0), 7.01 (1H, m), 7.39 (1H, m), 7.45–7.60 (2H, m), 7.65–7.75 (2H, m), 8.32 (1H, m).

Reference Example 76

4-(1-t-Butoxycarbonylpiperidin-4-yloxy)-3-(N-methylcarbamoyl)nitrobenzene

To a solution of 4-(1-t-butoxycarbonylpiperidin-4-yloxy)-3-carboxynitrobenzene (3.3 g) in dichloromethane (50 ml) were added isobutyl chloroformate (1.4 ml) and triethylamine (1.4 ml) in an ice bath and the mixture was stirred at the same temperature for 0.5 hours. To the reaction mixture was added 40% aqueous methylamine (1.1 ml) and the resulting mixture was stirred at room temperature for 3 hours. The reaction mixture was concentrated in vacuo. The residue was purified by chromatography on a silica gel column using dichloromethane/methanol=19/1 as an eluant to give the desired compound (3.5 g, yield quantitative) as a yellow amorphous solid.

$^1$H NMR (500 MHz, $CDCl_3$) δ ppm: 1.48 (9H, s), 1.80–1.90 (2H, m), 2.05–2.15 (2H, m), 3.04 (3H, m), 3.30–3.40 (2H, m), 3.75–3.85 (2H, m), 4.79 (1H, m), 7.08 (1H, d, J=9.0), 8.29 (1H, dd, J=9.0, 3.0), 9.07 (1H, d, J=3.0).

Reference Example 77

4-(1-t-Butoxycarbonylpiperidin-4-yloxy)-3-(N-methylcarbamoyl)aniline

To a solution of 4-(1-t-butoxycarbonylpiperidin-4-yloxy)-3-(N-methylcarbamoyl)nitrobenzene (3.5 g) in methanol (50 ml) was added palladium on carbon (0.4 g) and the mixture was stirred under a hydrogen atmosphere at room temperature for 1 hour. The reaction mixture was filtered. The filtrate was concentrated in vacuo. The residue was purified by chromatography on a silica gel column using dichloromethane/methanol=19/1 as an eluant to give the desired compound (2.9 g, yield 92%) as a yellow amorphous solid.

$^1$H NMR (500 MHz, $CDCl_3$) δ ppm: 1.47 (9H, s), 1.65–1.75 (2H, m), 1.95–2.05 (2H, m), 2.99 (3H, m), 3.20 (2H, m), 3.75–3.85 (2H, m), 4.40 (1H, m), 6.74 (1H, dd, J=9.0, 3.0), 6.81 (1H, d, J=9.0), 7.50 (1H, d, J=3.0).

Reference Example 78

Ethyl N-[4-(1-t-Butoxycarbonylpiperidin-4-yloxy)-3-(N'-methylcarbamoyl)phenyl]sulfamoylacetate To a solution of 4-(1-t-butoxycarbonylpiperidin-4-yloxy)-3-(N-methylcarbamoyl)aniline (2.9 g) and pyridine (0.8 ml) in dichloromethane (50 ml) was added dropwise ethyl chlorosulfonylacetate (1.3 ml) in an ice bath and the mixture was stirred at room temperature for 1 hour. The reaction mixture was concentrated in vacuo. The residue was purified by chromatography on a silica gel column using dichloromethane/ethyl acetate 2/1 as an eluant to give the desired compound (3.0 g, yield 72%) as a pale yellow solid.

$^1$H NMR (500 MHz, $CDCl_3$) δ ppm: 1.28 (3H, t, J=7.0), 1.48 (9H, s), 1.70–1.85 (2H, m), 2.00–2.15 (2H, m), 3.05 (3H, m), 3.29 (2H, m), 3.70–3.85 (2H, m), 3.95 (2H, s), 4.22 (2H, q, J=7.0), 4.63 (1H, m), 7.00 (1H, d, J=9.0), 7.61 (1H, dd, J=9.0, 3.0), 8.27 (1H, d, J=3.0).

Reference Example 79

Ethyl N-[4-(1-t-Butoxycarbonylpiperidin-4-yloxy)-3-(N'-methylcarbamoyl)phenyl]-N-[3-(3-cyanophenyl)-2-(E)-propenyl]sulfamoylacetate To a solution of 3-(3-cyanophenyl)-2-(E)-propen-1-ol (0.5 g), ethyl N-[4-(1-t-butoxycarbonylpiperidin-4-yloxy)-3-(N'-methylcarbamoyl)phenyl]sulfamoylacetate (1.5 g) and triphenylphosphine (1.0 g) in dichloromethane (40 ml) was added dropwise diethyl azodicarboxylate (0.6 ml) in an ice bath and the mixture was stirred at room temperature for 3 hours. The reaction mixture was concentrated in vacuo. The residue was purified by chromatography on a silica gel column using hexane/ethyl acetate=1/2 as an eluant to give the desired compound (1.5 g, yield 77%) as a colorless amorphous solid.

$^1$H NMR (500 MHz, $CDCl_3$) δ ppm: 1.36 (3H, t, J=7.0), 1.47 (9H, s), 1.75–1.85 (2H, m), 2.00–2.10 (2H, m), 3.01 (3H, m), 3.30 (2H, m), 3.70–3.80 (2H, m), 3.99 (2H, s), 4.32 (2H, q, J=7.0), 4.53 (2H, d, J=7.0), 4.64 (1H, m), 6.22 (1H, dt, J=16.0, 7.0), 6.42 (1H, d, J=16.0), 6.98 (1H, m), 7.35–7.45 (1H, m), 7.45–7.55 (4H, m), 8.33 (1H, m).

Reference Example 80

4-(1-t-Butoxycarbonylpiperidin-4-yloxy)-3-(N,N-dimethylcarbamoyl)nitrobenzene

To a solution of 4-(1-t-butoxycarbonylpiperidin-4-yloxy)-3-carboxynitrobenzene (3.4 g) in dichloromethane (60 ml) were added isobutyl chloroformate (1.4 ml) and triethylamine (1.5 ml) in an ice bath and the mixture was stirred at the same temperature for 0.5 hours. To the reaction mixture was added 50% aqueous dimethylamine (1.1 ml) and the resulting mixture was stirred at room temperature for 2 hours. The reaction mixture was concentrated in vacuo. The residue was purified by chromatography on a silica gel column using dichloromethane/methanol=19/1 as an eluant to give the desired compound (3.1 g, yield 83%) as a pale yellow amorphous solid.

$^1$H NMR (400 MHz, $CDCl_3$) δ ppm 1.47 (9H, s), 1.75–2.10 (4H, m), 2.89 (3H, s), 3.14 (3H, s), 3.35–3.65 (4H, m), 4.69 (1H, m), 7.00 (1H, d, J=9.0), 8.20 (1H, d, J=3.0), 8.25 (1H, dd, J=9.0, 3.0).

Reference Example 81

4-(1-t-Butoxycarbonylpiperidin-4-yloxy)-3-(N,N-dimethylcarbamoyl)aniline

To a solution of 4-(1-t-butoxycarbonylpiperidin-4-yloxy)-3-(N,N-dimethylcarbamoyl)nitrobenzene (3.1 g) in methanol (30 ml) was added palladium on carbon (0.3 g) and the mixture was stirred under a hydrogen atmosphere at room temperature for 1 hour. The reaction mixture was filtered. The filtrate was concentrated in vacuo. The residue was purified by chromatography on a silica gel column using dichloromethane/methanol 19/1 as an eluant to give the desired compound (2.8 g, yield 99%) as a yellow amorphous solid.

$^1$H NMR (400 NHz, $CDCl_3$) δ ppm: 1.45 (9H, s), 1.55–1.95 (4H, m), 2.89 (3H, s), 3.09 (3H, s), 3.25–3.40 (2H, m); 3.50–3.65 (2H, m), 4.20–4.30 (1H, m), 6.61 (1H, d, J=3.0), 6.64 (1H, dd, J=9.0, 3.0), 6.76 (1H, d, J=9.0).

Reference Example 82

Ethyl N-[4-(1-t-Butoxycarbonylpiperidin-4-yloxy)-3-(N',N'-dimethylcarbamoyl)phenyl]sulfamoylacetate To a solution of 4-(1-t-butoxycarbonylpiperidin-4-yloxy)-3-(N,N-dimethylcarbamoyl)aniline (2.8 g) and pyridine (0.7 ml) in dichloromethane (30 ml) was added dropwise ethyl chlorosulfonylacetate (1.2 ml) in an ice bath and the mixture was stirred at room temperature for 1 hour. The reaction mixture was concentrated in vacuo. The residue was purified by chromatography on a silica gel column using dichloromethane/ethyl acetate 1/1 as an eluant to give the desired compound (3.3 g, yield 79%) as a yellow amorphous solid.

$^1$H NMR (400 MHz, $CDCl_3$) δ ppm: 1.32 (3H, t, J=7.0), 1.46 (9H, s), 1.70–2.00 (4H, m), 2.87 (3H, s), 3.10 (3H, s), 3.30–3.50 (2H, m), 3.50–3.60 (2H, m), 3.93 (2H, s), 4.28 (2H, q, J=7.0), 4.48 (1H, m), 6.91 (1H, d, J=9.0), 7.22 (1H, d, J=3.0), 7.34 (1H, dd, J=9.0, 3.0).

Reference Example 83

Ethyl N-[4-(1-t-Butoxycarbonylpiperidin-4-yloxy)-3-(N',N'-dimethylcarbamoyl)phenyl]-N-[3-(3-cyanophenyl)-2-(E)-propenyl]sulfamoylacetate To a solution of 3-(3-cyanophenyl)-2-(E)-propen-1-ol (0.5 g), ethyl N-(4-(1-t-butoxycarbonylpiperidin-4-yloxy)-

3-(N',N'-dimethylcarbamoyl)phenyl]sulfamoylacetate (1.5 g) and triphenylphosphine (1.0 g) in dichloromethane (30 ml) was added dropwise diethyl azodicarboxylate (0.6 ml) in an ice bath and the mixture was stirred at room temperature for 3 hours. The reaction mixture was concentrated in vacuo. The residue was purified by chromatography on a silica gel column using hexane/ethyl acetate=1/2 as an eluant to give the desired compound (1.7 g, yield 88%) as a coloress amorphous solid.

$^1$H NMR (400 MHz, $CDCl_3$) δ ppm: 1.34 (3H, t, J=7.0), 1.46 (9H, s), 1.75–2.00 (4H, m), 2.83 (3H, s), 3.10 (3H, s), 3.30–3.60 (4H, m), 3.95–4.05 (2H, m), 4.30 (2H, q, J=7.0), 4.47 (2H, d, J=7.0), 4.52 (1H, m), 6.23 (1H, dt, J=16.0, 7.0), 6.42 (1H, d, J=16.0), 6.92 (1H, m), 7.35–7.55 (6H, m).

Reference Example 84

5-Cyano-2-hydroxybenzaldehyde

To a solution of 4-cyanophenol (25.0 g) in trifluoroacetic acid (150 ml) was added hexamethylenetetramine (50.0 g) and the mixture was stirred at 100° C. for 9 hours. After cooling to room temperature, sulfuric acid (50 ml) and water (300 ml) were added to the reaction mixture. The resulting mixture was stirred at room temperature for 1 hour. The reaction mixture was extracted with dichloromethane. The extract was washed with water and brine. The organic layer was dried over anhydrous magnesium sulfate, filtered and the filtrate concentrated in vacuo. The residue was purified by chromatography on a silica gel column using dichloromethane/ethyl acetate=19/1 as an eluant to give the desired compound (4.3 g, yield 13%) as a colorless solid.

$^1$H NMR (400 MHz, $CDCl_3$) δ ppm: 7.11 (1H, d, J=9.0), 7.78 (1H, dd, J=9.0, 2.0), 7.94 (1H, d, J=2.0), 9.93 (1H, s).

Reference Example 85

5-Cyano-2-hydroxycinnamaldehyde

A solution of 5-cyano-2-hydroxybenzaldehyde (4.3 g) and (triphenylphosphoranylidene)acetaldehyde (9.4 g) in toluene (150 ml) was stirred at 70° C. for 2 hours. The reaction mixture was concentrated in vacuo. The residue was purified by chromatography on a silica gel column using dichloromethane/ethyl acetate=3/1 as an eluant to give the desired compound (2.3 g, yield 44%) as a colorless solid.

$^1$H NMR (400 MHz, DMSO-$d_6$) δ ppm: 6.98 (1H, dd, J=16.0, 8.0), 7.08 (1H, d, J=9.0), 7.73 (1H, d, J=9.0), 7.83 (1H, d, J=16.0), 8.22 (1H, s), 9.67 (1H, d, J=8.0).

Reference Example 86

5-Cyano-2-methoxymethoxycinnamaldehyde

To a solution of 5-cyano-2-hydroxycinnamaldehyde (2.3 g) in N,N-dimethylformamide (25 ml) were added methoxymethyl chloride (1.5 ml) and triethylamine (2.8 ml) in an ice bath and the mixture was stirred at room temperature for 1 hour. The reaction mixture was extracted with ethyl acetate. The extract was washed with brine. The organic layer was dried over anhydrous magnesium sulfate, filtered and the filtrate concentrated in vacuo to give the desired compound (2.8 g, yield 98%) as a colorless solid.

$^1$H NMR (400 MHz, $CDCl_3$) δ ppm: 3.52 (3H, s), 5.36 (2H, s), 6.80 (1H, dd, J=16.0, 8.0), 7.30 (1H, d, J=9.0), 7.66 (1H, dd, J=9.0, 2.0), 7.75 (1H, d, J=16.0), 7.84 (1H, d, J=2.0), 9.74 (1H, d, J=8.0).

Reference Example 87

3-(5-Cyano-2-methoxymethoxyphenyl)-2-(E)-propen-1-ol

To a solution of 5-cyano-2-methoxymethoxycinnamaldehyde (2.8 g) in a mixture of dichloromethane (20 ml) and ethanol (40 ml) was added cerium chloride (1.7 g) in an ice bath and the mixture was stirred at the same temperature for 0.5 hours. To the resulting mixture was added sodium borohydride (0.9 g) and the mixture was stirred at the same temperature for 2 hours. After addition of saturated aqueous ammonium chloride, the reaction mixture was extracted with dichloromethane. The extract was washed with water and brine. The organic layer was dried over anhydrous magnesium sulfate, filtered and the filtrate concentrated in vacuo. The residue was purified by chromatography on a silica gel column using hexane/ethyl acetate=1/1 as an eluant to give the desired compound (2.6 g, yield 93%) as a yellow oil.

$^1$H NMR (500 MHz, $CDCl_3$) δ ppm: 3.49 (3H, s), 4.37 (2H, d, J=5.0), 5.27 (2H, s), 6.41 (1H, dt, J=16.0, 5.0), 6.90 (1H, d, J=16.0), 7.18 (1H, d, J=9.0), 7.49 (1H, dd, J=9.0, 2.0), 7.72 (1H, d, J=2.0).

Reference Example 88

Ethyl N-[4-(1-t-Butoxycarbonylpiperidin-4-yloxy)-3-chlorophenyl]-N-[3-(5-cyano-2-methoxymethoxyphenyl)-2-(E)-propenyl]sulfamoylacetate To a solution of 3-(5-cyano-2-methoxymethoxyphenyl)-2-(E)-propen-1-ol (0.6 g), ethyl N-[4-(1-t-butoxycarbonylpiperidin-4-yloxy)-3-chlorophenyl]sulfamoylacetate (1.3 g) and triphenylphosphine (0.9 g) in dichloromethane (40 ml) was added dropwise diethyl azodicarboxylate (0.6 ml) in an ice bath and the mixture was stirred at room temperature for 1.5 hours. The reaction mixture was concentrated in vacuo. The residue was purified by chromatography on a silica gel column using dichloromethane/ethyl acetate=9/1 as an eluant to give the desired compound (1.4 g, yield 74%) as a yellow amorphous solid.

$^1$H NMR (500 MHz, $CDCl_3$) δ ppm: 1.36 (3H, t, J=7.0), 1.47 (9H, s), 1.75–1.85 (2H, m), 1.85–1.95 (2H, m), 3.40–3.50 (2H, m), 3.44 (3H, s), 3.55–3.65 (2H, m), 3.99 (2H, s), 4.31 (2H, q, J=7.0), 4.48 (2H, d, J=7.0), 4.55 (1H, m), 5.23 (2H, s), 6.17 (1H, dt, J=16.0, 7.0), 6.70 (1H, d, J=16.0), 6.94 (1H, d, J=9.0), 7.13 (1H, d, J=9.0), 7.34 (1H, dd, J=9.0, 3.0), 7.47 (1H, dd, J=9.0, 2.0), 7.55 (1H, d, J=3.0), 7.61 (1H, d, J=2.0).

Reference Example 89

Methyl 3-Chloro-5-nitrosalicylate

To a solution of 3-chlorosalicylic acid (4.5 g) in a mixture of methanol (10 ml) and benzene (40 ml) was added a solution of 2M (trimethylsilyl)diazomethane in hexane (20 ml) in an ice bath and the mixture was stirred at room temperature for 2 hours. The reaction mixture was concentrated in vacuo. To the residual colorless oil were added 69% nitric acid (15 ml) and concentrated sulfuric acid (15 ml) and the mixture was stirred at room temperature for 0.5 hours. The reaction mixture was poured into iced water and extracted with ethyl acetate. The extract was washed with water and brine. The organic layer was dried over anhydrous magnesium sulfate, filtered and the filtrate concentrated in vacuo to afford a yellow solid. To the solid was added hexane and the mixture was filtered to give the desired compound (2.4 g, yield 39%) as a yellow solid.

$^1$H NMR (500 MHz, $CDCl_3$) δ ppm: 4.07 (3H, s), 8.47 (1H, d, J=3.0), 8.72 (1H, d, J=3.0).

Reference Example 90

4-(1-t-Butoxycarbonylpiperidin-4-yloxy)-3-chloro-5-methoxycarbonylnitrobenzene To a solution of 1-t-butoxycarbonyl-4-hydroxypiperidine (6.3 9), methyl 3-chloro-5-nitrosalicylate (2.4 g) and triphenylphosphine (10.8 g) in dichloromethane (100 ml) was added diethyl azodicarboxylate (6.6 ml) and the mixture was stirred at room temperature for 4 hours. The reaction mixture was concentrated in vacuo. The residue was purified by chromatography on a silica gel column using hexane/ethyl acetate=4/1 as an eluant to give the desired compound (3.4 g, yield 79%) as a pink solid.

$^1$H NMR (500 MHz, $CDCl_3$) δ ppm: 1.47 (9H, s), 1.75–1.85 (2H, m), 1.85–1.95 (2H, m), 3.11 (2H, m), 3.85–3.95 (2H, m), 3.97 (3H, s), 4.44 (1H, m), 8.43 (1H, d, J=3.0), 8.56 (1H, d, J=3.0).

Reference Example 91

4-(1-t-Butoxycarbonylpiperidin-4-yloxy)-5-carboxy-3-chloronitrobenzene

A solution of 4-(1-t-butoxycarbonylpiperidin-4-yloxy)-3-chloro-5-methoxycarbonylnitrobenzene (3.4 g) in concentrated hydrochloric acid (30 ml) was stirred at 75° C. for 16 hours. The reaction mixture was concentrated in vacuo. To a solution of the residual colorless solid in a mixture of water (15 ml) and acetone (15 ml) were added sodium hydrogencarbonate (1.6 g) and di-t-butyldicarbonate (2.2 g) in an ice bath. The resulting mixture was stirred at 40° C. for 1 hour. The reaction mixture was extracted with ethyl acetate. The extract was washed with 0.5M hydrochloric acid, water and brine. The organic layer was dried over anhydrous magnesium sulfate, filtered and the filtrate concentrated in vacuo to afford a pale yellow solid. To the solid was added hexane and the mixture was filtered to give the desired compound (2.6 g, yield 79%) as a pale yellow solid.

$^1$H NMR (500 MHz, $CDCl_3$) δ ppm: 1.48 (9H, s), 1.85–1.95 (2H, m), 1.95–2.05 (2H, m), 3.16 (2H, m), 3.90–4.00 (2H, m), 4.54 (1H, m), 8.45 (1H, d, J=3.0), 8.70 (1H, d, J=3.0).

Reference Example 92

4-(1-t-Butoxycarbonylpiperidin-4-yloxy)-5-carbamoyl-3-chloronitrobenzene

To a solution of 4-(1-t-butoxycarbonylpiperidin-4-yloxy)-5-carboxy-3-chloronitrobenzene (2.6 g) in dichloromethane (80 ml) were added isobutyl chloroformate (1.0 ml) and triethylamine (1.1 ml) in an ice bath and the mixture was stirred at the same temperature for 0.5 hours. To the reaction mixture was added 28% aqueous ammonia (0.5 ml) and the resulting mixture was stirred at room temperature for 1 hour. The reaction mixture was concentrated in vacuo. The residue was purified by chromatography on a silica gel column using dichloromethane/methanol 19/1 as an eluant to give the desired compound (2.2 g, yield 84%) as a pale yellow amorphous solid.

$^1$H NMR (500 MHz, $CDCl_3$) δ ppm: 1.47 (9H, s), 1.75–1.85 (2H, m), 2.00–2.10 (2H, m), 2.85 (2H, m), 4.05–4.15 (2H, m), 4.51 (1H, m), 8.42 (1H, d, J=3.0), 8.79 (1H, d, J=3.0).

Reference Example 93

4-(1-t-Butoxycarbonylpiperidin-4-yloxy)-5-carbamoyl-3-chloroaniline

To a solution of 4-(1-t-butoxycarbonylpiperidin-4-yloxy)-5-carbamoyl-3-chloronitrobenzene (2.2 g) in acetic acid (100 ml) was added tin powder (9.9 g) and the mixture was stirred at room temperature for 11 hours. The reaction mixture was filtered through Celite (trade mark) and the filtrate was concentrated in vacuo. The residual pale yellow solid was dissolved in aqueous potassium carbonate and extracted with ethyl acetate. The extract was washed with water and brine. The organic layer was dried over anhydrous magnesium sulfate, filtered and the filtrate concentrated in vacuo to give the desired compound (1.7 g, yield 83%) as a yellow amorphous solid.

$^1$H NMR (500 MHz, $CDCl_3$) δ ppm: 1.46 (9H, s), 1.65–1.75 (2H, m), 1.95–2.05 (2H, m), 2.77 (2H, m), 3.70–3.80 (2H, m), 4.17 (1H, m), 6.84 (1H, d, J=3.0), 7.19 (1H, d, J=3.0).

Reference Example 94

Ethyl N-[4-(1-t-Butoxycarbonylpiperidin-4-yloxy)-5-carbamoyl-3-chlorophenyl]sulfamoylacetate To a solution of 4-(1-t-butoxycarbonylpiperidin-4-yloxy)-5-carbamoyl-3-chloroaniline (1.7 g) and pyridine (0.7 ml) in dichloromethane (30 ml) was added dropwise ethyl chlorosulfonylacetate (0.7 ml) in an ice bath and the mixture was stirred at room temperature for 1 hour. The reaction mixture was concentrated in vacuo. The residue was purified by chromatography on a silica gel column using dichloromethane/methanol=1/1 as an eluant to give the desired compound (1.2 g, yield 48%) as a pale yellow solid.

$^1$H NMR (500 MHz, DMSO-$d_6$) δ ppm: 1.17 (3H, t, J=7.0), 1.40 (9H, s), 1.55–1.65 (2H, m), 1.80–1.90 (2H, m), 2.95–3.05 (2H, m), 3.70–3.80 (2H, m), 4.10 (2H, q, J=7.0), 4.21 (1H, m), 4.27 (2H, s), 7.28 (1H, d, J=3.0), 7.36 (1H, d, J=3.0).

Reference Example 95

Ethyl N-[4-(1-t-Butoxycarbonylpiperidin-4-yloxy)-5-carbamoyl-3-chlorophenyl]-N-[3-(3-cyanophenyl)-2-(E)-propenyl]sulfamoylacetate To a solution of 3-(3-cyanophenyl)-2-(E)-propen-1-ol (0.4 g), ethyl N-[4-(1-t-butoxycarbonylpiperidin-4-yloxy)-5-carbamoyl-3-chlorophenyl]sulfamoylacetate (1.2 g) and triphenylphosphine (0.8 g) in a mixture of dichloromethane (50 ml) and tetrahydrofuran (20 ml) was added dropwise diethyl azodicarboxylate (0.5 ml) in an ice bath and the mixture was stirred at room temperature for 1 hour. The reaction mixture was concentrated in vacuo. The residue was purified by chromatography on a silica gel column using dichloromethane/ethyl acetate=3/2 as an eluant to give the desired compound (1.5 g, yield quantitative) as a yellow amorphous solid.

$^1$H NMR (400 MHz, $CDCl_3$) δ ppm: 1.35 (3H, t, J=7.0), 1.46 (9H, s), 1.65–1.80 (2H, m), 1.95–2.05 (2H, m), 2.79 (2H, m), 4.00 (2H, s), 4.00–4.15 (2H, m), 4.31 (2H, q, J=7.0), 4.38 (1H, m), 4.53 (2H, d, J=7.0), 6.21 (1H, dt, J=16.0, 7.0), 6.46 (1H, d, J=16.0), 7.23 (1H, m), 7.41 (1H, m), 7.50–7.60 (3H, m), 8.03 (1H, m).

Reference Example 96

Methyl 3-Methyl-5-nitrosalicylate

To a solution of 3-methylsalicylic acid (5.1 g) in a mixture of methanol (10 ml) and benzene (40 ml) was added a solution of 2M (trimethylsilyl)diazomethane in hexane (25 ml) in an ice bath and the mixture was stirred at room temperature for 1 hour. The reaction mixture was concentrated in vacuo. The residual colorless oil was added to 69% nitric acid (15 ml) and concentrated sulfuric acid (15 ml) and the mixture was stirred at room temperature for 1 hour. The reaction mixture was poured into iced water and extracted with ethyl acetate. The extract was washed with water and brine. The organic layer was dried over anhydrous magnesium sulfate, filtered and the filtrate concentrated in vacuo. The residue was purified by chromatography on a silica gel column using hexane/ethyl acetate=2/1 as an eluant to afford a yellow solid. To the solid was added hexane and the mixture was filtered to give the desired compound (1.8 g, yield 25%) as a pale yellow solid.

$^1$H NMR (500 MHz, $CDCl_3$) δ ppm: 2.35 (3H, s), 4.03 (3H, s), 8.21 (1H, d, J=3.0), 8.66 (1H, d, J=3.0).

Reference Example 97

4-(1-t-Butoxycarbonylpiperidin-4-yloxy)-3-methoxycarbonyl-5-methylnitrobenzene

To a solution of 1-t-butoxycarbonyl-4-hydroxypiperidine (4.2 g), methyl 3-methyl-5-nitrosalicylate (1.8 g) and triphenylphosphine (6.8 g) in dichloromethane (100 ml) was added diethyl azodicarboxylate (4.1 ml) and the mixture was stirred at room temperature for 3 hours. The reaction mixture was concentrated in vacuo. The residue was purified by chromatography on a silica gel column using hexane/ethyl acetate=4/1 as an eluant to give the desired compound (3.1 g, yield 91%) as a rose oil.

$^1$H NMR (400 MHz, $CDCl_3$) δ ppm: 1.47 (9H, s), 1.65–1.75 (2H, m), 1.85–1.95 (2H, m), 2.39 (3H, s), 2.97 (2H, m), 3.90–4.00 (2H, m), 3.95 (3H, s), 4.16 (1H, m), 8.22 (1H, d, J=3.0), 8.52 (1H, d, J=3.0).

Reference Example 98

4-(1-t-Butoxycarbonylpiperidin-4-yloxy)-3-carboxy-5-methylnitrobenzene

A solution of 4-(1-t-butoxycarbonylpiperidin-4-yloxy)-3-methoxycarbonyl-5-methylnitrobenzene (4.0 g) in concentrated hydrochloric acid (40 ml) was stirred at 75° C. for 7 hours. The reaction mixture was concentrated in vacuo. To a solution of the residual colorless solid in a mixture of water (20 ml) and acetone (20 ml) were added sodium hydrogencarbonate (1.9 g) and di-t-butyl dicarbonate (2.7 g) in an ice bath. The resulting mixture was stirred at 40° C. for 2 hours. The reaction mixture was extracted with ethyl acetate. The extractant was washed with 0.5M hydrochloric acid, water and brine. The organic layer was dried over anhydrous magnesium sulfate, filtered and the filtrate concentrated in vacuo to afford a pale yellow solid. To the solid was added hexane and the mixture was filtered to give the desired compound (3.6 g, yield 79%) as a pale yellow solid.

$^1$H NMR (400 MHz, $CDCl_3$) δ ppm: 1.47 (9H, s), 1.70–1.85 (2H, m), 1.90–2.05 (2H, m), 2.43 (3H, s), 2.95 (2H, m), 4.00–4.10 (2H, m), 4.26 (1H, m), 8.26 (1H, d, J=3.0), 8.69 (1H, d, J=3.0).

Reference Example 99

4-(1-t-Butoxycarbonylpiperidin-4-yloxy)-3-carbamoyl-5-methylnitrobenzene

To a solution of 4-(1-t-butoxycarbonylpiperidin-4-yloxy)-3-carboxy-5-methylnitrobenzene (3.6 g) in dichloromethane (60 ml) were added isobutyl chloroformate (1.4 ml) and triethylamine (1.6 ml) in an ice bath and the mixture was stirred at the same temperature for 0.5 hours. To the reaction mixture was added 28% aqueous ammonia (0.7 ml) and the resulting mixture was stirred at room temperature for 1.5 hours. The reaction mixture was concentrated in vacuo. The residue was purified by chromatography on a silica gel column using dichloromethane/methanol=19/1 as an eluant to give the desired compound (3.9 g, yield quantitative) as a yellow oil.

$^1$H NMR (500 MHz, $CDCl_3$) δ ppm: 1.46 (9H, s), 1.70–1.80 (2H, m), 1.90–2.00 (2H, m), 2.43 (3H, s), 2.79 (2H, m), 4.05–4.15 (2H, m), 4.17 (1H, m), 8.20 (1H, d, J=3.0), 8.66 (1H, d, J=3.0).

Reference Example 100

4-(1-t-Butoxycarbonylpiperidin-4-yloxy)-3-carbamoyl-5-methylaniline

To a solution of 4-(1-t-butoxycarbonylpiperidin-4-yloxy)-3-carbamoyl-5-methylnitrobenzene (3.9 g) in methanol (100 ml) was added palladium on carbon (0.5 g) and the mixture was stirred under a hydrogen atmosphere at room temperature for 1.5 hours. The reaction mixture was filtered and the filtrate concentrated in vacuo to give the desired compound (3.5 g, yield 97%) as a dark green amorphous solid.

$^1$H NMR (500 MHz, $CDCl_3$) δ ppm: 1.46 (9H, s), 1.60–1.70 (2H, m), 1.90–2.00 (2H, m), 2.23 (3H, s), 2.71 (2H, m), 3.62 (2H, m), 3.80–3.90 (1H, m), 6.65 (1H, d, J=3.0), 7.11 (1H, d, J=3.0).

Reference Example 101

Ethyl N-[4-(1-t-Butoxycarbonylpiperidin-4-yloxy)-3-carbamoyl-5-methylphenyl]sulfamoylacetate To a solution of 4-(1-t-butoxycarbonylpiperidin-4-yloxy)-3-carbamoyl-5-methylaniline (3.5 g) and pyridine (1.0 ml) in dichloromethane (80 ml) was added dropwise ethyl chlorosulfonylacetate (1.6 ml) in an ice bath and the mixture was stirred at room temperature for 0.5 hours. The reaction mixture was concentrated in vacuo. The residue was purified by chromatography on a silica gel column using dichloromethane/methanol=19/1 as an eluant to give the desired compound (2.6 g, yield 51%) as a pale yellow solid.

$^1$H NMR (500 MHz, $CDCl_3$) δ ppm: 1.31 (3H, t, J=7.0), 1.46 (9H, s), 1.65–1.75 (2H, m), 1.90–2.00 (2H, m), 2.33 (3H, s), 2.74 (2H, m), 3.90–4.00 (1H, m), 3.97 (2H, s), 4.00–4.15 (2H, m), 4.27 (2H, q, J=7.0), 7.44 (1H, d, J=3.0), 7.72 (1H, d, J=3.0).

Reference Example 102

Ethyl N-[4-(1-t-Butoxycarbonylpiperidin-4-yloxy)-3-carbamoyl-5-methylphenyl]-N-[3-(3-cyanophenyl)-2-(E)-propenyl]sulfamoylacetate To a solution of 3-(3-cyanophenyl)-2-(E)-propen-1-ol (0.8 g), ethyl N-[4-(1-t-butoxycarbonylpiperidin-4-yloxy)-3-carbamoyl-5-methylphenyl]sulfamoylacetate (2.6 g) and triphenylphosphine (1.7 g) in a mixture of dichloromethane (50 ml) and tetrahydrofuran (50 ml) was added dropwise diethyl azodicarboxylate (1.0 ml) in an ice bath and the mixture was stirred at room temperature for 1.5 hours. The reaction mixture was concentrated in vacuo. The residue was purified by chromatography on a silica gel column using hexane/ethyl acetate 1/2 as an eluant to give the desired compound (3.2 g, yield 96%) as a pale yellow amorphous solid.

$^1$H NMR (500 MHz, $CDCl_3$) δ ppm: 1.35 (3H, t, J=7.0), 1.46 (9H, s), 1.65–1.75 (2H, m), 1.85–1.95 (2H, m), 2.32 (3H, s), 2.73 (2H, m), 3.95–4.05 (1H, m), 4.00 (2H, s), 4.05–4.15 (2H, m), 4.31 (2H, q, J=7.0), 4.52 (2H, d, J=7.0), 6.22 (1H, dt, J=16.0, 7.0), 6.44 (1H, d, J=16.0), 7.22 (1H, m), 7.40 (1H, m), 7.50–7.60 (3H, m), 7.91 (1H, m).

Reference Example 103

2,6-Difluoro-4-nitrophenol

To a solution of 2,6-difluorophenol (2.00 g) in acetic acid (20 ml) was added dropwise 60% nitric acid (1.20 ml) in an ice bath and the mixture was stirred at room temperature for 1 hour. After pouring into iced water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=3/1→2/1 as an eluant to give the desired compound (1.37 g, yield 51%) as a pale yellow solid.

$^1$H NMR (400 MHz, $CDCl_3$) δ ppm: 7.95 (2H, m).

Reference Example 104

4-(1-t-Butoxycarbonylpiperidin-4-yloxy)-3,5-difluoronitrobenzene

To a solution of 1-t-butoxycarbonyl-4-hydroxypiperidine (1.73 g), 2,6-difluoro-4-nitrophenol (1.37 g) and triphenylphosphine (2.67 g) in dichloromethane (30 ml) was added dropwise diethyl azodicarboxylate (1.57 ml) in an ice bath and the mixture was stirred at room temperature for 9 hours. The reaction mixture was concentrated in vacuo. The residue was purified by chromatography on a silica gel column using hexane/ethyl acetate=6/1 as an eluant to give the desired compound (2.13 g, yield 76%) as a pale yellow solid.

$^1$H NMR (400 MHz, $CDCl_3$) δ ppm: 1.47 (9H, s), 1.77–1.85 (2H, m), 1.89–1.96 (2H, m), 3.35 (2H, m), 3.72 (2H, m), 4.62 (1H, m), 7.87 (2H, m).

Reference Example 105

4-(1-t-Butoxycarbonylpiperidin-4-yloxy)-3,5-difluoroaniline

To a solution of 4-(1-t-butoxycarbonylpiperidin-4-yloxy)-3,5-difluoronitrobenzene (2.13 g) in ethanol (40 ml) was added palladium on carbon (0.20 g) and the mixture was stirred under a hydrogen atmosphere at room temperature for 1 hour. The reaction mixture was filtered and the filtrate concentrated in vacuo. The residue was purified by chromatography on a silica gel column using hexane/ethyl acetate=2/1 as an eluant to give the desired compound (1.70 g, yield 87%) as a colorless solid.

$^1$H NMR (400 MHz, $CDCl_3$) δ ppm: 1.46 (9H, s), 1.72–1.78 (2H, m), 1.83–1.89 (2H, m), 3.23 (2H, m), 3.77 (2H, m), 4.11 (1H, m), 6.21 (2H, m).

Reference Example 106

Ethyl N-[4-(1-t-Butoxycarbonylpiperidin-4-yloxy)-3,5-difluorophenyl]sulfamoylacetate To a solution of 4-(1-t-butoxycarbonylpiperidin-4-yloxy)-3,5-difluoroaniline (1.70 g) and pyridine (0.84 ml) in dichloromethane (30 ml) was added dropwise ethyl chlorosulfonylacetate (0.76 ml) in an ice bath and the mixture was stirred at room temperature for 1.5 hours. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=2/1 as an eluant to give the desired compound (2.48 g, yield quantitative) as a yellow oil.

$^1$H NMR (400 MHz, $CDCl_3$) δ ppm: 1.34 (3H, t, J=7.0), 1.47 (9H, s), 1.72–1.82 (2H, m), 1.83–1.93 (2H, m), 3.28 (2H, m), 3.75 (2H, m), 3.95 (2H, s), 4.30 (2H, q, J=7.0), 4.31 (1H, m), 6.95 (2H, m).

Reference Example 107

Ethyl N-[4-(1-t-Butoxycarbonylpiperidin-4-yloxy)-3,5-difluorophenyl]-N-[3-(3-cyanophenyl)-2-(E)-propenyl]sulfamoylacetate To a solution of 3-(3-cyanophenyl)-2-(E)-propen-1-ol (0.52 g), ethyl N-[4-(1-t-butoxycarbonylpiperidin-4-yloxy)-3,5-difluorophenyl]sulfamoylacetate (1.55 g) and triphenylphosphine (1.02 g) in dichloromethane (30 ml) was added dropwise diethyl azodicarboxylate (0.60 ml) in an ice bath and the mixture was stirred at room temperature for 1 hour. The reaction mixture was concentrated in vacuo. The residue was purified by chromatography on a silica gel column using hexane/ethyl acetate=2/1 as an eluant to give the desired compound (1.82 g, yield 91%) as a colorless amorphous solid.

$^1$H NMR (400 MHz, $CDCl_3$) δ ppm: 1.36 (3H, t, J=7.0), 1.46 (9H, s), 1.72–1.82 (2H, m), 1.83–1.93 (2H, m), 3.29 (2H, m), 3.73 (2H, m), 3.99 (2H, s), 4.31 (2H, q, J=7.0), 4.37 (1H, m), 4.47 (2H, d, J=6.5), 6.20 (1H, dt, J=16.0, 6.5), 6.43 (1H, d, J=16.0), 7.12 (2H, m), 7.41 (1H, t, J=7.5), 7.53 (1H, d, J=7.5), 7.54 (1H, d, J=7.5), 7.57 (1H, s).

Reference Example 108

4-(1-t-Butoxycarbonylpiperidin-4-yloxy)-3,5-dichloronitrobenzene

To a solution of 1-t-butoxycarbonyl-4-hydroxypiperidine (677 mg), 2,6-dichloro-4-nitrophenol (700 mg) and triphenylphosphine (1150 mg) in dichloromethane (40 ml) was added dropwise diethyl azodicarboxylate (0.67 ml) in an ice bath and the mixture was stirred at room temperature for 2 hours. The reaction mixture was concentrated in vacuo. The residue was purified by chromatography on a silica gel column using hexane/ethyl acetate=6/1 as an eluant to give the desired compound (950 mg, yield 72%) as a colorless solid.

$^1$H NMR (400 MHz, $CDCl_3$) δ ppm: 1.48 (9H, s), 1.85–2.00 (4H, m), 3.20 (2H, m), 3.91 (2H, m), 4.59 (1H, m), 8.23 (2H, s).

Reference Example 109

4-(1-t-Butoxycarbonylpiperidin-4-yloxy)-3,5-dichloroaniline

To a solution of 4-(1-t-butoxycarbonypiperidin-4-yloxy)-3,5-dichloronitrobenzene (1.95 g) in acetic acid (50 ml) was added zinc powder (11.10 g) in five portions at room temperature and the mixture was stirred at 50° C. for 6 hours. The reaction mixture was filtered and the filtrate concentrated in vacuo. The residue was partitioned between ethyl acetate and water. The extract was washed with brine. The organic layer was dried over anhydrous magnesium sulfate, filtered and the filtrate concentrated in vacuo. The residue was purified by chromatography on a silica gel column using hexane/ethyl acetate=3/1 as an eluant to give the desired compound (1.40 g, yield 78%) as a colorless solid.

$^1H$ NMR (500 MHz, $CDCl_3$) δ ppm: 1.47 (9H, s), 1.80–1.95 (4H, m), 3.09 (2H, m), 3.92 (2H, m), 4.22 (1H, m), 6.61 (2H, s).

Reference Example 110

Ethyl N-[4-(1-t-Butoxycarbonylpiperidin-4-yloxy)-3,5-dichlorophenyl]sulfamoylacetate To a solution of 4-(1-t-butoxycarbonylpiperidin-4-yloxy)-3,5-dichloroaniline (1.40 g) and pyridine (0.63 ml) in dichloromethane (30 ml) was added dropwise ethyl chlorosulfonylacetate (0.57 ml) in an ice bath and the mixture was stirred at room temperature for 1.5 hours. The reaction mixture was partitioned between ethyl acetate and water. The extract was washed with brine. The organic layer was dried over anhydrous magnesium sulfate, filtered and the filtrate concentrated in vacuo. The residue was purified by chromatography on a silica gel column using hexane/ethyl acetate 2/1 as an eluant to give the desired compound (1.89 g, yield 95%) as a pale yellow amorphous solid.

$^1H$ NMR (400 MHz, $CDCl_3$) δ ppm: 1.34 (3H, t, J=7.0), 1.47 (9H, s), 1.80–2.00 (4H, m), 3.14 (2H, m), 3.92 (2H, m), 3.96 (2H, s), 4.30 (2H, q, J=7.0), 4.37 (1H, m), 7.33 (2H, s).

Reference Example 111

N-[4-(1-t-Butoxycarbonylpiperidin-4-yloxy)-3,5-dichlorophenyl]-N-[3-(3-cyanophenyl)-2-(E)-propenyl]sulfamoylacetate To a solution of 3-(3-cyanophenyl)-2-(E)-propen-1-ol (0.59 g), ethyl N-[4-(1-t-butoxycarbonylpiperidin-4-yloxy)-3,5-dichlorophenyl]sulfamoylacetate (1.89 g) and triphenylphosphine (1.16 g) in dichloromethane (30 ml) was added dropwise diethyl azodicarboxylate (0.68 ml) in an ice bath and the mixture was stirred at the same temperature for 4 hours. The reaction mixture was concentrated in vacuo. The residue was purified by chromatography on a silica gel column using hexane/ethyl acetate=3/1 as an eluant to give the desired compound (2.06 g, yield 86%) as a colorless amorphous solid.

$^1H$ NMR (400 MHz, $CDCl_3$) δ ppm: 1.36 (3H, t, J=7.0), 1.47 (9H, s), 1.80–2.00 (4H, m), 3.15 (2H, m), 3.90 (2H, m), 4.00 (2H, s), 4.31 (2H, q, J=7.0), 4.41 (1H, m), 4.47 (2H, d, J=6.5), 6.20 (1H, dt, J=16.0, 6.5), 6.44 (1H, d, J=16.0), 7.42 (1H, t, J=8.0), 7.47 (2H, s), 7.53 (2H, m), 7.58 (1H, s).

Reference Example 112

4-(1-t-Butoxycarbonylpiperidin-4-yloxy)-3,5-dimethylnitrobenzene

To a solution of 1-t-butoxycarbonyl-4-hydroxypiperidine (2.40 g), 2,6-dimethyl-4-nitrophenol (1.50 g) and triphenylphosphine (3.06 g) in dichloromethane (60 ml) was added dropwise diethyl azodicarboxylate (1.80 ml) in an ice bath and the mixture was stirred at room temperature for 19 hours. The reaction mixture was concentrated in vacuo. The residue was purified by chromatography on a silica gel column using hexane/ethyl acetate=5/1 as an eluant to give the desired compound (2.25 g, yield 71%) as a colorless solid.

$^1H$ NMR (500 MHz, $CDCl_3$) δ ppm: 1.48 (9H, s), 1.73 (2H, m), 1.93 (2H, m), 2.35 (6H, s), 2.93 (2H, m), 4.00–4.10 (3H, m), 7.92 (2H, s).

Reference Example 113

4-(1-t-Butoxycarbonylpiperidin-4-yloxy)-3,5-dimethylaniline

To a solution of 4-(1-t-butoxycarbonylpiperidin-4-yloxy)-3,5-dimethylnitrobenzene (2.24 g) in a mixture of ethanol (30 ml) and tetrahydrofuran (10 ml) was added palladium on carbon (0.20 g) and the mixture was stirred under a hydrogen atmosphere at room temperature for 1 hour. The reaction mixture was filtered and the filtrate concentrated in vacuo. The residue was purified by chromatography on a silica gel column using hexane/ethyl acetate=2/1 as an eluant to give the desired compound (1.94 g, yield 95%) as a pale rose solid.

$^1H$ NMR (500 MHz, $CDCl_3$) δ ppm: 1.47 (9H, s), 1.66 (2H, m), 1.92 (2H, m), 2.19 (6H, s), 2.86 (2H, m), 3.79 (1H, m), 4.02 (2H, m), 6.36 (2H, s).

Reference Example 114

Ethyl N-[4-(1-t-Butoxycarbonylpiperidin-4-yloxy)-3,5-dimethylphenyl]sulfamoylacetate To a solution of 4-(1-t-butoxycarbonylpiperidin-4-yloxy)-3,5-dimethylaniline (1.94 g) and pyridine (0.98 ml) in dichloromethane (30 ml) was added dropwise ethyl chlorosulfonylacetate (0.97 ml) in an ice bath and the mixture was stirred at room temperature for 14 hours. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=2/1 as an eluant to give the desired compound (2.00 g, yield 70%) as a pale yellow solid.

$^1H$ NMR (400 MHz, $CDCl_3$) δ ppm: 1.33 (3H, t, J=7.0), 1.47 (9H, s), 1.69 (2H, m), 1.91 (2H, m), 2.26 (6H, s), 2.89 (2H, m), 3.90 (1H, m), 3.93 (2H, s), 4.03 (2H, m), 4.29 (2H, q, J=7.0), 6.98 (2H, s).

Reference Example 115

Ethyl N-[4-(1-t-Butoxycarbonylpiperidin-4-yloxy)-3,5-dimethylphenyl]-N-[3-(3-cyanophenyl)-2-(E)-propenyl]sulfamoylacetate To a solution of 3-(3-cyanophenyl)-2-(E)-propen-1-ol (0.55 g), ethyl N-[4-(1-t-butoxycarbonylpiperidin in-4-yloxy)-3,5-dimethylphenyl]sulfamoylacetate (1.50 g) and triphenylphosphine (1.08 g) in dichloromethane (20 ml) was added dropwise diethyl azodicarboxylate (0.63 ml) in an ice bath and the mixture was stirred at room temperature for 1.5 hours. The reaction mixture was concentrated in vacuo. The residue was purified by chromatography on a silica gel column using hexane/ethyl acetate=2/1 as an eluant to give the desired compound (1.75 g, yield 90%) as a colorless amorphous solid.

$^1H$ NMR (400 MHz, $CDCl_3$) δ ppm: 1.36 (3H, t, J=7.0), 1.47 (9H, s), 1.70 (2H, m), 1.91 (2H, m), 2.26 (6H, s), 2.90 (2H, m), 3.93 (1H, m), 3.99 (2H, s), 4.00 (2H, m), 4.30 (2H, q, J=7.0), 4.47 (2H, d, J=6.5), 6.23 (1H, dt, J=16.0, 6.5), 6.42 (1H, d, J=16.0), 7.11 (2H, s), 7.40 (1H, t, J=8.0), 7.52 (2H, m), 7.56 (1H, s).

Reference Example 116

Ethyl 4-[N-[4-(1-t-Butoxycarbonypiperidin-4-yloxy)phenyl]-N-[3-(3-cyanophenyl)-2-(E)-propenyl]amino]butyrate To a solution of 3-(3-[N-[4-(1-t-butoxycarbonylpiperidin-4-yloxy)phenyl]amino]-1-(E)-propenyl]benzonitrile (2.00 g) in N,N-dimethylformamide (40 ml) were added potassium carbonate (6.50 g) and ethyl bromobutyrate (5.00 ml) in five portions and the mixture was stirred at 140° C. for 16 hours. After addition of water, the reaction mixture was extracted with ethyl acetate. The extract was washed with brine. The organic layer was dried over anhydrous magnesium sulfate, filtered and the filtrate concentrated in vacuo. The residue was purified by chromatography on a silica gel column using hexane/ethyl acetate=2/1 as an eluant to give the desired compound (1.20 g, yield 48%) as a yellow oil.

$^1$H NMR (400 MHz, $CDCl_3$) δ ppm: 1.25 (3H, t, J=7.0), 1.46 (9H, s), 1.65–1.75 (2H, m), 1.80–2.00 (4H, m), 2.36 (2H, t, J=7.0), 3.20–3.35 (4H, m), 3.65–3.75 (2H, m), 4.02 (2H, d, J=5.0), 4.13 (2H, q, J=7.0), 4.27 (1H, m), 6.29 (1H, dt, J=16.0, 5.0), 6.47 (1H, d, J=16.0), 6.70 (2H, d, J=9.0), 6.84 (2H, d, J=9.0), 7.39 (1H, t, J=8.0), 7.49 (1H, d, J=8.0), 7.54 (1H, d, J=8.0), 7.61 (1H, s).

Reference Example 117

3-(3-Cyanophenyl)-2-fluoro-2-(Z)-propen-1-ol

To a solution of 2-diethylphosphono-2-fluoroacetic acid (4.35 g) [which was prepared according to the method described in *J. Organomet. Chem.*, 332, 1 (1987)] in,tetrahydrofuran (90 ml) was added dropwise a 1.6M solution of butyllithium in hexane (28 ml) at −78° C. and the mixture was stirred at the same temperature for 1 hour. To the reaction mixture was added dropwise a solution of 3-cyanobenzaldehyde (2.66 g) in tetrahydrofuran (10 ml) over 10 minutes. The resulting mixture was stirred at −78° C. for 3 hours and then the temperature of the reaction mixture was raised to 0° C. After addition of water, the organic layer of the resulting mixture was extracted with saturated aqueous sodium hydrogencarbonate twice. The combined aqueous layer was adjusted to pH 4 with concentrated hydrochloric acid and then extracted with t-butyl methyl ether five times. The extract was dried over anhydrous sodium sulfate, filtered and the filtrate concentrated in vacuo to afford a desired intermediate (3.47 g) as a white solid.

To a solution of the intermediate (1.15 g) and triethylamine (0.92 ml) in dichloromethane (10 ml) was added ethyl chloroformate (0.63 ml) in an ice bath and the mixture was stirred at room temperature for 15 minutes. The reaction mixture was concentrated in vacuo. To the residue was added ethyl acetate, the mixture was filtered, and then the filtrate was concentrated in vacuo. To a solution of the residue in tetrahydrofuran (10 ml) was added a solution of sodium borohydride (0.45 g) in water (5 ml) in an ice bath and the mixture was stirred at room temperature for 18 hours. After addition of saturated aqueous ammonium chloride, the reaction mixture was extracted with t-butyl methyl ether three times. The extractant was washed with brine. The organic layer was dried over anhydrous sodium sulfate, filtered and the concentrated in vacuo. The residue was purified by chromatography on a silica gel column using hexane/ethyl acetate=3/2 as an eluant to give the desired compound (0.33 g, yield 31%) as a colorless solid.

$^1$H NMR (500 MHz, $CDCl_3$) δ ppm: 4.32 (2H, dd, J=12.5, 5.5), 5.82 (1H, d, J=37.5), 7.45 (1H, t, J=8.0), 7.53 (1H, d, J=8.0), 7.70 (1H, d, J=8.0), 7.81 (1H, s).

Reference Example 118

Ethyl N-[4-(1-t-Butoxycarbonylpiperidin-4-yloxy) phenyl]-N-[3-(3-cyanophenyl)-2-fluoro-2-(Z)-propenyl]sulfamoylacetate To a solution of 3-(3-cyanophenyl)-2-fluoro-2-(Z)-propen-1-ol (0.45 g), ethyl N-[4-(1-t-butoxycarbonylpiperidin-4-yloxy)phenyl]sulfamoylacetate (1.12 g) and triphenylphosphine (0.80 g) in dichloromethane (20 ml) was added dropwise diethyl azodicarboxylate (0.48 ml) in an ice bath and the mixture was stirred at the same temperature for 2 hours. The reaction mixture was concentrated in vacuo. The residue was purified by chromatography on a silica gel column using dichloromethane/ethyl acetate=15/1 as an eluant to give the desired compound (1.40 g, yield 92%) as a colorless oil.

$^1$H NMR (400 MHz, $CDCl_3$) δ ppm: 1.35 (3H, t, J=7.0), 1.47 (9H, s), 1.74 (2H, m), 1.90 (2H, m), 3.34 (2H, m), 3.68 (2H, m), 4.00 (2H, s), 4.30 (2H, q, J=7.0), 4.46 (1H, m), 4.54 (2H. d, J=15.0), 5.62 (1H, d, J=36.5), 6.92 (2H, d, J=9.5), 7.42 (3H, m), 7.51 (1H, d, J=7.0), 7.63 (1H, d, J=8.0), 7.71 (1H, s).

Reference Example 119

2-Hydroxyisophthalic Acid

A solution of 2-methoxyisophthalic acid (1.0 g) in 55% hydriodic acid (10 ml) was heated at 80° C. for 1 hour. The reaction mixture was poured into iced water and the precipitate was collected by filtration to give the desired compound (0.9 g, yield 95%) as a pale yellow solid.

$^1$H NMR (400 MHz, DMSO-$d_6$) δ ppm: 6.93 (1H, t, J=8.0), 7.96 (2H, d, J=8.0).

Reference Example 120

Dimethyl 2-Hydroxyisophthalate

To a solution of 2-hydroxyisophthalic acid (1.9 g) in methanol (20 ml) was added thionyl chloride (1.5 ml) in an ice bath and the mixture was stirred at 70° C. for 4 hours. The reaction mixture was concentrated in vacuo to give the desired compound (1.5 g, yield 68%) as a white solid.

$^1$H NMR (500 MHz, $CDCl_3$) δ ppm: 3.96 (6H, s), 6.94 (1H, t, J=8.0), 8.06 (2H, d, J=8.0).

Reference Example 121

Dimethyl 2-Hydroxy-5-nitroisophthalate

Dimethyl 2-hydroxyisophthalate (1.5 g) was added to a mixture of 69% nitric acid (5 ml) and concentrated sulfuric acid (5 ml) and the mixture was stirred in an ice bath for 0.5 hours. After pouring into iced water, the reaction mixture was extracted with ethyl acetate. The extract was washed with water and brine. The organic layer was dried over anhydrous magnesium sulfate, filtered and the filtrate concentrated in vacuo to afford a yellow solid. To the solid was added hexane and the mixture was filtered to give the desired compound (1.6 g, yield 89%) as a yellow solid.

$^1$H NMR (500 MHz, $CDCl_3$) δ ppm: 4.03 (6H, s), 8.94 (2H, s).

Reference Example 122

Dimethyl 2-(1-t-Butoxycarbonylpiperidin-4-yloxy)-5-nitroisophthalate

To a solution of 1-t-butoxycarbonyl-4-hydroxypiperidine (2.6 g), dimethyl 2-hydroxy-5-nitroisophthalate (1.6 g) and triphenylphosphine (4.4 g) in a mixture of dichloromethane (40 ml) and tetrahydrofuran (20 ml) was added diethyl azodicarboxylate (2.6 ml) and the mixture was stirred at room temperature for 4 hours. The reaction mixture was concentrated in vacuo. The residue was purified by chromatography on a silica gel column using dichloromethane/ethyl acetate=19/1 as an eluant to afford a yellow solid. To the solid was added hexane/ethyl acetate=4/1 and then the mixture was filtered to give the desired compound (2.2 g, yield 78%) as a white solid.

$^1$H NMR (400 MHz, $CDCl_3$) δ ppm: 1.46 (9H, s), 1.70–1.80 (2H, m), 1.85–1.95 (2H, m), 3.05 (2H, m), 3.80–3.95 (2H, m), 3.97 (6H, s), 4.29 (1H, m), 8.74 (2H, s).

Reference Example 123

2-(1-t-Butoxycarbonylpiperidin-4-yloxy)-5-nitroisophthalic Acid

A solution of dimethyl 2-(1-t-butoxycarbonylpiperidin-4-yloxy)-5-nitroisophthalate (10.7 g) in concentrated hydrochloric acid (100 ml) was stirred at 80° C. for 10 hours. The reaction mixture was concentrated in vacuo. To the residue was added hexane to afford a white solid which was collected by filtration. To a solution of the solid in a mixture of water (50 ml) and acetone (50 ml) were added sodium hydrogencarbonate (4.6 g) and di-t-butyl dicarbonate (5.9 g) at room temperature. The resulting mixture was stirred at 40° C. for 1 hour. The reaction mixture was extracted with ethyl acetate. The extract was washed with brine. The organic layer was dried over anhydrous magnesium sulfate, filtered and the filtrate was concentrated in vacuo. To the residue was added hexane and the mixture was filtered to give the desired compound (4.1 g, yield 40%) as a pale yellow solid.

$^1$H NMR (500 MHz, DMSO-$d_6$) δ ppm: 1.40 (9H, s), 1.55–1.65 (2H, m), 1.75–1.85 (2H, m), 3.05–3.15 (2H, m), 3.55–3.65 (2H, m), 4.40 (1H, m), 8.54 (2H, s).

Reference Example 124

4-(1-t-Butoxycarbonylpiperidin-4-yloxy)-3,5-dicarbamoylnitrobenzene

To a solution of 2-(1-t-butoxycarbonylpiperidin-4-yloxy)-5-nitroisophthalic acid (4.6 g) in dichloromethane (150 ml) were added isobutyl chloroformate (4.3 ml) and triethylamine (4.8 ml) in an ice bath and the mixture was stirred at the same temperature for 0.5 hours. To the reaction mixture was added 28% aqueous ammonia (1.9 ml) and the resulting mixture was stirred at room temperature for 1 hour. The precipitate of the reaction mixture was filtered to give the desired compound (3.0 g, yield 64%) as a pale yellow solid.

$^1$H NMR (500 MHz, DMSO-$d_6$) δ ppm: 1.40 (9H, s), 1.60–1.70 (2H, m), 1.75–1.85 (2H, m), 3.05–3.15 (2H, m), 3.55–3.65 (2H, m), 4.48 (1H, m), 8.31 (2H, s).

Reference Example 125

4-(1-t-Butoxycarbonylpiperidin-4-yloxy)-3,5-dicarbamoylaniline

To a solution of 4-(1-t-butoxycarbonylpiperidin-4-yloxy)-3,5-dicarbamoylnitrobenzene (3.0 g) in methanol (60 ml) was added palladium on carbon (0.3 g) and the mixture was stirred under a hydrogen atmosphere at room temperature for 1 hour. The reaction mixture was filtered and the filtrate concentrated in vacuo to give the desired compound (2.8 g, yield quantitative) as a yellow solid.

$^1$H NMR (500 MHz, $CDCl_3$) δ ppm: 1.45 (9H, s), 1.55–1.70 (2H, m), 1.85–2.00 (2H, m), 2.67 (2H, m), 3.80–3.90 (2H, m), 4.02 (1H, m), 7.34 (2H, s).

Reference Example 126

Ethyl N-[4-(1-t-Butoxycarbonylpiperidin-4-yloxy)-3,5-dicarbamoylphenyl]sulfamoylacetate To a solution of 4-(1-t-butoxycarbonylpiperidin-4-yloxy)-3,5-dicarbamoylaniline (2.8 g) and pyridine (1.4 ml) in dichloromethane (80 ml) was added dropwise ethyl chlorosulfonylacetate (2.4 ml) in an ice bath and the mixture was stirred at room temperature for 2 hours. The reaction mixture was concentrated in vacuo. The residue was purified by chromatography on a silica gel column using dichloromethane/methanol 4/1 as an eluant to give the desired compound (0.9 g, yield 23%) as a pale yellow solid.

$^1$H NMR (500 MHz, DMSO-$d_6$) δ ppm: 1.18 (3H, t, J=7.0), 1.40 (9H, s), 1.50–1.60 (2H, m), 1.75–1.85 (2H, m), 2.90–3.00 (2H, m), 3.30 (2H, s), 3.65–3.75 (2H, m), 4.10 (2H, q, J=7.0), 4.15–4.20 (1H, m), 7.43 (2H, s).

Reference Example 127

Ethyl N-[4-(1-t-Butoxycarbonylpiperidin-4-yloxy)-3,5-dicarbamoylphenyl]-N-[3-(3-cyanophenyl)-2-(E)-propenyl]sulfamoylacetate To a solution of 3-(3-cyanophenyl)-2-(E)-propen-1-ol (0.9 g), ethyl N-[4-(1-t-butoxycarbonylpiperidin-4-yloxy)-3,5-dicarbamoylphenyl]sulfamoylacetate (0.9 g) and triphenylphosphine (1.8 g) in a mixture of dichloromethane (30 ml) and tetrahydrofuran (30 ml) was added diethyl azodicarboxylate (1.1 ml) in an ice bath and the mixture was stirred at room temperature for 1 hour. The reaction mixture was concentrated in vacuo. The residue was purified by chromatography on a silica gel column using dichloromethane/ethyl acetate=1/2 as an eluant to give the desired compound (0.8 g, yield 73%) as a pale yellow amorphous solid.

$^1$H NMR (500 MHz, $CDCl_3$) δ ppm: 1.26 (3H, t, J=7.0), 1.45 (9H, s), 1.60–1.75 (2H, m), 1.85–2.00 (2H, m), 2.60–2.75 (2H, m), 4.00–4.15 (2H, m), 4.03 (2H, s), 4.15–4.25 (1H, m), 4.31 (2H, q, J=7.0), 4.55 (2H, d, J=7.0), 6.22 (1H, dt, J=16.0, 7.0), 6.46 (1H, d, J=16.0), 7.35–7.45 (2H, m), 7.50–7.60 (3H, m), 8.16 (1H, m).

Reference Example 128

Methyl 4-Methyl-5-nitrosalicylate

To a solution of 4-methylsalicylic acid (3.5 g) in a mixture of methanol (8 ml) and benzene (32 ml) was added a solution of 2.0M (trimethylsilyl)diazomethane in hexane (15.0 ml) in an ice bath and the mixture was stirred at room temperature for 0.5 hours. The reaction mixture was concentrated in vacuo. To the residual yellow oil was added 69% nitric acid (20 ml) in an ice bath and the mixture was stirred at the same temperature for 2 hours. The reaction mixture was poured into iced Water and extracted with ethyl acetate. The extract was washed with water and brine. The organic layer was dried over anhydrous magnesium sulfate, filtered and the filtrate concentrated in vacuo. The residue was purified by chromatography on a silica gel column using hexane/ethyl acetate=4/1 as an eluant to give the desired compound (1.3 g, yield 21%) as a pale yellow solid.

$^1$H NMR (500 MHz, $CDCl_3$) δ ppm: 2.66 (3H, s), 4.01 (3H, s), 6.92 (1H, s), 8.66 (1H, s).

Reference Example 129

4-(1-t-Butoxycarbonylpiperidin-4-yloxy)-5-methoxycarbonyl-2-methylnitrobenzene To a solution of 1-t-butoxycarbonyl-4-hydroxypiperidine (5.4 g), methyl 4-methyl-5-nitrosalicylate (2.8 g) and triphenylphosphine (9.0 g) in dichloromethane (100 ml) was added diethyl azodicarboxylate (5.4 ml) and the mixture was stirred at room temperature for 9 hours. The reaction mixture was concentrated in vacuo. The residue was purified by chromatography on a silica gel column using hexane/ethyl acetate=4/1 as an eluant to give the desired compound (4.9 g, yield 93%) as a yellow oil.

$^1$H NMR (400 MHz, $CDCl_3$) δ ppm: 1.47 (9H, s), 1.85–1.95 (4H, m), 2.68 (3H, s), 3.50–3.65 (4H, m), 3.91 (3H, s), 4.78 (1H, m), 6.84 (1H, s), 8.63 (1H, s).

Reference Example 130

4-(1-t-Butoxycarbonylpiperidin-4-yloxy)-5-carboxy-2-methylnitrobenzene

A solution of 4-(1-t-butoxycarbonylpiperidin-4-yloxy)-5-methoxycarbonyl-2-methylnitrobenzene (4.9 g) in concentrated hydrochloric acid (100 ml) was stirred at 80° C. for 5 hours. The reaction mixture was concentrated in vacuo. To a solution of the residual white solid in a mixture of water (30 ml) and acetone (30 ml) were added sodium hydrogencarbonate (2.3 g) and di-t-butyl dicarbonate (3.3 g) at room temperature. The resulting mixture was stirred at 40° C. for 1 hour. The reaction mixture was extracted with ethyl acetate. The extract was washed with brine. The organic layer was dried over anhydrous magnesium sulfate, filtered and the filtrate concentrated in vacuo to give the desired compound (4.8 g, yield quantitative) as a yellow amorphous solid.

$^1$H NMR (500 MHz, $CDCl_3$) δ ppm: 1.48 (9H, s), 1.85–1.95 (2H, m), 2.05–2.15 (2H, m), 2.71 (3H, s), 3.35–3.45 (2H, m), 3.70–3.80 (2H, m), 4.85 (1H, m), 6.93 (1H, s), 8.84 (1H, s).

Reference Example 131

4-(1-t-Butoxycarbonylpiperidin-4-yloxy)-5-carbamoyl-2-methylnitrobenzene

To a solution of 4-(1-t-butoxycarbonylpiperidin-4-yloxy)-5-carboxy-2-methylnitrobenzene (4.8 g) in dichloromethane (100 ml) were added isobutyl chloroformate (1.7 ml) and triethylamine (1.8 ml) in an ice bath and the mixture was stirred at the same temperature for 1 hour. To the reaction mixture was added 28% aqueous ammonia (0.8 ml) and the resulting mixture was stirred for 2 hours. The reaction mixture was concentrated in vacuo. The residue was purified by chromatography on a silica gel column using dichloromethane/methanol=19/1 as an eluant to give the desired compound (4.7 g, yield 97%) as a white solid.

$^1$H NMR (500 MHz, DMSO-$d_6$) δ ppm: 1.41 (9H, s), 1.75–1.85 (2H, m), 1.90–2.00 (2H, m), 2.61 (3H, s), 3.20–3.30 (2H, m), 3.60–3.70 (2H, m), 4.93 (1H, m), 7.35 (1H, s), 8.42 (1H, s).

Reference Example 132

4-(1-t-Butoxycarbonylpiperidin-4-yloxy)-5-carbamoyl-2-methylaniline

To a solution of 4-(1-t-butoxycarbonylpiperidin-4-yloxy)-5-carbamoyl-2-methylnitrobenzene (4.7 g) in methanol (120 ml) was added palladium on carbon (0.5 g) and the mixture was stirred under a hydrogen atmosphere at room temperature for 2 hours. The reaction mixture was filtered. The filtrate was concentrated in vacuo to give the desired compound (4.0 g, yield 93%) as a yellow amorphous solid.

$^1$H NMR (500 MHz, $CDCl_3$) δ ppm: 1.47 (9H, s), 1.65–1.75 (2H, m), 1.95–2.05 (2H, m), 2.20 (3H, s), 3.18 (2H, m), 3.75–3.85 (2H, m), 4.45 (1H, m), 6.74 (1 H, s), 7.47 (1H, s).

Reference Example 133

Ethyl N-[4-(1-t-Butoxycarbonylpiperidin-4-yloxy)-5-carbamoyl-2-methylphenyl]sulfamoylacetate To a solution of 4-(1-t-butoxycarbonylpiperidin-4-yloxy)-5-carbamoyl-2-methylaniline (4.0 g) and pyridine (1.2 ml) in dichloromethane (60 ml) was added dropwise ethyl chlorosulfonylacetate (1.9 ml) in an ice bath and the mixture was stirred at room temperature for 0.5 hours. The reaction mixture was concentrated in vacuo. The residue was purified by chromatography on a silica gel column using dichloromethane/methanol=19/1 as an eluant to give the desired compound (2.8 g, yield 48%) as a pale yellow solid.

$^1$H NMR (500 MHz, $CDCl_3$) δ ppm: 1.35 (3H, t, J=7.0), 1.48 (9H, s), 1.75–1.85 (2H, m), 2.00–2.10 (2H, m), 2.49 (3H, s), 3.29 (2H, m), 3.75–3.85 (2H, m), 4.06 (2H, s), 4.33 (2H, q, J=7.0), 4.66 (1H, m), 6.90 (1H, s), 8.16 (1H, s).

Reference Example 134

Ethyl N-[4-(1-t-Butoxycarbonylpiperidin-4-yloxy)-5-carbamoyl-2-methylphenyl]-N-[3-(3-cyanophenyl)-2-(E)-propenyl]sulfamoylacetate To a solution of 3-(3-cyanophenyl)-2-(E)-propen-1-ol (0.9 g), ethyl N-[4-(1-t-butoxycarbonylpiperidin-4-yloxy)-5-carbamoyl-2-methylphenyl]sulfamoylacetate (2.8 g) and triphenylphosphine (2.0 g) in dichloromethane (100 ml) was added diethyl azodicarboxylate (1.2 ml) in an ice bath and the mixture was stirred at room temperature for 3 hours. The reaction mixture was concentrated in vacuo. The residue was purified by chromatography on a silica gel column using hexane/ethyl acetate=1/4 as an eluant to give the desired compound (2.1 g, yield 58%) as a yellow amorphous solid.

$^1$H NMR (500 MHz, $CDCl_3$) δ ppm: 1.37 (3H, t, J=7.0), 1.47 (9H, s), 1.75–1.85 (2H, m), 2.00–2.10 (2H, m), 2.41 (3H, s), 3.25–3.35 (2H, m), 3.75–3.85 (2H, m), 4.02 (1H, d, J=14.0), 4.16 (1H, d, J=14.0), 4.20–4.25 (1H, m), 4.30–4.40 (2H, m), 4.65–4.75 (2H, m), 6.20–6.30 (1H, m), 6.35 (1H, d, J=16.0), 6.88 (1H, s), 7.41 (1H, m), 7.50–7.55 (3H, m), 8.30 (1H, s).

Reference Example 135

3-(5-Cyano-2-methylphenyl)-2-(E)-propen-1-ol

Catecholborane (1.5 ml) was added to 1-t-butyldimethylsilyloxy-2-propyne (2.45 g) and the mixture was stirred at 60° C. for 4 hours. The reaction mixture was cooled to room temperature and to this mixture were added toluene (40 ml), 3-bromo-4-methylbenzonitrile (2.02 g), tetrakis(triphenylphosphine)palladium complex (0.58 g) and a 20% solution of sodium ethoxide in ethanol (5.0 ml). The resulting mixture was stirred at 90° C. for 4 hours. The reaction mixture was partitioned between water and ethyl acetate. The extract was washed with 1M aqueous sodium hydroxide, water and brine, dried over anhydrous sodium sulfate, and then concentrated in vacuo. The residue was purified by chromatography on a silica gel column using hexane/ethyl acetate=8/1 as an eluant to give a desired intermediate (2.23 g).

To a solution of the intermediate in tetrahydrofuran (60 ml) was added a 1M solution of tetrabutylammonium fluoride in tetrahydrofuran (12 ml) in an ice bath and the mixture was stirred at the same temperature for 1 hour. The reaction mixture was partitioned between water and t-butyl methyl ether. The extract was washed with water and brine, dried over anhydrous sodium sulfate and then concentrated in vacuo. The residue was purified by chromatography on a silica gel column using hexane/ethyl acetate=3/2 as an eluant to give the desired compound (0.64 g, two step yield 36%) as a colorless solid.

$^1$H NMR (500 MHz, $CDCl_3$) δ ppm: 2.41 (3H, s), 4.39 (2H, bs), 6.30 (1H, dt, J=16.0, 5.5), 6.80 (1H, d, J=16.0), 7.25 (1H, d, J=8.0), 7.43 (1H, dd, J=8.0, 2.0), 7.70 (1H, d, J=2.0).

Reference Example 136

Ethyl N-[4-(1-t-Butoxycarbonylpiperidin-4-yloxy)phenyl]-N-[3-(5-cyano-2-methylphenyl)-2-(E)-propenyl]sulfamoylacetate To a solution of 3-(5-cyano-2-methylphenyl)-2-(E)-propen-1-ol (0.64 g), ethyl N-[4-(1-t-butoxycarbonylpiperidin-4-yloxy)phenyl]sulfamoylacetate (1.62 g) and triphenylphosphine (1.16 g) in dichloromethane (30 ml) was added dropwise diethyl azodicarboxylate (0.70 ml) in an ice bath and the mixture was stirred at the same temperature for 2 hours. The reaction mixture was concentrated in vacuo. The residue was purified by chromatography on a silica gel column using dichloromethane/ethyl acetate=12/1 as an eluant to give the desired compound (2.03 g, yield 92%) as a colorless amorphous solid.

$^1$H NMR (500 MHz, $CDCl_3$) δ ppm: 1.36 (3H, t, J=7.0), 1.47 (9H, s), 1.75 (2H, m), 1.91 (2H, m), 2.25 (3H, s), 3.43 (2H, m), 3.69 (2H, m), 3.98 (2H, s), 4.31 (2H, q, J=7.0), 4.47 (1H, m), 4.49 (2H, d, J=6.5), 6.05 (1H, dt, J=15.5, 6.5), 6.56 (1H, d, J=15.5), 6.92 (2H, d, J=10.0), 7.19 (1H, d, J=7.5), 7.40 (3H, m), 7.55 (1H, s).

Reference Example 137

3-(5-Cyano-2-fluorophenyl)-2-(E)-propen-1-ol

Catecholborane (1.07 ml) was added to 1-t-butyldimethylsilyloxy-2-propyne (1.70 g) and the mixture was stirred at 60° C. for 3 hours. The reaction mixture was cooled to room temperature and to this mixture were added toluene (20 ml), 3-bromo-4-fluorobenzonitrile (1.40 g), tetrakis(triphenylphosphine)palladium complex (0.41 g) and a 20% solution of sodium ethoxide in ethanol (3.4 ml). The resulting mixture was stirred at 100° C. for 6 hours. After addition of 1M aqueous sodium hydroxide, the reaction mixture was extracted with ether. The extract was washed with 1 M aqueous sodium hydroxide, water and brine, dried over anhydrous sodium sulfate and then concentrated in vacuo. The residue was purified by chromatography on a silica gel column using hexane/ethyl acetate 10/1 as an eluant to give a desired intermediate (1.29 g).

To a solution of the intermediate in tetrahydrofuran (10 ml) was added a 1 M solution of tetrabutylammonium fluoride in tetrahydrofuran (5.30 ml) in an ice bath and the mixture was stirred at the same temperature for 1.5 hours. The reaction mixture was partitioned between water and ethyl acetate. The extract was washed with water and brine, dried over anhydrous magnesium sulfate and then concentrated in vacuo. The residue was purified by chromatography on a silica gel column using hexane/ethyl acetate=1/1 as an eluant to give the desired compound (0.46 g, two step yield 37%) as a colorless solid.

$^1$H NMR (400 MHz, $CDCl_3$) δ ppm: 4.40 (2H, m), 6.52 (1 H, dt, J=16.5, 5.0), 6.75 (1H, d, J=16.5), 7.16 (1H, dd, J=10.0, 8.5), 7.53 (1H, ddd, J=8.5, 5.0, 2.0), 7.70 (1H, dd, J=7.0, 2.0).

Reference Example 138

N-[4-(1-t-Butoxycarbonylpiperidin-4-yloxy)phenyl]-N-[3-(5-cyano-2-fluorophenyl)-2-(E)-propenyl]ethanesulfonamide To a solution of 3-(5-cyano-2-fluorophenyl)-2-(E)-propen-1-ol (0.72 g), N-[4-(1-t-butoxycarbonylpiperidin-4-yloxy)phenyl]ethanesulfonamide (1.63 g) and triphenylphosphine (1.37 g) in dichloromethane (40 ml) was added dropwise diethyl azodicarboxylate (0.83 ml) in an ice bath and the mixture was stirred at room temperature for 2 hours. The reaction mixture was concentrated in vacuo. The residue was purified by chromatography on a silica gel column using dichloromethane/ethyl acetate=10/1 as an eluant to give the desired compound (2.00 g, yield 91%) as a colorless oil.

$^1$H NMR (400 MHz, $CDCl_3$) δ ppm: 1.42 (3H, t, J=7.5), 1.47 (9H, s), 1.74 (2H, m), 1.90 (2H, m), 3.06 (2H, q, J=7.5), 3.33 (2H, m), 3.68 (2H, m), 4.45 (3H, m), 6.34 (1H, dt, J=16.0, 6.0), 6.54 (1H, d, J=16.0), 6.90 (2H, d, J=9.0), 7.12 (1H, dd, J=10.5, 9.0), 7.27 (2H, d, J=9.0), 7.51 (1H, ddd, J=9.0, 5.0, 2.0), 7.68 (1H, dd, J=6.5, 2.0).

Test Example 1

Determination of Anti-factor Xa Activity

Anti-factor Xa activity was determined according to the method of Hara et al. (*Thromb. Haemost*, 71, 314 (1994), with slight modifications. A 50 mM tris-HCl buffer (pH 8.4) containing 0.9% NaCl, 0.4 mM chromogenic substrate, S-2222 (Daiichi Pure Chemicals Co., Ltd., Tokyo, Japan), and a test compound were mixed, and the reaction was started by adding 0.25 unit/ml human factor Xa (Cosmo Bio Co., Ltd, Tokyo, Japan). Distilled water instead of the test compound was added to the buffer in the control group. The reaction mixture in a total volume of 0.1 ml was incubated for 5 min at room temperature. The absorbance at 405 nm was measured continuously using a 96-well microplate reader (model 550, BioRad), and the increase in absorbance for 5 min was calculated as an index of factor Xa activity. The $IC_{50}$ values, the concentration at which the compound inhibits factor Xa activity by 50%, was determined to estimate the anti-factor Xa activity of the test compound.

The results indicate that the benzamidine derivatives of formula (I) reported below exhibit excellent inhibitory effects against factor Xa activity. The compounds with $IC_{50}$ values less than 10 nM are listed in Table 2, where compound A indicates N-[4-[1-acetimidoyl-4-piperidyloxy]phenyl]-N-[2-(3-amidinophenoxy)ethyl]sulfamoylacetic acid dihydrochloride salt, which has already been described in WO 98/31661 (EP 976722).

TABLE 2

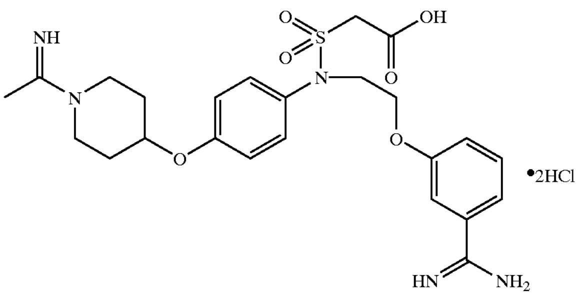

| Example number of test compound | Factor Xa inhibitory activity [$IC_{50}$ (nM)] |
|---|---|
| 3 | 8.6 |
| 4 | 6.4 |
| 8 | 4.5 |
| 9 | 7.4 |
| 10 | 4.6 |

TABLE 2-continued

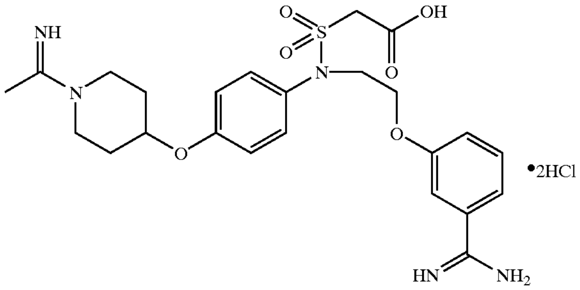

| Example number of test compound | Factor Xa inhibitory activity $[IC_{50}$ (nM)] |
|---|---|
| 11 | 8.1 |
| 22 | 8.3 |
| 23 | 8.3 |
| 28 | 9.0 |
| 29 | 9.0 |
| 31 | 10.0 |
| 34 | 10.0 |
| 36 | 7.1 |
| 38 | 8.7 |
| 41 | 7.5 |
| 46 | 6.8 |
| 47 | 3.7 |
| 49 | 9.8 |
| 54 | 4.6 |
| 55 | 5.0 |
| 56 | 10.0 |
| 57 | 9.3 |
| Compound A | 130 |

Test Example 2

Determination of Anti-trypsin Activity

Anti-trypsin activity was determined according to the method of Taniuchi et al. [*Thromb. Haemost.*, 79, 543 (1998)] with slight modifications. First, 85 μl of a 50 mM tris-HCl buffer (pH 8.4) containing 0.9% NaCl, 5 μl of chromogenic substrate, S-2222 (final concentration of 0.4 mM, Daiichi Pure Chemicals Co., Ltd., Tokyo, Japan) and 5 μl of a test compound were mixed, and the reaction was started by adding 5 μl of bovine trypsin (final concentration of 0.25 μg-protein/ml, Sigma). Distilled water instead of the test compound was added to the buffer in the control group. The reaction mixture in a total volume of 0.1 ml was incubated at room temperature. The absorbance at 405 nm was measured continuously using a 96-well microplate reader (model 550, BioRad), and the increase in absorbance for 5 min was calculated as an index of trypsin activity. The $IC_{50}$ value, the concentration at which the compound inhibits trypsin activity by 50%, was determined to estimate the anti-trypsin activity of the test compound. The results are shown in Table 3.

TABLE 3

| Example number of test compound | Anti-trypsin activity $[IC_{50}$(nM)] |
|---|---|
| 9 | 520 |
| 11 | 840 |

Formulation Example 1

Hard Capsule

A powder of the compound obtained in Example 9 (50 mg), lactose (128.7 mg), cellulose (70 mg) and magnesium stearate (1.3 mg) were blended, passed through a No. 60 mesh sieve and filled into a No. 3 hard gelatin capsule in 250 mg quantity.

Formulation Example 2

Tablet

A powder of the compound obtained in Example 9 (50 mg), lactose (124 mg), cellulose (25 mg) and magnesium stearate (1 mg) are blended and compressed by a tablet machine to form a tablet weighing 200 mg. If necessary, these tablets can be coated with sugar in a conventional manner.

Formulation Example 3

Injectable Formulation

The compound obtained in Example 9 (1.5% weight) is stirred in propylene glycol (10% volume). The mixture is adjusted with water for injection according to a definite volume and sterilized to afford an injectable formulation.

Industrial Applicability

Benzamidine derivatives of formula (I) and pharmaceutically acceptable salts thereof exhibit excellent inhibitory activity against factor Xa and low toxicity. They are useful for treating or preventing (especially treating) blood coagulation disorders (for example, thrombotic diseases such as cerebral infarction, myocardial infarction, peripheral circulation disease or the like).

When the compound (I) or a pharmaceutically acceptable salt of the present invention is used as a therapeutic or prophylactic agent for the diseaes described above, it can be administered alone, or a mixture of it and pharmaceutically acceptable excipient(s), diluent(s) and the like can be administered in various dosage forms such as tablets, capsules, granules, powders, syrups or the like for oral administration; and injections, suppositories or the like for parenteral administration.

These dosage forms can be prepared using additives such as excipients, lubricants, binders, disintegrants, emulsifiers, stabilizers, corrigents, diluents and the like in a conventional manner.

Examples of excipients include organic excipients, for example, sugar derivatives such as lactose, sucrose, glucose, mannitol or sorbitol; starch derivatives such as corn starch, potato starch, α-starch or dextrin; cellulose derivatives such as crystalline cellulose; acacia; dextran; pullulan; and inorganic excipients, for example, silicate derivatives such as light silicic acid, synthetic aluminum silicate, calcium silicate or magnesium aluminate metasilicate; phosphate derivatives such as calcium phosphate; carbonate derivatives such as calcium carbonate; or sulfate derivatives such as calcium sulfate.

Examples of lubricants include metal stearate derivatives such as stearic acid, calcium stearate or magnesium stearate; talc; colloidal silica; waxes such as beeswax or spermaceti; boric acid; adipic acid; sulfate derivatives such as sodium sulfate; glycol; fumaric acid; sodium benzoate; DL-leucine; lauryl sulfate derivatives such as sodium lauryl sulfate and magnesium lauryl sulfate; silicic acid derivatives such as silicic acid anhydride and silicic acid hydrate; and the starch derivatives described above in relation to excipients.

Examples of binders include hydroxypropylcellulose, hydroxypropylmethylcellulose, polyvinylpyrrolidone, Macrogol (trade mark) and the excipients as described above.

Examples of disintegrants include cellulose derivatives such as low-substituted hydroxypropylcellulose, carboxymethylcellulose, calcium carboxymethylcellulose and internally cross-linked sodium carboxymethylcellulose; chemically modified starch.cellulose derivatives such as carboxymethylstarch, sodium carboxymethylstarch; and cross-linked polyvinylpyrrolidone.

Examples of emulsifiers include colloidal clays such as bentonite or veegum; metal hydroxides such as magnesium hydroxide or aluminium hydroxide; anionic surfactants such as sodium lauryl sulfate or calcium stearate; cationic surfactants such as benzalkonium chloride or non-ionic surfactants such as polyoxyethylene alkyl ether, polyoxyethylenesorbitan esters of fatty acids, or sucrose esters of fatty acids.

Examples of stabilizers include para-hydroxybenzoates such as methylparaben or propylparaben; alcohols such as chlorobutanol, benzyl alcohol or phenethyl alcohol; benzalkonium chloride; phenol derivatives such as phenol or cresol; thimerosal; dehydroacetic acid, or sorbic acid.

Examples of corrigents include sweetening, souring and flavoring agents all of which are conventionally used.

The dose of the compound of formula (I) or a pharmaceutically acceptable salt thereof varies depending on a variety of factors such as the symptoms and age of the patient (e.g. a human). A suitable dosage level for oral administration is from 1 mg (preferably 10 mg) per dose as a lower limit to 1000 mg (preferably 500 mg) per dose as a an upper limit for an adult. A suitable dosage level for intravenous administration is from 0.5 mg (preferably 5 mg) per dose as a lower limit to 500 mg (preferably 250 mg) per dose as a an upper limit for an adult. The dosage level of the compound of formula (I) or a pharmaceutically acceptable salt thereof can be administered from 1 to 6 times per day depending upon the symptoms of the patient.

What is claimed is:

1. A benzamidine derivative of the following formula (I) or a pharmaceutically acceptable salt thereof:

(I)

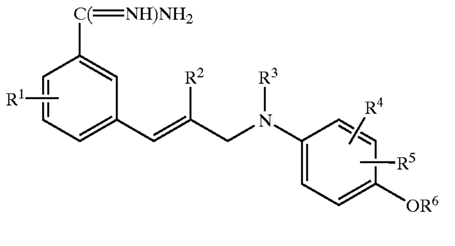

wherein:

$R^1$ is selected from the group consisting of a hydrogen atom, a halogen atom, a $C_1$–$C_6$ alkyl group and a hydroxyl group;

$R^2$ is selected from the group consisting of a hydrogen atom, a halogen atom and a $C_1$–$C_6$ alkyl group;

$R^3$ is selected from the group consisting of ethoxycarbonylmethanesulfonyl group and a carboxymethansulfonyl;

$R^4$ and $R^5$ are the same as or different from each other and each is selected from the group consisting of a hydrogen atom, a halogen atom, a $C_1$–$C_6$ alkyl group, a halogeno-$C_1$–$C_6$-alkyl group, a $C_1$–$C_6$ alkoxy group, a carboxyl group, a ($C_1$–$C_6$ alkoxy)carbonyl group, a carbamoyl group, a ($C_1$–$C_6$ alkyl)carbamoyl group and a di($C_1$–$C_6$ alkyl)carbamoyl group; and $R^6$ is selected from the group consisting of a 1-acetimidoylpyrrolidin-3-yl group and a 1-acetimidoylpiperidin-4-yl group.

2. A benzamidine derivative or a pharmaceutically acceptable salt thereof according to claim 1, wherein $R^1$ is selected from the group consisting of a hydrogen atom, a fluorine atom, a chlorine atom, a bromine atom, a $C_1$–$C_4$ alkyl group and a hydroxyl group.

3. A benzamidine derivative or a pharmaceutically acceptable salt thereof according to claim 1, wherein $R^1$ is selected from the group consisting of a hydrogen atom, a fluorine atom, a chlorine atom, a methyl group, an ethyl group and a hydroxyl group.

4. A benzamidine derivative or a pharmaceutically acceptable salt thereof according to claim 1, wherein $R^1$ is selected from the group consisting of a hydrogen atom, a fluorine atom, a methyl group and a hydroxyl group.

5. A benzamidine derivative or a pharmaceutically acceptable salt thereof according to claim 1, wherein $R^1$ is selected from the group consisting of a hydrogen atom and a hydroxyl group.

6. A benzamidine derivative or a pharmaceutically acceptable salt thereof according to claim 1, wherein $R^2$ is selected from the group consisting of a hydrogen atom, a fluorine atom, a chlorine atom, a bromine atom and a $C_1$–$C_4$ alkyl group.

7. A benzamidine derivative or a pharmaceutically acceptable salt thereof according to claim 1, wherein $R^2$ is selected from the group consisting of a hydrogen atom, a fluorine atom, a chlorine atom, a methyl group and an ethyl group.

8. A benzamidine derivative or a pharmaceutically acceptable salt thereof according to claim 1, wherein $R^2$ is selected from the group consisting of a hydrogen atom, a fluorine atom and a methyl group.

9. A benzamidine derivative or a pharmaceutically acceptable salt thereof according to claim 1, wherein $R^2$ is selected from the group consisting of a hydrogen atom and a fluorine atom.

10. A benzamidine derivative or a pharmaceutically acceptable salt thereof according to claim 1, wherein $R^2$ is a hydrogen atom.

11. A benzamidine derivative or a pharmaceutically acceptable salt thereof according to claim 1, wherein $R^3$ is a carboxymethanesulfonyl group.

12. A benzamidine derivative or a pharmaceutically acceptable salt thereof according to claim 1, wherein $R^3$ is an ethoxycarbonylmethanesulfonyl group.

13. A benzamidine derivative or a pharmaceutically acceptable salt thereof according to claim 1, wherein $R^4$ and $R^5$ are the same as or different from each other and each is selected from the group consisting of a hydrogen atom, a fluorine atom, a chlorine atom, a bromine atom, a $C_1$–$C_4$ alkyl group, a fluoromethyl group, a difluoromethyl group, a trifluoromethyl group, a 2-fluoroethyl group, a 2,2-difluoroethyl group, a 2,2,2-trifluoroethyl group, a $C_1$–$C_4$ alkoxy group, a carboxyl group, a methoxycarbonyl group, an ethoxycarbonyl group, a carbamoyl group, a methylcarbamoyl group and an N,N-dimethylcarbamoyl group.

14. A benzamidine derivative or a pharmaceutically acceptable salt thereof according to claim 1, wherein $R^4$ is selected from the group consisting of a hydrogen atom, a fluorine atom, a chlorine atom and a trifluoromethyl group, and $R^5$ is selected from the group consisting of a hydrogen atom, a fluorine atom, a chlorine atom, a bromine atom, a $C_1$–$C_4$ alkyl group, a fluoromethyl group, a difluoromethyl group, a trifluoromethyl group, a 2-fluoroethyl group, a 2,2-difluoroethyl group, a 2,2,2-trifluoroethyl group, a $C_1$–$C_4$ alkoxy group, a carboxyl group, a methoxycarbonyl group, an ethoxycarbonyl group, a carbamoyl group, a methylcarbamoyl group and an N,N-dimethylcarbamoyl group.

15. A benzamidine derivative or a pharmaceutically acceptable salt thereof according to claim 1, wherein $R^4$ is selected from the group consisting of a hydrogen atom, a fluorine atom and a chlorine atom and $R^5$ is selected from the group consisting of a hydrogen atom, a fluorine atom, a chlorine atom, a bromine atom, a methyl group, an ethyl group, a trifluoromethyl group, a methoxy group, an ethoxy group and a carbamoyl group.

16. A benzamidine derivative or a pharmaceutically acceptable salt thereof according to claim 1, wherein $R^4$ is a hydrogen atom and $R^5$ is selected from the group consisting of a hydrogen atom, a fluorine atom, a chlorine atom, a methyl group, a trifluoromethyl group and a carbamoyl group.

17. A benzamidine derivative or a pharmaceutically acceptable salt thereof according to claim 1, wherein $R^4$ is a hydrogen atom and $R^5$ is selected from the group consisting of a hydrogen atom, a chlorine atom, a methyl group and a carbamoyl group.

18. A benzamidine derivative or a pharmaceutically acceptable salt thereof according to claim 1, wherein $R^6$ is a 1-acetimidoylpiperidin-4-yl group.

19. A benzamidine derivative or a pharmaceutically acceptable salt thereof according to claim 1, wherein:

$R^1$ is selected from the group consisting of a hydrogen atom, a fluorine atom, a chlorine atom, a bromine atom, a $C_1$–$C_4$ alkyl group and a hydroxyl group;

$R^2$ is selected from the group consisting of a hydrogen atom, a fluorine atom, a chlorine atom, a bromine atom and a $C_1$–$C_4$ alkyl group; and $R^4$ and $R^5$ are the same as or different from each other and each is selected from the group consisting of a hydrogen atom, a fluorine atom, a chlorine atom, a bromine atom, a $C_1$–$C_4$ alkyl group, a fluoromethyl group, a difluoromethyl group, a trifluoromethyl group, a 2-fluoroethyl group, a 2,2-difluoroethyl group, a 2,2,2-trifluoroethyl group, a $C_1$–$C_4$ alkoxy group, a carboxyl group, a methoxycarbonyl group, an ethoxycarbonyl group, a carbamoyl group, a methylcarbamoyl group and an N,N-dimethylcarbamoyl group.

20. A benzamidine derivative or a pharmaceutically acceptable salt thereof according to claim 1, wherein:

$R^1$ is selected from the group consisting of a hydrogen atom, a fluorine atom, a chlorine atom, a methyl group, an ethyl group and a hydroxyl group;

$R^2$ is selected from the group consisting of a hydrogen atom, a fluorine atom, a chlorine atom, a methyl group and an ethyl group;

$R^4$ is selected from the group consisting of a hydrogen atom, a fluorine atom, a chlorine atom and a trifluoromethyl group, and $R^5$ is selected from the group consisting of a hydrogen atom, a fluorine atom, a chlorine atom, a bromine atom, a $C_1$–$C_4$ alkyl group, a fluoromethyl group, a difluoromethyl group, a trifluoromethyl group, a 2-fluoroethyl group, a 2,2-difluoroethyl group, a 2,2,2-trifluoroethyl group, a $C_1$–$C_4$ alkoxy group, a carboxyl group, a methoxycarbonyl group, an ethoxycarbonyl group, a carbamoyl group, a methylcarbamoyl group and an N,N-dimethylcarbamoyl group; and $R^6$ is a 1-acetimidoylpiperidin-4-yl group.

21. A benzamidine derivative or a pharmaceutically acceptable salt thereof according to claim 1, wherein:

$R^1$ is selected from the group consisting of a hydrogen atom, a fluorine atom, a methyl group and a hydroxyl group;

$R^2$ is selected from the group consisting of a hydrogen atom, a fluorine atom and a methyl group;

$R^4$ is selected from the group consisting of a hydrogen atom, a fluorine atom and a chlorine atom, and $R^5$ is selected from the group consisting of a hydrogen atom, a fluorine atom, a chlorine atom, a bromine atom, a methyl group, an ethyl group, a trifluoromethyl group, a methoxy group, an ethoxy group and a carbamoyl group; and $R^6$ is a 1-acetimidoylpiperidin-4-yl group.

22. A benzamidine derivative or a pharmaceutically acceptable salt thereof according to claim 1, wherein:

$R^1$ is selected from the group consisting of a hydrogen atom and a hydroxyl group;

$R^2$ is selected from the group consisting of a hydrogen atom and a fluorine atom;

$R^4$ is a hydrogen atom, and $R^5$ is selected from the group consisting of a hydrogen atom, a fluorine atom, a chlorine atom, a methyl group, a trifluoromethyl group and a carbamoyl group; and $R^6$ is a 1-acetimidoylpiperidin-4-yl group.

23. A benzamidine derivative or a pharmaceutically acceptable salt thereof according to claim 1, wherein:

$R^1$ is selected from the group consisting of a hydrogen atom and a hydroxyl group;

$R^2$ is selected from the group consisting of a hydrogen atom and a fluorine atom;

$R^4$ is a hydrogen atom, and $R^5$ is selected from the group consisting of a hydrogen atom, a chlorine atom, a methyl group and a carbamoyl group; and $R^6$ is a 1-acetimidoylpiperidin-4-yl group.

24. A benzamidine derivative or a pharmaceutically acceptable salt thereof according to claim 1, wherein:

$R^1$ is selected from the group consisting of a hydrogen atom and a hydroxyl group;

$R^2$ is selected from the group consisting of a hydrogen atom and a fluorine atom;

$R^4$ is a hydrogen atom, and $R^5$ is selected from the group consisting of a hydrogen atom, a chlorine atom, a methyl group and a carbamoyl group; and $R^6$ is a 1-acetimidoylpiperidin-4-yl group.

25. A benzamidine derivative according to claim 1 which is selected from the group consisting of the following compounds, or a pharmaceutically acceptable salt thereof:

ethyl N-[4-(1-acetimidoylpiperidin-4-yloxy)phenyl]-N-[3-(3-amidinophenyl)-2-(E)-propenyl]sulfamoylacetate, ethyl N-[4-(1-acetimidoylpiperidin-4-yloxy)-3-chlorophenyl]-N-[3-(3-amidinophenyl)-2-(E)-propenyl]sulfamoylacetate, ethyl N-[4-(1-acetimidoylpiperidin-4-yloxy)-3-methylphenyl]-N-[3-(3-amidinophenyl)-2-(E)-propenyl]sulfamoylacetate, ethyl N-[4-(1-acetimidoylpiperidin-4-yloxy)-3-carbamoylphenyl]-N-[3-(3-amidinophenyl)-2-(E)-propenyl]sulfamoylacetate, N-[4-(1-acetimidoylpiperidin-4-yloxy)phenyl]-N-[3-(3-amidinophenyl)-2-(E)-propenyl]sulfamoylacetic acid, N-[4-(1-acetimidoylpiperidin-4-yloxy)-3-fluorophenyl]-N-[3-(3-amidinophenyl)-2-(E)-propenyl]sulfamoylacetic acid, N-[4-(1-acetimidoylpiperidin-4-yloxy)-3-chlorophenyl]-N-[3-(3-amidinophenyl)-2-(E)-propenyl]sulfamoylacetic acid, N-[4-(1-acetimidoylpiperidin-4-yloxy)-3-methylphenyl]-N-[3-(3-amidinophenyl)-2-(E)-propenyl]sulfamoylacetic acid, N-[4-(1-acetimidoylpiperidin-4-yloxy)-3-trifluoromethylphenyl]-N-[3-(3-amidinophenyl)-2-(E)-propenyl]sulfamoylacetic acid, N-[4-(1-acetimidoylpiperidin-4-yloxy)-3-carbamoylphenyl]-N-[3-(3-amidinophenyl)-2-(E)-propenyl]sulfamoylacetic acid, ethyl N-[4-(1-acetimidoylpiperidin-4-yloxy)-3,5-dichlorophenyl]-N-[3-(3-amidinophenyl)-2-(E)-propenyl]sulfamoylacetate, N-[4-(1-acetimidoylpiperidin-4-yloxy)-3,5-dichlorophenyl]-N-[3-(3-amidinophenyl)-2-(E)-propenyl]sulfamoylacetic acid, and N-[4-(1-acetimidoylpiperidin-4-yloxy)phenyl]-N-[3-(3-amidinophenyl)-2-fluoro-2-(Z)-propenyl]sulfamoylacetic acid.

26. A benzamidine derivative according to claim 25, which is selected from the group consisting of the following compound and pharmaceutically acceptable salt thereof:

ethyl N-[4-(1-acetimidoylpiperidin-4-yloxy)phenyl]-N-[3-(3-amidinophenyl)-2-(E)-propenyl]sulfamoylacetate.

27. A benzamidine derivative according to claim 25 which is selected from the group consisting of the following compound and pharmaceutically acceptable salt thereof:

ethyl N-[4-(1-acetimidoylpiperidin-4-yloxy)-3-chlorophenyl]-N-[3-(3-amidinophenyl)-2-(E)-propenyl]sulfamoylacetate.

28. A benzamidine derivative according to claim 25 which is selected from the group consisting of the following compound and pharmaceutically acceptable salt thereof:

ethyl N-[4-(1-acetimidoylpiperidin-4-yloxy)-3-methylphenyl]-N-[3-(3-amidinophenyl)-2-(E)-propenyl]sulfamoylacetate.

29. A benzamidine derivative according to claim 25 which is selected from the group consisting of the following compound and pharmaceutically acceptable salt thereof:

ethyl N-[4-(1-acetimidoylpiperidin-4-yloxy)-3-carbamoylphenyl]-N-[3-(3-amidinophenyl)-2-(E)-propenyl]sulfamoylacetate.

30. A benzamidine derivative according to claim 25 which is selected from the group consisting of the following compound and pharmaceutically acceptable salt thereof:

N-[4-(1-acetimidoylpiperidin-4-yloxy)phenyl]-N-[3-(3-amidinophenyl)-2-(E)-propenyl]sulfamoylacetic acid.

31. A benzamidine derivative according to claim 25 which is selected from the group consisting of the following compound and pharmaceutically acceptable salt thereof:

N-[4-(1-acetimidoylpiperidin-4-yloxy)-3-fluorophenyl]-N-[3-(3-amidinophenyl)-2-(E)-propenyl]sulfamoylacetic acid.

32. A benzamidine derivative according to claim 25 which is selected from the group consisting of the following compound and pharmaceutically acceptable salt thereof:

N-[4-(1-acetimidoylpiperidin-4-yloxy)-3-chlorophenyl]-N-[3-(3-amidinophenyl)-2-(E)-propenyl]sulfamoylacetic acid.

33. A benzamidine derivative according to claim 25 which is selected from the group consisting of the following compound and pharmaceutically acceptable salt thereof:

N-[4-(1-acetimidoylpiperidin-4-yloxy)-3-methylphenyl]-N-[3-(3-amidinophenyl)-2-(E)-propenyl]sulfamoylacetic acid.

34. A benzamidine derivative according to claim 25 which is selected from the group consisting of the following compound and pharmaceutically acceptable salt thereof:

N-[4-(1-acetimidoylpiperidin-4-yloxy)-3-trifluoromethylphenyl]-N-[3-(3-amidinophenyl)-2-(E)-propenyl]sulfamoylacetic acid.

35. A benzamidine derivative according to claim 25 which is selected from the group consisting of the following compound and pharmaceutically acceptable salt thereof:

N-[4-(1-acetimidoylpiperidin-4-yloxy)-3-carbamoylphenyl]-N-[3-(3-amidinophenyl)-2-(E)-propenyl]sulfamoylacetic acid.

36. A benzamidine derivative according to claim 25 which is selected from the group consisting of the following compound and pharmaceutically acceptable salt thereof:

ethyl N-[4-(1-acetimidoylpiperidin-4-yloxy)-3,5-dichlorophenyl]-N-[3-(3-amidinophenyl)-2-(E)-propenyl]sulfamoylacetate.

37. A benzamidine derivative according to claim 25 which is selected from the group consisting of the following compound and pharmaceutically acceptable salt thereof:

N-[4-(1-acetimidoylpiperidin-4-yloxy)-3,5-dichlorophenyl]-N-[3-(3-amidinophenyl)-2-(E)-propenyl]sulfamoylacetic acid.

38. A benzamidine derivative according to claim 25 which is selected from the group consisting of the following compound and pharmaceutically acceptable salt thereof:

N-[4-(1-acetimidoylpiperidin-4-yloxy)phenyl]-N-[3-(3-amidinophenyl)-2-fluoro-2-(Z)-propenyl]sulfamoylacetic acid.

39. A pharmaceutical composition comprising a therapeutically effective amount of a benzamidine derivative or a pharmaceutically acceptable salt thereof according to claim 25, together with a pharmaceutically acceptable carrier or diluent.

40. A method for the treatment or prevention of a blood coagulation disorder, thrombotic disease, cerebral infarction, myocardial infarction, or peripheral circulation disorder in a warm-blooded animal, which comprises administering to a warm-blooded animal in need of such treatment or prevention an effective amount of a benzamidine derivative or a pharmaceutically acceptable salt thereof according to claim 25.

41. A method according to claim 40 wherein the warm-blooded animal is a human.

42. A pharmaceutical composition comprising a therapeutically effective amount of a benzamidine derivative or a pharmaceutically acceptable salt thereof according to claim 1, together with a pharmaceutically acceptable carrier or diluent.

43. A method for the treatment or prevention of a blood coagulation disorder, thrombotic disease, cerebral infarction, myocardial infarction, or peripheral circulation disorder in a warm-blooded animal, which comprises administering to a warm-blooded animal in need of such treatment or prevention an effective amount of a benzamidine derivative or a pharmaceutically acceptable salt thereof according to claim 1.

44. A method according to claim 43 wherein the warm-blooded animal is a human.

45. A benzamidine derivative according to claim 1 which is N-[4-(1-acetimidoylpiperidin-4-yl)oxy-3-carbamoylphenyl]-N-[(Z)-3-(3-amidinophenyl)-2-fluoro-2-propenyl]sulfamoylacetic acid dihydrochloride.

46. A pharmaceutical composition comprising a therapeutically effective amount of a benzamidine derivative according to claim 45, together with a pharmaceutically acceptable carrier or diluent.

47. A benzamidine derivative according to claim 1 which is N-[4-(1-acetimidoylpiperidin-4-yl)oxyphenyl]-N-[(E)-3-(3-amidinophenyl)-2-methyl-2-propenyl]sulfamoylacetic acid dihydrochloride.

48. A pharmaceutical composition comprising a therapeutically effective amount of a benzamidine derivative according to claim 47, together with a pharmaceutically acceptable carrier or diluent.

* * * * *